(12) United States Patent
Apt et al.

(10) Patent No.: US 9,540,666 B2
(45) Date of Patent: Jan. 10, 2017

(54) POLYUNSATURATED FATTY ACID SYNTHASE NUCLEIC ACID MOLECULES AND POLYPEPTIDES, COMPOSITIONS, AND METHODS OF MAKING AND USES THEREOF

(71) Applicant: DSM IP Assets B.V., Heerlen (NL)

(72) Inventors: Kirk E. Apt, Ellicott City, MD (US); Leslie Richter, Broomfield, CO (US); David Simpson, Boulder, CO (US); Ross Zirkle, Mt. Airy, MD (US)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 14/566,458

(22) Filed: Dec. 10, 2014

(65) Prior Publication Data

US 2015/0152450 A1 Jun. 4, 2015

Related U.S. Application Data

(62) Division of application No. 12/727,851, filed on Mar. 19, 2010, now Pat. No. 8,940,884.

(60) Provisional application No. 61/161,742, filed on Mar. 19, 2009, provisional application No. 61/296,460, filed on Jan. 19, 2010.

(51) Int. Cl.
| | |
|---|---|
| *C12P 7/64* | (2006.01) |
| *C12N 9/04* | (2006.01) |
| *C12N 15/82* | (2006.01) |
| *C12N 9/02* | (2006.01) |
| *C12N 9/88* | (2006.01) |
| *A61K 38/00* | (2006.01) |

(52) U.S. Cl.
CPC ............ *C12P 7/6427* (2013.01); *C12N 9/001* (2013.01); *C12N 9/0006* (2013.01); *C12N 9/88* (2013.01); *C12N 15/8247* (2013.01); *C12P 7/6472* (2013.01); *A61K 38/00* (2013.01); *C12Y 103/01* (2013.01); *C12Y 402/01* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,721,626 A | 1/1988 | Rule | |
| 5,601,860 A | 2/1997 | Lien et al. | |
| 5,952,544 A | 9/1999 | Browse et al. | |
| 5,981,781 A | 11/1999 | Knowlton | |
| 6,036,992 A | 3/2000 | Borror et al. | |
| 6,051,754 A | 4/2000 | Knutzon | |
| 6,160,007 A | 12/2000 | DeMichele et al. | |
| 6,372,965 B1 | 4/2002 | Lightner et al. | |
| 6,432,684 B1 | 8/2002 | Mukerji et al. | |
| 8,003,772 B2 | 8/2011 | Weaver et al. | |
| 8,426,686 B2 | 4/2013 | Metz et al. | |
| 8,829,274 B2 | 9/2014 | Facciotti et al. | |
| 2003/0101486 A1 | 5/2003 | Facciotti et al. | |
| 2004/0235127 A1 | 11/2004 | Metz et al. | |
| 2005/0014231 A1 | 1/2005 | Mukerji et al. | |
| 2005/0100995 A1 | 5/2005 | Weaver et al. | |
| 2005/0255440 A1 | 11/2005 | Downing | |
| 2005/0273883 A1 | 12/2005 | Metz et al. | |
| 2005/0273884 A1 | 12/2005 | Metz et al. | |
| 2008/0044871 A1 | 2/2008 | Metz et al. | |
| 2008/0144473 A1 | 6/2008 | Morimoto | |

FOREIGN PATENT DOCUMENTS

| | | |
|---|---|---|
| AU | 2007226510 A1 | 9/2007 |
| AU | 201325 201 A1 | 11/2013 |
| CA | 2646317 A1 | 9/2007 |
| CA | 2755639 A1 | 9/2010 |
| CN | 1535312 A | 10/2004 |
| CN | 104073505 A | 10/2014 |
| WO | WO9844917 | 10/1998 |
| WO | WO0294861 | 11/2002 |
| WO | WO2006037947 | 4/2006 |
| WO | WO2006125231 A2 | 11/2006 |
| WO | WO2006135866 | 12/2006 |
| WO | WO2007106903 | 9/2007 |
| WO | WO2007106908 | 9/2007 |

OTHER PUBLICATIONS

Witkowski et al.; Conversion of beta-ketoacyl synthase to a malonyl decarboxylase by replacement of the active site cysteine with glutamine; Biochemistry 38:11643-11650, 1999.*
Seffernick et al.; Melanine deaminase and atrazine chlorohydrolase: 98 percent identical but functionally different; J. Bacteriol. 183(8):2405-2410, 2001.*
Branden et al.; Introduction to Protein Structure, Garland Publishing Inc., New York, p. 247, (1991).*
2005, EMBL-EBI Database Accession No. AY730618, Thalassiosira Peudona long chain acyl-coA Synthetase (lacsA) mRNA, complete cds, AY730618, accessed at http://www.ebi.ac.uk/ena/data/view/AY730618, May 19, 2005, 2 pages.
Kendrick et al., Lipids of Selected Molds Grown for Production of n-3 and n-6 Polyunsaturated Fatty Acids, Department of Applied Biology, 1992, 15-20, 27(1).

(Continued)

*Primary Examiner* — Antonio Galisteo Gonzalez
(74) *Attorney, Agent, or Firm* — Xi Chen; Shannon McGarrah

(57) ABSTRACT

The present invention is directed to isolated nucleic acid molecules and polypeptides of thraustochytrid polyunsaturated fatty acid (PUFA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

12 Claims, 38 Drawing Sheets

(56) References Cited

OTHER PUBLICATIONS

Old et al., Principles of Gene Manipulation, An Introduction to Gene Engineering, 1987, p. 115, None.
Sefferenick et al., Melamine Deaminase and Atrazine Chlorohydrolase: 98 Percent Identical but Functionally Different, Journal of Bacteriology, 2001, pp, 2405-2410, vol. 183, No. 8.
Tonon et al., Identification of a long chain polyunsaturated fatty acid acyl-coenzyme a Synthetase from Diatom Thalassiosira pseudonana, Plant Physiology, 2005, 402-408, 138, American Society of Plant Biologists.
Witkowski et al., Conversion of a B-Ketoacyi Synthase to a Malonyl Decarboxylase by Replacement of the Active-Site Cysterine with Glutamine, Biochemistry, 1999, pp. 11643-11650, vol. 38.

* cited by examiner

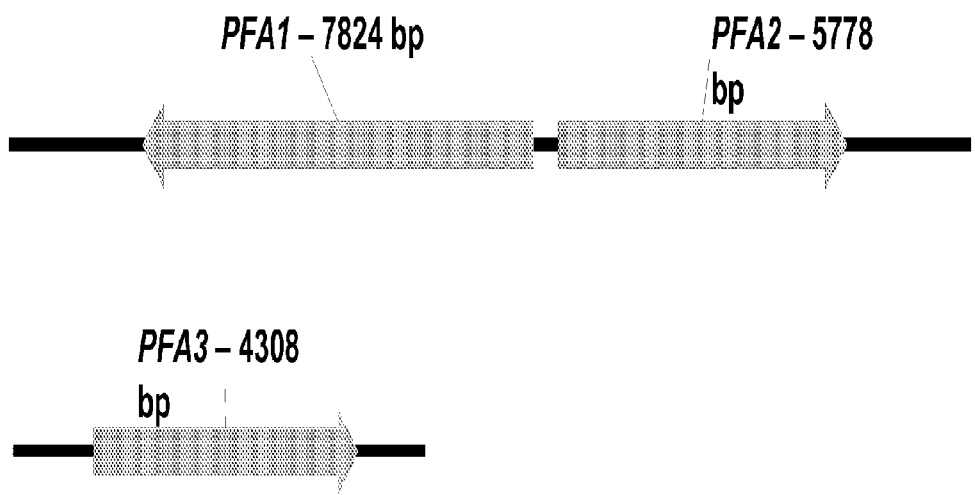
Figure 1. *Schizochytrium sp.* ATCC PTA-9695 Gene architecture

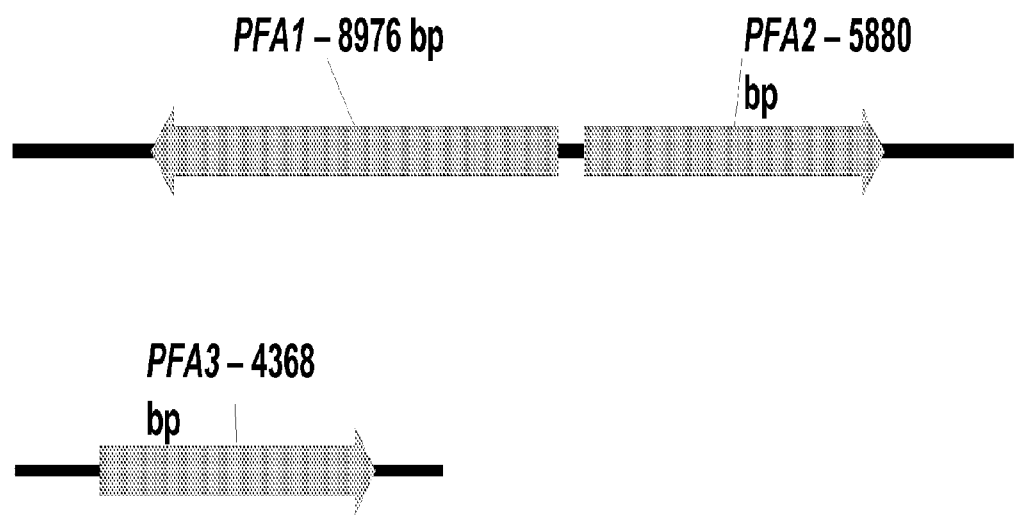
Figure 2. *Thraustochutrium sp.* ATCC PTA-10212 Gene architecture

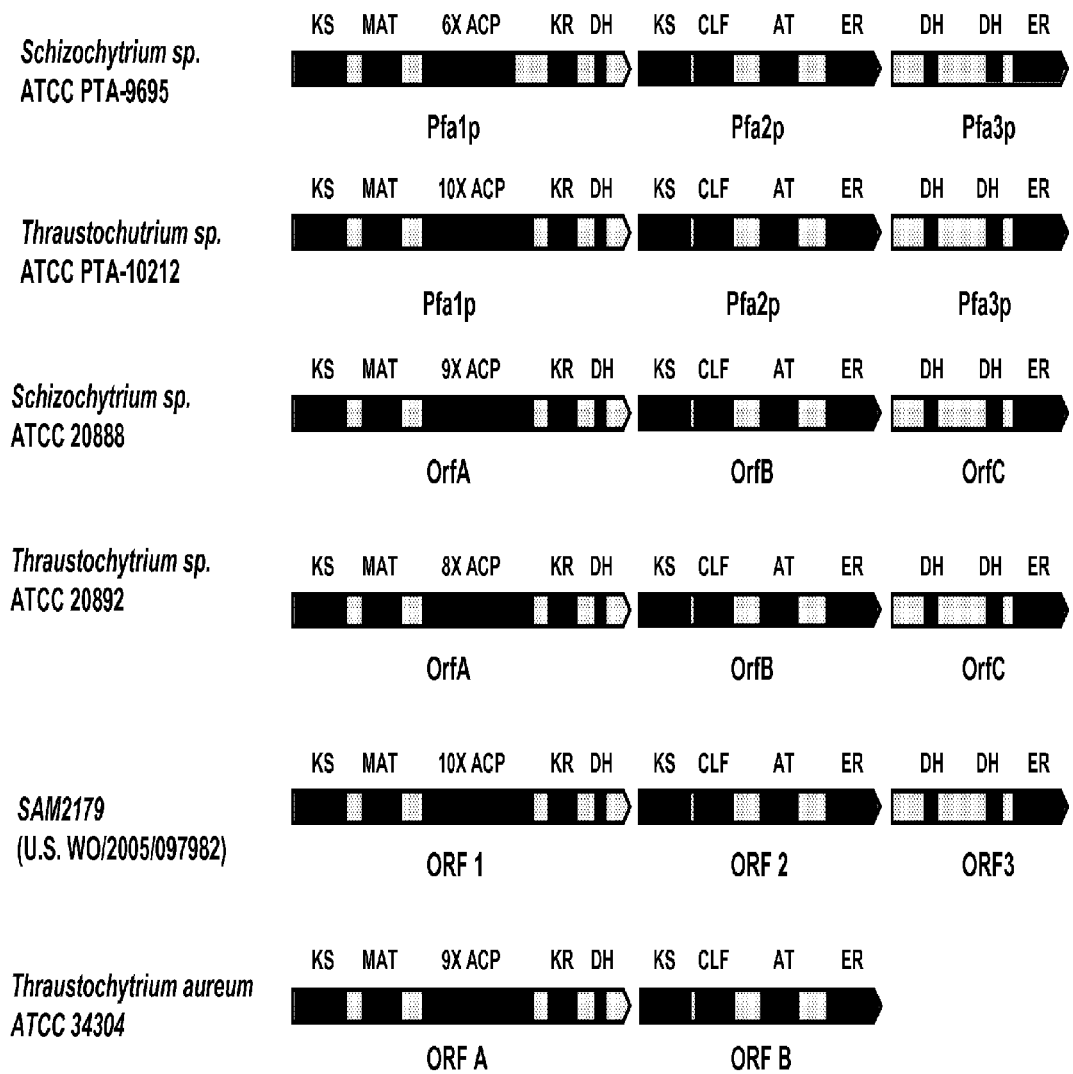
Figure 3. Domain architecture:

FIG. 4

```
                              1                                                  50
Sch. sp.  9695 Pfa1p      (1) --------------------------------------------------
   Thr. aureum ORF1       (1) RKCIRPSLGHHWAIIGVLGRALRIVRPIRYEATNLRRLPRSGWLVALGLF
Sch. sp. 20888 OrfA       (1) --------------------------------------------------
Thr. sp. 10212 Pfa1p      (1) --------------------------------------------------
Thr. sp. 20892 OrfA       (1) --------------------------------------------------

51                                                100
Sch. sp.  9695 Pfa1p      (1) -------------------------------------------------M
   Thr. aureum ORF1      (51) CDLSSCAGKLDLQTRDTAKDPCCKRKWSASRAPPRPRAEADKASNEMETK
Sch. sp. 20888 OrfA       (1) ----------------------------------------MAARLQEQKGGEM
Thr. sp. 10212 Pfa1p      (1) ------------------------------------------------ME
Thr. sp. 20892 OrfA       (1) -----------------------------------------------MKDME 101                                               150
Sch. sp.  9695 Pfa1p      (2) DTRIAIVGMSAILPSGENVRESWEAIRDGLDCLSDLPADRVDVTAYYPE
   Thr. aureum ORF1    (101) DDRWAIVGMSAILPCGESVRESWEAIRDGLDCLQDLPADRVDVTAYYDPN
Sch. sp. 20888 OrfA     (14) DTRIAIVGMSAILPGGTTVRESWETIRACVCLSDLPEDRVDVTAYYDPV
Thr. sp. 10212 Pfa1p     (3) DQRIAIVGMSAILPSGENVRESWEAIRDGLNCLSDLPADRVDVTAYYPT
Thr. sp. 20892 OrfA      (6) DRRWAIVGMSAHLPCGTDVRESWQAIRDCVCLSDLPADRVDVTAYYPN 151                                               200
Sch. sp.  9695 Pfa1p     (52) KPPKDKIYCKRGGFIPEYPDAREFGLNMEQMEDSDANQTVLLKVKEAL
   Thr. aureum ORF1    (151) KPPKDKIYCKRGGFIPEYPDAREFGLNMEQMEDSDANQTVLLKVKEAL
Sch. sp. 20888 OrfA     (64) KPPKDKIYCKRGGFIPEYPDAREFGLNMEQMEDSDANQTVLLKVKEAL
Thr. sp. 10212 Pfa1p    (53) KGVKDKIYCKRGGFIPEYPFDSREFGLNMLQMEDSDANQTVLLKVKEAL
Thr. sp. 20892 OrfA     (56) KAPKDKIYCKRGGFIPNYPDPREFGLNMEQMEDSDANQTVLLKVKQAL 201                                               250
Sch. sp.  9695 Pfa1p    (102) TDANIPEPESGKKNIGCVLGIGGGQKASHEFYSRLNYVVVVKVLRKMGLP
   Thr. aureum ORF1    (201) PDAGIPPTEKKKNIGCVLGIGGGQKASHEFYSRLNYVVVVEKVLRKMNLP
Sch. sp. 20888 OrfA    (114) QDAGIPALGKEKKNIGCVLGIGGGQKASHEFYSRLNYVVVVEKVLRKMGNP
Thr. sp. 10212 Pfa1p   (103) PDANIPEPTNEKKNIGCVLGIGGGQKASHEFYSRLNYVVVVKVLRKMGLP
Thr. sp. 20892 OrfA    (106) PDASIPPTEKKKNIGCVLGIGGGQKASHEFYSRLNYVVVVEKVLRKMGLP 251                                               300
Sch. sp.  9695 Pfa1p    (152) PEDVAAAVEKPKASFPEWRLDSFPGFLGNVTAGRCCNPFNMEGMNCVVDA
   Thr. aureum ORF1    (251) PEVVEAAVEKPKANFPEWRLDSFPGFLGNVTAGRCPNVFNMEGMNCVVDA
Sch. sp. 20888 OrfA    (164) PEDVKVAVEKPKANFPEWRLDSFPGFLGNVTAGRCPNPFNMEGMNCVVDA
Thr. sp. 10212 Pfa1p   (153) PEDVETAVEKPKANFPEWRLDSFPGFLGNVTAGRCPNPFNMEGMNCVVDA
Thr. sp. 20892 OrfA    (156) PADVEEAVEKPKANFPEWRLDSFPGFLGNVTAGRCPNPFNMEGMNCVVDA 301                                               350
Sch. sp.  9695 Pfa1p    (202) ACASSLIAPKVAPDELLPGDCDAMPAGATCTDNSPGMYMAFSKTPVFSTD
   Thr. aureum ORF1    (301) ACASSLIAPKVAPDELLPGDCDTMPAGATCTDNSPGMYMAFSKTPVFSTD
Sch. sp. 20888 OrfA    (214) ACASSLIAPKVAPDELLPGDCDMMPTGATCTDNSPGMYMAFSKTPVFSTD
Thr. sp. 10212 Pfa1p   (203) ACASSLIAPKVAPDELLPGDCDAMPAGATCTDNSPGMYMAFSKTPVFSTD
Thr. sp. 20892 OrfA    (206) ACASSLIAPKVAPELLPGDCDTMPGATCTDNSPGMYMAFSKTPVFSTD 351                                               400
Sch. sp.  9695 Pfa1p    (252) PSVPAYDAATKGMLIGEGSAMPVLKRYADAVRDGDPPHAVIPGCPSSSDG
   Thr. aureum ORF1    (351) QSVPAYDAPTKGMLIGEGSAMPVLKRYADAVRDGDEPHAVIPACPSSSDG
Sch. sp. 20888 OrfA    (264) PSVPAYDEPTKGMLIGEGSAMPVLKRYADAVRDGDEPHAVIPGCPSSSDG
Thr. sp. 10212 Pfa1p   (253) QSCLAYDEPTKGMLIGEGSAMFVLKRYADAVRDGDPPHAVIPCPSSSDG
Thr. sp. 20892 OrfA    (256) PSVPAYDEPTKGMLIGEGSAMFVLKRYADAVRDGDPHAVIPSCPSSSDG 401                                               450
Sch. sp.  9695 Pfa1p    (302) KAEGIYPPTPSGQEEALERAYARANVPFPTVPLVEGHGTGTPVGDPIELT
   Thr. aureum ORF1    (401) KAEGIYAPTVSGQEEALERAYARACVPFPTVPLVEGHGTGTPVGDPIELT
Sch. sp. 20888 OrfA    (314) KAEGIYPPTPSGQEEALERAYNRACVPFPTVPLVEGHGTGTPVGDPIELT
Thr. sp. 10212 Pfa1p   (303) KAEGIYPPTPSGQEEALPLRAYRRACVSPNTVPLVEGHGTGTPVGDPIELT
Thr. sp. 20892 OrfA    (306) KAEGIYPPTPSGQEEALERAYARACVCPPTPGLVEGHGTGTPVGDPIELT 451                                               500
Sch. sp.  9695 Pfa1p    (352) ALSNIFSPAPSANGGGAEEAEQPAVGSIKSQIGHLKPVAGLAGPVKVPPA
   Thr. aureum ORF1    (451) ALRNPFPAANKGR------KETPAVGSIKSQIGHLKPVAGFAGPVKPPMA
Sch. sp. 20888 OrfA    (364) ALRNIFDPAPPEG-----NTEKPAVGSIKSSIGHLKPVAGLAGPVKPPMA
Thr. sp. 10212 Pfa1p   (353) ALRNIFDPAPPPG-----HPEEPAVGSIKSQIGHLKPVAGCAGPVKPPMA
Thr. sp. 20892 OrfA    (356) ALRNIFDPAPPSK------REQPAVGSIKSQIGHLKPVAGFAGPVKAPVA
```

FIG. 4 (cont'd)

```
                              501                                                550
Sch. sp. 9695  Pfalp    (402) LKHKTLPGTINVDKPPSLVDGTPIQQSPLYVNTMNRPWTTPVGVPRRAGV
    Thr. aureum ORF1    (495) LKHKTLPGTINVHDPPALKDGSPIQDSSLYINTMNRPWTTAPGVPRRAGI
Sch. sp. 20888 OrfA     (409) LKHKTLPGTINVDNPPNLKDNTPINSSLYINTMNRPWTPPEGVPRRAGI
Thr. sp. 10212 Pfalp    (398) LKHKTLPGSINVENPPNLVDGTVISDEKLYINTMNRPWITKEGVPRRAGI
Thr. sp. 20892 OrfA     (400) LKHKTLPGSINVDQPPLLSDGTQIQDSSLYINKTNRPWTTQNKLPRRAGV
                              551                                                600
Sch. sp. 9695  Pfalp    (452) SSFGFGGANYHAVLEEFEPEHESAYRYNNSPQVALLHAGDVATLAATVRA
    Thr. aureum ORF1    (545) SSFGFGGANYHAVLEEAEPEHAKPYRMNQTPCPVLLHASSASALASTCRA
Sch. sp. 20888 OrfA     (459) SSFGFGGANYHAVLEEAEPEHTTAYRLNKRFCPVLMMAASPAALQSLCEA
Thr. sp. 10212 Pfalp    (448) SSFGFGGANYHAVLEEFEPEQTKPYRLNVSACPMLLHAVNANSLQKLCED
Thr. sp. 20892 OrfA     (450) SSFGFGGANYHAVLEEFEPEHEKPYRLNTVGHPVLLYAPSVEALKVICND
                              601                                                650
Sch. sp. 9695  Pfalp    (502) KEALATNEQEEARVVKNADYRAYHRFLDECKIEGAVPQAHARVGLLVRDL
    Thr. aureum ORF1    (595) QADALQRANSP-EASKHADYRAIVAFHSAEHLAGVPAGHARIGFVSGSA
Sch. sp. 20888 OrfA     (509) QLKEFEAAIKENETVKNTAYIKCVKFGLQFKFPGSIPATNARLGFLVKDA
Thr. sp. 10212 Pfalp    (498) QLKLIKESREKCVNTKHTDYVAFSKFQDSIKLKGSSVPIQHARVGFASKSI
Thr. sp. 20892 OrfA     (500) QHALITIAEEEAKTHKNVEKVCGYKFLDESQLQGSCPPENPRVGEEATLP
                              651                                                700
Sch. sp. 9695  Pfalp    (552) SSLIAVIEAAAAKLAGSESATENTVSVATGEAAFRVRGVATENNVAALFS
    Thr. aureum ORF1    (644) ASTIAVIRAASALKQSSATLDVTLSN  GVTYRSAAMITPGSVAALFS
Sch. sp. 20888 OrfA     (559) EDACSTIRAICAQFAKDVIKEAAVRLPSL-GVSFRAKGIATN-GAVAALFS
Thr. sp. 10212 Pfalp    (548) EDTISSAIVNSFQKDIITTSMALPSI-GAIFRSTALLNDNKSVAALFS
Thr. sp. 20892 OrfA     (550) TSNIIVALKSILAQLDAKPDAKKWDLPHKKSFGATFASSVKGSVAALFS
                              701                                                750
Sch. sp. 9695  Pfalp    (602) GQGAQYTHMFSDVAMSWPFFRESVAAMDRAQRERFG--SPAKRSSVLYP
    Thr. aureum ORF1    (692) GQGAQYTHMFTDVAMSWPFFRSAVQEMDAAQVTAAAP----KRLSEVLYP
Sch. sp. 20888 OrfA     (607) GQGAQYTHMFSEVAMSWPQFRQSLAAMDAAQSKVASSDKDFERNSQVLYP
Thr. sp. 10212 Pfalp    (597) GQGAQYTHMFNDVAMSWPQFRLCVNDMKKAQEEEVIN-DSSVKRISQVMSP
Thr. sp. 20892 OrfA     (600) GQGTQYLNMFSDVAMSWPFFRDSIVAMSEAQTEVFEG--QVEPISKVLSP
                              751                                                800
Sch. sp. 9695  Pfalp    (650) RKPYGDEPRQDHKEISQTRYSQPATHACWVGAPDIFKAAGLAPSEAAGHS
    Thr. aureum ORF1    (738) RKPYAAETEQDNKAISNTINSQPALMACAAGAPLVFRQAGLAPDHVAGHS
Sch. sp. 20888 OrfA     (657) PKPYEREFEQNPKKISNTAYSQPSTHACAWGAFEIFKEAGFTPDFAAGHS
Thr. sp. 10212 Pfalp    (646) RKPYARESPLDNKEISKTEYSQTNTVASSVGLFEIFRDAGFAPAEVAGHS
Thr. sp. 20892 OrfA     (648) RERYSGESESEOGNELLCNTEYSQPHIAAAAGAFDIFKAAGIKPDMVGGHS
                              801                                                850
Sch. sp. 9695  Pfalp    (700) LGEFSALYAAGSSDRDANTDLVCARAKAMSDFTAQASSSGCAMAAVIGAK
    Thr. aureum ORF1    (788) LGEFSALIAAGCASRSELFRLVCSRAKAMQDVPQG---------------
Sch. sp. 20888 OrfA     (707) LGEFAALYAAGCVDRDSLFELVCRRASIMGGKDAP-ASPKGCMAAVIGEN
Thr. sp. 10212 Pfalp    (696) LGEFSALYAAGLIDREDLFKLVCNRAMSMRDAPK--KSADGAMAAVIGEN
Thr. sp. 20892 OrfA     (698) LGEFSALYAAGSESRDDLYKLVCKRAKAMANASDG------AMAAVIGED
                              851                                                900
Sch. sp. 9695  Pfalp    (750) ADQSSGGAPLVAIANSNSFSQTVITGSAENVAAASDKLRCSGNFRVVEL
    Thr. aureum ORF1    (823) -----DG----ATLANCNSFSQVVISGDKTNVERESSRLAGLG-FRVVEL
Sch. sp. 20888 OrfA     (756) AENIKVQ-AANVTLGNSNSFSQTVITGNVESTQAETSARLQKEG-FRVVEL
Thr. sp. 10212 Pfalp    (744) ASSIKISS-APFVVANNNSFSQTVIFGANSGTQAETSKLKTQG-FRVVHL
Thr. sp. 20892 OrfA     (742) ARLSTPQ-NSIVIVANFNSAIQVVISGIVQGVKEESSKLLISKG-FRVVEL
                              901                                                950
Sch. sp. 9695  Pfalp    (800) ACERAFHSPHMRGAEQIFASALSQAPVAPAAARFYSNVTGGAAVTSPAD
    Thr. aureum ORF1    (863) ACEGAFHSPIMTAAQATFQAALDSIKIGTPTNGARLYNNVSGKTCRSLGI
Sch. sp. 20888 OrfA     (804) ACESAFHSPQMENASSAFKDVIKVSFRTPKSE--TKLFSNVSGETYPTI
Thr. sp. 10212 Pfalp    (792) ACEGAFHSPIMENASKQFQKAISAVKFNKPTQS--SPKIFSNVTGGVFTI
Thr. sp. 20892 OrfA     (790) KCQGAFHSPLMGPSDSFKSTIFETCTSSPPKNVK--FFCNVSGKFSP---N
                              951                                               1000
Sch. sp. 9695  Pfalp    (850) VKTNLGNHMTSPVQFVQQSRAMIAAGARVFVEFGPKQVLSRLVKETIGIA
    Thr. aureum ORF1    (913) LSDCLGNHMTSPVLFQAQSENMYAAGARIFVEFGPKQVLSKLVGETIAQK
Sch. sp. 20888 OrfA     (852) ASEMLTQHMTSSVKFSTQSRNMSQAGARIFEEFGPKQVLSKLVSETIKID
Thr. sp. 10212 Pfalp    (840) PKTALSRHMTSSVQFSTQIRNMYAAGARVFEEFGPKQVLSKLVNEIFPGD
Thr. sp. 20892 OrfA     (836) PKQTLKSHMTSSVQFEEQIRNMYDAGARVFLEFGPKQVLKKLIAEMFP--
```

FIG. 4 (cont'd)

```
                               1001                                              1050
Sch. sp. 9695 Pfa1p    (900)  CDYVTVAVNPDSKKDSDTQLRQAASTLAVAGVPLKDFDNWQLPDATRLEP
    Thr. aureum ORF1   (963)  SDFVIVAVNSSSKKDSDVQLREAAAKLAVLGVPLANFDPWELCDARKLRE
Sch. sp. 20888 OrfA    (902)  PSVVTVSVNPASGTDSDIQLRDAAVQLVVAGVNLQGFDKWMAPEATRMQA
Thr. sp. 10212 Pfa1p   (890)  TSVIETVSVNPASKKDSDIQLRQAAVQMAVAGVALTDFDNWELKDPTRNKE
Thr. sp. 20892 OrfA    (884)  -SCTALSVNPASSGDSDVQLRLAAVKFAVSGAALSTFDPWEYRKPQDELI
                               1051                                             1100
Sch. sp. 9695 Pfa1p    (950)  VKKKKTTLRLSAATYVSAKTLRQREASSNDGYTKSGAT----------AV
    Thr. aureum ORF1  (1013)  CPRSKTTLRLSAATYVSNKTLAARERKMEDNCDFSSLFASG--------P
Sch. sp. 20888 OrfA   (952)  IKKKKTTLRLSAATYVSDKTKKVRSAANNDGKCYYIKGAAPLIKAPEPV
Thr. sp. 10212 Pfa1p  (940)  FPRKKTTLTLSAATYVSKKTLQERERKMNDGRTVSCVQ----------R
Thr. sp. 20892 OrfA   (933)  RKPRKTALVLSAATYVSPKTLAERKKAMEDIKLVSITPR----------D
                               1101                                             1150
Sch. sp. 9695 Pfa1p    (990)  NKEVDTANEERIVKQAQDLQRQLAELSTAAQASQKVAELERTIQDLEPK
    Thr. aureum ORF1  (1055)  ASQEMEREIANLRAELEAAQRQLDTAKTQLARKLVQDPTADRQRDMIRH
Sch. sp. 20888 OrfA  (1002)  SDEAAKEALNLQKELQDAQRQLDDAKRAAAEANGKLAAAKEEAKTARAS
Thr. sp. 10212 Pfa1p  (979)  SENTNTGELERLRKQLQDKENEVRVQALATQASADLQNTKAELQKAQAS
Thr. sp. 20892 OrfA   (973)  SMVSIGKIAQEVRTAKQPLETERRLNKELEHLKRELAAKASKKSASKS
                               1151                                             1200
Sch. sp. 9695 Pfa1p   (1040)  --------------------------------KQQQQQE---------
    Thr. aureum ORF1  (1105)  RSTLAAMVKEFEALAS---------GSPCAYPKAPKVDTAVEDVPFADKV
Sch. sp. 20888 OrfA  (1052)  -SKPAVDTAVVEHHAALLKSSLAASLGYGSVDASSSQQQQQQQTAPAPVK
Thr. sp. 10212 Pfa1p (1029)  KSSNAASDAVVAKHKALLANLESLTGKAVDKSSFSKGQVASPATVRVV
Thr. sp. 20892 OrfA  (1023)  ----SKERGVISKHRALLQNLLQRYDDLRVVPSKVRSVAVDNTAPYADQV
                               1201                                             1250
Sch. sp. 9695 Pfa1p   (1047)  -----------------------------K-GEN--S-----------
    Thr. aureum ORF1  (1146)  STSPPQ---------VTSAPIAELARAEAVMEVLAANKTGYEVDMIEALM
Sch. sp. 20888 OrfA  (1101)  AAAPAAP---VASAPAPAVSNELLEKAETVVMEVLAAKTGYETMIEALM
Thr. sp. 10212 Pfa1p (1079)  SAPVQAA---APVQVSASYDSGLLAKAFQVVIEVIASKTGYETESTELIM
Thr. sp. 20892 OrfA  (1069)  STPASERSASPLFEKRSSSYSSARLAEAEAAVLSVLADKTGYSSSMIEMIM
                               1251                                             1300
Sch. sp. 9695 Pfa1p   (1052)  ------------------ESNAAAEVLRKHKSLLQRMLQDCSEQAVPVRT
    Thr. aureum ORF1  (1187)  LESAELGIDSVKRVEILAAVQAQLGVEAKDVDALSRTKTVGEVVDAMKAE
Sch. sp. 20888 OrfA  (1148)  SLETELGIDSIKRVEILSEVQAMLNVEAKDVDALSRTKTVGEVVNAMKAE
Thr. sp. 10212 Pfa1p (1126)  SLETELGIDSIKRVEILSEVQAQLNVEAKDVDALSRTKTVGEVIDAMKAE
Thr. sp. 20892 OrfA  (1119)  DLESELGVDSIKRVEINSEVQTLLSVEVSDVDALSRTKTVGEVIEAMRLE
                               1301                                             1350
Sch. sp. 9695 Pfa1p   (1084)  SVPTPTSSPSPTSSPVSGN----------SKSTRGSSDLQASILAKAETV
    Thr. aureum ORF1  (1237)  ISGQATSAPSPMAQPQASAPSPSPTASVLPKEVALPASSDPAKIARAFAV
Sch. sp. 20888 OrfA  (1198)  IASSSAPAPAAASPAPAKA----------APASAPAVSNELLEKAETV
Thr. sp. 10212 Pfa1p (1176)  ISGGQPAAPVQVSAPTQVV----------APVQASAPVDSGLLAKAEQV
Thr. sp. 20892 OrfA  (1169)  SSPQGQTLRAESIRQPPVSEPAVPTS----SSSSIANVSSARLAEAEAA
                               1351                                             1400
Sch. sp. 9695 Pfa1p   (1123)  VMAVLAAKTGYEADMVEADMLLEAELGIDSIKRVEILSSVQQGLGVEAKD
    Thr. aureum ORF1  (1287)  VMEVLAAKTGYEVDMIEADMLLEAELGIDSKKRVEILAAVQAQLGVEAKD
Sch. sp. 20888 OrfA  (1237)  VMEVLAAKTGYETDMIESDMELETELGIDSIKRVEILSSVQAMLNVEAKD
Thr. sp. 10212 Pfa1p (1215)  VLEVLASKTGYETELIELDMELETELGIDSIKRVEILSSVQAQLSVEAKD
Thr. sp. 20892 OrfA  (1215)  VSSVLADKTGYSSSMIEMDMLLESELGVDSIKRVEINSSVQTLLSVEVSD
                               1401                                             1450
Sch. sp. 9695 Pfa1p   (1173)  VDALSRTRTVGEVVDAMKAEIVASS-----------------------
    Thr. aureum ORF1  (1337)  VDALSRTRTVGEVVDAMKAEISGGATSAPAVAQPQASAPSPSATTASVL
Sch. sp. 20888 OrfA  (1287)  VDALSRTRTVGEVVNAMKAEIAGSSAPAPAAAPGPAAAK----------
Thr. sp. 10212 Pfa1p (1265)  VDALSRTRTVGEVVDAMKAEIAGGQPAAPVQVAAPTQVVA---------
Thr. sp. 20892 OrfA  (1265)  VDALSRTRTVGEVVRAMKIESGGPQGQTLTAESTRQPPVSEPAVPTS---
                               1451                                             1500
Sch. sp. 9695 Pfa1p   (1198)  -------------------------------------------------
    Thr. aureum ORF1  (1387)  RKPVAAPTSADPSKLAAAEAVVMEVLAAKTGYEVDMIEADMLLDAELGID
Sch. sp. 20888 OrfA  (1327)  PAPAAAAPAVSNELLEKAETVVMEVLAAKTGYEVDMIESDMELETELGID
Thr. sp. 10212 Pfa1p (1305)  PVQASAP--VDSGLLAKAEQVVIEVLASKTGYETELIELDMELETELGID
Thr. sp. 20892 OrfA  (1312)  -S--SSSIANVSSARLAEAEAAVLSVLADKTGYDSSMIEMDMLESELGVD
```

FIG. 4 (cont'd)

```
                              1501                                              1550
Sch. sp. 9695 Pfa1p    (1198) ---------------------------------------------GGSAPAV
Thr. aureum ORF1       (1437) SIKPEILRAVQAQLGVEAKDVDALSRTRTVGEVVDAMKAEIGGQATSAP
Sch. sp. 20888 OrfA    (1377) SIKRVEILSEVQAMLNVEAKDVDALSRTRTVGEVVDAMKAEIAGGSAPA
Thr. sp. 10212 Pfa1p   (1353) SIKRVEILSEVQAQLSVEAKDVDALSRTRTVGEVVDAMKAEISGGQPAA
Thr. sp. 20892 OrfA    (1360) SIKRVEINSEVQTLLSVEVSDVDALSRTRTVGDVVDAMKLEGGPQGQTL
                              1551                                              1600
Sch. sp. 9695 Pfa1p    (1205) PSAPAASAAPTAASTAPSA-----DLQALLSKAETVVMAVLAAKTGYEA
Thr. aureum ORF1       (1487) ASVAQPQISVSPTPLAASPS-----ADPAKLARAEAVVMEVLAAKTGYEV
Sch. sp. 20888 OrfA    (1427) AAAPAPAAAAPAPAPAPS-----VSSELLEKAETVMEVLAAKTGYE
Thr. sp. 10212 Pfa1p   (1403) VQVAAPTQIVAPVQVSAP-------VDSGLLAKAEQVVLEVLASKTGYE
Thr. sp. 20892 OrfA    (1410) TAESIRQPPVSEPAVPTSSSSIANVLSARLAEAEAAVLSVLADKTGYD
                              1601                                              1650
Sch. sp. 9695 Pfa1p    (1250) DMVEADMQLEAELGIDSIKRVEILSEVQGQLGVEAKDVDALSRTRTVGEV
Thr. aureum ORF1       (1532) DMIEADMLLDAELGIDSKKRIEILAAVQAQLGVEAKDVDALSRTRTVGEV
Sch. sp. 20888 OrfA    (1472) DMIESDMELETELGIDSIKRVEILSEVQAMLNVEAKDVDALSRTRTVGEV
Thr. sp. 10212 Pfa1p   (1446) SMIELDMELETELGIDSKRVEILSEVQAQLSVEAKDVDALSRTRTVGEV
Thr. sp. 20892 OrfA    (1460) SMIEMDMQLESELGVDSKRVEINSEVQTLLSVEVSDVDALSRTRTVGDV
                              1651                                              1700
Sch. sp. 9695 Pfa1p    (1300) VDAMKAEIVAASAGSAP----APAVPSAPAASAAPTAAASTAPSADLQAL
Thr. aureum ORF1       (1582) VDAMKAEIGGQATSAPASVAQPQASAPSPSATAVLEKPVAAPTSADPAK
Sch. sp. 20888 OrfA    (1522) VDAMKAEIAGGSAPAPA----AAAPAPAAAAPAPAAPAPAPAPAYSSEL
Thr. sp. 10212 Pfa1p   (1496) VDAMKAEISGGQP-----------TAPVQVAAPTQIVAPVQVSAPVDSGL
Thr. sp. 20892 OrfA    (1510) VAMKLEGGPQG-Q---TLTAESIRQPEVSEPAVPTSSSSIANVSSAR
                              1701                                              1750
Sch. sp. 9695 Pfa1p    (1346) LSKAETVVMAVLAAKTGYEADMVEADMQLEAELGIDSIKRVEILSEVQGQ
Thr. aureum ORF1       (1632) LAKAEAVVMEVLAAKTGYEVDMIEADMLLDAELGIDSVKRIEILAAVQAQ
Sch. sp. 20888 OrfA    (1568) LEKAETVVMEVLAAKTGYEVDMIESDMELETELGIDSIKRVEILSEVQAM
Thr. sp. 10212 Pfa1p   (1535) LAKAEQVVLEVLASKTGYESMIELDMELETELGIDSKRVEILSEVQAQ
Thr. sp. 20892 OrfA    (1556) LAEAEAAVLSVLADKTGYDSMIEMDMQLESELGVDSKRVEINSEVQTL
                              1751                                              1800
Sch. sp. 9695 Pfa1p    (1396) LGVEAKDVDALSRTRTVGEVVDAMKAEIVAASGGSAPSPAVPSAPAASAA
Thr. aureum ORF1       (1682) LGVEAKDVDALSRTRTVGEVVDAMKAEIGGQAT-----SAPASMAQPQIS
Sch. sp. 20888 OrfA    (1618) LNVEAKDVDALSRTRTVGEVVDAMKAEIAGSS-----AAPAPAAAPAPAA
Thr. sp. 10212 Pfa1p   (1585) LSVEAKDVDALSRTRTVGEVVDAMKAEISGGQ-----PAAPVQVAAPTQI
Thr. sp. 20892 OrfA    (1606) LSVEVSDVDALSRTRTVGDVVDAMKLEGGPQGQTLTSEPIHQPPVSEPA
                              1801                                              1850
Sch. sp. 9695 Pfa1p    (1446) PTPAASTAPSSDLQALLAKAETVVMAVLAAKTGYEADMVEADMQLEAELG
Thr. aureum ORF1       (1727) VSPTPLAASPSADPAKLAKAEAVVMEVLAAKTGYEVDMIEADMLLDAELG
Sch. sp. 20888 OrfA    (1663) APAPAPAAAPAYSNELLEKAETVVMEVLAAKTGYEVDMIESDMELETELG
Thr. sp. 10212 Pfa1p   (1630) VAPVQASAP--VDSGLLAKAEQVVLEVLASKTGYETELELDMELETELG
Thr. sp. 20892 OrfA    (1656) VPTSSSSIANVSSARLAEAEAAVLSVLADKTGYDSMIEMDMQLESELG
                              1851                                              1900
Sch. sp. 9695 Pfa1p    (1496) IDSIKRVEILSEVQGQLGVEAKDVDALSRTRTVGSVVDAMKAEIVAASG
Thr. aureum ORF1       (1777) IDSVKRIEILAAVQAQLGVEAKDVDALSRTRTVGEVVDAMKAEIGGQATS
Sch. sp. 20888 OrfA    (1713) IDSIKRVEILSEVQAMLNVEAKDVDALSRTRTVGEVVDAMKAEIAGGSAP
Thr. sp. 10212 Pfa1p   (1678) IDSIKRVEILSEVQAQLSVEAKDVDALSRTRTVGEVVDAMKAEISGGQPA
Thr. sp. 20892 OrfA    (1706) VDSIKRVEINSEVQTLLSVEVSDVDALSRTRTVGDVVAMKMELGGPQGQ
                              1901                                              1950
Sch. sp. 9695 Pfa1p    (1546) SAPAPAVS--------------------------------
Thr. aureum ORF1       (1827) APASVAQS--------------------------------
Sch. sp. 20888 OrfA    (1763) APAAAP-----APAAAAPAVSNELLEKAETVVMEVLAAKTGYETDMIES
Thr. sp. 10212 Pfa1p   (1728) APVQVAATQIVAPVQVSAPVDSGLLAKAEQVVLEVLASKTGYETELIEL
Thr. sp. 20892 OrfA    (1756) TLTAESIR--------------------------------
                              1951                                              2000
Sch. sp. 9695 Pfa1p    (1554) ----------------------------------------
Thr. aureum ORF1       (1835) -----------------------------------QASAP-----
Sch. sp. 20888 OrfA    (1808) DMELETELGIDSIKRVEILSEVQAMLNVEAKDVDALSRTRTVGEVVDAMK
Thr. sp. 10212 Pfa1p   (1778) DMELETELGIDSIKRVEILSEVQAQLNVEAKDVDALSRTRTVGEVIDAMK
Thr. sp. 20892 OrfA    (1764) ----------------------------------------
```

FIG. 4 (cont'd)

```
                              2001                                               2050
Sch. sp. 9695 Pfalp   (1554) -----------SAPAASAAPTPAASTAPSADLQAELSKAETVVAAVLAA
    Thr. aureum ORF1  (1840) -----------SPSATASAPVTLLAAPASVDPAKLARAEAAVVMEVLAA
   Sch. sp. 20888 OrfA (1858) AEIAGSSAPAPAAAAPAPSAAAPAPSAAAPAVSSEILEKAETVVMEVLAA
  Thr. sp. 10212 Pfalp (1828) AEIAGGQP--AAPVQVAAPAPVVAEVQVSTPVDSGLLAKAEQVVLEVLAC
   Thr. sp. 20892 OrfA (1764) -----------QPEVSEPAVPTSSSSIANVSSARLAEAEAAVLSVLAD
                              2051                                               2100
Sch. sp. 9695 Pfalp   (1592) KTGYEADMVEADMQLEAELGIDSIKRVEILSEVQGQLGVEAKDVDALSRT
    Thr. aureum ORF1  (1877) KTGYEVDMIEADMLLRAELGIDSVKRVEILAAVQAQLGVEAKDVDALSRT
   Sch. sp. 20888 OrfA (1908) KTGYEIDMIESDMELETELGIDSIKRVEILSEVQAMLNVEAKDVDALSRT
  Thr. sp. 10212 Pfalp (1876) KTGYEVELIELDMRLETELGIDSIKRVEILSEVQAQLSVEAKDVDALSRT
   Thr. sp. 20892 OrfA (1802) KTGYEVSMIEMDMQLEEELGVDSIKRVEILSEVQALLSVEVSDVDALSRT
                              2101                                               2150
Sch. sp. 9695 Pfalp   (1642) RTVGEVVDAMKAEIVAASGGSAPAAAVPSAPAASA------APTAATAPS
    Thr. aureum ORF1  (1927) RTVGEVVDAMKAEIGGQATSAPASVAQPQASAPSPSATASVLPKPVASPS
   Sch. sp. 20888 OrfA (1958) RTVGEVVDAMKAEIACGS----RPAPAAAAP--------APAAAAP
  Thr. sp. 10212 Pfalp (1926) RTVGEVVDAMKAEISGSQ-----PTAPVQVAAPTQ------VVAPVKVST
   Thr. sp. 20892 OrfA (1852) RTVGEVVDAMKMELGGPQG----QTLTAESIREPPVSEPAVPTSSSSIAS
                              2151                                               2200
Sch. sp. 9695 Pfalp   (1686) ADLQALLSKAETVVMAVLAAKTGYEADMVEADMELEAELGIDSIKRVEIL
    Thr. aureum ORF1  (1977) SVDPAKLARAEAAVVMEVLAAKTGYEVDMIDADMLLRAELGIDSVKRVEIL
   Sch. sp. 20888 OrfA (1992) AVSNEILEKAETVVMEVLAAKTGYEIPMELSDMELSEVQAMLNVEAKDVD
  Thr. sp. 10212 Pfalp (1965) PVDSQLLAKAEQVVLEVLASKTGYETEEVELDMELETELGIDSIKRVEIL
   Thr. sp. 20892 OrfA (1898) NVSSARLAEAEAAVLSVLADKTGYESSMIEMDMQLEEELGVDSIKRVEIL
                              2201                                               2250
Sch. sp. 9695 Pfalp   (1736) SEVQQQLGVEAKDVDALSRTRTVGEVVDAMKAEIVAASGGSAPAAPSAPS
    Thr. aureum ORF1  (2027) AAVQAQLGVEAKDVDALSRTRTVGEVVRAMKAEIGAAGPNDAQAAS----
   Sch. sp. 20888 OrfA (2042) SEVQAMLNVEAKDVDALSRTRTVGEVVDAMKAEIAGGRAPAPAAAAPASA
  Thr. sp. 10212 Pfalp (2015) SEVQAQLNVEAKDVDALSRTRTVGEVVDAMKAEIASDQPAPAVVPVQAKS
   Thr. sp. 20892 OrfA (1948) SEVQTLLSVEVSDVDALSRTRTVGEVVEAMKLELGESSSIETLNCTEVEH
                              2251                                               2300
Sch. sp. 9695 Pfalp   (1786) LLPT----------------------------------------------
    Thr. aureum ORF1  (2073) --------------------------------------------------
   Sch. sp. 20888 OrfA (2092) GAAP----------------------------------------------
  Thr. sp. 10212 Pfalp (2065) GVANPALLAKAEQVVLEVLASKTGYETELIELDMELETELGIDSIKRVEI
   Thr. sp. 20892 OrfA (1998) TSYKS---------------------------------------------
                              2301                                               2350
Sch. sp. 9695 Pfalp   (1790) --------------------------------------------------
    Thr. aureum ORF1  (2073) --------------------------------G-----------------
   Sch. sp. 20888 OrfA (2096) --------------------------------------------------
  Thr. sp. 10212 Pfalp (2115) LSEVQAELSVEAKDVDALSRTRTVGEVIDAMKAEIAGSAVTVATLDDSTI
   Thr. sp. 20892 OrfA (2003) --------------------------------------------------
                              2351                                               2400
Sch. sp. 9695 Pfalp   (1790) ---------------GSGRCEDLSLTEPVETTLPLEAELSGAEGGARP
    Thr. aureum ORF1  (2074) ---------------HERGTGCEDLSECSASVVEIARCSELALERPMRRP
   Sch. sp. 20888 OrfA (2096) ----------AVKIDSVHEARCDDLSLMHAKVVDIRREDELSLRPENRP
  Thr. sp. 10212 Pfalp (2165) MEETDDEDEDFILYDHVGSRCEDLSESFSSVKSIPRADKLLLENIAERP
   Thr. sp. 20892 OrfA (2003) ---------------VKASGCENVDTREAKVVQISLESKLKSTVSHERP
                              2401                                               2450
Sch. sp. 9695 Pfalp   (1824) VVVVVDGSALTSSLVSSIGDRAVILQVQSSSACSPR-STTHKLVTAADRS
    Thr. aureum ORF1  (2109) ILIVSDGSALPAALASRLGSCAVILTTAGELDQSVR   STKIIVDMEGWG
   Sch. sp. 20888 OrfA (2136) VEVVVDGSELTLALVRVLGACAVVLTREGLQLAQPKGAAAIKHVLAKDLS
  Thr. sp. 10212 Pfalp (2215) IVIVLCGKKLTTELAKAAGERAVVATESAQSLVSPS--FVGKSFTGNTE
   Thr. sp. 20892 OrfA (2037) VIVVEDGIPLTTELCKILGGNIVVLSSQGKPAGPRS------VESPDLS
                              2451                                               2500
Sch. sp. 9695 Pfalp   (1873) EKALQAALTSVEAQFGKSGEVFQFG-DDVQAQLGWALLAAKHLKTSLS
    Thr. aureum ORF1  (2156) EADLVRALEAVESREGVPSGVVVLERASETARDQLEPALLLAKHSSKALN
   Sch. sp. 20888 OrfA (2186) AESAEKAKEAEQREGAASGESSQAERFEPAEILLSTLMCAKFAKASLC
  Thr. sp. 10212 Pfalp (2263) RSEIEKMVSATTSSGKSGEVYQHFHDSHYGMQLLWALMAAKHLLKFSLN
   Thr. sp. 20892 OrfA (2080) EESIIQAAALERTVGVPIGESCQQVSNVSTKAQLCWALLAAKHLEKDLS
```

FIG. 4 (cont'd)

```
                                    2501                                              2550
Sch. sp. 9695 Pfa1p     (1922)  EQXXEGGRXEFXAVARLDGQLGLXG--K---STTAXVDXSRAQQGSVXGLC
    Thr. aureum ORF1    (2206)  QQXPGGRACFVGVXRXDGKLGLXG--XCAKGKXWAXAAEXAQQGAVAGLC
Sch. sp. 20888 OrfA     (2236)  TAXAGGRPAFXGVARLDGXLGFX-------SQGTXUAXKRAOFGAXFGLC
Thr. sp. 10212 Pfa1p    (2313)  DPXKNGRXEFXAVARXNGKLGXDN--XSVHDQXIVXSCGIXERGAXFGLC
Thr. sp. 20892 OrfA     (2130)  AVXPDSRXEFVGVVRLNGKLGTFENIXDFSKFDLXKAXDYGORGXXLGLC
                                    2551                                              2600
Sch. sp. 9695 Pfa1p     (1967)  KXXDLEWXA--VFCRGXDXAADXDAAQAARCXXGEXSDXDXAXREXGYXA
    Thr. aureum ORF1    (2254)  KXXDLEWXH--VFXRSXDXELGANEETAAQAXFEEXSCXPDXXREXGYXK
Sch. sp. 20888 OrfA     (2279)  KTXGLEWSESDVFXRGXDXAXQGXHPEDAAVAXXRENXCADXFXREVGIGA
Thr. sp. 10212 Pfa1p    (2361)  KTXDLEWXN--VFXRGXDXAEGXSYSLAAELXXDEXSCANXSXREXGYXI
Thr. sp. 20892 OrfA     (2180)  KXXDLEWEQ--VFCRGXDXACDXMPLQAARIXRNEXOGXNXRXREVGXDI
                                    2601                                              2650
Sch. sp. 9695 Pfa1p     (2015)  XXQRCTXTTKSXXTXGKXHQPXSXXDXXLVXGGARGITPXCXREXAQRXGG
    Thr. aureum ORF1    (2302)  DGKRXTXEARPXGLGXPKQALRXXDXXLVXGGARGITPXCVRELAXSXSG
Sch. sp. 20888 OrfA     (2329)  NQQRCTIRXAKLETGNXQRQIAKDDXLLVXGGARGITPXCXREXTXQXAG
Thr. sp. 10212 Pfa1p    (2409)  SXERXXTEAHKLVTGKXHAPIKKKDAFLVXGGARGITPXCXREXAKAXKG
Thr. sp. 20892 OrfA     (2228)  SXARXTISTDDXXLCGPSKAKVEXXDXXLVXGGARGITPHCXREXASRSPG
                                    2651                                              2700
Sch. sp. 9695 Pfa1p     (2065)  GXXXLXGRSELPTTXPAWXVGXESGKPXXXAAXAFLKAEXAAGXGAKPTP
    Thr. aureum ORF1    (2352)  GXXVLXGRS-PXADXPAWXCGV-EEANXGTAXNAHLKAEXAAGXGPKPTP
Sch. sp. 20888 OrfA     (2379)  GKXXILXGRSKVSASXPAWCAGXTDEKAXOXAXTQELKRAXSAGEGPKPTP
Thr. sp. 10212 Pfa1p    (2459)  GTXXILXGRS-AXAXXPLWXNGK-SGXDXXKAXXAFLKEXXAAGXGSKPTP
Thr. sp. 20892 OrfA     (2278)  TTXXILXGRS-EXXGXEPDWXVGH-YNXDXXQXTXKHLKXTHXAG-GVKPTP
                                    2701                                              2750
Sch. sp. 9695 Pfa1p     (2115)  MLXXKLXGXVXGAREVRXSXAEITAQGATAXYEXCDVXXAAKVREXVEXV
    Thr. aureum ORF1    (2400)  XAXXKAXVGXVXCAREVLGSLEXIRAQGAXAEYXXCDVXCAERVXAXVDDX
Sch. sp. 20888 OrfA     (2429)  XAVTKLVGXVXGAREVEXXAXIEALGXXAXYSSXCDVNXXADVAKAVRDA
Thr. sp. 10212 Pfa1p    (2507)  KVXRXLXDKVXGIREVRXSXANIEAHGAXAXYEXCDVXXAEKVXAAVQKX
Thr. sp. 20892 OrfA     (2325)  XAXXALXNRVTGXREVRXSLRXIQEAGANVEYXXCDVXDENKVRQXVQRX
                                    2751                                              2800
Sch. sp. 9695 Pfa1p     (2165)  QQQGXRXVXGXFHASGVLRDKXVXNXXXADFSAVXDTKVGGLXNLLXCVX
    Thr. aureum ORF1    (2450)  XRRVX-AVXGXVHASGVLRDKSVERLEXAXFXVVXGTKVDCGLXNLLQAVX
Sch. sp. 20888 OrfA     (2479)  XSQLXAXVXGIVHASGVLRDXXEKXLPXFXAVXGTKVXGLENLLXAVX
Thr. sp. 10212 Pfa1p    (2557)  XKEHLVXXGIXHASGVLRDKLVXNKXXDXFNAVXGTKVXGLXNLLXAVN
Thr. sp. 20892 OrfA     (2375)  XQKYXCEXXGIWHASGVLRDKLVXQKXXTDXFXAVXGTKVXGLXNXXXQVN
                                    2801                                              2850
Sch. sp. 9695 Pfa1p     (2215)  XXQXRHXVXFSSLAGXHGNXGQSXDYAXANEXLNKXXAHLXAVHXQXCAXX
    Thr. aureum ORF1    (2499)  RPKXRHXVXFSSLAGXHGNTGQXXVYAXANEXLNKXXFHLETAXXPGXSVKX
Sch. sp. 20888 OrfA     (2529)  RXNXRHXVXFSSLAGXHGNXGQSXDYAXANEXLNKXXLELXKDXS---VKX
Thr. sp. 10212 Pfa1p    (2607)  XNFXRHXVXFSSLAGXHGNXGQSXDYAXANEXLNKXXGFRLGXAYSQLCVKX
Thr. sp. 20892 OrfA     (2425)  XXKLXHFXLFSSLAGXHGNKGQXXDYAXANEXLNKXXAHTLXAFXXKLNAKV
                                    2851                                              2900
Sch. sp. 9695 Pfa1p     (2265)  XFGPWXG-GMVTXXLXAXFIRMGXQIIPXQXGAQTVAXNXXXSSPGQXXL
    Thr. aureum ORF1    (2549)  XEGFPWXG-GMVNDXLXAHFAXMGXVQIIPLXXGAXTVXRXXGXCXPTQXL
Sch. sp. 20888 OrfA     (2576)  XXFGPWXG-GMVXPQLKXXFQEMGXVQIIPRXXGAXTVARXXLGSXPAEXL
Thr. sp. 10212 Pfa1p    (2657)  XXFGPWXG-GMVXPXLKXXFQSMGXVQIIPEXXGAXTVARXVLXSNPSQXL
Thr. sp. 20892 OrfA     (2475)  XDFGPWVGSGMVTETLEXHFKXMGXVQTIPLXPGARTVXQXXLAXSSPPQSL
                                    2901                                              2950
Sch. sp. 9695 Pfa1p     (2314)  VGNWXXPXXVESXTEHXXLQTXLRQS-DXPFLDXHVIQGRXVLPMTXAXGX
    Thr. aureum ORF1    (2598)  VGNWXXPXXVENXSVHKXTVRLGGESAXXPFLSXXTIQGXXVLPMTXALGL
Sch. sp. 20888 OrfA     (2625)  VGNWRTPSKKVGSDXXTXHRKXSAK-SXXFLEDEVIQGRRVLPMTXAXGS
Thr. sp. 10212 Pfa1p    (2706)  VGNWXXPXXSFLXSKXATXVQXFXPX-LXXFLKSXEQIHGXNVLPMTXAXGX
Thr. sp. 20892 OrfA     (2525)  XGNWXFPATKXLQRSNVXTGXLSPX-EIEFXADXKIQGRXVLPMMAAXGX
                                    2951                                              3000
Sch. sp. 9695 Pfa1p     (2363)  XAHQXQSXXAGXXQLWXXYEDAQLFKGXAXDNXADVPXRXELSRRKXXQEDA
    Thr. aureum ORF1    (2648)  XAEAXRGLXVGHQXVGXEDAQXFCGXVXDKXATCEXQXRREXSTASP---
Sch. sp. 20888 OrfA     (2674)  XAETCLXXXXPGXSXXXXDDAQLFSGXVTXDGDVNCEXXTPSXAPSG----
Thr. sp. 10212 Pfa1p    (2755)  XAHLVKNFXAGXHXXXGXXDAQLFSGXVXDHXVQAQXXKXTEQXLDXXXG---
Thr. sp. 20892 OrfA     (2574)  XASIXEGXXPGXXXLQGXENAQLFQGXXTXNQETKFQXXTXIEEHNSXXN---
```

FIG. 4 (cont'd)

```
                                  3001                                              3050
Sch. sp.  9695 Pfa1p   (2413)  GKV  KV VL KSQVN-GKS PAY AT  LS-P PK  V T  FD T---
    Thr. aureum ORF1   (2695)  ---SEVV L AS LNVFAAGK   PAY  HV LGAS P TGG QL LKDLGVD
Sch. sp. 20888 OrfA    (2720)  ---  NV  T KTFSS-GK   PAY AV   LSNQ AP   NATMQPPSL---
Thr. sp. 10212 Pfa1p   (2802)  ---  KV  V TASNDNGK    PAY AV  LG-KTS   F  L   FS Q---
Thr. sp. 20892 OrfA    (2621)  ----  DVLTS  GVMLESGK   PAY  CV  CLNTTQQQ  KLSP  ILN  EVDP
                                  3051                                              3100
Sch. sp.  9695 Pfa1p   (2458)  --PDP  CTEHD  YDG   LFHGK A GG   V LSA  PKQLT  KC N   PE
    Thr. aureum ORF1   (2742)  ADP  C  VGKGA  YDG   LFHG   A   Y    E  LRC  PAELAV  C V   SAAQ
Sch. sp. 20888 OrfA    (2763)  --D  DPALQGS  YDG   LFHG  A  RG   D  LSC  KSQLVA  CSA  G  DA
Thr. sp. 10212 Pfa1p   (2845)  --E  N  RSADE  YDG   LFG  L  RG ITK  LNV  DTSLTTQCTN  D  AT
Thr. sp. 20892 OrfA    (2667)  ------ACEVNPYDG    LFHG  LL F  QQV LHS  TKGLV  KC  AL   KEA
                                  3101                                              3150
Sch. sp.  9695 Pfa1p   (2506)  QR  Q  VVNLSQQ   P QAD   F QA  LV ARM   Q  A  LP  C   FD     
    Thr. aureum ORF1   (2792)  DR  Q  VSRGVL     P  NDTVFQA  LV ARL  RDS A  LPS  V  R  S    GQP
Sch. sp. 20888 OrfA    (2811)  AR  E  ATDTDA        ND  A FQA  LV VRRTLGQA A LP  S  Q  IVQ    
Thr. sp. 10212 Pfa1p   (2893)  ER-GQFADIEPVNP   MADA A FQA  LV VRN   N  A  LP   C  E   DI    
Thr. sp. 20892 OrfA    (2711)  I  -GPFIKQTL    P I  DD   I FQL  L V CRNALG  A  LP  R    N   FGN
                                  3151                                              3200
Sch. sp.  9695 Pfa1p   (2556)    P-  AT         LAS  SP-LV     CKCTVA          G       F      ASV Y   K
    Thr. aureum ORF1   (2842)  PSE  EV    T  L  LDS  ASGPLD   AKAQ   T   RACGA T A  G  ASV V   K
Sch. sp. 20888 OrfA    (2861)  PQ-DKP  V  I    RSNQ  G---GH  QHKHALQF   N    G      IDVQASV  AT
Thr. sp. 10212 Pfa1p   (2942)    P-  EK         QALGNT---SG  S  LKSV   Y       G        L        ASV Y 
Thr. sp. 20892 OrfA    (2760)    E-  ST   A   TPVGPR-VPK  P  IKMQ  L  Q    SGNT   S  G E  SVV  S
                                  3201
Sch. sp.  9695 Pfa1p   (2604)  T  T
    Thr. aureum ORF1   (2892)  A  S  -
Sch. sp. 20888 OrfA    (2907)  S  A  -
Thr. sp. 10212 Pfa1p   (2988)  K  F  -
Thr. sp. 20892 OrfA    (2808)  E  V  -
```

FIG. 5

```
                              1                                                  50
Sch. sp.  9695 Pfa2p    (1)   ----------------------------------------MPCDN-
Sch. sp. 20888 OrfB     (1)   -------------------------------MAARNVSAAHEMHD-K--
Thr. sp. 10212 Pfa2p    (1)   -------------------------------------MVKLSVGDNICH-Q-
Thr. aureum    ORF2     (1)   QAIGHRAARWSCRSKSKARGHKAQKEMNQGGRNDEGVSVARADPCP-T-
Thr. sp. 20892 OrfB     (1)   ---------------------------------------MQLPPAHSAD-N-
                              51                                                 100
Sch. sp.  9695 Pfa2p    (7)   AVVGMAVQYAGC---QEFW--LMRKE----SPISAERLG-RYR-LH-H-QR
Sch. sp. 20888 OrfB    (19)   AVVGMAVQYAGC-T--EFW-VLM-GK-E--VISDKRLGSNYRAEHIKAER
Thr. sp. 10212 Pfa2p   (17)   AVVGMAVMYAGCQ-QHEFWQ-LQGKN---SISQNRLGSE-R-EH-K-ER
Thr. aureum    ORF2    (51)   AVVGMAVEYAGC-C--AFW--LM--K---ACISDDRLGSARR-EH-A-ER
Thr. sp. 20892 OrfB    (15)   AVVGMAVKYAGCD---EFWK-LM--S---SISAARLGSNKR-EH-V-ER
                              101                                                150
Sch. sp.  9695 Pfa2p   (57)   SKY-DTFCN-RYG--DASV-N--EH-LLADLA-RA-L-AGIN--LDDASTT
Sch. sp. 20888 OrfB    (69)   SKY-DTFCN-TYGT-DENEIDNEH-LL-NLA-QAL--TS---------V
Thr. sp. 10212 Pfa2p   (67)   SKY-DTFCN-RYG-IDEN-QS-EH-LL-KLA-DA-A-TKG--------S
Thr. aureum    ORF2   (101)   SKY-DTFCN-RYG-I-PK-EN--EH-LL-GLAAAA-Q--QDRRSDGGKFDP
Thr. sp. 20892 OrfB    (65)   SKY-DTFCN-RYG-IQQGT-N--EH-LL-GLAQEA-A--AGRMEKQ-PSEA
                              151                                                200
Sch. sp.  9695 Pfa2p  (104)   AN-RDFGIVSGCLSFPMDNLQG-LLN-YQV--EN--GAQR--D-R-PWS-
Sch. sp. 20888 OrfB   (109)   K-ST-CGIVSGCLSFPMDNLQG-LLN-YQNH-E-----ARV--A-S-HWS-
Thr. sp. 10212 Pfa2p  (107)   I--N-TGIVSGCLSFPMDNLQG-LLN-YQCH-E---GPNAL--VN-LWSK
Thr. aureum    ORF2   (150)   AQ-K-CGIVSGCLSFPMDNLQG-LLN-YQAH-E---GKHC-A-QT-PWST
Thr. sp. 20892 OrfB   (113)   F--ENTGIVSGCLSFPMDNLQG-LLN-YQSH-E-Q-PPSALV--VKLWS-
                              201                                                250
Sch. sp.  9695 Pfa2p  (153)   RP--VS-E-SDPRV-SDPASFVAN-LG-G--RY--DAACA-ALYCL-LAS
Sch. sp. 20888 OrfB   (158)   REQ-NK-EAGD--I-MDPASFVA-ELN-CA-HYS-DAACA-ALY-L-LAQ
Thr. sp. 10212 Pfa2p  (156)   RTTNG---KDD--A-FDPASFVA-QLD-C--HYS-DAACA-ALY-L-LAQ
Thr. aureum    ORF2   (199)   RT--LH-LP-DP-THRDPASFVAG-LG-G--HY--DAACA-ALY-L-LAQ
Thr. sp. 20892 OrfB   (163)   RQ--TKAH-G---R-IDPASFVA-KLN-G--HY--DAACA-ALY-L-LAQ
                              251                                                300
Sch. sp.  9695 Pfa2p  (203)   DHL-SR--D-MLCGA-C-P-PFFIL-GFSTF-AMP--PDDNP-S-PLRQ
Sch. sp. 20888 OrfB   (208)   DHL-S--AD-MLCGA-CLP-PFFIL-GFSTF-AMP--TGQ--NVS-PL--
Thr. sp. 10212 Pfa2p  (203)   DHL-S--A-DTMLCGA-CLP-PFFIL-GFSTFHAMP-S-----D-SAPL--
Thr. aureum    ORF2   (249)   DHL-S-EAD-MLCGA-C-P-PFFIL-GFSTFHAMP-GEN---GVS-PF--
Thr. sp. 20892 OrfB   (213)   DHL-S--AVD-MLCGA-C-P-PFFIL-GFSTF-AMPX--D---GV--PL--
                              301                                                350
Sch. sp.  9695 Pfa2p  (253)   G--GLTPGEGG--MVLKRLEDA-RDG-RIYG-LL-TS-SN-G-GLPL-P-
Sch. sp. 20888 OrfB   (256)   D--GLTPGEGG--MVLKRLDDA-RDG--IYG-LL--N-SN-GTGLPLKPL
Thr. sp. 10212 Pfa2p  (249)   T--GLTPGEGG--MVLKRLNDA-RDG-RIYG-LL-A--SN-G-GLPL-P-
Thr. aureum    ORF2   (296)   D--GLTPGEGG--MVLKRLADAERDG--YG-LL--S--SN-G-GLPLKP-
Thr. sp. 20892 OrfB   (260)   T--AGLTPGEGG--MVLKRLKDA-RDGN-IYGVLLE-N-SN-G-GLPL-P-
                              351                                                400
Sch. sp.  9695 Pfa2p  (303)   -PSEK--E-L-TS-G-D--SE-QY-ECHATGTP-GDVVE---A--HC-FR-
Sch. sp. 20888 OrfB   (306)   -PSEKKC-MD-T-T--NV-- -HK-QY-ECHATGTP-GDRVE--AV-A-FEG
Thr. sp. 10212 Pfa2p  (299)   -PSEFDC-EKALQ--HRL--SS-QY-ECHATGTP-GDKVE--A-TK-FGE
Thr. aureum    ORF2   (346)   QPSEE-C-KA--EL-G-P--RD-QY-ECHATGTP-GDTVE-QA-A-FEG
Thr. sp. 20892 OrfB   (310)   -PSEE-C-R-T-R-AG-AADQS-QY-ECHATGTPRGDVVE--A-ERVFKK
                              401                                                450
Sch. sp.  9695 Pfa2p  (352)   NTDHPPR-C-TKGNFGH-LVAAGFAGMAK-LL-MQ-GTIPPTPG-DRSN-
Sch. sp. 20888 OrfB   (355)   ---K-PRFC-TKGNFGH-LVAAGFAGMC-K-LL-MK-C-IPPTPG--DETK
Thr. sp. 10212 Pfa2p  (348)   ---H-PRFG-TKGNFGH-LVAAGFAGM-CK-LL-MQ-GE-IPPTPG--NPDN
Thr. aureum    ORF2   (395)   ---ASPR-G-TKGNFGH-LVAAGFAGM-K-LL-MERG-IPPTPG--SGT-
Thr. sp. 20892 OrfB   (360)   ---N-PR-G-TKGNFGH-LVAAGFAGMAK-LL-ME-G-IPPTPG-DASN-
                              451                                                500
Sch. sp.  9695 Pfa2p  (401)   C-DP-V-DE-I-PWPY-S-QA-AGKPGDELKCASLSAFGFGGTNAHC-FRE
Sch. sp. 20888 OrfB   (402)   MDPL-VSGE-I-PWP--NGE-KK---------AGLSAFGFGGTNAHA-FEE
Thr. sp. 10212 Pfa2p  (395)   I-HD-V-T-T-I-PWPN-N-DL-K---------ACLSAFGFGGTNAHA-FEE
Thr. aureum    ORF2   (441)   Q-DP-V-TAA--PWP-T-GG-KK---------AGLSAFGFGGTNAHA-FEE
Thr. sp. 20892 OrfB   (406)   QASEH V--KA-TW--HGA-K---------AGLSAFGFGGTNAHA-FEE
```

FIG. 5 (cont'd)

```
                            501                                              550
Sch. sp.  9695 Pfa2p  (451) HRQIAATATASPVLP-------EVIPGPIAIIGMDAIFGILKGLDAIEQA
Sch. sp. 20888 OrfB   (443) HDPSNAACTGHDSISALSARCGGESNMRLAITGMDAIFGALKGLDAIERA
Thr. sp. 10212 Pfa2p  (436) IRSDLQANKTLENE--S-KSHEIFSSFILAIVGMIEFGRLKGLQEIERA
    Thr. aureum ORF2  (482) HIPSRAPPAVLCQPRLG-----SGPNRLAIVGMDAIFGSLEGLSALEAA
Thr. sp. 20892 OrfB   (447) FNAEGISYRPGKPP------VESNIRPSVVITGMDCIFGSLEGLDAIETA
                            551                                              600
Sch. sp.  9695 Pfa2p  (494) IYKGTDGASDLPSKRWRFLGADTIFLTAIGIDAVPIGCIRDVDVDIKRL
Sch. sp. 20888 OrfB   (493) IYTGAIGAIPLPEKRWRFLGKDKIFLDLCGVKATPHGCIIEDVIVDIQRL
Thr. sp. 10212 Pfa2p  (483) IYNGGHGACDLPENRWRFLGEDKIFLQACGLQKLPIGCIIKGVITDIKRL
    Thr. aureum ORF2  (527) IYEARHAARPLPAKRWRFLGGDESFLHEIGIECSPHGCIIEDVDVDIKRL
Thr. sp. 20892 OrfB   (491) IYEGRDAARDLPAKRWRFLGEDLIFLRAIRLKEKPIGCINESVDVNEIRRL
                            601                                              650
Sch. sp.  9695 Pfa2p  (544) RSPMIPEDVLRPCQLLAVATNDRAIQDAGMATGGKVAVIVGLGTDTELYR
Sch. sp. 20888 OrfB   (543) RTPMTPEDNLLPCQLLAVSTIDRAILDSGNKKGGNVAVFVGLGTDLELYR
Thr. sp. 10212 Pfa2p  (533) RLPMIQEDILRPLQLLAVSIIDRAINASGVKPNGKVAVIVGLGTDLELYR
    Thr. aureum ORF2  (577) RIPMYPEDILRPCQLLAVSTIDRAILDSGIAKGGNVAVIVGLGTDLELYR
Thr. sp. 20892 OrfB   (541) RIPLTPEDMLRPCQLLAVSTNDRAILDACILEKGQHVAVIVGLGTDLELYR
                            651                                              700
Sch. sp.  9695 Pfa2p  (594) HRARVTLKERLDP---AAFSPEQIQELMDYINDCGTSTSYTSYIGNLVAT
Sch. sp. 20888 OrfB   (593) HRARVALKERIR-----PEASKKLIDIMCYINDCGTSTSYTSYIGNLVAT
Thr. sp. 10212 Pfa2p  (583) HRARVALKERLQTAI--KEDIPLLEKLMIYINDRGTSTSYTSYIGNLVAT
    Thr. aureum ORF2  (627) HRARVALKERLQGLVRSAEGGAITSRMIYINDCGTSTSYTSYIGNLVAT
Thr. sp. 20892 OrfB   (591) HRARVALKEVIHPSI--KSDTAILQRMQYINDAGTSTSYTSYIGNLVAT
                            701                                              750
Sch. sp.  9695 Pfa2p  (641) RVSSQWGFTGPSFTVTEGANSVIRCLELCKILLITHQVDAVVVAGVDLCA
Sch. sp. 20888 OrfB   (638) RVSSQWGFTGPSFTITEGNNSVIRCALLCKILLITGIVDIVVVAGVDLCG
Thr. sp. 10212 Pfa2p  (631) RVSSLWGFTGPSFTITEGENSVIRCLILCRIFLANGIVDAVVVAGVDLCG
    Thr. aureum ORF2  (677) RVSSQWGFTGPSFTVTEGANSVIRCAQLAKINLIRGIVDAVVVAGVDLCG
Thr. sp. 20892 OrfB   (639) RISSQWGFTGPSFTVTEGNNSVIRCAQLARDNLQVNRVDAVVIAGVDLNG
                            751                                              800
Sch. sp.  9695 Pfa2p  (691) IAENLYIKARRSAESRQDHPRANFIASADGYFAGIGSCAIVIKRQASVCS
Sch. sp. 20888 OrfB   (688) SAENLVIKSRRFKVSTSDTPRASFIAAADGYFVGIGCGAFVLKREISQTK
Thr. sp. 10212 Pfa2p  (681) SAENLFVKSRRSKVSTQNEPFANFIKNADGYFAGIDGCGAIVLKRISQCTD
    Thr. aureum ORF2  (727) SAEAFIVISRRMQISISQRPAAPFIRAADGIFAGIEGIGALVFKRLIDCVS
Thr. sp. 20892 OrfB   (689) SAESFIVRANRQKISILSHPCASFIRDADGIFAGIEGIGALVFKRLEICAP
                            801                                              850
Sch. sp.  9695 Pfa2p  (741) -DIKIYASVAGITCIAQPAEAVSPLILQVHNDDNIKRVIINELAAISGI
Sch. sp. 20888 OrfB   (738) -DIRIYACIDAIVPGNVPSACIREALDQAPIKPGI---IEMIELSAISAI
Thr. sp. 10212 Pfa2p  (731) STIKIYAIIDSIAVGDEVGPTIKQALKIASIAAKI---IEIAELSASSGK
    Thr. aureum ORF2  (777) -GIRIYASIDSVVVATTPRAAIIRAIAGSARIDPAS---IDINELSASSHI
Thr. sp. 20892 OrfB   (739) -QIKIYASIISIAIDKEPTSSAVKAIYGIDSSLSI---IEIIEISGISKI
                            851                                              900
Sch. sp.  9695 Pfa2p  (790) HAPHIINSPLSAFIQTIQVSKILAHQVPG----SVAIGSVIANVGDIGIA
Sch. sp. 20888 OrfB   (784) HLKDPSVIPKEITAEEIIGIIQTIIRDDDKLPRNVATGSVIATVGDTGIA
Thr. sp. 10212 Pfa2p  (778) HIISGRITCEDEINELGIIFNEG      IQRVAIGSVIANVGDIGIA
    Thr. aureum ORF2  (823) FVRAPITIAQPLIIEVIGAIREIIGTAGRGSRSVAIGSIIANVGDAGIA
Thr. sp. 20892 OrfB   (785) FAAFEIAIEIQSIIVIAQIKIISKIIEPAK--GQGVAIGSTIATVGDIGIA
                            901                                              950
Sch. sp.  9695 Pfa2p  (836) IGAASLIKTALCINNRYLP---AIPQWERPVIPVSEAIITCPRIRAWIKN
Sch. sp. 20888 OrfB   (834) IGAASLIKAALCIYNRYLPSNGDDIDEIAPEIPIDITLIACQTIRAWIKN
Thr. sp. 10212 Pfa2p  (819) IGAASLIKTALCLYNRYLP-KLPIINKITKDVEISKSFIVCEHIRAWIKN
    Thr. aureum ORF2  (873) IGAAILVKTALCIINRYLA-ATPGIDAIAAGVDIGIELIVCREIRAWIKN
Thr. sp. 20892 OrfB   (833) IGAAILIKTALCLYNRYLP-ALAIISGICEQSIAIGINIIICHEIRPWIKN
                            951                                             1000
Sch. sp.  9695 Pfa2p  (883) PGESRLAAVISASEIGSCIGVILIIDEYITIESSNIIGIDDAIPKIIAIRG
Sch. sp. 20888 OrfB   (884) PGERRIAAVIGVISETIRSCVSVILIIEIAEGHIERENEISLDEEAPELIVIRA
Thr. sp. 10212 Pfa2p  (868) VDINRIAVISGVCEINGSCVGIVMSIDVQGHIEESNLVSLIDKNEPIKVIGIYG
    Thr. aureum ORF2  (922) AIGVARIIAAISGVDEGGSCIGIVLSIVPGQIETGNIISTIQAEISPKIILIISA
Thr. sp. 20892 OrfB   (882) QNIKRCALIISGTDPSHICISILVLSDTG-CIEEHNITCFIVQAPQLVIIIHG
```

FIG. 5 (cont'd)

```
                            1001                                              1050
Sch. sp.  9695 Pfa2p  (933) DEVDDIKAEVNAELALERAHAETGSATDDDPKAAVAFTAHRLRFLRLVGE
Sch. sp. 20888 OrfB   (934) ESHEDIEGAEDKIRERFEQPTEAEPRESEERQARRIFLE--EEGEEEAQ
Thr. sp. 10212 Pfa2p  (918) ESVEDIEVQENKYEEKFEQETETAEAAQKVKEPTIDIDSN--EFAEMENL
Thr. aureum   ORF2    (972) PDHAAEEDEEAAEEAAEEQADEEEAAAAAEDR---------EEGEEEVG
Thr. sp. 20892 OrfB   (931) FDGKTEEEEEESYEEEEEEGHAEPE---------EYFHK--EEEQEELE
                            1051                                              1100
Sch. sp.  9695 Pfa2p  (983) TVESHGATATECEAEEETPEEEEEEEEAAEGEPRSAEAGENWMSPEGSA
Sch. sp. 20888 OrfB   (982) DEESEGSQEPEAEEEVETPSEEQEEEEEAAEGEPREEEMEEEDWSSPEGSR
Thr. sp. 10212 Pfa2p  (966) PQDKN---EEFAEAEEEETPNEEQEEEEEEEAVEGEEPREEEEAEEDWCSPEGSI
Thr. aureum   ORF2   (1012) CEEGE---GGEETECEVEASEPASLHEEEEALAHEGEEPREEEAEEDWASPEGSY
Thr. sp. 20892 OrfB   (969) NEKEE---E-EETEELVCNPNQLQEEEMLAIEGEQRSELTGEEDWVSPEGSC
                            1101                                              1150
Sch. sp.  9695 Pfa2p (1033) EAETPETSDEEVAFMYGEGRSPYYGEVGLEEHPEEWPELHERENDETAALWEN
Sch. sp. 20888 OrfB  (1032) EAEEPEEAEDEEVAFMYGEGRSPYYGETQEEEHPEEWPELHEVENEETNRLWAE
Thr. sp. 10212 Pfa2p (1013) EACNPEEKSENEEAFMYGEGRSPYAGEEGYDEHPEEWPMLHELEVNNEETTELWDQ
Thr. aureum   ORF2   (1059) EAEEPEEEEEDEEVAFMYGEGRSPYCGEVGREDLHPEEWPEELHEREVNAEETVNLWGE
Thr. sp. 20892 OrfB  (1015) EAEPNPEEEEEAEEVAFMYGEGRSPYCGEVGLGEEHPEEWPELHENEEVNNEETVDLWTE
                            1151                                              1200
Sch. sp.  9695 Pfa2p (1083) GDEEWEEEPREVDAEESQRAEEQTAFDEADQEEEMFRTGEEEVSEEGLTDYEEEREDVEEGE
Sch. sp. 20888 OrfB  (1082) GDRWEEEPRAEEFKSEEEESQQQEFDREEEMEMFRLGEEELTSEEAFTNEEEERDVEEEE
Thr. sp. 10212 Pfa2p (1063) GDEWYEEPREEEEEVAEKEKEEFGDFDKEEQEEEMFRLGEEEESMEEFTDEEATEEEEGE
Thr. aureum   ORF2   (1109) GDEWEEEEPRAEEEAEEEEEQEEECRNFDSEEEQVEMFRTGEEEEESMEEELTDEEAEPSEEEGE
Thr. sp. 20892 OrfB  (1065) GDGWEEYPRTLEEREEEHTKAIESFNEAEEQEEMFRAGEEEESMEEQTDYVMNEEEEGV
                            1201                                              1250
Sch. sp.  9695 Pfa2p (1133) QPKACFGLSLGEESMEEFAEESEEERNCEGLSEEQEETQREEETSEEVWEEEQLAVEFEEA
Sch. sp. 20888 OrfB  (1132) TPKAEEFGLSLGEESMEEFAFSEEENGEEEEEQEEEDLREEDVWNKALAVEFEEA
Thr. sp. 10212 Pfa2p (1113) KPKAEEFGLSLGEESMEEFAFSEEENTEESKEEEEEEREEEEEAVWEEEQLAVEFAA
Thr. aureum   ORF2   (1159) GPKAEEFGLSLGEEVSMEEFAEESESNCEEESEEEMTEEEEEEEEASEEVWNEELAVEFEEA
Thr. sp. 20892 OrfB  (1115) QPKAGFGLSLGEESMEEFAEESEEENCEEQSQEEEETNEEEGSEEVWEEEELAEEENEFEA
                            1251                                              1300
Sch. sp.  9695 Pfa2p (1183) EREEEWNEEPADAEEVEESFWQCYEEVEASEEAEEEEEKAEEEPEHREEFVRLEEEVNDSSE
Sch. sp. 20888 OrfB  (1182) EREAWGEEPQSVEEKEEEEFWQGYEEEVEGEEEQEEEEAAIEEPEESEEEVRLTEEEEEEEAEE
Thr. sp. 10212 Pfa2p (1163) ERDEWNEEPADKSEEDEEFWQGYFVYEEEEETIEVEEEETIE-EEEEEEEEEEEEE
Thr. aureum   ORF2   (1209) EREEEWGEEAPGAEEEEESEEEEFWQCGYEEEVEEATEEAQEEEQAEEEEEGEEEEEEEEEEE
Thr. sp. 20892 OrfB  (1165) EREEEWKEEPRGAEEEEEESFWQGYEEEVHEEETREEEVEHEEEAEEGLSEPEEVRLEEEEVNDSRE
                            1301                                              1350
Sch. sp.  9695 Pfa2p (1233) ALIAGKPAECLREEEEEEEEEEGEEEEPPEEFVKQGMEGHCEEVAEEEEEPGIEAEEEEHEEE
Sch. sp. 20888 OrfB  (1232) AEEESGKPEEACKEEAEEEEEEEEEGGNEEEPAEEPVEEEQGMCGHCEEEVGEEPEETKEEEEAKEEHAN
Thr. sp. 10212 Pfa2p (1212) CLIAGKPEEEECQKEEEEEEHEEEEPAEVEEVEEQGMEGHCEEEAIPEEELDQESEEEHEEEE
Thr. aureum   ORF2   (1259) VLIAGKPAEECEAVEEAEEEGSEEEEPPEEEQVEEQGMEGHCAEEEEEVEEPEETSEEEEEESEREHNNE
Thr. sp. 20892 OrfB  (1215) ALIAGKPEEDACQAEEEEEEEEEEEEEEEEEEEEEEKFPSEEPVKQGMEGHCEEEVRAEEIKEEEEQEEEIHEET
                            1351                                              1400
Sch. sp.  9695 Pfa2p (1283) LEEEEDSPVKMYTEEVTNAELRG-------------GENSEEETEEVQKEE
Sch. sp. 20888 OrfB  (1282) LEFEVVEGLDLWEEEINQEERLV-------PRATGAKDEWEPSEFGEEAEQEE
Thr. sp. 10212 Pfa2p (1262) LEEEKPEENVKLFEEESENE                  ELVSMKDEEEEGKLEEAEEE
Thr. aureum   ORF2   (1309) LRFEESQEEETGGCKMYSSVSNSRIGPVEESQMGPGTELVFSPEEEFEEEEVEEQEE
Thr. sp. 20892 OrfB  (1265) LREESNDYSDCQLFEEAVTEG---------------ALDSETMEEEKHEEVEEEE
                            1401                                              1450
Sch. sp.  9695 Pfa2p (1317) YEEEEAEDFPGIVEEKEVSRDE-EEDVEFVEVGPEEMRSEAVSDEEEGKAATPEEEEEV
Sch. sp. 20888 OrfB  (1325) YEEEQANFPEEIVEETEEEKQN-EDVEFVEVGPEEHEEHRSTAVREEETLGEQR-NEEEEAG
Thr. sp. 10212 Pfa2p (1296) YQHEEADFPEEIEVNKVKETCKTDEEFEEEEGSEEEYRSEAVEEETEEELGE---EIEEEV
Thr. aureum   ORF2   (1359) YSEEEADFPAITEEAEVEQQG-EDVEFEEVEEGEDHSRSAAVEEETLGEETR-RHEEEAEE
Thr. sp. 20892 OrfB  (1300) YSEEEEADFPQIEYNTVEESAG-EDVFEEEEEGCDASRSEAAVQNEEEGGQG-KFEEEET
                            1451                                              1500
Sch. sp.  9695 Pfa2p (1366) AEEDEEPSEEEEEAWEEEQTEEEKSEEALLEEEAHEERVPLHNPEEEEEEEEEELFADLYHPTFLTAIDEEAMQ
Sch. sp. 20888 OrfB  (1373) AEEDEEEQNEEEEEEDAWEEEEEEEEEEEEEEEEEAEEEEEEASEEEEEEAEEEEEHLVPGEEEEEEEEEEEPEEEYEEEEEESKEEEEEEEAEQACYEEEEAEEEEEELC
Thr. sp. 10212 Pfa2p (1343) AEEDEEEQNEEEEAWGEEEEEEEEEEEMEEEEEEEMEEEEEEEWEEEASEEEEEEEEEISHEEEEEVPSEEEEKKEEEEEEEEEEEEEEEEEEEEEKFDPQAKPNRF
Thr. aureum   ORF2   (1407) AEEMEDEEEKGEEEEEEESEEEEEAWEEEQEEEEEEEEEEEETEEREEEEEEMEEEEEEEEEEEEAEEEEEEEEEEASEEEHEEREVPEEEEEEEEEDEEEEEEEEEEEESMEEEEEEEPAEEEVEEEEEEEEFRCREEETEEEEAIEEEEEEEEAEEEEEEQR
Thr. sp. 20892 OrfB  (1348) AEEDEKGHEESEEEAWEEEEEEEEEQVEEEEEEEEEEEEEEEEEEEAEEEEEEEEETAEESEEEEEEEEEEEEELAAHEREVPEEEEEKEEEEEEEEEEEEEEEEEEEEEEEEEEEEEEEELDEEEEHPNFREMCCTMATT--
```

FIG. 5 (cont'd)

```
                              1501                                          1550
Sch. sp.  9695 Pfa2p   (1416) E-PPPKPNRFLPSVENGYPCPDQISKQVAAASAKPSTHCMRLHPAKAV
Sch. sp. 20888 OrfB    (1423) KGEKPKKNKFVRKQSNGRENSKADPSSSADRASFPPADPAEAASSRI
Thr. sp. 10212 Pfa2p   (1393) IRNIELNGFFDRTNISVDQQLSPADPKLAEISNNRNMPKDNYVPEERVK
Thr. aureum  ORF2      (1457) SGQPEQRNKFLRTTENGFSDPADATSPEAVAILPATAAISPPKSGAPH
Thr. sp. 20892 OrfB    (1396) ---PKVEDKFLRTQSNGRPEKEMIHSEDTTLSCLPAPSEANIAALQSRS
                              1551                                          1600
Sch. sp.  9695 Pfa2p   (1465) SVAASAVVADSTPVVKAKQSSSS--------------------------
Sch. sp. 20888 OrfB    (1473) NKPVAPKFYARLNIDEQDETRDPILNKSNAPSSSSSSSSSSSSSSPSPA
Thr. sp. 10212 Pfa2p   (1443) TMIKAEPSNLQVSVGSKPVVSERISSDTNSFEKLSEITKSFDG-------
Thr. aureum  ORF2      (1507) DSQPEAEARPVGEASVPRRASSSSKLARTLAIDACDSDVRAALLDLDAPI
Thr. sp. 20892 OrfB    (1443) SRSAAARSGQSHDCASHSHEENKDSCPSKSKLDSVSVAINFDN-------
                              1601                                          1650
Sch. sp.  9695 Pfa2p   (1489) --------------------------------------------------
Sch. sp. 20888 OrfB    (1523) PSAPVQKKAAPAAETKAVASADALRSALLDLDSMLALSSASASGNLVETA
Thr. sp. 10212 Pfa2p   (1486) -----------------------VN-------------------------
Thr. aureum  ORF2      (1557) AVG-----------------G-----------------------------
Thr. sp. 20892 OrfB    (1486) --------------------------------------------------
                              1651                                          1700
Sch. sp.  9695 Pfa2p   (1489) --------------LLSGDDAFRCYDVEMPLYMGAMAEGISSVDLVAAA
Sch. sp. 20888 OrfB    (1573) PSDASVIVPPCNSADLGSRAFMRTYGVSAPLYTGAMAKGIASADLVIAAG
Thr. sp. 10212 Pfa2p   (1488) ------ACTEAMSGDSG---FLRTYEVEYPLYTGAMAKGIASADLVIAAG
Thr. aureum  ORF2      (1561) --SSRAQVPPCPSSALGSAAFRAAHGVDYALYMGAMAKGVASRNVIAAG
Thr. sp. 20892 OrfB    (1486) ---------DDRIQSGHASFREMENTRYSLYTGAMAKGTASADLVIAAG
                              1701                                          1750
Sch. sp.  9695 Pfa2p   (1526) EATWLASFGAARLESDQVELQIREIQQRTSN-AFAVNLNPGPDEAAT---
Sch. sp. 20888 OrfB    (1623) RQGILASFGAGGLPSQVVRSSIRRIQAALPNGPSAVNLIHSPEDSNLRKG
Thr. sp. 10212 Pfa2p   (1529) KSKILASFGAGGLASQVVSDAKQIKAELGNGPSAVNLIHSPEDPSLRKG
Thr. aureum  ORF2      (1609) KARRLASFGAGGLESGEVSRASREIQAALPEGRSAVNLIHSPEDPNLREG
Thr. sp. 20892 OrfB    (1526) REGILASSGAGGLESATVRKGISRIQALPSGFSAVNLIHSPEDGNLEQG
                              1751                                          1800
Sch. sp.  9695 Pfa2p   (1572) -VDALLRTSVSLVEASSSTGALSADIVYRVTGLRPTSCGASVSATHRW
Sch. sp. 20888 OrfB    (1673) SVDLFLEKGVTFVEASAFM-SLTPQVVRYRAACLTRNASCSVNIRPRI
Thr. sp. 10212 Pfa2p   (1579) SVDLFLKYNVRFVEVSAFM-SLTPQVVRYRAACLARARSCSVKIQPRI
Thr. aureum  ORF2      (1659) SVELFLRRGIRLVEASAFH-SVTESLVRYRVAGLEAGPG-GTARPLRPVI
Thr. sp. 20892 OrfB    (1576) SVDLFLEKNVRRAECSAFT-SLIVPVVHYRAAGLVRQS-GSSLIKNRI
                              1801                                          1850
Sch. sp.  9695 Pfa2p   (1621) AKVSRIEVAEHFSRPAPAASVLALVAAKQISPEQAASLASEVANADDWAVE
Sch. sp. 20888 OrfB    (1721) GKVSRIEIAEMFMRPAPEHSLQKLSASGETNQFQAESARRVRSADDIAVE
Thr. sp. 10212 Pfa2p   (1627) AKISRTELAEIFLKPAPKNILDALVADGSISQFQAQSALLVPNADDITVE
Thr. aureum  ORF2      (1707) GKVSRAELAEMFMRPPPAAIVSKLLAQGLVSEEQASLAEIVESVDDVAIE
Thr. sp. 20892 OrfB    (1624) AKVSRIELAEMFIRPAPQISLLEKLVASEITSSSQARMAAKVPHADDIAVE
                              1851                                          1900
Sch. sp.  9695 Pfa2p   (1671) ADSGGHTDNRPIHVSLPISSAQRRR----WRSLVDTPVRSGAGGGIACPR
Sch. sp. 20888 OrfB    (1771) ADSGGHTDNRPIHVILPISSTNSRDRSHRECGYPANLRVRSGAGGGIGCPQ
Thr. sp. 10212 Pfa2p   (1677) ADSGGHTDNRPIHVSLPLITQRN  RICKQYPKIILKVRIGAGGGIGCPK
Thr. aureum  ORF2      (1757) ADSGGHTDNRPIHVSLPSSSALRDSKMRECKIPAANRVRSGAGGGISCPA
Thr. sp. 20892 OrfB    (1674) ADSGGHTDNRPMHVSLPLISSGRNTSLAEYGCATAFRTRSGAGGGIGCPS
                              1901                                          1950
Sch. sp.  9695 Pfa2p   (1717) AALLAFSRGAAFVTGSVNQLAREAGTSDAVRLLLATATYSDVAMAPGS-
Sch. sp. 20888 OrfB    (1821) AALATFNMGASFVTGSVNQVAKQSGTCDNVRKQLAKATYSDVCMAPAAE
Thr. sp. 10212 Pfa2p   (1725) AAFAAFSMGANSATGSVNQLSREAGTCDYVRKSLNKATYSDVTMAPAAE
Thr. aureum  ORF2      (1807) AARAAFSMGAREVTGSINQLTRQAGTSDSVRAALRATYSDVTMAPAAE
Thr. sp. 20892 OrfB    (1724) AALAAFSMGASFVTGSVNQSCREEAGTCDTVRESLANSSYSDVTMAPAAE
                              1951                                          2000
Sch. sp.  9695 Pfa2p   (1766) ------SQVLKKQTMFAARATMLAQLQAKSGSFDASPEPQLRRLERSVF
Sch. sp. 20888 OrfB    (1871) MEREGVKLQVLKKGTMFPSRANKLVELFCKSDSFESNPPAESARVERIF
Thr. sp. 10212 Pfa2p   (1775) MFDHGVELQVLKKGTMFPSRAKKLVTLFKKSKSSEESPADSSRLEQSVF
Thr. aureum  ORF2      (1857) MEDQGVELQVLKKGTMFPARANKLASLFTTSQSLDASPRASEARLEKVF
Thr. sp. 20892 OrfB    (1774) MFDQGVELQVLKKGTMFPSRANKLRKLFVNSESLETSPSKELSKYLENIF
```

FIG. 5 (cont'd)

```
                             2001                                               2050
Sch. sp.  9695 Pfa2p  (1809) KQSVADVWAAAREKRGVDATAAS--------PQERMRLCVRWYRSQSSRW
Sch. sp. 20888 OrfB   (1921) SRRDEVWRETRNEYINRLHNPERIORARRDPKLEMSLCERWYLSLASEW
Thr. sp. 10212 Pfa2p  (1825) KKSFDEVTRETRNEYINRLHSPERIERAERDAKLEMSLCERWYLSKSSRW
   Thr. aureum ORF2   (1907) RMSRDEVWNETRQEYETRLNNPAKYARAERDPKLEMSLCERWYLSKSSRW
Thr. sp. 20892 OrfB   (1824) KQRRDOVWRETRREYCERLNNPEKIARAMRDPKLEMSLCERWYLSKESGW
                             2051                                               2100
Sch. sp.  9695 Pfa2p  (1851) ATERTSRRKADYQRWCGPAIGSRNDRRRGRKLDATAGTGERPRVRDRNQH
Sch. sp. 20888 OrfB   (1971) ARTGASDRVRDYQRWCGPAIGSRNDFRKG-RYLDPARANERPCVRQRNKQ
Thr. sp. 10212 Pfa2p  (1875) ARTGESRRVQDYQRWCGPAIGSRNDFARGRPCLDPERLGSRPSVRQRNKH
   Thr. aureum ORF2   (1957) ASRGOVRGRERDYQRWCGPTIGRRNERRRGRSLDAERCGRRPCVRRRNQE
Thr. sp. 20892 OrfB   (1874) ARAGIKSRARDYQRWCGPARGSRNNFASG-RSLRDWKRTRVRPGVAERNMA
                             2101                             2140
Sch. sp.  9695 Pfa2p  (1901) ILLGASHYRRRQRQQQDDDVRRYIIV---------------
Sch. sp. 20888 OrfB   (2020) ILRGACRLRRREILRNARLSRGAAALVASIDDTYVPAEKL
Thr. sp. 10212 Pfa2p  (1925) ILRGACRYQRLSRLKYLNFNYEELDTLTYSASNFI
   Thr. aureum ORF2   (2007) ILCGAARREQRRARFMLLAGRRSADALAYTVAEAR------
Thr. sp. 20892 OrfB   (1923) ILDGARELAAKRR--------------------------
```

```
                            601                                               650
Sch. sp. 9695 Pfa3p   (563) DLALVTRVTSVADMESGPPYNSDVNPGQGTMVGEFDCPADAWFEGASSRD
Sch. sp. 20888 OrfC   (597) DLALVTRAVSVSIEKSVNSRNIDSDPSKGTMVGEFDCPADAWFKGAKRD
Thr. sp. 20892 OrfC   (572) DLALVTRWEVSNMESGKFINSDCHPSKGTMVGEFDCPQDANWFIDGSCRD
Thr. sp. 10212 Pfa3p  (557) DLALVTRWSVSDMRFKSHINIDVNPSKGTMSGEFDCPADAWFEQGSCRD
                            651                                               700
Sch. sp. 9695 Pfa3p   (613) DHMPYSIIMEIALQTSGVLTSVLKAPLTMBKDDILFRNLDADAEIVGDAM
Sch. sp. 20888 OrfC   (647) SHMPYSILMEIALQTSGVLTSVLKAPLTMRKDDILFRNLDANAEFVR-AS
Thr. sp. 20892 OrfC   (622) GHMPYSIIMEISLQTSGVLTSVLKAPLTMBKDDILFRNLDASAEMVR-PS
Thr. sp. 10212 Pfa3p  (607) GHMPYSIVMEIALQTSGVLTSVLKAPLTMBKDDILFRNLDASAEMVR-SD
                            701                                               750
Sch. sp. 9695 Pfa3p   (663) PDVRGKTIRNFTKCTGYSMLGKMGIHRFTFELSVDSAVFYKGSTSFGWFS
Sch. sp. 20888 OrfC   (696) SDYRGKTIPNVTKCTGYSMLGEMGSHRFTFELYVDDVSFYKGSTSFGWFV
Thr. sp. 20892 OrfC   (671) VDVRGKTIPNVTKCTGYSMLGKMGIHRFTFELSVDGVVFYKGSTSFGWFT
Thr. sp. 10212 Pfa3p  (656) VDCRGKTIRNFTQCTGYSMLGKMGIHRFTFELSVDDVVFYKGSTSFGWFT
                            751                                               800
Sch. sp. 9695 Pfa3p   (713) PEVFSSQTGLDNGKPRLPWSREN----------NVAVDTLSAPASSSSAQ
Sch. sp. 20888 OrfC   (746) PEVFASQAGLDNGKSSSPWSIENKVPASSVSSSDVRPNGSGRTAIFSNAP
Thr. sp. 20892 OrfC   (721) PEVFAQQAGLDNGKRSTEPWCKTNN--TSVRRVEIASAKGKEQLTEKLPDS
Thr. sp. 10212 Pfa3p  (706) PEVFSSQVGLDNGKSVQPWSREDKS--SRVVSDVASTAGKDLFSKIGS
                            801                                               850
Sch. sp. 9695 Pfa3p   (753) GSLQSQRRGSQASSLDSTISIAGSGSGVISQGYAHGEKAVNKQDWFFSCHF
Sch. sp. 20888 OrfC   (796) SGASQNRRSDQGSNLDASDSVSG-SGSKSLGYAHGSKTVNSNDWFFSCHF
Thr. sp. 20892 OrfC   (769) SSAQSLRRSEQCESLDYSNSAPD-SGLSSKGYAHGHKDVNSQDWFFSCHF
Thr. sp. 10212 Pfa3p  (754) KDAQVQRRNSQCESLDSHSIIPN-SGKSNKGYAHGSKKVNSNDWFFSCHF
                            851                                               900
Sch. sp. 9695 Pfa3p   (803) WFDEVMPGSLGIESMFQLIEASCSKOGLASSGISHPVESHAF-GATSWK
Sch. sp. 20888 OrfC   (845) WFDSVMPGSLGVESMFQLIEAIAAHEDLASKARHCSPHLCAPSPRASSWK
Thr. sp. 20892 OrfC   (818) WFDEVMPGSLGIESMFQLIEAFAVISQNSPGESNVSNPTFAHAF-GKTSWK
Thr. sp. 10212 Pfa3p  (803) WFDEVMPGSLGIESMFQLIEASSRDGSIASSEHGIVNPTFALSN-GKTSWK
                            901                                               950
Sch. sp. 9695 Pfa3p   (852) YRGQLTPKNDRMDSEVHIKSVAAFSS---SVDSVADGFLSVDGLRVYSAS
Sch. sp. 20888 OrfC   (895) YRGQLIPKSIKMDSEVHISSSDAHDG---VVDLSADGFLWADSLRVYSVS
Thr. sp. 20892 OrfC   (867) YRGQLIPKNIRAMDCEVHISITASPSNGGSVDSVADGALIVDGLRVYEAK
Thr. sp. 10212 Pfa3p  (852) YRGQLNNKGIRMDSEIHIKDIVKNSSG--TVDLSADGFLLSDSLRVYSAS
                            951                                              1000
Sch. sp. 9695 Pfa3p   (899) ILRVSIQESAGHVEEQEVAAKASSSN---------SSIVDVDADIQAL
Sch. sp. 20888 OrfC   (942) SIRVIASSERPAAASSAASVGSSASSVERTRSSPAVSSSPSQTIDLKQL
Thr. sp. 20892 OrfC   (917) ELRVSSSSAKPQAIPDVQQQPPSASADPG---------KSGVALSPTQL
Thr. sp. 10212 Pfa3p  (900) DLRVSIVPSTKAAPKSVAAARHVASPSPGV-----PSNTSSEISLESL
                            1001                                             1050
Sch. sp. 9695 Pfa3p   (939) KQALLTISRPLQLSAG-----------------SESEACASSDLGDRGFM
Sch. sp. 20888 OrfC   (992) KTSLLELSAPLYLSQPSSGQSKKHTSVASGQATSVQPCTSGDLGDRSFM
Thr. sp. 20892 OrfC   (957) RDVLLEVINPLYLGVSSNNLVQFESKPATSSRIVSSKPCSSGDLGDRSFM
Thr. sp. 10212 Pfa3p  (945) SKELLNLSRPLSLSTSSHI--SKQFGDSVNNGQASVSRPCTSNDLGSRSFM
                            1051                                             1100
Sch. sp. 9695 Pfa3p   (972) ETYGVVAPLYSGAMAKGIASADLVIAMGQRKSLGSFGAGGLPMHHVRASS
Sch. sp. 20888 OrfC   (1042) ETYGVVAPLYTGAMAKGIASADLVIAAGKRKSLGSFGAGGLPMHHVRAAL
Thr. sp. 20892 OrfC   (1007) ETYSVSAPLYTGAMAKGIASADLVIAAGKRKSLGSFGAGGLPSSIVRFAI
Thr. sp. 10212 Pfa3p  (993) ETYSVVAPLYTGAMAKGIASADLVIAAGKRKSLGSFGAGGLPMHHVRASS
                            1101                                             1150
Sch. sp. 9695 Pfa3p   (1022) EKIQAALPAGPYAVNLIHSPFDANLEKGNVDLFLEKGVRVVEASAFMELT
Sch. sp. 20888 OrfC   (1092) EKIQAALPQGPYAVNLIHSPFDSNLEKGNVDLFLEKGVIVVEESAFMTLT
Thr. sp. 20892 OrfC   (1057) EKTQQHIPHGPYAVNLIHSPFDSNLEKGNVDLFIEMGVSVVFCSAFMSLT
Thr. sp. 10212 Pfa3p  (1043) EKIQAALPEGPYAVNLIHSPFDSNLEKGNVDLFLEKGVHVVEASAFTALT
                            1151                                             1200
Sch. sp. 9695 Pfa3p   (1072) BQVVRYRASGLSRDSRGGSVRTAHKIIGKVSRTELAEMFIRPAPQASLEK
Sch. sp. 20888 OrfC   (1142) SQVVRYRAAGLSRNSDG-SVNIRSSIIGKVSRTELAEMFIRPAPESILSK
Thr. sp. 20892 OrfC   (1107) AQVVRYRASGLSSSADG-SSRTAHSIIGKVSRTELAEMFIRPAPQHILQK
Thr. sp. 10212 Pfa3p  (1093) TQVVRYRACGLSDSKDG-SVLIKNSIIGKVSRTELAEMFFRPAPQNILSK
```

FIG. 6 (cont'd)

```
                              1201                                              1250
Sch. sp.  9695 Pfa3p  (1122)  LVASGESTPEQAALALEVPRADDIAVEADSGGHTDNRPIHVILPLISSLR
Sch. sp. 20888 OrfC   (1191)  LIASGESTQEQAELARRVPVADDIAVEADSGGHTDNRPIHVILPLINLR
Thr. sp. 20892 OrfC   (1156)  LVASGESTAEQAELATQVPVADDIAVEADSGGHTDNRPIHVILPLINLR
Thr. sp. 10212 Pfa3p  (1142)  LIASGESTKEQASLALEVPRADDVAVEADSGGHTDNRPIHVILPLINLR
                              1251                                              1300
Sch. sp.  9695 Pfa3p  (1172)  NRLQRESKYPARHRVRVGAGGGIGCPQAALCAFHMGAAFVVTGIVNQSK
Sch. sp. 20888 OrfC   (1241)  NRLHRECGYPAHLRVRVGAGGGVGCPQAAAKALTMGAAFIVTGIVNQVK
Thr. sp. 20892 OrfC   (1206)  NRLHKERDYPSHLRVRVGAGGGTGCPQAALAAFQMGAAFLITGTVNQLA
Thr. sp. 10212 Pfa3p  (1192)  NRLHKECGRPAALRVRVGAGGGIGCPSAAVAAFNMGAAFLITGSVNQVK
                              1301                                              1350
Sch. sp.  9695 Pfa3p  (1222)  QSGTCDNVRRQLSRATYSDIKMAPAADMFLQGVELQVLKKGTMFPSRAKK
Sch. sp. 20888 OrfC   (1291)  QSGTCDNVRRQLSQATYSDICMAPAADMFEEGVKLQVLKKGTMFPSRANK
Thr. sp. 20892 OrfC   (1256)  ESGTCDNVRLQLSKATYSDVCMAPAADMFLQGVELQVLKKGTMFPSRAKK
Thr. sp. 10212 Pfa3p  (1242)  QSGTCDIVRRQLSEASYSDIKMAPAADMFDQGVELQVLKKGTMFPSRAKK
                              1351                                              1400
Sch. sp.  9695 Pfa3p  (1272)  LEELFHKYDSFKAMPRDELARVEKRIFSKSLAEVWAETKDFYITRLNNPE
Sch. sp. 20888 OrfC   (1341)  LYELFCKYDSFDSMPPAELERIEKRIFKRALQEVWEETKDFYINGLKNPE
Thr. sp. 20892 OrfC   (1306)  LYELFCKYDSFKAMPREELQRVEKRIFQKSLAEVWQETSDFYIHRKKNPE
Thr. sp. 10212 Pfa3p  (1292)  LYELFCMYNSFRDMPKSELQRLEKRIFQKSLAEVWEETKDFYINRLNNPE
                              1401                                              1450
Sch. sp.  9695 Pfa3p  (1322)  KIRKASNEDRKLKMSLCFRWYLGLSSFWANKGIARRTMDYQIWCGPAIGA
Sch. sp. 20888 OrfC   (1391)  -KIDRAEHDRKLKMSLCFRWYLGLSSRWANMGAPDRVMDYQVWCGPAIGA
Thr. sp. 20892 OrfC   (1356)  -KINRAASDGKLKMSLCFRWYLGLSSFWANSGAQDRVMDYQIWCGPAIGA
Thr. sp. 10212 Pfa3p  (1342)  KIEHARKKDRKLKMSLCFRWYLGLSSFWANKGIKKRSMDYQIWCGPAIGS
                              1451                                              1500
Sch. sp.  9695 Pfa3p  (1372)  ENDFIADSYLDVAVSGERPDVVQINLQILSGAAVLQRLLSVKLA--PRID
Sch. sp. 20888 OrfC   (1440)  ENDFIRGTYLDPAVSNEYPCVVQINLQILRGASVLRRLNADRND--PRID
Thr. sp. 20892 OrfC   (1405)  ENDFTRGTYLDKTVRKSYPCVAQINLQILQGAAVLKRIGVIRFDRMLLQA
Thr. sp. 10212 Pfa3p  (1392)  ENDFVKGTYLDPAVCSYPCVVQINMQILRGACFLQRYRAIKHD--PRID
                              1501        1517
Sch. sp.  9695 Pfa3p  (1420)  VDIRDESFIYRPDHAL-
Sch. sp. 20888 OrfC   (1488)  LRREDAAFVYEPSSAL-
Thr. sp. 20892 OrfC   (1455)  VDIDDPVFTYVPSPL-
Thr. sp. 10212 Pfa3p  (1440)  EDVSDYFTYRPESTL-
```

FIG. 7

(SEQ ID NO:1)

FIG. 8

MDTRIAIVGMSAILPSGENVRESWEAIRDGLDCLSDLPADRVDVTAYYNPEKTTKDKIYCKRGGFIPEYDFDAREFGLNMFQMEDSDANQTISLLKV
KEALTDANIPAFSSGKKNIGCVLGIGGGQKASHEFYSRLNYVVVDKVLRKMGLPEEDVAAAVDKYKASFPEWRLDSFPGFLGNVTAGRCCNTFNM
EGMNCVVDAACASSLIAVKVAIEELLYGDCDAMIAGATCTDNSIGMYMAFSKTPVFSTDPSVKAYDAATKGMLIGEGSAMLVLKRYADAVRDGD
TVHAVIKGCASSSDGKAAGIYTPTISGQEEALRRAYARANVDPATVTLVEGHGTGTPVGDKIELTALSNLFSKAFSANGGGAEEAEQVAVGSIKSQI
GHLKAVAGLAGLVKVVLALKHKTLPQTINVDKPPSLVDGTPIQQSPLYVNTMNRPWFTPVGVPRRAGVSSFGFGGANYHAVLEEFEPEHESAYRY
NNLPQVALLHAGDVATLAATVRAKLALATAEQEEARVVKNADYIAYHRFLDECKLRGAVPQAHARVGLLVRDLSSLIAVLEAAAAKLAGEESAT
EWTVSVATGEAAFRVRGVATEANVAALFSGQGAQYTHMFSDVAMNWPPFRESVAAMDRAQRERFGRPAKRVSSVLYPRKPYGDEPRQDHKEIS
QTRYSQPATLACSVGAFDIFKAAGLAPSFAAGHSLGEFAALYAAGSLDRDAVFDLVCARAKAMSDFTAQASSSGGAMAAVIGAKADQLSLGGAPD
VWLANSNSPSQTVITGTAEAVAAASDKLRCSGNFRVVPLACEAAFHSPHMRGAEQTFASALAQAPVSAPAAARFYSNVTGGAAVTSPADVKTNLG
KHMTSPVQFVQQVRAMHAAGARVFVEFGPKQVLSRLVKETLGEAGDVVTVAVNPDSAKDSDTQLRQAALTLAVAGVPLKDFDRWQLPDATRLE
PVKKKKTTLRLSAATYVSAKTLRQREAVLNDGYTVSGATAVVKEVDTANEERLVRQAQDLQRQLAEASTAAQAAQSKVAELERTIQDLERKVQQ
QQQEKGENSDSNAAAEVLRRHKELLQRMLQDCDEQAVPVATVVPTPTSSPTPTSSPVSGNSKSTRGSADLQALLAKAETVVMAVLAAKTGYEAD
MVEADMDLEAELGIDSIKRVEILSEVQGQLGVEAKDVDALSRTRTVGEVVDAMKAEIVAASGGSAPAVPSAPAASAAPTPAASTAPSADLQALLSK
AETVVMAVLAAKTGYEADMVEADMDLEAELGIDSIKRVEILSEVQGQLGVEAKDVDALSRTRTVGEVVDAMKAEIVAASAGSAPAPAVPSAPAA
SAAPTPAASTAPSADLQALLSKAETVVMAVLAAKTGYEADMVEADMDLEAELGIDSIKRVEILSEVQGQLGVEAKDVDALSRTRTVGEVVDAMK
AEIVAASGGSAPAPAVPSAPAASAAPTPAAATAPSADLQALLAKAETVVMAVLAAKTGYEADMVEADMDLEAELGIDSIKRVEILSEVQGQLGVE
AKDVDALSRTRTVGEVVDAMKAEIVAASAGSAPAPAVPSAPAASAAPTPAASTAPSADLQALLSKAETVVMAVLAAKTGYEADMVEADMDLEA
ELGIDSIKRVEILSEVQGQLGVEAKDVDALSRTRTVGEVVDAMKAEIVAASGGSAPAAAVPSAPAASAAPTPATAPSADLQALLSKAETVVMAVLA
AKTGYEADMVEADMDLEAELGIDSIKRVEILSEVQGQLGVEAKDVDALSRTRTVGEVVDAMKAEIVAASGGSAPAAPSAPALLPTLFGSECEDLSL
TFPVITTLPLPAELVLAEGGARPVVVVDDGSALTSSLVSSLGDRAVLLQVQSSSACSPRSTTHKLVTVADRSEAALQAALTSVEAQFGKVGGFVFQF
GDDDVQAQLGWALLAAKHLKTSLSEQIEGGRTFFVAVARLDGQLGLSGKSTTATVDLSRAQQGSVFGLCKTLDLEWPAVFCRGIDLAADLDAAQ
AARCLLGELSDPDVAVRESGYSASGQRCTITTKSLTTGKPHQPISSSDLFLVSGGARGITPLCVRELAQRVGGGTYVLIGRSELPTTEPAWAVGVESG
KPLEKAALAFLKAEFAAGRGAKPTPMLHKKLVGAVVGAREVRASLAEITAQGATAVYESCDVSSAAKVREMVERVQQQGGRRVSGVFHASGVL
RDKLVENKSLADFSAVYDTKVGGLINLLACVDLAQLRHLVLFSSLAGFHGNVGQSDYAMANEALNKLAAHLSAVHPQLCARSICFGPWDGGMVT
PALKANFIRMGIQIIPRQGGAQTVANMLVSSSPGQLLVGNWGVPPVVPSATEHTVLQTLRQSDNPFLDSHVIQGRRVLPMTLAVGYMAHQAQSIYA
GHQLWAVEDAQLFKGIAIDNGADVPVRVELSRRKEEQEDAGKVKVKVQVLLKSQVNGKSVPAYKATVVLSPAPRPSVITRDFDLTPDPACTEHDL
YDGKTLFHGKAFQGIEQVLSATPKQLTAKCRNLPLTPEQRGQFVVNLSQQDPFQADIAFQAMLVWARMLRQSAALPNNCERFDFYKPMAPGATY
YTSVKLASASPLVDSVCKCTVAMHDEQGEVYFSARASVVLNKTLTY (SEQ ID NO:2)

MPCDNIAVVGMAVQYAGCKNQDEFWDTLMRKEINSSPISAERLGTRYRDLHFHPQRSKYADTFCNDRYGCVDASVDNEHDLLADLARRALLDAG
INLDDASTTANLRDFGIVSGCLSFPMDNLQGELLNLYQVHVENRVGAQRFRDSRPWSERPRAVSPEASDPRVYSDPASFVANQLGLGPVRYSLDAA
CASALYCLKLASDHLLSRSADVMLCGATCFPDPFFILSGFSTFQAMPLGGPDDNPLSVPLRQGSQGLTPGEGGAIMVLKRLEDAVRDGDRIYGTLLG
TSLSNAGCGLPLSPHLPSEKSCMEDLYTSVGIDPSEVQYVECHATGTPQGDVVEVEALRHCFRGNTDHPPRMGSTKGNFGHTLVAAGFAGMAKVL
LSMQHGTIPPTPGVDRSNCIDPLVVDEAIPWPYSSAQARAGKPGDELKCASLSAFGFGGTNAHCVFREHRQIAATATASPVLPEVTPGPIAIIGMDAT
FGTLKGLDAFEQAIYKGTDGASDLPSKRWRFLGADTDFLTAMGLDAVPRGCYVRDVDVDYKRLRSPMIPEDVLRPQQLLAVATMDRALQDAGM
ATGGKVAVLVGLGTDTELYRHRARVTLKERLDPAAFSPEQVQEMMDYINDCGTSTSYTSYIGNLVATRVSSQWGFTGPSFTVTEGANSVYRCLEL
GKFLLDTHQVDAVVVAGVDLCATAENLYLKARRSAISRQDHPRANFEASADGYFAGEGSGALVLKRQADVGSDDKVYASVAGLTCAAQPAEAV
SPLLLQVHNDDNEKRVVEMVELAADSGRHAPHLANSPLSAESQLEQVSKLLAHQVPGSVAIGSVRANVGDVGYASGAASLIKTALCLHNRYLPAN
PQWERPVAPVSEALFTCPRSRAWLKNPGESRLAAVASASESGSCFGVLLTDEYATHESSNRLSLDDAAPKLIAIRGDTVDDIMAKVNAELALLRAH
AETGSATDDDPAAAVAFTAHRLRFLRLVGETVASHGATATLCLALLTTPEKLEKELELAAKGVPRSAKAGRNWMSPSGSAFAPTPVTSDRVAFMY
GEGRSPYYGVGLDLHRLWPALHERINDKTAALWENGDSWLMPRAVDADSQRAVQTAFDADQIEMFRTGIFVSICLTDYARDVLGVQPKACFGLSL
GEISMLFALSRRNCGLSDQLTQRLRTSPVWSTQLAVEFQALRKLWNVPADAPVESFWQGYLVRASRAEIEKAIGPDNRFVRLLIVNDSSSALIAGKP
AECLRVLERLGGRLPPMPVKQGMIGHCPEVAPYTPGIAHIHEILEIPDSPVKMYTSVTNAELRGGSNSSITEFVQKLYTRIADFPGIVDKVSRDGHDVF
VEVGPNNMRSAAVSDILGKAATPHVSVALDRPSESAWTQTLKSLALLTAHRVPLHNPTLFADLYHPTFLTAIDSAMQEPPPKPNRFLRSVEVNGYFC
PDGISKQVAAASAKPSTHCMVRLHPAKAVVVAAAGAVVADSTPVVKAKQTSSSLLVGDDAFLRCYDVDWPLYMGAMAEGISSVDLVVAAAEAR
MLASFGAARLPMDQVELQIREIQQRTSNAFAVNLMPGPDEAATVDALLRTGVSIVEASGYTGALSADLVRYRVTGLRRTSCGASVSATHRVVAKV
SRTEVAEHFLRPAPAAVLEALVAAKQITPEQAALASRVAMADDVAVEADSGGHTDNRPIHVLLPLVVAQRNRWRHLVDTPVRVGAGGGIACPRA
ALLAFSLGAAFVVTGSVNQLAREAGTSDAVRLLLATATYSDVAMAPGGVQVLKKQTMFAARATMLAQLQAKFGSFDAVPEPQLRKLERSVFKQS
VADVWAAAREKFGVDATAASPQERMALCVRWYMSQSSRWATEATSARKADYQIWCGPAIGSFNDFVRGTKLDATAGTGEFPRVVDINQHILLGA
SHYRRVQQQQQDDDVEYIIV (SEQ ID NO:4)

FIG. 11

(SEQ ID NO:5)

FIG. 12

MTSSKKTPVWEMSKEELLDGKTVVFDYNELLEFAEGDVGQVFGPEFDIIDKYRRRVRLPAREYLLVSRVTLMDAEVNNFRVGSRMVTEYDVPVNG
ELSEGGDVPWAVLVESGQCDLMLISYMGIDFQCKGDRVYRLLNTSLTFFGVAHEGETLVYDIRVTGFAKGAGGEISMFFFEYDCFVDGRLLIEMRD
GCAGFFTDAELAAGKGVLKTKAELAARAQIQKQDIAPFAPAPCSHKTSLDAREMRLLVDRQWARVFGSGMAGIDYKLCARKMLMIDRVTHLDPR
GGAHGLGLLIGEKVLERDHWYFPCHFVRDEVMAGSLVSDGCSQLLKVYMLWLGLHTTVGAFDFRPVSGHANKVRCRGQISPHKGKLVYVMEIKE
MGFDAKTGDPFAIADVDIIDVNFEEGQAFAGVEDLHSYGQGDLRKKIVVDFKGIALSLQKRKEQQKESMTVTTTTTTTSRVIAPPSGCLKGDPTAPT
SVTWHPMAEGNGGPGPTPSFSPSAYPPRAVCFSPFPNNPLDNDHTPGQMPLTWFNMSEFMCGKVSNCLGPEFARFDASKTSRSPAFDLALVTRVTS
VADMEHGPFYNVDVNPGQGTMVGEFDCPADAWFFGASSRDDHMPYSILMEIALQTSGVLTSVLKAPLTMDKDDILFRNLDADAELVGDAMPDVR
GKTIRNFTKCTGYSMLGKMGIHRFTFELSVDGAVFYKGSTSFGWFVPEVFESQTGLDNGKPRLPWYRENNVAVDTLSAPASASSAQGQLQLQRRG
SQAQFLDTIHLAGSGAGVHGQGYAHGEKAVNKQDWFFSCHFWFDPVMPGSLGIESMFQLVEAWCVKQGLAARHGIAHPVFAHAPGATSWKYRG
QLTPKNDRMDSEVHIKSVAAFSSWVDVVADGFLFVDGLRVYSADNLRVRIQTGAGHVEEQEVAAKATTKNSSIADVDVADLQALKQALLTLERPL
QLDAGSEVPACAVSDLGDRGFMETYGVVAPLYSGAMAKGIASADLVIAMGQRKMLGSFGAGGLPMHVVRAGIEKIQAALPAGPYAVNLIHSPFD
ANLEKGNVDLFLEKGVRVVEASAFMELTPQVVRYRATGLSRDARGGSVRTAHKIIGKVSRTELAEMFIRPAPQAILDKLVASGEITPEQAALALEVP
MADDIAVEADSGGHTDNRPIHVILPLILSLRNRLQRELKYPARHRVRVGAGGGIGCPQAALGAFHMGAAFVVTGTVNQLSRQAGTCDNVRRQLSR
ATYSDITMAPAADMFEQGVELQVLKKGTMFPSRAKKLFELFHKYDSFEAMPADELARVEKRIFSKSLAEVWAETKDFYITRLNNPEKIRKAENEDP
KLKMSLCFRWYLGLSSFWANNGIADRTMDYQIWCGPAIGAFNDFIADSYLDVAVSGEFPDVVQINLQILSGAAYLQRLLSVKLAPRIDVDTEDDLF
TYRPDHAL (SEQ ID NO:6)

FIG. 13

ATGGAAGATCAAAGAATTGCTATTGTTGGATTATCTGCGATTTTACCAAGTGGTGAAAATGTTAGAGAATCTTGGGAAGCAATACGTGATGGTTTGAATTGTTTAAGTGATTTA
CCTGCGGATCGTGTTGATGTTACTGCGTATTATAATCCAACAAAAGGTGTAAAGGATAAAATTTATTGTAAACGTGGTGGGTTTATTCCTGAATATGAATTTGATTCTAGAGAA
TTTGGACTTAATATGTTACAAATGGAAGATTCTGATGCTAATCAAACGTTAACTTTATTAAAGGTTAAAGAAGCATTAGATGATGCTAATATACCTGCATTTACTAATGAGAAA
AAAAATATTGGTTGTGTTCTTGGTATTGGTGGTGGTCAAAAAGCATCTCATGAATTTTATTCAAGACTTAATTATGTTGTTGTGGATAAAGTTTTAAGAAAAATGGGATTACCT
GATGAGGATGTTGAAACTGCTGTTGAAAAGTTTAAAGCTAATTTTCCTGAATGGAGATTAGATTCCTTTCCTGGTTTTCTTGGTAATGTTACTGCTGGCCGTTGTACTAATACAT
TCAATATGGAAGGTATGAATTGTGTTGTAGATGCTGCTTGTGCTAGTTCTTTAATTGCTATTAAAGTTGCTATTGATGAATTATTACATGGTGATTGTGATGCAATGATTGCTGG
TGCAACTTGTACTGATAACGCTCTTGGTATGTATATGGCATTTTCAAAAACACCTGTTTTTTCAACTGATCAAAGTTGTCTTGCATATGATGAAAAAACAAAAGGTATGCTTATT
GGTGAAGGTTCAGCTATGTTTGTTTTAAAACGTTATGCTGACGCAGTGAGAGATGGTGATACTGTACATGCTGTTATACGTTCATGTTCATCATCATCTGACGGTAAAGCATCT
GGTATTTATACACCAACTATTTCTGGTCAAGAAGAAGCTATTCTTAGAGCATATCGTAGAGCTGGTGTATCACCAAATACTATTACTTTAGTTGAAGGACATGGTACTGGTACA
CCAGTGGGTGATAAAATTGAATTAACAGCTTTACGCAATGTATTTGATAAAGCATATGGTCCTGGTCATAAGGAAGAAGTTGCTGTTGGAAGTATTAAAAGTCAAATTGGTCA
TTTGAAAGCTGTTGCTGGTTGTGCTGGTCTTGTGAAATTGGTTATGGCATTGAAACATAAAACACTACCTCAAAGTATTAATGTTGAAAATCCACCTAATTTAGTGGATGGTAC
TGTCATTAGTGATACTACTTTATATATTAATACAATGAATCGTCCATGGATTACTAAGCCTGGTGTTCCAAGAAGAGCTGGTATATCTAGTTTCGGATTTGGTGGTGCAAATTAT
CATGCTGTTTTAGAAGAATTTGAGCCGGAACAAACTAAACCATATAGATTGAATGTATCTGCACAACCAATGCTTCTTCATGCGGTAAATGCAAATTCATTACAAAAGCTATGT
GAAGATCAATTAAAACTTTTGAAAGAATCAAGAGAAAAATGTGTCAACACCAAAAACACTGATTATGTTGCGTTTTCAAAATTTCAAGATTCTTTTAAATTGAAAGGTTCTGTT
CCATCACAACATGCTAGAGTTGGTTTTGCATCAAAATCTATTGAAGATACTATTTCTATTTTATCTGCTATCGTTAATAGATTTCAAAAAGATATTACAACAACTAGTTGGGCTT
TACCAAAAGAAGGTGCTATTTTTAGATCTACTGCATTGATTAATGACAATAAAAGTGTAGCTGCTTTATTTTCTGGACAAGGCGCACAATATACCCATATGTTTAATGATGTTG
CAATGCAATGGCCACAATTTCGTTTATGTGTAAATGATATGGAGAAAGCACAGGAAGAAGTTATCAATGATAAAAGTGTGAAACGTATCAGTCAAGTTATGTTTCCTCGTAAA
CCATATGCAAGAGAATCACCTTTAGACAATAAAGAAATCTCTAAGACTGAATATTCTCAAACAACAACTGTCGCTAGTTCAGTAGGTTTATTTGAAATTTTCCGTGATGCTGGT
TTCGCTCCTGCTTTTGTTGCTGGTCATTCTTTAGGTGAAATTTAGTGCATTGTATGCAGCTGGATTGATTGATCGCGAAGATTTATTCAAGTTGGTATGTAATCGTGCAATGGCTA
TGAGAGATGCACCAAAAAAATCTGCTGATGGAGCAATGGCTGCTGTTATTGGTCCAAATGCTTCTTCAATTAAGCTTTCAGCTCCTGAAGTATGGGTTGCTAACAATAACTCTC
CATCTCAAACTGTTATTACCGGTGCAAATTCTGGTGTACAAGCTGAAACAAGTAAATTGAAAACTCAAGGTTTCCGTGTGGTTCATTTGGCATGTGATGGGGCATTTCATTCGC
CTCATATGGAAAATGCTGAAAAGCAATTTCAAAAAAGCTCTTTCAGCAGTTAAGTTTAATAAACCAACTGGTTCTTCTCCAAAAATTTTCAGCAATGTAACTGGTGGTGTATTTA
CGGATCCAAAAACTGCTTTGTCAAGACATATGACTAGTTCTGTACAATTTCTTACTCAAATTAAGAATATGTACGCGGCTGGAGCTCGTGTCTTTATTGAATTTGGACCAAAAC
AAGTACTTTCCAAATTGGTCAATGAAATTTTTCCTGGTGATACAAGCGTTTTAACTGTTTCGGTGAATCCAGCTAGTGCTAAAGATAGTGACATTCAATTGCGTCAAGCTGCAG
TTCAAATGGCCGTTGCTGGTGTAGCTCTTACCGATTTTGATAAATGGGAACTCAAAGATCCTACCCGTATGAAGGAATTCCCACGTAAGAAGACTACTTTGACTTTGTCTGCAG
CAACTTATGTCTCCAAGAAAACTCTACAGGAGCGTGAACGAATCATGAATGATGGGCGAACTGTTTCATGTGTTCAACGTATTGAAAACACTAATACTGGTGAGTTGGAGAAA
TTGAAGAAGCAATTGCAAGATAAAGAAAATGAGGTTGTAAGAGTTCAAGCTCTTGCAACTCAAGCTTCAGCTGATTTGCAAAATACCAAAGCAGAATTACAAAAAGCTCAAG
CAACAAAATCTAGTAATGCAGCATCTGATGCGGTGGTGGCAAAAACATAAGGCAATTTTATTGGCAATGTTAGAAGAACTTGAAACCGGCAAGGCTGTAGATTATTCTTCATTT
TCGAAAGGTCAAGTTGCAAGTCCAGCTACCGTTCGTGTCGTTTCAGCTCCTGTTCAAGCGGCTGCTCCTGTGCAGGTATCTGCTTCTGTTGATTCTGGTTTGTTGGCAAAAGCGG
AACAAGTTGTATTGGAAGTATTGGCATCGAAGACTGGTTATGAGACTGAGTTGATTGAATTGGATATGGAATTGGAAACTGAACTTGGTATTGATTCTATCAAGAGAGTAGAA
ATTCTTTCTGAAGTTCAAGCTCAATTGAATGTTGAAGCTAAAGATGTAGATGCTCTTAGTAGAACTCGTACTGTTGGTGAAGTGATTGATGCAATGAAAGCCGAAATTGCTGGT
GGTCAACCAGCTGCTCCTGTTCAAGTTGCAGCTCCTACTCAAGTAGTTGCTCCTGTTCAAGCATCTGCTCCTGTTGATTCTGGTTTGTTAGCAAAAGCGGAACAAGTTGTATTGG
AAGTATTGGCATCGAAGACTGGTTATGAGACTGAGTTGATTGAATTGGATATGGAATTGGAAACCGAACTTGGTATTGATTCTATCAAGAGAGTAGAAATTCTTTCTGAAGTT
CAAGCTCAATTGAGTGTTGAAGCTAAAGATGTAGATGCTCTTAGTAGAACTCGTACTGTTGGTGAAGTGATTGATGCAATGAAAGCCGAAATTGCTGGTGGTCAACCAGCTGC
TCCTGTTCAAGTTGCAGCTCCTACTCAAGTAGTTGCTCCTGTTCAAGCATCTGCTCCTGTTGATTCTGGTTTGTTAGCAAAAGCGGAACAAGTTGTATTGGAAGTATTGGCATCG
AAGACTGGTTATGAGACTGAGTTGATTGAATTGGATATGGAATTGGAAACCGAACTTGGTATTGATTCTATCAAGAGAGTAGAAATTCTTTCTGAAGTTCAAGCTCAATTGAG
TGTTGAAGCTAAAGATGTAGATGCTCTTAGTAGAACTCGTACTGTTGGTGAAGTGATTGATGCAATGAAAGCTGAAATTTCTGGTGGTCAGCCAGCTGCTCCTGTTCAAGTTGC
AGCTCCTACTCAAATAGTTGCTCCTGTTCAAGTATCCGCTCCTGTTGATTCTGGTTTGTTAGCAAAGGCGGAACAAGTAGTATTGGAAGTATTGGCATCGAAGACTGGTTATGA
GACTGAGTTGATTGAATTGGATATGGAATTGGAAACTGAACTTGGTATTGATTCTATCAAGAGAGTAGAAATTCTTTCTGAAGTTCAAGCTCAATTGAGTGTTGAAGCTAAAG
ATGTAGATGCTCTTAGTAGAACTCGTACTGTTGGTGAAGTGATTGATGCAATGAAAGCTGAAATTTCTGGTGGTCAACCAACTGCTCCTGTTCAAGTTGCAGCTCCTACTCAAA
TAGTTGCTCCTGTTCAAGTATCTGCTCCTGTTGATTCTGGTTTGTTAGCAAAGGCGGAACAAGTTGTATTGGAAGTATTGGCATCGAAGACTGGTTATGAGACTGAGTTGATTG

FIG. 13 (cont'd)

```
AATTGGATATGGAATTGGAAACCGAACTTGGTATTGATTCTATCAAGAGAGTAGAAATTCTTTCTGAAGTTCAAGCTCAATTGAGTGTTGAAGCTAAAGATGTAGATGCTCTTA
GTAGAACTCGTACTGTTGGTGAAGTGATTGATGCAATGAAAGCCGAAATTTCTGGTGGTCAGCCAGCTGCTCCTGTTCAAGTTGCAGCTCCTACTCAAATAGTTGCTCCTGTTC
AAGCATCTGCTCCTGTTGATTCTGGTTTGTTGGCAAAAGCGGAACAAGTTGTATTGGAAGTGTTAGCATCCAAGACTGGTTATGAAACTGAGTTGATTGAATTAGATATGGAAT
TGGAAACCGAACTTGGTATTGATTCTATCAAGAGAGTAGAAATTCTTTCTGAAGTTCAAGCTCAATTGAGTGTTGAAGCTAAAGATGTAGATGCTCTTAGTAGAACTCGTACTG
TTGGTGAAGTGATTGATGCAATGAAAGCTGAAATTTCTGGTGGTCAACCAGCTGCTCCTGTTCAAGTTGCAGCTCCTACTCAAATAGTTGCTCCTGTTCAAGTATCTGCTCCTGT
TGATTCTGGTTTGTTAGCAAAGGCGGAACAAGTTGTATTGGAAGTATTGGCATCTAAGACTGGTTATGAGACTGAGTTGATTGAATTGGATATGGAATTGGAAACTGAACTTG
GTATTGATTCTATCAAGAGAGTAGAAATTCTTTCTGAAGTTCAAGCTCAATTGAATGTTGAAGCTAAAGATGTAGATGCTCTTAGTAGAACTCGTACTGTTGGTGAAGTGATTG
ATGCAATGAAAGCCGAAATTGCTGGTGGTCAACCAGCTGCTCCTGTTCAAGTTGCAGCTCCTGCTCCAGTAGTTGCTCCTGTTCAAGTATCTACTCCTGTTGATTCTGGTTTGTT
GGCAAAAGCGGAACAAGTTGTATTGGAAGTGTTAGCATGCAAGACTGGTTATGAAACTGAGTTGATTGAATTGGATATGGAATTGGAAACTGAACTTGGTATTGATTCTATCA
AGAGAGTAGAAATTCTTTCTGAAGTTCAAGCTCAATTGAGTGTTGAAGCTAAAGATGTAGATGCTCTTAGTAGAACTCGTACTGTTGGTGAAGTGATTGATGCAATGAAAGCC
GAAATTTCTGGTGGTCAACCAACTGCTCCTGTTCAAGTTGCAGCTCCTACTCAAGTAGTTGCTCCTGTTAAAGTATCTACTCCTGTTGATTCTGGTTTGTTAGCAAAGGCGGAAC
AAGTAGTATTGGAAGTATTGGCATCTAAGACTGGTTATGAAACTGAGTTGATTGAATTAGATATGGAATTGGAAACTGAACTTGGTATTGATTCTATCAAGAGAGTAGAAATT
CTTTCTGAAGTTCAAGCTCAATTGAATGTGGAAGCTAAAGATGTGGATGCTCTTAGTAGAACTCGTACTGTTGGTGAAGTGATTGATGCAATGAAAGCCGAAATTGCTGGTGA
TCAACCTGCTCCAGCTGTAGTTCCAGTTCAAGCTAAGAGTGGTGTAGCCAACCCTGCACTTTTGGCAAAGGCGGAACAAGTAGTATTGGAAGTATTGGCATCCAAGACCGGTT
ATGAAACTGAGCTGATTGAATTGGATATGGAATTGGAAACTGAACTTGGTATTGATTCAATCAAGAGAGTAGAAATTCTGTCCGAAGTTCAAGCAGAATTGAGTGTTGAAGCA
AAAGATGTAGACGCTCTAAGTAGAACCCGTACTGTTGGGGAAGTGATCGATGCAATGAAAGCTGAAATTGCTGGCAGTGCTGTCACGGTTGCAACTTTGGATGATTCAACAAT
TATGGAGGAGACAGATGATGAAGATGAAGACTTTATTTTATACGATCATGTATACGGAAGCGAATGTGAAGATCTTAGTCTGAGTTTTTCATCCGTAAAGAGCATCCCGCGCG
CTGATAAACTTTTGTTGGATAACATTGCTGAAAGGCCAATTGTTATTGTGGATTGTGGAACAAAGCTTACAACTGAACTTGCAAAAGCTATTGGAGAACGTGCCGTGGTTGCTA
CATTCAGTGCACAGAGCTTGGTATCCCGTGGATTCGTTGGTAAATCATTTACTCTAGGAAATACAGAAGAAAGTGAGATCGAAAAGATGGTTTCAAGCATTGAATCTTCGTAT
GGAAAAATTGGTGGCTTTGTTTATCAACATTTTCATGATAGCGACTATGGTATGCAACTTGGATGGGCGTTAATGGCAGCGAAACATTTGAAAGAGTCCCTCAACGACCCGAT
TAAGAATGGAAGAACCTTCTTTTTGGCTGTTGCGCGTATGAATGGTAAACTTGGTATGGACAATGCTTCAGTTCATGATCAAGGAATAGTGGAATCATGCGGTATCGCCGAAC
GTGGTGCTATCTTTGGTTTGTGCAAAACTTTGGATTTGGAATGGCCTAATGTTTTTGCTCGTGGTGTTGATATTGCTGAAGGTATGAGTTATAGTTTGGCTGCGGAATTGATTGT
TGATGAGATTTCTTGTGCAAATCTTTCCATTCGGGAATCTGGTTACACGATTAGCGGAGAAAGATTCACAACTGAAGCTCACAAATTGGTTACTGGAAAGCCTCATGCTCCGAT
TAAGAAGAAGGATGCTTTCCTAGTATCTGGTGGTGCTCGTGGTATTACTCCACTTTGTATTCGTGAAATTGCTAAAGCAGTGAAAGGTGGCACTTACATTTTGATGGGTCGATC
AGCTTTGGCTGATGAACCCTTGTGGGCTAATGGTAAATCCGGAAAAGATTTAGATAAAGCTGGTTTTGGCATTTTTGAAGGAAGAGTTTGCAGCTGGGCGTGGTAGTAAACCAA
CTCCAAAAGTTCACAAATCTTTGATTGATAAAGTGCTCGGTATTAGGGAGGTTAGAGCATCTATTGCAAATATAGAAGCCCATGGAGCAAAAGCTATATATTTGTCTTGCGAT
GTATCTTCCGCTGAGAAAGTAAAGGCTGCAGTGCAAAAAGTTGAAAAGGAGCATCTAGTTCGTATTACTGGTATTGTGCATGCATCAGGCGTTTTGAGGGATAAATTGGTTGA
GAACAAAACTTTGGATGATTTCAACGCAGTATATGGAACCAAAGTAACTGGACTAGTAAACTTGCTGTCAGCAGTGAACATGAATTTTGTTCGTCATTTGGTTATGTTTAGTTC
TTTGGCTGGATATCATGGGAAATGTTGGTCAATCTGATTATGCAATGGCTAACGAATCACTTAACAAGATTGGTTTTAGATTGGGTGCAGCTTATTCTCAATTGTGTGTTAAATCT
ATTTGTTTTGGACCTTGGGATGGTGGAATGGTAACTCCAGCTTTGAAAAAACAATTTCAATCAATGGGTGTCCAGATTATTCCTCGTGAAGGTGGCGCGGAGACTGTTGCAAG
AATAGTCTTATCTTCAAATCCTTCTCAAGTTTTAGTTGGCAACTGGGGTGTTCCTCCAGTTTCACCTTTGTCAAAATCGGCAACTATTGTTCAAACTTTTACCCCTGAGTTAAATC
CATTTCTAAAGTCTCATCAAATTCATGGTAAAAATGTTTTGCCTATGACTGTAGCAATTGGATATCTTGCTCACTTGGTTAAGAATTTTTATGCTGGTCATCATTTGTGGGGAGT
TGAAGATGCTCAATTGTTCAGTGGTGTTGTAATTGACCATGCGGTGCAAGCTCAAGTGAAATTAACGGAACAGAGTTTGGATGATGATGGCAAGGTAAAAGTTCAAGCTGTTC
TGACTGCTTCAAACGATAATGGGAAAAATGGTACCTGCATACAAAGCAGTGATTGTTTTGGGAAAAACAAGTAGACCTGCGTTTATTTTGAAAGATTTTTCATTGCAAGAATCT
AATTCTCGCAGTGCTGATGAGTTGTATGATGGTAAAACTTTGTTTCATGGTCCATTATTTCGTGGAATTACCAAGTTGTTGAATGTATCTGATACTTCACTAACAACTCAATGTA
CCAATATTGATTTGACTGCTACTGAACGTGGTCAATTTGCGGATATCGAACCTGTGAATCCTTTTATGGCGGATGCTGCATTTCAAGCTATGCTTGTATGGGTTAGAAATTTAA
GGAATAGTGCATCTTTACCAAACAATTGTGAAAGAGTAGATATCTATAAACCAATAGCACCTGGTGAAAAGTATTACACTACTTTGCAAGCTTTGGGTAATACCTCCGGTTCTG
TTCTCAAGTCTGTATTTTATATGCACGATGAACAAGGAGAAGTATTTCTATCTGGAAGAGCTAGTGTTGTTGTGAATGACAAGATGGAGTTTTAG
```

(SEQ ID NO:68)

FIG. 14

ATGGAGGACCAGCGTATTGCGATCGTTGGCCTTAGCGCGATCCTTCCCTCGGGCGAGAACGTCCGCGAGTCGTGGGAGGCGATCCGTGACGGCCTCAACTGCCTTTCCGACCT
GCCCGCCGACCGCGTTGACGTCACTGCCTACTACAACCCCACGAAGGGCGTCAAGGACAAGATCTACTGCAAGCGTGGTGGCTTCATCCCCGAGTACGAGTTTGACTCGCGCG
AGTTCGGCCTCAACATGCTTCAGATGGAGGACTCGGACGCCAACCAGACCCTCACCCTGCTCAAGGTTAAGGAGGCCCTCGACGACGCCAACATTCCCGCGTTTACCAACGAG
AAGAAGAACATCGGTTGCGTCCTCGGTATTGGCGGTGGTCAGAAGGCCTCGCATGAGTTCTACAGCCGCCTCAACTACGTCGTCGTGGATAAGGTCCTCCGCAAGATGGGCCT
CCCGGACGAGGACGTCGAGACTGCTGTCGAGAAGTTCAAGGCCAACTTTCCCGAGTGGCGCCTTGACTCCTTCCCCGGCTTTCTCGGTAACGTCACTGCGGGCCGCTGCACCA
ACACCTTCAACATGGAGGGCATGAACTGCGTGGTCGATGCCGCCTGCGCCTCGTCCCTCATCGCTATCAAGGTCGCCATCGATGAGCTGCTCCACGGCGATTGCGACGCGATG
ATTGCTGGCGCGACGTGCACCGACAACGCCCTTGGCATGTACATGGCCTTTTCCAAGACCCCCGTCTTTTCCACGGACCAGAGCTGCCTCGCCTACGACGAGAAAACCAAGGG
TATGCTCATTGGCGAGGGTTCCGCCATGTTCGTCCTTAAGCGCTACGCCGACGCCGTCCGCGATGGCGACACCGTCCACGCCGTCATCCGCTCGTGCTCGTCCTCCTCCGACGG
CAAGGCCGTCGGGTATCTACACCCCGACCATCTCGGGCCAGGAGGAGGCCATCCTTCGCGCCTACGTCGTGCCGGCGTGAGCCCGAACACGATCACCCTTGTGGAGGGCCATG
GCACCGGCACCCCCGTCGGCGACAAGATCGAGCTGACCGCCCTCCGCAACGTCTTTGACAAGGCCTACGGCCCTGGCCACAAGGAGGAGGTCGCTGTGGGCTCCATCAAGTC
GCAGATCGGTCACCTCAAGGCCGTCGCCGGCTGCGCTGGCCTCGTCAAGCTCGTGATGGCTCTCAAGCATAAGACGCTCCCGCAGTCCATCAACGTCGAGAACCCGCCCAACC
TCGTCGATGGCACTGTCATCTCGGACACCACGCTCTACATCAACACCATGAACCGCCCGTGGATCACCAAGCCGGGCGTCCCCCGTCGTGCGGGCATCTCCAGCTTCGGCTTTG
GCGGCGCTAACTACCACGCTGTCCTTGAGGAGTTCGAGCCCGAGCAGACCAAGCCCTACCGCCTGAACGTTTCGGCCCAGCCGATGCTCCTCCACGCCGTCAACGCGAACTCG
CTCCAGAAGCTCTGCGAGGACCAGCTCAAGCTCCTCAAGGAGTCCCGCGAGAAGTGCGTCAACACGAAGAACACCGACTACGTCGCTTTTTCCAAGTTTCAGGACTCCTTTAA
GCTCAAGGGCTCCGTCCCCAGCCAGCACGCTCGCGTGGGCTTTGCTTCCAAGAGCATCGAGGACACGATTTCCATTCTTAGCGCCATTGTCAACCGCTTCCAGAAGGACATCAC
GACCACCAGCTGGGCGCTCCCGAAGGAGGGCGCCATCTTTCGCAGCACCGCCCTCATCAACGACAACAAGTCCGTGGCCGCCCTGTTCTCGGGTCAGGGCGCTCAGTACACCC
ACATGTTCAACGACGTCGCGATGCAGTGGCCGCAGTTCCGCCTCTGCGTTAACGATATGGAGAAGGCCCAGGAGGAGGTGATCAACGACAAGTCGGTTAAGCGCATTAGCCA
GGTCATGTTTCCCGCAAGCCCTACGCGCGCGAGAGCCCCCTCGACAACAAGGAGATCAGCAAGACCGAGTACTCGCAGACGACGACCGTCGCCTCGTCCGTCGGCCTCTTTG
AGATTTTCCGCGACGCCGGCTTTGCCCCGGCTTTTGTTGCGGGCCACTCGCTCGGTGAGTTCTCCGCCCTTTACGCCGCTGGCCTCATCGACCGCGAGGACCTCTTTAAGCTCGT
GTGCAACCGCGCCATGGCTATGCGCGACGCCCCCAAGAAGTCCGCTGACGGCGCCATGGCTGCCGTCATCGGTCCGAACGCCTCGTCCATCAAGCTCTCGGCTCCCGAGGTTT
GGGTCGCGAACAACAACTCGCCCTCGCAGACCGTCATCACTGGTGCCAACAGCGGCGTCCAGGCCGAGACTTCGAAGCTCAAGACGCAGGGTTTCCGCGTGGTCCACCTCGCC
TGCGACGGCGCGTTTCACAGCCCGCACATGGAGAACGCCGAGAAGCAGTTTCAGAAGGCCCTCTCGGCCGTCAAGTTCAACAAGCCCACCGGCTCGTCCCCCAAGATTTTCAG
CAACGTCACCGGCGGTGTCTTTACCGATCCTAAGACGGCCCTCTCCCGCCACATGACTAGCTCGGTCCAGTTTCTCACCCAGATCAAGAACATGTACGCCGCTGGCGCCCGCGT
TTTCATCGAGTTCGGCCCCAAGCAGGTCCTCTCGAAGCTCGTCAACGAGATTTTCCCGGGCGACACCAGCGTCCTCACTGTTAGCGTGAACCCTGCCTCCGCCAAGGACTCGGA
CATCCAGCTCCGCCAGGCGGCCGTGCAGATGGCGGTCGCTGGCGTCGCTCTCACCGACTTTGATAAGTGGGAGCTTAAGGACCCGACCCGCATGAAGGAGTTCCCTCGCAAGA
AAACGACCCTCACCCTCTCCGCCGCTACCTACGTTAGCAAGAAAACGCTCCAGGAGCGCGAGCGTATCATGAACGACGGTCGCACTGTCAGCTGCGTGCAGCGCATCGAGAA
CACGAACACGGGCGAGCTTGAGAAGCTCAAGAAGCAGCTCCAGGACAAGGAGAACGAGGTTGTCCGCGTCCAGGCCCTTGCCACCCAGGCCAGCGCCGACCTTCAGAACACC
AAGGCTGAGCTTCAGAAGGGCTCAGGCCACCAAGTCGTCGAACGCTGCCTCGGACGCCGTCGTCGCCAAGCACAAGGCCATCCTCCTCGCTATGCTGGAGGAGCTGGAGACTG
GCAAGGCCGTCGATTACTCCAGCTTTTCCAAGGGTCAGGTTGCCTCCCCTGCGACCGTTCGTGTCGTGTCGGCTCCCGTGCAGGCTGCCGCACCGGTTCAGGTCAGCGCCTCCG
TGGACTCGGGCCTGCTCGCGAAGGCGGAGCAGGTCGTGCTTGAGGTCCTCGCCTCCAAGACCGGCTACGAGACTGAGCTTATCGAGCTGGACATGGAGCTTGAGACTGAGCTT
GGTATCGATTCGATCAAGCGCGTCGAGATTCTTTCGGAGGTCCAGGCCCAGCTCAACGTGGAGGCCAAGGACGTTGACGCCCTGTCGCGCACCCGTACGGTCGGCGAGGTCAT
CGATGCCATGAAGGCGGAGATTGCCGGCGGTCAGCCTGCTGCCCCCGTCCAGGTCGCTGCGCCGACGCAGGTCGTCGCCCCGGTCCAGGCCTCCGCGCCTGTCGATAGCGGCC
TCCTCGCCAAGGCGGAGCAGGTCGTCCTTGAGGTGCTCGCTTCCAAGACTGGTTACGAGACTGAGCTTATTGAGCTTGACATGGAGCTGGAGACTGAGCTTGGCATTGACTCC
ATCAAGCGCGTGGAGATTCTGAGCGAGGTCCAGGCCCAGCTCAGCGTGGAGGCCAAGGATGTCGATGCCCTCTCCCGTACGCGCACCGTCGGCGAGGTCATTGACGCGATGA
AGGCCGAGATCGCGGGTGGTCAGCCGGCCGCCCCCGTCCAGGTCGCTGCCCCTACGCAGGTCGTCGCTCCCGTCCAGGCCAGCGCTCCCGTCGACTCGGGCCTTCTTGCTAAG
GCCGAGCAGGTCGTCCTTGAGGTCCTTGCCAGCAAGACTGGCTACGAGACTGAGCTTATTGAGCTTGACATGGAGCTTGAGACTGAGCTTGGCATCGACTCGATTAAGCGCGT
CGAGATCCTCAGCGAGGTCCAGGCCCAGCTCTCCGTCGAGGCTAAGGATGTGGATGCTCTCAGCCGCACGCGCACGGTGGGCGAGGTCATTGATGCCATGAAGGCGGAGATT
TCCGGCGGTCAGCCCGCTGCCCCCGTCCAGGTCGCTGCTCCGACCCAGATCGTCGCCCCGGTCCAGGTTCGGCTCCGGTGGACAGCGGCCTCCTTGCCAAGGCCGAGCAGGT
CGTCCTTGAGGTCCTCGCCAGCAAGACCGGCTACGAGACTGAGCTGATCGAGCTTGACATGGAGCTTGAGACTGAGCTGGGCATCGATTCCATTAAGCGCGTCGAGATCCTCT
CGGAGGTCCAGGCCCAGCTCAGCGTGGAGGCCAAGGATGTCGATGCCCTCTCGCGTACCCGTACCGTCGGCGAGGTTATCGATGCTATGAAGGCCGAGATCAGCGGCGGTCA
GCCCACGGCGCCCGTTCAGGTCGCTGCCCCTACGCAGATCGTTGCCCCTGTCCAGGTCAGCGCTCCCGTGGACAGCGGCCTCCTCGCTAAGGCCTGAGCAGGTGGTGCTGGAGG
TCCTGGCCTCCAAGACCGGCTACGAGACTGAGCTTATCGAGCTTGACATGGAGCTTGAGACTGAGCTTGGCATTGACAGCATCAAGCGTGTCGAGATCCTCTCCGAGGTGCAG

FIG. 14 (cont'd)

```
GCCCAGCTCAGCGTGGAGGCCAAGGACGTTGACGCGCTCAGCCGTACGCGCACCGTTGGCGAGGTGATCGACGCCATGAAGGCCGAGATTAGCGGTGGTCAGCCCGCTGCCC
CGGTTCAGGTGGCTGCCCCTACGCAGATCGTCGCCCCCGTGCAAGCTTCCGCCCCTGTGGACAGCGGCCTTCTCGCCAAGGCCGAGCAGGTCGTCCTTGAGGTGCTGGCCTCCA
AGACCGGCTACGAGACTGAGCTGATCGAGCTTGACATGGAGCTGGAGACTGAGCTTGGCATCGACTCGATCAAGCGCGTGGAGATTCTCTCGGAGGTCCAGGCCCAGCTCTCG
GTCGAGGCCAAGGACGTCGATGCGCTCTCCCGCACCCGCACCGTGGGCGAGGTCATCGACGCTATGAAGGCGGAGATCAGCGGCGGTCAGCCGGCGGCCCCTGTGCAGGTGG
CCGCTCCGACCCAGATCGTCGCTCCTGTCCAGGTTTCCGCCCCGGTGGACTCGGGCCTCCTGGCTAAGGCCGAGCAGGTCGTCCTTGAGGTCCTCGCTTCCAAGACCGGCTACG
AGACTGAGCTGATCGAGCTGGACATGGAGCTTGAGACTGAGCTGGGCATCGATTCGATCAAGCGCGTCGAGATTCTCTCGGAGGTCCAGGCCCAGCTCAACGTTGAGGCCAA
GGACGTGGACGCCCTCTCGCGTACTCGCACCGTTGGCGAGGTTATTGATGCTATGAAGGCCGAGATCGCCGGTGGTCAGCCGGCTGCCCCTGTTCAGGTTGCTGCCCCTGCGCC
GGTGGTCGCCCCGGTCCAGGTGTCCACCCCGGTTGACAGCGGCCTCCTTGCCAAGGCCGAGCAGGTTGTGCTGGAGGTCCTCGCCTGCAAGACGGGCTACGAGACTGAGCTTA
TCGAGCTTGACATGGAGCTGGAGACTGAGCTTGGCATCGACTCCATCAAACGCGTCGAGATTCTTTCGGAGGTCCAGGCCCAGCTGTCGGTGGAGGCTAAGGATGTCGATGCC
CTCAGCCGCACGCGCACGGTCGGTGAGGTCATCGATGCTATGAAGGCCGAGATTTCGGGCGGTCAGCCCACCGCCCCCGTGCAGGTCGCCGCGCCCACCCAGGTCGTGGCCCC
GGTCAAGGTTTCCACGCCCGTGGACTCGGGCCTTCTCGCCAAGGCCGAGCAGGTCGTGCTGGAGGTTCTCGCCTCCAAGACGGGTTACGAGACTGAGCTGATTGAGCTTGACA
TGGAGCTGGAGACTGAGCTGGGCATTGACTCCATCAAGCGCGTCGAGATCCTCTCGGAGGTCCAGGCCCAGCTCAACGTCGAGGCCAAGGACGTCGATGCCCTCTCGCGCACC
CGCACCGTCGGCGAGGTCATTGATGCCATGAAGGCCGAGATCGCTGGCGATCAGCCTGCCCCGGCTGTGGTCCCGGTGCAGGCCAAGTCGGGTGTCGCGAACCCCGCCCTCCT
CGCCAAGGCGGAGCAGGTCGTGCTGGAGGTCCTGGCCAGCAAGACGGGCTACGAGACTGAGCTTATCGAGCTTGACATGGAGCTTGAGACTGAGCTTGGTATTGACTCGATT
AAGCGCGTTGAGATCCTTTCCGAGGTCCAGGCCGAGCTGTCCGTGGAGGCCAAGGATGTCGATGCGCTCTCCCGCACCCGCACGGTGGGCGAGGTCATCGACGCTATGAAGGC
CGAGATTGCCGGCTCCGCGGTCACTGTCGCTACCCTTGACGACTCGACCATTATGGAGGAGACTGACGACGAGGACGAGGACTTTATCCTGTACGACCACGTCTACGGCTCCG
AGTGCGAGGATCTCTCGCTCTCGTTCTCGTCGGTCAAGTCGATTCCTCGCGCGGACAAGCTCCTGCTGGACAACATTGCCGAGCGCCCCATTGTCATTGTCGATTGCGGCACGA
AGCTCACGACCGAGCTGGCGAAGGCCATCGGCGAGCGCGCTGTCGTTGCCACGTTCTCGGCCCAGTCGCTCGTGTCCCGTGGCTTCGTGGGCAAGAGCTTCACCCTCGGCAAC
ACCGAGGAGTCGGAGATCGAGAAGATGGTGTCCTCCATCGAGTCGTCCTACGGCAAGATCGGCGGCTTTGTCTACCAGCACTTTCATGACAGCGACTACGGTATGCAGCTCGG
CTGGGCTCTCATGGCCGCGAAGCACCTCAAGGAGTCCCTCAACGACCCGATCAAGAACGGCCGCACCTTTTTCCTGGCTGTCGCCCGCATGAACGGCAAGCTCGGCATGGACA
ACGCCTCCGTCCACGACCAGGGCATCGTCGAGAGCTGCGGTATCGCTGAGCGTGGTGCCATCTTTGGCCTCTGCAAGACCCTGGACCTGGAGTGGCCTAACGTGTTTGCGCGC
GGTGTGGACATCGCGGAGGGCATGTCCTACTCCCTCGCGGCCGAGCTGATCGTCGATGAGATCAGCTGCGCCAACCTTTCGATCCGCGAGAGCGGCTACACTATTAGCGGCGA
GCGCTTCACCACGGAGGCGCACAAGCTCGTCACGGGCAAGCCTCACGCGCCCATCAAGAAGAAGGACGCCTTTCTCGTGTCGGGTGGTGCTCGCGGCATCACGCCCCTGTGCA
TTCGCGAGATTGCCAAGGCCGTCAAGGGTGGCACCTACATTCTCATGGGCCGCTCGGCGCTCGCGGACGAGCCCCTCTGGGCTAACGGCAAGAGCGGCAAGGACCTCGACAA
GGCCGGCCTCGCCTTCCTTAAGGAGGAGTTCGCTGCCGGCCGTGGCTCGAAGCCCACCCCCAAGGTCCACAAGTCGCTCATCGACAAGGTCCTCGGCATCCGCGAGGTTCGCG
CGTCCATCGCCAACATCGAGGCGCACGGCGCTAAGGCCATCTACCTCTCGTGCGATGTGTCGAGCGCCGAGAAGGTCAAGGCCTGCCGTCCAGAAGGTCGAGAAGGAGCATCT
CGTCCGCATCACGGGCATCGTGCACGCCTCCGGCGTCCTGCGCGACAAGCTCGTCGAGAACAAGACCCTCGACGACTTTAACGCGTGTGTACGGCACGAAGGTCACGGGCCTCG
TCAACCTCCTTAGCGCCGTCAACATGAACTTCGTCCGCCACCTGGTGATGTTCTCGTCGCTCGCTGGTTACCACGGCAACGTCGGCCAGTCGGACTACGCTATGGCCAACGAGA
GCCTTAACAAGATCGGCTTCCGTCTTGGTGCCGCGTACTCCCAGCTCTGCGTCAAGTCCATCTGCTTCGGGCCCTTGGGATGGCGGCATGGTGACGCCGGCGCTCAAGAAGCAGT
TCCAGTCCATGGGCGTTCAGATCATCCCTCGCGAGGGTGGCGCCGAGACTGTCGCTCGCATTGTGCTCTCGTCCAACCCCAGCCAGGTCCTCGTCGGCAACTGGGGCGTCCCGC
CCGTCAGCCCCCTCTCCAAGTCGGCCACCATCGTCCAGACCTTTACCCCTGAGCTTAACCCCTTCCTCAAGTCCCACCAGATCCACGGCAAGAACGTCCTGCCCATGACGGTCG
CCATTGGTTACCTCGCCCACCTCGTGAAGAACTTTTACGCCGGCCACCACCTCTGGGGCGTGGAGGACGCGCAGCTCTTCTCCGGCGTCGTCATCGACCACGCCGTGCAGGCCC
AGGTCAAGCTCACTGAGCAGAGCCTGGATGACGATGGCAAGGTCAAGGTCCAGGCGGTGCTCACCGCCTCGAACGACAACGGCAAGATGGTGCCGGCCTACAAGGCCGTCAT
CGTGCTCGGCAAGACTTCCCGTCCGGCCTTCATCCTCAAGGACTTTTCGCTCCAGGAGTCCAACTCGCGCTCGGCCGACGAGCTGTACGACGGCAAGACCCTGTTCCACGGCCC
GCTGTTCCGTGGCATCACCAAGCTCCTCAACGTGTCCGACACTAGCCTCACGACCCAGTGCACCAACATCGATCTCACCGCCACTGAGCGCGGCCAGTTTGCCGACATCGAGC
CGGTCAACCCCTTTCATGGCGGACGCCGCCTTCCAGGCCATGCTCGTCTGGGTCCGCAACCTCCGTAACTCCGCCAGCCTTCCGAACAACTGCGAGCGCGTCGATATCTACAAGC
CCATCGCGCCCGGCGAGAAGTACTACACCACGCTGCAGGCCCTCGGCAACACCTCCGGCTCGGTTCTCAAGTCCGTTTTCTACATGCATGACGAGCAGGGCGAGGTGTTCCTC
TCGGGCCGCGCCAGCGTCGTGGTCAACGATAAGATGGAATTCTAA  (SEQ ID NO: 120)
```

FIG. 15

MEDQRIAIVGLSAILPSGENVRESWEAIRDGLNCLSDLPADRVDVTAYYNPTKGVKDKIYCKRGGFIPEYEFDSREFGLNMLQMEDSDANQTLTLLKVKEALDDANIPAFTNEKKNIG
CVLGIGGGQKASHEFYSRLNYVVVDKVLRKMGLPDEDVETAVEKFKANFPEWRLDSFPGFLGNVTAGRCTNTFNMEGMNCVVDAACASSLIAIKVAIDELLHGDCDAMIAGATCTD
NALGMYMAFSKTPVFSTDQSCLAYDEKTKGMLIGEGSAMFVLKRYADAVRDGDTVHAVIRSCSSSSDGKASGIYTPTISGQEEAILRAYRRAGVSPNTITLVEGHGTGTPVGDKIELT
ALRNVFDKAYGPGHKEEVAVGSIKSQIGHLKAVAGCAGLVKLVMALKHKTLPQSINVENPPNLVDGTVISDTTLYINTMNRPWITKPGVPRRAGISSFGFGGANYHAVLEEFEPEQTK
PYRLNVSAQPMLLIAVNANSLQKLCEDQLKLLKESREKCVNTKNTDYVAFSKFQDSFKLKGSVPSQIIARVGFASKSIEDTISILSAIVNRFQKDITTTSWALPKEGAIFRSTALINDNKS
VAALFSGQGAQYTHMFNDVAMQWPQFRLCVNDMEKAQEEVINDKSVKRISQVMFPRKPYARESPLDNKEISKTEYSQTTTVASSVGLFEIFRDAGFAPAFVAGHSLGEFSALYAAGL
IDREDLFKLVCNRAMAMRDAPKKSADGAMAAVIGPNASSIKLSAPEVWVANNNSPSQTVITGANSGVQAETSKLKTQGFRVVHLACDGAFHSPHMENAEKQFQKALSAVKFNKPTG
SSPKIFSNVTGGVFTDPKTALSRIIMTSSVQFLTQIKNMYAAGARVFIEFGPKQVLSKLVNEIFPGDTSVLTVSVNPASAKDSDIQLRQAAVQMAVAGVALTDFDKWELKDPTRMKEFP
RKKTTLTLSAATYVSKKTLQERERIMNDGRTVSCVQRIENTNTGELEKLKKQLQDKENEVVRVQALATQASADLQNTKAELQKAQATKSSNAASDAVVAKHKAILLAMLEELETGK
AVDYSSFSKGQVASPATVRVVSAPVQAAAPVQVSASVDSGLLAKAEQVVLEVLASKTGYETELIELDMELETELGIDSIKRVEILSEVQAQLNVEAKDVDALSRTRTVGEVIDAMKAE
IAGGQPAAPVQVAAPTQVVAPVQASAPVDSGLLAKAEQVVLEVLASKTGYETELIELDMELETELGIDSIKRVEILSEVQAQLSVEAKDVDALSRTRTVGEVIDAMKAEIAGGQPAAP
VQVAAPTQVVAPVQASAPVDSGLLAKAEQVVLEVLASKTGYETELIELDMELETELGIDSIKRVEILSEVQAQLSVEAKDVDALSRTRTVGEVIDAMKAEISGGQPAAPVQVAAPTQI
VAPVQVSAPVDSGLLAKAEQVVLEVLASKTGYETELIELDMELETELGIDSIKRVEILSEVQAQLSVEAKDVDALSRTRTVGEVIDAMKAEISGGQPTAPVQVAAPTQIVAPVQVSAPV
DSGLLAKAEQVVLEVLASKTGYETELIELDMELETELGIDSIKRVEILSEVQAQLSVEAKDVDALSRTRTVGEVIDAMKAEISGGQPAAPVQVAAPTQIVAPVQASAPVDSGLLAKAEQ
VVLEVLASKTGYETELIELDMELETELGIDSIKRVEILSEVQAQLSVEAKDVDALSRTRTVGEVIDAMKAEISGGQPAAPVQVAAPTQIVAPVQVSAPVDSGLLAKAEQVVLEVLASKT
GYETELIELDMELETELGIDSIKRVEILSEVQAQLNVEAKDVDALSRTRTVGEVIDAMKAEIAGGQPAAPVQVAAPAPVVAPVQVSTPVDSGLLAKAEQVVLEVLACKTGYETELIELD
MELETELGIDSIKRVEILSEVQAQLSVEAKDVDALSRTRTVGEVIDAMKAEISGGQPTAPVQVAAPTQVVAPVKVSTPVDSGLLAKAEQVVLEVLASKTGYETELIELDMELETELGID
SIKRVEILSEVQAQLNVEAKDVDALSRTRTVGEVIDAMKAEIAGDQPAPAVVPVQAKSGVANPALLAKAEQVVLEVLASKTGYETELIELDMELETELGIDSIKRVEILSEVQAELSVE
AKDVDALSRTRTVGEVIDAMKAEIAGSAVTVATLDDSTIMEETDDEDEDFILYDHVYGSECEDLSLSFSSVKSIPRADKLLLDNIAERPIVIVDCGTKLTTELAKAIGERAVVATFSAQS
LVSRGFVGKSFTLGNTEESEIEKMVSSIESSYGKIGGFVYQHFHDSDYGMQLGWALMAAKHLKESLNDPIKNGRTFFLAVARMNGKLGMDNASVHDQGIVESCGIAERGAIFGLCKT
LDLEWPNVFARGVDIAEGMSYSLAAELIVDEISCANLSIRESGYTISGERFTTEAHKLVTGKPHAPIKKKDAFLVSGGARGITPLCIREIAKAVKGGTYILMGRSALADEPLWANGKSGK
DLDKAGLAFLKEEFAAGRGSKPTPKVHKSLIDKVLGIREVRASIANIEAHGAKAIYLSCDVSSAEKVKAAVQKVEKEHLVRITGIVHASGVLRDKLVENKTLDDFNAVYGTKVTGLVN
LLSAVNMNFVRHLVMFSSLAGYHGNVGQSDYAMANESLNKIGFRLGAAYSQLCVKSICFGPWDGGMVTPALKKQFQSMGVQIIPREGGAETVARIVLSSNPSQVLVGNWGVPPVSP
LSKSATIVQTFTPELNPFLKSHQIHGKNVLPMTVAIGYLAHLVKNFYAGHHLWGVEDAQLFSGVVIDHAVQAQVKLTEQSLDDDGKVKVQAVLTASNDNGKMVPAYKAVTVLGKTS
RPAFILKDFSLQESNSRSADELYDGKTLFHGPLFRGITKLLNVSDTSLTTQCTNIDLTATERGQFADIEPVNPFMADAAFQAMLVWVRNLRNSASLPNNCERVDIYKPIAPGEKYYTTLQ
ALGNTSGSVLKSVFYMHDFQGFVFLSGRASVVVNDKMEF (SEQ ID NO:69)

FIG. 16

ATGGTGAAATTAAGTGTTGGTGATAATATTTGTCATGATCAACGTGTTGCTGTTGTTGGTATGGCTGTTATGTATGCTGGTTGTCAAAATCAACATGAATTTTGGCAATCTTTAC
AAGGTAAAAATATGAATTCAAAATCGATTTCACAAAATCGTTTAGGTTCTGAGTATAGAGAAGAACATTTTAAACCTGAAAGAAGTAAATATTCCGATACCTTTTGTAATGAA
AGATATGGTTGTATTGATGAGAATGTTCAAAGTGAACATGAACTTTTATTAAAACTTGCAAAAGATGCTATTGCGGATACAAAAGGTTCTATTGATTTGAATAAAACCGGAAT
CGTTAGTGGTTGCTTATCTTTTCCAATGGATAATTTACAAGGTGATTTATTAAATTTGTATCAATGTCACATTGAAAAGAAAATTGGGCCAAATGCATTAAAAGATGTGAATTT
ATGGTCTAAAAGAACCACCAACGGAAAAGATGATAAAAAAGCTTATTTTGATCCTGCCTCTTTCGTAGCTGAACAATTAGATATGGGACCATTACATTATAGTTTAGATGCTG
CTTGTGCGTCTGCACTTTATGTATTAAGACTTGCTCAAGATCATTTATTAAGTGGTGCTGCTGATACAATGTTATGTGGTGCATCTTGTTTACCTGAACCTTTTTTTATTTTATCT
GGTTTTTCTACTTTTCATGCAATGCCATTATCTGGTGATGTTTCTGCTCCTTTGCATAAAACTTCACAAGGTCTTACACCTGGTGAAGGTGGTGCTATTATGGTACTTAAACGAT
TAAATGATGCAATCCGTGATGGTGATAGAATTTATGGTACTTTACTTGGTGCTGAATTAAGTAATGCTGGTTGTGGTTTACCATTGAGTCCACATATGCCAAGTGAATTTGATT
GTATGGAAAAAGCTTTACAAAGAGTACACAGATTACCATCATCTATTCAATATGTTGAGTGTCATGCAACTGGTACACCACAAGGTGATAAAGTTGAAATTGATGCTATGACA
AAATGTTTTGGTGAACATTTACCAAGGTTTGGTTCAACGAAAGGGAATTTTGGTCATACACTTGTTGCTGCTGGTTTTTGCTGGTATGTGTAAAGTTTTATTATCAATGCAATATG
GTGAAATACCACCAACTCCAGGTCTTGAAAATCCAGACAATATTATGCATGATTTAGTTGTTACTGAAACAATTCCATGGCCTAATACAAATGGTGATTTGAAACGTGCATGTT
TATCTGCTTTTGGATTCGGTGGTACTAATGCACATGCTGTATTTGAAGAGTATCGTTCAGATTTACAAGCAAATAAAACTCTTGAAAATGAAAGTAAAAGTCATGAAATCTTTT
CTTCATTTAAAATTGCTATTGTTGGTATGGAATCTGAATTTGGTACTTTGAAAGGATTACAAGAATTTGAACGTGCTATTTACAATGGTGGTCATGGTGCATGTGATTTACCTGA
AAATAGATGGAGATTTCTTGGAGAAGATAAAGAATTTTTACAAGCTTGTGGTTTACAAAAATTACCAAGAGGTTGTTATATTAAAGAAGTGGAAACTGATTTTAAAAGGTTAC
GTTTACCAATGATACAGGAGGATATTCTAAGACCTTTACAGTTGTTAGCTGTTTCGATTATCGACAGAGCACTTAACGCATCTGGTGTTAAACCAAATGGCAAAGTTGCAGTTT
TAGTTGGATTAGGTACTGATCTTGAATTATATCGTCATCGTGCTCGTGTTGCATTAAAGGAACGCCTCCAAACTGCGGTCAAAGAAGATATTCCTTTACTTGAAAAGTTAATGA
ACTATGTCAATGATAGAGGTACAAGTACATCATATACATCTTATATTGGAAATTTGGTTGCAACTCGAGTTTCATCATTATGGGGTTTTACTGGTCCATCATTCACGATTACTGA
AGGTGAAAATTCCGTATATCGTTGTCTTGATTTGGGAAGATGGTTCTTAGCTAATGGTGAAGTAGATGCTGTTGTTGTTGCCGGGGTTGATTTATGTGGTAGTGCTGAAAATCT
TTTTGTAAAATCTCGTAGAAGTAAAGTTTCCACACAAAATGAACCATTTGCAAATTTTGAATCAAATGCTGATGGATATTTTGCTGGAGATGGTTGTGGAGCTTTGGTTTTGAA
ACGATTGAGTGATTGTACGGATTCAACTGAAAAAATTTATGCAACGGTGGATTCAATTGCTGTTGGTGATGAAGTTGGCCCAACTATTAAACAAGCTTTGAAGAATGCATCCA
TAGCAGCGAAAGATATTGAACTGGCAGAGCTATCAGCCAAGTTCAGGCAAACATCATTCTGGTAGAATCACTTGTGAAGATGAACTAAATGAACTGGGTGAAATTTCAATGA
AGGTATACAAAGAGTTGCAATTGGTAGTGTGAAAGCTAATGTTGGAGATGTGGATATGCATCTGGTGCAGCAAGTTTAATCAAAACGGCTTTGTGCCTGTACAACCGATATT
TACCAAAGTTACCAAATTGGAATAAGCCAACGAAAGATGTTGAATGGTCCAAATCATTTTTTGTATGTGAACATTCTAGAGCATGGTTGAAAAATGTTGATGAAAATAGACAT
GCTGTCGTTTCTGGAGTTTGCGAAAATGGTTCGTGTTATGGAATCGTAATGTCTGATGTACAAGGACATCATGAAGAATCGAATCTTGTTAGTTTAGACAAAAATGAACCAAA
AGTACTGGGTATTTACGGAGATTCAGTTGATGATATCCTAGTTCAGCTCAACAAATATCTTGAAAAATTCCTTCAAGAAACTGGAACGGCTGCGGCTGCACAAAAAGTTAAAT
CACCTACAATAGATATTGACTCCAATGTGTTTGCTGAGATGCTTAATCTACCGCAGGATAAAAACAAAAAATTTGCGGTCGCATTGGTTACCACACCAAATAAACTCCAGCGT
GAAAATAGAACTTGCTGTGAAGGGTATTCCACGTTGCGTAAAAGCAAAAAGAGATTGGTGTTCTCCATCTGGAAGTATTTTTGCTTGTAATCCACTCAAAAGTGATAATATTGCA
TTTATGTATGGTGAAGGCCGAAGCCCATATGCTGGACTGGGATATGATTTGCATCGAATTTGGCCTATGCTACACGAGTTGGTTAACAATAGAACTACAGAACTTTGGGATCA
AGGTGATAGTTGGTATTTACCTCGATCTAGCTCTGTTGCTGAAAAAGAAAAAGTCTTCGGAGATTTTGATAAGAATCAAATTGAAATGTTTAGATTGGGTATTTTTGTATCAAT
GTGTTTCACTGATATGGCCACTGAACTTTTGGGTTTAAAACCCAAAGCCGCGTTTGGTTTAAGTTTGGGTGAAATATCTATGCTTTTTGCATTTTCTAAAAAGAATACCAAGTTG
TCCAAAGAATTGACCCGTCGTCTAAAAGAAGCAAAAGTTTGGGCATCACAATTAGCTGTTGAATTTGCAGCTATTCGAGATTTGTGGAATATTCCAGCTGATAAATCTATTGAT
GAATTTTGGCAAGGGTATTTTGTTTACGCAAATCGAACCCTGGTCGAGAACACAATTGGGGAGAATAAATTTGTTCGTTTGTTGATTGTAAATGATTCGCAAAGTTGTCTAATT
GCCGGGAAACCAGATGAATGTCAAAAAGTTATTGAGAAGCTTCATTTGAAGCTACCGGCGGTTCCAGTAACTCAGGGTATGATCGGTCATTGCCCAGAAGCAATTCCTTATCT
AGATCAAATCAGTCATATTCATGAAATGCTTGAAATTCCAAAACCCGAAAATGTGAAATTGTTTACAACTAGTGAAAACAGAGAATTAGTGTCGATGAAAGATTCCGTGTCAA
AATTGGTTGCTGAGATTTATCAGCATGTTGCTGATTTTCCAAACATCGTGAACAAGGTTAAAGAAACTTGCAAAACTGATATATTTATTGAATTGGGATCGAACAATTATCGAT
CTGGAGCTGTCAAAACAATTTTAGGTCCAGAAATCGTTTCTGTTGCAATTGATAGGCAAAATGAAACTGCATGGGGTCAACTAATGAAGATGGTTGCATCGTTGATAAGTCAT
CGAGTTCCGGGTGTTGAATTGAAAAAACTCTATCATCCTGAATTGCTGAAATTTGATCCACAGGCAAAACCGAATCGTTTCATCAGAAATATAGAACTGAATGGATTTTTTGAT
CGTACGAATATTATTGTTGATAAGCAACTATCCCCTGCCGGATCCGAAACTCGCTGAAATTGTGAACAATCGAAATATGCCTAAAGATAATGTTTATGTACCAATTGAACGGGT
GAAAACGATGATAAAGGCGGAACCAGCTAATTTACAAGTCAGCGTGGGAAGTAAACCAGTTGTTACTGAAAGAATTAGTTCGGACGATAATCTATTTGAAAAGTTGTCAGAA
ATTACAAAATCTTTTGATGGTGTAAATGCGTGTACTGAAGCAATGTTGGGAGACTCTGGATTTCTCAAAACATATGAGGTTGACTATCCTTTGTACACAGGTGCCATGGCTAAA
GGAATTGCGTCTGCTGATTTGGTTATTGCTGCTGGTAAATCAAAGATCTTGGCATCATTTGGAGCTGGTGGGTTGGCCTTACAAGTGGTAGAAGATGCCATTAAACAAATTAAA
GCTGAATTGGGGAACGGTCCGTTTGCTGTAAATTTGATTCATTCACCATTCGATCCTAGCTTGGGAGAAGGGTAACGTTGATCTTTTTCTAAAATATAACGTTCGATTTGTTGAAG

FIG. 16 (cont'd)

TATCCGCATTTATGTCATTAACCCCTCAGGTTGTACGATACAGAGCCGCTGGTTTGGCCAAAGCAAGAGATGGATCTGTGAAAATTCAAAATCGTATTATTGCCAAAATTTCAA
GAACAGAGTTAGCGGAACTGTTCTTGAAACCAGCACCCAAAAATATTTTAGATGCATTGGTTGCGGATGGATCTATTAGTCAAGAACAAGCCCAACTTGCATTACTTGTGCCA
ATGGCTGATGATATTACTGTGGAAGCTGATTCTGGTGGGCATACTGACAATCGACCAATTCATGTTTTGTTACCTTTGATAATTCAGCAAAGAAATAGAATTTGTAAACAATAC
CCAAAACATTTAAAAGTTCGAATCGGAGCAGCTGGTGGTATTGGATGCCCGAAGGCAGCATTTGCTGCGTTTGAGATGGGTGCTGCATACATTGCAACTGGAACGGTAAATCA
ACTTTCAAAGGAAGCAGGTACTTGTGACTATGTACGTAAAGTATTGAATAAAGCTACATATTCGGATGTTACCATGGCTCCAGCCGCAGATATGTTCGATCATGGTGTTGAATT
ACAAGTTTTGAAGAAAGGTACTATGTTTCCTTCACGTGCTAAAAAACTATACGATTTGTTCAAAAAATACAAATCGATTGAGGAATTACCAGCAGATGAGGTGAAAAAACTTG
AGCAAAAAGTTTTCAAAAAGTCGTTTGATGAAGTATGGGATGAGACCAAGAATTACTATATTAATCGTTTACATTCTCCCGAAAAAATTGAACGTGCTGAAAGAGATGCAAAA
CTTAAAATGTCGTTATGTTTTCGTTGGTATTTGTCGAAGTCTTCCAGATGGGCTAATACCGGTGAATCTGGAAGAGTGCAGGATTATCAAATTTGGTGTGGTCCAGCAATTGGG
TCATATAATGATTTTGCGAAAGGATCACCATGTTTGGATCCTGAGATTTTGGGTAGTTTTCCAAGTGTTGTTCAGATTAATAAACATATTTTACGTGGTGCTTGTTTCTATCAAA
GACTCTCTCAGTTGAAATATCTGAATTTTAACTATGAGGAATTAGATACGTTAACATACTCTGCATCGAATTTTATTTAA (SEQ ID NO:70)

FIG. 17

ATGGTGAAGCTTTCCGTTGGTGACAACATTTGCCACGATCAGCGCGTCGCCGTGGTCGGCATGGCCGTCATGTACGCCGGCTGCCAGAACCAGCACGAGTTTTGGCAGAGCCT
CCAGGGTAAGAACATGAACAGCAAGAGCATCAGCCAGAACCGCCTGGGCTCCGAGTACCGCGAGGAGCACTTTAAGCCGGAGCGCTCGAAGTACAGCGACACCTTCTGCAAC
GAGCGTTACGGCTGCATCGACGAGAACGTCCAGAGCGAGCATGAGCTCCTCCTGAAGCTCGCTAAGGACGCGATCGCCGATACCAAGGGCAGCATCGACCTTAACAAGACCG
GCATTGTCTCCGGCTGCCTCTCGTTCCCTATGGATAACCTCCAGGGCGACCTTCTCAACCTCTACCAGTGCCATATTGAGAAGAAGATCGGCCCGAACGCCCTCAAGGATGTCA
ACCTCTGGTCGAAGCGCACGACCAACGGTAAGGACGATAAGAAGGCCTACTTCGATCCCGCCAGCTTCGTCGCTGAGCAGCTTGACATGGGTCCCCTCCACTACTCGCTCGAC
GCTGCCTGCGCCTCCGCTCTCTACGTCCTCCGCCTCGCCCAGGACCACCTCCTCAGCGGTGCCGCCGACACCATGCTCTGCGGCGCCTCGTGCCTCCCGGAGCCCTTTTTCATCC
TTTCGGGCTTTTCGACCTTCCACGCCATGCCCCTTTCGGGTGACGTGTCGGCCCCTCTTCACAAGACGAGCCAGGGCCTCACTCCGGGCGAGGGCGGTGCTATCATGGTCCTGA
AGCGCCTCAACGATGCCATTCGCGACGGCGACCGCATCTACGGCACGCTCCTGGGCGCCGAGCTTTCCAACGCGGGTTGCGGCCTCCCGCTCTCCCCGCACATGCCGTCCGAG
TTCGACTGCATGGAGAAGGCCCTCCAGCGCGTTCACCGCCTCCCGTCCTCCATCCAGTACGTGGAGTGCCACGCCACTGGCACCCCGCAGGGCGACAAGGTCGAGATCGACGC
CATGACGAAGTGCTTCGGCGAGCATCTGCCTCGCTTCGGCTCCACCAAGGGTAACTTCGGCCACACCCTCGTGGCTGCTGGCTTTGCGGGCATGTGCAAGGTCCTCCTCTCGAT
GCAGTACGGTGAGATTCCTCCTACGCCTGGCCTGGAGAACCCCGACAACATTATGCACGATCTTGTCGTTACCGAGACTATTCCCTGGCCGAACACCAACGGCGATCTTAAGC
GTGCCGTGCCTCAGCGCCTTTGGCTTTGGCGGTACTAACGCCCACGCCGTGTTCGAGGAGTACCGCAGCGACCTTCAGGCCAACAAGACCCTTGAGAACGAGAGCAAGTCCCAC
GAGATCTTTTCCTCCTTTAAGATTGCCATTGTTGGCATGGAGTCCGAGTTTGGCACTCTCAAGGGCCTCCAGGAGTTCGAGCGTGCCATCTACAACGGCGGCCACGGCGCGTGC
GACCTTCCGGAGAACCGCTGGCGCTTTCTCGGTGAGGACAAGGAGTTTCTCCAGGCCTGCGGCCTCCAGAAGCTCCCGCGTGGCTGCTACATCAAGGAGGTCGAGACTGACTT
TAAGCGCCTTCGCCTCCCCATGATCCAGGAGGACATCCTCCGCCCCCTCCAGCTCCTCGCCGTGTCGATCATCGACCGCGCCCTCAACGCCAGCGGCGTTAAGCCCAACGGCA
AGGTCGCCGTCCTCGTGGGCCTCGGCACCGATCTTGAGCTCTACCGCCACCGCGCTCGCGTCGCCCTGAAGGAGCGCCTTCAGACCGCCGTCAAGGAGGACATCCCCCTGCTG
GAGAAGCTCATGAACTACGTGAACGACCGCGGCACCTCCACGTCCTACACCTCGTACATCGGCAACCTCGTTGCGACCCGCGTCAGCTCGCTCTGGGGCTTCACCGGCCCTAG
CTTCACGATCACGGAGGGCGAGAACTCGGTTTACCGTTGCCTCGACCTCGGCCGCTGGTTCCTCGCCAACGGTGAGGTCGATGCCGTGGTTGTCGCTGGCGTGGATCTCTGCGG
CTCGGCCGAGAACCTGTTCGTCAAGTCGCGCCGCTCCAAGGTGTCCACCCAGAACGAGCCCTTTGCTAACTTTGAGTCGAACGCCGACGGCTACTTCGCCGGCGACGGCTGCG
GTGCCCTCGTTCTCAAGCGCCTTTCGGACTGCACTGACTCCACCGAGAAGATCTACGCGACCGTGGACAGCATTGCTGTCGGCGACGAGGTGGGCCCGACTATTAAGCAGGCC
CTGAAGAACGCCTCGATCGCCGCGAAGGACATCGAGCTCGCGGAGCTCTCCGCCTCCAGCGGCAAGCACCACTCCGGCCGCATCACCTGCGAGGACGAGCTTAACGAGCTCG
GCGAGATCTTCAACGAGGGCATTCAGCGCGTGGCCATCGGCAGCGTCAAGGCCAACGTCGGCGACGTCGGCTACGCCTCCGGTGCTGCCAGCCTCATCAAGACGGCCCTCTGC
CTCTACAACCGCTACCTCCCCAAGCTCCCCAACTGGAACAAGCCGACCAAGGACGTCGAGTGGTCGAAGAGCTTCTTTGTCTGCGAGCACTCGCGCGCCTGGCTCAAGAACGT
GGACGAGAACCGCCACGCGGTCGTGAGCGGCGTCTGCGAGAACGGCTCCTGCTACGGCATCGTCATGAGCGACGTCCAGGGCCCACCATGAGGAGTCGAACCTCGTGTCCCTC
GATAAGAACGAGCCCAAGGTGCTCGGTATCTACGGCGATTCCGTGGACGATATTCTGGTCCAGCTGAACAAGTACCTGGAGAAGTTCCTTCAGGAGACTGGCACTGCTGCGGC
TGCGCAGAAGGTGAAGAGCCCTACCATTGACATCGACTCGAACGTCTTTGCCGAGATGCTGAACCTTCCCCAGGACAAGAACAAGAAGTTTGCCGTCGCTCTGGTCACGACCC
CCAACAAGCTCCAGCGCGAGATTGAGCTCGCCGTTAAGGGCATCCCTCGCTGCGTGAAGGCCAAGCGCGACTGGTGCTCCCCCTCCGGCAGCATCTTTGCGTGCAACCCGCTC
AAGTCGGACAACATTGCCTTTATGTACGGCGAGGGCCGCTCGCCTTACGCCGGCCTCGGCTACGATCTCCACCGCATCTGGCCCATGCTTCACGAGCTCGTGAACAACCGCAC
GACTGAGCTGTGGGACCAGGGTGACTCGTGGTACCTGCCGCGCAGCTCCTCCGTGGCCGAGAAGGAGAAGGTCTTTGGCGACTTCGACAAGAACCAGATCGAGATGTTCCGC
CTCGGTATTTTCGTCAGCATGTGCTTTACCGACATGGCGACGGAGCTCCTCGGCCTTAAGCCGAAGGCCGCTTTCGGCCTCTCCCTCGGCGAGATCAGCATGCTCTTTGCTTTCT
CGAAGAAGAACACCAAGCTCTCCAAGGGAGCTTACTCGCCGCCTCAAGGAGGCCAAGGTGTGGGCGTCGCAGCTGGCCGTCGAGTTCGCCGCCATCCGCGACCTTTGGAACAT
CCCGGCCGACAAGTCCATCGATGAGTTCTGGCAGGGTTACTTCGTTTACGCCAACCGTACGCTCGTGGAGAACACCATTGGCGAGAACAAGTTCGTCCGCCTCCTTATCGTCAA
CGACTCCCAGTCCTGCCTCATTGCCGGTAAGCCCGATGAGTGCCAGAAGGTCATCGAGAAGCTCCACCTTAAGCTCCCCGCCGTCCCCGTCACCCAGGGCATGATTGGCCACT
GCCCGGAGGCCATTCCCTACCTCGACCAGATCAGCCACATCCACGAGATGCTTGAGATCCCGAAGCCTGAGAACGTCAAGCTCTTCACGACGTCCGAGAACCGCGAGCTTGTC
TCGATGAAGGACTCCGTTAGCAAGCTCGTCGCGGAGATCTACCAGCACGTCGCTGACTTCCCCAACATTGTCAACAAGGTCAAGGAGACTTGCAAGACGGACATTTTCATCGA
GCTGGGCAGCAACAACTACCGTTCCGGTGCCGTCAAGACTATCCTCGGTCCGGAGATCGTGAGCGTTGCCATCGACCGTCAGAACGAGACTGCCTGGGGCCAGCTCATGAAGA
TGGTCGCCAGCCTGATCTCCCACCGCGTCCCCGGCGTCGAGCTCAAGAAGCTGTACCATCCGGAGCTCCTGAAGTTCGATCCCCAGGCCAAGCCCAACCGCTTTATCCGCAAC
ATCGAGCTCAACGGCTTTTTCGACCGCACGAACATCATCGTCGATAAGCAGCTTTCCCCTGCGGACCCGAAGCTCGCCGAGATCGTCAACAACCGCAACATGCCGAAGGATAA
CGTGTACGTCCCCATTGAGCGCGTCAAGACGATGATCAAGGCCGAGCCCGCTAACCTCCAGGTGTCCGTCGGCTCGAAGCCCGTGGTCACCGAGCGTATCTCGTCGGACGACA
ACCTCTTTGAGAAGCTCTCGGAGATCACTAAGTCCTTCGACGGTGTCAACGCCTGCACCGAGGCCATGCTCGGCGATTCGGGCTTTCTCAAGACGTACGAGGTTGACTACCCGC
TCTACACCGGCGCTATGGCCAAGGGTATCGCCTCCGCCGACCTCGTCATTGCGGCGGGTAAGTCGAAGATCCTTGCGTCCTTTGGTGCTGGCGGCCTCGCTCTCCAGGTGGTCG

FIG. 17 (cont'd)

AGGATGCCATTAAGCAGATCAAGGCTGAGCTTGGCAACGGTCCCTTTGCCGTCAACCTCATCCACTCGCCTTTCGACCCCTCGCTTGAGAAGGGCAACGTTGACCTTTTCCTCA
AGTACAACGTCCGCTTTGTCGAGGTGAGCGCGTTCATGAGCCTCACCCCCCAGGTCGTTCGCTACCGCGCTGCCGGCCTTGCCAAGGCCCGTGACGGCTCGGTCAAGATTCAG
AACCGCATCATCGCCAAGATTTCGCGCACGGAGCTGGCCGAGCTCTTCCTCAAGCCCGCTCCGAAGAACATCCTCGATGCCCTCGTTGCCGACGGCTCGATTTCCCAGGAGCA
GGCTCAGCTCGCGCTCCTCGTCCCTATGGCCGATGACATCACCGTTGAGGCCGACTCCGGTGGCCACACCGACAACCGCCCCATTCATGTGCTCCTCCCCCTCATCATCCAGCA
GCGCAACCGCATTTGCAAGCAGTACCCGAAGCACCTCAAGGTCCGCATCGGCGCTGCCGGTGGCATCGGTTGCCCTAAGGCGGCTTTTGCCGCCTTTGAGATGGGTGCGGCCT
ACATCGCCACGGGCACCGTTAACCAGCTCTCGAAGGAGGCCGGCACCTGCGACTACGTGCGCAAGGTGCTCAACAAGGCCACCTACTCCGACGTCACGATGGCTCCCGCTGCC
GACATGTTCGACCACGGTGTCGAGCTCCAGGTTCTCAAGAAGGGCACCATGTTTCCGTCGCGCGCCAAGAAGCTCTACGACCTCTTTAAGAAGTACAAGTCGATCGAGGAGCT
CCCTGCCGACGAGGTCAAGAAGCTGGAGCAGAAGGTTTTTAAGAAGTCGTTCGACGAGGTCTGGGACGAGACTAAGAACTACTACATTAACCGCCTCCACTCCCCTGAGAAG
ATCGAGCGCGCGGAGCGTGACGCCAAGCTGAAGATGTCGCTCTGCTTTCGTTGGTACCTGAGCAAGTCGTCCCGCTGGGCCAACACCGGCGAGTCGGGCCGTGTCCAGGACTA
CCAGATCTGGTGCGGCCCCGCCATCGGCTCGTACAACGACTTCGCGAAGGGCTCGCCCTGCCTTGACCCTGAGATCCTTGGCTCGTTCCCGTCGGTTGTCCAGATCAACAAGCA
TATTCTGCGCGGCGCTTGCTTCTACCAGCGTCTTTCGCAGCTCAAGTACCTTAACTTCAACTACGAGGAGCTCGATACGCTCACCTACAGCGCTAGCAACTTTATCTAA (SEQ ID NO: 121)

FIG. 18

MVKLSVGDNICHDQRVAVVGMAVMYAGCQNQHEFWQSLQGKNMNSKSISQNRLGSEYREEHFKPERSKYSDTFCNERYGCIDENVQSEHELLLKLAKDAIADTKGSIDLNKTGIVS
GCLSFPMDNLQGDLLNLYQCHIEKKIGPNALKDVNLWSKRTTNGKDDKKAYFDPASFVAEQLDMGPLIIYSLDAACASALYVLRLAQDIILLSGAADTMLCGASCLPEPFFILSGFSTF
HAMPLSGDVSAPLHKTSQGLTPGEGGAIMVLKRLNDAIRDGDRIYGTLLGAFLSNAGCGLPLSPHMPSFFDCMFKALQRVHRLPSSIQYVFCHATGTPQGDKVEIDAMTKCFGFHLPR
FGSTKGNFGHTLVAAGFAGMCKVLLSMQYGFIPPTPGLFNPDNIMHDLVVTETIPWPNTNGDLKRACLSAFGFGGTNAHAVFFEYRSDLQANKTLENFSKSHFIFSSFKIAIVGMFSFF
GTLKGLQEFFERAIYNGGHGACDLPENRWRFLGEDKEFLQACGLQKLPRGCYIKEVETDFKRLRLPMIQEDILRPLQLLAVSIIDRALNASGVKPNGKVAVLVGLGTDLELYRHRARVA
LKERLQTAVKEDIPLLEKLMNYVNDRGTSTSYTSYIGNLVATRVSSLWGFTGPSFTITEGENSVYRCLDLGRWFLANGEVDAVVVAGVDLCGSAENLFVKSRRSKVSTQNEPFANFES
NADGYFAGDGCGALVLKRLSDCTDSTEKIYATVDSIAVGDEVGPTIKQALKNASIAAKDIELAELSASSGKHHSGRITCEDELNELGEIFNEGIQRVAIGSVKANVGDVGYASGAASLI
KTALCLYNRYLPKLPNWNKPTKDVEWSKSFFVCEHSRAWLKNVDENRHAVVSGVCENGSCYGIVMSDVQGHHEEESNLVSLDKNEPKVLGIYGDSVDDILVQLNKYLEKFLQETGT
AAAAQKVKSPTIDIDSNVFAEMLNLPQDKNKKFAVALVTTPNKLQRFIELAVKGIPRCVKAKRDWCSPSGSIFACNPLKSDNIAFMYGEGRSPYAGLGYDLHRIWPMLHELVNNRTTE
LWDQGDSWYLPRSSSVAEKEKVFGDFDKNQIEMFRLGIFVSMCFTDMATELLGLKPKAAFGLSLGEISMLFAFSKKKNTKLSKELTRRLKEAKVWASQLAVEFAAIRDLWNIPADKSID
EFWQGYFVYANRTLVENTIGENKFVRLLIVNDSQSCLIAGKPDECQKVIEKLIILKLPAVPVTQGMIGIICPEAIPYLDQISIIIIEMLEIPKPENVKLFTTSENRELVSMKDSVSKLVAEIY
QHVADFPNIVNKVKETCKTDIFIELGSNNYRSGAVKTILGPEIVSVAIDRQNETAWGQLMKMVASLISHRVPGVELKKLYHPELLKFDPQAKPNRFIRNIELNGFFDRTNIIVDKQLSPA
DPKLAEIVNNRNMPKDNVYVPIERVKTMIKAEPANLQVSVGSKPVVTERISSDDNLFEKLSEITKSFDGVNACTEAMLGDSGFLKTYEVDYPLYTGAMAKGIASADLVIAAGKSKILA
SFGAGGLALQVVEDAIKQIKAELGNGPFAVNLIHSPFDPSLEKGNVDLFLKYNVRFVEVSAFMSLTPQVVRYRAAGLAKARDGSVKIQNRIIAKISRTELAELFLKPAPKNILDALVAD
GSISQEQAQLALLVPMADDITVEADSGGHTDNRPIHVLLPLIIQQRNRICKQYPKHLKVRIGAAGGIGCPKAAFAAFEMGAAYIATGTVNQLSKEAGTCDYVRKVLNKATYSDVTMAP
AADMFDHGVELQVLKKGTMFPSRAKKLYDLFKKYKSIEELPADEVKKLEQKVFKKSFDEVWDETKNYYINRLHSPEKIERAERDAKLKMSLCFRWYLSKSSRWANTGESGRVQDY
QIWCGPAIGSYNDFAKGSPCLDPEILGSFPSVVQINKHILRGACFYQRLSQLKYLNFNYEELDTLTYSASNFI (SEQ ID NO:71)

FIG. 19

ATGGTTGGTTTACAAATGAAAAAGAAACCAGTATGGGAGATGAGTAAGGAAGAACAAAGTTCTGGAAAGAATGTTGTATTTGACTATGATGAATTGTTGGAATTTGCTGAAG
GTGATATTGGTAAAGTCTTTGGACCTAAGTTTGATATTATCGATAAGTATAGTCGACGTGTACGTTTACCTGCGAGAGAATATCTTCTAGTTACCAGAGTTACTTTGATGGATG
CTGAAGTTGGGAATTTCAGAGTTGGATCTAGAATGGTTACTGAATATGATGTTCCAGTAAATGGTGAACTTTCACAAGGTGGTGATGTTCCATGGGCTGTTCTTGTTGAATCTG
GACAATGTGATCTTATGTTAATATCTTATATGGGTATTGATTTTCAATGTAAAGGTGATCGTGTCTATCGATTATTAAATACTACGTTGACGTTTTACGGTGTTGCTCATGAGGG
TGAAACACTAGTATACGATATTCGTGTAACTGGATTTGCAAAAGGTATGCACGGTGAAATCTCCATGTTTTTTTTTGAAATATGATTGTTATGTGAATGGACGATTATTAATCGA
AATGAGAGATGGTTGTGCGGGATTTTTTACTGATGAAGAACTTGCAGCAGGTAAAGGAGTTATTAAAACTGTTGCTGAACTTCATAAAAGAAAATCTATTGTTCCAAAATCCA
TTAAACCTTTTGCTCTAAATCCAGCAGTACACAAAACAATGTTTTCTGAAAATGATATGGAAAAATTGTGTGAGCGTCAATGGGAAAATGTATTGGGTAGTGGACTTCAAGGT
ATTGACTACAAGTTATGTGCACGGAAAATGCTTATGATTGATCGTATTACTAAAATACAACATAATGGTGGTGCATATGGTCTTGGATTATTGGTTGGCGAAAAAATTCTTGAA
CGTGATCATTGGTATTTTCCATGCCATTTTGTAAAGGATCAAGTTATGGCTGGCTCACTTGTTAGTGATGGTTGCAGTCAGCTACTAAAACTTTATATGTTATGGTTGGGTTTAC
ATGATGTGGTTCCAGATTTTCAATTTCGTCCAGTTCCTGGACAACCAAATAAAGTTCGTTGCCGTGGACAAATTAGTCCACATCGTGGTAAACTTGTTTATGTTATGGAAATAA
GAGAAATGGGATTCAATGAATCAACTGGACAACCATATGCTATTGCTGATGTTGATATTATTGATGTAAACTATGAACTTGGTCAATCATTTGATATGGCTGATATTGATAGTT
ATGGACGTGGTAATTTGTCAAAGAAAATTGTGGTTGATTTTAAAGGAATTGCTTTGCAAATGGAAGGTACCGTGAAATCATCAAATATCATTGATTCTTCACCAAAATCAACTA
TTATACAACCACCTCCAAATTGTCTTCGTGGTGATCCACTGGCACCATCACAAGTTACATGGCATCCAATGGCAGGAGTTAATGGGGCACCAGCTCCTTCATTTAGTCCATCTG
ATTATCCACCACGTGCTGTTTGCTTCAAACCATTTCCTGGTAATCCTTTAGATAACGATCATACACCTGGTAAAATGCCTTTAACATGGTTTAATATGTCCGAGTTTATGTGTGG
TAAAGTATCAAATTGTCTTGGACCAGAATTTAAGAGATTTGATAACTCTAAAACATCCAGAAGTCCTGCCTTTGATCTTGCACTTGTTACACGTGTTGTGAGTGTATCAGATAT
GGAATTTAAACCTCATTTAAATATTGATGTTAATCCAAGTAAGGGGTACAATGATAGGTGAATTTGATTGCCCTGCAGATGCGTGGTTTTTTCAAGGATCATGTAACGATGGTCA
TATGCCGTATTCTATTGTTATGGAAATTGCTCTTCAAACTTCTGGTGTATTAACTTCAGTTTTGAAAGCACCTTTGACTATGGATAAAGATGATATTCTTTTCCGCAATTTGGAT
GCCCACTGCTGAAATGGTTCGAAGTGATGTTGATTGTAGAGGTAAAACTATCAAAAACTTTACTCAATGTACCGGTTACAGTATGCTCGGAAAAATGGGAATTCATAGATTCAC
ATTTGAATTATCTGTTGATGATGTAGTTTTCTACAAAGGATCAACATCTTTTGGTTGGTTCACCCCTGAAGTATTCGAGTCACAAGTTGGTCTTGATAATGGTAAAAAAGTACA
ACCATGGTATTTGGAACAAAAATCATCTAATGTAGTAACTTATGACGTTGCGTCCACTGCTGGCAAGGATAAGTTATTTTCAAAGATTGGATCTAAGGATGCACAAGTTCAAA
GAAGAAATACACAATGTGAGTTTCTAGATACTATGCATATTATTCCAAATACTGGAAAGTACAACAAAGGTTATGCTCATGGAGAAAAGAAAGTTAATCCAAACGACTGGTTC
TTTTCCTGTCATTTCTGGTTTGATCCTGTGATGCCTGGTTCATTAGGTATTGAAAGTATGTTTCAACTCATTGAAGCATTTTCAATTGATCAAGGAATCGCTTCAAAACATGGTA
TTGTGAATCCAACTTTTGCTCATTCCAATGGAAAAACTTCTTGGAAATACAGAGGTCAATTGAATAACAAAGGTAAACGAATGGATAGTGAAATTCATATCAAAGATATTGTC
AAAAAATGCTGATGGTACTGTTGATTTGATTGCTGATGGATTTTTATTGGTTGATTCACTAAGAGTATACTCTGCAGATGATCTTCGCGTAAAAATTGTACCGGGAACCAAAGCT
GCACCTAAATCAGTAGCTGCTGCTCCAAGACATGTTGCAACACCAATTCCAGGAGTGCCTTCGAATACAAGCAGTGTTGAAATCAGTTTGGAATCTTTGAAGAAAGAATTGTT
AAATCTTGAGAAACCATTGTATCTTGAAACTTCCAATCATATTGTAAAACAATTCGGTGACGTTAACAATGGCCAAGCATCCGTTATTCCACCATGCACCATCAATGATTTGGG
TGAGCGTAGTTTTATGGAAACATACAATGTTGTTGCACCCACTTTACACTGGAGCCATGGCTAAAGGTATTGCATCTGCTGATTTGGTAATTGCAGCTGGTAAAAGAAAAATTTT
GGGTTCTTTTGGCGCTGGAGGCTTACCAATGCACTTGGTTCGTGCTTCTGTTGAAAAAATCCAAGCCGCACTTCCAGAAGGTCCATACGCTGTCAACTTGATTCATAGTCCATT
CGACTCAAATCTTGAAAAGGGAAATGTAGATCTATTTTTGGAAAAAGGTGTTCATGTTGTTGAAGCATCTGCATTCACTGCTCTGACCACTCAAGTAGTTCGTTACCGTGCATG
TGGTTTATCTCGGGCTAAAGACGGATCTGTATTGATCAAAAATAGAATCATCGGTAAAGTTTCAAGAACCGAATTGGCTGAAATGTTTTTCAGACCTGCACCACAAAACTTGCT
TGACAAGCTTATTGCTAGTGGAGAAATCACTAAAGAACAAGCTTCATTGGCTTTGGAAGTACCAATGGCTGATGATGTAGCTGTTGAAGCTGATAGCGGTGGACATACTGATA
ATAGACCAATTCATGTAATCCTACCTTTGATTATCAATCTACGAAATAGAATTCATAAAGAATGTGGTTTTCCTGCTGCTTTGAGAGTTCGCGTTGGTGCTGGTGGTGGAATTG
GTTGTCCAAGTGCTGCAGTTGCTGCATTCAATATGGGAGCTGCATTCTTGATTACTGGCAGCGTCAACCAAGTTAGCAAACAATCTGGTACGTGTGATATCGTTAGAAAGCAAT
TATCTGAAGCTTCGTATTCAGATATTACCATGGCACCAGCGGCTGATATGTTTGATCAAGGAGTCGAGCTTCAAGTATTAAAAAAAGGAACTATGTTTCCATCTCGTGCAAAGA
AATTGTATGAATTATTCTGTATGTACAACTCATTTGATGACATGCCAAAAAGCGAACTTCAAAGACTAGAGAAGCGAATTTTTCAAAAATCGCTTGCCGGAAGTTTGGGAAGAA
ACTAAAGATTTTTATATCAATCGTTTGAATAATCCTGAGAAGATTGAACATGCTGAGAAGAAAGATCCAAAGTTGAAGATGTCATTATGCTTTAGATGGTATTTGGGTTTAAGT
TCATTTTGGGCAAACAATGGAATTAAAGAAAGATCAATGGACTATCAAATTTGGTGTGGTCCAGCGATTGGTTCATACAATGATTTTGTAAAAGGAACTTATTTGGATCCTGCA
GTAGCAGGTTCATATCCATGTGTTGTTCAAATTAACATGCAAATTCTACGCGGTGCTTGTTTTCTTCAACGAGTTCGTGCAATCAAGCACGATCCACGATTGGATATTGATGTC
GATGAAGATGTATTTACCTATCGTCCAGAATCAACCCTATAG     (SEQ ID NO:72)

FIG. 20

ATGGTTGGCCTGCAGATGAAGAAGAAGCCTGTGTGGGAGATGTCGAAGGAGGAGCAGTCGTCCGGCAAGAACGTCGTCTTTGACTACGACGAGCTCCTCGAATTCGCGGAGG
GTGACATCGGCAAGGTGTTCGGCCCCAAGTTTGACATCATCGACAAGTACAGCCGCCGTGTGCGCCTCCCGGCCCGCGAGTACCTCCTCGTCACCCGTGTCACGCTCATGGAT
GCCGAGGTCGGCAACTTCCGCGTCGGCTCGCGCATGGTCACCGAGTACGACGTCCCGGTGAACGGCGAGCTTTCCCAGGGCGGCGACGTTCCCTGGGCCGTCCTCGTCGAGTC
GGGCCAGTGCGACCTCATGCTTATCTCGTACATGGGCATTGACTTTCAGTGCAAGGGTGACCGCGTTTACCGCCTTCTCAACACGACCCTCACGTTCTACGGTGTCGCCCACGA
GGGCGAGACTCTCGTTTACGACATCCGCGTCACTGGTTTCGCCAAGGGCATGCACGGCGAGATTAGCATGTTCTTCTTCGAGTACGACTGCTACGTCAACGGCCGCCTGCTCAT
CGAGATGCGCGACGGTTGCGCTGGCTTCTTCACGGACGAGGAGCTCGCCGCGGGCAAGGGCGTCATCAAGACCGTCGCTGAGCTCCACAAGCGCAAGTCGATTGTGCCCAAG
TCGATCAAGCCTTTTGCCCTCAACCCCGCCGTCCACAAGACGATGTTCAGCGAGAACGACATGGAGAAGCTTTGCGAGCGCCAGTGGGAGAACGTCCTCGGCTCCGGCCTCCA
GGGCATCGACTACAAGCTGTGCGCCCGCAAGATGCTCATGATCGACCGCATCACGAAGATCCAGCACAACGGCGGTGCGTACGGCCTCGGCCTCCTCGTTGGCGAGAAGATTC
TTGAGCGCGACCATTGGTACTTCCCCTTGCCACTTCGTCAAGGACCAGGTGATGGCGGGCTCCCTCGTTAGCGACGGCTGCTCGCAGCTGCTCAAGCTTTACATGCTTTGGCTCG
GCCTCCACGACGTGGTCCCCGATTTCCAGTTCCGTCCTGTCCCTGGCCAGCCCAACAAGGTGCGCTGCCGTGGCCAGATCAGCCCCCATCGTGGCAAGCTCGTGTACGTGATGG
AGATTCGCGAGATGGGTTTCAACGAGTCCACCGGCCAGCCCTACGCGATCGCTGACGTTGACATTATCGATGTGAACTACGAGCTCGGCCAGTCCTTCGACATGGCCGACATC
GACTCGTACGGCCGTGGCAACCTCTCCAAGAAGATTGTCGTCGATTTCAAGGGGCATTGCGCTCCAGATGGAGGGCACCGTCAAGAGCTCCAACATCATCGATTCGTCCCCCAA
GTCCACGATTATCCAGCCGCCGCCCAACTGCCTCCGCGGCGATCCTCTCGCCCCCTCGCAGGTCACCTGGCACCCGATGGCCGGTGTCAACGGCGCCCCGCCCCCTCCTTCAG
CCCGTCGGATTACCCTCCTCGTGCCGTTTGCTTTAAGCCCTTCCCTGGCAACCCCCTCGACAACGATCATACGCCGGGCAAGATGCCGCTGACCTGGTTTAACATGTCGGAGTT
TATGTGCGGCAAGGTCAGCAACTGCCTTGGCCCTGAGTTTAAGCGCTTCGACAACTCCAAGACGAGCCGCTCCCCGGCCTTCGACCTGGCCCTGGTTACGCGCGTGGTGTCGGT
CAGCGATATGGAGTTCAAGCCCCACCTCAACATCGACGTCAACCCGTCGAAGGGCACGATGATTGGCGAGTTCGACTGCCCCGCTGACGCCTGGTTCTTTCAGGGCTCCTGCA
ACGACGGCCACATGCCGTACAGCATCGTCATGGAGATCGCCCTTCAGACCAGCGGTGTCCTCACCTCCGTCCTCAAGGCCCCGCTCACTATGGACAAGGACGACATTCTCTTTC
GCAACCTCGACGCCACCGCCGAGATGGTCCGTTCCGACGTCGATTGCCGCGGTAAGACCATCAAGAACTTCACCCAGTGCACCGGCTACAGCATGCTTGGCAAGATGGGCATC
CACCGCTTCACTTTTGAGCTCTCGGTCGATGACGTCGTGTTTTACAAGGGCTCGACCAGCTTTGGTTGGTTCACGCCGGAGGTGTTTGAGTCGCAGGTCGGCCTCGATAACGGC
AAGAAGGTCCAGCCGTGGTATCTGGAGCAGAAGTCGTCGAACGTGGTGACGTACGATGTCGCCTCGACCGCCGGCAAGGACAAGCTCTTCTCGAAGATCGGCTCGAAGGACG
CTCAGGTCCAGCGTCGCAACACCCAGTGCGAGTTTCTCGACACGATGCACATTATTCCGAACACCGGCAAGTACAACAAGGGCTACGCGCACGGTGAGAAGAAGGTCAACCC
CAACGACTGGTTCTTCTCCTGCCACTTTTGGTTCGACCCGGTGATGCCCGGCTCCCTCGGTATTGAGTCCATGTTCCAGCTCATCGAGGCCTTTCGATTGACCAGGGTATCGCG
TCCAAGCATGGCATCGTGAACCCTACCTTCGCGCACTCGAACGGCAAGACCTCGTGGAAGTACCGCGGCCAGCTCAACAACAAGGGCAAGCGCATGGACAGCGAGATTCACA
TCAAGGATATTGTCAAGAACGCCGACGGTACTGTCGATCTCATCGCCGATGGTTTTCTTCTCGTGGACTCGCTTCGCGTTTACAGCGCCGATGACCTCCGCGTCAAGATCGTCC
CCGGCACTAAGGCTGCTCCCAAGAGCGTCGCGGCCGCTCCGCGCCATGTGGCCACTCCGATCCCCGGCGTCCCCTCCAACACCTCCTCGGTGGAGATCTCGCTTGAGTCCCTTA
AGAAGGAGCTCCTCAACCTGGAGAAGCCCCTCTACCTTGAGACTTCCAACCACATCGTCAAGCAGTTCGGCGACGTTAACAACGGCCAGGCCTCCGTCATCCCTCCGTGCACC
ATTAACGATCTCGGTGAGCGCTCGTTTATGGAGACTTACAACGTCGTCGCTCCCCTCTACACCGGCGCGATGGCGAAGGGCATCGCTTCGGCGGACCTCGTCATCGCTGCCGGT
AAGCGCAAGATCCTCGGCAGCTTCGGCGCCGGTGGCCTCCCGATGCACCTCGTGCGCGCCTCGGTCGAGAAGATCCAGGCCGCCTCCCGGAGGGCCGTACGCGGTCAACCT
CATCCACTCGCCTTTCGACTCGAACCTTGAGAAGGGTAACGTGGACCTCTTTCTGGAGAAGGGCGTCCACGTGGTCGAGGCCTCCGCCTTTACCGCCCTCACGACCCAGGTCGT
TCGCTACCGCGCCTGCGGCCTCTCGCGTGCTAAGGACGGTTCCGTGCTGATTAAGAACCGCATCATCGGTAAGGTCAGCCGCACGGAGCTTGCCGAGATGTTCTTTCGCCCTGC
CCCCCAGAACCTCCTCGATAAGCTCATCGCCAGCGGCGAGATCACCAAGGAGCAGGCGTCCCTCGCTCTTGAGGTTCCTATGGCCGACGATGTCGCTGTTGAGGCCGACTCCG
GCGGCCACACCGATAACCGTCCCATCCACGTCATCCTCCCGCTGATTATTAACCTCCGCAACCGTATCCACAAGGAGTGCGGCTTTCCTGCCGCTCTCCGCGTCCGCGTCGGCG
CTGGTGGTGGCATCGGTTGCCCCTCGGCCGCTGTCGCCGCCTTCAACATGGGCGCGGCCTTCCTGATCACCGGCTCCGTTAACCAGGTGAGCAAGCAGTCCGGCACGTGCGAC
ATTGTGCGCAAGCAGCTTAGCGAGGCCAGCTACTCCGACATCACGATGGCTCCCGCCGCTGACATGTTCGACCAGGGCGTGGAGCTCCAGGTCCTCAAGAAGGGTACGATGTT
TCCCTCGCGCGCCAAGAAGCTCTACGAGCTCTTTTGCATGTACAACAGCTTTGACGACATGCCGAAGTCCGAGCTCCAGCGCCTGGAGAAGCGCATTTTCCAGAAGAGCCTCG
CCGAGGTCTGGGAGGAGACTAAGGACTTTTACATCAACCGCCTCAACAACCCGGAGAAGATCGAGCACGCCGAGAAGAAGGACCCCAAGCTCAAGATGTCCCTTTGCTTTCG
CTGGTATCTCGGCCTTTCGAGCTTTTGGGCCAACAACGGCATCAAGGAGCGCAGCATGGATTACCAGATTTGGTGCGGCCCGGCCATTGGCAGCTACAACGACTTCGTGAAGG
GCACCTACCTCGACCCCGCCGTCGCCGGTTCGTACCCCTGCGTGGTCCAGATCAACATGCAGATCCTCCGCGGTGCGTGCTTCCTCCAGCGCGTCCGCGCCATTAAGCACGACC
CGCGCCTCGATATCGACGTTGATGAGGACGTCTTTACCTACCGCCCCGAGAGCACCCTCTAA (SEQ ID NO:122)

FIG. 21

MVGLQMKKKPVWEMSKEFQSSGKNVVFDYDFLLEFAEGDIGKVFGPKFDIIDKYSRRVRLPAREYLLVTRVTLMDAEVGNFRVGSRMVTEYDVPVNGFLSQGGDVPWAVLVESGQ
CDLMLISYMGIDFQCKGDRVYRLLNTTLTFYGVAHEGETLVYDIRVTGFAKGMHGEISMFFFEYDCYVNGRLLIEMRDGCAGFFTDEELAAGKGVIKTVAELHKRKSIVPKSIKPFAL
NPAVHKTMFSENDMEKLCERQWENVLGSGLQGIDYKLCARKMLMIDRITKIQHNGGAYGLGLLVGEKILERDHWYFPCHFVKDQVMAGSLVSDGCSQLLKLYMLWLGLHDVVPD
FQFRPVPGQPNKVRCRGQISPHRGKLVYVMEIREMGFNESTGQPYALADVDIDVNYELGQSFDMADIDSYGRGNLSKKIVVDFKGIALQMEGTVKSSNIIDSSPKSTIIQPPPNCLRGDP
LAPSQVTWIIPMAGVNGAPAPSFSPSDYPPRAVCFKPFPGNPLDNDIITPGKMPLTWFNMSEFMCGKVSNCLGPEFKRFDNSKTSRSPAFDLALVTRVVSVSDMEFKPIILNIDVNPSKG
TMIGEFDCPADAWFFQGSCVNDGHMPYSIVMFIALQTSGVLTSVLKAPLTMDKDDILFRNLDATAFMVRSDVDCRGKTIKNFTQCTGYSMLGKMGIHRFTFFLSVDDVVFYKGSTSFG
WFTPEVFESQVGLDNGKKVQPWYLEQKSSNVVTYDVASTAGKDKLFSKIGSKDAQVQRRNTQCEFLDTMHIIPNTGKYNKGYAHGEKKVNPNDWFFSCHFWFDPVMPGSLGIESMF
QLIEAFSIDQGIASKHGIVNPTFAHSNGKTSWKYRGQLNNKGKRMDSEIHIKDIVKNADGTVDLIADGFLLVDSLRVYSADDLRVKIVPGTKAAPKSVAAAPRHVATPIPGVPSNTSSV
EISLESLKKELLNLEKPLYLETSNIIIVKQFGDVNNGQASVIPPCTINDLGERSFMETYNVVAPLYTGAMAKGIASADLVIAAGKRKILGSFGAGGLPMIILVRASVEKIQAALPEGPYAV
NLIHSPFDSNLFKGNVDLFLFKGVHVVEASAFTALTTQVVRYRACGLSRAKDGSVLIKNRIIGKVSRTELAFMFFRPAPQNLLDKLIASGFITKFQASLALFVPMADDVAVFADSGGHT
DNRPIHVILPLIINLRNRIHKECGFPAALRVRVGAGGGIGCPSAAVAAFNMGAAFLITGSVNQVSKQSGTCDIVRKQLSEASYSDITMAPAADMFDQGVELQVLKKGTMFPSRAKKLYE
LFCMYNSFDDMPKSELQRLEKRIFQKSLAEVWEETKDFYINRLNNPEKIEHAEKKDPKLKMSLCFRWYLGLSSFWANNGIKERSMDYQIWCGPAIGSYNDFVKGTYLDPAVAGSYPC
VVQINMQILRGACFLQRVRAIKHDPRLDIDVDEDVFTYRPESTL (SEQ ID NO:73)

FIG. 22

*Schizochytrium* Codon Usage

| AA* | Codon | Fraction | AA* | Codon | Fraction | AA* | Codon | Fraction | AA* | Codon | Fraction |
|---|---|---|---|---|---|---|---|---|---|---|---|
| Ala | GCC | 0.64 | End | TAA | 0.34 | Leu | CTT | 0.16 | Ser | TCG | 0.33 |
| Ala | GCA | 0.03 | End | TGA | 0.33 | Leu | TTG | 0.02 | Ser | TCC | 0.31 |
| Ala | GCT | 0.18 | End | TAG | 0.33 | Leu | CTG | 0.12 | Ser | AGT | 0.03 |
| Ala | GCG | 0.16 | Gln | CAA | 0.08 | Leu | CTC | 0.69 | Ser | TCA | 0 |
| Arg | CGG | 0.01 | Gln | CAG | 0.92 | Leu | TTA | 0 | Ser | TCT | 0.09 |
| Arg | AGA | 0 | Glu | GAA | 0.09 | Leu | CTA | 0 | Thr | ACG | 0.3 |
| Arg | CGC | 0.8 | Glu | GAG | 0.91 | Lys | AAA | 0.04 | Thr | ACC | 0.54 |
| Arg | CGA | 0.01 | Gly | GGA | 0.1 | Lys | AAG | 0.96 | Thr | ACA | 0.02 |
| Arg | AGG | 0 | Gly | GGT | 0.2 | Met | ATG | 1 | Thr | ACT | 0.14 |
| Arg | CGT | 0.17 | Gly | GGG | 0 | Phe | TTT | 0.45 | Trp | TGG | 1 |
| Asn | AAC | 0.94 | Gly | GGC | 0.7 | Phe | TTC | 0.55 | Tyr | TAC | 0.94 |
| Asn | AAT | 0.06 | His | CAC | 0.83 | Pro | CCT | 0.21 | Tyr | TAT | 0.06 |
| Asp | GAT | 0.24 | His | CAT | 0.17 | Pro | CCG | 0.34 | Val | GTC | 0.62 |
| Asp | GAC | 0.76 | Ile | ATC | 0.7 | Pro | CCC | 0.43 | Val | GTA | 0 |
| Cys | TGC | 0.95 | Ile | ATA | 0 | Pro | CCA | 0.02 | Val | GTT | 0.14 |
| Cys | TGT | 0.05 | Ile | ATT | 0.3 | Ser | AGC | 0.24 | Val | GTG | 0.24 |

* AA=Amino Acid

SEQUENCE LISTING

```
<160> NUMBER OF SEQ ID NOS: 127

<210> SEQ ID NO 1
<211> LENGTH: 7824
<212> TYPE: DNA
<213> ORGANISM: Schizochytrium sp.

<400> SEQUENCE: 1
atggatactc gcatcgcgat cgtggggatg tcggcgatcc tgccgagcgg ggagaacgtg      60
cgcgagagct gggaggcgat ccgcgatggg ctggattgcc tgagcgatct gccggcggac     120
cgcgtggacg tgacggccta ctacaacccg gagaagacga ccaaggacaa gatctactgc     180
```

-continued

| | | |
|---|---|---|
| aagcgcggcg ggttcatccc ggagtacgac ttcgacgcgc gtgagttcgg gctcaacatg | 240 | |
| ttccagatgg aggactcgga cgccaaccag acgatctcgc tgctcaaggt gaaggaggcg | 300 | |
| ctgacggacg ccaacatccc ggcgttctcg agcggtaaga agaacatcgg ctgcgtgctg | 360 | |
| ggcatcggcg gcggccagaa ggcgagccac gagttctact cgcggctcaa ctacgtggtc | 420 | |
| gtggacaagg tgctgcgcaa gatgggcctg ccggaggaag acgtggcggc ggcggtggac | 480 | |
| aagtacaagg cgagtttccc cgagtggcgc ctcgactctt tccccgggtt cctgggcaac | 540 | |
| gtcacggcgg ggcgctgctg caataccttc aacatggagg catgaactg cgtcgtggac | 600 | |
| gcggcctgcg cgtcgtcgct gatcgcggtc aaagtggcga tcgaggagct gctctacggc | 660 | |
| gactgcgatg cgatgatcgc gggtgccacc tgcacggaca actcgatcgg gatgtacatg | 720 | |
| gccttctcca agacgcccgt gttttccacg gacccgagcg tcaaggcgta cgacgccgcc | 780 | |
| accaaaggca tgctcatcgg cgagggctcg gcgatgctcg tgctgaagcg ctacgcggac | 840 | |
| gccgtgcgcg acggcgacac cgtgcacgcc gtcatcaagg ggtgcgcgtc ctcgagcgac | 900 | |
| ggcaaggcgg cgggcatcta cacgccgaca atctcgggcc aggaggaggc cctgcgccgc | 960 | |
| gcctacgccc gcgccaatgt cgacccggcc actgtgacgc tggtggaggg ccacggcacg | 1020 | |
| ggtacgccgg tgggcgacaa gatcgagctg acggcgctga gcaacctctt ctccaaggcg | 1080 | |
| ttttctgcca acggtggcgg cgcggaggaa gcagagcagg tggcggtggg cagcatcaag | 1140 | |
| tcgcagatcg ggcacctcaa ggcggtggcc gggctggccg gctggtcaa ggtggtgctg | 1200 | |
| gcgctcaagc acaagacgct gccgcagacg atcaacgtcg acaagccgcc gtcgctggtg | 1260 | |
| gacgggaccc cgatccagca gtcgccgctg tacgtcaaca cgatgaaccg cccctggttc | 1320 | |
| acgcccgtag gggtgccgcg ccgcgccggc gtgtcgtcgt ttgggtttgg cggtgccaac | 1380 | |
| taccacgccg tgctggagga gtttgagccc gagcacgaga gcgcgtaccg gtacaacaac | 1440 | |
| ctgccgcagg tggcgctgct gcacgcgggg gacgtcgcga ccttggcggc gacggttcgc | 1500 | |
| gccaagctgg cgctggccac cgccgagcag gaagaggcgc gtgtggtgaa gaacgcggac | 1560 | |
| tacatcgcgt accaccggtt cctggacgag tgcaagttgc gcggcgctgt gccgcaggcg | 1620 | |
| cacgcgcggg tgggactgct cgtacgggac ctgagctcgc tcatcgccgt gctcgaggcc | 1680 | |
| gctgccgcca agctcgcggg cgaagagagc gcgacggagt ggacggtcag cgttgctacg | 1740 | |
| ggcgaggcgg ccttccgcgt gcgcggtgtg gctacggagg ccaacgtggc ggcgctgttc | 1800 | |
| tcgggccagg gcgcgcagta cacgcacatg ttcagcgacg tggcgatgaa ctggccccg | 1860 | |
| ttccgcgaga gcgtcgccgc catggaccgc gcccagcgcg agcgcttcgg gcggcctgcc | 1920 | |
| aagcgcgtga gcagcgtgct gtacccgcgc aagccgtacg gcgacgaacc gcggcaggac | 1980 | |
| cacaaggaga tctcgcaaac gcgctactcg cagcccgcaa cgctcgcgtg ctcggtcggc | 2040 | |
| gcctttgaca tcttcaaagc ggcgggactg gcgccgagct ttgcggcggg ccactcgctg | 2100 | |
| ggcgagtttg cggcgctcta cgcggcccgg tcgctcgatc gcgacgccgt cttcgacctg | 2160 | |
| gtctgcgcgc gcgccaaggc catgagcgac ttcacggccc aggccagcag cagcggtggc | 2220 | |
| gccatggcgg ccgtgattgg cgccaaggcg gaccagctct cgctgggtgg cgcgcccgac | 2280 | |
| gtgtggctcg ccaacagcaa ctcgcccctg cagaccgtga tcacgggaac cgccgaagca | 2340 | |
| gtggctgcgg cctctgacaa gttgcgctgc agcggcaact tccgcgtcgt gcctctggcc | 2400 | |
| tgcgaggcgc ccttccactc gccgcacatg cgcggcgcgg agcagacgtt tgcgtcggcg | 2460 | |
| ctcgcgcagg cgcccgtgtc ggcaccgcg gctgctcggt tctactctaa cgtgacgggg | 2520 | |
| ggcgccgcgg taacctcgcc cgcggacgtc aaaacgaacc tgggcaagca catgacgagc | 2580 | |

```
cctgtgcagt tcgtgcagca ggtgcgagcc atgcacgcgg cgggcgcgcg tgtgtttgtg    2640
gagtttgggc ccaagcaggt cctgtcgcgc ctcgtcaagg agaccttggc gaggccggc     2700 gacgtggtca cggtcgccgt caacccagac tcggccaagg acagcgacac gcagctgcgc    2760
caggcggcgc tcacgttggc ggtcgccggc gtgccgctca aggactttga ccgctggcag    2820
ctgccggatg ccacgcgcct cgagcctgtc aagaagaaga agaccacgtt gcggctctcg    2880
gcagccacct acgtctccgc caagacgttg cgccagcgcg aggccgtgct caacgacggc    2940
tacactgtca gtggtgccac ggcggtagtc aaggaagtgg acacggccaa cgaggagcgt    3000
ctcgtccgcc aagcccagga tctccagcgc cagctcgcgg aggcctcgac ggcagcccag    3060
gcggcgcagt ccaaggtcgc ggagctcgag cgcacgatcc aggacttgga gcgcaaggtg    3120
cagcagcagc agcaagagaa gggtgagaac tcagacagca acgctgccgc cgaagtgctg    3180
cggcgccaca aggagctgct ccagcgcatg ctgcaggact gtgacgagca ggcagtgccc    3240
gtagccacgg tggttccgac acctacgtcc tccccgacgc ctacatcctc acccgtatcc    3300
ggcaacagca agagcactcg tggcagtgct gatctgcaag cgctgctggc caaggcggag    3360
actgtggtga tggctgtgct ggctgccaag actggctacg aggccgacat ggttgaggcg    3420
gacatggacc tggaggccga gctcggcatc gactcgatca agcgcgtgga gatcctttcc    3480
gaggtgcagg gccagctggg cgtcgaggcc aaggacgtgg atgcgctgag ccgcacgcgc    3540
acggtcggtg aggttgtgga cgccatgaag gcggagatcg tggctgcctc tggtggtagt    3600
gctcctgcgg ttccttcggc gcccgctgct tctgcagctc cgactcccgc tgcttcgact    3660
gcgccttctg ctgatctgca agcgctgctg tccaaggcgg agactgtggt gatggctgtg    3720
ctggcggcca agactggcta cgaggccgac atggtcgagg cggacatgga cctggaggcc    3780
gagctcggca tcgactcgat caagcgcgtg agatcctct cggaggtgca gggccagctg    3840
ggcgtcgagg ccaaggacgt ggatgcgctg agccgcacgc gcacggtcgg tgaggttgtg    3900
gatgccatga aggcggaaat cgtggctgcc tctgctggta gtgctcctgc tcctgctgtt    3960
ccttcggcgc ccgctgcttc tgcagctccg actcccgctg cttcgactgc gccttctgct    4020
gatctgcaag cgctgctgtc caaggcggag acggtggtga tggctgtgct ggcggccaag    4080
actggctacg aggccgacat ggtcgaggcg gacatggacc tggaggccga gctcggcatc    4140
gactcgatca agcgcgtgga gatcctctcg gaggtgcagg gccagctggg cgtcgaggcc    4200
aaggacgtgg atgcgctgag ccgcacgcgc acggtcggtg aggttgtgga tgccatgaag    4260
gcggaaatcg tggctgcctc tggtggtagt gctcctgctc ctgcggttcc ttcggcgccc    4320
gctgcttctg cagctccgac tcccgcggct gcgacagcgc cttctgctga tctgcaagcg    4380
ctgctggcca aggcggagac tgtggtgatg gctgtgctgg cggccaagac tggctacgag    4440
gccgacatgg tcgaggcgga catggacctg gaggccgagc tcggcatcga ctcgatcaag    4500
cgcgtggaga tcctttccga ggtgcagggc cagctgggcg tcgaggccaa ggacgtagat    4560
gcgctgagcc gcacgcgcac ggtcggtgag gttgtggatg ccatgaaggc ggagatcgtg    4620
gctgcctctg ctggtagtgc tcctgctcct gctgttcctt cggcgcccgc tgcttctgca    4680
gctccgactc ccgctgcttc gactgcgcct tctgctgatc tgcaagcgct gctgtccaag    4740
gcggagactg tggtgatggc tgtgctggcg gccaagactg gctacgaggc cgacatggtc    4800
gaggcggaca tggacctgga ggccgagctc ggcatcgact cgatcaagcg cgtggagatc    4860
ctctcggagg tgcagggcca gctgggcgtc gaggccaagg acgtggatgc gctgagccgc    4920
```

```
acgcgcacgg tcggtgaggt tgtggatgcc atgaaggcgg aaatcgtggc tgcctctggt    4980
ggtagtgctc ctgctgctgc tgttccttcg gcgcccgctg cttctgcagc tccgactcct    5040
gcgactgcgc cttctgctga tctgcaagcg ctgctgtcca aggcggagac tgtggtgatg    5100
gctgtgctgg cggccaagac tggctacgag gccgacatgg tcgaggcgga catggacctg    5160
gaggccgagc tcggcatcga ctcgatcaag cgcgtggaga tcctttccga ggtgcagggc    5220
cagctgggcg tcgaggccaa ggacgtagat gcgctgagcc gcacgcgcac ggtcggtgaa    5280
gtggtggacg ccatgaaggc ggagatcgtg gctgcctctg gtggtagtgc tcctgctgct    5340
ccttcggcgc ccgcgcttct tccaacgctg tttggttccg agtgcgagga cctgtctctg    5400
acctttcccg tgataacgac cctgccgctt cctgcagagc ttgtgctggc cgagggcggc    5460
gctcgccctg tagtcgtggt ggatgatgga tctgcactca cctcgtcgct ggtgtcctcg    5520
ctcggcgatc gtgcggtgct gctgcaggtg cagtcttcct ctgcctgctc gccgcgctcg    5580
accacgcaca agttggtgac cgtagcagac cgctctgaag cggcgctaca ggcggcgctc    5640
acgtccgtcg aggcgcagtt cggcaaggtg ggtggctttg tgttccagtt cggcgacgac    5700
gacgtgcaag cgcagctcgg ctgggcgctg ctcgcggcca agcacctcaa aacttcgctg    5760
tcagaacaga tcgagggcgg tcgcaccttt ttcgtggccg tcgcgcggct cgacggccag    5820
ctggggctct ccggcaagtc gacgaccgct accgttgatc tctcccgcgc gcagcagggc    5880
agcgtgttcg gcctgtgcaa gacactcgac ctggagtggc ccgctgtctt ctgccgcgga    5940
atcgacctgg ccgccgacct cgacgccgca caggccgcgc ggtgcctgct gggcgagctg    6000
tcagaccccg acgtggccgt gcgcgagtct ggttactccg cctcgggcca cgctgcacg     6060
acaactacga agtcgctgac tacgggcaag ccgcaccagc cgatctcctc gtcggacctc    6120
tttctggtgt cgggcggcgc gcgcggcatc accccgctgt gcgtgcgcga gctggcgcag    6180
cgcgtgggcg gcggcacgta cgtgctcatc ggccgctcgg agctgcccac gacggagcct    6240
gcctgggcgg tcgcgtgga gtctggcaag ccgctggaga aggccgcgct ggcgttcctg    6300
aaggcggagt ttgcagcggg ccgcggggcc aagccgacgc cgatgctgca caagaagctc    6360
gtgggcgccg tggtcggagc gcgcgaggtg cgagcctcgc tcgccgagat cactgcacag    6420
ggcgccacgg ctgtgtacga gtcgtgcgac gtgagctctg ccgccaaggt gcgtgagatg    6480
gtagagcgcg tgcagcagca gggcgggcgg cgcgtgtcgg gcgtgttcca cgcgtcgggc    6540
gtgctgcgcg acaagctcgt ggagaacaag tcgctggcgg acttcagcgc cgtgtacgac    6600
accaaggtgg gcgccctcat caacctgctg gcctgcgtgg acctggcgca gctgcgtcac    6660
ctcgtgctct tcagctcgct cgcgggcttc cacggcaacg tcgggcagtc ggactacgca    6720
atggccaacg aggcgctcaa caagctggcg gcgcacctgt cggcggtgca cccgcagctg    6780
tgcgcgcgct cgatctgctt cggaccgtgg gacggcggca tggtgacccc cgcgctcaag    6840
gccaacttca tccgcatggg catccagatc atcccgcgcc aaggcggcgc gcagaccgtc    6900
gccaacatgc tcgtcagtag ctcccccggt cagctgctcg tgggcaactg ggcgtgcca     6960
cccgtcgtgc cgagtgccac cgagcacacc gtgctgcaga cgctccgcca gagcgacaac    7020
cccttcctcg actcgcacgt gatccagggc cgccgcgtgc tgcccatgac cctggccgtg    7080
ggctacatgg cgcaccaggc gcagagcatc tacgcgggcc accagctgtg ggccgtcgag    7140
gacgcccagc tcttcaaggg catcgccatc gacaatggcg ccgacgtgcc cgtgcgcgtg    7200
gagctgtcgc gccgcaagga ggagcaggag gacgccggca aggtcaaggt caaggtgcag    7260
gtgctgctca aatcgcaggt caacggcaag tcggtgcccg cgtacaaggc gaccgtcgtg    7320
```

-continued

```
ctgtccctg cgccgcgccc cagcgtcatc acgcgtgact tcgacctcac cccggacccg    7380
gcctgcacgg agcacgacct ctacgacggc aagacgctct tccacggcaa ggccttccag    7440
ggcatcgagc aggtgctctc ggcgacgccc aagcagctca ccgccaagtg ccgcaatttg    7500
cccctcacgc ccgagcagcg cggccagttc gtcgttaacc tcagccagca ggacccgttc    7560
caggcggaca ttgcgttcca ggcgatgctc gtctgggcgc gcatgctgcg ccaatcggcg    7620
gccctgccca caactgcga gcgcttcgac ttttacaagc cgatggcccc gggcgccacc     7680
tactacacgt cggtcaagct ggcctcggcc tcacccttgg tggactctgt gtgcaagtgc    7740
accgtggcga tgcacgatga gcaaggtgag gtgtacttt ctgctcgtgc agcgtcgtc     7800 ctcaacaaga ccctcacgta ctaa                                            7824
```

<210> SEQ ID NO 2
<211> LENGTH: 2607
<212> TYPE: PRT
<213> ORGANISM: Schizochytrium sp.

<400> SEQUENCE: 2

```
Met Asp Thr Arg Ile Ala Ile Val Gly Met Ser Ala Ile Leu Pro Ser
1               5                   10                  15

Gly Glu Asn Val Arg Glu Ser Trp Glu Ala Ile Arg Asp Gly Leu Asp
            20                  25                  30

Cys Leu Ser Asp Leu Pro Ala Asp Arg Val Asp Val Thr Ala Tyr Tyr
        35                  40                  45

Asn Pro Glu Lys Thr Thr Lys Asp Lys Ile Tyr Cys Lys Arg Gly Gly
    50                  55                  60

Phe Ile Pro Glu Tyr Asp Phe Asp Ala Arg Glu Phe Gly Leu Asn Met
65                  70                  75                  80

Phe Gln Met Glu Asp Ser Asp Ala Asn Gln Thr Ile Ser Leu Leu Lys
                85                  90                  95

Val Lys Glu Ala Leu Thr Asp Ala Asn Ile Pro Ala Phe Ser Ser Gly
            100                 105                 110

Lys Lys Asn Ile Gly Cys Val Leu Gly Ile Gly Gly Gly Gln Lys Ala
        115                 120                 125

Ser His Glu Phe Tyr Ser Arg Leu Asn Tyr Val Val Asp Lys Val
    130                 135                 140

Leu Arg Lys Met Gly Leu Pro Glu Glu Asp Val Ala Ala Val Asp
145                 150                 155                 160

Lys Tyr Lys Ala Ser Phe Pro Gly Trp Arg Leu Asp Ser Phe Pro Gly
                165                 170                 175

Phe Leu Gly Asn Val Thr Ala Gly Arg Cys Cys Asn Thr Phe Asn Met
            180                 185                 190

Glu Gly Met Asn Cys Val Val Asp Ala Ala Cys Ala Ser Ser Leu Ile
        195                 200                 205

Ala Val Lys Val Ala Ile Glu Glu Leu Leu Tyr Gly Asp Cys Asp Ala
    210                 215                 220

Met Ile Ala Gly Ala Thr Cys Thr Asp Asn Ser Ile Gly Met Tyr Met
225                 230                 235                 240

Ala Phe Ser Lys Thr Pro Val Phe Ser Thr Asp Pro Ser Val Lys Ala
                245                 250                 255

Tyr Asp Ala Ala Thr Lys Gly Met Leu Ile Gly Glu Gly Ser Ala Met
            260                 265                 270

Leu Val Leu Lys Arg Tyr Ala Asp Ala Val Arg Asp Gly Asp Thr Val
```

-continued

```
              275                 280                 285
His Ala Val Ile Lys Gly Cys Ala Ser Ser Asp Gly Lys Ala Ala
290                 295                 300
Gly Ile Tyr Thr Pro Thr Ile Ser Gly Gln Glu Ala Leu Arg Arg
305                 310                 315                 320
Ala Tyr Ala Arg Ala Asn Val Asp Pro Ala Thr Val Thr Leu Val Glu
                325                 330                 335
Gly His Gly Thr Gly Thr Pro Val Gly Asp Lys Ile Glu Leu Thr Ala
                340                 345                 350
Leu Ser Asn Leu Phe Ser Lys Ala Phe Ser Ala Asn Gly Gly Gly Ala
                355                 360                 365
Glu Glu Ala Glu Gln Val Ala Val Gly Ser Ile Lys Ser Gln Ile Gly
370                 375                 380
His Leu Lys Ala Val Ala Gly Leu Ala Gly Leu Val Lys Val Val Leu
385                 390                 395                 400
Ala Leu Lys His Lys Thr Leu Pro Gln Thr Ile Asn Val Asp Lys Pro
                405                 410                 415
Pro Ser Leu Val Asp Gly Thr Pro Ile Gln Gln Ser Pro Leu Tyr Val
                420                 425                 430
Asn Thr Met Asn Arg Pro Trp Phe Thr Pro Val Gly Val Pro Arg Arg
                435                 440                 445
Ala Gly Val Ser Ser Phe Gly Phe Gly Gly Ala Asn Tyr His Ala Val
                450                 455                 460
Leu Glu Glu Phe Glu Pro Glu His Gly Ser Ala Tyr Arg Tyr Asn Asn
465                 470                 475                 480
Leu Pro Gln Val Ala Leu Leu His Ala Gly Asp Val Ala Thr Leu Ala
                485                 490                 495
Ala Thr Val Arg Ala Lys Leu Ala Leu Ala Thr Ala Glu Gln Glu Glu
                500                 505                 510
Ala Arg Val Val Lys Asn Ala Asp Tyr Ile Ala Tyr His Arg Phe Leu
                515                 520                 525
Asp Glu Cys Lys Leu Arg Gly Ala Val Pro Gln Ala His Ala Arg Val
                530                 535                 540
Gly Leu Leu Val Arg Asp Leu Ser Ser Leu Ile Ala Val Leu Glu Ala
545                 550                 555                 560
Ala Ala Ala Lys Leu Ala Gly Glu Glu Ser Ala Thr Glu Trp Thr Val
                565                 570                 575
Ser Val Ala Thr Gly Glu Ala Ala Phe Arg Val Arg Gly Val Ala Thr
                580                 585                 590
Glu Ala Asn Val Ala Ala Leu Phe Ser Gly Gln Gly Ala Gln Tyr Thr
                595                 600                 605
His Met Phe Ser Asp Val Ala Met Asn Trp Pro Pro Phe Arg Glu Ser
                610                 615                 620
Val Ala Ala Met Asp Arg Ala Gln Arg Glu Arg Phe Gly Arg Pro Ala
625                 630                 635                 640
Lys Arg Val Ser Ser Val Leu Tyr Pro Arg Lys Pro Tyr Gly Asp Glu
                645                 650                 655
Pro Arg Gln Asp His Lys Glu Ile Ser Gln Thr Arg Tyr Ser Gln Pro
                660                 665                 670
Ala Thr Leu Ala Cys Ser Val Gly Ala Phe Asp Ile Phe Lys Ala Ala
                675                 680                 685
Gly Leu Ala Pro Ser Phe Ala Ala Gly His Ser Leu Gly Glu Phe Ala
                690                 695                 700
```

```
Ala Leu Tyr Ala Ala Gly Ser Leu Asp Arg Asp Ala Val Phe Asp Leu
705                 710                 715                 720

Val Cys Ala Arg Ala Lys Ala Met Ser Asp Phe Thr Ala Gln Ala Ser
            725                 730                 735

Ser Ser Gly Gly Ala Met Ala Ala Val Ile Gly Ala Lys Ala Asp Gln
        740                 745                 750

Leu Ser Leu Gly Gly Ala Pro Asp Val Trp Leu Ala Asn Ser Asn Ser
    755                 760                 765

Pro Ser Gln Thr Val Ile Thr Gly Thr Ala Glu Ala Val Ala Ala
770                 775                 780

Ser Asp Lys Leu Arg Cys Ser Gly Asn Phe Arg Val Val Pro Leu Ala
785                 790                 795                 800

Cys Glu Ala Ala Phe His Ser Pro His Met Arg Gly Ala Glu Gln Thr
            805                 810                 815

Phe Ala Ser Ala Leu Ala Gln Ala Pro Val Ser Ala Pro Ala Ala Ala
        820                 825                 830

Arg Phe Tyr Ser Asn Val Thr Gly Gly Ala Ala Val Thr Ser Pro Ala
    835                 840                 845

Asp Val Lys Thr Asn Leu Gly Lys His Met Thr Ser Pro Val Gln Phe
850                 855                 860

Val Gln Gln Val Arg Ala Met His Ala Ala Gly Ala Arg Val Phe Val
865                 870                 875                 880

Glu Phe Gly Pro Lys Gln Val Leu Ser Arg Leu Val Lys Glu Thr Leu
            885                 890                 895

Gly Glu Ala Gly Asp Val Val Thr Ala Val Asn Pro Asp Ser Ala
        900                 905                 910

Lys Asp Ser Asp Thr Gln Leu Arg Gln Ala Ala Leu Thr Leu Ala Val
    915                 920                 925

Ala Gly Val Pro Leu Lys Asp Phe Asp Arg Trp Gln Leu Pro Asp Ala
930                 935                 940

Thr Arg Leu Glu Pro Val Lys Lys Lys Thr Thr Leu Arg Leu Ser
945                 950                 955                 960

Ala Ala Thr Tyr Val Ser Ala Lys Thr Leu Arg Gln Arg Glu Ala Val
            965                 970                 975

Leu Asn Asp Gly Tyr Thr Val Ser Gly Ala Thr Ala Val Val Lys Glu
        980                 985                 990

Val Asp Thr Ala Asn Glu Glu Arg  Leu Val Arg Gln Ala  Gln Asp Leu
    995                 1000               1005

Gln Arg  Gln Leu Ala Glu Ala  Ser Thr Ala Ala Gln  Ala Ala Gln
   1010               1015               1020

Ser Lys  Val Ala Glu Leu Glu  Arg Thr Ile Gln Asp  Leu Glu Arg
   1025               1030               1035

Lys Val  Gln Gln Gln Gln Glu  Lys Gly Glu Asn  Ser Asp Ser
   1040               1045               1050

Asn Ala  Ala Ala Glu Val Leu  Arg Arg His Lys Glu  Leu Leu Gln
   1055               1060               1065

Arg Met  Leu Gln Asp Cys Asp  Glu Gln Ala Val Pro  Val Ala Thr
   1070               1075               1080

Val Val  Pro Thr Pro Thr Ser  Ser Pro Thr Pro Thr  Ser Ser Pro
   1085               1090               1095

Val Ser  Gly Asn Ser Lys Ser  Thr Arg Gly Ser Ala  Asp Leu Gln
   1100               1105               1110
```

-continued

```
Ala Leu Leu Ala Lys Ala Glu Thr Val Val Met Ala Val Leu Ala
1115                1120                1125

Ala Lys Thr Gly Tyr Glu Ala Asp Met Val Glu Ala Asp Met Asp
1130                1135                1140

Leu Glu Ala Glu Leu Gly Ile Asp Ser Ile Lys Arg Val Glu Ile
1145                1150                1155

Leu Ser Glu Val Gln Gly Gln Leu Gly Val Glu Ala Lys Asp Val
1160                1165                1170

Asp Ala Leu Ser Arg Thr Arg Thr Val Gly Glu Val Val Asp Ala
1175                1180                1185

Met Lys Ala Glu Ile Val Ala Ala Ser Gly Gly Ser Ala Pro Ala
1190                1195                1200

Val Pro Ser Ala Pro Ala Ala Ser Ala Ala Pro Thr Pro Ala Ala
1205                1210                1215

Ser Thr Ala Pro Ser Ala Asp Leu Gln Ala Leu Leu Ser Lys Ala
1220                1225                1230

Glu Thr Val Val Met Ala Val Leu Ala Ala Lys Thr Gly Tyr Glu
1235                1240                1245

Ala Asp Met Val Glu Ala Asp Met Asp Leu Glu Ala Glu Leu Gly
1250                1255                1260

Ile Asp Ser Ile Lys Arg Val Glu Ile Leu Ser Glu Val Gln Gly
1265                1270                1275

Gln Leu Gly Val Glu Ala Lys Asp Val Asp Ala Leu Ser Arg Thr
1280                1285                1290

Arg Thr Val Gly Glu Val Val Asp Ala Met Lys Ala Glu Ile Val
1295                1300                1305

Ala Ala Ser Ala Gly Ser Ala Pro Ala Pro Ala Val Pro Ser Ala
1310                1315                1320

Pro Ala Ala Ser Ala Ala Pro Thr Pro Ala Ala Ser Thr Ala Pro
1325                1330                1335

Ser Ala Asp Leu Gln Ala Leu Leu Ser Lys Ala Glu Thr Val Val
1340                1345                1350

Met Ala Val Leu Ala Ala Lys Thr Gly Tyr Glu Ala Asp Met Val
1355                1360                1365

Glu Ala Asp Met Asp Leu Glu Ala Glu Leu Gly Ile Asp Ser Ile
1370                1375                1380

Lys Arg Val Glu Ile Leu Ser Glu Val Gln Gly Gln Leu Gly Val
1385                1390                1395

Glu Ala Lys Asp Val Asp Ala Leu Ser Arg Thr Arg Thr Val Gly
1400                1405                1410

Glu Val Val Asp Ala Met Lys Ala Glu Ile Val Ala Ala Ser Gly
1415                1420                1425

Gly Ser Ala Pro Ala Pro Ala Val Pro Ser Ala Pro Ala Ala Ser
1430                1435                1440

Ala Ala Pro Thr Pro Ala Ala Thr Ala Pro Ser Ala Asp Leu
1445                1450                1455

Gln Ala Leu Leu Ala Lys Ala Glu Thr Val Val Met Ala Val Leu
1460                1465                1470

Ala Ala Lys Thr Gly Tyr Glu Ala Asp Met Val Glu Ala Asp Met
1475                1480                1485

Asp Leu Glu Ala Glu Leu Gly Ile Asp Ser Ile Lys Arg Val Glu
1490                1495                1500

Ile Leu Ser Glu Val Gln Gly Gln Leu Gly Val Glu Ala Lys Asp
```

```
                1505                1510                1515

Val Asp Ala Leu Ser Arg Thr Arg Thr Val Gly Glu Val Val Asp
        1520                1525                1530

Ala Met Lys Ala Glu Ile Val Ala Ala Ser Ala Gly Ser Ala Pro
        1535                1540                1545

Ala Pro Ala Val Pro Ser Ala Pro Ala Ser Ala Ala Pro Thr
        1550                1555                1560

Pro Ala Ala Ser Thr Ala Pro Ser Ala Asp Leu Gln Ala Leu Leu
        1565                1570                1575

Ser Lys Ala Glu Thr Val Val Met Ala Val Leu Ala Ala Lys Thr
        1580                1585                1590

Gly Tyr Glu Ala Asp Met Val Glu Ala Asp Met Asp Leu Glu Ala
        1595                1600                1605

Glu Leu Gly Ile Asp Ser Ile Lys Arg Val Glu Ile Leu Ser Glu
        1610                1615                1620

Val Gln Gly Gln Leu Gly Val Glu Ala Lys Asp Val Asp Ala Leu
        1625                1630                1635

Ser Arg Thr Arg Thr Val Gly Glu Val Val Asp Ala Met Lys Ala
        1640                1645                1650

Glu Ile Val Ala Ala Ser Gly Gly Ser Ala Pro Ala Ala Ala Val
        1655                1660                1665

Pro Ser Ala Pro Ala Ala Ser Ala Ala Pro Thr Pro Ala Thr Ala
        1670                1675                1680

Pro Ser Ala Asp Leu Gln Ala Leu Leu Ser Lys Ala Glu Thr Val
        1685                1690                1695

Val Met Ala Val Leu Ala Ala Lys Thr Gly Tyr Glu Ala Asp Met
        1700                1705                1710

Val Glu Ala Asp Met Asp Leu Glu Ala Glu Leu Gly Ile Asp Ser
        1715                1720                1725

Ile Lys Arg Val Glu Ile Leu Ser Glu Val Gln Gly Gln Leu Gly
        1730                1735                1740

Val Glu Ala Lys Asp Val Asp Ala Leu Ser Arg Thr Arg Thr Val
        1745                1750                1755

Gly Glu Val Val Asp Ala Met Lys Ala Glu Ile Val Ala Ala Ser
        1760                1765                1770

Gly Gly Ser Ala Pro Ala Ala Pro Ser Ala Pro Ala Leu Leu Pro
        1775                1780                1785

Thr Leu Phe Gly Ser Glu Cys Glu Asp Leu Ser Leu Thr Phe Pro
        1790                1795                1800

Val Ile Thr Thr Leu Pro Leu Pro Ala Glu Leu Val Leu Ala Glu
        1805                1810                1815

Gly Gly Ala Arg Pro Val Val Val Val Asp Asp Gly Ser Ala Leu
        1820                1825                1830

Thr Ser Ser Leu Val Ser Ser Leu Gly Asp Arg Ala Val Leu Leu
        1835                1840                1845

Gln Val Gln Ser Ser Ser Ala Cys Ser Pro Arg Ser Thr Thr His
        1850                1855                1860

Lys Leu Val Thr Val Ala Asp Arg Ser Glu Ala Ala Leu Gln Ala
        1865                1870                1875

Ala Leu Thr Ser Val Glu Ala Gln Phe Gly Lys Val Gly Gly Phe
        1880                1885                1890

Val Phe Gln Phe Gly Asp Asp Asp Val Gln Ala Gln Leu Gly Trp
        1895                1900                1905
```

Ala Leu Leu Ala Ala Lys His Leu Lys Thr Ser Leu Ser Glu Gln
1910            1915                1920

Ile Glu Gly Gly Arg Thr Phe Phe Val Ala Val Ala Arg Leu Asp
1925            1930                1935

Gly Gln Leu Gly Leu Ser Gly Lys Ser Thr Thr Ala Thr Val Asp
1940            1945                1950

Leu Ser Arg Ala Gln Gln Gly Ser Val Phe Gly Leu Cys Lys Thr
1955            1960                1965

Leu Asp Leu Glu Trp Pro Ala Val Phe Cys Arg Gly Ile Asp Leu
1970            1975                1980

Ala Ala Asp Leu Asp Ala Ala Gln Ala Ala Arg Cys Leu Leu Gly
1985            1990                1995

Glu Leu Ser Asp Pro Asp Val Ala Val Arg Glu Ser Gly Tyr Ser
2000            2005                2010

Ala Ser Gly Gln Arg Cys Thr Thr Thr Thr Lys Ser Leu Thr Thr
2015            2020                2025

Gly Lys Pro His Gln Pro Ile Ser Ser Ser Asp Leu Phe Leu Val
2030            2035                2040

Ser Gly Gly Ala Arg Gly Ile Thr Pro Leu Cys Val Arg Glu Leu
2045            2050                2055

Ala Gln Arg Val Gly Gly Gly Thr Tyr Val Leu Ile Gly Arg Ser
2060            2065                2070

Glu Leu Pro Thr Thr Glu Pro Ala Trp Ala Val Gly Val Glu Ser
2075            2080                2085

Gly Lys Pro Leu Glu Lys Ala Ala Leu Ala Phe Leu Lys Ala Glu
2090            2095                2100

Phe Ala Ala Gly Arg Gly Ala Lys Pro Thr Pro Met Leu His Lys
2105            2110                2115

Lys Leu Val Gly Ala Val Val Gly Ala Arg Glu Val Arg Ala Ser
2120            2125                2130

Leu Ala Glu Ile Thr Ala Gln Gly Ala Thr Ala Val Tyr Glu Ser
2135            2140                2145

Cys Asp Val Ser Ser Ala Ala Lys Val Arg Glu Met Val Glu Arg
2150            2155                2160

Val Gln Gln Gln Gly Gly Arg Arg Val Ser Gly Val Phe His Ala
2165            2170                2175

Ser Gly Val Leu Arg Asp Lys Leu Val Glu Asn Lys Ser Leu Ala
2180            2185                2190

Asp Phe Ser Ala Val Tyr Asp Thr Lys Val Gly Gly Leu Ile Asn
2195            2200                2205

Leu Leu Ala Cys Val Asp Leu Ala Gln Leu Arg His Leu Val Leu
2210            2215                2220

Phe Ser Ser Leu Ala Gly Phe His Gly Asn Val Gly Gln Ser Asp
2225            2230                2235

Tyr Ala Met Ala Asn Glu Ala Leu Asn Lys Leu Ala Ala His Leu
2240            2245                2250

Ser Ala Val His Pro Gln Leu Cys Ala Arg Ser Ile Cys Phe Gly
2255            2260                2265

Pro Trp Asp Gly Gly Met Val Thr Pro Ala Leu Lys Ala Asn Phe
2270            2275                2280

Ile Arg Met Gly Ile Gln Ile Ile Pro Arg Gln Gly Gly Ala Gln
2285            2290                2295

```
Thr Val Ala Asn Met Leu Val Ser Ser Ser Pro Gly Gln Leu Leu
    2300            2305                2310

Val Gly Asn Trp Gly Val Pro Pro Val Pro Ser Ala Thr Glu
    2315            2320                2325

His Thr Val Leu Gln Thr Leu Arg Gln Ser Asp Asn Pro Phe Leu
    2330            2335                2340

Asp Ser His Val Ile Gln Gly Arg Arg Val Leu Pro Met Thr Leu
    2345            2350                2355

Ala Val Gly Tyr Met Ala His Gln Ala Gln Ser Ile Tyr Ala Gly
    2360            2365                2370

His Gln Leu Trp Ala Val Glu Asp Ala Gln Leu Phe Lys Gly Ile
    2375            2380                2385

Ala Ile Asp Asn Gly Ala Asp Val Pro Val Arg Val Glu Leu Ser
    2390            2395                2400

Arg Arg Lys Glu Glu Gln Glu Asp Ala Gly Lys Val Lys Val Lys
    2405            2410                2415

Val Gln Val Leu Leu Lys Ser Gln Val Asn Gly Lys Ser Val Pro
    2420            2425                2430

Ala Tyr Lys Ala Thr Val Val Leu Ser Pro Ala Pro Arg Pro Ser
    2435            2440                2445

Val Ile Thr Arg Asp Phe Asp Leu Thr Pro Asp Pro Ala Cys Thr
    2450            2455                2460

Glu His Asp Leu Tyr Asp Gly Lys Thr Leu Phe His Gly Lys Ala
    2465            2470                2475

Phe Gln Gly Ile Glu Gln Val Leu Ser Ala Thr Pro Lys Gln Leu
    2480            2485                2490

Thr Ala Lys Cys Arg Asn Leu Pro Leu Thr Pro Glu Gln Arg Gly
    2495            2500                2505

Gln Phe Val Val Asn Leu Ser Gln Gln Asp Pro Phe Gln Ala Asp
    2510            2515                2520

Ile Ala Phe Gln Ala Met Leu Val Trp Ala Arg Met Leu Arg Gln
    2525            2530                2535

Ser Ala Ala Leu Pro Asn Asn Cys Glu Arg Phe Asp Phe Tyr Lys
    2540            2545                2550

Pro Met Ala Pro Gly Ala Thr Tyr Tyr Thr Ser Val Lys Leu Ala
    2555            2560                2565

Ser Ala Ser Pro Leu Val Asp Ser Val Cys Lys Cys Thr Val Ala
    2570            2575                2580

Met His Asp Glu Gln Gly Glu Val Tyr Phe Ser Ala Arg Ala Ser
    2585            2590                2595

Val Val Leu Asn Lys Thr Leu Thr Tyr
    2600            2605

<210> SEQ ID NO 3
<211> LENGTH: 5778
<212> TYPE: DNA
<213> ORGANISM: Schizochytrium sp.

<400> SEQUENCE: 3
atgccgtgcg ataacattgc ggtcgtgggc atggcggtgc agtatgccgg atgcaagaac      60
caggacgagt tctgggatac gctgatgcgt aaggagatca actcgagccc gatctcggcg     120
gagcgcctcg gtacgcgcta ccgcgacctc cacttccacc cgcagcgcag caagtacgcc     180
gacaccttct gcaacgatcg ctacggctgc gtcgatgcca cgtcgacaa cgagcacgac     240
```

```
ctcctcgccg  acctggcccg  gcgcgccctg  ctcgacgccg  gaattaacct  cgacgacgcc   300
agcaccaccg  ccaacctacg  cgacttcggc  atcgtgagcg  gctgcctgtc  gttccccatg   360
gacaatctgc  agggcgagct  gctcaatctg  taccaagtgc  atgtggagaa  ccgcgtgggc   420
gcccagcgct  tccgcgactc  cgcgccctgg  tcggagcgcc  cgcgcgctgt  ctcgcccgag   480
gccagcgacc  cgcgcgtgta  ctccgacccg  gcgtccttcg  tggccaacca  gctcggcctg   540
gggcccgtgc  gctacagcct  cgatgcagcc  tgcgcgtcgg  cgctgtactg  cctcaagctg   600
gcgtccgacc  acttgctctc  gcgcagcgcg  gacgtgatgc  tgtgcggcgc  cacatgcttt   660
ccggacccgt  tcttcattct  ctcggggttc  tccaccttcc  aggcgatgcc  gctgggcgga   720
ccggacgata  acccactgtc  cgtgccgctg  cggcagggca  gccagggcct  gacgcccgga   780
gagggcggcg  ccatcatggt  gctgaagcgc  ctcgaggacg  ccgtgcgcga  cggcgaccgc   840
atctacggca  ccttgctcgg  cacgagtctg  agcaacgccg  ggtgcggcct  gccgctgagc   900
ccgcacctgc  cgagcgagaa  gtcgtgcatg  gaggacctgt  acacgagcgt  cggcatcgac   960
ccaagcgagg  tgcagtacgt  ggagtgccac  gccacgggca  ctccgcaggg  cgacgtcgtg  1020
gaggtagagg  cgctgcgcca  ctgctttcga  ggtaacacgg  accacccgcc  gcgcatgggc  1080
tccaccaagg  gcaactttgg  ccacactctc  gtggcggccg  ggttcgcagg  catggccaag  1140
gtgctgctgt  cgatgcagca  cggcacgatc  ccgcccacgc  ccggtgtcga  ccgctccaac  1200
tgcatcgacc  cgctcgtcgt  ggacgaggcc  atcccttggc  cgtactcgtc  ggcgcaggcg  1260
cgggcaggca  aaccaggcga  tgagctcaag  tgcgcctcgc  tctccgcctt  tggctttggt  1320
ggaaccaacg  cgcactgtgt  cttccgtgag  caccgccaaa  ttgctgctac  tgcgacagcc  1380
tcgccggtgc  ttcccgaggt  gactcctgga  ccgattgcca  tcatcgggat  ggacgcgacg  1440
tttggtaccc  tcaagggcct  ggacgcgttt  gagcaggcca  tctacaaggg  cacggacggc  1500
gccagcgacc  tgccgagcaa  gcgctggcgg  ttcctgggcg  ccgacacgga  cttcttgacc  1560
gccatgggcc  tcgacgccgt  gccgcgcggg  tgctacgtgc  gcgacgtgga  cgtggactac  1620
aagcggctgc  ggtcgccgat  gatccctgag  gacgtcctgc  gcccgcaaca  gctgctggcg  1680
gtggctacga  tggaccgcgc  gctgcaggac  gctggaatgg  cgacgggagg  caaggtggcg  1740
gtgctggtgg  ggctcggcac  ggacaccgag  ctgtaccggc  accgcgcgcg  cgtgacactc  1800
aaggagcggc  tcgacccggc  cgcgttctcg  cccgagcagg  tgcaggagat  gatggactac  1860
atcaacgact  gcggcacctc  gacgtcgtac  acgtcgtaca  tcggcaacct  cgtggccacg  1920
cgcgtgtcct  cgcagtgggg  ctttacgggc  ccgtccttca  ccgtcaccga  aggcgcaaac  1980
tcggtctacc  gctgcctcga  gctgggcaag  ttcctgctcg  acacgcacca  ggtggacgcc  2040
gtcgtggtgg  ccggcgtcga  cctctgtgcc  accgccgaga  cctttacct   caaggcgcgc  2100 cgctccgcca  tcagccgaca  ggaccaccct  cgcgccaact  tgaggccag   cgccgacggg  2160 tactttgccg  gcgagggcag  cggcgccctg  gtcctcaagc  gccaggccga  cgttggctca  2220
gacgacaagg  tctacgccag  tgtcgcgggc  ctcacgtgcg  ccgcgcagcc  cgctgaagcc  2280
gtgtcgccgc  tactactcca  agtccacaac  gacgacaacg  agaagagggt  ggtggagatg  2340
gtggagctcg  ccgccgactc  gggtcgccat  gcgccgcact  tggccaactc  gccgctgagc  2400
gccgagtcgc  agctggagca  agtgtccaag  ttgctcgcgc  accaggtgcc  gggctcggtg  2460
gccatcggca  gcgtcgcgcgc  caacgtggga  gacgtcgggt  acgcctcggg  cgccgcgagc  2520
ctcatcaaga  cggcgctgtg  cctccacaac  cgctacctcc  cggccaaccc  gcagtgggag  2580
cggccggtgg  cgccggtctc  cgaggcgctg  tttacttgcc  cgcgctcgcg  tgcctggctg  2640
```

```
aagaacccgg gcgagtcgcg actggcggct gtcgccagtg cctccgagag cgggtcctgc   2700
tttggcgtgc tcctcacaga cgagtacgcc actcatgaga gcagcaaccg cctctcgctg   2760
gatgacgccg cccccaagct catcgcgatc cgtggcgaca ccgttgacga tatcatggcc   2820
aaggtcaacg ccgagctggc gctcctccga gcgcacgccg aaaccgggtc tgctactgac   2880
gacgacccag ctgctgctgt cgcttttcact gctcatcgct tgcgcttttt gcggctcgta   2940
ggggagacgg tggctagtca cggtgccacg gcgaccttgt gtttggccct gctgacaacg   3000
ccggagaagc tggagaagga gttggagctg gcagccaagg gtgtaccgcg aagcgccaag   3060
gccgggcgca actggatgtc gccatcgggc agcgcctttg cgccgacacc tgtgaccagc   3120
gaccgcgtcg cgttcatgta cggcgagggc cgcagcccct actacggcgt cgggctcgac   3180
ctgcaccgcc tgtggccggc tttgcacgag cgcatcaacg acaagaccgc ggcgctgtgg   3240
gagaacggcg actcgtggct catgccgcgc gcggtggatg ccgactcgca gcgcgccgtg   3300
cagacggcct ttgacgcgga ccagatcgag atgttccgca cgggcatctt cgtgtccatc   3360
tgcctcaccg actacgcgcg cgacgtgctc ggggtgcagc ccaaggcgtg cttcggcctc   3420
agcctcggcg agatctccat gctctttgcg ctgtcgcgac gcaactgcgg cctgtcggac   3480
cagctcacgc agcgcctacg cacctcgccg gtgtggtcga cacagctggc ggtggagttc   3540
caggccttgc gcaagctatg gaacgtgccg gcggacgccc ccgtggagtc cttctggcag   3600
ggctacttgg ttcgcgccag ccgcgccgaa atcgagaagg cgatcgggcc cgacaaccgc   3660
ttcgtgcgcc tgctgatcgt caacgactcg agcagcgcgc tgatcgccgg caaacctgcc   3720
gagtgtctgc gcgtgctgga gcgcctgggc gggcggttgc cgccgatgcc cgtcaagcaa   3780
ggcatgattg ggcactgccc cgaagtggcg ccctacacgc cgggcatcgc gcacatccac   3840
gagattttgg agattccgga cagccccgtc aagatgtaca cctcggtcac caacgccgag   3900
ctgcgcgggg gcagcaacag cagcatcacc gagttcgtgc agaagttgta cacgcgcatc   3960
gccgactttc cgggcatcgt cgacaaggtc agccgtgacg gccacgatgt cttcgtcgag   4020
gtggggccga caacatgcg ctccgccgcg gtcagtgaca ttcttggcaa ggctgccacc   4080
ccgcatgtct ccgtggcgct ggaccgcccc agtgagtcgg cgtggacgca gaccctcaag   4140
tcgctggcgc tgctgaccgc ccaccgcgtg cccctgcaca acccgactct gtttgcggac   4200
ctgtaccacc ccacgttcct gacggctatc gactctgcga tgcaggagcc cccgcccaag   4260
cccaaccgct tccttcgcag cgtagaggtc aacgggtact tttgccccga cggcatcagc   4320
aagcaggttg ctgctgcaag tgccaaaccc tcgacgcatt gcatggttcg tttgcaccca   4380
gccaaggcag ttgtggttgc tgctgctggt gctgtggttg ctgattcgac gcccgtggtc   4440
aaggccaagc agacgtcgtc gtcgttgttg gttggggatg acgcctttct gcgctgctac   4500
gacgtggact ggccgctcta catgggcgcc atggcggaag gcatctcgtc ggtagacctg   4560
gtggtcgctg ccgccgaggc ccgcatgctg gcatcattcg gagcggcccg cttgcctatg   4620
gaccaggtgg aactccagat ccgtgagatc cagcaacgca cctccaacgc ctttgctgtc   4680
aacctgatgc cgggtcctga cgaggccgcg acggtggacg cgctgctgcg cacgggcgtc   4740
tcaatcgtcg aggcatcggg ctacaccggc gcgctctctg cagacctggt gcgctaccgt   4800
gtcacgggtc tgcgacgaac tagttgcggt gcttctgtgt cggcgactca ccgtgtggtc   4860
gccaaggtgt cgcgcaccga ggtggccgag cactttctgc gcccggcgcc ggccgccgta   4920
ctagaggctt tggtcgccgc caaacagatt acgcccgagc aggccgcgct ggccagccgc   4980
```

```
gtcgccatgg ccgacgacgt cgcggtggag gccgactcgg gcgggcacac cgacaaccga    5040
ccgatccacg tgctgctgcc gctcgtggtg gcgcagcgca accgctggcg ccacctggtg    5100
gacacgccag tgcgcgtcgg cgccggcggc gggatcgcct gtccgcgcgc cgcgctgctc    5160
gccttttccc tgggcgccgc ctttgtggtc accgggtccg tcaaccaact ggcccgcgag    5220
gctggcacca gcgacgcggt ccgactactg ctggcgacgg ccacctactc ggacgtggcc    5280
atggcgccgg cgccgtcca ggtgctcaag aagcagacca tgttcgccgc gcgggccacg    5340
atgctcgccc agctgcaggc caagttcggc tcctttgacg ccgtgccgga gccgcagctg    5400
cgcaagctcg agcgctccgt gttcaagcag tccgtggcgg acgtgtgggc tgctgcacgc    5460
gaaaagtttg tgtcgacgc taccgctgca agtccgcagg agaggatggc gctctgtgtg    5520
cgctggtaca tgtcgcagtc gtcgcgatgg gctaccgagg cgacgtccgc gcgcaaggcg    5580
gactaccaga tctggtgcgg ccccgccatc ggcagcttca cgacttcgt tcgcggcacc    5640 aagctggacg cgaccgctgg caccggcgag tttccgcgcg tcgtggacat caaccagcac    5700
atcctcctcg gagcctcgca ctaccgccgc gtgcagcaac aacaacagga cgacgacgta    5760
gaatacatca tcgtataa                                                  5778

<210> SEQ ID NO 4
<211> LENGTH: 1925
<212> TYPE: PRT
<213> ORGANISM: Schizochytrium sp.

<400> SEQUENCE: 4

Met Pro Cys Asp Asn Ile Ala Val Val Gly Met Ala Val Gln Tyr Ala
1               5                   10                  15

Gly Cys Lys Asn Gln Asp Glu Phe Trp Asp Thr Leu Met Arg Lys Glu
            20                  25                  30

Ile Asn Ser Ser Pro Ile Ser Ala Glu Arg Leu Gly Thr Arg Tyr Arg
        35                  40                  45

Asp Leu His Phe His Pro Gln Arg Ser Lys Tyr Ala Asp Thr Phe Cys
    50                  55                  60

Asn Asp Arg Tyr Gly Cys Val Asp Ala Ser Val Asp Asn Glu His Asp
65                  70                  75                  80

Leu Leu Ala Asp Leu Ala Arg Arg Ala Leu Leu Asp Ala Gly Ile Asn
                85                  90                  95

Leu Asp Asp Ala Ser Thr Thr Ala Asn Leu Arg Asp Phe Gly Ile Val
            100                 105                 110

Ser Gly Cys Leu Ser Phe Pro Met Asp Asn Leu Gln Gly Glu Leu Leu
        115                 120                 125

Asn Leu Tyr Gln Val His Val Glu Asn Arg Val Gly Ala Gln Arg Phe
    130                 135                 140

Arg Asp Ser Arg Pro Trp Ser Glu Arg Pro Arg Ala Val Ser Pro Glu
145                 150                 155                 160

Ala Ser Asp Pro Arg Val Tyr Ser Asp Pro Ala Ser Phe Val Ala Asn
                165                 170                 175

Gln Leu Gly Leu Gly Pro Val Arg Tyr Ser Leu Asp Ala Ala Cys Ala
            180                 185                 190

Ser Ala Leu Tyr Cys Leu Lys Leu Ala Ser Asp His Leu Leu Ser Arg
        195                 200                 205

Ser Ala Asp Val Met Leu Cys Gly Ala Thr Cys Phe Pro Asp Pro Phe
    210                 215                 220

Phe Ile Leu Ser Gly Phe Ser Thr Phe Gln Ala Met Pro Leu Gly Gly
```

-continued

```
                225                 230                 235                 240
        Pro Asp Asp Asn Pro Leu Ser Val Pro Leu Arg Gln Gly Ser Gln Gly
                        245                 250                 255
        Leu Thr Pro Gly Glu Gly Gly Ala Ile Met Val Leu Lys Arg Leu Glu
                        260                 265                 270
        Asp Ala Val Arg Asp Gly Asp Arg Ile Tyr Gly Thr Leu Leu Gly Thr
                        275                 280                 285
        Ser Leu Ser Asn Ala Gly Cys Gly Leu Pro Leu Ser Pro His Leu Pro
                        290                 295                 300
        Ser Glu Lys Ser Cys Met Glu Asp Leu Tyr Thr Ser Val Gly Ile Asp
        305                 310                 315                 320
        Pro Ser Glu Val Gln Tyr Val Glu Cys His Ala Thr Gly Thr Pro Gln
                        325                 330                 335
        Gly Asp Val Val Glu Val Glu Ala Leu Arg His Cys Phe Arg Gly Asn
                        340                 345                 350
        Thr Asp His Pro Pro Arg Met Gly Ser Thr Lys Gly Asn Phe Gly His
                        355                 360                 365
        Thr Leu Val Ala Ala Gly Phe Ala Gly Met Ala Lys Val Leu Leu Ser
                        370                 375                 380
        Met Gln His Gly Thr Ile Pro Pro Thr Pro Gly Val Asp Arg Ser Asn
        385                 390                 395                 400
        Cys Ile Asp Pro Leu Val Val Asp Glu Ala Ile Pro Trp Pro Tyr Ser
                        405                 410                 415
        Ser Ala Gln Ala Arg Ala Gly Lys Pro Gly Asp Glu Leu Lys Cys Ala
                        420                 425                 430
        Ser Leu Ser Ala Phe Gly Phe Gly Gly Thr Asn Ala His Cys Val Phe
                        435                 440                 445
        Arg Glu His Arg Gln Ile Ala Ala Thr Ala Thr Ala Ser Pro Val Leu
                        450                 455                 460
        Pro Glu Val Thr Pro Gly Pro Ile Ala Ile Ile Gly Met Asp Ala Thr
        465                 470                 475                 480
        Phe Gly Thr Leu Lys Gly Leu Asp Ala Phe Glu Gln Ala Ile Tyr Lys
                        485                 490                 495
        Gly Thr Asp Gly Ala Ser Asp Leu Pro Ser Lys Arg Trp Arg Phe Leu
                        500                 505                 510
        Gly Ala Asp Thr Asp Phe Leu Thr Ala Met Gly Leu Asp Ala Val Pro
                        515                 520                 525
        Arg Gly Cys Tyr Val Arg Asp Val Asp Val Asp Tyr Lys Arg Leu Arg
                        530                 535                 540
        Ser Pro Met Ile Pro Glu Asp Val Leu Arg Pro Gln Gln Leu Leu Ala
        545                 550                 555                 560
        Val Ala Thr Met Asp Arg Ala Leu Gln Asp Ala Gly Met Ala Thr Gly
                        565                 570                 575
        Gly Lys Val Ala Val Leu Val Gly Leu Gly Thr Asp Thr Glu Leu Tyr
                        580                 585                 590
        Arg His Arg Ala Arg Val Thr Leu Lys Glu Arg Leu Asp Pro Ala Ala
                        595                 600                 605
        Phe Ser Pro Glu Gln Val Gln Glu Met Met Asp Tyr Ile Asn Asp Cys
                        610                 615                 620
        Gly Thr Ser Thr Ser Tyr Thr Ser Tyr Ile Gly Asn Leu Val Ala Thr
        625                 630                 635                 640
        Arg Val Ser Ser Gln Trp Gly Phe Thr Gly Pro Ser Phe Thr Val Thr
                        645                 650                 655
```

```
Glu Gly Ala Asn Ser Val Tyr Arg Cys Leu Glu Leu Gly Lys Phe Leu
            660                 665                 670

Leu Asp Thr His Gln Val Asp Ala Val Val Ala Gly Val Asp Leu
        675                 680                 685

Cys Ala Thr Ala Glu Asn Leu Tyr Leu Lys Ala Arg Arg Ser Ala Ile
        690                 695                 700

Ser Arg Gln Asp His Pro Arg Ala Asn Phe Glu Ala Ser Ala Asp Gly
705                 710                 715                 720

Tyr Phe Ala Gly Glu Gly Ser Gly Ala Leu Val Leu Lys Arg Gln Ala
                725                 730                 735

Asp Val Gly Ser Asp Lys Val Tyr Ala Ser Val Ala Gly Leu Thr
            740                 745                 750

Cys Ala Ala Gln Pro Ala Glu Ala Val Ser Pro Leu Leu Gln Val
        755                 760                 765

His Asn Asp Asp Asn Glu Lys Arg Val Val Glu Met Val Glu Leu Ala
        770                 775                 780

Ala Asp Ser Gly Arg His Ala Pro His Leu Ala Asn Ser Pro Leu Ser
785                 790                 795                 800

Ala Glu Ser Gln Leu Glu Gln Val Ser Lys Leu Leu Ala His Gln Val
                805                 810                 815

Pro Gly Ser Val Ala Ile Gly Ser Val Arg Ala Asn Val Gly Asp Val
            820                 825                 830

Gly Tyr Ala Ser Gly Ala Ala Ser Leu Ile Lys Thr Ala Leu Cys Leu
                835                 840                 845

His Asn Arg Tyr Leu Pro Ala Asn Pro Gln Trp Glu Arg Pro Val Ala
850                 855                 860

Pro Val Ser Glu Ala Leu Phe Thr Cys Pro Arg Ser Arg Ala Trp Leu
865                 870                 875                 880

Lys Asn Pro Gly Glu Ser Arg Leu Ala Ala Val Ala Ser Ala Ser Glu
                885                 890                 895

Ser Gly Ser Cys Phe Gly Val Leu Leu Thr Asp Glu Tyr Ala Thr His
            900                 905                 910

Glu Ser Ser Asn Arg Leu Ser Leu Asp Asp Ala Ala Pro Lys Leu Ile
            915                 920                 925

Ala Ile Arg Gly Asp Thr Val Asp Ile Met Ala Lys Val Asn Ala
            930                 935                 940

Glu Leu Ala Leu Leu Arg Ala His Ala Glu Thr Gly Ser Ala Thr Asp
945                 950                 955                 960

Asp Asp Pro Ala Ala Ala Val Ala Phe Thr Ala His Arg Leu Arg Phe
                965                 970                 975

Leu Arg Leu Val Gly Glu Thr Val Ala Ser His Gly Ala Thr Ala Thr
            980                 985                 990

Leu Cys Leu Ala Leu Leu Thr Thr Pro Glu Lys Leu Glu Lys Glu Leu
        995                 1000                1005

Glu Leu Ala Ala Lys Gly Val Pro Arg Ser Ala Lys Ala Gly Arg
        1010                1015                1020

Asn Trp Met Ser Pro Ser Gly Ser Ala Phe Ala Pro Thr Pro Val
        1025                1030                1035

Thr Ser Asp Arg Val Ala Phe Met Tyr Gly Glu Gly Arg Ser Pro
        1040                1045                1050

Tyr Tyr Gly Val Gly Leu Asp Leu His Arg Leu Trp Pro Ala Leu
        1055                1060                1065
```

```
His Glu Arg Ile Asn Asp Lys Thr Ala Ala Leu Trp Glu Asn Gly
    1070            1075            1080

Asp Ser Trp Leu Met Pro Arg Ala Val Asp Ala Asp Ser Gln Arg
    1085            1090            1095

Ala Val Gln Thr Ala Phe Asp Ala Asp Gln Ile Glu Met Phe Arg
    1100            1105            1110

Thr Gly Ile Phe Val Ser Ile Cys Leu Thr Asp Tyr Ala Arg Asp
    1115            1120            1125

Val Leu Gly Val Gln Pro Lys Ala Cys Phe Gly Leu Ser Leu Gly
    1130            1135            1140

Glu Ile Ser Met Leu Phe Ala Leu Ser Arg Arg Asn Cys Gly Leu
    1145            1150            1155

Ser Asp Gln Leu Thr Gln Arg Leu Arg Thr Ser Pro Val Trp Ser
    1160            1165            1170

Thr Gln Leu Ala Val Glu Phe Gln Ala Leu Arg Lys Leu Trp Asn
    1175            1180            1185

Val Pro Ala Asp Ala Pro Val Glu Ser Phe Trp Gln Gly Tyr Leu
    1190            1195            1200

Val Arg Ala Ser Arg Ala Glu Ile Glu Lys Ala Ile Gly Pro Asp
    1205            1210            1215

Asn Arg Phe Val Arg Leu Leu Ile Val Asn Asp Ser Ser Ser Ala
    1220            1225            1230

Leu Ile Ala Gly Lys Pro Ala Glu Cys Leu Arg Val Leu Glu Arg
    1235            1240            1245

Leu Gly Gly Arg Leu Pro Pro Met Pro Val Lys Gln Gly Met Ile
    1250            1255            1260

Gly His Cys Pro Glu Val Ala Pro Tyr Thr Pro Gly Ile Ala His
    1265            1270            1275

Ile His Glu Ile Leu Glu Ile Pro Asp Ser Pro Val Lys Met Tyr
    1280            1285            1290

Thr Ser Val Thr Asn Ala Glu Leu Arg Gly Gly Ser Asn Ser Ser
    1295            1300            1305

Ile Thr Glu Phe Val Gln Lys Leu Tyr Thr Arg Ile Ala Asp Phe
    1310            1315            1320

Pro Gly Ile Val Asp Lys Val Ser Arg Asp Gly His Asp Val Phe
    1325            1330            1335

Val Glu Val Gly Pro Asn Asn Met Arg Ser Ala Ala Val Ser Asp
    1340            1345            1350

Ile Leu Gly Lys Ala Ala Thr Pro His Val Ser Val Ala Leu Asp
    1355            1360            1365

Arg Pro Ser Glu Ser Ala Trp Thr Gln Thr Leu Lys Ser Leu Ala
    1370            1375            1380

Leu Leu Thr Ala His Arg Val Pro Leu His Asn Pro Thr Leu Phe
    1385            1390            1395

Ala Asp Leu Tyr His Pro Thr Phe Leu Thr Ala Ile Asp Ser Ala
    1400            1405            1410

Met Gln Glu Pro Pro Lys Pro Asn Arg Phe Leu Arg Ser Val
    1415            1420            1425

Glu Val Asn Gly Tyr Phe Cys Pro Asp Gly Ile Ser Lys Gln Val
    1430            1435            1440

Ala Ala Ala Ser Ala Lys Pro Ser Thr His Cys Met Val Arg Leu
    1445            1450            1455

His Pro Ala Lys Ala Val Val Val Ala Ala Ala Gly Ala Val Val
```

-continued

```
            1460                1465                1470
Ala Asp Ser Thr Pro Val Val Lys Ala Lys Gln Thr Ser Ser Ser
    1475                1480                1485

Leu Leu Val Gly Asp Asp Ala Phe Leu Arg Cys Tyr Asp Val Asp
    1490                1495                1500

Trp Pro Leu Tyr Met Gly Ala Met Ala Glu Gly Ile Ser Ser Val
    1505                1510                1515

Asp Leu Val Val Ala Ala Glu Ala Arg Met Leu Ala Ser Phe
    1520                1525                1530

Gly Ala Ala Arg Leu Pro Met Asp Gln Val Glu Leu Gln Ile Arg
    1535                1540                1545

Glu Ile Gln Gln Arg Thr Ser Asn Ala Phe Ala Val Asn Leu Met
    1550                1555                1560

Pro Gly Pro Asp Glu Ala Ala Thr Val Asp Ala Leu Leu Arg Thr
    1565                1570                1575

Gly Val Ser Ile Val Glu Ala Ser Gly Tyr Thr Gly Ala Leu Ser
    1580                1585                1590

Ala Asp Leu Val Arg Tyr Arg Val Thr Gly Leu Arg Arg Thr Ser
    1595                1600                1605

Cys Gly Ala Ser Val Ser Ala Thr His Arg Val Val Ala Lys Val
    1610                1615                1620

Ser Arg Thr Glu Val Ala Glu His Phe Leu Arg Pro Ala Pro Ala
    1625                1630                1635

Ala Val Leu Glu Ala Leu Val Ala Ala Lys Gln Ile Thr Pro Glu
    1640                1645                1650

Gln Ala Ala Leu Ala Ser Arg Val Ala Met Ala Asp Asp Val Ala
    1655                1660                1665

Val Glu Ala Asp Ser Gly Gly His Thr Asp Asn Arg Pro Ile His
    1670                1675                1680

Val Leu Leu Pro Leu Val Val Ala Gln Arg Asn Arg Trp Arg His
    1685                1690                1695

Leu Val Asp Thr Pro Val Arg Val Gly Ala Gly Gly Gly Ile Ala
    1700                1705                1710

Cys Pro Arg Ala Ala Leu Leu Ala Phe Ser Leu Gly Ala Ala Phe
    1715                1720                1725

Val Val Thr Gly Ser Val Asn Gln Leu Ala Arg Glu Ala Gly Thr
    1730                1735                1740

Ser Asp Ala Val Arg Leu Leu Leu Ala Thr Ala Thr Tyr Ser Asp
    1745                1750                1755

Val Ala Met Ala Pro Gly Gly Val Gln Val Leu Lys Lys Gln Thr
    1760                1765                1770

Met Phe Ala Ala Arg Ala Thr Met Leu Ala Gln Leu Gln Ala Lys
    1775                1780                1785

Phe Gly Ser Phe Asp Ala Val Pro Glu Pro Gln Leu Arg Lys Leu
    1790                1795                1800

Glu Arg Ser Val Phe Lys Gln Ser Val Ala Asp Val Trp Ala Ala
    1805                1810                1815

Ala Arg Glu Lys Phe Gly Val Asp Ala Thr Ala Ala Ser Pro Gln
    1820                1825                1830

Glu Arg Met Ala Leu Cys Val Arg Trp Tyr Met Ser Gln Ser Ser
    1835                1840                1845

Arg Trp Ala Thr Glu Ala Thr Ser Ala Arg Lys Ala Asp Tyr Gln
    1850                1855                1860
```

```
Ile Trp Cys Gly Pro Ala Ile Gly Ser Phe Asn Asp Phe Val Arg
    1865                1870                1875

Gly Thr Lys Leu Asp Ala Thr Ala Gly Thr Gly Glu Phe Pro Arg
        1880                1885                1890

Val Val Asp Ile Asn Gln His Ile Leu Leu Gly Ala Ser His Tyr
    1895                1900                1905

Arg Arg Val Gln Gln Gln Gln Asp Asp Asp Val Glu Tyr Ile
1910                1915                1920

Ile Val
    1925

<210> SEQ ID NO 5
<211> LENGTH: 4308
<212> TYPE: DNA
<213> ORGANISM: Schizochytrium sp.

<400> SEQUENCE: 5
atgacatcat cgaagaagac tcccgtgtgg gagatgagca aggaggagct gctggacggc      60
aagacggtgg tcttcgacta caacgagctg ctcgaattcg ccgagggcga cgtgggccaa     120
gtgttcggac ccgagttcga catcatcgac aagtaccggc gtcgcgtgcg gctgccggcg     180
cgcgagtacc tgctcgtgtc gcgcgtgacg ctgatggacg ccgaggtgaa caacttccgc     240
gtcgggtcgc gcatggtgac cgagtacgac gtgcccgtga acggggagct gtcggagggc     300
ggggacgtgc cgtgggcggt gctggtggag tcggggcagt gcgacctgat gctcatctcg     360
tacatgggca tcgacttcca gtgcaagggc gaccgcgtgt accgcctgct caacacatcg     420
ctcaccttct tcggggtggc gcacgagggc gagacgctgg tgtacgacat ccgcgtcacg     480
gggttcgcca agggcgcggg cggggagatc tcgatgttct tcttcgagta cgactgcttc     540
gtggacggcc gcctgctgat cgagatgcgc gacgggtgcg ccgggttctt cacggacgcc     600
gagctggccg ccgcaagggc cgtgcttaag accaaggcgg agctggcggc gcgcgcgcag     660
atccagaagc aggacatcgc gcccttcgcg ccggcgccgt gctcgcacaa gacctcgctg     720
gacgcgcgcg agatgcggct gctcgtggac gccagtgggg cgcgcgtctt cggcagcggc     780
atggcgggca tcgactacaa gttgtgcgct cgcaagatgc tcatgatcga ccgcgtcacg     840
cacctcgacc cgcgcggcgg cgcgcacggc tcgggctgc tgatcgggga gaaggtgctg      900
gagcgcgacc actggtactt ccctgccac tttgtgcgcg acgaggtgat ggccgggtcg      960
ctggtcagcg acgctgctc gcagctcctc aaggtgtaca tgctgtggct cggcctgcac     1020
acgaccgtgg gcgcgttcga ctttcgtccc gtgagcgggc acgccaacaa ggtgcggtgc     1080
cgcgggcaga tctcaccgca aagggcaag ctcgtgtacg tgatggagat caaggaaatg     1140
ggctttgacg cgaagacggg cgatccgttt gcgatcgcgg acgtggacat catcgacgtc     1200
aacttcgagg agggacaggc gtttgcggga gtggaagacc tgcacagcta cggccagggc     1260
gacctccgca agaagatcgt cgtcgacttc aagggcatcg cgctctccct gcagaagcgg     1320
aaggagcagc agaaggaaag catgaccgtg actacgacga cgacgacgac gagccgggtg     1380
attgcgccgc ccagcgggtg cctcaagggc gacccgacgg cgccgacgag cgtgacgtgg     1440
cacccgatgg cggagggcaa cggcgggccc ggaccgacgc cgtcgttctc gccgtccgcg     1500
tacccgccgc gggcggtgtg cttctcgccg ttccccaaca accgcttga caacgaccac     1560 acgccgggcc agatgccgtt gacctggttc aacatgtccg aattcatgtg cggcaaagtg     1620
tccaactgcc tgggccccga gtttgcgcgc ttcgacgcga gcaagacgag ccgcagcccg     1680
```

```
gcctttgacc tggcgctcgt gacgcgggtg acgagcgtgg cggacatgga gcacgggccg    1740
ttctacaacg tggacgtcaa cccgggccag ggcacgatgg tgggcgagtt cgactgtccc    1800
gcggacgcgt ggttcttcgg cgcctcgagc cgcgacgacc acatgccgta ctcgatcctg    1860
atggagatcg cgctgcagac gtcgggcgtc ctcacctcgg tgctcaaggc gccgctgacg    1920
atggacaagg acgacatcct cttccgcaac ctcgacgcag acgccgagct cgtgggcgac    1980
gccatgccgg acgtgcgcgg caagacgatc cgcaacttca ccaagtgcac aggctacagc    2040
atgctcggca agatgggcat ccaccgcttc acctttgagc tcagcgtcga cggcgccgtc    2100
ttctacaagg gcagcacctc gtttggctgg ttcgtccccg aggtcttcga gtcgcagacc    2160
ggtctcgaca acggcaagcc gcgcctgcct tggtaccgcg agaacaacgt cgccgtcgac    2220
acgtctccg cgcccgcctc cgcttcctcc gcgcaaggtc agctgcagct gcagcgacgc    2280
gggtcgcagg cgcagttcct ggacacaatc cacctggcgg gcagcggcgc cggcgtgcac    2340
ggccagggct acgcgcacgg ggagaaggcc gtgaacaagc aagattggtt cttctcgtgc    2400
cacttctggt tcgaccccgt gatgcccggg tccctgggca tcgagtcgat gttccagctc    2460
gtcgaggcgt ggtgcgtgaa gcagggactc gcggcgcggc acggcatcgc tcacccagtg    2520
ttcgcgcacg cgcccggggc cacgagctgg aagtaccgcg ggcagctaac ccccaagaac    2580
gaccgcatgg acagcgaggt gcacatcaag tcggtggcgg ccttctcctc ctgggtcgac    2640
gtcgtcgcgg acgggttcct cttcgtcgac ggcctccgcg tctactcggc agacaacctc    2700
cgcgtccgca tccagaccgg cgccggccac gttgaagagc aagaggttgc tgccaaggcc    2760
acaaccaaga acagcagtat tgctgatgtg gacgtggcgg acctgcaagc gctcaagcag    2820
gcgttgctga cgctggagcg accgctgcag ctggacgcgg ggagcgaggt gcccgcctgc    2880
gcggtgagcg acctgggcga tagggcttc atggagacgt acggggtggt ggcgccgctg    2940
tacagcgggg cgatggccaa gggcatcgcg tcggcggacc tggtgatcgc gatgggccag    3000
cgcaagatgc tgggggtcgtt tggcgcgggc gggctcccga tgcacgtcgt gcgcgcgggg    3060
attgagaaga tccaggcagc gctgccagcg gggccatacg cggtcaacct gattcactcg    3120
cctttgacg ccaacctgga aagggcaac gtggacctct tcctggagaa gggcgtgcgc    3180
gtcgtggagg cgtcgccctt catggagctc acgccccagg tggtgcgcta ccgcgcgacg    3240
ggcctctctc gcgacgcgcg cggcggctcc gtgcgcacgg cccacaagat catcggcaag    3300
gtcagccgca ccgagctggc cgagatgttt atccggcccg cgccgcaagc cattctcgac    3360
aagcttgtgg cgtccggcga gatcaccccc gagcaggcgg cgctggcgct cgaggtgccc    3420
atggcggacg acatcgccgt cgaggccgat tcgggcgggc acaccgacaa ccgccccatc    3480
cacgtcatcc tgcccctcat cctcagcctg cgcaaccgcc tccagcgcga gctcaagtac    3540
cctgcgcgac accgcgtgcg cgtcggcgcc ggggcggca tcgggtgccc gcaagcggct    3600
ctgggcgcct tccacatggg cgccgcgttt gtggtgacgg gcacggtcaa ccagctgagc    3660
cggcaggccg ggacatgcga caatgtgcgg cggcagctgt cgcgcgcgac gtactcggac    3720
atcacgatgg cgccggcggc ggacatgttc gagcagggcg tcgagctgca ggtgctcaag    3780
aagggcacga tgtttccctc gcgcgccaag aagctgttcg agctgtttca agtacgac    3840
tcgttcgagg cgatgccggc ggacgagctg cgcgcgtcg agaagcgcat cttcagcaag    3900
tcactcgccg aggtgtgggc cgagaccaag gacttctaca tcacgcggct caacaacccg    3960
gagaagatcc gcaaggcgga gaacgaggac cccaagctca agatgtcact ctgcttccgc    4020
```

-continued

```
tggtacctcg ggctcagctc gttctgggcc aacaacggca tcgcggaccg cacgatggac   4080
taccagatct ggtgcggccc tgccatcggc gccttcaacg acttcatcgc cgactcgtac   4140
ctcgacgtgg ccgtctcggg cgagttcccc gacgtcgtgc agatcaacct gcagatcctg   4200
tcgggcgcag cctacctcca gcgcctcctc tccgtcaagc tcgcaccgcg gatcgacgtc   4260
gacaccgagg acgacctctt cacctaccgc cccgaccacg cactctaa              4308
```

<210> SEQ ID NO 6  
<211> LENGTH: 1435  
<212> TYPE: PRT  
<213> ORGANISM: Schizochytrium sp.

<400> SEQUENCE: 6

```
Met Thr Ser Ser Lys Lys Thr Pro Val Trp Glu Met Ser Lys Glu Glu
1               5                   10                  15

Leu Leu Asp Gly Lys Thr Val Val Phe Asp Tyr Asn Glu Leu Leu Glu
            20                  25                  30

Phe Ala Glu Gly Asp Val Gly Gln Val Phe Gly Pro Glu Phe Asp Ile
        35                  40                  45

Ile Asp Lys Tyr Arg Arg Arg Val Arg Leu Pro Ala Arg Glu Tyr Leu
    50                  55                  60

Leu Val Ser Arg Val Thr Leu Met Asp Ala Glu Val Asn Asn Phe Arg
65                  70                  75                  80

Val Gly Ser Arg Met Val Thr Glu Tyr Asp Val Pro Val Asn Gly Glu
                85                  90                  95

Leu Ser Glu Gly Gly Asp Val Pro Trp Ala Val Leu Val Glu Ser Gly
            100                 105                 110

Gln Cys Asp Leu Met Leu Ile Ser Tyr Met Gly Ile Asp Phe Gln Cys
        115                 120                 125

Lys Gly Asp Arg Val Tyr Arg Leu Leu Asn Thr Ser Leu Thr Phe Phe
    130                 135                 140

Gly Val Ala His Glu Gly Glu Thr Leu Val Tyr Asp Ile Arg Val Thr
145                 150                 155                 160

Gly Phe Ala Lys Gly Ala Gly Glu Ile Ser Met Phe Phe Phe Glu
                165                 170                 175

Tyr Asp Cys Phe Val Asp Gly Arg Leu Leu Ile Glu Met Arg Asp Gly
            180                 185                 190

Cys Ala Gly Phe Phe Thr Asp Ala Glu Leu Ala Ala Gly Lys Gly Val
        195                 200                 205

Leu Lys Thr Lys Ala Glu Leu Ala Ala Arg Ala Gln Ile Gln Lys Gln
    210                 215                 220

Asp Ile Ala Pro Phe Ala Pro Ala Pro Cys Ser His Lys Thr Ser Leu
225                 230                 235                 240

Asp Ala Arg Glu Met Arg Leu Leu Val Asp Arg Gln Trp Ala Arg Val
                245                 250                 255

Phe Gly Ser Gly Met Ala Gly Ile Asp Tyr Lys Leu Cys Ala Arg Lys
            260                 265                 270

Met Leu Met Ile Asp Arg Val Thr His Leu Asp Pro Arg Gly Gly Ala
        275                 280                 285

His Gly Leu Gly Leu Leu Ile Gly Glu Lys Val Leu Glu Arg Asp His
    290                 295                 300

Trp Tyr Phe Pro Cys His Phe Val Arg Asp Glu Val Met Ala Gly Ser
305                 310                 315                 320

Leu Val Ser Asp Gly Cys Ser Gln Leu Leu Lys Val Tyr Met Leu Trp
```

-continued

```
                    325                 330                 335
Leu Gly Leu His Thr Val Gly Ala Phe Asp Phe Arg Pro Val Ser
            340                 345                 350

Gly His Ala Asn Lys Val Arg Cys Arg Gly Gln Ile Ser Pro His Lys
            355                 360                 365

Gly Lys Leu Val Tyr Val Met Glu Ile Lys Glu Met Gly Phe Asp Ala
        370                 375                 380

Lys Thr Gly Asp Pro Phe Ala Ile Ala Asp Val Asp Ile Ile Asp Val
385                 390                 395                 400

Asn Phe Glu Glu Gly Gln Ala Phe Ala Gly Val Glu Asp Leu His Ser
                405                 410                 415

Tyr Gly Gln Gly Asp Leu Arg Lys Lys Ile Val Val Asp Phe Lys Gly
            420                 425                 430

Ile Ala Leu Ser Leu Gln Lys Arg Lys Glu Gln Lys Glu Ser Met
            435                 440                 445

Thr Val Thr Thr Thr Thr Thr Thr Ser Arg Val Ile Ala Pro Pro
        450                 455                 460

Ser Gly Cys Leu Lys Gly Asp Pro Thr Ala Pro Thr Ser Val Thr Trp
465                 470                 475                 480

His Pro Met Ala Glu Gly Asn Gly Gly Pro Gly Thr Pro Ser Phe
                485                 490                 495

Ser Pro Ser Ala Tyr Pro Pro Arg Ala Val Cys Phe Ser Pro Phe Pro
                500                 505                 510

Asn Asn Pro Leu Asp Asn Asp His Thr Pro Gly Gln Met Pro Leu Thr
            515                 520                 525

Trp Phe Asn Met Ser Glu Phe Met Cys Gly Lys Val Ser Asn Cys Leu
        530                 535                 540

Gly Pro Glu Phe Ala Arg Phe Asp Ala Ser Lys Thr Ser Arg Ser Pro
545                 550                 555                 560

Ala Phe Asp Leu Ala Leu Val Thr Arg Val Thr Ser Val Ala Asp Met
                565                 570                 575

Glu His Gly Pro Phe Tyr Asn Val Asp Val Asn Pro Gly Gln Gly Thr
            580                 585                 590

Met Val Gly Glu Phe Asp Cys Pro Ala Asp Ala Trp Phe Phe Gly Ala
        595                 600                 605

Ser Ser Arg Asp Asp His Met Pro Tyr Ser Ile Leu Met Glu Ile Ala
        610                 615                 620

Leu Gln Thr Ser Gly Val Leu Thr Ser Val Leu Lys Ala Pro Leu Thr
625                 630                 635                 640

Met Asp Lys Asp Asp Ile Leu Phe Arg Asn Leu Asp Ala Asp Ala Glu
                645                 650                 655

Leu Val Gly Asp Ala Met Pro Asp Val Arg Gly Lys Thr Ile Arg Asn
            660                 665                 670

Phe Thr Lys Cys Thr Gly Tyr Ser Met Leu Gly Lys Met Gly Ile His
        675                 680                 685

Arg Phe Thr Phe Glu Leu Ser Val Asp Gly Ala Val Phe Tyr Lys Gly
        690                 695                 700

Ser Thr Ser Phe Gly Trp Phe Val Pro Glu Val Phe Glu Ser Gln Thr
705                 710                 715                 720

Gly Leu Asp Asn Gly Lys Pro Arg Leu Pro Trp Tyr Arg Glu Asn Asn
                725                 730                 735

Val Ala Val Asp Thr Leu Ser Ala Pro Ala Ser Ala Ser Ala Gln
            740                 745                 750
```

```
Gly Gln Leu Gln Leu Gln Arg Arg Gly Ser Gln Ala Gln Phe Leu Asp
        755                 760                 765

Thr Ile His Leu Ala Gly Ser Gly Ala Gly Val His Gly Gln Gly Tyr
770                 775                 780

Ala His Gly Glu Lys Ala Val Asn Lys Gln Asp Trp Phe Phe Ser Cys
785                 790                 795                 800

His Phe Trp Phe Asp Pro Val Met Pro Gly Ser Leu Gly Ile Glu Ser
                805                 810                 815

Met Phe Gln Leu Val Glu Ala Trp Cys Val Lys Gln Gly Leu Ala Ala
                820                 825                 830

Arg His Gly Ile Ala His Pro Val Phe Ala His Ala Pro Gly Ala Thr
                835                 840                 845

Ser Trp Lys Tyr Arg Gly Gln Leu Thr Pro Lys Asn Asp Arg Met Asp
850                 855                 860

Ser Glu Val His Ile Lys Ser Val Ala Ala Phe Ser Ser Trp Val Asp
865                 870                 875                 880

Val Val Ala Asp Gly Phe Leu Phe Val Asp Gly Leu Arg Val Tyr Ser
                885                 890                 895

Ala Asp Asn Leu Arg Val Arg Ile Gln Thr Gly Ala Gly His Val Glu
                900                 905                 910

Glu Gln Glu Val Ala Ala Lys Ala Thr Thr Lys Asn Ser Ser Ile Ala
            915                 920                 925

Asp Val Asp Val Ala Asp Leu Gln Ala Leu Lys Gln Ala Leu Leu Thr
    930                 935                 940

Leu Glu Arg Pro Leu Gln Leu Asp Ala Gly Ser Glu Val Pro Ala Cys
945                 950                 955                 960

Ala Val Ser Asp Leu Gly Asp Arg Gly Phe Met Glu Thr Tyr Gly Val
                965                 970                 975

Val Ala Pro Leu Tyr Ser Gly Ala Met Ala Lys Gly Ile Ala Ser Ala
                980                 985                 990

Asp Leu Val Ile Ala Met Gly Gln Arg Lys Met Leu Gly Ser Phe Gly
        995                 1000                1005

Ala Gly Gly Leu Pro Met His Val Val Arg Ala Gly Ile Glu Lys
    1010                1015                1020

Ile Gln Ala Ala Leu Pro Ala Gly Pro Tyr Ala Val Asn Leu Ile
    1025                1030                1035

His Ser Pro Phe Asp Ala Asn Leu Glu Lys Gly Asn Val Asp Leu
    1040                1045                1050

Phe Leu Glu Lys Gly Val Arg Val Val Glu Ala Ser Ala Phe Met
    1055                1060                1065

Glu Leu Thr Pro Gln Val Val Arg Tyr Arg Ala Thr Gly Leu Ser
    1070                1075                1080

Arg Asp Ala Arg Gly Gly Ser Val Arg Thr Ala His Lys Ile Ile
    1085                1090                1095

Gly Lys Val Ser Arg Thr Glu Leu Ala Glu Met Phe Ile Arg Pro
    1100                1105                1110

Ala Pro Gln Ala Ile Leu Asp Lys Leu Val Ala Ser Gly Glu Ile
    1115                1120                1125

Thr Pro Glu Gln Ala Ala Leu Ala Leu Glu Val Pro Met Ala Asp
    1130                1135                1140

Asp Ile Ala Val Glu Ala Asp Ser Gly Gly His Thr Asp Asn Arg
    1145                1150                1155
```

```
Pro Ile His Val Ile Leu Pro Leu Ile Leu Ser Leu Arg Asn Arg
    1160                1165                1170

Leu Gln Arg Glu Leu Lys Tyr Pro Ala Arg His Arg Val Arg Val
    1175                1180                1185

Gly Ala Gly Gly Gly Ile Gly Cys Pro Gln Ala Ala Leu Gly Ala
    1190                1195                1200

Phe His Met Gly Ala Ala Phe Val Val Thr Gly Thr Val Asn Gln
    1205                1210                1215

Leu Ser Arg Gln Ala Gly Thr Cys Asp Asn Val Arg Arg Gln Leu
    1220                1225                1230

Ser Arg Ala Thr Tyr Ser Asp Ile Thr Met Ala Pro Ala Ala Asp
    1235                1240                1245

Met Phe Glu Gln Gly Val Glu Leu Gln Val Leu Lys Lys Gly Thr
    1250                1255                1260

Met Phe Pro Ser Arg Ala Lys Lys Leu Phe Glu Leu Phe His Lys
    1265                1270                1275

Tyr Asp Ser Phe Glu Ala Met Pro Ala Asp Glu Leu Ala Arg Val
    1280                1285                1290

Glu Lys Arg Ile Phe Ser Lys Ser Leu Ala Glu Val Trp Ala Glu
    1295                1300                1305

Thr Lys Asp Phe Tyr Ile Thr Arg Leu Asn Asn Pro Glu Lys Ile
    1310                1315                1320

Arg Lys Ala Glu Asn Glu Asp Pro Lys Leu Lys Met Ser Leu Cys
    1325                1330                1335

Phe Arg Trp Tyr Leu Gly Leu Ser Ser Phe Trp Ala Asn Asn Gly
    1340                1345                1350

Ile Ala Asp Arg Thr Met Asp Tyr Gln Ile Trp Cys Gly Pro Ala
    1355                1360                1365

Ile Gly Ala Phe Asn Asp Phe Ile Ala Asp Ser Tyr Leu Asp Val
    1370                1375                1380

Ala Val Ser Gly Glu Phe Pro Asp Val Val Gln Ile Asn Leu Gln
    1385                1390                1395

Ile Leu Ser Gly Ala Ala Tyr Leu Gln Arg Leu Leu Ser Val Lys
    1400                1405                1410

Leu Ala Pro Arg Ile Asp Val Asp Thr Glu Asp Leu Phe Thr
    1415                1420                1425

Tyr Arg Pro Asp His Ala Leu
    1430                1435

<210> SEQ ID NO 7
<211> LENGTH: 1395
<212> TYPE: DNA
<213> ORGANISM: Schizochytrium sp.

<400> SEQUENCE: 7
actcgcatcg cgatcgtggg gatgtcggcg atcctgccga gcggggagaa cgtgcgcgag      60
agctgggagg cgatccgcga tgggctggat tgcctgagcg atctgccggc ggaccgcgtg     120
gacgtgacgg cctactacaa cccggagaag acgaccaagg acaagatcta ctgcaagcgc     180
ggcgggttca tcccggagta cgacttcgac gcgcgtgagt cgggctcaa catgttccag      240 atggaggact cggacgccaa ccagacgatc tcgctgctca aggtgaagga ggcgctgacg     300
gacgccaaca tccggcgtt ctcgagcggt aagaagaaca tcggctgcgt gctgggcatc      360
ggcggcggcc agaaggcgag ccacgagttc tactcgcggc tcaactacgt ggtcgtggac     420
```

```
aaggtgctgc gcaagatggg cctgccggag gaagacgtgg cggcggcggt ggacaagtac    480
aaggcgagtt ccccgagtg gcgcctcgac tctttccccg ggttcctggg caacgtcacg    540
gcggggcgct gctgcaatac cttcaacatg gagggcatga actgcgtcgt ggacgcggcc    600
tgcgcgtcgt cgctgatcgc ggtcaaagtg gcgatcgagg agctgctcta cggcgactgc    660
gatgcgatga tcgcgggtgc cacctgcacg gacaactcga tcgggatgta catggccttc    720
tccaagacgc ccgtgttttc cacgacccg agcgtcaagg cgtacgacgc cgccaccaaa    780
ggcatgctca tcggcgaggg ctcggcgatg ctcgtgctga gcgctacgc ggacgccgtg    840
cgcgacggcg acaccgtgca cgccgtcatc aagggggtgcg cgtcctcgag cgacggcaag    900
gcggcgggca tctacacgcc gacaatctcg gccaggagg aggccctgcg ccgcgcctac    960
gcccgcgcca atgtcgaccc ggccactgtg acgctggtgg agggccacgg cacgggtacg   1020
ccggtgggcg acaagatcga gctgacggcg ctgagcaacc tcttctccaa ggcgttttct   1080
gccaacggtg gcggcgcgga ggaagcagag caggtggcgg tgggcagcat caagtcgcag   1140
atcgggcacc tcaaggcggt ggccgggctg ccgggctgg tcaaggtggt gctggcgctc   1200
aagcacaaga cgctgccgca gacgatcaac gtcgacaagc cgccgtcgct ggtggacggg   1260
accccgatcc agcagtcgcc gctgtacgtc aacacgatga accgcccctg gttcacgccc   1320
gtaggggtgc cgcgccgcgc cggcgtgtcg tcgtttgggt ttggcggtgc caactaccac   1380
gccgtgctgg aggag                                                    1395

<210> SEQ ID NO 8
<211> LENGTH: 465
<212> TYPE: PRT
<213> ORGANISM: Schizochytrium sp.

<400> SEQUENCE: 8

Thr Arg Ile Ala Ile Val Gly Met Ser Ala Ile Leu Pro Ser Gly Glu
1               5                  10                  15

Asn Val Arg Glu Ser Trp Glu Ala Ile Arg Asp Gly Leu Asp Cys Leu
            20                  25                  30

Ser Asp Leu Pro Ala Asp Arg Val Asp Val Thr Ala Tyr Tyr Asn Pro
        35                  40                  45

Glu Lys Thr Thr Lys Asp Lys Ile Tyr Cys Lys Arg Gly Gly Phe Ile
    50                  55                  60

Pro Glu Tyr Asp Phe Asp Ala Arg Glu Phe Gly Leu Asn Met Phe Gln
65                  70                  75                  80

Met Glu Asp Ser Asp Ala Asn Gln Thr Ile Ser Leu Leu Lys Val Lys
                85                  90                  95

Glu Ala Leu Thr Asp Ala Asn Ile Pro Ala Phe Ser Ser Gly Lys Lys
            100                 105                 110

Asn Ile Gly Cys Val Leu Gly Ile Gly Gly Gln Lys Ala Ser His
        115                 120                 125

Glu Phe Tyr Ser Arg Leu Asn Tyr Val Val Asp Lys Val Leu Arg
    130                 135                 140

Lys Met Gly Leu Pro Glu Glu Asp Val Ala Ala Val Asp Lys Tyr
145                 150                 155                 160

Lys Ala Ser Phe Pro Glu Trp Arg Leu Asp Ser Phe Pro Gly Phe Leu
                165                 170                 175

Gly Asn Val Thr Ala Gly Arg Cys Cys Asn Thr Phe Asn Met Glu Gly
            180                 185                 190

Met Asn Cys Val Val Asp Ala Ala Cys Ala Ser Ser Leu Ile Ala Val
```

-continued

|  | 195 |  |  | 200 |  |  | 205 |  |  |  |
| - | - | - | - | - | - | - | - | - | - | - |

Lys Val Ala Ile Glu Leu Leu Tyr Gly Asp Cys Asp Ala Met Ile
210              215              220

Ala Gly Ala Thr Cys Thr Asp Asn Ser Ile Gly Met Tyr Met Ala Phe
225              230              235              240

Ser Lys Thr Pro Val Phe Ser Thr Asp Pro Ser Val Lys Ala Tyr Asp
              245              250              255

Ala Ala Thr Lys Gly Met Leu Ile Gly Glu Gly Ser Ala Met Leu Val
              260              265              270

Leu Lys Arg Tyr Ala Asp Ala Val Arg Asp Gly Asp Thr Val His Ala
              275              280              285

Val Ile Lys Gly Cys Ala Ser Ser Asp Gly Lys Ala Ala Gly Ile
290              295              300

Tyr Thr Pro Thr Ile Ser Gly Gln Glu Glu Ala Leu Arg Arg Ala Tyr
305              310              315              320

Ala Arg Ala Asn Val Asp Pro Ala Thr Val Thr Leu Val Glu Gly His
              325              330              335

Gly Thr Gly Thr Pro Val Gly Asp Lys Ile Glu Leu Thr Ala Leu Ser
              340              345              350

Asn Leu Phe Ser Lys Ala Phe Ser Ala Asn Gly Gly Ala Glu Glu
              355              360              365

Ala Glu Gln Val Ala Val Gly Ser Ile Lys Ser Gln Ile Gly His Leu
370              375              380

Lys Ala Val Ala Gly Leu Ala Gly Leu Val Lys Val Val Leu Ala Leu
385              390              395              400

Lys His Lys Thr Leu Pro Gln Thr Ile Asn Val Asp Lys Pro Pro Ser
              405              410              415

Leu Val Asp Gly Thr Pro Ile Gln Gln Ser Pro Leu Tyr Val Asn Thr
              420              425              430

Met Asn Arg Pro Trp Phe Thr Pro Val Gly Val Pro Arg Arg Ala Gly
              435              440              445

Val Ser Ser Phe Gly Phe Gly Gly Ala Asn Tyr His Ala Val Leu Glu
              450              455              460

Glu
465

```
<210> SEQ ID NO 9
<211> LENGTH: 903
<212> TYPE: DNA
<213> ORGANISM: Schizochytrium sp.

<400> SEQUENCE: 9
ttctcgggcc agggcgcgca gtacacgcac atgttcagcg acgtggcgat gaactggccc      60
ccgttccgcg agagcgtcgc cgccatggac cgcgcccagc gcgagcgctt cgggcggcct     120
gccaagcgcg tgagcagcgt gctgtacccg cgcaagccgt acggcgacga accgcggcag     180
gaccacaagg agatctcgca aacgcgctac tcgcagcccg caacgctcgc gtgctcggtc     240
ggcgcctttg acatcttcaa agcggcggga ctggcgccga gctttgcggc gggccactcg     300
ctgggcgagt tgcggcgct ctacgcggcc gggtcgctcg atcgcgacgc cgtcttcgac     360
ctggtctgcg cgcgcgccaa ggccatgagc gacttcacgg cccaggccag cagcagcggt     420
ggcgccatgg cggccgtgat ggcgccaag gcggaccagc tctcgctggg tggcgcgccc     480
gacgtgtggc tcgccaacag caactcgccc tcgcagaccg tgatcacggg aaccgccgaa     540
```

-continued

```
gcagtggctg cggcctctga caagttgcgc tgcagcggca acttccgcgt cgtgcctctg    600
gcctgcgagg cggccttcca ctcgccgcac atgcgcggcg cggagcagac gtttgcgtcg    660
gcgctcgcgc aggcgcccgt gtcggcaccg gcggctgctc ggttctactc taacgtgacg    720
gggggcgccg cggtaacctc gcccgcggac gtcaaaacga acctgggcaa gcacatgacg    780
agccctgtgc agttcgtgca gcaggtgcga gccatgcacg cggcgggcgc gcgtgtgttt    840
gtggagtttg gcccaagca ggtcctgtcg cgcctcgtca aggagaccct tggcgaggcc    900
ggc                                                                  903
```

<210> SEQ ID NO 10
<211> LENGTH: 301
<212> TYPE: PRT
<213> ORGANISM: Schizochytrium sp.

<400> SEQUENCE: 10

```
Phe Ser Gly Gln Gly Ala Gln Tyr Thr His Met Phe Ser Asp Val Ala
1               5                   10                  15

Met Asn Trp Pro Pro Phe Arg Glu Ser Val Ala Ala Met Asp Arg Ala
            20                  25                  30

Gln Arg Glu Arg Phe Gly Arg Pro Ala Lys Arg Val Ser Ser Val Leu
        35                  40                  45

Tyr Pro Arg Lys Pro Tyr Gly Asp Glu Pro Arg Gln Asp His Lys Glu
    50                  55                  60

Ile Ser Gln Thr Arg Tyr Ser Gln Pro Ala Thr Leu Ala Cys Ser Val
65                  70                  75                  80

Gly Ala Phe Asp Ile Phe Lys Ala Ala Gly Leu Ala Pro Ser Phe Ala
                85                  90                  95

Ala Gly His Ser Leu Gly Glu Phe Ala Ala Leu Tyr Ala Ala Gly Ser
            100                 105                 110

Leu Asp Arg Asp Ala Val Phe Asp Leu Val Cys Ala Arg Ala Lys Ala
        115                 120                 125

Met Ser Asp Phe Thr Ala Gln Ala Ser Ser Ser Gly Gly Ala Met Ala
    130                 135                 140

Ala Val Ile Gly Ala Lys Ala Asp Gln Leu Ser Leu Gly Gly Ala Pro
145                 150                 155                 160

Asp Val Trp Leu Ala Asn Ser Asn Ser Pro Ser Gln Thr Val Ile Thr
                165                 170                 175

Gly Thr Ala Glu Ala Val Ala Ala Ser Asp Lys Leu Arg Cys Ser
            180                 185                 190

Gly Asn Phe Arg Val Val Pro Leu Ala Cys Glu Ala Ala Phe His Ser
        195                 200                 205

Pro His Met Arg Gly Ala Glu Gln Thr Phe Ala Ser Ala Leu Ala Gln
    210                 215                 220

Ala Pro Val Ser Ala Pro Ala Ala Ala Arg Phe Tyr Ser Asn Val Thr
225                 230                 235                 240

Gly Gly Ala Ala Val Thr Ser Pro Ala Asp Val Lys Thr Asn Leu Gly
                245                 250                 255

Lys His Met Thr Ser Pro Val Gln Phe Val Gln Gln Val Arg Ala Met
            260                 265                 270

His Ala Ala Gly Ala Arg Val Phe Val Glu Phe Gly Pro Lys Gln Val
        275                 280                 285

Leu Ser Arg Leu Val Lys Glu Thr Leu Gly Glu Ala Gly
    290                 295                 300
```

<210> SEQ ID NO 11
<211> LENGTH: 2103
<212> TYPE: DNA
<213> ORGANISM: Schizochytrium sp.

<400> SEQUENCE: 11

| | | | | | |
|---|---|---|---|---|---|
| tccggcaaca | gcaagagcac | tcgtggcagt | gctgatctgc | aagcgctgct | ggccaaggcg | 60 |
| gagactgtgg | tgatggctgt | gctggctgcc | aagactggct | acgaggccga | catggttgag | 120 |
| gcggacatgg | acctggaggc | cgagctcggc | atcgactcga | tcaagcgcgt | ggagatcctt | 180 |
| tccgaggtgc | agggccagct | gggcgtcgag | gccaaggacg | tggatgcgct | gagccgcacg | 240 |
| cgcacggtcg | gtgaggttgt | ggacgccatg | aaggcggaga | tcgtggctgc | ctctggtggt | 300 |
| agtgctcctg | cggttccttc | ggcgcccgct | gcttctgcag | ctccgactcc | cgctgcttcg | 360 |
| actgcgcctt | ctgctgatct | gcaagcgctg | ctgtccaagg | cggagactgt | ggtgatggct | 420 |
| gtgctggcgg | ccaagactgg | ctacgaggcc | gacatggtcg | aggcggacat | ggacctggag | 480 |
| gccgagctcg | gcatcgactc | gatcaagcgc | gtggagatcc | tctcggaggt | gcagggccag | 540 |
| ctgggcgtcg | aggccaagga | cgtggatgcg | ctgagccgca | cgcgcacggt | cggtgaggtt | 600 |
| gtggatgcca | tgaaggcgga | aatcgtggct | gcctctgctg | gtagtgctcc | tgctcctgct | 660 |
| gttccttcgg | cgcccgctgc | ttctgcagct | ccgactcccg | ctgcttcgac | tgcgccttct | 720 |
| gctgatctgc | aagcgctgct | gtccaaggcg | gagacggtgg | tgatggctgt | gctggcggcc | 780 |
| aagactggct | acgaggccga | catggtcgag | gcggacatgg | acctggaggc | cgagctcggc | 840 |
| atcgactcga | tcaagcgcgt | ggagatcctc | tcggaggtgc | agggccagct | gggcgtcgag | 900 |
| gccaaggacg | tggatgcgct | gagccgcacg | cgcacggtcg | gtgaggttgt | ggatgccatg | 960 |
| aaggcggaaa | tcgtggctgc | ctctggtggt | agtgctcctg | ctcctgcggt | tccttcggcg | 1020 |
| cccgctgctt | ctgcagctcc | gactcccgcg | gctgcgacag | cgccttctgc | tgatctgcaa | 1080 |
| gcgctgctgg | ccaaggcgga | gactgtggtg | atggctgtgc | tggcggccaa | gactggctac | 1140 |
| gaggccgaca | tggtcgaggc | ggacatggac | ctggaggccg | agctcggcat | cgactcgatc | 1200 |
| aagcgcgtgg | agatcctttc | cgaggtgcag | ggccagctgg | gcgtcgaggc | caaggacgta | 1260 |
| gatgcgctga | gccgcacgcg | cacggtcggt | gaggttgtgg | atgccatgaa | ggcggagatc | 1320 |
| gtggctgcct | gctggtag | tgctcctgct | cctgctgttc | cttcggcgcc | cgctgcttct | 1380 |
| gcagctccga | ctcccgctgc | ttcgactgcg | ccttctgctg | atctgcaagc | gctgctgtcc | 1440 |
| aaggcggaga | ctgtggtgat | ggctgtgctg | gcggccaaga | ctggctacga | ggccgacatg | 1500 |
| gtcgaggcgg | acatggacct | ggaggccgag | ctcggcatcg | actcgatcaa | gcgcgtggag | 1560 |
| atcctctcgg | aggtgcaggg | ccagctgggc | gtcgaggcca | aggacgtgga | tgcgctgagc | 1620 |
| cgcacgcgca | cggtcggtga | ggttgtggat | gccatgaagg | cggaaatcgt | ggctgcctct | 1680 |
| ggtggtagtg | ctcctgctgc | tgctgttcct | tcggcgcccg | ctgcttctgc | agctccgact | 1740 |
| cctgcgactg | cgccttctgc | tgatctgcaa | gcgctgctgt | ccaaggcgga | gactgtggtg | 1800 |
| atggctgtgc | tggcggccaa | gactggctac | gaggccgaca | tggtcgaggc | ggacatggac | 1860 |
| ctggaggccg | agctcggcat | cgactcgatc | aagcgcgtgg | agatcctttc | cgaggtgcag | 1920 |
| ggccagctgg | gcgtcgaggc | caaggacgta | gatgcgctga | gccgcacgcg | cacggtcggt | 1980 |
| gaagtggtgg | acgccatgaa | ggcggagatc | gtggctgcct | ctggtggtag | tgctcctgct | 2040 |
| gctccttcgg | cgcccgcgct | tcttccaacg | ctgtttggtt | ccgagtgcga | ggacctgtct | 2100 |
| ctg | | | | | | 2103 |

<210> SEQ ID NO 12
<211> LENGTH: 701
<212> TYPE: PRT
<213> ORGANISM: Schizochytrium sp.

<400> SEQUENCE: 12

```
Ser Gly Asn Ser Lys Ser Thr Arg Gly Ser Ala Asp Leu Gln Ala Leu
1               5                   10                  15

Leu Ala Lys Ala Glu Thr Val Val Met Ala Val Leu Ala Ala Lys Thr
                20                  25                  30

Gly Tyr Glu Ala Asp Met Val Glu Ala Asp Met Asp Leu Glu Ala Glu
            35                  40                  45

Leu Gly Ile Asp Ser Ile Lys Arg Val Glu Ile Leu Ser Glu Val Gln
50                  55                  60

Gly Gln Leu Gly Val Glu Ala Lys Asp Val Asp Ala Leu Ser Arg Thr
65                  70                  75                  80

Arg Thr Val Gly Glu Val Val Asp Ala Met Lys Ala Glu Ile Val Ala
                85                  90                  95

Ala Ser Gly Gly Ser Ala Pro Ala Val Pro Ser Ala Pro Ala Ala Ser
            100                 105                 110

Ala Ala Pro Thr Pro Ala Ala Ser Thr Ala Pro Ser Ala Asp Leu Gln
        115                 120                 125

Ala Leu Leu Ser Lys Ala Glu Thr Val Val Met Ala Val Leu Ala Ala
130                 135                 140

Lys Thr Gly Tyr Glu Ala Asp Met Val Glu Ala Asp Met Asp Leu Glu
145                 150                 155                 160

Ala Glu Leu Gly Ile Asp Ser Ile Lys Arg Val Glu Ile Leu Ser Glu
                165                 170                 175

Val Gln Gly Gln Leu Gly Val Glu Ala Lys Asp Val Asp Ala Leu Ser
            180                 185                 190

Arg Thr Arg Thr Val Gly Glu Val Val Asp Ala Met Lys Ala Glu Ile
        195                 200                 205

Val Ala Ala Ser Ala Gly Ser Ala Pro Ala Pro Ala Val Pro Ser Ala
210                 215                 220

Pro Ala Ser Ala Ala Pro Thr Pro Ala Ala Ser Thr Ala Pro Ser
225                 230                 235                 240

Ala Asp Leu Gln Ala Leu Leu Ser Lys Ala Glu Thr Val Val Met Ala
                245                 250                 255

Val Leu Ala Ala Lys Thr Gly Tyr Glu Ala Asp Met Val Glu Ala Asp
            260                 265                 270

Met Asp Leu Glu Ala Glu Leu Gly Ile Asp Ser Ile Lys Arg Val Glu
        275                 280                 285

Ile Leu Ser Glu Val Gln Gly Gln Leu Gly Val Glu Ala Lys Asp Val
290                 295                 300

Asp Ala Leu Ser Arg Thr Arg Thr Val Gly Glu Val Val Asp Ala Met
305                 310                 315                 320

Lys Ala Glu Ile Val Ala Ala Ser Gly Gly Ser Ala Pro Ala Pro Ala
                325                 330                 335

Val Pro Ser Ala Pro Ala Ala Ser Ala Ala Pro Thr Pro Ala Ala
            340                 345                 350

Thr Ala Pro Ser Ala Asp Leu Gln Ala Leu Leu Ala Lys Ala Glu Thr
        355                 360                 365

Val Val Met Ala Val Leu Ala Ala Lys Thr Gly Tyr Glu Ala Asp Met
```

Val Glu Ala Asp Met Asp Leu Glu Ala Glu Leu Gly Ile Asp Ser Ile
385                 390                 395                 400

Lys Arg Val Glu Ile Leu Ser Glu Val Gln Gly Gln Leu Gly Val Glu
            405                 410                 415

Ala Lys Asp Val Asp Ala Leu Ser Arg Thr Arg Thr Val Gly Glu Val
            420                 425                 430

Val Asp Ala Met Lys Ala Glu Ile Val Ala Ala Ser Ala Gly Ser Ala
            435                 440                 445

Pro Ala Pro Ala Val Pro Ser Ala Pro Ala Ala Ser Ala Ala Pro Thr
450                 455                 460

Pro Ala Ala Ser Thr Ala Pro Ser Ala Asp Leu Gln Ala Leu Leu Ser
465                 470                 475                 480

Lys Ala Glu Thr Val Val Met Ala Val Leu Ala Ala Lys Thr Gly Tyr
                485                 490                 495

Glu Ala Asp Met Val Glu Ala Asp Met Asp Leu Glu Ala Glu Leu Gly
                500                 505                 510

Ile Asp Ser Ile Lys Arg Val Glu Ile Leu Ser Glu Val Gln Gly Gln
            515                 520                 525

Leu Gly Val Glu Ala Lys Asp Val Asp Ala Leu Ser Arg Thr Arg Thr
530                 535                 540

Val Gly Glu Val Val Asp Ala Met Lys Ala Glu Ile Val Ala Ala Ser
545                 550                 555                 560

Gly Gly Ser Ala Pro Ala Ala Val Pro Ser Ala Pro Ala Ala Ser
                565                 570                 575

Ala Ala Pro Thr Pro Ala Thr Ala Pro Ser Ala Asp Leu Gln Ala Leu
            580                 585                 590

Leu Ser Lys Ala Glu Thr Val Val Met Ala Val Leu Ala Ala Lys Thr
            595                 600                 605

Gly Tyr Glu Ala Asp Met Val Glu Ala Asp Met Asp Leu Glu Ala Glu
610                 615                 620

Leu Gly Ile Asp Ser Ile Lys Arg Val Glu Ile Leu Ser Glu Val Gln
625                 630                 635                 640

Gly Gln Leu Gly Val Glu Ala Lys Asp Val Asp Ala Leu Ser Arg Thr
                645                 650                 655

Arg Thr Val Gly Glu Val Val Asp Ala Met Lys Ala Glu Ile Val Ala
                660                 665                 670

Ala Ser Gly Gly Ser Ala Pro Ala Ala Pro Ser Ala Pro Ala Leu Leu
            675                 680                 685

Pro Thr Leu Phe Gly Ser Glu Cys Glu Asp Leu Ser Leu
690                 695                 700

<210> SEQ ID NO 13
<211> LENGTH: 276
<212> TYPE: DNA
<213> ORGANISM: Schizochytrium sp.

<400> SEQUENCE: 13
agtgctgatc tgcaagcgct gctggccaag gcggagactg tggtgatggc tgtgctggct      60
gccaagactg gctacgaggc cgacatggtt gaggcggaca tggacctgga ggccgagctc     120
ggcatcgact cgatcaagcg cgtggagatc ctttccgagg tgcagggcca gctgggcgtc     180
gaggccaagg acgtggatgc gctgagccgc acgcgcacgg tcggtgaggt tgtggacgcc     240
atgaaggcgg agatcgtggc tgcctctggt ggtagt                               276

<210> SEQ ID NO 14
<211> LENGTH: 92
<212> TYPE: PRT
<213> ORGANISM: Schizochytrium sp.

<400> SEQUENCE: 14

Ser Ala Asp Leu Gln Ala Leu Leu Ala Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Gly Gly Ser
                85                  90

<210> SEQ ID NO 15
<211> LENGTH: 276
<212> TYPE: DNA
<213> ORGANISM: Schizochytrium sp.

<400> SEQUENCE: 15
tctgctgatc tgcaagcgct gctgtccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcggtgaggt tgtggatgcc     240
atgaaggcgg aaatcgtggc tgcctctgct ggtagt                              276

<210> SEQ ID NO 16
<211> LENGTH: 92
<212> TYPE: PRT
<213> ORGANISM: Schizochytrium sp.

<400> SEQUENCE: 16

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Ala Gly Ser
                85                  90

<210> SEQ ID NO 17
<211> LENGTH: 276
<212> TYPE: DNA
<213> ORGANISM: Schizochytrium sp.

<400> SEQUENCE: 17

```
tctgctgatc tgcaagcgct gctgtccaag gcggagacgg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcggtgaggt tgtggatgcc     240
atgaaggcgg aaatcgtggc tgcctctggt ggtagt                                276
```

<210> SEQ ID NO 18
<211> LENGTH: 92
<212> TYPE: PRT
<213> ORGANISM: Schizochytrium sp.

<400> SEQUENCE: 18

```
Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Val Val Asp Ala
65                  70                  75                  80

Met Lys Ala Glu Ile Val Ala Ala Ser Gly Gly Ser
                85                  90
```

<210> SEQ ID NO 19
<211> LENGTH: 276
<212> TYPE: DNA
<213> ORGANISM: Schizochytrium sp.

<400> SEQUENCE: 19

```
tctgctgatc tgcaagcgct gctggccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctttccgagg tgcagggcca gctgggcgtc     180
gaggccaagg acgtagatgc gctgagccgc acgcgcacgg tcggtgaggt tgtggatgcc     240
atgaaggcgg agatcgtggc tgcctctgct ggtagt                                276
```

<210> SEQ ID NO 20
<211> LENGTH: 92
<212> TYPE: PRT
<213> ORGANISM: Schizochytrium sp.

<400> SEQUENCE: 20

```
Ser Ala Asp Leu Gln Ala Leu Leu Ala Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Val Val Asp Ala
65                  70                  75                  80

Met Lys Ala Glu Ile Val Ala Ala Ser Ala Gly Ser
                85                  90
```

<210> SEQ ID NO 21
<211> LENGTH: 276
<212> TYPE: DNA
<213> ORGANISM: Schizochytrium sp.

<400> SEQUENCE: 21

```
tctgctgatc tgcaagcgct gctgtccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcggtgaggt tgtggatgcc     240
atgaaggcgg aaatcgtggc tgcctctggt ggtagt                                276
```

<210> SEQ ID NO 22
<211> LENGTH: 92
<212> TYPE: PRT
<213> ORGANISM: Schizochytrium sp.

<400> SEQUENCE: 22

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Val Val Asp Ala
65                  70                  75                  80

Met Lys Ala Glu Ile Val Ala Ala Ser Gly Gly Ser
                85                  90

<210> SEQ ID NO 23
<211> LENGTH: 276
<212> TYPE: DNA
<213> ORGANISM: Schizochytrium sp.

<400> SEQUENCE: 23

```
tctgctgatc tgcaagcgct gctgtccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctttccgagg tgcagggcca gctgggcgtc     180
gaggccaagg acgtagatgc gctgagccgc acgcgcacgg tcggtgaagt ggtggacgcc     240
atgaaggcgg agatcgtggc tgcctctggt ggtagt                                276
```

<210> SEQ ID NO 24
<211> LENGTH: 92
<212> TYPE: PRT
<213> ORGANISM: Schizochytrium sp.

<400> SEQUENCE: 24

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

```
Glu Ile Leu Ser Glu Val Gln Gly Gln Leu Gly Val Glu Ala Lys Asp
 50                  55                  60

Val Asp Ala Leu Ser Arg Thr Arg Thr Val Gly Glu Val Val Asp Ala
 65                  70                  75                  80

Met Lys Ala Glu Ile Val Ala Ala Ser Gly Gly Ser
                 85                  90

<210> SEQ ID NO 25
<211> LENGTH: 2178
<212> TYPE: DNA
<213> ORGANISM: Schizochytrium sp.

<400> SEQUENCE: 25
```

| | | | | |
|---|---|---|---|---|
| gcgctacagg cggcgctcac gtccgtcgag gcgcagttcg gcaaggtggg tggctttgtg | 60 |
| ttccagttcg gcgacgacga cgtgcaagcg cagctcggct gggcgctgct cgcggccaag | 120 |
| cacctcaaaa cttcgctgtc agaacagatc gagggcggtc gcaccttttt cgtggccgtc | 180 |
| gcgcggctcg acgccagct gggggctctcc ggcaagtcga cgaccgctac cgttgatctc | 240 |
| tcccgcgcgc agcagggcag cgtgttcggc ctgtgcaaga cactcgacct ggagtggccc | 300 |
| gctgtcttct gccgcggaat cgacctggcc gccgacctcg acgccgcaca ggccgcgcgg | 360 |
| tgcctgctgg gcgagctgtc agaccccgac gtggccgtgc gcgagtctgg ttactccgcc | 420 |
| tcgggccagc gctgcacgac aactacgaag tcgctgacta cgggcaagcc gcaccagccg | 480 |
| atctcctcgt cggacctctt tctggtgtcg ggcggcgcgc gcggcatcac cccgctgtgc | 540 |
| gtgcgcgagc tggcgcagcg cgtgggcggc ggcacgtacg tgctcatcgg ccgctcggag | 600 |
| ctgcccacga cggagcctgc ctgggcggtc ggcgtggagt ctggcaagcc gctggagaag | 660 |
| gccgcgctgg cgttcctgaa ggcggagttt cagcgggcc gcggggccaa gccgacgccg | 720 |
| atgctgcaca agaagctcgt gggcgccgtg gtcggagcgc gcgaggtgcg agcctcgctc | 780 |
| gccgagatca ctgcacaggg cgccacggct gtgtacgagt cgtgcgacgt gagctctgcc | 840 |
| gccaaggtgc gtgagatggt agagcgcgtg cagcagcagg gcgggcggcg cgtgtcgggc | 900 |
| gtgttccacg cgtcgggcgt gctgcgcgac aagctcgtgg agaacaagtc gctggcggac | 960 |
| ttcagcgccg tgtacgacac caaggtgggc ggcctcatca acctgctggc ctgcgtggac | 1020 |
| ctggcgcagc tgcgtcacct cgtgctcttc agctcgctcg cgggcttcca cggcaacgtc | 1080 |
| gggcagtcgg actacgcaat ggccaacgag gcgctcaaca agctggcggc gcacctgtcg | 1140 |
| gcggtgcacc cgcagctgtg cgcgcgctcg atctgcttcg gaccgtggga cggcggcatg | 1200 |
| gtgacccccg cgctcaaggc caacttcatc cgcatgggca tccagatcat cccgcgccaa | 1260 |
| ggcggcgcgc agaccgtcgc caacatgctc gtcagtagct cccccggtca gctgctcgtg | 1320 |
| ggcaactggg gcgtgccacc cgtcgtgccg agtgccaccg agcacaccgt gctgcagacg | 1380 |
| ctccgccaga gcgacaaccc cttcctcgac tcgcacgtga tccagggccg ccgcgtgctg | 1440 |
| cccatgaccc tggccgtggg ctacatgcg caccaggcgc agagcatcta cgcgggccac | 1500 |
| cagctgtggg ccgtcgagga cgcccagctc ttcaagggca tcgccatcga caatggcgcc | 1560 |
| gacgtgcccg tgcgcgtgga gctgtcgcgc cgcaaggagg agcaggagga cgccggcaag | 1620 |
| gtcaaggtca aggtgcaggt gctgctcaaa tcgcaggtca acggcaagtc ggtgcccgcg | 1680 |
| tacaaggcga ccgtcgtgct gtcccctgcg ccgcgcccca gcgtcatcac gcgtgacttc | 1740 |
| gacctcaccc cggacccggc ctgcacggag cacgacctct acgacggcaa gacgctcttc | 1800 |
| cacggcaagg ccttccaggg catcgagcag gtgctctcgg cgacgcccaa gcagctcacc | 1860 |

-continued

```
gccaagtgcc gcaatttgcc cctcacgccc gagcagcgcg gccagttcgt cgttaacctc    1920
agccagcagg acccgttcca ggcggacatt gcgttccagg cgatgctcgt ctgggcgcgc    1980
atgctgcgcc aatcggcggc cctgcccaac aactgcgagc gcttcgactt ttacaagccg    2040
atggccccgg cgccacctca ctacacgtcg gtcaagctgg cctcggcctc acccttggtg    2100
gactctgtgt gcaagtgcac cgtggcgatg cacgatgagc aaggtgaggt gtacttttct    2160
gctcgtgcca gcgtcgtc                                                  2178
```

<210> SEQ ID NO 26
<211> LENGTH: 726
<212> TYPE: PRT
<213> ORGANISM: Schizochytrium sp.

<400> SEQUENCE: 26

```
Ala Leu Gln Ala Ala Leu Thr Ser Val Glu Ala Gln Phe Gly Lys Val
1               5                   10                  15

Gly Gly Phe Val Phe Gln Phe Gly Asp Asp Val Gln Ala Gln Leu
            20                  25                  30

Gly Trp Ala Leu Leu Ala Ala Lys His Leu Lys Thr Ser Leu Ser Glu
        35                  40                  45

Gln Ile Glu Gly Gly Arg Thr Phe Phe Val Ala Val Ala Arg Leu Asp
    50                  55                  60

Gly Gln Leu Gly Leu Ser Gly Lys Ser Thr Thr Ala Thr Val Asp Leu
65                  70                  75                  80

Ser Arg Ala Gln Gln Gly Ser Val Phe Gly Leu Cys Lys Thr Leu Asp
                85                  90                  95

Leu Glu Trp Pro Ala Val Phe Cys Arg Gly Ile Asp Leu Ala Ala Asp
            100                 105                 110

Leu Asp Ala Ala Gln Ala Ala Arg Cys Leu Leu Gly Glu Leu Ser Asp
        115                 120                 125

Pro Asp Val Ala Val Arg Glu Ser Gly Tyr Ser Ala Ser Gly Gln Arg
    130                 135                 140

Cys Thr Thr Thr Thr Lys Ser Leu Thr Thr Gly Lys Pro His Gln Pro
145                 150                 155                 160

Ile Ser Ser Ser Asp Leu Phe Leu Val Ser Gly Gly Ala Arg Gly Ile
                165                 170                 175

Thr Pro Leu Cys Val Arg Glu Leu Ala Gln Arg Val Gly Gly Gly Thr
            180                 185                 190

Tyr Val Leu Ile Gly Arg Ser Glu Leu Pro Thr Thr Glu Pro Ala Trp
        195                 200                 205

Ala Val Gly Val Glu Ser Gly Lys Pro Leu Glu Lys Ala Ala Leu Ala
    210                 215                 220

Phe Leu Lys Ala Glu Phe Ala Ala Gly Arg Gly Ala Lys Pro Thr Pro
225                 230                 235                 240

Met Leu His Lys Lys Leu Val Gly Ala Val Gly Ala Arg Glu Val
                245                 250                 255

Arg Ala Ser Leu Ala Glu Ile Thr Ala Gln Gly Ala Thr Ala Val Tyr
            260                 265                 270

Glu Ser Cys Asp Val Ser Ser Ala Lys Val Arg Glu Met Val Glu
        275                 280                 285

Arg Val Gln Gln Gln Gly Gly Arg Arg Val Ser Gly Val Phe His Ala
    290                 295                 300

Ser Gly Val Leu Arg Asp Lys Leu Val Glu Asn Lys Ser Leu Ala Asp
```

```
            305                 310                 315                 320
        Phe Ser Ala Val Tyr Asp Thr Lys Val Gly Gly Leu Ile Asn Leu Leu
                        325                 330                 335
        Ala Cys Val Asp Leu Ala Gln Leu Arg His Leu Val Leu Phe Ser Ser
                        340                 345                 350
        Leu Ala Gly Phe His Gly Asn Val Gly Gln Ser Asp Tyr Ala Met Ala
                        355                 360                 365
        Asn Glu Ala Leu Asn Lys Leu Ala Ala His Leu Ser Ala Val His Pro
                370                 375                 380
        Gln Leu Cys Ala Arg Ser Ile Cys Phe Gly Pro Trp Asp Gly Gly Met
        385                 390                 395                 400
        Val Thr Pro Ala Leu Lys Ala Asn Phe Ile Arg Met Gly Ile Gln Ile
                        405                 410                 415
        Ile Pro Arg Gln Gly Gly Ala Gln Thr Val Ala Asn Met Leu Val Ser
                        420                 425                 430
        Ser Ser Pro Gly Gln Leu Leu Val Gly Asn Trp Gly Val Pro Pro Val
                        435                 440                 445
        Val Pro Ser Ala Thr Glu His Thr Val Leu Gln Thr Leu Arg Gln Ser
                        450                 455                 460
        Asp Asn Pro Phe Leu Asp Ser His Val Ile Gln Gly Arg Arg Val Leu
        465                 470                 475                 480
        Pro Met Thr Leu Ala Val Gly Tyr Met Ala His Gln Ala Gln Ser Ile
                        485                 490                 495
        Tyr Ala Gly His Gln Leu Trp Ala Val Glu Asp Ala Gln Leu Phe Lys
                        500                 505                 510
        Gly Ile Ala Ile Asp Asn Gly Ala Asp Val Pro Val Arg Val Glu Leu
                        515                 520                 525
        Ser Arg Arg Lys Glu Glu Gln Glu Asp Ala Gly Lys Val Lys Val Lys
                        530                 535                 540
        Val Gln Val Leu Leu Lys Ser Gln Val Asn Gly Lys Ser Val Pro Ala
        545                 550                 555                 560
        Tyr Lys Ala Thr Val Val Leu Ser Pro Ala Pro Arg Pro Ser Val Ile
                        565                 570                 575
        Thr Arg Asp Phe Asp Leu Thr Pro Asp Pro Ala Cys Thr Glu His Asp
                        580                 585                 590
        Leu Tyr Asp Gly Lys Thr Leu Phe His Gly Lys Ala Phe Gln Gly Ile
                        595                 600                 605
        Glu Gln Val Leu Ser Ala Thr Pro Lys Gln Leu Thr Ala Lys Cys Arg
                        610                 615                 620
        Asn Leu Pro Leu Thr Pro Glu Gln Arg Gly Gln Phe Val Val Asn Leu
        625                 630                 635                 640
        Ser Gln Gln Asp Pro Phe Gln Ala Asp Ile Ala Phe Gln Ala Met Leu
                        645                 650                 655
        Val Trp Ala Arg Met Leu Arg Gln Ser Ala Ala Leu Pro Asn Asn Cys
                        660                 665                 670
        Glu Arg Phe Asp Phe Tyr Lys Pro Met Ala Pro Gly Ala Thr Tyr Tyr
                        675                 680                 685
        Thr Ser Val Lys Leu Ala Ser Ala Ser Pro Leu Val Asp Ser Val Cys
                        690                 695                 700
        Lys Cys Thr Val Ala Met His Asp Glu Gln Gly Glu Val Tyr Phe Ser
        705                 710                 715                 720
        Ala Arg Ala Ser Val Val
                        725
```

<210> SEQ ID NO 27
<211> LENGTH: 39
<212> TYPE: DNA
<213> ORGANISM: Schizochytrium sp.

<400> SEQUENCE: 27
ctcgactcgc acgtgatcca gggccgccgc gtgctgccc                              39

<210> SEQ ID NO 28
<211> LENGTH: 13
<212> TYPE: PRT
<213> ORGANISM: Schizochytrium sp.

<400> SEQUENCE: 28

Leu Asp Ser His Val Ile Gln Gly Arg Arg Val Leu Pro
1               5                   10

<210> SEQ ID NO 29
<211> LENGTH: 1341
<212> TYPE: DNA
<213> ORGANISM: Schizochytrium sp.

<400> SEQUENCE: 29
gataacattg cggtcgtggg catggcggtg cagtatgccg atgcaagaa ccaggacgag         60
ttctgggata cgctgatgcg taaggagatc aactcgagcc cgatctcggc ggagcgcctc       120
ggtacgcgct accgcgacct ccacttccac ccgcagcgca gcaagtacgc cgacaccttc       180
tgcaacgatc gctacggctg cgtcgatgcc agcgtcgaca acgagcacga cctcctcgcc       240
gacctggccc ggcgcgccct gctcgacgcc ggaattaacc tcgacgacgc cagcaccacc       300
gccaacctac gcgacttcgg catcgtgagc ggctgcctgt cgttccccat ggacaatctg       360
cagggcgagc tgctcaatct gtaccaagtg catgtggaga accgcgtggg cgcccagcgc       420
ttccgcgact cgcgccctg tcggagcgc ccgcgcgctg tctcgcccga ggccagcgac         480
ccgcgcgtgt actccgaccc ggcgtccttc gtggccaacc agctcggcct ggggcccgtg       540
cgctacagcc tcgatgcagc ctgcgcgtcg gcgctgtact gcctcaagct ggcgtccgac       600
cacttgctct cgcgcagcgc ggacgtgatg ctgtgcggcg ccacatgctt tccggacccg       660
ttcttcattc tctcggggtt ctccaccttc caggcgatgc cgctgggcgg accggacgat       720
aacccactgt ccgtgccgct gcggcagggc agccagggcc tgacgcccgg agagggcggc       780
gccatcatgg tgctgaagcg cctcgaggac gccgtgcgcg acggcgaccg catctacggc       840
accttgctcg gcacgagtct gagcaacgcc gggtgcggcc tgccgctgag cccgcacctg       900
ccgagcgaga agtcgtgcat ggaggacctg tacacgagcg tcggcatcga cccaagcgag       960
gtgcagtacg tggagtgcca cgccacgggc actccgcagg gcgacgtcgt ggaggtagag      1020
gcgctgcgcc actgctttcg aggtaacacg gaccacccgc cgcgcatggg ctccaccaag      1080
ggcaactttg ccacactct cgtggcggcc gggttcgcag gcatggccaa ggtgctgctg       1140
tcgatgcagc acggcacgat cccgcccacg cccggtgtcg accgctccaa ctgcatcgac      1200
ccgctcgtcg tggacgaggc catcccttgg ccgtactcgt cggcgcaggc gcgggcaggc      1260
aaaccaggcg atgagctcaa gtgcgcctcg ctctccgcct ttggctttgg tggaaccaac      1320
gcgcactgtg tcttccgtga g                                                1341

<210> SEQ ID NO 30
<211> LENGTH: 447

-continued

```
<212> TYPE: PRT
<213> ORGANISM: Schizochytrium sp.

<400> SEQUENCE: 30
```

| | | | | | | | | | | | | | | | |
|---|---|---|---|---|---|---|---|---|---|---|---|---|---|---|---|
| Asp | Asn | Ile | Ala | Val | Val | Gly | Met | Ala | Val | Gln | Tyr | Ala | Gly | Cys | Lys |
| 1 | | | | 5 | | | | | 10 | | | | | 15 | |
| Asn | Gln | Asp | Glu | Phe | Trp | Asp | Thr | Leu | Met | Arg | Lys | Glu | Ile | Asn | Ser |
| | | | 20 | | | | | 25 | | | | | 30 | | |
| Ser | Pro | Ile | Ser | Ala | Glu | Arg | Leu | Gly | Thr | Arg | Tyr | Arg | Asp | Leu | His |
| | | 35 | | | | | 40 | | | | | 45 | | | |
| Phe | His | Pro | Gln | Arg | Ser | Lys | Tyr | Ala | Asp | Thr | Phe | Cys | Asn | Asp | Arg |
| | 50 | | | | | 55 | | | | | 60 | | | | |
| Tyr | Gly | Cys | Val | Asp | Ala | Ser | Val | Asp | Asn | Glu | His | Asp | Leu | Leu | Ala |
| 65 | | | | | 70 | | | | | 75 | | | | | 80 |
| Asp | Leu | Ala | Arg | Arg | Ala | Leu | Leu | Asp | Ala | Gly | Ile | Asn | Leu | Asp | Asp |
| | | | | 85 | | | | | 90 | | | | | 95 | |
| Ala | Ser | Thr | Thr | Ala | Asn | Leu | Arg | Asp | Phe | Gly | Ile | Val | Ser | Gly | Cys |
| | | | 100 | | | | | 105 | | | | | 110 | | |
| Leu | Ser | Phe | Pro | Met | Asp | Asn | Leu | Gln | Gly | Glu | Leu | Leu | Asn | Leu | Tyr |
| | | 115 | | | | | 120 | | | | | 125 | | | |
| Gln | Val | His | Val | Glu | Asn | Arg | Val | Gly | Ala | Gln | Arg | Phe | Arg | Asp | Ser |
| | 130 | | | | | 135 | | | | | 140 | | | | |
| Arg | Pro | Trp | Ser | Glu | Arg | Pro | Arg | Ala | Val | Ser | Pro | Glu | Ala | Ser | Asp |
| 145 | | | | | 150 | | | | | 155 | | | | | 160 |
| Pro | Arg | Val | Tyr | Ser | Asp | Pro | Ala | Ser | Phe | Val | Ala | Asn | Gln | Leu | Gly |
| | | | | 165 | | | | | 170 | | | | | 175 | |
| Leu | Gly | Pro | Val | Arg | Tyr | Ser | Leu | Asp | Ala | Ala | Cys | Ala | Ser | Ala | Leu |
| | | | 180 | | | | | 185 | | | | | 190 | | |
| Tyr | Cys | Leu | Lys | Leu | Ala | Ser | Asp | His | Leu | Leu | Ser | Arg | Ser | Ala | Asp |
| | | 195 | | | | | 200 | | | | | 205 | | | |
| Val | Met | Leu | Cys | Gly | Ala | Thr | Cys | Phe | Pro | Asp | Pro | Phe | Phe | Ile | Leu |
| | 210 | | | | | 215 | | | | | 220 | | | | |
| Ser | Gly | Phe | Ser | Thr | Phe | Gln | Ala | Met | Pro | Leu | Gly | Gly | Pro | Asp | Asp |
| 225 | | | | | 230 | | | | | 235 | | | | | 240 |
| Asn | Pro | Leu | Ser | Val | Pro | Leu | Arg | Gln | Gly | Ser | Gln | Gly | Leu | Thr | Pro |
| | | | | 245 | | | | | 250 | | | | | 255 | |
| Gly | Glu | Gly | Gly | Ala | Ile | Met | Val | Leu | Lys | Arg | Leu | Glu | Asp | Ala | Val |
| | | | 260 | | | | | 265 | | | | | 270 | | |
| Arg | Asp | Gly | Asp | Arg | Ile | Tyr | Gly | Thr | Leu | Leu | Gly | Thr | Ser | Leu | Ser |
| | | 275 | | | | | 280 | | | | | 285 | | | |
| Asn | Ala | Gly | Cys | Gly | Leu | Pro | Leu | Ser | Pro | His | Leu | Pro | Ser | Glu | Lys |
| | 290 | | | | | 295 | | | | | 300 | | | | |
| Ser | Cys | Met | Glu | Asp | Leu | Tyr | Thr | Ser | Val | Gly | Ile | Asp | Pro | Ser | Glu |
| 305 | | | | | 310 | | | | | 315 | | | | | 320 |
| Val | Gln | Tyr | Val | Glu | Cys | His | Ala | Thr | Gly | Thr | Pro | Gln | Gly | Asp | Val |
| | | | | 325 | | | | | 330 | | | | | 335 | |
| Val | Glu | Val | Glu | Ala | Leu | Arg | His | Cys | Phe | Arg | Gly | Asn | Thr | Asp | His |
| | | | 340 | | | | | 345 | | | | | 350 | | |
| Pro | Pro | Arg | Met | Gly | Ser | Thr | Lys | Gly | Asn | Phe | Gly | His | Thr | Leu | Val |
| | | 355 | | | | | 360 | | | | | 365 | | | |
| Ala | Ala | Gly | Phe | Ala | Gly | Met | Ala | Lys | Val | Leu | Leu | Ser | Met | Gln | His |
| | 370 | | | | | 375 | | | | | 380 | | | | |
| Gly | Thr | Ile | Pro | Pro | Thr | Pro | Gly | Val | Asp | Arg | Ser | Asn | Cys | Ile | Asp |
| 385 | | | | | 390 | | | | | 395 | | | | | 400 |

```
Pro Leu Val Val Asp Glu Ala Ile Pro Trp Pro Tyr Ser Ser Ala Gln
            405                 410                 415

Ala Arg Ala Gly Lys Pro Gly Asp Glu Leu Lys Cys Ala Ser Leu Ser
            420                 425                 430

Ala Phe Gly Phe Gly Gly Thr Asn Ala His Cys Val Phe Arg Glu
            435                 440                 445

<210> SEQ ID NO 31
<211> LENGTH: 1293
<212> TYPE: DNA
<213> ORGANISM: Schizochytrium sp.

<400> SEQUENCE: 31
ggaccgattg ccatcatcgg gatggacgcg acgtttggta ccctcaaggg cctggacgcg      60
tttgagcagg ccatctacaa gggcacggac ggcgccagcg acctgccgag caagcgctgg     120
cggttcctgg cgccgacac ggacttcttg accgccatgg gcctcgacgc cgtgccgcgc      180
gggtgctacg tgcgcgacgt ggacgtggac tacaagcggc tgcggtcgcc gatgatccct     240
gaggacgtcc tgcgcccgca acagctgctg gcggtggcta cgatggaccg cgcgctgcag     300
gacgctggaa tggcgacggg aggcaaggtg gcggtgctgg tggggctcgg cacggacacc     360
gagctgtacc ggcaccgcgc gcgcgtgaca ctcaaggagc ggctcgaccc ggccgcgttc     420
tcgcccgagc aggtgcagga gatgatggac tacatcaacg actgcggcac ctcgacgtcg     480
tacacgtcgt acatcggcaa cctcgtggcc acgcgcgtgt cctcgcagtg gggctttacg     540
ggcccgtcct tcaccgtcac cgaaggcgca aactcggtct accgctgcct cgagctgggc     600
aagttcctgc tcgacacgca ccaggtggac gccgtcgtgg tggccggcgt cgacctctgt     660
gccaccgccg agaaccttta cctcaaggcg cgccgctccg ccatcagccg acaggaccac     720
cctcgcgcca actttgaggc cagcgccgac gggtactttg ccggcgaggg cagcggcgcc     780
ctggtcctca gcgccaggc cgacgttggc tcagacgaca aggtctacgc cagtgtcgcg     840
ggcctcacgt gcgccgcgca gcccgctgaa gccgtgtcgc cgctactact ccaagtccac     900
aacgacgaca cgagaagag ggtggtggag atggtggagc tcgccgccga ctcgggtcgc     960
catgcgccgc acttggccaa ctcgccgctg agcgccgagt cgcagctgga gcaagtgtcc    1020
aagttgctcg cgcaccaggt gccgggctcg gtggccatcg gcagcgtgcg cgccaacgtg    1080
ggagacgtcg ggtacgcctc gggcgccgcg agcctcatca agacggcgct gtgcctccac    1140
aaccgctacc tcccggccaa cccgcagtgg gagcggccgg tggcgccggt ctccgaggcg    1200
ctgtttactt gcccgcgctc gcgtgcctgg ctgaagaacc cgggcgagtc gcgactggcg    1260
gctgtcgcca gtgcctccga gagcgggtcc tgc                                 1293

<210> SEQ ID NO 32
<211> LENGTH: 431
<212> TYPE: PRT
<213> ORGANISM: Schizochytrium sp.

<400> SEQUENCE: 32

Gly Pro Ile Ala Ile Ile Gly Met Asp Ala Thr Phe Gly Thr Leu Lys
1               5                   10                  15

Gly Leu Asp Ala Phe Glu Gln Ala Ile Tyr Lys Gly Thr Asp Gly Ala
            20                  25                  30

Ser Asp Leu Pro Ser Lys Arg Trp Arg Phe Leu Gly Ala Asp Thr Asp
        35                  40                  45
```

```
Phe Leu Thr Ala Met Gly Leu Asp Ala Val Pro Arg Gly Cys Tyr Val
 50                  55                  60

Arg Asp Val Asp Val Asp Tyr Lys Arg Leu Arg Ser Pro Met Ile Pro
 65                  70                  75                  80

Glu Asp Val Leu Arg Pro Gln Gln Leu Leu Ala Val Ala Thr Met Asp
                 85                  90                  95

Arg Ala Leu Gln Asp Ala Gly Met Ala Thr Gly Gly Lys Val Ala Val
                100                 105                 110

Leu Val Gly Leu Gly Thr Asp Thr Glu Leu Tyr Arg His Arg Ala Arg
            115                 120                 125

Val Thr Leu Lys Glu Arg Leu Asp Pro Ala Ala Phe Ser Pro Glu Gln
130                 135                 140

Val Gln Glu Met Met Asp Tyr Ile Asn Asp Cys Gly Thr Ser Thr Ser
145                 150                 155                 160

Tyr Thr Ser Tyr Ile Gly Asn Leu Val Ala Thr Arg Val Ser Gln
                165                 170                 175

Trp Gly Phe Thr Gly Pro Ser Phe Thr Val Thr Glu Gly Ala Asn Ser
                180                 185                 190

Val Tyr Arg Cys Leu Glu Leu Gly Lys Phe Leu Leu Asp Thr His Gln
            195                 200                 205

Val Asp Ala Val Val Ala Gly Val Asp Leu Cys Ala Thr Ala Glu
210                 215                 220

Asn Leu Tyr Leu Lys Ala Arg Arg Ser Ala Ile Ser Arg Gln Asp His
225                 230                 235                 240

Pro Arg Ala Asn Phe Glu Ala Ser Ala Asp Gly Tyr Phe Ala Gly Glu
                245                 250                 255

Gly Ser Gly Ala Leu Val Leu Lys Arg Gln Ala Asp Val Gly Ser Asp
            260                 265                 270

Asp Lys Val Tyr Ala Ser Val Ala Gly Leu Thr Cys Ala Ala Gln Pro
        275                 280                 285

Ala Glu Ala Val Ser Pro Leu Leu Leu Gln Val His Asn Asp Asp Asn
    290                 295                 300

Glu Lys Arg Val Val Glu Met Val Glu Leu Ala Ala Asp Ser Gly Arg
305                 310                 315                 320

His Ala Pro His Leu Ala Asn Ser Pro Leu Ser Ala Glu Ser Gln Leu
                325                 330                 335

Glu Gln Val Ser Lys Leu Leu Ala His Gln Val Pro Gly Ser Val Ala
            340                 345                 350

Ile Gly Ser Val Arg Ala Asn Val Gly Asp Val Gly Tyr Ala Ser Gly
        355                 360                 365

Ala Ala Ser Leu Ile Lys Thr Ala Leu Cys Leu His Asn Arg Tyr Leu
    370                 375                 380

Pro Ala Asn Pro Gln Trp Glu Arg Pro Val Ala Pro Val Ser Glu Ala
385                 390                 395                 400

Leu Phe Thr Cys Pro Arg Ser Arg Ala Trp Leu Lys Asn Pro Gly Glu
                405                 410                 415

Ser Arg Leu Ala Ala Val Ala Ser Ala Ser Glu Ser Gly Ser Cys
            420                 425                 430

<210> SEQ ID NO 33
<211> LENGTH: 1203
<212> TYPE: DNA
<213> ORGANISM: Schizochytrium sp.

<400> SEQUENCE: 33
```

```
acgccggaga agctggagaa ggagttggag ctggcagcca agggtgtacc gcgaagcgcc      60
aaggccgggc gcaactggat gtcgccatcg ggcagcgcct tgcgccgac  acctgtgacc     120
agcgaccgcg tcgcgttcat gtacggcgag ggccgcagcc cctactacgg cgtcgggctc     180
gacctgcacc gcctgtggcc ggcttttgcac gagcgcatca acgacaagac cgcggcgctg    240
tgggagaacg cgactcgtg  gctcatgccg cgcgcggtgg atgccgactc gcagcgcgcc     300
gtgcagacgg cctttgacgc ggaccagatc gagatgttcc gcacgggcat cttcgtgtcc     360
atctgcctca ccgactacgc gcgcgacgtg ctcggggtgc agcccaaggc gtgcttcggc     420
ctcagcctcg gcgagatctc catgctctt  gcgctgtcgc gacgcaactg cggcctgtcg     480
gaccagctca cgcagcgcct acgcacctcg ccggtgtggt cgacacagct ggcggtggag     540
ttccaggcct tgcgcaagct atggaacgtg ccggcggacg cccccgtgga gtccttctgg     600
cagggctact tggttcgcgc cagccgcgcc gaaatcgaga aggcgatcgg gcccgacaac     660
cgcttcgtgc gcctgctgat cgtcaacgac tcgagcagcg cgctgatcgc cggcaaacct    720
gccgagtgtc tgcgcgtgct ggagcgcctg ggcgggcggt tgccgccgat gcccgtcaag     780
caaggcatga ttgggcactg ccccgaagtg gcgccctaca cgccgggcat cgcgcacatc     840
cacgagattt tggagattcc ggacagcccc gtcaagatgt acacctcggt caccaacgcc     900
gagctgcgcg ggggcagcaa cagcagcatc accgagttcg tgcagaagtt gtacacgcgc     960
atcgccgact ttccgggcat cgtcgacaag gtcagccgtg acggccacga tgtcttcgtc    1020
gaggtggggc cgaacaacat cgctccgcc  gcggtcagtg acattcttgg caaggctgcc    1080
accccgcatg tctccgtggc gctggaccgc cccagtgagt cggcgtggac gcagaccctc    1140
aagtcgctgg cgctgctgac cgcccaccgc gtgcccctgc acaacccgac tctgtttgcg    1200
gac                                                                  1203
```

<210> SEQ ID NO 34
<211> LENGTH: 401
<212> TYPE: PRT
<213> ORGANISM: Schizochytrium sp.

<400> SEQUENCE: 34

Thr Pro Glu Lys Leu Glu Lys Glu Leu Glu Leu Ala Ala Lys Gly Val
1               5                   10                  15

Pro Arg Ser Ala Lys Ala Gly Arg Asn Trp Met Ser Pro Ser Gly Ser
                20                  25                  30

Ala Phe Ala Pro Thr Pro Val Thr Ser Asp Arg Val Ala Phe Met Tyr
            35                  40                  45

Gly Glu Gly Arg Ser Pro Tyr Tyr Gly Val Gly Leu Asp Leu His Arg
        50                  55                  60

Leu Trp Pro Ala Leu His Glu Arg Ile Asn Asp Lys Thr Ala Ala Leu
65                  70                  75                  80

Trp Glu Asn Gly Asp Ser Trp Leu Met Pro Arg Ala Val Asp Ala Asp
                85                  90                  95

Ser Gln Arg Ala Val Gln Thr Ala Phe Asp Ala Asp Gln Ile Glu Met
            100                 105                 110

Phe Arg Thr Gly Ile Phe Val Ser Ile Cys Leu Thr Asp Tyr Ala Arg
        115                 120                 125

Asp Val Leu Gly Val Gln Pro Lys Ala Cys Phe Gly Leu Ser Leu Gly
    130                 135                 140

Glu Ile Ser Met Leu Phe Ala Leu Ser Arg Arg Asn Cys Gly Leu Ser

```
         145                 150                 155                 160
Asp Gln Leu Thr Gln Arg Leu Arg Thr Ser Pro Val Trp Ser Thr Gln
                165                 170                 175

Leu Ala Val Glu Phe Gln Ala Leu Arg Lys Leu Trp Asn Val Pro Ala
            180                 185                 190

Asp Ala Pro Val Glu Ser Phe Trp Gln Gly Tyr Leu Val Arg Ala Ser
        195                 200                 205

Arg Ala Glu Ile Glu Lys Ala Ile Gly Pro Asp Asn Arg Phe Val Arg
    210                 215                 220

Leu Leu Ile Val Asn Asp Ser Ser Ala Leu Ile Ala Gly Lys Pro
225                 230                 235                 240

Ala Glu Cys Leu Arg Val Leu Glu Arg Leu Gly Arg Leu Pro Pro
                245                 250                 255

Met Pro Val Lys Gln Gly Met Ile Gly His Cys Pro Glu Val Ala Pro
            260                 265                 270

Tyr Thr Pro Gly Ile Ala His Ile His Glu Ile Leu Glu Ile Pro Asp
        275                 280                 285

Ser Pro Val Lys Met Tyr Thr Ser Val Thr Asn Ala Glu Leu Arg Gly
    290                 295                 300

Gly Ser Asn Ser Ser Ile Thr Glu Phe Val Gln Lys Leu Tyr Thr Arg
305                 310                 315                 320

Ile Ala Asp Phe Pro Gly Ile Val Asp Lys Val Ser Arg Asp Gly His
                325                 330                 335

Asp Val Phe Val Glu Val Gly Pro Asn Asn Met Arg Ser Ala Ala Val
            340                 345                 350

Ser Asp Ile Leu Gly Lys Ala Ala Thr Pro His Val Ser Val Ala Leu
        355                 360                 365

Asp Arg Pro Ser Glu Ser Ala Trp Thr Gln Thr Leu Lys Ser Leu Ala
    370                 375                 380

Leu Leu Thr Ala His Arg Val Pro Leu His Asn Pro Thr Leu Phe Ala
385                 390                 395                 400

Asp
```

<210> SEQ ID NO 35
<211> LENGTH: 1273
<212> TYPE: DNA
<213> ORGANISM: Schizochytrium sp.

<400> SEQUENCE: 35

```
tacgacgtgg actggccgct ctacatgggc gccatggcgg aaggcatctc gtcggtagac    60
ctggtggtcg ctgccgccga ggcccgcatg ctggcatcat tcggagcggc ccgcttgcct   120
atggaccagg tggaactcca gatccgtgag atccagcaac gcacctccaa cgcctttgct   180
gtcaacctga tgccgggtcc tgacgaggcc gcgacggtgg acgcgctgct gcgcacgggc   240
gtctcaatcg tcgaggcatc gggctacacc ggcgcgctct ctgcagacct ggtgcgctac   300
cgtgtcacgg gtctgcgacg aactagttgc ggtgcttctg tgtcggcgac tcaccgtgtg   360
gtcgccaagg tgtcgcgcac cgaggtggcc gagcactttc tgcgcccggc cggcgccgcc   420
gtactagagg cttttggtcgc cgccaaacag attacgcccg agcaggccgc gctggccagc   480
cgcgtcgcca tggccgacga cgtcgcggtg gaggccgact cgggcgggca caccgacaac   540
cgaccgatcc acgtgctgct gccgctcgtg gtggcgcagc gcaaccgctg cgccacctg   600
gtggacacgc cagtgcgcgt cggcgccggc ggcgggatcg cctgtccgcg cgccgcgctg   660
```

```
ctcgcctttt ccctgggcgc cgcctttgtg gtcaccgggt ccgtcaacca actggcccgc    720
gaggctggca ccagcgacgc ggtccgacta ctgctggcga cggccaccta ctcggacgtg    780
gccatggcgc cgggcggcgt ccaggtgctc aagaagcaga ccatgttcgc cgcgcgggcc    840
acgatgctcg cccagctgca ggccaagttc ggctcctttg acgccgtgcc ggagccgcag    900
ctgcgcaagc tcgagcgctc cgtgttcaag cagtccgtgg cggacgtgtg ggctgctgca    960
cgcgaaaagt ttggtgtcga cgctaccgct gcaagtccgc aggagaggat ggcgctctgt   1020
gtgcgctggt acatgtcgca gtcgtcgcga tgggctaccg aggcgacgtc cgcgcgcaag   1080
gcggactacc agatctggtg cggccccgcc atcggcagct tcaacgactt cgttcgcggc   1140
accaagctgg acgcgaccgc tggcaccggc gagtttccgc gcgtcgtgga catcaaccag   1200
cacatcctcc tcggagcctc gcactaccgc cgcgtgcagc aacaacaaca ggacgacgac   1260
gtagaataca tca                                                      1273
```

<210> SEQ ID NO 36
<211> LENGTH: 401
<212> TYPE: PRT
<213> ORGANISM: Schizochytrium sp.

<400> SEQUENCE: 36

```
Tyr Asp Val Asp Trp Pro Leu Tyr Met Gly Ala Met Ala Glu Gly Ile
1               5                   10                  15

Ser Ser Val Asp Leu Val Val Ala Ala Glu Ala Arg Met Leu Ala
            20                  25                  30

Ser Phe Gly Ala Ala Arg Leu Pro Met Asp Gln Val Glu Leu Gln Ile
        35                  40                  45

Arg Glu Ile Gln Gln Arg Thr Ser Asn Ala Phe Ala Val Asn Leu Met
    50                  55                  60

Pro Gly Pro Asp Glu Ala Ala Thr Val Asp Ala Leu Leu Arg Thr Gly
65                  70                  75                  80

Val Ser Ile Val Glu Ala Ser Gly Tyr Thr Gly Ala Leu Ser Ala Asp
                85                  90                  95

Leu Val Arg Tyr Arg Val Thr Gly Leu Arg Arg Thr Ser Cys Gly Ala
            100                 105                 110

Ser Val Ser Ala Thr His Arg Val Ala Lys Val Ser Arg Thr Glu
        115                 120                 125

Val Ala Glu His Phe Leu Arg Pro Ala Pro Ala Ala Val Leu Glu Ala
    130                 135                 140

Leu Val Ala Ala Lys Gln Ile Thr Pro Glu Gln Ala Ala Leu Ala Ser
145                 150                 155                 160

Arg Val Ala Met Ala Asp Asp Val Ala Val Glu Ala Asp Ser Gly Gly
                165                 170                 175

His Thr Asp Asn Arg Pro Ile His Val Leu Pro Leu Val Val Ala
            180                 185                 190

Gln Arg Asn Arg Trp Arg His Leu Val Asp Thr Pro Val Arg Val Gly
        195                 200                 205

Ala Gly Gly Gly Ile Ala Cys Pro Arg Ala Ala Leu Leu Ala Phe Ser
    210                 215                 220

Leu Gly Ala Ala Phe Val Val Thr Gly Ser Val Asn Gln Leu Ala Arg
225                 230                 235                 240

Glu Ala Gly Thr Ser Asp Ala Val Arg Leu Leu Leu Ala Thr Ala Thr
                245                 250                 255

Tyr Ser Asp Val Ala Met Ala Pro Gly Gly Val Gln Val Leu Lys Lys
```

```
                     260                 265                 270
Gln Thr Met Phe Ala Ala Arg Ala Thr Met Leu Ala Gln Leu Gln Ala
            275                 280                 285

Lys Phe Gly Ser Phe Asp Ala Val Pro Glu Pro Gln Leu Arg Lys Leu
            290                 295                 300

Glu Arg Ser Val Phe Lys Gln Ser Val Ala Asp Val Trp Ala Ala Ala
305                 310                 315                 320

Arg Glu Lys Phe Gly Val Asp Ala Thr Ala Ala Ser Pro Gln Glu Arg
                325                 330                 335

Met Ala Leu Cys Val Arg Trp Tyr Met Ser Gln Ser Ser Arg Trp Ala
            340                 345                 350

Thr Glu Ala Thr Ser Ala Arg Lys Ala Asp Tyr Gln Ile Trp Cys Gly
            355                 360                 365

Pro Ala Ile Gly Ser Phe Asn Asp Phe Val Arg Gly Thr Lys Leu Asp
            370                 375                 380

Ala Thr Ala Gly Thr Gly Glu Phe Pro Arg Val Val Asp Ile Asn Gln
385                 390                 395                 400

His

<210> SEQ ID NO 37
<211> LENGTH: 1350
<212> TYPE: DNA
<213> ORGANISM: Schizochytrium sp.

<400> SEQUENCE: 37
atgacatcat cgaagaagac tcccgtgtgg gagatgagca aggaggagct gctggacggc     60
aagacggtgg tcttcgacta caacgagctg ctcgaattcg ccgagggcga cgtgggccaa    120
gtgttcggac ccgagttcga catcatcgac aagtaccggc gtcgcgtgcg gctgccggcg    180
cgcgagtacc tgctcgtgtc gcgcgtgacg ctgatggacg ccgaggtgaa caacttccgc    240
gtcgggtcgc gcatggtgac cgagtacgac gtgcccgtga acggggagct gtcggagggc    300
ggggacgtgc cgtgggcggt gctggtggag tcggggcagt gcgacctgat gctcatctcg    360
tacatgggca tcgacttcca gtgcaagggc gaccgcgtgt accgcctgct caacacatcg    420
ctcaccttct tcgggtggc gcacgagggc gagacgctgg tgtacgacat ccgcgtcacg    480
gggttcgcca agggcgcggg cggggagatc tcgatgttct tcttcgagta cgactgcttc    540
gtggacggcc gcctgctgat cgagatgcgc gacgggtgcg ccgggttctt cacggacgcc    600
gagctggccg ccggcaaggg cgtgcttaag accaaggcgg agctggcggc gcgcgcgcag    660
atccagaagc aggacatcgc gcccttttgcg ccggcgccgt gctcgcacaa gacctcgctg    720
gacgcgcgcg agatgcggct gctcgtggac cgccagtggg cgcgcgtctt cggcagcggc    780
atggcgggca tcgactacaa gttgtgcgct cgcaagatgc tcatgatcga ccgcgtcacg    840
cacctcgacc cgcgcggcgg cgcgcacggc ctcgggctgc tgatcgggga aaggtgctg    900 gagcgcgacc actggtactt ccctgccac tttgtgcgcg acgaggtgat ggccgggtcg    960
ctggtcagcg acggctgctc gcagctcctc aaggtgtaca tgctgtggct cggcctgcac    1020
acgaccgtgg gcgcgttcga ctttcgtccc gtgagcgggc acgccaacaa ggtgcgtgc    1080 cgcgggcaga tctcaccgca caagggcaag ctcgtgtacg tgatggagat caaggaaatg    1140
ggctttgacg cgaagacggg cgatccgttt gcgatcgcgg acgtggacat catcgacgtc    1200
aacttcgagg agggacaggc gttgcggga gtggaagacc tgcacagcta cggccagggc    1260
gacctccgca agaagatcgt cgtcgacttc aagggcatcg cgctctcccct gcagaagcgg    1320
```
aaggagcagc agaaggaaag catgaccgtg                1350

<210> SEQ ID NO 38
<211> LENGTH: 450
<212> TYPE: PRT
<213> ORGANISM: Schizochytrium sp.

<400> SEQUENCE: 38

Met Thr Ser Ser Lys Lys Thr Pro Val Trp Glu Met Ser Lys Glu Glu
1               5                   10                  15

Leu Leu Asp Gly Lys Thr Val Val Phe Asp Tyr Asn Glu Leu Leu Glu
            20                  25                  30

Phe Ala Glu Gly Asp Val Gly Gln Val Phe Gly Pro Glu Phe Asp Ile
        35                  40                  45

Ile Asp Lys Tyr Arg Arg Val Arg Leu Pro Ala Arg Glu Tyr Leu
    50                  55                  60

Leu Val Ser Arg Val Thr Leu Met Asp Ala Glu Val Asn Asn Phe Arg
65                  70                  75                  80

Val Gly Ser Arg Met Val Thr Glu Tyr Asp Val Pro Val Asn Gly Glu
                85                  90                  95

Leu Ser Glu Gly Gly Asp Val Pro Trp Ala Val Leu Val Glu Ser Gly
            100                 105                 110

Gln Cys Asp Leu Met Leu Ile Ser Tyr Met Gly Ile Asp Phe Gln Cys
        115                 120                 125

Lys Gly Asp Arg Val Tyr Arg Leu Leu Asn Thr Ser Leu Thr Phe Phe
    130                 135                 140

Gly Val Ala His Glu Gly Glu Thr Leu Val Tyr Asp Ile Arg Val Thr
145                 150                 155                 160

Gly Phe Ala Lys Gly Ala Gly Gly Glu Ile Ser Met Phe Phe Phe Glu
                165                 170                 175

Tyr Asp Cys Phe Val Asp Gly Arg Leu Leu Ile Glu Met Arg Asp Gly
            180                 185                 190

Cys Ala Gly Phe Phe Thr Asp Ala Glu Leu Ala Ala Gly Lys Gly Val
        195                 200                 205

Leu Lys Thr Lys Ala Glu Leu Ala Ala Arg Ala Gln Ile Gln Lys Gln
    210                 215                 220

Asp Ile Ala Pro Phe Ala Pro Ala Pro Cys Ser His Lys Thr Ser Leu
225                 230                 235                 240

Asp Ala Arg Glu Met Arg Leu Leu Val Asp Arg Gln Trp Ala Arg Val
                245                 250                 255

Phe Gly Ser Gly Met Ala Gly Ile Asp Tyr Lys Leu Cys Ala Arg Lys
            260                 265                 270

Met Leu Met Ile Asp Arg Val Thr His Leu Asp Pro Arg Gly Gly Ala
        275                 280                 285

His Gly Leu Gly Leu Leu Ile Gly Glu Lys Val Leu Glu Arg Asp His
    290                 295                 300

Trp Tyr Phe Pro Cys His Phe Val Arg Asp Glu Val Met Ala Gly Ser
305                 310                 315                 320

Leu Val Ser Asp Gly Cys Ser Gln Leu Leu Lys Val Tyr Met Leu Trp
                325                 330                 335

Leu Gly Leu His Thr Thr Val Gly Ala Phe Asp Phe Arg Pro Val Ser
            340                 345                 350

Gly His Ala Asn Lys Val Arg Cys Arg Gly Gln Ile Ser Pro His Lys
        355                 360                 365

Gly Lys Leu Val Tyr Val Met Glu Ile Lys Glu Met Gly Phe Asp Ala
    370                 375                 380

Lys Thr Gly Asp Pro Phe Ala Ile Ala Asp Val Asp Ile Ile Asp Val
385                 390                 395                 400

Asn Phe Glu Glu Gly Gln Ala Phe Ala Gly Val Glu Asp Leu His Ser
                405                 410                 415

Tyr Gly Gln Gly Asp Leu Arg Lys Lys Ile Val Val Asp Phe Lys Gly
            420                 425                 430

Ile Ala Leu Ser Leu Gln Lys Arg Lys Glu Gln Gln Lys Glu Ser Met
        435                 440                 445

Thr Val
    450

<210> SEQ ID NO 39
<211> LENGTH: 1200
<212> TYPE: DNA
<213> ORGANISM: Schizochytrium sp.

<400> SEQUENCE: 39
tacccgccgc gggcggtgtg cttctcgccg ttccccaaca acccgcttga caacgaccac        60
acgccgggcc agatgccgtt gacctggttc aacatgtccg aattcatgtg cggcaaagtg       120
tccaactgcc tggccccga gtttgcgcgc ttcgacgcga gcaagacgag ccgcagcccg        180
gcctttgacc tggcgctcgt gacgcgggtg acgagcgtgg cggacatgga gcacgggccg       240
ttctacaacg tggacgtcaa cccgggccag ggcacgatgg tgggcgagtt cgactgtccc       300
gcggacgcgt ggttcttcgg cgcctcgagc cgcgacgacc acatgccgta ctcgatcctg       360
atggagatcg cgctgcagac gtcgggcgtc ctcacctcgg tgctcaaggc gccgctgacg       420
atggacaagg acgacatcct cttccgcaac ctcgacgcag acgccgagct cgtgggcgac       480
gccatgccgg acgtgcgcgg caagacgatc cgcaacttca ccaagtgcac aggctacagc       540
atgctcggca agatgggcat ccaccgcttc acctttgagc tcagcgtcga cggcgccgtc       600
ttctacaagg gcagcacctc gtttggctgg ttcgtccccg aggtcttcga gtcgcagacc       660
ggtctcgaca acggcaagcc gcgcctgcct tggtaccgcg agaacaacgt cgccgtcgac       720
acgctctccg cgcccgcctc cgcttcctcc gcgcaaggtc agctgcagct gcagcgacgc       780
gggtcgcagg cgcagttcct ggacacaatc cacctggcgg cagcggcgc cggcgtgcac        840 ggccagggct acgcgcacgg ggagaaggcc gtgaacaagc aagattggtt cttctcgtgc       900
cacttctggt cgaccccgt gatgcccggg tccctgggca tcgagtcgat gttccagctc        960
gtcgaggcgt ggtgcgtgaa gcagggactc gcggcgcggc acggcatcgc tcacccagtg      1020
ttcgcgcacg cgcccggggc cacgagctgg aagtaccgcg ggcagctaac ccccaagaac      1080
gaccgcatgg acagcgaggt gcacatcaag tcggtggcgg ccttctcctc ctgggtcgac      1140
gtcgtcgcgg acgggttcct cttcgtcgac ggcctccgcg tctactcggc agacaacctc      1200

<210> SEQ ID NO 40
<211> LENGTH: 400
<212> TYPE: PRT
<213> ORGANISM: Schizochytrium sp.

<400> SEQUENCE: 40

Tyr Pro Pro Arg Ala Val Cys Phe Ser Pro Phe Pro Asn Asn Pro Leu
1               5                   10                  15

Asp Asn Asp His Thr Pro Gly Gln Met Pro Leu Thr Trp Phe Asn Met

```
                    20                  25                  30
Ser Glu Phe Met Cys Gly Lys Val Ser Asn Cys Leu Gly Pro Glu Phe
            35                  40                  45

Ala Arg Phe Asp Ala Ser Lys Thr Ser Arg Ser Pro Ala Phe Asp Leu
        50                  55                  60

Ala Leu Val Thr Arg Val Thr Ser Val Ala Asp Met Glu His Gly Pro
65                  70                  75                  80

Phe Tyr Asn Val Asp Val Asn Pro Gly Gln Gly Thr Met Val Gly Glu
                85                  90                  95

Phe Asp Cys Pro Ala Asp Ala Trp Phe Phe Gly Ala Ser Ser Arg Asp
            100                 105                 110

Asp His Met Pro Tyr Ser Ile Leu Met Glu Ile Ala Leu Gln Thr Ser
        115                 120                 125

Gly Val Leu Thr Ser Val Leu Lys Ala Pro Leu Thr Met Asp Lys Asp
    130                 135                 140

Asp Ile Leu Phe Arg Asn Leu Asp Ala Asp Ala Glu Leu Val Gly Asp
145                 150                 155                 160

Ala Met Pro Asp Val Arg Gly Lys Thr Ile Arg Asn Phe Thr Lys Cys
                165                 170                 175

Thr Gly Tyr Ser Met Leu Gly Lys Met Gly Ile His Arg Phe Thr Phe
            180                 185                 190

Glu Leu Ser Val Asp Gly Ala Val Phe Tyr Lys Gly Ser Thr Ser Phe
        195                 200                 205

Gly Trp Phe Val Pro Glu Val Phe Glu Ser Gln Thr Gly Leu Asp Asn
    210                 215                 220

Gly Lys Pro Arg Leu Pro Trp Tyr Arg Glu Asn Asn Val Ala Val Asp
225                 230                 235                 240

Thr Leu Ser Ala Pro Ala Ser Ala Ser Ala Gln Gly Gln Leu Gln
                245                 250                 255

Leu Gln Arg Arg Gly Ser Gln Ala Gln Phe Leu Asp Thr Ile His Leu
        260                 265                 270

Ala Gly Ser Gly Ala Gly Val His Gly Gln Gly Tyr Ala His Gly Glu
    275                 280                 285

Lys Ala Val Asn Lys Gln Asp Trp Phe Phe Ser Cys His Phe Trp Phe
290                 295                 300

Asp Pro Val Met Pro Gly Ser Leu Gly Ile Glu Ser Met Phe Gln Leu
305                 310                 315                 320

Val Glu Ala Trp Cys Val Lys Gln Gly Leu Ala Ala Arg His Gly Ile
                325                 330                 335

Ala His Pro Val Phe Ala His Ala Pro Gly Ala Thr Ser Trp Lys Tyr
            340                 345                 350

Arg Gly Gln Leu Thr Pro Lys Asn Asp Arg Met Asp Ser Glu Val His
        355                 360                 365

Ile Lys Ser Val Ala Ala Phe Ser Ser Trp Val Asp Val Ala Asp
    370                 375                 380

Gly Phe Leu Phe Val Asp Gly Leu Arg Val Tyr Ser Ala Asp Asn Leu
385                 390                 395                 400
```

<210> SEQ ID NO 41
<211> LENGTH: 1353
<212> TYPE: DNA
<213> ORGANISM: Schizochytrium sp.

<400> SEQUENCE: 41

```
cagctggacg cggggagcga ggtgcccgcc tgcgcggtga gcgacctggg cgataggggc      60
ttcatggaga cgtacggggt ggtggcgccg ctgtacagcg gggcgatggc caagggcatc     120
gcgtcggcgg acctggtgat cgcgatgggc cagcgcaaga tgctggggtc gtttggcgcg     180
ggcgggctcc cgatgcacgt cgtgcgcgcg gggattgaga agatccaggc agcgctgcca     240
gcggggccat acgcggtcaa cctgattcac tcgccttttg acgccaacct ggagaagggc     300
aacgtggacc tcttcctgga agggcgtg cgcgtcgtgg aggcgtcggc cttcatggag      360
ctcacgcccc aggtggtgcg ctaccgcgcg acgggcctct ctcgcgacgc gcgcggcggc     420
tccgtgcgca cggcccacaa gatcatcggc aaggtcagcc gcaccgagct ggccgagatg     480
tttatccggc ccgcgccgca agccattctc gacaagcttg tggcgtccgg cgagatcacc     540
cccgagcagg cggcgctggc gctcgaggtg cccatggcgg acgacatcgc cgtcgaggcc     600
gattcgggcg ggcacaccga caaccgcccc atccacgtca tcctgcccct catcctcagc     660
ctgcgcaacc gcctccagcg cgagctcaag taccctgcgc gacaccgcgt gcgcgtcggc     720 gccggggcg gcatcgggtg cccgcaagcg gctctgggcg ccttccacat gggcgccgcg     780
tttgtggtga cgggcacggt caaccagctg agccggcagg ccgggacatg cgacaatgtg     840
cggcggcagc tgtcgcgcgc gacgtactcg gacatcacga tggcgccggc ggcggacatg     900
ttcgagcagg gcgtcgagct gcaggtgctc aagaagggca cgatgtttcc ctcgcgcgcc     960
aagaagctgt tcgagctgtt tcacaagtac gactcgttcg aggcgatgcc ggcggacgag    1020
ctggcgcgcg tcgagaagcg catcttcagc aagtcactcg ccgaggtgtg ggccgagacc    1080
aaggacttct acatcacgcg gctcaacaac ccggagaaga tccgcaaggc ggagaacgag    1140 gacccaagc tcaagatgtc actctgcttc cgctggtacc tcgggctcag ctcgttctgg    1200
gccaacaacg gcatcgcgga ccgcacgatg gactaccaga tctggtgcgg ccctgccatc    1260
ggcgccttca cgacttcat cgccgactcg tacctcgacg tggccgtctc gggcgagttc    1320
cccgacgtcg tgcagatcaa cctgcagatc ctg                                 1353
```

<210> SEQ ID NO 42
<211> LENGTH: 451
<212> TYPE: PRT
<213> ORGANISM: Schizochytrium sp.

<400> SEQUENCE: 42

```
Gln Leu Asp Ala Gly Ser Glu Val Pro Ala Cys Ala Val Ser Asp Leu
1               5                   10                  15

Gly Asp Arg Gly Phe Met Glu Thr Tyr Gly Val Val Ala Pro Leu Tyr
            20                  25                  30

Ser Gly Ala Met Ala Lys Gly Ile Ala Ser Ala Asp Leu Val Ile Ala
        35                  40                  45

Met Gly Gln Arg Lys Met Leu Gly Ser Phe Gly Ala Gly Leu Pro
    50                  55                  60

Met His Val Val Arg Ala Gly Ile Glu Lys Ile Gln Ala Ala Leu Pro
65                  70                  75                  80

Ala Gly Pro Tyr Ala Val Asn Leu Ile His Ser Pro Phe Asp Ala Asn
                85                  90                  95

Leu Glu Lys Gly Asn Val Asp Leu Phe Leu Glu Lys Gly Val Arg Val
            100                 105                 110

Val Glu Ala Ser Ala Phe Met Glu Leu Thr Pro Gln Val Val Arg Tyr
        115                 120                 125

Arg Ala Thr Gly Leu Ser Arg Asp Ala Arg Gly Gly Ser Val Arg Thr
```

```
            130                 135                 140
Ala His Lys Ile Ile Gly Lys Val Ser Arg Thr Glu Leu Ala Glu Met
145                 150                 155                 160

Phe Ile Arg Pro Ala Pro Gln Ala Ile Leu Asp Lys Leu Val Ala Ser
                165                 170                 175

Gly Glu Ile Thr Pro Glu Gln Ala Ala Leu Ala Leu Glu Val Pro Met
                180                 185                 190

Ala Asp Asp Ile Ala Val Glu Ala Asp Ser Gly Gly His Thr Asp Asn
                195                 200                 205

Arg Pro Ile His Val Ile Leu Pro Leu Ile Leu Ser Leu Arg Asn Arg
                210                 215                 220

Leu Gln Arg Glu Leu Lys Tyr Pro Ala Arg His Arg Val Arg Val Gly
225                 230                 235                 240

Ala Gly Gly Gly Ile Gly Cys Pro Gln Ala Ala Leu Gly Ala Phe His
                245                 250                 255

Met Gly Ala Ala Phe Val Val Thr Gly Thr Val Asn Gln Leu Ser Arg
                260                 265                 270

Gln Ala Gly Thr Cys Asp Asn Val Arg Arg Gln Leu Ser Arg Ala Thr
                275                 280                 285

Tyr Ser Asp Ile Thr Met Ala Pro Ala Asp Met Phe Glu Gln Gly
                290                 295                 300

Val Glu Leu Gln Val Leu Lys Lys Gly Thr Met Phe Pro Ser Arg Ala
305                 310                 315                 320

Lys Lys Leu Phe Glu Leu Phe His Lys Tyr Asp Ser Phe Glu Ala Met
                325                 330                 335

Pro Ala Asp Glu Leu Ala Arg Val Glu Lys Arg Ile Phe Ser Lys Ser
                340                 345                 350

Leu Ala Glu Val Trp Ala Glu Thr Lys Asp Phe Tyr Ile Thr Arg Leu
                355                 360                 365

Asn Asn Pro Glu Lys Ile Arg Lys Ala Glu Asn Glu Asp Pro Lys Leu
                370                 375                 380

Lys Met Ser Leu Cys Phe Arg Trp Tyr Leu Gly Leu Ser Ser Phe Trp
385                 390                 395                 400

Ala Asn Asn Gly Ile Ala Asp Arg Thr Met Asp Tyr Gln Ile Trp Cys
                405                 410                 415

Gly Pro Ala Ile Gly Ala Phe Asn Asp Phe Ile Ala Asp Ser Tyr Leu
                420                 425                 430

Asp Val Ala Val Ser Gly Glu Phe Pro Asp Val Val Gln Ile Asn Leu
                435                 440                 445

Gln Ile Leu
      450

<210> SEQ ID NO 43
<211> LENGTH: 4
<212> TYPE: PRT
<213> ORGANISM: Schizochytrium sp.
<220> FEATURE:
<221> NAME/KEY: misc_feature
<222> LOCATION: (2)..(2)
<223> OTHER INFORMATION: Xaa can be any naturally occurring amino acid

<400> SEQUENCE: 43

Asp Xaa Ala Cys
1

<210> SEQ ID NO 44
```

```
<211> LENGTH: 4
<212> TYPE: PRT
<213> ORGANISM: Schizochytrium sp.

<400> SEQUENCE: 44

Gly Phe Gly Gly
1

<210> SEQ ID NO 45
<211> LENGTH: 12
<212> TYPE: DNA
<213> ORGANISM: Schizochytrium sp.

<400> SEQUENCE: 45
gggtttggcg gt                                                            12

<210> SEQ ID NO 46
<211> LENGTH: 5
<212> TYPE: PRT
<213> ORGANISM: Schizochytrium sp.

<400> SEQUENCE: 46

Gly Phe Ser Leu Gly
1               5

<210> SEQ ID NO 47
<211> LENGTH: 5
<212> TYPE: PRT
<213> ORGANISM: Schizochytrium sp.

<400> SEQUENCE: 47

Leu Gly Ile Asp Ser
1               5

<210> SEQ ID NO 48
<211> LENGTH: 903
<212> TYPE: DNA
<213> ORGANISM: Schizochytrium sp.

<400> SEQUENCE: 48
ctgtcagacc ccgacgtggc cgtgcgcgag tctggttact ccgcctcggg ccagcgctgc        60
acgacaacta cgaagtcgct gactacgggc aagccgcacc agccgatctc ctcgtcggac       120
ctctttctgg tgtcgggcgg cgcgcgcggc atcaccccgc tgtgcgtgcg cgagctggcg       180
cagcgcgtgg gcggcggcac gtacgtgctc atcggccgct cggagctgcc cacgacggag       240
cctgcctggg cggtcggcgt ggagtctggc aagccgctgg agaaggccgc gctggcgttc       300
ctgaaggcgg agtttgcagc gggccgcggg gccaagccga cgccgatgct gcacaagaag       360
ctcgtgggcg ccgtggtcgg agcgcgcgag gtgcagcgcc cgctcgccga gatcactgca       420
cagggcgcca cggctgtgta cgagtcgtgc gacgtgagct ctgccgccaa ggtgcgtgag       480
atggtagagc gcgtgcagca gcagggcggg cggcgcgtgt cggcgtgtt ccacgcgtcg        540 ggcgtgctgc gcgacaagct cgtggagaac aagtcgctgg cggacttcag cgccgtgtac       600
gacaccaagg tgggcggcct catcaacctg ctggcctgcg tggacctggc gcagctgcgt       660
cacctcgtgc tcttcagctc gctcgcgggc ttccacggca acgtcgggca gtcggactac       720
gcaatggcca acgaggcgct caacaagctg gcggcgcacc tgtcggcggt gcacccgcag       780
ctgtgcgcgc gctcgatctg cttcggaccg tgggacggcg gcatggtgac ccccgcgctc       840
aaggccaact tcatccgcat gggcatccag atcatcccgc gccaaggcgg cgcgcagacc       900
```

```
gtc                                                                          903
```

<210> SEQ ID NO 49
<211> LENGTH: 301
<212> TYPE: PRT
<213> ORGANISM: Schizochytrium sp.

<400> SEQUENCE: 49

Leu Ser Asp Pro Asp Val Ala Val Arg Glu Ser Gly Tyr Ser Ala Ser
1               5                   10                  15

Gly Gln Arg Cys Thr Thr Thr Lys Ser Leu Thr Gly Lys Pro
            20                  25                  30

His Gln Pro Ile Ser Ser Asp Leu Phe Leu Val Ser Gly Gly Ala
                35                  40                  45

Arg Gly Ile Thr Pro Leu Cys Val Arg Glu Leu Ala Gln Arg Val Gly
            50                  55                  60

Gly Gly Thr Tyr Val Leu Ile Gly Arg Ser Glu Leu Pro Thr Thr Glu
65                  70                  75                  80

Pro Ala Trp Ala Val Gly Val Glu Ser Gly Lys Pro Leu Glu Lys Ala
                85                  90                  95

Ala Leu Ala Phe Leu Lys Ala Glu Phe Ala Ala Gly Arg Gly Ala Lys
            100                 105                 110

Pro Thr Pro Met Leu His Lys Lys Leu Val Gly Ala Val Val Gly Ala
            115                 120                 125

Arg Glu Val Arg Ala Ser Leu Ala Glu Ile Thr Ala Gln Gly Ala Thr
130                 135                 140

Ala Val Tyr Glu Ser Cys Asp Val Ser Ser Ala Ala Lys Val Arg Glu
145                 150                 155                 160

Met Val Glu Arg Val Gln Gln Gln Gly Gly Arg Arg Val Ser Gly Val
                165                 170                 175

Phe His Ala Ser Gly Val Leu Arg Asp Lys Leu Val Glu Asn Lys Ser
            180                 185                 190

Leu Ala Asp Phe Ser Ala Val Tyr Asp Thr Lys Val Gly Gly Leu Ile
            195                 200                 205

Asn Leu Leu Ala Cys Val Asp Leu Ala Gln Leu Arg His Leu Val Leu
210                 215                 220

Phe Ser Ser Leu Ala Gly Phe His Gly Asn Val Gly Gln Ser Asp Tyr
225                 230                 235                 240

Ala Met Ala Asn Glu Ala Leu Asn Lys Leu Ala Ala His Leu Ser Ala
                245                 250                 255

Val His Pro Gln Leu Cys Ala Arg Ser Ile Cys Phe Gly Pro Trp Asp
            260                 265                 270

Gly Gly Met Val Thr Pro Ala Leu Lys Ala Asn Phe Ile Arg Met Gly
            275                 280                 285

Ile Gln Ile Ile Pro Arg Gln Gly Gly Ala Gln Thr Val
290                 295                 300

<210> SEQ ID NO 50
<211> LENGTH: 13
<212> TYPE: PRT
<213> ORGANISM: Schizochytrium sp.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)

```
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid

<400> SEQUENCE: 50

Leu Xaa Xaa His Xaa Xaa Xaa Gly Xaa Xaa Xaa Xaa Pro
1               5                   10

<210> SEQ ID NO 51
<211> LENGTH: 12
<212> TYPE: DNA
<213> ORGANISM: Schizochytrium sp.

<400> SEQUENCE: 51
ggctttggtg ga                                                           12

<210> SEQ ID NO 52
<211> LENGTH: 5
<212> TYPE: PRT
<213> ORGANISM: Schizochytrium sp.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 52

Gly Xaa Ser Xaa Gly
1               5

<210> SEQ ID NO 53
<211> LENGTH: 5
<212> TYPE: PRT
<213> ORGANISM: Schizochytrium sp.
<220> FEATURE:
<221> NAME/KEY: misc_feature
<222> LOCATION: (2)..(3)
<223> OTHER INFORMATION: Xaa can be any naturally occurring amino acid

<400> SEQUENCE: 53

Phe Xaa Xaa His Phe
1               5

<210> SEQ ID NO 54
<211> LENGTH: 2910
<212> TYPE: PRT
<213> ORGANISM: Schizochytrium sp.

<400> SEQUENCE: 54

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
```

```
                    85                  90                  95
Asp Ser Asp Ala Asn Gln Thr Ile Ser Leu Leu Lys Val Lys Glu Ala
                100                 105                 110

Leu Gln Asp Ala Gly Ile Asp Ala Leu Gly Lys Glu Lys Lys Asn Ile
                115                 120                 125

Gly Cys Val Leu Gly Ile Gly Gly Gln Lys Ser Ser His Glu Phe
                130                 135                 140

Tyr Ser Arg Leu Asn Tyr Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
                180                 185                 190

Val Thr Ala Gly Arg Cys Thr Asn Thr Phe Asn Leu Asp Gly Met Asn
                195                 200                 205

Cys Val Val Asp Ala Ala Cys Ala Ser Ser Leu Ile Ala Val Lys Val
                210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
                260                 265                 270

Thr Lys Gly Met Leu Ile Gly Glu Gly Ser Ala Met Leu Val Leu Lys
                275                 280                 285

Arg Tyr Ala Asp Ala Val Arg Asp Gly Asp Glu Ile His Ala Val Ile
                290                 295                 300

Arg Gly Cys Ala Ser Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
                325                 330                 335

Ala Cys Val Asp Pro Ala Thr Val Thr Leu Val Glu Gly His Gly Thr
                340                 345                 350

Gly Thr Pro Val Gly Asp Arg Ile Glu Leu Thr Ala Leu Arg Asn Leu
                355                 360                 365

Phe Asp Lys Ala Tyr Gly Glu Gly Asn Thr Glu Lys Val Ala Val Gly
                370                 375                 380

Ser Ile Lys Ser Ser Ile Gly His Leu Lys Ala Val Ala Gly Leu Ala
385                 390                 395                 400

Gly Met Ile Lys Val Ile Met Ala Leu Lys His Lys Thr Leu Pro Gly
                405                 410                 415

Thr Ile Asn Val Asp Asn Pro Asn Leu Tyr Asp Asn Thr Pro Ile
                420                 425                 430

Asn Glu Ser Ser Leu Tyr Ile Asn Thr Met Asn Arg Pro Trp Phe Pro
                435                 440                 445

Pro Pro Gly Val Pro Arg Arg Ala Gly Ile Ser Ser Phe Gly Phe Gly
                450                 455                 460

Gly Ala Asn Tyr His Ala Val Leu Glu Glu Ala Glu Pro Glu His Thr
465                 470                 475                 480

Thr Ala Tyr Arg Leu Asn Lys Arg Pro Gln Pro Val Leu Met Met Ala
                485                 490                 495

Ala Thr Pro Ala Ala Leu Gln Ser Leu Cys Glu Ala Gln Leu Lys Glu
                500                 505                 510
```

```
Phe Glu Ala Ala Ile Lys Glu Asn Glu Thr Val Lys Asn Thr Ala Tyr
            515                 520                 525

Ile Lys Cys Val Lys Phe Gly Glu Gln Phe Lys Phe Pro Gly Ser Ile
        530                 535                 540

Pro Ala Thr Asn Ala Arg Leu Gly Phe Leu Val Lys Asp Ala Glu Asp
545                 550                 555                 560

Ala Cys Ser Thr Leu Arg Ala Ile Cys Ala Gln Phe Ala Lys Asp Val
                565                 570                 575

Thr Lys Glu Ala Trp Arg Leu Pro Arg Glu Gly Val Ser Phe Arg Ala
            580                 585                 590

Lys Gly Ile Ala Thr Asn Gly Ala Val Ala Leu Phe Ser Gly Gln
        595                 600                 605

Gly Ala Gln Tyr Thr His Met Phe Ser Glu Val Ala Met Asn Trp Pro
        610                 615                 620

Gln Phe Arg Gln Ser Ile Ala Ala Met Asp Ala Ala Gln Ser Lys Val
625                 630                 635                 640

Ala Gly Ser Asp Lys Asp Phe Glu Arg Val Ser Gln Val Leu Tyr Pro
                645                 650                 655

Arg Lys Pro Tyr Glu Arg Glu Pro Glu Gln Asn Pro Lys Lys Ile Ser
            660                 665                 670

Leu Thr Ala Tyr Ser Gln Pro Ser Thr Leu Ala Cys Ala Leu Gly Ala
        675                 680                 685

Phe Glu Ile Phe Lys Glu Ala Gly Phe Thr Pro Asp Phe Ala Ala Gly
        690                 695                 700

His Ser Leu Gly Glu Phe Ala Ala Leu Tyr Ala Ala Gly Cys Val Asp
705                 710                 715                 720

Arg Asp Glu Leu Phe Glu Leu Val Cys Arg Arg Ala Arg Ile Met Gly
                725                 730                 735

Gly Lys Asp Ala Pro Ala Thr Pro Lys Gly Cys Met Ala Ala Val Ile
            740                 745                 750

Gly Pro Asn Ala Glu Asn Ile Lys Val Gln Ala Ala Asn Val Trp Leu
        755                 760                 765

Gly Asn Ser Asn Ser Pro Ser Gln Thr Val Ile Thr Gly Ser Val Glu
        770                 775                 780

Gly Ile Gln Ala Glu Ser Ala Arg Leu Gln Lys Glu Gly Phe Arg Val
785                 790                 795                 800

Val Pro Leu Ala Cys Glu Ser Ala Phe His Ser Pro Gln Met Glu Asn
                805                 810                 815

Ala Ser Ser Ala Phe Lys Asp Val Ile Ser Lys Val Ser Phe Arg Thr
            820                 825                 830

Pro Lys Ala Glu Thr Lys Leu Phe Ser Asn Val Ser Gly Glu Thr Tyr
        835                 840                 845

Pro Thr Asp Ala Arg Glu Met Leu Thr Gln His Met Thr Ser Ser Val
850                 855                 860

Lys Phe Leu Thr Gln Val Arg Asn Met His Gln Ala Gly Ala Arg Ile
865                 870                 875                 880

Phe Val Glu Phe Gly Pro Lys Gln Val Leu Ser Lys Leu Val Ser Glu
                885                 890                 895

Thr Leu Lys Asp Asp Pro Ser Val Val Thr Val Ser Val Asn Pro Ala
            900                 905                 910

Ser Gly Thr Asp Ser Asp Ile Gln Leu Arg Asp Ala Ala Val Gln Leu
        915                 920                 925
```

```
Val Val Ala Gly Val Asn Leu Gln Gly Phe Asp Lys Trp Asp Ala Pro
930                 935                 940

Asp Ala Thr Arg Met Gln Ala Ile Lys Lys Arg Thr Thr Leu Arg
945                 950                 955                 960

Leu Ser Ala Ala Thr Tyr Val Ser Asp Lys Thr Lys Lys Val Arg Asp
            965                 970                 975

Ala Ala Met Asn Asp Gly Arg Cys Val Thr Tyr Leu Lys Gly Ala Ala
                980                 985                 990

Pro Leu Ile Lys Ala Pro Glu Pro Val Val Asp Glu Ala Ala Lys Arg
            995                 1000                1005

Glu Ala Glu Arg Leu Gln Lys Glu Leu Gln Asp Ala Gln Arg Gln
    1010                1015                1020

Leu Asp Asp Ala Lys Arg Ala Ala Glu Ala Asn Ser Lys Leu
1025                1030                1035

Ala Ala Ala Lys Glu Glu Ala Lys Thr Ala Ala Ala Ser Ala Lys
    1040                1045                1050

Pro Ala Val Asp Thr Ala Val Val Glu Lys His Arg Ala Ile Leu
    1055                1060                1065

Lys Ser Met Leu Ala Glu Leu Asp Gly Tyr Gly Ser Val Asp Ala
    1070                1075                1080

Ser Ser Leu Gln Gln Gln Gln Gln Gln Thr Ala Pro Ala Pro
    1085                1090                1095

Val Lys Ala Ala Ala Pro Ala Ala Pro Val Ala Ser Ala Pro Ala
    1100                1105                1110

Pro Ala Val Ser Asn Glu Leu Leu Glu Lys Ala Glu Thr Val Val
    1115                1120                1125

Met Glu Val Leu Ala Ala Lys Thr Gly Tyr Glu Thr Asp Met Ile
    1130                1135                1140

Glu Ala Asp Met Glu Leu Glu Thr Glu Leu Gly Ile Asp Ser Ile
    1145                1150                1155

Lys Arg Val Glu Ile Leu Ser Glu Val Gln Ala Met Leu Asn Val
    1160                1165                1170

Glu Ala Lys Asp Val Asp Ala Leu Ser Arg Thr Arg Thr Val Gly
    1175                1180                1185

Glu Val Val Asn Ala Met Lys Ala Glu Ile Ala Gly Ser Ser Ala
    1190                1195                1200

Pro Ala Pro Ala Ala Ala Pro Ala Pro Ala Lys Ala Ala Pro
    1205                1210                1215

Ala Ala Ala Ala Pro Ala Val Ser Asn Glu Leu Leu Glu Lys Ala
    1220                1225                1230

Glu Thr Val Val Met Glu Val Leu Ala Ala Lys Thr Gly Tyr Glu
    1235                1240                1245

Thr Asp Met Ile Glu Ser Asp Met Glu Leu Glu Thr Glu Leu Gly
    1250                1255                1260

Ile Asp Ser Ile Lys Arg Val Glu Ile Leu Ser Glu Val Gln Ala
    1265                1270                1275

Met Leu Asn Val Glu Ala Lys Asp Val Asp Ala Leu Ser Arg Thr
    1280                1285                1290

Arg Thr Val Gly Glu Val Val Asn Ala Met Lys Ala Glu Ile Ala
    1295                1300                1305

Gly Gly Ser Ala Pro Ala Pro Ala Ala Ala Ala Pro Gly Pro Ala
    1310                1315                1320

Ala Ala Ala Pro Ala Pro Ala Ala Ala Ala Pro Ala Val Ser Asn
```

-continued

```
            1325                1330                1335

Glu Leu Leu Glu Lys Ala Glu Thr Val Val Met Glu Val Leu Ala
            1340                1345                1350

Ala Lys Thr Gly Tyr Glu Thr Asp Met Ile Glu Ser Asp Met Glu
            1355                1360                1365

Leu Glu Thr Glu Leu Gly Ile Asp Ser Ile Lys Arg Val Glu Ile
            1370                1375                1380

Leu Ser Glu Val Gln Ala Met Leu Asn Val Glu Ala Lys Asp Val
            1385                1390                1395

Asp Ala Leu Ser Arg Thr Arg Thr Val Gly Glu Val Val Asp Ala
            1400                1405                1410

Met Lys Ala Glu Ile Ala Gly Gly Ser Ala Pro Ala Pro Ala Ala
            1415                1420                1425

Ala Ala Pro Ala Pro Ala Ala Ala Ala Pro Ala Pro Ala Ala Pro
            1430                1435                1440

Ala Pro Ala Val Ser Ser Glu Leu Leu Glu Lys Ala Glu Thr Val
            1445                1450                1455

Val Met Glu Val Leu Ala Ala Lys Thr Gly Tyr Glu Thr Asp Met
            1460                1465                1470

Ile Glu Ser Asp Met Glu Leu Glu Thr Glu Leu Gly Ile Asp Ser
            1475                1480                1485

Ile Lys Arg Val Glu Ile Leu Ser Glu Val Gln Ala Met Leu Asn
            1490                1495                1500

Val Glu Ala Lys Asp Val Asp Ala Leu Ser Arg Thr Arg Thr Val
            1505                1510                1515

Gly Glu Val Val Asp Ala Met Lys Ala Glu Ile Ala Gly Gly Ser
            1520                1525                1530

Ala Pro Ala Pro Ala Ala Ala Pro Ala Pro Ala Ala Ala Ala
            1535                1540                1545

Pro Ala Pro Ala Ala Pro Ala Pro Ala Ala Pro Ala Pro Ala Val
            1550                1555                1560

Ser Ser Glu Leu Leu Glu Lys Ala Glu Thr Val Val Met Glu Val
            1565                1570                1575

Leu Ala Ala Lys Thr Gly Tyr Glu Thr Asp Met Ile Glu Ser Asp
            1580                1585                1590

Met Glu Leu Glu Thr Glu Leu Gly Ile Asp Ser Ile Lys Arg Val
            1595                1600                1605

Glu Ile Leu Ser Glu Val Gln Ala Met Leu Asn Val Glu Ala Lys
            1610                1615                1620

Asp Val Asp Ala Leu Ser Arg Thr Arg Thr Val Gly Glu Val Val
            1625                1630                1635

Asp Ala Met Lys Ala Glu Ile Ala Gly Ser Ser Ala Ser Ala Pro
            1640                1645                1650

Ala Ala Ala Ala Pro Ala Pro Ala Ala Ala Ala Pro Ala Pro Ala
            1655                1660                1665

Ala Ala Ala Pro Ala Val Ser Asn Glu Leu Leu Glu Lys Ala Glu
            1670                1675                1680

Thr Val Val Met Glu Val Leu Ala Ala Lys Thr Gly Tyr Glu Thr
            1685                1690                1695

Asp Met Ile Glu Ser Asp Met Glu Leu Glu Thr Glu Leu Gly Ile
            1700                1705                1710

Asp Ser Ile Lys Arg Val Glu Ile Leu Ser Glu Val Gln Ala Met
            1715                1720                1725
```

-continued

```
Leu Asn Val Glu Ala Lys Asp Val Asp Ala Leu Ser Arg Thr Arg
1730                1735                1740

Thr Val Gly Glu Val Val Asp Ala Met Lys Ala Glu Ile Ala Gly
1745                1750                1755

Gly Ser Ala Pro Ala Pro Ala Ala Ala Pro Ala Pro Ala Ala
1760                1765                1770

Ala Ala Pro Ala Val Ser Asn Glu Leu Leu Glu Lys Ala Glu Thr
1775                1780                1785

Val Val Met Glu Val Leu Ala Ala Lys Thr Gly Tyr Glu Thr Asp
1790                1795                1800

Met Ile Glu Ser Asp Met Glu Leu Glu Thr Glu Leu Gly Ile Asp
1805                1810                1815

Ser Ile Lys Arg Val Glu Ile Leu Ser Glu Val Gln Ala Met Leu
1820                1825                1830

Asn Val Glu Ala Lys Asp Val Asp Ala Leu Ser Arg Thr Arg Thr
1835                1840                1845

Val Gly Glu Val Val Asp Ala Met Lys Ala Glu Ile Ala Gly Ser
1850                1855                1860

Ser Ala Pro Ala Pro Ala Ala Ala Pro Ala Pro Ala Ala Ala
1865                1870                1875

Ala Pro Ala Pro Ala Ala Ala Ala Pro Ala Val Ser Ser Glu Leu
1880                1885                1890

Leu Glu Lys Ala Glu Thr Val Val Met Glu Val Leu Ala Ala Lys
1895                1900                1905

Thr Gly Tyr Glu Thr Asp Met Ile Glu Ser Asp Met Glu Leu Glu
1910                1915                1920

Thr Glu Leu Gly Ile Asp Ser Ile Lys Arg Val Glu Ile Leu Ser
1925                1930                1935

Glu Val Gln Ala Met Leu Asn Val Glu Ala Lys Asp Val Asp Ala
1940                1945                1950

Leu Ser Arg Thr Arg Thr Val Gly Glu Val Val Asp Ala Met Lys
1955                1960                1965

Ala Glu Ile Ala Gly Gly Ser Ala Pro Ala Pro Ala Ala Ala Ala
1970                1975                1980

Pro Ala Pro Ala Ala Ala Pro Ala Val Ser Asn Glu Leu Leu
1985                1990                1995

Glu Lys Ala Glu Thr Val Val Met Glu Val Leu Ala Ala Lys Thr
2000                2005                2010

Gly Tyr Glu Thr Asp Met Ile Glu Ser Asp Met Glu Leu Glu Thr
2015                2020                2025

Glu Leu Gly Ile Asp Ser Ile Lys Arg Val Glu Ile Leu Ser Glu
2030                2035                2040

Val Gln Ala Met Leu Asn Val Glu Ala Lys Asp Val Asp Ala Leu
2045                2050                2055

Ser Arg Thr Arg Thr Val Gly Glu Val Val Asp Ala Met Lys Ala
2060                2065                2070

Glu Ile Ala Gly Gly Ser Ala Pro Ala Pro Ala Ala Ala Pro
2075                2080                2085

Ala Ser Ala Gly Ala Ala Pro Ala Val Lys Ile Asp Ser Val His
2090                2095                2100

Gly Ala Asp Cys Asp Asp Leu Ser Leu Met His Ala Lys Val Val
2105                2110                2115
```

```
Asp Ile Arg Arg Pro Asp Glu Leu Ile Leu Glu Arg Pro Glu Asn
2120                2125                2130

Arg Pro Val Leu Val Val Asp Asp Gly Ser Glu Leu Thr Leu Ala
2135                2140                2145

Leu Val Arg Val Leu Gly Ala Cys Ala Val Val Leu Thr Phe Glu
2150                2155                2160

Gly Leu Gln Leu Ala Gln Arg Ala Gly Ala Ala Ile Arg His
2165                2170                2175

Lys Ala Ile Lys Glu Ala Glu Gln Arg Phe Gly Ala Leu Gly Gly
2180                2185                2190

Phe Ile Ser Gln Gln Ala Glu Arg Phe Glu Pro Ala Glu Ile Leu
2195                2200                2205

Gly Phe Thr Leu Met Cys Ala Lys Phe Ala Lys Ala Ser Leu Cys
2210                2215                2220

Thr Ala Val Ala Gly Val Leu Ala Lys Asp Leu Ser Ala Glu Ser
2225                2230                2235

Ala Glu Gly Arg Pro Ala Phe Ile Gly Val Ala Arg Leu Asp Gly
2240                2245                2250

Arg Leu Gly Phe Thr Ser Gln Gly Thr Ser Asp Ala Leu Lys Arg
2255                2260                2265

Ala Gln Arg Gly Ala Ile Phe Gly Leu Cys Lys Thr Ile Gly Leu
2270                2275                2280

Glu Trp Ser Glu Ser Asp Val Phe Ser Arg Gly Val Asp Ile Ala
2285                2290                2295

Gln Gly Met His Pro Glu Asp Ala Ala Val Ala Ile Val Arg Glu
2300                2305                2310

Met Ala Cys Ala Asp Ile Arg Ile Arg Glu Val Gly Ile Gly Ala
2315                2320                2325

Asn Gln Gln Arg Cys Thr Ile Arg Ala Ala Lys Leu Glu Thr Gly
2330                2335                2340

Asn Pro Gln Arg Gln Ile Ala Lys Asp Asp Val Leu Leu Val Ser
2345                2350                2355

Gly Gly Ala Arg Gly Ile Thr Pro Leu Cys Ile Arg Glu Ile Thr
2360                2365                2370

Arg Gln Ile Ala Gly Gly Lys Tyr Ile Leu Leu Gly Arg Ser Lys
2375                2380                2385

Val Ser Ala Ser Glu Pro Ala Trp Cys Ala Gly Ile Thr Asp Glu
2390                2395                2400

Lys Ala Val Gln Lys Ala Ala Thr Gln Glu Leu Lys Arg Ala Phe
2405                2410                2415

Ser Ala Gly Glu Gly Pro Lys Pro Thr Pro Arg Ala Val Thr Lys
2420                2425                2430

Leu Val Gly Ser Val Leu Gly Ala Arg Glu Val Arg Ser Ser Ile
2435                2440                2445

Ala Ala Ile Glu Ala Leu Gly Gly Lys Ala Ile Tyr Ser Ser Cys
2450                2455                2460

Asp Val Asn Ser Ala Ala Asp Val Ala Lys Ala Val Arg Asp Ala
2465                2470                2475

Glu Ser Gln Leu Gly Ala Arg Val Ser Gly Ile Val His Ala Ser
2480                2485                2490

Gly Val Leu Arg Asp Arg Leu Ile Glu Lys Lys Leu Pro Asp Glu
2495                2500                2505

Phe Asp Ala Val Phe Gly Thr Lys Val Thr Gly Leu Glu Asn Leu
```

```
            2510                2515                2520

Leu Ala Ala Val Asp Arg Ala Asn Leu Lys His Met Val Leu Phe
    2525                2530                2535

Ser Ser Leu Ala Gly Phe His Gly Asn Val Gly Gln Ser Asp Tyr
    2540                2545                2550

Ala Met Ala Asn Glu Ala Leu Asn Lys Met Gly Leu Glu Leu Ala
    2555                2560                2565

Lys Asp Val Ser Val Lys Ser Ile Cys Phe Gly Pro Trp Asp Gly
    2570                2575                2580

Gly Met Val Thr Pro Gln Leu Lys Lys Gln Phe Gln Glu Met Gly
    2585                2590                2595

Val Gln Ile Ile Pro Arg Glu Gly Gly Ala Asp Thr Val Ala Arg
    2600                2605                2610

Ile Val Leu Gly Ser Ser Pro Ala Glu Ile Leu Val Gly Asn Trp
    2615                2620                2625

Arg Thr Pro Ser Lys Lys Val Gly Ser Asp Thr Ile Thr Leu His
    2630                2635                2640

Arg Lys Ile Ser Ala Lys Ser Asn Pro Phe Leu Glu Asp His Val
    2645                2650                2655

Ile Gln Gly Arg Arg Val Leu Pro Met Thr Leu Ala Ile Gly Ser
    2660                2665                2670

Leu Ala Glu Thr Cys Leu Gly Leu Phe Pro Gly Tyr Ser Leu Trp
    2675                2680                2685

Ala Ile Asp Asp Ala Gln Leu Phe Lys Gly Val Thr Val Asp Gly
    2690                2695                2700

Asp Val Asn Cys Glu Val Thr Leu Thr Pro Ser Thr Ala Pro Ser
    2705                2710                2715

Gly Arg Val Asn Val Gln Ala Thr Leu Lys Thr Phe Ser Ser Gly
    2720                2725                2730

Lys Leu Val Pro Ala Tyr Arg Ala Val Ile Val Leu Ser Asn Gln
    2735                2740                2745

Gly Ala Pro Pro Ala Asn Ala Thr Met Gln Pro Pro Ser Leu Asp
    2750                2755                2760

Ala Asp Pro Ala Leu Gln Gly Ser Val Tyr Asp Gly Lys Thr Leu
    2765                2770                2775

Phe His Gly Pro Ala Phe Arg Gly Ile Asp Asp Val Leu Ser Cys
    2780                2785                2790

Thr Lys Ser Gln Leu Val Ala Lys Cys Ser Ala Val Pro Gly Ser
    2795                2800                2805

Asp Ala Ala Arg Gly Glu Phe Ala Thr Asp Thr Asp Ala His Asp
    2810                2815                2820

Pro Phe Val Asn Asp Leu Ala Phe Gln Ala Met Leu Val Trp Val
    2825                2830                2835

Arg Arg Thr Leu Gly Gln Ala Ala Leu Pro Asn Ser Ile Gln Arg
    2840                2845                2850

Ile Val Gln His Arg Pro Val Pro Gln Asp Lys Pro Phe Tyr Ile
    2855                2860                2865

Thr Leu Arg Ser Asn Gln Ser Gly Gly His Ser Gln His Lys His
    2870                2875                2880

Ala Leu Gln Phe His Asn Glu Gln Gly Asp Leu Phe Ile Asp Val
    2885                2890                2895

Gln Ala Ser Val Ile Ala Thr Asp Ser Leu Ala Phe
    2900                2905                2910
```

<210> SEQ ID NO 55
<211> LENGTH: 2895
<212> TYPE: PRT
<213> ORGANISM: Thraustochytrium aureum

<400> SEQUENCE: 55

| | | | | | | | | | | | | | | |
|---|---|---|---|---|---|---|---|---|---|---|---|---|---|---|
| Arg | Lys | Cys | Ile | Arg | Pro | Ser | Leu | Gly | His | His | Trp | Ala | Ile | Ile | Gly |
| 1 | | | | 5 | | | | | 10 | | | | | 15 | |
| Val | Leu | Gly | Arg | Ala | Leu | Arg | Ile | Val | Arg | Pro | Ile | Arg | Tyr | Glu | Ala |
| | | | 20 | | | | | 25 | | | | | 30 | | |
| Thr | Asn | Leu | Arg | Arg | Leu | Pro | Arg | Ser | Gly | Trp | Leu | Val | Ala | Leu | Gly |
| | | | 35 | | | | | 40 | | | | | 45 | | |
| Leu | Phe | Cys | Asp | Leu | Ser | Ser | Cys | Ala | Gly | Lys | Leu | Asp | Leu | Gln | Thr |
| | | 50 | | | | | 55 | | | | | 60 | | | |
| Arg | Asp | Thr | Ala | Lys | Asp | Pro | Cys | Cys | Lys | Arg | Lys | Trp | Ser | Ala | Ser |
| 65 | | | | | 70 | | | | | 75 | | | | | 80 |
| Arg | Ala | Pro | Pro | Arg | Pro | Arg | Ala | Glu | Ala | Asp | Lys | Ala | Ser | Asn | Glu |
| | | | | 85 | | | | | 90 | | | | | 95 | |
| Met | Glu | Thr | Lys | Asp | Asp | Arg | Val | Ala | Ile | Val | Gly | Met | Ser | Ala | Ile |
| | | | 100 | | | | | 105 | | | | | 110 | | |
| Leu | Pro | Cys | Gly | Glu | Ser | Val | Arg | Glu | Ser | Trp | Glu | Ala | Ile | Arg | Glu |
| | | | 115 | | | | | 120 | | | | | 125 | | |
| Gly | Leu | Asp | Cys | Leu | Gln | Leu | Pro | Ala | Asp | Arg | Val | Asp | Ile | Thr | |
| | | 130 | | | | | 135 | | | | | 140 | | | |
| Ala | Tyr | Tyr | Asp | Pro | Asn | Lys | Thr | Thr | Lys | Asp | Lys | Ile | Tyr | Cys | Lys |
| 145 | | | | | 150 | | | | | 155 | | | | | 160 |
| Arg | Gly | Gly | Phe | Ile | Pro | Glu | Tyr | Asp | Phe | Asp | Ala | Arg | Glu | Phe | Gly |
| | | | | 165 | | | | | 170 | | | | | 175 | |
| Leu | Asn | Met | Phe | Gln | Met | Glu | Asp | Ser | Asp | Ala | Asn | Gln | Thr | Val | Thr |
| | | | 180 | | | | | 185 | | | | | 190 | | |
| Leu | Leu | Lys | Val | Lys | Glu | Ala | Leu | Glu | Asp | Ala | Gly | Val | Glu | Pro | Phe |
| | | | 195 | | | | | 200 | | | | | 205 | | |
| Thr | Lys | Lys | Lys | Asn | Ile | Gly | Cys | Val | Leu | Gly | Ile | Gly | Gly | Gly | |
| | | 210 | | | | | 215 | | | | | 220 | | | |
| Gln | Lys | Ala | Ser | His | Glu | Phe | Tyr | Ser | Arg | Leu | Asn | Tyr | Val | Val | Val |
| 225 | | | | | 230 | | | | | 235 | | | | | 240 |
| Glu | Lys | Val | Leu | Arg | Lys | Met | Asn | Leu | Pro | Asp | Glu | Val | Val | Glu | Ala |
| | | | | 245 | | | | | 250 | | | | | 255 | |
| Ala | Val | Glu | Lys | Tyr | Lys | Ala | Asn | Phe | Pro | Glu | Trp | Arg | Leu | Asp | Ser |
| | | | 260 | | | | | 265 | | | | | 270 | | |
| Phe | Pro | Gly | Phe | Leu | Gly | Asn | Val | Thr | Ala | Gly | Arg | Cys | Ser | Asn | Val |
| | | | 275 | | | | | 280 | | | | | 285 | | |
| Phe | Asn | Met | Glu | Gly | Met | Asn | Cys | Val | Val | Asp | Ala | Ala | Cys | Ala | Ser |
| | | 290 | | | | | 295 | | | | | 300 | | | |
| Ser | Leu | Ile | Ala | Ile | Lys | Val | Ala | Ile | Asp | Glu | Leu | Leu | His | Gly | Asp |
| 305 | | | | | 310 | | | | | 315 | | | | | 320 |
| Cys | Asp | Thr | Met | Ile | Ala | Gly | Ala | Thr | Cys | Thr | Asp | Asn | Ser | Ile | Gly |
| | | | | 325 | | | | | 330 | | | | | 335 | |
| Met | Tyr | Met | Ala | Phe | Ser | Lys | Thr | Pro | Val | Phe | Ser | Thr | Asp | Gln | Ser |
| | | | 340 | | | | | 345 | | | | | 350 | | |
| Val | Lys | Ala | Tyr | Asp | Ala | Lys | Thr | Lys | Gly | Met | Leu | Ile | Gly | Glu | Gly |
| | | | 355 | | | | | 360 | | | | | 365 | | |
| Ser | Ala | Met | Val | Val | Leu | Lys | Arg | Tyr | Ala | Asp | Ala | Val | Arg | Asp | Gly |

```
              370                 375                 380
Asp Glu Ile His Ala Val Ile Arg Ala Cys Ala Ser Ser Asp Gly
385                 390                 395                 400

Lys Ala Ala Gly Ile Tyr Ala Pro Thr Val Ser Gly Gln Glu Ala
                405                 410                 415

Leu Arg Arg Ala Tyr Ala Arg Ala Gly Val Asp Pro Ser Thr Val Thr
                420                 425                 430

Leu Val Glu Gly His Gly Thr Gly Thr Pro Val Gly Asp Arg Ile Glu
                435                 440                 445

Leu Thr Ala Leu Arg Asn Val Phe Asp Ala Ala Asn Lys Gly Arg Lys
                450                 455                 460

Glu Thr Val Ala Val Gly Ser Ile Lys Ser Gln Ile Gly His Leu Lys
465                 470                 475                 480

Ala Val Ala Gly Phe Ala Gly Leu Val Lys Val Val Met Ala Leu Lys
                485                 490                 495

His Lys Thr Leu Pro Gln Thr Ile Asn Val His Asp Pro Pro Ala Leu
                500                 505                 510

His Asp Gly Ser Pro Ile Gln Asp Ser Ser Leu Tyr Ile Asn Thr Met
                515                 520                 525

Asn Arg Pro Trp Phe Thr Ala Pro Gly Val Pro Arg Arg Ala Gly Ile
530                 535                 540

Ser Ser Phe Gly Phe Gly Gly Ala Asn Tyr His Ala Val Leu Glu Glu
545                 550                 555                 560

Ala Glu Pro Glu His Ala Lys Pro Tyr Arg Met Asn Gln Val Pro Gln
                565                 570                 575

Pro Val Leu Leu His Ala Ser Ser Ala Ser Ala Leu Ala Ser Ile Cys
                580                 585                 590

Asp Ala Gln Ala Asp Ala Leu Gln Ala Ala Val Ser Pro Glu Ala Ser
                595                 600                 605

Lys His Ala Asp Tyr Arg Ala Ile Val Ala Phe His Glu Ala Phe Lys
                610                 615                 620

Leu Arg Ala Gly Val Pro Ala Gly His Ala Arg Ile Gly Phe Val Ser
625                 630                 635                 640

Gly Ser Ala Ala Ala Thr Leu Ala Val Leu Arg Ala Ala Ser Ala Lys
                645                 650                 655

Leu Lys Gln Ser Ser Ala Thr Leu Glu Trp Thr Leu Leu Arg Glu Gly
                660                 665                 670

Val Thr Tyr Arg Ser Ala Ala Met His Thr Pro Gly Ser Val Ala Ala
                675                 680                 685

Leu Phe Ala Gly Gln Gly Ala Gln Tyr Thr His Met Phe Ala Asp Val
                690                 695                 700

Ala Met Asn Trp Pro Pro Phe Arg Ser Ala Val Gln Glu Met Asp Ala
705                 710                 715                 720

Ala Gln Val Thr Ala Ala Pro Lys Arg Leu Ser Glu Val Leu Tyr
                725                 730                 735

Pro Arg Lys Pro Tyr Ala Ala Glu Pro Glu Gln Asp Asn Lys Ala Ile
                740                 745                 750

Ser Met Thr Ile Asn Ser Gln Pro Ala Leu Met Ala Cys Ala Ala Gly
                755                 760                 765

Ala Phe Glu Val Phe Arg Gln Ala Gly Leu Ala Pro Asp His Val Ala
                770                 775                 780

Gly His Ser Leu Gly Glu Phe Gly Ala Leu Leu Ala Ala Gly Cys Ala
785                 790                 795                 800
```

```
Ser Arg Glu Glu Leu Phe Arg Leu Val Cys Ser Arg Ala Lys Ala Met
            805                 810                 815

Gln Asp Val Pro Gln Gly Asp Gly Ala Trp Leu Ala Asn Cys Asn Ser
            820                 825                 830

Pro Ser Gln Val Val Ile Ser Gly Asp Lys Thr Ala Val Glu Arg Glu
            835                 840                 845

Ser Ser Arg Leu Ala Gly Leu Gly Phe Arg Ile Ile Pro Leu Ala Cys
            850                 855                 860

Glu Gly Ala Phe His Ser Pro His Met Thr Ala Ala Gln Ala Thr Phe
865                 870                 875                 880

Gln Ala Ala Leu Asp Ser Leu Lys Ile Ser Thr Pro Thr Asn Gly Ala
            885                 890                 895

Arg Leu Tyr Asn Asn Val Ser Gly Lys Thr Cys Arg Ser Leu Gly Glu
            900                 905                 910

Leu Arg Asp Cys Leu Gly Lys His Met Thr Ser Pro Val Leu Phe Gln
            915                 920                 925

Ala Gln Val Glu Asn Met Tyr Ala Ala Gly Ala Arg Ile Phe Val Glu
            930                 935                 940

Phe Gly Pro Lys Gln Val Leu Ser Lys Leu Val Gly Glu Ile Leu Ala
945                 950                 955                 960

Asp Lys Ser Asp Phe Val Thr Val Ala Val Asn Ser Ser Ser Ser Lys
            965                 970                 975

Asp Ser Asp Val Gln Leu Arg Glu Ala Ala Lys Leu Ala Val Leu
            980                 985                 990

Gly Val Pro Leu Ala Asn Phe Asp Pro Trp Glu Leu Cys Asp Ala Arg
            995                 1000                1005

Arg Leu Arg Glu Cys Pro Arg Ser Lys Thr Thr Leu Arg Leu Ser
            1010                1015                1020

Ala Ala Thr Tyr Val Ser Asn Lys Thr Leu Ala Ala Arg Glu Lys
            1025                1030                1035

Val Met Glu Asp Asn Cys Asp Phe Ser Ser Leu Phe Ala Ser Gly
            1040                1045                1050

Pro Ala Ser Gln Glu Met Glu Arg Glu Ile Ala Asn Leu Arg Ala
            1055                1060                1065

Glu Leu Glu Ala Ala Gln Arg Gln Leu Asp Thr Ala Lys Thr Gln
            1070                1075                1080

Leu Ala Arg Lys Gln Val Gln Asp Pro Thr Ala Asp Arg Gln Arg
            1085                1090                1095

Asp Met Ile Ala Lys His Arg Ser Thr Leu Ala Ala Met Val Lys
            1100                1105                1110

Glu Phe Glu Ala Leu Ala Ser Gly Ser Pro Cys Ala Val Pro Phe
            1115                1120                1125

Ala Pro Val Val Asp Thr Val Glu Asp Val Pro Phe Ala Asp
            1130                1135                1140

Lys Val Ser Thr Pro Pro Gln Val Thr Ser Ala Pro Ile Ala
            1145                1150                1155

Glu Leu Ala Arg Ala Glu Val Val Met Glu Val Leu Ala Ala
            1160                1165                1170

Lys Thr Gly Tyr Glu Val Asp Met Ile Glu Ala Asp Met Leu Leu
            1175                1180                1185

Asp Ala Glu Leu Gly Ile Asp Ser Val Lys Arg Ile Glu Ile Leu
            1190                1195                1200
```

-continued

| | | | | | | | | | | | | |
|---|---|---|---|---|---|---|---|---|---|---|---|---|
| Ala | Ala | Val | Gln | Ala | Gln | Leu | Gly | Val | Glu | Ala | Lys | Asp | Val | Asp |
| 1205 | | | | | 1210 | | | | | 1215 | | |
| Ala | Leu | Ser | Arg | Thr | Arg | Thr | Val | Gly | Glu | Val | Val | Asp | Ala | Met |
| 1220 | | | | | 1225 | | | | | 1230 | | |
| Lys | Ala | Glu | Ile | Gly | Gly | Gln | Ala | Thr | Ser | Ala | Pro | Ser | Pro | Met |
| 1235 | | | | | 1240 | | | | | 1245 | | |
| Ala | Gln | Pro | Gln | Ala | Ser | Ala | Pro | Ser | Pro | Ser | Pro | Thr | Ala | Ser |
| 1250 | | | | | 1255 | | | | | 1260 | | |
| Val | Leu | Pro | Lys | Pro | Val | Ala | Leu | Pro | Ala | Ser | Val | Asp | Pro | Ala |
| 1265 | | | | | 1270 | | | | | 1275 | | |
| Lys | Leu | Ala | Arg | Ala | Glu | Ala | Val | Val | Met | Glu | Val | Leu | Ala | Ala |
| 1280 | | | | | 1285 | | | | | 1290 | | |
| Lys | Thr | Gly | Tyr | Glu | Val | Asp | Met | Ile | Glu | Ala | Asp | Met | Leu | Leu |
| 1295 | | | | | 1300 | | | | | 1305 | | |
| Asp | Ala | Glu | Leu | Gly | Ile | Asp | Ser | Val | Lys | Arg | Ile | Glu | Ile | Leu |
| 1310 | | | | | 1315 | | | | | 1320 | | |
| Ala | Ala | Val | Gln | Ala | Gln | Leu | Gly | Val | Glu | Ala | Lys | Asp | Val | Asp |
| 1325 | | | | | 1330 | | | | | 1335 | | |
| Ala | Leu | Ser | Arg | Thr | Arg | Thr | Val | Gly | Glu | Val | Val | Asp | Ala | Met |
| 1340 | | | | | 1345 | | | | | 1350 | | |
| Lys | Ala | Glu | Ile | Gly | Gly | Gln | Ala | Thr | Ser | Ala | Pro | Ala | Ser | Val |
| 1355 | | | | | 1360 | | | | | 1365 | | |
| Ala | Gln | Pro | Gln | Ala | Ser | Ala | Pro | Ser | Pro | Ser | Ala | Thr | Thr | Ala |
| 1370 | | | | | 1375 | | | | | 1380 | | |
| Ser | Val | Leu | Pro | Lys | Pro | Val | Ala | Ala | Pro | Thr | Ser | Ala | Asp | Pro |
| 1385 | | | | | 1390 | | | | | 1395 | | |
| Ala | Lys | Leu | Ala | Arg | Ala | Glu | Ala | Val | Val | Met | Glu | Val | Leu | Ala |
| 1400 | | | | | 1405 | | | | | 1410 | | |
| Ala | Lys | Thr | Gly | Tyr | Glu | Val | Asp | Met | Ile | Glu | Ala | Asp | Met | Leu |
| 1415 | | | | | 1420 | | | | | 1425 | | |
| Leu | Asp | Ala | Glu | Leu | Gly | Ile | Asp | Ser | Val | Lys | Arg | Ile | Glu | Ile |
| 1430 | | | | | 1435 | | | | | 1440 | | |
| Leu | Ala | Ala | Val | Gln | Ala | Gln | Leu | Gly | Val | Glu | Ala | Lys | Asp | Val |
| 1445 | | | | | 1450 | | | | | 1455 | | |
| Asp | Ala | Leu | Ser | Arg | Thr | Arg | Thr | Val | Gly | Glu | Val | Val | Glu | Ala |
| 1460 | | | | | 1465 | | | | | 1470 | | |
| Met | Lys | Ala | Glu | Ile | Gly | Gly | Gln | Ala | Thr | Ser | Ala | Pro | Ala | Ser |
| 1475 | | | | | 1480 | | | | | 1485 | | |
| Val | Ala | Gln | Pro | Gln | Ile | Ser | Val | Ser | Pro | Thr | Pro | Leu | Ala | Ala |
| 1490 | | | | | 1495 | | | | | 1500 | | |
| Ser | Pro | Ser | Ala | Asp | Pro | Ala | Lys | Leu | Ala | Arg | Ala | Glu | Ala | Val |
| 1505 | | | | | 1510 | | | | | 1515 | | |
| Val | Met | Glu | Val | Leu | Ala | Ala | Lys | Thr | Gly | Tyr | Glu | Val | Asp | Met |
| 1520 | | | | | 1525 | | | | | 1530 | | |
| Ile | Glu | Ala | Asp | Met | Leu | Leu | Asp | Ala | Glu | Leu | Gly | Ile | Asp | Ser |
| 1535 | | | | | 1540 | | | | | 1545 | | |
| Val | Lys | Arg | Ile | Glu | Ile | Leu | Ala | Ala | Val | Gln | Ala | Gln | Leu | Gly |
| 1550 | | | | | 1555 | | | | | 1560 | | |
| Val | Glu | Ala | Lys | Asp | Val | Asp | Ala | Leu | Ser | Arg | Thr | Arg | Thr | Val |
| 1565 | | | | | 1570 | | | | | 1575 | | |
| Gly | Glu | Val | Val | Asp | Ala | Met | Lys | Ala | Glu | Ile | Gly | Gly | Gln | Ala |
| 1580 | | | | | 1585 | | | | | 1590 | | |
| Thr | Ser | Ala | Pro | Ala | Ser | Val | Ala | Gln | Pro | Gln | Ala | Ser | Ala | Pro |

-continued

```
            1595                1600                1605

Ser Pro Ser Ala Thr Ala Ser  Val Leu Pro Lys Pro  Val Ala Ala
    1610                1615                1620

Pro Thr Ser Ala Asp Pro Ala  Lys Leu Ala Arg Ala  Glu Ala Val
    1625                1630                1635

Val Met Glu Val Leu Ala Ala  Lys Thr Gly Tyr Glu  Val Asp Met
    1640                1645                1650

Ile Glu Ala Asp Met Leu Leu  Asp Ala Glu Leu Gly  Ile Asp Ser
    1655                1660                1665

Val Lys Arg Ile Glu Ile Leu  Ala Ala Val Gln Ala  Gln Leu Gly
    1670                1675                1680

Val Glu Ala Lys Asp Val Asp  Ala Leu Ser Arg Thr  Arg Thr Val
    1685                1690                1695

Gly Glu Val Val Glu Ala Met  Lys Ala Glu Ile Gly  Gly Gln Ala
    1700                1705                1710

Thr Ser Ala Pro Ala Ser Met  Ala Gln Pro Gln Ile  Ser Val Ser
    1715                1720                1725

Pro Thr Pro Leu Ala Ala Ser  Pro Ser Ala Asp Pro  Ala Lys Leu
    1730                1735                1740

Ala Arg Ala Glu Ala Val Val  Met Glu Val Leu Ala  Ala Lys Thr
    1745                1750                1755

Gly Tyr Glu Val Asp Met Ile  Glu Ala Asp Met Leu  Leu Asp Ala
    1760                1765                1770

Glu Leu Gly Ile Asp Ser Val  Lys Arg Ile Glu Ile  Leu Ala Ala
    1775                1780                1785

Val Gln Ala Gln Leu Gly Val  Glu Ala Lys Asp Val  Asp Ala Leu
    1790                1795                1800

Ser Arg Thr Arg Thr Val Gly  Glu Val Val Asp Ala  Met Lys Ala
    1805                1810                1815

Glu Ile Gly Gly Gln Ala Thr  Ser Ala Pro Ala Ser  Val Ala Gln
    1820                1825                1830

Pro Gln Ala Ser Ala Pro Ser  Pro Ser Ala Thr Ala  Ser Ala Pro
    1835                1840                1845

Val Thr Pro Leu Ala Ala Pro  Ala Ser Val Asp Pro  Ala Lys Leu
    1850                1855                1860

Ala Arg Ala Glu Ala Val Val  Met Glu Val Leu Ala  Ala Lys Thr
    1865                1870                1875

Gly Tyr Glu Val Asp Met Ile  Glu Ala Asp Met Leu  Leu Asp Ala
    1880                1885                1890

Glu Leu Gly Ile Asp Ser Val  Lys Arg Ile Glu Ile  Leu Ala Ala
    1895                1900                1905

Val Gln Ala Gln Leu Gly Val  Glu Ala Lys Asp Val  Asp Ala Leu
    1910                1915                1920

Ser Arg Thr Arg Thr Val Gly  Glu Val Val Asp Ala  Met Lys Ala
    1925                1930                1935

Glu Ile Gly Gly Gln Ala Thr  Ser Ala Pro Ala Ser  Val Ala Gln
    1940                1945                1950

Pro Gln Ala Ser Ala Pro Ser  Pro Ser Ala Thr Ala  Ser Val Leu
    1955                1960                1965

Pro Lys Pro Val Ala Ser Pro  Ala Ser Val Asp Pro  Ala Lys Leu
    1970                1975                1980

Ala Arg Ala Glu Ala Val Val  Met Glu Val Leu Ala  Ala Lys Thr
    1985                1990                1995
```

```
Gly Tyr Glu Val Asp Met Ile Asp Ala Asp Met Leu Leu Asp Ala
    2000                2005                2010

Glu Leu Gly Ile Asp Ser Val Lys Arg Ile Glu Ile Leu Ala Ala
    2015                2020                2025

Val Gln Ala Gln Leu Gly Val Glu Ala Lys Asp Val Asp Ala Leu
    2030                2035                2040

Ser Arg Thr Arg Thr Val Gly Glu Val Val Glu Ala Met Lys Ala
    2045                2050                2055

Glu Ile Gly Ala Ala Gly Pro Asn Asp Ala Gln Ala Ala Ser Gly
    2060                2065                2070

His Leu Phe Gly Thr Gly Cys Glu Asp Leu Ser Leu Cys Ser Ala
    2075                2080                2085

Ser Val Val Glu Ile Ala Arg Cys Ser Glu Leu Ala Leu Glu Arg
    2090                2095                2100

Pro Met Asp Arg Pro Ile Leu Ile Val Ser Asp Gly Ser Ala Leu
    2105                2110                2115

Pro Ala Ala Leu Ala Ser Arg Leu Gly Ser Cys Ala Val Ile Leu
    2120                2125                2130

Thr Thr Ala Gly Glu Thr Asp Gln Ser Val Arg Ser Thr Lys His
    2135                2140                2145

Val Asp Met Glu Gly Trp Gly Glu Ala Asp Leu Val Arg Ala Leu
    2150                2155                2160

Glu Ala Val Glu Ser Arg Phe Gly Val Pro Gly Gly Val Val Val
    2165                2170                2175

Leu Glu Arg Ala Ser Glu Thr Ala Arg Asp Gln Leu Gly Phe Ala
    2180                2185                2190

Leu Leu Leu Ala Lys His Ser Ser Lys Ala Leu Asn Gln Gln Ile
    2195                2200                2205

Pro Gly Gly Arg Ala Cys Phe Val Gly Val Ser Arg Ile Asp Gly
    2210                2215                2220

Lys Leu Gly Leu Ser Gly Ala Cys Ala Lys Gly Lys Gly Trp Ala
    2225                2230                2235

Glu Ala Ala Glu Ile Ala Gln Gln Gly Ala Val Ala Gly Leu Cys
    2240                2245                2250

Lys Thr Leu Asp Leu Glu Trp Pro His Val Phe Ala Arg Ser Ile
    2255                2260                2265

Asp Ile Glu Leu Gly Ala Asn Glu Glu Thr Ala Ala Gln Ala Ile
    2270                2275                2280

Phe Glu Glu Leu Ser Cys Pro Asp Leu Thr Val Arg Glu Ala Gly
    2285                2290                2295

Tyr Thr Lys Asp Gly Lys Arg Trp Thr Thr Glu Ala Arg Pro Val
    2300                2305                2310

Gly Leu Gly Lys Pro Lys Gln Ala Leu Arg Ser Ser Asp Val Phe
    2315                2320                2325

Leu Val Ser Gly Gly Ala Arg Gly Ile Thr Pro Val Cys Val Arg
    2330                2335                2340

Glu Leu Ala Lys Ser Ile Ser Gly Gly Thr Phe Val Leu Leu Gly
    2345                2350                2355

Arg Ser Pro Leu Ala Asp Asp Pro Ala Trp Ala Cys Gly Val Glu
    2360                2365                2370

Glu Ala Asn Ile Gly Thr Ala Ala Met Ala His Leu Lys Ala Glu
    2375                2380                2385
```

-continued

```
Phe Ala Ala Gly Arg Gly Pro Lys Pro Thr Pro Lys Ala His Lys
    2390                2395                2400

Ala Leu Val Gly Ser Val Leu Gly Ala Arg Glu Val Leu Gly Ser
    2405                2410                2415

Leu Glu Ser Ile Arg Ala Gln Gly Ala Arg Ala Glu Tyr Val Ser
    2420                2425                2430

Cys Asp Val Ser Cys Ala Glu Arg Val Lys Ala Val Val Asp Asp
    2435                2440                2445

Leu Glu Arg Arg Val Gly Ala Val Thr Gly Val Val His Ala Ser
    2450                2455                2460

Gly Val Leu Arg Asp Lys Ser Val Glu Arg Leu Glu Leu Ala Asp
    2465                2470                2475

Phe Glu Val Val Tyr Gly Thr Lys Val Asp Gly Leu Leu Asn Leu
    2480                2485                2490

Leu Gln Ala Val Asp Arg Pro Lys Leu Arg His Leu Val Leu Phe
    2495                2500                2505

Ser Ser Leu Ala Gly Phe His Gly Asn Thr Gly Gln Ala Val Tyr
    2510                2515                2520

Ala Met Ala Asn Glu Ala Leu Asn Lys Met Ala Phe His Leu Glu
    2525                2530                2535

Thr Ala Met Pro Gly Leu Ser Val Lys Thr Ile Gly Phe Gly Pro
    2540                2545                2550

Trp Asp Gly Gly Met Val Asn Asp Ala Leu Lys Ala His Phe Ala
    2555                2560                2565

Ser Met Gly Val Gln Ile Ile Pro Leu Asp Gly Gly Ala Glu Thr
    2570                2575                2580

Val Ser Arg Ile Ile Gly Ala Cys Ser Pro Thr Gln Val Leu Val
    2585                2590                2595

Gly Asn Trp Gly Leu Pro Pro Val Val Pro Asn Ala Ser Val His
    2600                2605                2610

Lys Ile Thr Val Arg Leu Gly Gly Glu Ser Ala Asn Pro Phe Leu
    2615                2620                2625

Ser Ser His Thr Ile Gln Gly Arg Lys Val Leu Pro Met Thr Val
    2630                2635                2640

Ala Leu Gly Leu Leu Ala Glu Ala Ala Arg Gly Leu Tyr Val Gly
    2645                2650                2655

His Gln Val Val Gly Ile Glu Asp Ala Gln Val Phe Gln Gly Val
    2660                2665                2670

Val Leu Asp Lys Gly Ala Thr Cys Glu Val Gln Leu Arg Arg Glu
    2675                2680                2685

Ser Ser Thr Ala Ser Pro Ser Glu Val Val Leu Ser Ala Ser Leu
    2690                2695                2700

Asn Val Phe Ala Ala Gly Lys Val Val Pro Ala Tyr Arg Ala His
    2705                2710                2715

Val Val Leu Gly Ala Ser Gly Pro Arg Thr Gly Val Gln Leu
    2720                2725                2730

Glu Leu Lys Asp Leu Gly Val Asp Ala Asp Pro Ala Cys Ser Val
    2735                2740                2745

Gly Lys Gly Ala Leu Tyr Asp Gly Arg Thr Leu Phe His Gly Pro
    2750                2755                2760

Ala Phe Gln Tyr Met Asp Glu Val Leu Arg Cys Ser Pro Ala Glu
    2765                2770                2775

Leu Ala Val Arg Cys Arg Val Val Pro Ser Ala Ala Gln Asp Arg
```

```
                    2780                2785                2790

Gly Gln Phe Val Ser Arg Gly Val Leu Tyr Asp Pro Phe Leu Asn
    2795                2800                2805

Asp Thr Val Phe Gln Ala Leu Leu Val Trp Ala Arg Leu Val Arg
    2810                2815                2820

Asp Ser Ala Ser Leu Pro Ser Asn Val Glu Arg Ile Ser Phe His
    2825                2830                2835

Gly Gln Pro Pro Ser Glu Gly Glu Val Phe Tyr Thr Thr Leu Lys
    2840                2845                2850

Leu Asp Ser Ala Ala Ser Gly Pro Leu Asp Pro Ile Ala Lys Ala
    2855                2860                2865

Gln Phe Phe Leu His Arg Ala Cys Gly Ala Val Phe Ala Ser Gly
    2870                2875                2880

Arg Ala Ser Val Val Leu Asn Lys Ala Leu Ser Phe
    2885                2890                2895

<210> SEQ ID NO 56
<211> LENGTH: 2811
<212> TYPE: PRT
<213> ORGANISM: Thraustochytrium sp.

<400> SEQUENCE: 56

Met Lys Asp Met Glu Asp Arg Arg Val Ala Ile Val Gly Met Ser Ala
1               5                   10                  15

His Leu Pro Cys Gly Thr Asp Val Lys Glu Ser Trp Gln Ala Ile Arg
                20                  25                  30

Asp Gly Ile Asp Cys Leu Ser Asp Leu Pro Ala Asp Arg Leu Asp Val
            35                  40                  45

Thr Ala Tyr Tyr Asn Pro Asn Lys Ala Thr Lys Asp Lys Ile Tyr Cys
        50                  55                  60

Lys Arg Gly Gly Phe Ile Pro Asn Tyr Asp Phe Asp Pro Arg Glu Phe
65                  70                  75                  80

Gly Leu Asn Met Phe Gln Met Glu Asp Ser Asp Ala Asn Gln Thr Leu
                85                  90                  95

Thr Leu Leu Lys Val Lys Gln Ala Leu Glu Asp Ala Ser Ile Glu Pro
            100                 105                 110

Phe Thr Lys Glu Lys Lys Asn Ile Gly Cys Val Leu Gly Ile Gly Gly
        115                 120                 125

Gly Gln Lys Ala Ser His Glu Phe Tyr Ser Arg Leu Asn Tyr Val Val
    130                 135                 140

Val Glu Lys Val Leu Arg Lys Met Gly Leu Pro Asp Ala Asp Val Glu
145                 150                 155                 160

Glu Ala Val Glu Lys Tyr Lys Ala Asn Phe Pro Glu Trp Arg Leu Asp
                165                 170                 175

Ser Phe Pro Gly Phe Leu Gly Asn Val Thr Ala Gly Arg Cys Ser Asn
            180                 185                 190

Thr Phe Asn Met Glu Gly Met Asn Cys Val Val Asp Ala Ala Cys Ala
        195                 200                 205

Ser Ser Leu Ile Ala Ile Lys Val Ala Val Glu Glu Leu Leu Phe Gly
    210                 215                 220

Asp Cys Asp Thr Met Ile Ala Gly Ala Thr Cys Thr Asp Asn Ser Leu
225                 230                 235                 240

Gly Met Tyr Met Ala Phe Ser Lys Thr Pro Val Phe Ser Thr Asp Pro
                245                 250                 255
```

```
Ser Val Arg Ala Tyr Asp Glu Lys Thr Lys Gly Met Leu Ile Gly Glu
            260                 265                 270

Gly Ser Ala Met Phe Val Leu Lys Arg Tyr Ala Asp Ala Val Arg Asp
        275                 280                 285

Gly Asp Thr Ile His Ala Val Leu Arg Ser Cys Ser Ser Ser Ser Asp
    290                 295                 300

Gly Lys Ala Ala Gly Ile Tyr Thr Pro Thr Ile Ser Gly Gln Glu Glu
305                 310                 315                 320

Ala Leu Arg Arg Ala Tyr Ala Arg Ala Gly Val Cys Pro Ser Thr Ile
                325                 330                 335

Gly Leu Val Glu Gly His Gly Thr Gly Thr Pro Val Gly Asp Arg Ile
            340                 345                 350

Glu Leu Thr Ala Leu Arg Asn Leu Phe Asp Lys Ala Phe Gly Ser Lys
        355                 360                 365

Lys Glu Gln Ile Ala Val Gly Ser Ile Lys Ser Gln Ile Gly His Leu
    370                 375                 380

Lys Ser Val Ala Gly Phe Ala Gly Leu Val Lys Ala Val Leu Ala Leu
385                 390                 395                 400

Lys His Lys Thr Leu Pro Gly Ser Ile Asn Val Asp Gln Pro Pro Leu
                405                 410                 415

Leu Tyr Asp Gly Thr Gln Ile Gln Asp Ser Ser Leu Tyr Ile Asn Lys
            420                 425                 430

Thr Asn Arg Pro Trp Phe Thr Gln Asn Lys Leu Pro Arg Arg Ala Gly
        435                 440                 445

Val Ser Ser Phe Gly Phe Gly Gly Ala Asn Tyr His Ala Val Leu Glu
    450                 455                 460

Glu Phe Glu Pro Glu His Glu Lys Pro Tyr Arg Leu Asn Thr Val Gly
465                 470                 475                 480

His Pro Val Leu Leu Tyr Ala Pro Ser Val Glu Ala Leu Lys Val Leu
                485                 490                 495

Cys Asn Asp Gln Leu Ala Glu Leu Thr Ile Ala Leu Glu Glu Ala Lys
            500                 505                 510

Thr His Lys Asn Val Asp Lys Val Cys Gly Tyr Lys Phe Ile Asp Glu
        515                 520                 525

Phe Gln Leu Gln Gly Ser Cys Pro Pro Glu Asn Pro Arg Val Gly Phe
    530                 535                 540

Leu Ala Thr Leu Pro Thr Ser Asn Ile Ile Val Ala Leu Lys Ala Ile
545                 550                 555                 560

Leu Ala Gln Leu Asp Ala Lys Pro Asp Ala Lys Lys Trp Asp Leu Pro
                565                 570                 575

His Lys Lys Ala Phe Gly Ala Thr Phe Ala Ser Ser Ser Val Lys Gly
            580                 585                 590

Ser Val Ala Ala Leu Phe Ala Gly Gln Gly Thr Gln Tyr Leu Asn Met
        595                 600                 605

Phe Ser Asp Val Ala Met Asn Trp Pro Pro Phe Arg Asp Ser Ile Val
    610                 615                 620

Ala Met Glu Glu Ala Gln Thr Glu Val Phe Glu Gly Gln Val Glu Pro
625                 630                 635                 640

Ile Ser Lys Val Leu Phe Pro Arg Glu Arg Tyr Ala Ser Glu Ser Glu
                645                 650                 655

Gln Gly Asn Glu Leu Leu Cys Leu Thr Glu Tyr Ser Gln Pro Thr Thr
            660                 665                 670

Ile Ala Ala Ala Val Gly Ala Phe Asp Ile Phe Lys Ala Ala Gly Phe
```

```
                    675                 680                 685
Lys Pro Asp Met Val Gly Gly His Ser Leu Gly Glu Phe Ala Ala Leu
690                 695                 700

Tyr Ala Ala Gly Ser Ile Ser Arg Asp Asp Leu Tyr Lys Leu Val Cys
705                 710                 715                 720

Lys Arg Ala Lys Ala Met Ala Asn Ala Ser Asp Gly Ala Met Ala Ala
                725                 730                 735

Val Ile Gly Pro Asp Ala Arg Leu Val Thr Pro Gln Asn Ser Asp Val
            740                 745                 750

Tyr Val Ala Asn Phe Asn Ser Ala Thr Gln Val Val Ile Ser Gly Thr
        755                 760                 765

Val Gln Gly Val Lys Glu Glu Ser Lys Leu Leu Ile Ser Lys Gly Phe
770                 775                 780

Arg Val Leu Pro Leu Lys Cys Gln Gly Ala Phe His Ser Pro Leu Met
785                 790                 795                 800

Gly Pro Ser Glu Asp Ser Phe Lys Ser Leu Val Glu Thr Cys Thr Ile
                805                 810                 815

Ser Pro Pro Lys Asn Val Lys Phe Phe Cys Asn Val Ser Gly Lys Glu
            820                 825                 830

Ser Pro Asn Pro Lys Gln Thr Leu Lys Ser His Met Thr Ser Ser Val
        835                 840                 845

Gln Phe Glu Glu Gln Ile Arg Asn Met Tyr Asp Ala Gly Ala Arg Val
850                 855                 860

Phe Leu Glu Phe Gly Pro Arg Gln Val Leu Ala Lys Leu Ile Ala Glu
865                 870                 875                 880

Met Phe Pro Ser Cys Thr Ala Ile Ser Val Asn Pro Ala Ser Ser Gly
                885                 890                 895

Asp Ser Asp Val Gln Leu Arg Leu Ala Ala Val Lys Phe Ala Val Ser
            900                 905                 910

Gly Ala Ala Leu Ser Thr Phe Asp Pro Trp Glu Tyr Arg Lys Pro Gln
        915                 920                 925

Asp Leu Leu Ile Arg Lys Pro Arg Lys Thr Ala Leu Val Leu Ser Ala
930                 935                 940

Ala Thr Tyr Val Ser Pro Lys Thr Leu Ala Glu Arg Lys Lys Ala Met
945                 950                 955                 960

Glu Asp Ile Lys Leu Val Ser Ile Thr Pro Arg Asp Ser Met Val Ser
                965                 970                 975

Ile Gly Lys Ile Ala Gln Glu Val Arg Thr Ala Lys Gln Pro Leu Glu
            980                 985                 990

Thr Glu Ile Arg Arg Leu Asn Lys Glu Leu Glu His Leu Lys Arg Glu
        995                 1000                1005

Leu Ala Ala Ala Lys Ala Ser Val Lys Ser Ala Ser Lys Ser Ser
        1010                1015                1020

Lys Glu Arg Ser Val Leu Ser Lys His Arg Ala Leu Leu Gln Asn
        1025                1030                1035

Ile Leu Gln Asp Tyr Asp Asp Leu Arg Val Val Pro Phe Ala Val
        1040                1045                1050

Arg Ser Val Ala Val Asp Asn Thr Ala Pro Tyr Ala Asp Gln Val
        1055                1060                1065

Ser Thr Pro Ala Ser Glu Arg Ser Ala Ser Pro Leu Phe Glu Lys
        1070                1075                1080

Arg Ser Ser Val Ser Ser Ala Arg Leu Ala Glu Ala Glu Ala Ala
        1085                1090                1095
```

```
Val Leu Ser Val Leu Ala Asp Lys Thr Gly Tyr Asp Ser Ser Met
        1100                1105                1110

Ile Glu Met Asp Met Asp Leu Glu Ser Glu Leu Gly Val Asp Ser
        1115                1120                1125

Ile Lys Arg Val Glu Ile Met Ser Glu Val Gln Thr Leu Leu Ser
        1130                1135                1140

Val Glu Val Ser Asp Val Asp Ala Leu Ser Arg Thr Lys Thr Val
        1145                1150                1155

Gly Asp Val Ile Glu Ala Met Lys Leu Glu Leu Gly Gly Pro Gln
        1160                1165                1170

Gly Gln Thr Leu Thr Ala Glu Ser Ile Arg Gln Pro Pro Val Ser
        1175                1180                1185

Glu Pro Ala Val Pro Thr Ser Ser Ser Ser Ile Ala Asn Val
        1190                1195                1200

Ser Ser Ala Arg Leu Ala Glu Ala Glu Ala Ala Val Leu Ser Val
        1205                1210                1215

Leu Ala Asp Lys Thr Gly Tyr Asp Ser Ser Met Ile Glu Met Asp
        1220                1225                1230

Met Asp Leu Glu Ser Glu Leu Gly Val Asp Ser Ile Lys Arg Val
        1235                1240                1245

Glu Ile Met Ser Glu Val Gln Thr Leu Leu Ser Val Glu Val Ser
        1250                1255                1260

Asp Val Asp Ala Leu Ser Arg Thr Lys Thr Val Gly Asp Val Ile
        1265                1270                1275

Glu Ala Met Lys Leu Glu Leu Gly Gly Pro Gln Gly Gln Thr Leu
        1280                1285                1290

Thr Ala Glu Ser Ile Arg Gln Pro Pro Val Ser Glu Pro Ala Val
        1295                1300                1305

Pro Thr Ser Ser Ser Ser Ile Ala Asn Val Ser Ser Ala Arg
        1310                1315                1320

Leu Ala Glu Ala Glu Ala Ala Val Leu Ser Val Leu Ala Asp Lys
        1325                1330                1335

Thr Gly Tyr Asp Ser Ser Met Ile Glu Met Asp Met Asp Leu Glu
        1340                1345                1350

Ser Glu Leu Gly Val Asp Ser Ile Lys Arg Val Glu Ile Met Ser
        1355                1360                1365

Glu Val Gln Thr Leu Leu Ser Val Glu Val Ser Asp Val Asp Ala
        1370                1375                1380

Leu Ser Arg Thr Lys Thr Val Gly Asp Val Ile Glu Ala Met Lys
        1385                1390                1395

Leu Glu Leu Gly Gly Pro Gln Gly Gln Thr Leu Thr Ala Glu Ser
        1400                1405                1410

Ile Arg Gln Pro Pro Val Ser Glu Pro Ala Val Pro Thr Ser Ser
        1415                1420                1425

Ser Ser Ile Ala Asn Val Leu Ser Ala Arg Leu Ala Glu Ala
        1430                1435                1440

Glu Ala Ala Val Leu Ser Val Leu Ala Asp Lys Thr Gly Tyr Asp
        1445                1450                1455

Ser Ser Met Ile Glu Met Asp Met Asp Leu Glu Ser Glu Leu Gly
        1460                1465                1470

Val Asp Ser Ile Lys Arg Val Glu Ile Met Ser Glu Val Gln Thr
        1475                1480                1485
```

```
Leu Leu Ser Val Glu Val Ser Asp Val Asp Ala Leu Ser Arg Thr
    1490            1495                1500
Lys Thr Val Gly Asp Val Ile Glu Ala Met Lys Leu Glu Leu Gly
1505            1510                1515
Gly Pro Gln Gly Gln Thr Leu Thr Ala Glu Ser Ile Arg Gln Pro
1520            1525                1530
Pro Val Ser Glu Pro Ala Val Pro Thr Ser Ser Ser Ser Ser Ile
1535            1540                1545
Ala Asn Val Ser Ser Ala Arg Leu Ala Glu Ala Glu Ala Ala Val
1550            1555                1560
Leu Ser Val Leu Ala Asp Lys Thr Gly Tyr Asp Ser Ser Met Ile
1565            1570                1575
Glu Met Asp Met Asp Leu Glu Ser Glu Leu Gly Val Asp Ser Ile
1580            1585                1590
Lys Arg Val Glu Ile Met Ser Glu Val Gln Thr Leu Leu Ser Val
1595            1600                1605
Glu Val Ser Asp Val Asp Ala Leu Ser Arg Thr Lys Thr Val Gly
1610            1615                1620
Asp Val Ile Glu Ala Met Lys Leu Glu Leu Gly Gly Pro Gln Gly
1625            1630                1635
Gln Thr Leu Thr Ser Glu Pro Ile His Gln Pro Val Ser Glu
1640            1645                1650
Pro Ala Val Pro Thr Ser Ser Ser Ser Ile Ala Asn Val Ser
1655            1660                1665
Ser Ala Arg Leu Ala Glu Ala Glu Ala Val Leu Ser Val Leu
1670            1675                1680
Ala Asp Lys Thr Gly Tyr Asp Ser Ser Met Ile Glu Met Asp Met
1685            1690                1695
Asp Leu Glu Ser Glu Leu Gly Val Asp Ser Ile Lys Arg Val Glu
1700            1705                1710
Ile Met Ser Glu Val Gln Thr Leu Leu Ser Val Glu Val Ser Asp
1715            1720                1725
Val Asp Ala Leu Ser Arg Thr Lys Thr Val Gly Asp Val Ile Glu
1730            1735                1740
Ala Met Lys Met Glu Leu Gly Gly Pro Gln Gly Gln Thr Leu Thr
1745            1750                1755
Ala Glu Ser Ile Arg Gln Pro Pro Val Ser Glu Pro Ala Val Pro
1760            1765                1770
Thr Ser Ser Ser Ser Ser Ile Ala Asn Val Ser Ser Ala Arg Leu
1775            1780                1785
Ala Glu Ala Glu Ala Ala Val Leu Ser Val Leu Ala Asp Lys Thr
1790            1795                1800
Gly Tyr Asp Ser Ser Met Ile Glu Met Asp Met Asp Leu Glu Ser
1805            1810                1815
Glu Leu Gly Val Asp Ser Ile Lys Arg Val Glu Ile Met Ser Glu
1820            1825                1830
Val Gln Ala Leu Leu Ser Val Glu Val Ser Asp Val Asp Ala Leu
1835            1840                1845
Ser Arg Thr Lys Thr Val Gly Asp Val Ile Glu Ala Met Lys Met
1850            1855                1860
Glu Leu Gly Gly Pro Gln Gly Gln Thr Leu Thr Ala Glu Ser Ile
1865            1870                1875
Arg Glu Pro Pro Val Ser Glu Pro Ala Val Pro Thr Ser Ser Ser
```

-continued

Ser Ser Ile Ala Asn Val Ser Ser Ala Arg Leu Ala Glu Ala Glu
     1895                1900                1905

Ala Ala Val Leu Ser Val Leu Ala Asp Lys Thr Gly Tyr Asp Ser
     1910                1915                1920

Ser Met Ile Glu Met Asp Met Asp Leu Glu Ser Glu Leu Gly Val
     1925                1930                1935

Asp Ser Ile Lys Arg Val Glu Ile Met Ser Glu Val Gln Thr Leu
     1940                1945                1950

Leu Ser Val Glu Val Ser Asp Val Asp Ala Leu Ser Arg Thr Lys
     1955                1960                1965

Thr Val Gly Asp Val Ile Glu Ala Met Lys Leu Glu Leu Gly Glu
     1970                1975                1980

Ser Ser Ser Ile Glu Thr Leu Asn Cys Thr Glu Val Glu His Thr
     1985                1990                1995

Ser Tyr Lys Ser Val Lys Ala Ser Gly Cys Glu Asn Val Asp Thr
     2000                2005                2010

Arg Phe Ala Lys Val Val Gln Ile Ser Leu Pro Ser Lys Leu Lys
     2015                2020                2025

Ser Thr Val Ser His Asp Arg Pro Val Ile Val Asp Asp Gly
     2030                2035                2040

Thr Pro Leu Thr Thr Glu Leu Cys Lys Ile Leu Gly Gly Asn Ile
     2045                2050                2055

Val Val Leu Ser Tyr Gln Gly Lys Pro Ala Gly Pro Arg Gly Val
     2060                2065                2070

Glu Val Pro Asp Leu Ser Glu Glu Ala Leu Ile Gln Ala Leu Ala
     2075                2080                2085

Leu Ile Arg Ser Thr Tyr Gly Val Pro Ile Gly Phe Ile Cys Gln
     2090                2095                2100

Gln Val Ser Asn Val Ser Thr Lys Ala Gln Leu Cys Trp Ala Leu
     2105                2110                2115

Leu Ala Ala Lys His Leu Lys Lys Asp Leu Asn Ala Val Leu Pro
     2120                2125                2130

Asp Ser Arg Ser Phe Phe Val Gly Val Val Arg Leu Asn Gly Lys
     2135                2140                2145

Leu Gly Thr Phe Glu Asn Ile Ser Asp Phe Ser Lys Phe Asp Leu
     2150                2155                2160

Thr Lys Ala Leu Asp Tyr Gly Gln Arg Gly Ser Leu Leu Gly Leu
     2165                2170                2175

Cys Lys Ser Leu Asp Leu Glu Trp Glu Gln Val Phe Cys Arg Gly
     2180                2185                2190

Ile Asp Leu Ala Cys Asp Leu Met Pro Leu Gln Ala Ala Arg Ile
     2195                2200                2205

Leu Arg Asn Glu Leu Gln Cys Pro Asn Met Arg Leu Arg Glu Val
     2210                2215                2220

Gly Tyr Asp Ile Ser Gly Ala Arg Tyr Thr Ile Ser Thr Asp Asp
     2225                2230                2235

Leu Leu Cys Gly Pro Ser Lys Ala Lys Val Glu Ala Ala Asp Leu
     2240                2245                2250

Phe Leu Val Thr Gly Gly Ala Arg Gly Ile Thr Pro His Cys Val
     2255                2260                2265

Arg Glu Ile Ala Ser Arg Ser Pro Gly Thr Thr Phe Val Leu Val
     2270                2275                2280

-continued

Gly Arg Ser Glu Met Ser Asp Glu Pro Asp Trp Ala Val Gly His
2285                2290                2295

Tyr Asn Lys Asp Leu Asp Gln Ser Thr Met Lys His Leu Lys Ala
2300                2305                2310

Thr His Ala Ala Gly Gly Val Lys Pro Thr Pro Lys Ala His Arg
2315                2320                2325

Ala Leu Val Asn Arg Val Thr Gly Ser Arg Glu Val Arg Glu Ser
2330                2335                2340

Leu Arg Ala Ile Gln Glu Ala Gly Ala Asn Val Glu Tyr Ile Ala
2345                2350                2355

Cys Asp Val Ser Asp Glu Asn Lys Val Arg Gln Leu Val Gln Arg
2360                2365                2370

Val Glu Gln Lys Tyr Gly Cys Glu Ile Thr Gly Ile Trp His Ala
2375                2380                2385

Ser Gly Val Leu Arg Asp Lys Leu Val Glu Gln Lys Thr Thr Asp
2390                2395                2400

Asp Phe Glu Ala Val Phe Gly Thr Lys Val Thr Gly Leu Val Asn
2405                2410                2415

Ile Val Ser Gln Val Asn Met Ser Lys Leu Arg His Phe Ile Leu
2420                2425                2430

Phe Ser Ser Leu Ala Gly Phe His Gly Asn Lys Gly Gln Thr Asp
2435                2440                2445

Tyr Ala Ile Ala Asn Glu Ala Leu Asn Lys Ile Ala His Thr Leu
2450                2455                2460

Ser Ala Phe Leu Pro Lys Leu Asn Ala Lys Val Leu Asp Phe Gly
2465                2470                2475

Pro Trp Val Gly Ser Gly Met Val Thr Glu Thr Leu Glu Lys His
2480                2485                2490

Phe Lys Ala Met Gly Val Gln Thr Ile Pro Leu Glu Pro Gly Ala
2495                2500                2505

Arg Thr Val Ala Gln Ile Ile Leu Ala Ser Ser Pro Pro Gln Ser
2510                2515                2520

Leu Leu Gly Asn Trp Gly Phe Pro Ala Thr Lys Pro Leu Gln Arg
2525                2530                2535

Ser Asn Val Val Thr Gly Thr Leu Ser Pro Glu Glu Ile Glu Phe
2540                2545                2550

Ile Ala Asp His Lys Ile Gln Gly Arg Lys Val Leu Pro Met Met
2555                2560                2565

Ala Ala Ile Gly Phe Met Ala Ser Ile Ala Glu Gly Leu Tyr Pro
2570                2575                2580

Gly Tyr Asn Leu Gln Gly Val Glu Asn Ala Gln Leu Phe Gln Gly
2585                2590                2595

Leu Thr Ile Asn Gln Glu Thr Lys Phe Gln Ile Thr Leu Ile Glu
2600                2605                2610

Glu His Asn Ser Glu Glu Asn Leu Asp Val Leu Thr Ser Leu Gly
2615                2620                2625

Val Met Leu Glu Ser Gly Lys Val Leu Pro Ala Tyr Arg Cys Val
2630                2635                2640

Val Cys Leu Asn Thr Thr Gln Gln Pro Lys Leu Ser Pro Lys
2645                2650                2655

Ile Leu Asn Leu Glu Val Asp Pro Ala Cys Glu Val Asn Pro Tyr
2660                2665                2670

```
Asp Gly Lys Ser Leu Phe His Gly Pro Leu Leu Gln Phe Val Gln
    2675                2680                2685

Gln Val Leu His Ser Ser Thr Lys Gly Leu Val Ala Lys Cys Arg
    2690                2695                2700

Ala Leu Pro Ile Lys Glu Ala Ile Arg Gly Pro Phe Ile Lys Gln
    2705                2710                2715

Thr Leu His Asp Pro Ile Leu Asp Val Ile Phe Gln Leu Met
    2720                2725                2730

Leu Val Trp Cys Arg Asn Ala Leu Gly Ser Ala Ser Leu Pro Asn
    2735                2740                2745

Arg Ile Glu Lys Met Ser Tyr Phe Gly Asn Val Ser Glu Gly Ser
    2750                2755                2760

Thr Phe Phe Ala Ser Val Thr Pro Val Gly Pro Arg Val Pro Lys
    2765                2770                2775

Asp Pro Val Ile Lys Met Gln Phe Leu Leu Gln Asp Glu Ser Gly
    2780                2785                2790

Asn Thr Phe Ser Ser Gly Glu Gly Ser Val Val Leu Ser Asp Glu
    2795                2800                2805

Leu Val Phe
    2810

<210> SEQ ID NO 57
<211> LENGTH: 2059
<212> TYPE: PRT
<213> ORGANISM: Schizochytrium sp.

<400> SEQUENCE: 57

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
        195                 200                 205

His Leu Val Ser Gly Ala Ala Asp Val Met Leu Cys Gly Ala Thr Cys
    210                 215                 220
```

```
Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
            245                 250                 255

Ser Gln Gly Leu Thr Pro Gly Glu Gly Gly Ser Ile Met Val Leu Lys
        260                 265                 270

Arg Leu Asp Asp Ala Ile Arg Asp Gly Asp His Ile Tyr Gly Thr Leu
    275                 280                 285

Leu Gly Ala Asn Val Ser Asn Ser Gly Thr Gly Leu Pro Leu Lys Pro
290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
                340                 345                 350

Glu Gly Lys Val Pro Arg Phe Gly Thr Thr Lys Gly Asn Phe Gly His
            355                 360                 365

Thr Leu Val Ala Ala Gly Phe Ala Gly Met Cys Lys Val Leu Leu Ser
370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
            420                 425                 430

Gly Thr Asn Ala His Ala Val Phe Glu Glu His Asp Pro Ser Asn Ala
        435                 440                 445

Ala Cys Thr Gly His Asp Ser Ile Ser Ala Leu Ser Ala Arg Cys Gly
    450                 455                 460

Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
                485                 490                 495

Ala His Gly Ala Ile Pro Leu Pro Glu Lys Arg Trp Arg Phe Leu Gly
            500                 505                 510

Lys Asp Lys Asp Phe Leu Asp Leu Cys Gly Val Lys Ala Thr Pro His
        515                 520                 525

Gly Cys Tyr Ile Glu Asp Val Glu Val Asp Phe Gln Arg Leu Arg Thr
    530                 535                 540

Pro Met Thr Pro Glu Asp Met Leu Leu Pro Gln Gln Leu Leu Ala Val
545                 550                 555                 560

Thr Thr Ile Asp Arg Ala Ile Leu Asp Ser Gly Met Lys Lys Gly Gly
                565                 570                 575

Asn Val Ala Val Phe Val Gly Leu Gly Thr Asp Leu Glu Leu Tyr Arg
            580                 585                 590

His Arg Ala Arg Val Ala Leu Lys Glu Arg Val Arg Pro Glu Ala Ser
        595                 600                 605

Lys Lys Leu Asn Asp Met Met Gln Tyr Ile Asn Asp Cys Gly Thr Ser
    610                 615                 620

Thr Ser Tyr Thr Ser Tyr Ile Gly Asn Leu Val Ala Thr Arg Val Ser
625                 630                 635                 640
```

```
Ser Gln Trp Gly Phe Thr Gly Pro Ser Phe Thr Ile Thr Glu Gly Asn
            645                 650                 655

Asn Ser Val Tyr Arg Cys Ala Glu Leu Gly Lys Tyr Leu Leu Glu Thr
            660                 665                 670

Gly Glu Val Asp Gly Val Val Ala Gly Val Asp Leu Cys Gly Ser
            675                 680             685

Ala Glu Asn Leu Tyr Val Lys Ser Arg Arg Phe Lys Val Ser Thr Ser
690                 695                 700

Asp Thr Pro Arg Ala Ser Phe Asp Ala Ala Asp Gly Tyr Phe Val
705                 710                 715                 720

Gly Glu Gly Cys Gly Ala Phe Val Leu Lys Arg Glu Thr Ser Cys Thr
                725                 730                 735

Lys Asp Asp Arg Ile Tyr Ala Cys Met Asp Ala Ile Val Pro Gly Asn
                740                 745                 750

Val Pro Ser Ala Cys Leu Arg Glu Ala Leu Asp Gln Ala Arg Val Lys
            755                 760                 765

Pro Gly Asp Ile Glu Met Leu Glu Leu Ser Ala Asp Ser Ala Arg His
            770                 775                 780

Leu Lys Asp Pro Ser Val Leu Pro Lys Glu Leu Thr Ala Glu Glu
785                 790                 795                 800

Ile Gly Gly Leu Gln Thr Ile Leu Arg Asp Asp Lys Leu Pro Arg
                805                 810                 815

Asn Val Ala Thr Gly Ser Val Lys Ala Thr Val Gly Asp Thr Gly Tyr
                820                 825                 830

Ala Ser Gly Ala Ala Ser Leu Ile Lys Ala Ala Leu Cys Ile Tyr Asn
            835                 840                 845

Arg Tyr Leu Pro Ser Asn Gly Asp Asp Trp Asp Glu Pro Ala Pro Glu
850                 855                 860

Ala Pro Trp Asp Ser Thr Leu Phe Ala Cys Gln Thr Ser Arg Ala Trp
865                 870                 875                 880

Leu Lys Asn Pro Gly Glu Arg Arg Tyr Ala Ala Val Ser Gly Val Ser
                885                 890                 895

Glu Thr Arg Ser Cys Tyr Ser Val Leu Leu Ser Glu Ala Glu Gly His
            900                 905                 910

Tyr Glu Arg Glu Asn Arg Ile Ser Leu Asp Glu Glu Ala Pro Lys Leu
            915                 920                 925

Ile Val Leu Arg Ala Asp Ser His Glu Glu Ile Leu Gly Arg Leu Asp
            930                 935                 940

Lys Ile Arg Glu Arg Phe Leu Gln Pro Thr Gly Ala Ala Pro Arg Glu
945                 950                 955                 960

Ser Glu Leu Lys Ala Gln Ala Arg Arg Ile Phe Leu Glu Leu Gly
                965                 970                 975

Glu Thr Leu Ala Gln Asp Ala Ala Ser Ser Gly Ser Gln Lys Pro Leu
            980                 985                 990

Ala Leu Ser Leu Val Ser Thr Pro Ser Lys Leu Gln Arg Glu Val Glu
            995                 1000                1005

Leu Ala Ala Lys Gly Ile Pro Arg Cys Leu Lys Met Arg Arg Asp
        1010                1015                1020

Trp Ser Ser Pro Ala Gly Ser Arg Tyr Ala Pro Glu Pro Leu Ala
        1025                1030                1035

Ser Asp Arg Val Ala Phe Met Tyr Gly Glu Gly Arg Ser Pro Tyr
        1040                1045                1050

Tyr Gly Ile Thr Gln Asp Ile His Arg Ile Trp Pro Glu Leu His
```

-continued

```
          1055                1060                1065
Glu Val Ile Asn Glu Lys Thr Asn Arg Leu Trp Ala Glu Gly Asp
          1070                1075                1080
Arg Trp Val Met Pro Arg Ala Ser Phe Lys Ser Glu Leu Glu Ser
          1085                1090                1095
Gln Gln Gln Glu Phe Asp Arg Asn Met Ile Glu Met Phe Arg Leu
          1100                1105                1110
Gly Ile Leu Thr Ser Ile Ala Phe Thr Asn Leu Ala Arg Asp Val
          1115                1120                1125
Leu Asn Ile Thr Pro Lys Ala Ala Phe Gly Leu Ser Leu Gly Glu
          1130                1135                1140
Ile Ser Met Ile Phe Ala Phe Ser Lys Lys Asn Gly Leu Ile Ser
          1145                1150                1155
Asp Gln Leu Thr Lys Asp Leu Arg Glu Ser Asp Val Trp Asn Lys
          1160                1165                1170
Ala Leu Ala Val Glu Phe Asn Ala Leu Arg Glu Ala Trp Gly Ile
          1175                1180                1185
Pro Gln Ser Val Pro Lys Asp Glu Phe Trp Gln Gly Tyr Ile Val
          1190                1195                1200
Arg Gly Thr Lys Gln Asp Ile Glu Ala Ala Ile Ala Pro Asp Ser
          1205                1210                1215
Lys Tyr Val Arg Leu Thr Ile Ile Asn Asp Ala Asn Thr Ala Leu
          1220                1225                1230
Ile Ser Gly Lys Pro Asp Ala Cys Lys Ala Ala Ile Ala Arg Leu
          1235                1240                1245
Gly Gly Asn Ile Pro Ala Leu Pro Val Thr Gln Gly Met Cys Gly
          1250                1255                1260
His Cys Pro Glu Val Gly Pro Tyr Thr Lys Asp Ile Ala Lys Ile
          1265                1270                1275
His Ala Asn Leu Glu Phe Pro Val Val Asp Gly Leu Asp Leu Trp
          1280                1285                1290
Thr Thr Ile Asn Gln Lys Arg Leu Val Pro Arg Ala Thr Gly Ala
          1295                1300                1305
Lys Asp Glu Trp Ala Pro Ser Ser Phe Gly Glu Tyr Ala Gly Gln
          1310                1315                1320
Leu Tyr Glu Lys Gln Ala Asn Phe Pro Gln Ile Val Glu Thr Ile
          1325                1330                1335
Tyr Lys Gln Asn Tyr Asp Val Phe Val Glu Val Gly Pro Asn Asn
          1340                1345                1350
His Arg Ser Thr Ala Val Arg Thr Thr Leu Gly Pro Gln Arg Asn
          1355                1360                1365
His Leu Ala Gly Ala Ile Asp Lys Gln Asn Glu Asp Ala Trp Thr
          1370                1375                1380
Thr Ile Val Lys Leu Val Ala Ser Leu Lys Ala His Leu Val Pro
          1385                1390                1395
Gly Val Thr Ile Ser Pro Leu Tyr His Ser Lys Leu Val Ala Glu
          1400                1405                1410
Ala Gln Ala Cys Tyr Ala Ala Leu Cys Lys Gly Glu Lys Pro Lys
          1415                1420                1425
Lys Asn Lys Phe Val Arg Lys Ile Gln Leu Asn Gly Arg Phe Asn
          1430                1435                1440
Ser Lys Ala Asp Pro Ile Ser Ser Ala Asp Leu Ala Ser Phe Pro
          1445                1450                1455
```

```
Pro Ala Asp Pro Ala Ile Glu Ala Ala Ile Ser Ser Arg Ile Met
    1460            1465                1470

Lys Pro Val Ala Pro Lys Phe Tyr Ala Arg Leu Asn Ile Asp Glu
    1475            1480                1485

Gln Asp Glu Thr Arg Asp Pro Ile Leu Asn Lys Asp Asn Ala Pro
    1490            1495                1500

Ser Ser Ser Ser Ser Ser Ser Ser Ser Ser Ser Ser Ser Ser Ser
    1505            1510                1515

Pro Ser Pro Ala Pro Ser Ala Pro Val Gln Lys Lys Ala Ala Pro
    1520            1525                1530

Ala Ala Glu Thr Lys Ala Val Ala Ser Ala Asp Ala Leu Arg Ser
    1535            1540                1545

Ala Leu Leu Asp Leu Asp Ser Met Leu Ala Leu Ser Ser Ala Ser
    1550            1555                1560

Ala Ser Gly Asn Leu Val Glu Thr Ala Pro Ser Asp Ala Ser Val
    1565            1570                1575

Ile Val Pro Pro Cys Asn Ile Ala Asp Leu Gly Ser Arg Ala Phe
    1580            1585                1590

Met Lys Thr Tyr Gly Val Ser Ala Pro Leu Tyr Thr Gly Ala Met
    1595            1600                1605

Ala Lys Gly Ile Ala Ser Ala Asp Leu Val Ile Ala Ala Gly Arg
    1610            1615                1620

Gln Gly Ile Leu Ala Ser Phe Gly Ala Gly Gly Leu Pro Met Gln
    1625            1630                1635

Val Val Arg Glu Ser Ile Glu Lys Ile Gln Ala Ala Leu Pro Asn
    1640            1645                1650

Gly Pro Tyr Ala Val Asn Leu Ile His Ser Pro Phe Asp Ser Asn
    1655            1660                1665

Leu Glu Lys Gly Asn Val Asp Leu Phe Leu Glu Lys Gly Val Thr
    1670            1675                1680

Phe Val Glu Ala Ser Ala Phe Met Thr Leu Thr Pro Gln Val Val
    1685            1690                1695

Arg Tyr Arg Ala Ala Gly Leu Thr Arg Asn Ala Asp Gly Ser Val
    1700            1705                1710

Asn Ile Arg Asn Arg Ile Ile Gly Lys Val Ser Arg Thr Glu Leu
    1715            1720                1725

Ala Glu Met Phe Met Arg Pro Ala Pro Glu His Leu Leu Gln Lys
    1730            1735                1740

Leu Ile Ala Ser Gly Glu Ile Asn Gln Glu Gln Ala Glu Leu Ala
    1745            1750                1755

Arg Arg Val Pro Val Ala Asp Asp Ile Ala Val Glu Ala Asp Ser
    1760            1765                1770

Gly Gly His Thr Asp Asn Arg Pro Ile His Val Ile Leu Pro Leu
    1775            1780                1785

Ile Ile Asn Leu Arg Asp Arg Leu His Arg Glu Cys Gly Tyr Pro
    1790            1795                1800

Ala Asn Leu Arg Val Arg Val Gly Ala Gly Gly Ile Gly Cys
    1805            1810                1815

Pro Gln Ala Ala Leu Ala Thr Phe Asn Met Gly Ala Ser Phe Ile
    1820            1825                1830

Val Thr Gly Thr Val Asn Gln Val Ala Lys Gln Ser Gly Thr Cys
    1835            1840                1845
```

Asp Asn Val Arg Lys Gln Leu Ala Lys Ala Thr Tyr Ser Asp Val
1850                1855                1860

Cys Met Ala Pro Ala Ala Asp Met Phe Glu Glu Gly Val Lys Leu
1865                1870                1875

Gln Val Leu Lys Lys Gly Thr Met Phe Pro Ser Arg Ala Asn Lys
1880                1885                1890

Leu Tyr Glu Leu Phe Cys Lys Tyr Asp Ser Phe Glu Ser Met Pro
1895                1900                1905

Pro Ala Glu Leu Ala Arg Val Glu Lys Arg Ile Phe Ser Arg Ala
1910                1915                1920

Leu Glu Glu Val Trp Asp Glu Thr Lys Asn Phe Tyr Ile Asn Arg
1925                1930                1935

Leu His Asn Pro Glu Lys Ile Gln Arg Ala Glu Arg Asp Pro Lys
1940                1945                1950

Leu Lys Met Ser Leu Cys Phe Arg Trp Tyr Leu Ser Leu Ala Ser
1955                1960                1965

Arg Trp Ala Asn Thr Gly Ala Ser Asp Arg Val Met Asp Tyr Gln
1970                1975                1980

Val Trp Cys Gly Pro Ala Ile Gly Ser Phe Asn Asp Phe Ile Lys
1985                1990                1995

Gly Thr Tyr Leu Asp Pro Val Ala Asn Glu Tyr Pro Cys Val
2000                2005                2010

Val Gln Ile Asn Lys Gln Ile Leu Arg Gly Ala Cys Phe Leu Arg
2015                2020                2025

Arg Leu Glu Ile Leu Arg Asn Ala Arg Leu Ser Asp Gly Ala Ala
2030                2035                2040

Ala Leu Val Ala Ser Ile Asp Asp Thr Tyr Val Pro Ala Glu Lys
2045                2050                2055

Leu

<210> SEQ ID NO 58
<211> LENGTH: 1935
<212> TYPE: PRT
<213> ORGANISM: Thraustochytrium sp.

<400> SEQUENCE: 58

Met Gln Leu Pro Pro Ala His Ser Ala Asp Glu Asn Arg Ile Ala Val
1               5                   10                  15

Val Gly Met Ala Val Lys Tyr Ala Gly Cys Asp Asn Lys Glu Glu Phe
                20                  25                  30

Trp Lys Thr Leu Met Asn Gly Ser Ile Asn Thr Lys Ser Ile Ser Ala
            35                  40                  45

Ala Arg Leu Gly Ser Asn Lys Arg Asp Glu His Tyr Val Pro Glu Arg
        50                  55                  60

Ser Lys Tyr Ala Asp Thr Phe Cys Asn Glu Arg Tyr Gly Cys Ile Gln
65                  70                  75                  80

Gln Gly Thr Asp Asn Glu His Asp Leu Leu Gly Leu Ala Gln Glu
                85                  90                  95

Ala Leu Ala Asp Ala Ala Gly Arg Met Glu Lys Gln Pro Ser Glu Ala
            100                 105                 110

Phe Asp Leu Glu Asn Thr Gly Ile Val Ser Gly Cys Leu Ser Phe Pro
        115                 120                 125

Met Asp Asn Leu Gln Gly Glu Leu Leu Asn Leu Tyr Gln Ser His Val
    130                 135                 140

```
Glu Lys Gln Leu Pro Ser Ala Leu Val Glu Ala Val Lys Leu Trp
145                 150                 155                 160

Ser Glu Arg Gln Lys Ser Thr Lys Ala His Ala Gly Asp Lys Arg Arg
            165                 170                 175

Phe Ile Asp Pro Ala Ser Phe Val Ala Asp Lys Leu Asn Leu Gly Pro
            180                 185                 190

Leu His Tyr Ala Ile Asp Ala Ala Cys Ala Ser Ala Leu Tyr Val Leu
            195                 200                 205

Lys Leu Ala Gln Asp His Leu Val Ser Gly Ala Val Asp Met Met Leu
            210                 215                 220

Cys Gly Ala Thr Cys Phe Pro Glu Pro Phe Phe Ile Leu Ser Gly Phe
225                 230                 235                 240

Ser Thr Phe Gln Ala Met Pro Val Gly Ala Asp Gly Val Ser Leu Pro
            245                 250                 255

Leu His Lys Thr Ser Ala Gly Leu Thr Pro Gly Glu Gly Gly Ser Ile
            260                 265                 270

Met Val Leu Lys Arg Leu Lys Asp Ala Ile Arg Asp Gly Asn His Ile
            275                 280                 285

Tyr Gly Val Leu Leu Glu Ala Asn Leu Ser Asn Ala Gly Cys Gly Leu
            290                 295                 300

Pro Leu Ser Pro His Leu Pro Ser Glu Glu Ser Cys Ile Arg Asp Thr
305                 310                 315                 320

Tyr Arg Arg Ala Gly Val Ala Ala Asp Gln Ser Ile Gln Tyr Ile Glu
            325                 330                 335

Cys His Ala Thr Gly Thr Pro Arg Gly Asp Val Val Glu Ile Glu Ala
            340                 345                 350

Val Glu Arg Val Phe Lys Lys Asn Val Pro Arg Leu Gly Ser Thr Lys
            355                 360                 365

Gly Asn Phe Gly His Ser Leu Val Ala Ala Gly Phe Ala Gly Met Ala
            370                 375                 380

Lys Leu Leu Leu Ala Met Glu His Gly Val Ile Pro Pro Thr Pro Gly
385                 390                 395                 400

Leu Asp Ala Ser Asn Gln Ala Ser Glu His Val Val Thr Lys Ala Ile
            405                 410                 415

Thr Trp Pro Glu Thr His Gly Ala Pro Lys Arg Ala Gly Leu Ser Ala
            420                 425                 430

Phe Gly Phe Gly Gly Thr Asn Ala His Ala Leu Phe Glu Glu Phe Asn
            435                 440                 445

Ala Glu Gly Ile Ser Tyr Arg Pro Gly Lys Pro Pro Val Glu Ser Asn
            450                 455                 460

Thr Arg Pro Ser Val Val Ile Thr Gly Met Asp Cys Thr Phe Gly Ser
465                 470                 475                 480

Leu Glu Gly Ile Asp Ala Phe Glu Thr Ala Leu Tyr Glu Gly Arg Asp
            485                 490                 495

Ala Ala Arg Asp Leu Pro Ala Lys Arg Trp Arg Phe Leu Gly Glu Asp
            500                 505                 510

Leu Glu Phe Leu Arg Ala Ile Arg Leu Lys Glu Lys Pro Arg Gly Cys
            515                 520                 525

Phe Val Glu Ser Val Asp Val Asn Phe Arg Arg Leu Lys Thr Pro Leu
            530                 535                 540

Thr Pro Glu Asp Met Leu Arg Pro Gln Gln Leu Leu Ala Val Ser Thr
545                 550                 555                 560

Met Asp Arg Ala Ile Ile Asp Ala Gly Leu Lys Lys Gly Gln His Val
```

-continued

```
                565                 570                 575
Ala Val Leu Val Gly Leu Gly Thr Asp Leu Glu Leu Tyr Arg His Arg
                580                 585                 590
Ala Arg Val Ala Leu Lys Glu Val Leu His Pro Ser Leu Lys Ser Asp
                595                 600                 605
Thr Ala Ile Leu Gln Lys Ile Met Gln Tyr Val Asn Asp Ala Gly Thr
                610                 615                 620
Ser Thr Ser Tyr Thr Ser Tyr Ile Gly Asn Leu Val Ala Thr Arg Ile
625                 630                 635                 640
Ser Ser Gln Trp Gly Phe Thr Gly Pro Ser Phe Thr Val Thr Glu Gly
                645                 650                 655
Asn Asn Ser Val Tyr Arg Cys Ala Gln Leu Ala Lys Asp Met Leu Gln
                660                 665                 670
Val Asn Arg Val Asp Ala Val Ile Ala Gly Val Asp Leu Asn Gly
                675                 680                 685
Ser Ala Glu Ser Phe Phe Val Arg Ala Asn Arg Gln Lys Ile Ser Lys
                690                 695                 700
Leu Ser His Pro Cys Ala Ser Phe Asp Arg Asp Ala Asp Gly Phe Phe
705                 710                 715                 720
Ala Gly Glu Gly Cys Gly Ala Leu Val Phe Lys Arg Leu Glu Asp Cys
                725                 730                 735
Ala Pro Gln Glu Lys Ile Tyr Ala Ser Ile Asp Ser Ile Ala Ile Asp
                740                 745                 750
Lys Glu Pro Thr Ser Ser Ala Val Lys Ala Val Tyr Gln Ser Asp Ser
                755                 760                 765
Ser Leu Ser Asp Ile Glu Leu Leu Glu Ile Ser Gly Asp Ser Lys Arg
770                 775                 780
Phe Ala Ala Phe Glu Gly Ala Val Glu Ile Gln Ser Ser Val Glu Ala
785                 790                 795                 800
Gln Leu Lys Gly Leu Ser Lys Val Leu Glu Pro Ala Lys Gly Gln Gly
                805                 810                 815
Val Ala Val Gly Ser Thr Arg Ala Thr Val Gly Asp Ile Gly Tyr Ala
                820                 825                 830
Thr Gly Ala Ala Ser Leu Ile Lys Thr Ala Leu Cys Leu Tyr Asn Arg
                835                 840                 845
Tyr Leu Pro Ala Leu Ala Asn Trp Ser Gly Pro Cys Glu Gln Ser Ala
                850                 855                 860
Trp Gly Ser Asn Met Phe Val Cys His Glu Thr Arg Pro Trp Met Lys
865                 870                 875                 880
Asn Gln Asn Glu Lys Arg Cys Ala Leu Ile Ser Gly Thr Asp Pro Ser
                885                 890                 895
His Thr Cys Phe Ser Leu Val Leu Ser Asp Thr Gly Cys Tyr Glu Glu
                900                 905                 910
His Asn Arg Thr Cys Phe Asp Val Gln Ala Pro Gln Leu Val Leu Ile
                915                 920                 925
His Gly Phe Asp Gly Lys Thr Ile Val Arg Arg Leu Glu Gly Tyr Leu
                930                 935                 940
Leu Glu Leu Val Glu Gly His Ala Ser Pro Ser Glu Tyr Phe His Lys
945                 950                 955                 960
Leu Ile Gly Gln Ser Leu Leu Glu Asn Ser Glu Ser Lys Leu Thr
                965                 970                 975
Leu Ser Leu Val Cys Asn Pro Asn Gln Leu Gln Lys Glu Leu Met Leu
                980                 985                 990
```

-continued

```
Ala Ile Lys Gly Val Gln Arg Ser Met Leu Thr Gly Lys Asp Trp Val
        995                 1000                1005

Ser Pro Ser Gly Ser Cys Phe Ala Pro Asn Pro Leu Ser Ser Ala
    1010                1015                1020

Lys Val Ala Phe Met Tyr Gly Glu Gly Arg Ser Pro Tyr Cys Gly
    1025                1030                1035

Val Gly Leu Gly Leu His Arg Leu Trp Pro Gly Leu His Glu Asn
    1040                1045                1050

Val Asn Asn Lys Thr Val Asp Leu Trp Thr Glu Gly Asp Gly Trp
    1055                1060                1065

Leu Tyr Pro Arg Thr Leu Thr Arg Glu Glu His Thr Lys Ala Ile
    1070                1075                1080

Glu Ser Phe Asn Ala Asn Gln Ile Glu Met Phe Arg Ala Gly Ile
    1085                1090                1095

Phe Ile Ser Met Cys Gln Thr Asp Tyr Val Met Asn Val Leu Gly
    1100                1105                1110

Val Gln Pro Lys Ala Gly Phe Gly Leu Ser Leu Gly Glu Ile Ser
    1115                1120                1125

Met Leu Phe Ala Met Ser Lys Glu Asn Cys Arg Gln Ser Gln Glu
    1130                1135                1140

Met Thr Asn Arg Leu Arg Gly Ser Pro Val Trp Ser Asn Glu Leu
    1145                1150                1155

Ala Ile Asn Phe Asn Ala Ile Arg Lys Leu Trp Lys Ile Pro Arg
    1160                1165                1170

Gly Ala Pro Leu Glu Ser Phe Trp Gln Gly Tyr Leu Val His Gly
    1175                1180                1185

Thr Arg Glu Glu Val Glu His Ala Ile Gly Leu Ser Glu Pro Tyr
    1190                1195                1200

Val Arg Leu Leu Ile Val Asn Asp Ser Arg Ser Ala Leu Ile Ala
    1205                1210                1215

Gly Lys Pro Asp Ala Cys Gln Ala Val Ile Ser Arg Leu Asn Ser
    1220                1225                1230

Lys Phe Pro Ser Leu Pro Val Lys Gln Gly Met Ile Gly His Cys
    1235                1240                1245

Pro Glu Val Arg Ala Phe Ile Lys Asp Ile Gly Tyr Ile His Glu
    1250                1255                1260

Thr Leu Arg Ile Ser Asn Asp Tyr Ser Asp Cys Gln Leu Phe Ser
    1265                1270                1275

Ala Val Thr Lys Gly Ala Leu Asp Ser Ser Thr Met Glu Ile Lys
    1280                1285                1290

His Phe Val Gly Glu Val Tyr Ser Arg Ile Ala Asp Phe Pro Gln
    1295                1300                1305

Ile Val Asn Thr Val His Ser Ala Gly Tyr Asp Val Phe Leu Glu
    1310                1315                1320

Leu Gly Cys Asp Ala Ser Arg Ser Ala Ala Val Gln Asn Ile Leu
    1325                1330                1335

Gly Gly Gln Gly Lys Phe Leu Ser Thr Ala Ile Asp Lys Lys Gly
    1340                1345                1350

His Ser Ala Trp Ser Gln Val Leu Arg Ala Thr Ala Ser Leu Ala
    1355                1360                1365

Ala His Arg Val Pro Gly Ile Ser Ile Leu Asp Leu Phe His Pro
    1370                1375                1380
```

```
Asn Phe Arg Glu Met Cys Cys Thr Met Ala Thr Thr Pro Lys Val
    1385                1390                1395

Glu Asp Lys Phe Leu Arg Thr Ile Gln Ile Asn Gly Arg Phe Glu
    1400                1405                1410

Lys Glu Met Ile His Leu Glu Asp Thr Thr Leu Ser Cys Leu Pro
    1415                1420                1425

Ala Pro Ser Glu Ala Asn Ile Ala Ala Ile Gln Ser Arg Ser Ile
    1430                1435                1440

Arg Ser Ala Ala Ala Arg Ser Gly Gln Ser His Asp Cys Ala Ser
    1445                1450                1455

His Ser His Glu Glu Asn Lys Asp Ser Cys Pro Glu Lys Leu Lys
    1460                1465                1470

Leu Asp Ser Val Ser Val Ala Ile Asn Phe Asp Asn Asp Asp Arg
    1475                1480                1485

Ile Gln Leu Gly His Ala Gly Phe Arg Glu Met Tyr Asn Thr Arg
    1490                1495                1500

Tyr Ser Leu Tyr Thr Gly Ala Met Ala Lys Gly Ile Ala Ser Ala
    1505                1510                1515

Asp Leu Val Ile Ala Ala Gly Lys Glu Gly Ile Leu Ala Ser Tyr
    1520                1525                1530

Gly Ala Gly Gly Leu Pro Leu Ala Thr Val Arg Lys Gly Ile Asp
    1535                1540                1545

Lys Ile Gln Gln Ala Leu Pro Ser Gly Pro Tyr Ala Val Asn Leu
    1550                1555                1560

Ile His Ser Pro Phe Asp Gly Asn Leu Glu Gln Gly Asn Val Asp
    1565                1570                1575

Leu Phe Leu Glu Lys Asn Val Arg Val Ala Glu Cys Ser Ala Phe
    1580                1585                1590

Thr Thr Leu Thr Val Pro Val Val His Tyr Arg Ala Ala Gly Leu
    1595                1600                1605

Val Arg Arg Gln Asp Gly Ser Ile Leu Ile Lys Asn Arg Ile Ile
    1610                1615                1620

Ala Lys Val Ser Arg Thr Glu Leu Ala Glu Met Phe Leu Arg Pro
    1625                1630                1635

Ala Pro Gln Ile Ile Leu Glu Lys Leu Val Ala Ala Glu Ile Ile
    1640                1645                1650

Ser Ser Asp Gln Ala Arg Met Ala Ala Lys Val Pro Met Ala Asp
    1655                1660                1665

Asp Ile Ala Val Glu Ala Asp Ser Gly Gly His Thr Asp Asn Arg
    1670                1675                1680

Pro Met His Val Ile Leu Pro Leu Ile Ile Gln Leu Arg Asn Thr
    1685                1690                1695

Ile Leu Ala Glu Tyr Gly Cys Ala Thr Ala Phe Arg Thr Arg Ile
    1700                1705                1710

Gly Ala Gly Gly Gly Ile Gly Cys Pro Ser Ala Ala Leu Ala Ala
    1715                1720                1725

Phe Asp Met Gly Ala Ser Phe Val Val Thr Gly Ser Ile Asn Gln
    1730                1735                1740

Ile Cys Arg Glu Ala Gly Thr Cys Asp Thr Val Arg Glu Leu Leu
    1745                1750                1755

Ala Asn Ser Ser Tyr Ser Asp Val Thr Met Ala Pro Ala Ala Asp
    1760                1765                1770

Met Phe Asp Gln Gly Val Lys Leu Gln Val Leu Lys Arg Gly Thr
```

```
                    1775                1780                1785
Met Phe Pro Ser Arg Ala Asn Lys Leu Arg Lys Leu Phe Val Asn
    1790                1795                1800

Tyr Glu Ser Leu Glu Thr Leu Pro Ser Lys Glu Leu Lys Tyr Leu
    1805                1810                1815

Glu Asn Ile Ile Phe Lys Gln Ala Val Asp Gln Val Trp Glu Glu
    1820                1825                1830

Thr Lys Arg Phe Tyr Cys Glu Lys Leu Asn Asn Pro Asp Lys Ile
    1835                1840                1845

Ala Arg Ala Met Lys Asp Pro Lys Leu Lys Met Ser Leu Cys Phe
    1850                1855                1860

Arg Trp Tyr Leu Ser Lys Ser Ser Gly Trp Ala Asn Ala Gly Ile
    1865                1870                1875

Lys Ser Arg Ala Leu Asp Tyr Gln Ile Trp Cys Gly Pro Ala Met
    1880                1885                1890

Gly Ser Phe Asn Asn Phe Ala Ser Gly Thr Ser Leu Asp Trp Lys
    1895                1900                1905

Val Thr Gly Val Phe Pro Gly Val Ala Glu Val Asn Met Ala Ile
    1910                1915                1920

Leu Asp Gly Ala Arg Glu Leu Ala Ala Lys Arg Asn
    1925                1930                1935

<210> SEQ ID NO 59
<211> LENGTH: 2037
<212> TYPE: PRT
<213> ORGANISM: Thraustochytrium aureum

<400> SEQUENCE: 59

Gln Ala Ile Gly His Arg Ala Ala Arg Trp Ser Cys Arg Ser Lys Ser
1               5                   10                  15

Lys Ala Arg Gly His Lys Ala Gln Lys Glu Met Asn Gln Gly Gly Arg
                20                  25                  30

Asn Asp Glu Gly Val Ser Val Ala Arg Ala Asp Pro Cys Pro Asp Thr
            35                  40                  45

Arg Ile Ala Val Val Gly Met Ala Val Glu Tyr Ala Gly Cys Arg Gly
        50                  55                  60

Lys Glu Ala Phe Trp Asp Thr Leu Met Asn Gly Lys Ile Asn Ser Ala
65                  70                  75                  80

Cys Ile Ser Asp Asp Arg Leu Gly Ser Ala Arg Arg Glu Glu His Tyr
                85                  90                  95

Ala Pro Glu Arg Ser Lys Tyr Ala Asp Thr Phe Cys Asn Glu Arg Tyr
            100                 105                 110

Gly Cys Ile Asp Pro Lys Val Asp Asn Glu His Asp Leu Leu Leu Gly
        115                 120                 125

Leu Ala Ala Ala Ala Leu Gln Asp Ala Gln Asp Arg Arg Ser Asp Gly
    130                 135                 140

Gly Lys Phe Asp Pro Ala Gln Leu Lys Arg Cys Gly Ile Val Ser Gly
145                 150                 155                 160

Cys Leu Ser Phe Pro Met Asp Asn Leu Gln Gly Glu Leu Leu Asn Leu
                165                 170                 175

Tyr Gln Ala His Ala Glu Arg Arg Ile Gly Lys His Cys Phe Ala Asp
            180                 185                 190

Gln Thr Pro Trp Ser Thr Arg Thr Arg Ala Leu His Pro Leu Pro Gly
        195                 200                 205
```

```
Asp Pro Arg Thr His Arg Asp Pro Ala Ser Phe Val Ala Gly Gln Leu
    210                 215                 220

Gly Leu Gly Pro Leu His Tyr Ser Leu Asp Ala Ala Cys Ala Ser Ala
225                 230                 235                 240

Leu Tyr Val Leu Arg Leu Ala Gln Asp His Leu Leu Ser Gly Glu Ala
                245                 250                 255

Asp Leu Met Leu Cys Gly Ala Thr Cys Phe Pro Glu Pro Phe Phe Ile
            260                 265                 270

Leu Thr Gly Phe Ser Thr Phe His Ala Met Pro Val Gly Glu Asn Gly
        275                 280                 285

Val Ser Met Pro Phe His Arg Asp His Leu Leu Ser Gly Glu Ala Asp
    290                 295                 300

Leu Met Leu Cys Gly Ala Thr Cys Phe Pro Glu Pro Phe Phe Ile Leu
305                 310                 315                 320

Thr Gly Phe Ser Thr Phe His Ala Met Pro Val Gly Glu Asn Gly Val
                325                 330                 335

Ser Met Pro Phe His Arg Gln Pro Ser Glu Glu Ala Cys Leu Lys Ala
            340                 345                 350

Thr Tyr Glu Leu Val Gly Val Pro Pro Arg Asp Val Gln Tyr Val Glu
        355                 360                 365

Cys His Ala Thr Gly Thr Pro Gln Gly Asp Thr Val Glu Leu Gln Ala
    370                 375                 380

Val Lys Ala Cys Phe Glu Gly Ala Ser Pro Arg Ile Gly Ser Thr Lys
385                 390                 395                 400

Gly Asn Phe Gly His Thr Leu Val Ala Ala Gly Phe Ala Gly Met Cys
                405                 410                 415

Lys Val Leu Leu Ala Met Glu Arg Gly Val Ile Pro Pro Thr Pro Gly
            420                 425                 430

Val Asp Ser Gly Thr Gln Ile Asp Pro Leu Val Val Thr Ala Ala Leu
        435                 440                 445

Pro Trp Pro Asp Thr Arg Gly Pro Lys Arg Ala Gly Leu Ser Ala
    450                 455                 460

Phe Gly Phe Gly Gly Thr Asn Ala His Ala Val Phe Glu Glu His Ile
465                 470                 475                 480

Pro Ser Arg Ala Pro Pro Ala Val Leu Cys Gln Pro Arg Leu Gly Ser
                485                 490                 495

Gly Pro Asn Arg Lys Leu Ala Ile Val Gly Met Asp Ala Thr Phe Gly
            500                 505                 510

Ser Leu Lys Gly Leu Ser Ala Leu Glu Ala Ala Leu Tyr Glu Ala Arg
        515                 520                 525

His Ala Ala Arg Pro Leu Pro Ala Lys Arg Trp Arg Phe Leu Gly Gly
    530                 535                 540

Asp Glu Ser Phe Leu His Glu Ile Gly Leu Glu Cys Ser Pro His Gly
545                 550                 555                 560

Cys Tyr Ile Glu Asp Val Asp Val Asp Phe Lys Arg Leu Arg Thr Pro
                565                 570                 575

Met Val Pro Glu Asp Leu Leu Arg Pro Gln Gln Leu Leu Ala Val Ser
            580                 585                 590

Thr Ile Asp Lys Ala Ile Leu Asp Ser Gly Leu Ala Lys Gly Gly Asn
        595                 600                 605

Val Ala Val Leu Val Gly Leu Gly Thr Asp Leu Glu Leu Tyr Arg His
    610                 615                 620

Arg Ala Arg Val Ala Leu Lys Glu Arg Leu Gln Gly Leu Val Arg Ser
```

-continued

```
            625                 630                 635                 640
        Ala Glu Gly Gly Ala Leu Thr Ser Arg Leu Met Asn Tyr Ile Asn Asp
                        645                 650                 655

Ser Gly Thr Ser Thr Ser Tyr Thr Ser Tyr Ile Gly Asn Leu Val Ala
                        660                 665                 670

Thr Arg Val Ser Ser Gln Trp Gly Phe Thr Gly Pro Ser Phe Thr Val
                        675                 680                 685

Thr Glu Gly Ala Asn Ser Val His Arg Cys Ala Gln Leu Ala Lys Tyr
                        690                 695                 700

Met Leu Asp Arg Gly Glu Val Asp Ala Val Val Ala Gly Val Asp
        705                 710                 715                 720

Leu Cys Gly Ser Ala Glu Ala Phe Phe Val Arg Ser Arg Met Gln
                        725                 730                 735

Ile Ser Lys Ser Gln Arg Pro Ala Ala Pro Phe Asp Arg Ala Ala Asp
                        740                 745                 750

Gly Phe Phe Ala Gly Glu Gly Cys Gly Ala Leu Val Phe Lys Arg Leu
                        755                 760                 765

Thr Asp Cys Val Ser Gly Glu Arg Ile Tyr Ala Ser Leu Asp Ser Val
                        770                 775                 780

Val Val Ala Thr Thr Pro Arg Ala Ala Leu Arg Ala Ala Gly Ser
        785                 790                 795                 800

Ala Arg Val Asp Pro Ala Ser Ile Asp Met Val Glu Leu Ser Ala Asp
                        805                 810                 815

Ser His Arg Phe Val Arg Ala Pro Gly Thr Val Ala Gln Pro Leu Thr
                        820                 825                 830

Ala Glu Val Glu Val Gly Ala Val Arg Glu Val Ile Gly Thr Ala Gly
                        835                 840                 845

Arg Gly Ser Arg Ser Val Ala Val Gly Ser Val Arg Ala Asn Val Gly
                        850                 855                 860

Asp Ala Gly Phe Ala Ser Gly Ala Ala Ala Leu Val Lys Thr Ala Leu
        865                 870                 875                 880

Cys Leu His Asn Arg Tyr Leu Ala Ala Thr Pro Gly Trp Asp Ala Pro
                        885                 890                 895

Ala Ala Gly Val Asp Phe Gly Ala Glu Leu Tyr Val Cys Arg Glu Ser
                        900                 905                 910

Arg Ala Trp Val Lys Asn Ala Gly Val Ala Arg His Ala Ala Ile Ser
                        915                 920                 925

Gly Val Asp Glu Gly Gly Ser Cys Tyr Gly Leu Val Leu Ser Asp Val
                        930                 935                 940

Pro Gly Gln Tyr Glu Thr Gly Asn Arg Ile Ser Leu Gln Ala Glu Ser
        945                 950                 955                 960

Pro Lys Leu Leu Leu Leu Ser Ala Pro Asp His Ala Ala Leu Leu Asp
                        965                 970                 975

Lys Val Ala Ala Glu Leu Ala Leu Glu Gln Ala Asp Gly Leu Ser
                        980                 985                 990

Ala Ala Ala Ala Ala Val Asp Arg Leu Leu Gly Glu Ser Leu Val Gly
                        995                1000                1005

Cys Ala  Ala Gly Ser Gly Gly  Leu Thr Leu Cys Leu  Val Ala Ser
                       1010                1015                1020

Pro Ala  Ser Leu His Lys Glu  Leu Ala Leu Ala His  Arg Gly Ile
                       1025                1030                1035

Pro Arg  Cys Ile Lys Ala Arg  Arg Asp Trp Ala Ser  Pro Ala Gly
                       1040                1045                1050
```

```
Ser Tyr Phe Ala Pro Glu Pro Ile Ala Ser Asp Arg Val Ala Phe
1055                1060                1065

Met Tyr Gly Glu Gly Arg Ser Pro Tyr Cys Gly Val Gly Arg Asp
1070                1075                1080

Leu His Arg Ile Trp Pro Ala Leu His Glu Arg Val Asn Ala Lys
1085                1090                1095

Thr Val Asn Leu Trp Gly Asp Gly Asp Ala Trp Leu Leu Pro Arg
1100                1105                1110

Ala Thr Ser Ala Glu Glu Glu Gln Leu Cys Arg Asn Phe Asp
1115                1120                1125

Ser Asn Gln Val Glu Met Phe Arg Thr Gly Val Tyr Ile Ser Met
1130                1135                1140

Cys Leu Thr Asp Leu Ala Arg Ser Leu Ile Gly Leu Gly Pro Lys
1145                1150                1155

Ala Ser Phe Gly Leu Ser Leu Gly Glu Val Ser Met Leu Phe Ala
1160                1165                1170

Leu Ser Glu Ser Asn Cys Arg Leu Ser Glu Glu Met Thr Arg Arg
1175                1180                1185

Leu Arg Ala Ser Pro Val Trp Asn Ser Glu Leu Ala Val Glu Phe
1190                1195                1200

Asn Ala Leu Arg Lys Leu Trp Gly Val Ala Pro Gly Ala Pro Val
1205                1210                1215

Asp Ser Phe Trp Gln Gly Tyr Val Val Arg Ala Thr Arg Ala Gln
1220                1225                1230

Val Glu Gln Ala Ile Gly Glu Asp Asn Gln Phe Val Arg Leu Leu
1235                1240                1245

Ile Val Asn Asp Ser Gln Ser Val Leu Ile Ala Gly Lys Pro Ala
1250                1255                1260

Ala Cys Glu Ala Val Ile Ala Arg Ile Gly Ser Ile Leu Pro Pro
1265                1270                1275

Leu Gln Val Ser Gln Gly Met Val Gly His Cys Ala Glu Val Leu
1280                1285                1290

Pro Tyr Thr Ser Glu Ile Gly Arg Ile His Asn Met Leu Arg Phe
1295                1300                1305

Pro Ser Gln Asp Glu Thr Gly Gly Cys Lys Met Tyr Ser Ser Val
1310                1315                1320

Ser Asn Ser Arg Ile Gly Pro Val Glu Glu Ser Gln Met Gly Pro
1325                1330                1335

Gly Thr Glu Leu Val Phe Ser Pro Ser Met Glu Asp Phe Val Ala
1340                1345                1350

Gln Leu Tyr Ser Arg Val Ala Asp Phe Pro Ala Ile Thr Glu Ala
1355                1360                1365

Val Tyr Gln Gln Gly His Asp Val Phe Val Glu Val Gly Pro Asp
1370                1375                1380

His Ser Arg Ser Ala Ala Val Arg Ser Thr Leu Gly Pro Thr Arg
1385                1390                1395

Arg His Ile Ala Val Ala Met Asp Arg Lys Gly Glu Ser Ala Trp
1400                1405                1410

Ser Gln Leu Leu Lys Met Leu Ala Thr Leu Ala Ser His Arg Val
1415                1420                1425

Pro Gly Leu Asp Leu Ser Ser Met Tyr His Pro Ala Val Val Glu
1430                1435                1440
```

```
Arg Cys Arg Leu Ala Leu Ala Ala Gln Arg Ser Gly Gln Pro Glu
    1445                1450                1455

Gln Arg Asn Lys Phe Leu Arg Thr Ile Glu Val Asn Gly Phe Tyr
    1460                1465                1470

Asp Pro Ala Asp Ala Thr Ile Pro Glu Ala Val Ala Thr Ile Leu
    1475                1480                1485

Pro Ala Thr Ala Ala Ile Ser Pro Pro Lys Leu Gly Ala Pro His
    1490                1495                1500

Asp Ser Gln Pro Glu Ala Glu Ala Arg Pro Val Gly Glu Ala Ser
    1505                1510                1515

Val Pro Arg Arg Ala Thr Ser Ser Ser Lys Leu Ala Arg Thr Leu
    1520                1525                1530

Ala Ile Asp Ala Cys Asp Ser Asp Val Arg Ala Ala Leu Leu Asp
    1535                1540                1545

Leu Asp Ala Pro Ile Ala Val Gly Gly Ser Ser Arg Ala Gln Val
    1550                1555                1560

Pro Pro Cys Pro Val Ser Ala Leu Gly Ser Ala Ala Phe Arg Ala
    1565                1570                1575

Ala His Gly Val Asp Tyr Ala Leu Tyr Met Gly Ala Met Ala Lys
    1580                1585                1590

Gly Val Ala Ser Ala Glu Met Val Ile Ala Ala Gly Lys Ala Arg
    1595                1600                1605

Met Leu Ala Ser Phe Gly Ala Gly Gly Leu Pro Leu Gly Glu Val
    1610                1615                1620

Glu Glu Ala Leu Asp Lys Ile Gln Ala Ala Leu Pro Glu Gly Pro
    1625                1630                1635

Phe Ala Val Asn Leu Ile His Ser Pro Phe Asp Pro Asn Leu Glu
    1640                1645                1650

Glu Gly Asn Val Glu Leu Phe Leu Arg Arg Gly Ile Arg Leu Val
    1655                1660                1665

Glu Ala Ser Ala Phe Met Ser Val Thr Pro Ser Leu Val Arg Tyr
    1670                1675                1680

Arg Val Ala Gly Leu Glu Arg Gly Pro Gly Gly Thr Ala Arg Val
    1685                1690                1695

Leu Asn Arg Val Ile Gly Lys Val Ser Arg Ala Glu Leu Ala Glu
    1700                1705                1710

Met Phe Met Arg Pro Pro Ala Ala Ile Val Ser Lys Leu Leu
    1715                1720                1725

Ala Gln Gly Leu Val Thr Glu Glu Gln Ala Ser Leu Ala Glu Ile
    1730                1735                1740

Val Pro Leu Val Asp Asp Val Ala Ile Glu Ala Asp Ser Gly Gly
    1745                1750                1755

His Thr Asp Asn Arg Pro Ile His Val Val Leu Pro Val Val Leu
    1760                1765                1770

Ala Leu Arg Asp Arg Val Met Arg Glu Cys Lys Tyr Pro Ala Ala
    1775                1780                1785

Asn Arg Val Arg Val Gly Ala Gly Gly Gly Ile Gly Cys Pro Ala
    1790                1795                1800

Ala Ala Arg Ala Ala Phe Asp Met Gly Ala Ala Phe Val Leu Thr
    1805                1810                1815

Gly Ser Ile Asn Gln Leu Thr Arg Gln Ala Gly Thr Ser Asp Ser
    1820                1825                1830

Val Arg Ala Ala Leu Ala Arg Ala Thr Tyr Ser Asp Val Thr Met
```

```
              1835                1840                1845

Ala Pro Ala Ala Asp Met Phe Asp Gln Gly Val Lys Leu Gln Val
        1850                1855                1860

Leu Lys Arg Gly Thr Met Phe Pro Ala Arg Ala Asn Lys Leu Tyr
    1865                1870                1875

Glu Leu Phe Thr Thr Tyr Gln Ser Leu Asp Ala Ile Pro Arg Ala
    1880                1885                1890

Glu Leu Ala Arg Leu Glu Lys Arg Val Phe Arg Met Ser Ile Asp
    1895                1900                1905

Glu Val Trp Asn Glu Thr Lys Gln Phe Tyr Glu Thr Arg Leu Asn
    1910                1915                1920

Asn Pro Ala Lys Val Ala Arg Ala Glu Arg Asp Pro Lys Leu Lys
    1925                1930                1935

Met Ser Leu Cys Phe Arg Trp Tyr Leu Ser Lys Ser Ser Lys Trp
    1940                1945                1950

Ala Ser Thr Gly Gln Val Gly Arg Glu Leu Asp Tyr Gln Val Trp
    1955                1960                1965

Cys Gly Pro Thr Ile Gly Ala Phe Asn Glu Phe Val Lys Gly Ser
    1970                1975                1980

Ser Leu Asp Ala Glu Ala Cys Gly Gly Arg Phe Pro Cys Val Val
    1985                1990                1995

Arg Val Asn Gln Glu Ile Leu Cys Gly Ala Ala Tyr Glu Gln Arg
    2000                2005                2010

Leu Ala Arg Phe Met Leu Leu Ala Gly Arg Glu Ser Ala Asp Ala
    2015                2020                2025

Leu Ala Tyr Thr Val Ala Glu Ala Arg
    2030                2035

<210> SEQ ID NO 60
<211> LENGTH: 1470
<212> TYPE: PRT
<213> ORGANISM: Thraustochytrium sp.

<400> SEQUENCE: 60

Met Gly Pro Arg Val Ala Ser Gly Lys Val Pro Ala Trp Glu Met Ser
1               5                   10                  15

Lys Ser Glu Leu Cys Asp Asp Arg Thr Val Val Phe Asp Tyr Glu Glu
            20                  25                  30

Leu Leu Glu Phe Ala Glu Gly Asp Ile Ser Lys Val Phe Gly Pro Glu
        35                  40                  45

Phe Lys Val Val Asp Gly Phe Arg Arg Val Arg Leu Pro Ala Arg
    50                  55                  60

Glu Tyr Leu Leu Val Thr Arg Val Thr Leu Met Asp Ala Glu Val Gly
65                  70                  75                  80

Asn Phe Arg Val Gly Ala Arg Met Val Thr Glu Tyr Asp Val Pro Val
                85                  90                  95

Asn Gly Glu Leu Ser Glu Gly Gly Asp Val Pro Trp Ala Val Leu Val
            100                 105                 110

Glu Ala Gly Gln Cys Asp Leu Leu Leu Ile Ser Tyr Met Gly Ile Asp
        115                 120                 125

Phe Gln Cys Lys Gly Glu Arg Val Tyr Arg Leu Leu Asn Thr Thr Leu
    130                 135                 140

Thr Phe Phe Gly Val Ala Lys Glu Gly Glu Thr Leu Val Tyr Asp Ile
145                 150                 155                 160
```

-continued

Arg Val Thr Gly Phe Ala Lys Arg Pro Asp Gly Asp Ile Ser Met Phe
              165                 170                 175

Phe Phe Glu Tyr Asp Cys Tyr Cys Asn Gly Lys Leu Leu Ile Glu Met
          180                 185                 190

Arg Asp Gly Ser Ala Gly Phe Phe Thr Asp Glu Glu Leu Ala Ala Gly
          195                 200                 205

Lys Gly Val Val Val Thr Arg Ala Gln Gln Asn Met Arg Asp Lys Ile
        210                 215                 220

Val Arg Gln Ser Ile Glu Pro Phe Ala Leu Ala Cys Thr His Lys
225                 230                 235                 240

Thr Thr Leu Asn Glu Ser Asp Met Gln Ser Leu Val Glu Arg Asn Trp
              245                 250                 255

Ala Asn Val Phe Gly Thr Ser Asn Lys Met Ala Glu Leu Asn Tyr Lys
          260                 265                 270

Ile Cys Ala Arg Lys Met Leu Met Ile Asp Arg Val Thr His Ile Asp
          275                 280                 285

His His Gly Gly Ala Tyr Gly Leu Gly Leu Leu Val Gly Glu Lys Ile
      290                 295                 300

Leu Asp Arg Asn His Trp Tyr Phe Pro Cys His Phe Val Asn Asp Gln
305                 310                 315                 320

Val Met Ala Gly Ser Leu Val Ser Asp Gly Cys Ser Gln Leu Leu Lys
              325                 330                 335

Leu Tyr Met Ile Trp Leu Gly Leu His Leu Lys Met Glu Glu Phe Asp
          340                 345                 350

Phe Leu Pro Val Ser Gly His Lys Asn Lys Val Arg Cys Arg Gly Gln
          355                 360                 365

Ile Ser Pro His Lys Gly Lys Leu Val Tyr Val Met Glu Ile Lys Lys
      370                 375                 380

Met Gly Tyr Asp Gln Ala Ser Gly Ser Pro Tyr Ala Ile Ala Asp Val
385                 390                 395                 400

Asp Ile Ile Asp Val Asn Glu Glu Leu Gly Gln Ser Phe Asp Ile Asn
              405                 410                 415

Asp Leu Ala Ser Tyr Gly Lys Gly Asp Leu Ser Lys Lys Ile Val Val
          420                 425                 430

Asp Phe Lys Gly Ile Ala Leu Gln Leu Lys Gly Arg Ala Phe Ser Arg
          435                 440                 445

Met Ser Ser Ser Ser Leu Asn Glu Gly Trp Gln Cys Val Pro Lys
      450                 455                 460

Pro Ser Gln Arg Met Glu His Glu Gln Pro Ala His Cys Leu Ala
465                 470                 475                 480

Ser Asp Pro Glu Ala Pro Ser Thr Val Thr Trp His Pro Met Ser Lys
              485                 490                 495

Leu Pro Gly Asn Pro Thr Pro Phe Phe Ser Pro Ser Ser Tyr Pro Pro
          500                 505                 510

Arg Ala Ile Cys Phe Ile Pro Pro Gly Asn Pro Leu Asp Asn Asn
          515                 520                 525

Cys Lys Ala Gly Glu Met Pro Leu Asn Trp Tyr Asn Met Ser Glu Phe
      530                 535                 540

Met Cys Gly Lys Val Ser Asn Cys Leu Gly Pro Glu Phe Ala Arg Phe
545                 550                 555                 560

Asp Lys Ser Asn Thr Ser Arg Ser Pro Ala Phe Asp Leu Ala Leu Val
              565                 570                 575

Thr Arg Val Val Glu Val Thr Asn Met Glu His Gly Lys Phe Leu Asn

```
                580             585             590
Val Asp Cys Asn Pro Ser Lys Gly Thr Met Val Gly Glu Phe Asp Cys
                595             600             605
Pro Gln Asp Ala Trp Phe Phe Asp Gly Ser Cys Asn Asp Gly His Met
        610             615             620
Pro Tyr Ser Ile Ile Met Glu Ile Gly Leu Gln Thr Ser Gly Val Leu
625             630             635             640
Thr Ser Val Leu Lys Ala Pro Leu Thr Met Asp Lys Asp Asp Ile Leu
                645             650             655
Phe Arg Asn Leu Asp Ala Ser Ala Glu Met Val Arg Pro Asp Val Asp
        660             665             670
Val Arg Gly Lys Thr Ile Arg Asn Val Thr Lys Cys Thr Gly Tyr Ala
            675             680             685
Met Leu Gly Lys Met Gly Ile His Arg Phe Thr Phe Glu Leu Ser Val
        690             695             700
Asp Gly Val Val Phe Tyr Lys Gly Ser Thr Ser Phe Gly Trp Phe Thr
705             710             715             720
Pro Glu Val Phe Ala Gln Gln Ala Gly Leu Asp Asn Gly Lys Lys Thr
                725             730             735
Glu Pro Trp Cys Lys Thr Asn Asn Thr Ser Val Arg Arg Val Glu Ile
            740             745             750
Ala Ser Ala Lys Gly Lys Glu Gln Leu Thr Glu Lys Leu Pro Asp Ala
            755             760             765
Thr Asn Ala Gln Val Leu Arg Arg Ser Glu Gln Cys Glu Tyr Leu Asp
        770             775             780
Tyr Leu Asn Ile Ala Pro Asp Ser Gly Leu His Gly Lys Gly Tyr Ala
785             790             795             800
His Gly His Lys Asp Val Asn Pro Gln Asp Trp Phe Phe Ser Cys His
                805             810             815
Phe Trp Phe Asp Pro Val Met Pro Gly Ser Leu Gly Ile Glu Ser Met
            820             825             830
Phe Gln Leu Ile Glu Ala Phe Ala Val Asp Gln Asn Ile Pro Gly Glu
        835             840             845
Tyr Asn Val Ser Asn Pro Thr Phe Ala His Ala Pro Gly Lys Thr Ala
        850             855             860
Trp Lys Tyr Arg Gly Gln Leu Thr Pro Lys Asn Arg Ala Met Asp Cys
865             870             875             880
Glu Val His Ile Val Ser Ile Thr Ala Ser Pro Glu Asn Gly Gly Tyr
                885             890             895
Val Asp Ile Val Ala Asp Gly Ala Leu Trp Val Asp Gly Leu Arg Val
            900             905             910
Tyr Glu Ala Lys Glu Leu Arg Val Arg Val Val Ser Ala Lys Pro Gln
            915             920             925
Ala Ile Pro Asp Val Gln Gln Gln Pro Pro Ser Ala Lys Ala Asp Pro
        930             935             940
Gly Lys Thr Gly Val Ala Leu Ser Pro Thr Gln Leu Arg Asp Val Leu
945             950             955             960
Leu Glu Val Asp Asn Pro Leu Tyr Leu Gly Val Glu Asn Ser Asn Leu
                965             970             975
Val Gln Phe Glu Ser Lys Pro Ala Thr Ser Ser Arg Ile Val Ser Ile
            980             985             990
Lys Pro Cys Ser Ile Ser Asp Leu Gly Asp Lys Ser Phe Met Glu Thr
        995             1000            1005
```

-continued

```
Tyr Asn Val Ser Ala Pro Leu Tyr Thr Gly Ala Met Ala Lys Gly
1010                1015                1020

Ile Ala Ser Ala Asp Leu Val Ile Ala Ala Gly Lys Arg Lys Ile
1025                1030                1035

Leu Gly Ser Phe Gly Ala Gly Gly Leu Pro Ile Ser Ile Val Arg
1040                1045                1050

Glu Ala Leu Glu Lys Ile Gln Gln His Leu Pro His Gly Pro Tyr
1055                1060                1065

Ala Val Asn Leu Ile His Ser Pro Phe Asp Ser Asn Leu Glu Lys
1070                1075                1080

Gly Asn Val Asp Leu Phe Leu Glu Met Gly Val Thr Val Val Glu
1085                1090                1095

Cys Ser Ala Phe Met Glu Leu Thr Ala Gln Val Val Arg Tyr Arg
1100                1105                1110

Ala Ser Gly Leu Ser Lys Ser Ala Asp Gly Ser Ile Arg Ile Ala
1115                1120                1125

His Arg Ile Ile Gly Lys Val Ser Arg Thr Glu Leu Ala Glu Met
1130                1135                1140

Phe Ile Arg Pro Ala Pro Gln His Leu Leu Gln Lys Leu Val Ala
1145                1150                1155

Ser Gly Glu Leu Thr Ala Glu Gln Ala Glu Leu Ala Thr Gln Val
1160                1165                1170

Pro Val Ala Asp Asp Ile Ala Val Glu Ala Asp Ser Gly Gly His
1175                1180                1185

Thr Asp Asn Arg Pro Ile His Val Ile Leu Pro Leu Ile Ile Asn
1190                1195                1200

Leu Arg Asn Arg Leu His Lys Glu Leu Asp Tyr Pro Ser His Leu
1205                1210                1215

Arg Val Arg Val Gly Ala Gly Gly Gly Ile Gly Cys Pro Gln Ala
1220                1225                1230

Ala Leu Ala Ala Phe Gln Met Gly Ala Ala Phe Leu Ile Thr Gly
1235                1240                1245

Thr Val Asn Gln Leu Ala Arg Glu Ser Gly Thr Cys Asp Asn Val
1250                1255                1260

Arg Leu Gln Leu Ser Lys Ala Thr Tyr Ser Asp Val Cys Met Ala
1265                1270                1275

Pro Ala Ala Asp Met Phe Asp Gln Gly Val Glu Leu Gln Val Leu
1280                1285                1290

Lys Lys Gly Thr Leu Phe Pro Ser Arg Ala Lys Lys Leu Tyr Glu
1295                1300                1305

Leu Phe Cys Lys Tyr Asp Ser Phe Glu Ala Met Pro Ala Glu Glu
1310                1315                1320

Leu Gln Arg Val Glu Lys Arg Ile Phe Gln Lys Ser Leu Ala Glu
1325                1330                1335

Val Trp Gln Glu Thr Ser Asp Phe Tyr Ile His Arg Ile Lys Asn
1340                1345                1350

Pro Glu Lys Ile Asn Arg Ala Ala Ser Asp Gly Lys Leu Lys Met
1355                1360                1365

Ser Leu Cys Phe Arg Trp Tyr Leu Gly Leu Ser Ser Phe Trp Ala
1370                1375                1380

Asn Ser Gly Ala Gln Asp Arg Val Met Asp Tyr Gln Ile Trp Cys
1385                1390                1395
```

-continued

Gly Pro Ala Ile Gly Ala Phe Asn Asp Phe Thr Lys Gly Thr Tyr
    1400                1405                1410

Leu Asp Val Thr Val Ala Lys Ser Tyr Pro Cys Val Ala Gln Ile
    1415                1420                1425

Asn Leu Gln Ile Leu Gln Gly Ala Ala Tyr Leu Lys Arg Leu Gly
    1430                1435                1440

Val Ile Arg Phe Asp Arg Met Leu Leu Gln Ala Val Asp Ile Asp
    1445                1450                1455

Asp Pro Val Phe Thr Tyr Val Pro Thr Gln Pro Leu
    1460                1465                1470

<210> SEQ ID NO 61
<211> LENGTH: 1503
<212> TYPE: PRT
<213> ORGANISM: Schizochytrium sp.

<400> SEQUENCE: 61

Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
            20                  25                  30

Leu Leu Glu Phe Ala Glu Gly Asp Ile Ala Lys Val Phe Gly Pro Glu
        35                  40                  45

Phe Ala Val Ile Asp Lys Tyr Pro Arg Arg Val Arg Leu Pro Ala Arg
    50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
        115                 120                 125

Phe Gln Asn Gln Gly Asp Arg Val Tyr Arg Leu Leu Asn Thr Thr Leu
    130                 135                 140

Thr Phe Tyr Gly Val Ala His Glu Gly Glu Thr Leu Glu Tyr Asp Ile
145                 150                 155                 160

Arg Val Thr Gly Phe Ala Lys Arg Leu Asp Gly Gly Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Asp Ala Gly
        195                 200                 205

Lys Gly Val Val Phe Thr Arg Gly Asp Leu Ala Ala Arg Ala Lys Ile
    210                 215                 220

Pro Lys Gln Asp Val Ser Pro Tyr Ala Val Ala Pro Cys Leu His Lys
225                 230                 235                 240

Thr Lys Leu Asn Glu Lys Glu Met Gln Thr Leu Val Asp Lys Asp Trp
                245                 250                 255

Ala Ser Val Phe Gly Ser Lys Asn Gly Met Pro Glu Ile Asn Tyr Lys
            260                 265                 270

Leu Cys Ala Arg Lys Met Leu Met Ile Asp Arg Val Thr Ser Ile Asp
        275                 280                 285

His Lys Gly Gly Val Tyr Gly Leu Gly Gln Leu Val Gly Glu Lys Ile
    290                 295                 300

```
Leu Glu Arg Asp His Trp Tyr Phe Pro Cys His Phe Val Lys Asp Gln
305                 310                 315                 320

Val Met Ala Gly Ser Leu Val Ser Asp Gly Cys Ser Gln Met Leu Lys
            325                 330                 335

Met Tyr Met Ile Trp Leu Gly Leu His Leu Thr Thr Gly Pro Phe Asp
        340                 345                 350

Phe Arg Pro Val Asn Gly His Pro Asn Lys Val Arg Cys Arg Gly Gln
    355                 360                 365

Ile Ser Pro His Lys Gly Lys Leu Val Tyr Val Met Glu Ile Lys Glu
370                 375                 380

Met Gly Phe Asp Glu Asp Asn Asp Pro Tyr Ala Ile Ala Asp Val Asn
385                 390                 395                 400

Ile Ile Asp Val Asp Phe Glu Lys Gly Gln Asp Phe Ser Leu Asp Arg
            405                 410                 415

Ile Ser Asp Tyr Gly Lys Gly Asp Leu Asn Lys Lys Ile Val Val Asp
        420                 425                 430

Phe Lys Gly Ile Ala Leu Lys Met Gln Lys Arg Ser Thr Asn Lys Asn
    435                 440                 445

Pro Ser Lys Val Gln Pro Val Phe Ala Asn Gly Ala Ala Thr Val Gly
450                 455                 460

Pro Glu Ala Ser Lys Ala Ser Ser Gly Ala Ser Ala Ser Ala Ser Ala
465                 470                 475                 480

Ala Pro Ala Lys Pro Ala Phe Ser Ala Asp Val Leu Ala Pro Lys Pro
            485                 490                 495

Val Ala Leu Pro Glu His Ile Leu Lys Gly Asp Ala Leu Ala Pro Lys
        500                 505                 510

Glu Met Ser Trp His Pro Met Ala Arg Ile Pro Gly Asn Pro Thr Pro
    515                 520                 525

Ser Phe Ala Pro Ser Ala Tyr Lys Pro Arg Asn Ile Ala Phe Thr Pro
530                 535                 540

Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
            565                 570                 575

Cys Leu Gly Pro Glu Phe Ala Lys Phe Asp Asp Ser Asn Thr Ser Arg
        580                 585                 590

Ser Pro Ala Trp Asp Leu Ala Leu Val Thr Arg Ala Val Ser Val Ser
    595                 600                 605

Asp Leu Lys His Val Asn Tyr Arg Asn Ile Asp Leu Asp Pro Ser Lys
610                 615                 620

Gly Thr Met Val Gly Glu Phe Asp Cys Pro Ala Asp Ala Trp Phe Tyr
625                 630                 635                 640

Lys Gly Ala Cys Asn Asp Ala His Met Pro Tyr Ser Ile Leu Met Glu
            645                 650                 655

Ile Ala Leu Gln Thr Ser Gly Val Leu Thr Ser Val Leu Lys Ala Pro
        660                 665                 670

Leu Thr Met Glu Lys Asp Asp Ile Leu Phe Arg Asn Leu Asp Ala Asn
    675                 680                 685

Ala Glu Phe Val Arg Ala Asp Leu Asp Tyr Arg Gly Lys Thr Ile Arg
    690                 695                 700

Asn Val Thr Lys Cys Thr Gly Tyr Ser Met Leu Gly Glu Met Gly Val
705                 710                 715                 720
```

-continued

His Arg Phe Thr Phe Glu Leu Tyr Val Asp Asp Val Leu Phe Tyr Lys
            725                 730                 735

Gly Ser Thr Ser Phe Gly Trp Phe Val Pro Glu Val Phe Ala Ala Gln
            740                 745                 750

Ala Gly Leu Asp Asn Gly Arg Lys Ser Glu Pro Trp Phe Ile Glu Asn
            755                 760                 765

Lys Val Pro Ala Ser Gln Val Ser Ser Phe Asp Val Arg Pro Asn Gly
            770                 775                 780

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
                805                 810                 815

Ser Gly Ser Gly Lys Lys Ser Leu Gly Tyr Ala His Gly Ser Lys Thr
            820                 825                 830

Val Asn Pro Asn Asp Trp Phe Phe Ser Cys His Phe Trp Phe Asp Ser
            835                 840                 845

Val Met Pro Gly Ser Leu Gly Val Glu Ser Met Phe Gln Leu Val Glu
            850                 855                 860

Ala Ile Ala Ala His Glu Asp Leu Ala Gly Lys Ala Arg His Cys Gln
865                 870                 875                 880

Pro His Leu Cys Ala Arg Pro Arg Ala Arg Ser Ser Trp Lys Tyr Arg
                885                 890                 895

Gly Gln Leu Thr Pro Lys Ser Lys Lys Met Asp Ser Glu Val His Ile
            900                 905                 910

Val Ser Val Asp Ala His Asp Gly Val Val Asp Leu Val Ala Asp Gly
            915                 920                 925

Phe Leu Trp Ala Asp Ser Leu Arg Val Tyr Ser Val Ser Asn Ile Arg
930                 935                 940

Val Arg Ile Ala Ser Gly Glu Ala Pro Ala Ala Ser Ser Ala Ala
945                 950                 955                 960

Ser Val Gly Ser Ser Ala Ser Ser Val Glu Arg Thr Arg Ser Ser Pro
                965                 970                 975

Ala Val Ala Ser Gly Pro Ala Gln Thr Ile Asp Leu Lys Gln Leu Lys
            980                 985                 990

Thr Glu Leu Leu Glu Leu Asp Ala Pro Leu Tyr Leu Ser Gln Asp Pro
            995                 1000                1005

Thr Ser Gly Gln Leu Lys Lys His Thr Asp Val Ala Ser Gly Gln
            1010                1015                1020

Ala Thr Ile Val Gln Pro Cys Thr Leu Gly Asp Leu Gly Asp Arg
            1025                1030                1035

Ser Phe Met Glu Thr Tyr Gly Val Val Ala Pro Leu Tyr Thr Gly
            1040                1045                1050

Ala Met Ala Lys Gly Ile Ala Ser Ala Asp Leu Val Ile Ala Ala
            1055                1060                1065

Gly Lys Arg Lys Ile Leu Gly Ser Phe Gly Ala Gly Gly Leu Pro
            1070                1075                1080

Met His His Val Arg Ala Ala Leu Glu Lys Ile Gln Ala Ala Leu
            1085                1090                1095

Pro Gln Gly Pro Tyr Ala Val Asn Leu Ile His Ser Pro Phe Asp
            1100                1105                1110

Ser Asn Leu Glu Lys Gly Asn Val Asp Leu Phe Leu Glu Lys Gly
            1115                1120                1125

Val Thr Val Val Glu Ala Ser Ala Phe Met Thr Leu Thr Pro Gln 1130                1135                1140

Val Val Arg Tyr Arg Ala Ala Gly Leu Ser Arg Asn Ala Asp Gly
    1145                1150                1155

Ser Val Asn Ile Arg Asn Arg Ile Ile Gly Lys Val Ser Arg Thr
    1160                1165                1170

Glu Leu Ala Glu Met Phe Ile Arg Pro Ala Pro Glu His Leu Leu
    1175                1180                1185

Glu Lys Leu Ile Ala Ser Gly Glu Ile Thr Gln Glu Gln Ala Glu
    1190                1195                1200

Leu Ala Arg Arg Val Pro Val Ala Asp Asp Ile Ala Val Glu Ala
    1205                1210                1215

Asp Ser Gly Gly His Thr Asp Asn Arg Pro Ile His Val Ile Leu
    1220                1225                1230

Pro Leu Ile Ile Asn Leu Arg Asn Arg Leu His Arg Glu Cys Gly
    1235                1240                1245

Tyr Pro Ala His Leu Arg Val Arg Val Gly Ala Gly Gly Gly Val
    1250                1255                1260

Gly Cys Pro Gln Ala Ala Ala Ala Leu Thr Met Gly Ala Ala
    1265                1270                1275

Phe Ile Val Thr Gly Thr Val Asn Gln Val Ala Lys Gln Ser Gly
    1280                1285                1290

Thr Cys Asp Asn Val Arg Lys Gln Leu Ser Gln Ala Thr Tyr Ser
    1295                1300                1305

Asp Ile Cys Met Ala Pro Ala Ala Asp Met Phe Glu Glu Gly Val
    1310                1315                1320

Lys Leu Gln Val Leu Lys Lys Gly Thr Met Phe Pro Ser Arg Ala
    1325                1330                1335

Asn Lys Leu Tyr Glu Leu Phe Cys Lys Tyr Asp Ser Phe Asp Ser
    1340                1345                1350

Met Pro Pro Ala Glu Leu Glu Arg Ile Glu Lys Arg Ile Phe Lys
    1355                1360                1365

Arg Ala Leu Gln Glu Val Trp Glu Glu Thr Lys Asp Phe Tyr Ile
    1370                1375                1380

Asn Gly Leu Lys Asn Pro Glu Lys Ile Gln Arg Ala Glu His Asp
    1385                1390                1395

Pro Lys Leu Lys Met Ser Leu Cys Phe Arg Trp Tyr Leu Gly Leu
    1400                1405                1410

Ala Ser Arg Trp Ala Asn Met Gly Ala Pro Asp Arg Val Met Asp
    1415                1420                1425

Tyr Gln Val Trp Cys Gly Pro Ala Ile Gly Ala Phe Asn Asp Phe
    1430                1435                1440

Ile Lys Gly Thr Tyr Leu Asp Pro Ala Val Ser Asn Glu Tyr Pro
    1445                1450                1455

Cys Val Val Gln Ile Asn Leu Gln Ile Leu Arg Gly Ala Cys Tyr
    1460                1465                1470

Leu Arg Arg Leu Asn Ala Leu Arg Asn Asp Pro Arg Ile Asp Leu
    1475                1480                1485

Glu Thr Glu Asp Ala Ala Phe Val Tyr Glu Pro Thr Asn Ala Leu
    1490                1495                1500

<210> SEQ ID NO 62
<211> LENGTH: 27
<212> TYPE: DNA
<213> ORGANISM: Artificial

```
<220> FEATURE:
<223> OTHER INFORMATION: Synthetic Primer prDS173
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 62
gatctactgc aagcgcggng gnttyat                                          27

<210> SEQ ID NO 63
<211> LENGTH: 21
<212> TYPE: DNA
<213> ORGANISM: Artificial
<220> FEATURE:
<223> OTHER INFORMATION: Synthetic Primer prDS174
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 63
ggcgcaggcg gcrtcnacna c                                                21

<210> SEQ ID NO 64
<211> LENGTH: 23
<212> TYPE: DNA
<213> ORGANISM: Artificial
<220> FEATURE:
<223> OTHER INFORMATION: Synthetic Primer JGM190
<220> FEATURE:
<221> NAME/KEY: misc_feature
<222> LOCATION: (15)..(15)
<223> OTHER INFORMATION: n is a, c, g, or t

<400> SEQUENCE: 64
caytggtayt tyccntgyca ytt                                              23

<210> SEQ ID NO 65
<211> LENGTH: 17
<212> TYPE: DNA
<213> ORGANISM: Artificial
<220> FEATURE:
<223> OTHER INFORMATION: Synthetic Primer BLR242
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 65
ccnggcatna cnggrtc                                                     17

<210> SEQ ID NO 66
<211> LENGTH: 27
<212> TYPE: DNA
```

```
<213> ORGANISM: Artificial
<220> FEATURE:
<223> OTHER INFORMATION: Synthetic Primer CAX055

<400> SEQUENCE: 66
gtcatgattg aacaagatgg attgcac                                          27

<210> SEQ ID NO 67
<211> LENGTH: 27
<212> TYPE: DNA
<213> ORGANISM: Artificial
<220> FEATURE:
<223> OTHER INFORMATION: Synthetic Primer CAX056

<400> SEQUENCE: 67
ccacgtgtca gaagaactcg tcaagaa                                          27

<210> SEQ ID NO 68
<211> LENGTH: 8976
<212> TYPE: DNA
<213> ORGANISM: Thraustochytrium sp.

<400> SEQUENCE: 68
atggaagatc aaagaattgc tattgttgga ttatctgcga ttttaccaag tggtgaaaat       60
gttagagaat cttgggaagc aatacgtgat ggtttgaatt gtttaagtga tttacctgcg      120
gatcgtgttg atgttactgc gtattataat ccaacaaaag gtgtaaagga taaaatttat      180
tgtaaacgtg gtgggtttat tcctgaatat gaatttgatt ctagagaatt tggacttaat      240
atgttacaaa tggaagattc tgatgctaat caaacgttaa cttattaaa ggttaaagaa       300 gcattagatg atgctaatat acctgcattt actaatgaga aaaaaaatat tggttgtgtt      360
cttggtattg tggtggtca aaaagcatct catgaattt attcaagact taattatgtt       420
gttgtggata agttttaag aaaaatggga ttacctgatg aggatgttga aactgctgtt      480
gaaaagttta agctaatttt tcctgaatgg agattagatt cctttcctgg ttttcttggt      540
aatgttactg ctggccgttg tactaataca ttcaatatgg aaggtatgaa ttgtgttgta      600
gatgctgctt gtgctagttc tttaattgct attaaagttg ctattgatga attattacat      660
ggtgattgtg atgcaatgat tgctggtgca acttgtactg ataacgctct tggtatgtat      720
atggcatttt caaaacacc tgttttttca actgatcaaa gttgtcttgc atatgatgaa      780
aaaacaaaag gtatgcttat tggtgaaggt tcagctatgt ttgttttaaa acgttatgct      840
gacgcagtga gagatggtga tactgtacat gctgttatac gttcatgttc atcatcatct      900
gacggtaaag catctggtat ttatacacca actatttctg gtcaagaaga agctattctt      960
agagcatatc gtagagctgg tgtatcacca aatactatta ctttagttga aggacatggt     1020
actggtacac cagtgggtga taaaattgaa ttaacagctt acgcaatgt atttgataaa     1080 gcatatggtc ctggtcataa ggaagaagtt gctgttggaa gtattaaaag tcaaattggt     1140
catttgaaag ctgttgctgg ttgtgctggt cttgtgaaat ggttatggc attgaaacat     1200 aaaacactac ctcaaagtat taatgttgaa aatccaccta atttagtgga tggtactgtc     1260
attagtgata ctacttata tattaataca atgaatcgtc catggattac taagcctggt     1320
gttccaagaa gagctggtat atctagtttc ggatttggtg gtgcaaatta tcatgctgtt     1380
ttagaagaat ttgagccgga acaaactaaa ccatatagat tgaatgtatc tgcacaacca     1440
atgcttcttc atgcgggtaaa atgcaaattca ttacaaaagc tatgtgaaga tcaattaaaa     1500 ctttttgaaag aatcaagaga aaatgtgtc aacaccaaaa acactgatta tgttgcgttt     1560
```

```
tcaaaatttc aagattctttt taaattgaaa ggttctgttc catcacaaca tgctagagtt   1620
ggttttgcat caaaatctat tgaagatact atttctattt tatctgctat cgttaataga   1680
tttcaaaaag atattacaac aactagttgg gctttaccaa agaaggtgc tatttttaga    1740 tctactgcat tgattaatga caataaaagt gtagctgctt tattttctgg acaaggcgca   1800
caatataccc atatgtttaa tgatgttgca atgcaatggc cacaatttcg tttatgtgta   1860
aatgatatgg agaaagcaca ggaagaagtt atcaatgata aaagtgtgaa acgtatcagt   1920
caagttatgt ttcctcgtaa accatatgca agagaatcac ctttagacaa taaagaaatc   1980
tctaagactg aatattctca aacaacaact gtcgctagtt cagtaggttt atttgaaatt   2040
ttccgtgatg ctggtttcgc tcctgctttt gttgctggtc attctttagg tgaatttagt   2100
gcattgtatg cagctggatt gattgatcgc gaagatttat tcaagttggt atgtaatcgt   2160
gcaatggcta tgagagatgc accaaaaaaa tctgctgatg gagcaatggc tgctgttatt   2220
ggtccaaatg cttcttcaat taagctttca gctcctgaag tatgggttgc taacaataac   2280
tctccatctc aaactgttat taccggtgca aattctggtg tacaagctga aacaagtaaa   2340
ttgaaaactc aaggtttccg tgtggttcat ttggcatgtg atggggcatt tcattcgcct   2400
catatggaaa atgctgaaaa gcaatttcaa aaagctcttt cagcagttaa gtttaataaa   2460
ccaactggtt cttctccaaa aattttcagc aatgtaactg gtggtgtatt tacgatcca   2520 aaaactgctt tgtcaagaca tatgactagt tctgtacaat ttcttactca aattaagaat   2580
atgtacgcgg ctggagctcg tgtctttatt gaatttggac caaaacaagt actttccaaa   2640
ttggtcaatg aaattttttcc tggtgataca agcgttttaa ctgtttcggt gaatccagct   2700
agtgctaaag atagtgacat tcaattgcgt caagctgcag ttcaaatggc cgttgctggt   2760
gtagctctta ccgattttga taaatgggaa ctcaaagatc ctacccgtat gaaggaattc   2820
ccacgtaaga agactacttt gactttgtct gcagcaactt atgtctccaa gaaaactcta   2880
caggagcgtg aacgaatcat gaatgatggg cgaactgttt catgtgttca acgtattgaa   2940
aacactaata ctggtgagtt ggagaaattg aagaagcaat tgcaagataa agaaaatgag   3000
gttgtaagag ttcaagctct tgcaactcaa gcttcagctg atttgcaaaa taccaaagca   3060
gaattacaaa aagctcaagc aacaaaatct agtaatgcag catctgatgc ggtggtggca   3120
aaacataagg caattttatt ggcaatgtta gaagaacttg aaaccggcaa ggctgtagat   3180
tattcttcat tttcgaaagg tcaagttgca agtccagcta ccgttcgtgt cgtttcagct   3240
cctgttcaag cggctgctcc tgtgcaggta tctgcttctg ttgattctgg tttgttggca   3300
aaagcggaac aagttgtatt ggaagtattg gcatcgaaga ctggttatga gactgagttg   3360
attgaattgg atatggaatt ggaaactgaa cttggtattg attctatcaa gagagtagaa   3420
attctttctg aagttcaagc tcaattgaat gttgaagcta aagatgtaga tgctcttagt   3480
agaactcgta ctgttggtga agtgattgat gcaatgaaag ccgaaattgc tggtggtcaa   3540
ccagctgctc ctgttcaagt tgcagctcct actcaagtag ttgctcctgt tcaagcatct   3600
gctcctgttg attctggttt gttagcaaaa gcggaacaag ttgtattgga agtattggca   3660
tcgaagactg gttatgagac tgagttgatt gaattggata tggaattgga aaccgaactt   3720
ggtattgatt ctatcaagag agtagaaatt ctttctgaag ttcaagctca attgagtgtt   3780
gaagctaaag atgtagatgc tcttagtaga actcgtactg ttggtgaagt gattgatgca   3840
atgaaagccg aaattgctgg tggtcaacca gctgctcctg ttcaagttgc agctcctact   3900
```

| | |
|---|---|
| caagtagttg ctcctgttca agcatctgct cctgttgatt ctggtttgtt agcaaaagcg | 3960 |
| gaacaagttg tattggaagt attggcatcg aagactggtt atgagactga gttgattgaa | 4020 |
| ttggatatgg aattggaaac cgaacttggt attgattcta tcaagagagt agaaattctt | 4080 |
| tctgaagttc aagctcaatt gagtgttgaa gctaaagatg tagatgctct tagtagaact | 4140 |
| cgtactgttg gtgaagtgat tgatgcaatg aaagctgaaa tttctggtgg tcagccagct | 4200 |
| gctcctgttc aagttgcagc tcctactcaa atagttgctc ctgttcaagt atccgctcct | 4260 |
| gttgattctg gtttgttagc aaaggcggaa caagtagtat tggaagtatt ggcatccaag | 4320 |
| actggttatg agactgagtt gattgaattg gatatggaat tggaaactga acttggtatt | 4380 |
| gattctatca agagagtaga aattctttct gaagttcaag ctcaattgag tgttgaagct | 4440 |
| aaagatgtag atgctcttag tagaactcgt actgttggtg aagtgattga tgcaatgaaa | 4500 |
| gctgaaattt ctggtggtca accaactgct cctgttcaag ttgcagctcc tactcaaata | 4560 |
| gttgctcctg ttcaagtatc tgctcctgtt gattctggtt tgttagcaaa ggcggaacaa | 4620 |
| gttgtattgg aagtattggc atcgaagact ggttatgaga ctgagttgat tgaattggat | 4680 |
| atggaattgg aaaccgaact tggtattgat tctatcaaga gagtagaaat tctttctgaa | 4740 |
| gttcaagctc aattgagtgt tgaagctaaa gatgtagatg ctcttagtag aactcgtact | 4800 |
| gttggtgaag tgattgatgc aatgaaagcc gaaatttctg gtggtcagcc agctgctcct | 4860 |
| gttcaagttg cagctcctac tcaaatagtt gctcctgttc aagcatctgc tcctgttgat | 4920 |
| tctggtttgt tggcaaaagc ggaacaagtt gtattggaag tgttagcatc caagactggt | 4980 |
| tatgaaactg agttgattga attagatatg aattggaaa ccgaacttgg tattgattct | 5040 |
| atcaagagag tagaaattct ttctgaagtt caagctcaat tgagtgttga agctaaagat | 5100 |
| gtagatgctc ttagtagaac tcgtactgtt ggtgaagtga ttgatgcaat gaaagctgaa | 5160 |
| atttctggtg gtcaaccagc tgctcctgtt caagttgcag ctcctactca atagttgct | 5220 |
| cctgttcaag tatctgctcc tgttgattct ggtttgttag caaaggcgga acaagttgta | 5280 |
| ttggaagtat tggcatctaa gactggttat gagactgagt tgattgaatt ggatatggaa | 5340 |
| ttggaaactg aacttggtat tgattctatc aagagagtag aaattctttc tgaagttcaa | 5400 |
| gctcaattga atgttgaagc taaagatgta gatgctctta gtagaactcg tactgttggt | 5460 |
| gaagtgattg atgcaatgaa agccgaaatt gctggtggtc aaccagctgc tcctgttcaa | 5520 |
| gttgcagctc ctgctccagt agttgctcct gttcaagtat ctactcctgt tgattctggt | 5580 |
| ttgttggcaa aagcggaaca agttgtattg gaagtgttag catgcaagac tggttatgaa | 5640 |
| actgagttga ttgaattgga tatggaattg gaaactgaac ttggtattga ttctatcaag | 5700 |
| agagtagaaa ttctttctga agttcaagct caattgagtg ttgaagctaa agatgtagat | 5760 |
| gctcttagta gaactcgtac tgttggtgaa gtgattgatg caatgaaagc cgaaatttct | 5820 |
| ggtggtcaac caactgctcc tgttcaagtt gcagctccta ctcaagtagt tgctcctgtt | 5880 |
| aaagtatcta ctcctgttga ttctggtttg ttagcaaagg cggaacaagt agtattggaa | 5940 |
| gtattggcat ctaagactgg ttatgaaact gagttgattg aattagatat ggaattggaa | 6000 |
| actgaacttg gtattgattc tatcaagaga gtagaaattc tttctgaagt tcaagctcaa | 6060 |
| ttgaatgtgg aagctaaaga tgtggatgct cttagtagaa ctcgtactgt tggtgaagtg | 6120 |
| attgatgcaa tgaaagccga aattgctggt gatcaacctg ctccagctgt agttccagtt | 6180 |
| caagctaaga gtggtgtagc caaccctgca cttttggcaa aggcggaaca agtagtattg | 6240 |
| gaagtattgg catccaagac cggttatgaa actgagctga ttgaattgga tatggaattg | 6300 |

```
gaaactgaac ttggtattga ttcaatcaag agagtagaaa ttctgtccga agttcaagca    6360
gaattgagtg ttgaagcaaa agatgtagac gctctaagta gaacccgtac tgttggggaa    6420
gtgatcgatg caatgaaagc tgaaattgct ggcagtgctg tcacggttgc aactttggat    6480
gattcaacaa ttatggagga gacagatgat gaagatgaag actttatttt atacgatcat    6540
gtatacggaa gcgaatgtga agatcttagt ctgagttttt catccgtaaa gagcatcccg    6600
cgcgctgata aacttttgtt ggataacatt gctgaaaggc caattgttat tgtggattgt    6660
ggaacaaagc ttacaactga acttgcaaaa gctattggag aacgtgccgt ggttgctaca    6720
ttcagtgcac agagcttggt atcccgtgga ttcgttggta aatcatttac tctaggaaat    6780
acagaagaaa gtgagatcga aaagatggtt tcaagcattg aatcttcgta tggaaaaatt    6840
ggtggctttg tttatcaaca ttttcatgat agcgactatg gtatgcaact tggatgggcg    6900
ttaatggcag cgaaacattt gaaagagtcc ctcaacgacc cgattaagaa tggaagaacc    6960 ttcttttttgg ctgttgcgcg tatgaatggt aaacttggta tggacaatgc ttcagttcat    7020
gatcaaggaa tagtggaatc atgcggtatc gccgaacgtg gtgctatctt tggtttgtgc    7080
aaaactttgg atttggaatg gcctaatgtt tttgctcgtg gtgttgatat tgctgaaggt    7140
atgagttata gtttggctgc ggaattgatt gttgatgaga tttcttgtgc aaatctttcc    7200
attcgggaat ctggttacac gattagcgga gaaagattca caactgaagc tcacaaattg    7260
gttactggaa agcctcatgc tccgattaag aagaaggatg ctttcctagt atctggtggt    7320
gctcgtggta ttactccact ttgtattcgt gaaattgcta aagcagtgaa aggtggcact    7380
tacattttga tgggtcgatc agctttggct gatgaaccct gtgggctaa tggtaaatcc    7440 ggaaaagatt tagataaagc tggttttggca tttttgaagg aagagtttgc agctgggcgt    7500
ggtagtaaac caactccaaa agttcacaaa tctttgattg ataaagtgct cggtattagg    7560
gaggttagag catctattgc aaatatgaaa gcccatggag caaaagctat atatttgtct    7620
tgcgatgtat cttccgctga gaaagtaaag gctgcagtgc aaaaagttga aaaggagcat    7680
ctagttcgta ttactggtat tgtgcatgca tcaggcgttt tgagggataa attggttgag    7740
aacaaaactt tggatgattt caacgcagta tatgaaacca aagtaactgg actagtaaac    7800
ttgctgtcag cagtgaacat gaattttgtt cgtcatttgg ttatgtttag ttctttggct    7860
ggatatcatg gaaatgttgg tcaatctgat tatgcaatgg ctaacgaatc acttaacaag    7920
attggtttta gattgggtgc agcttattct caattgtgtg ttaaatctat ttgttttgga    7980
ccttgggatg gtgaatggt aactccagct ttgaaaaaac aatttcaatc aatgggtgtc    8040
cagattattc ctcgtgaagg tggcgcggag actgttgcaa gaatagtctt atcttcaaat    8100
ccttctcaag ttttagttgg caactggggt gttcctccag tttcacccttt gtcaaaatcg    8160 gcaactattg ttcaaacttt taccccctgag ttaaatccat ttctaaagtc tcatcaaatt    8220
catggtaaaa atgttttgcc tatgactgta gcaattggat atcttgctca cttggttaag    8280 aattttatg ctggtcatca tttgtgggga gttgaagatg ctcaattgtt cagtggtgtt    8340
gtaattgacc atgcggtgca agctcaagtg aaattaacgg aacagagttt ggatgatgat    8400
ggcaaggtaa aagttcaagc tgttctgact gcttcaaacg ataatggaaa aatggtacct    8460
gcatacaaag cagtgattgt tttgggaaaa acaagtagac ctgcgtttat tttgaaagat    8520 tttttcattgc aagaatctaa ttctcgcagt gctgatgagt tgtatgatgg taaaactttg    8580
tttcatggtc cattatttcg tggaattacc aagttgttga atgtatctga tacttcacta    8640
```

```
acaactcaat gtaccaatat tgatttgact gctactgaac gtggtcaatt tgcggatatc   8700
gaacctgtga atccttttat ggcggatgct gcatttcaag ctatgcttgt atgggttaga   8760
aatttaagga atagtgcatc tttaccaaac aattgtgaaa gagtagatat ctataaacca   8820
atagcacctg gtgaaaagta ttacactact ttgcaagctt tgggtaatac ctccggttct   8880
gttctcaagt ctgtatttta tatgcacgat gaacaaggag aagtatttct atctggaaga   8940
gctagtgttg ttgtgaatga caagatggag ttttag                              8976

<210> SEQ ID NO 69
<211> LENGTH: 2991
<212> TYPE: PRT
<213> ORGANISM: Thraustochytrium sp.

<400> SEQUENCE: 69

Met Glu Asp Gln Arg Ile Ala Ile Val Gly Leu Ser Ala Ile Leu Pro
1               5                   10                  15

Ser Gly Glu Asn Val Arg Glu Ser Trp Glu Ala Ile Arg Asp Gly Leu
            20                  25                  30

Asn Cys Leu Ser Asp Leu Pro Ala Asp Arg Val Asp Val Thr Ala Tyr
        35                  40                  45

Tyr Asn Pro Thr Lys Gly Val Lys Asp Lys Ile Tyr Cys Lys Arg Gly
    50                  55                  60

Gly Phe Ile Pro Glu Tyr Glu Phe Asp Ser Arg Glu Phe Gly Leu Asn
65                  70                  75                  80

Met Leu Gln Met Glu Asp Ser Asp Ala Asn Gln Thr Leu Thr Leu Leu
                85                  90                  95

Lys Val Lys Glu Ala Leu Asp Asp Ala Asn Ile Pro Ala Phe Thr Asn
            100                 105                 110

Glu Lys Lys Asn Ile Gly Cys Val Leu Gly Ile Gly Gly Gly Gln Lys
        115                 120                 125

Ala Ser His Glu Phe Tyr Ser Arg Leu Asn Tyr Val Val Val Asp Lys
    130                 135                 140

Val Leu Arg Lys Met Gly Leu Pro Asp Glu Asp Val Glu Thr Ala Val
145                 150                 155                 160

Glu Lys Phe Lys Ala Asn Phe Pro Glu Trp Arg Leu Asp Ser Phe Pro
                165                 170                 175

Gly Phe Leu Gly Asn Val Thr Ala Gly Arg Cys Thr Asn Thr Phe Asn
            180                 185                 190

Met Glu Gly Met Asn Cys Val Val Asp Ala Ala Cys Ala Ser Ser Leu
        195                 200                 205

Ile Ala Ile Lys Val Ala Ile Asp Glu Leu Leu His Gly Asp Cys Asp
    210                 215                 220

Ala Met Ile Ala Gly Ala Thr Cys Thr Asp Asn Ala Leu Gly Met Tyr
225                 230                 235                 240

Met Ala Phe Ser Lys Thr Pro Val Phe Ser Thr Asp Gln Ser Cys Leu
                245                 250                 255

Ala Tyr Asp Glu Lys Thr Lys Gly Met Leu Ile Gly Glu Gly Ser Ala
            260                 265                 270

Met Phe Val Leu Lys Arg Tyr Ala Asp Ala Val Arg Asp Gly Asp Thr
        275                 280                 285

Val His Ala Val Ile Arg Ser Cys Ser Ser Ser Ser Asp Gly Lys Ala
    290                 295                 300

Ser Gly Ile Tyr Thr Pro Thr Ile Ser Gly Gln Glu Glu Ala Ile Leu
305                 310                 315                 320
```

```
Arg Ala Tyr Arg Arg Ala Gly Val Ser Pro Asn Thr Ile Thr Leu Val
                325                 330                 335

Glu Gly His Gly Thr Gly Thr Pro Val Gly Asp Lys Ile Glu Leu Thr
                340                 345                 350

Ala Leu Arg Asn Val Phe Asp Lys Ala Tyr Gly Pro Gly His Lys Glu
            355                 360                 365

Glu Val Ala Val Gly Ser Ile Lys Ser Gln Ile Gly His Leu Lys Ala
        370                 375                 380

Val Ala Gly Cys Ala Gly Leu Val Lys Leu Val Met Ala Leu Lys His
385                 390                 395                 400

Lys Thr Leu Pro Gln Ser Ile Asn Val Glu Asn Pro Pro Asn Leu Val
                405                 410                 415

Asp Gly Thr Val Ile Ser Asp Thr Thr Leu Tyr Ile Asn Thr Met Asn
                420                 425                 430

Arg Pro Trp Ile Thr Lys Pro Gly Val Pro Arg Arg Ala Gly Ile Ser
            435                 440                 445

Ser Phe Gly Phe Gly Gly Ala Asn Tyr His Ala Val Leu Glu Glu Phe
        450                 455                 460

Glu Pro Glu Gln Thr Lys Pro Tyr Arg Leu Asn Val Ser Ala Gln Pro
465                 470                 475                 480

Met Leu Leu His Ala Val Asn Ala Asn Ser Leu Gln Lys Leu Cys Glu
                485                 490                 495

Asp Gln Leu Lys Leu Leu Lys Glu Ser Arg Glu Lys Cys Val Asn Thr
                500                 505                 510

Lys Asn Thr Asp Tyr Val Ala Phe Ser Lys Phe Gln Asp Ser Phe Lys
            515                 520                 525

Leu Lys Gly Ser Val Pro Ser Gln His Ala Arg Val Gly Phe Ala Ser
        530                 535                 540

Lys Ser Ile Glu Asp Thr Ile Ser Ile Leu Ser Ala Ile Val Asn Arg
545                 550                 555                 560

Phe Gln Lys Asp Ile Thr Thr Thr Ser Trp Ala Leu Pro Lys Glu Gly
                565                 570                 575

Ala Ile Phe Arg Ser Thr Ala Leu Ile Asn Asp Asn Lys Ser Val Ala
            580                 585                 590

Ala Leu Phe Ser Gly Gln Gly Ala Gln Tyr Thr His Met Phe Asn Asp
        595                 600                 605

Val Ala Met Gln Trp Pro Gln Phe Arg Leu Cys Val Asn Asp Met Glu
610                 615                 620

Lys Ala Gln Glu Glu Val Ile Asn Asp Lys Ser Val Lys Arg Ile Ser
625                 630                 635                 640

Gln Val Met Phe Pro Arg Lys Pro Tyr Ala Arg Glu Ser Pro Leu Asp
                645                 650                 655

Asn Lys Glu Ile Ser Lys Thr Glu Tyr Ser Gln Thr Thr Thr Val Ala
            660                 665                 670

Ser Ser Val Gly Leu Phe Glu Ile Phe Arg Asp Ala Gly Phe Ala Pro
        675                 680                 685

Ala Phe Val Ala Gly His Ser Leu Gly Glu Phe Ser Ala Leu Tyr Ala
        690                 695                 700

Ala Gly Leu Ile Asp Arg Glu Asp Leu Phe Lys Leu Val Cys Asn Arg
705                 710                 715                 720

Ala Met Ala Met Arg Asp Ala Pro Lys Lys Ser Ala Asp Gly Ala Met
                725                 730                 735
```

-continued

Ala Ala Val Ile Gly Pro Asn Ala Ser Ser Ile Lys Leu Ser Ala Pro
            740                 745                 750

Glu Val Trp Val Ala Asn Asn Ser Pro Ser Gln Thr Val Ile Thr
    755                 760                 765

Gly Ala Asn Ser Gly Val Gln Ala Glu Thr Ser Lys Leu Lys Thr Gln
    770                 775                 780

Gly Phe Arg Val Val His Leu Ala Cys Asp Gly Ala Phe His Ser Pro
785                 790                 795                 800

His Met Glu Asn Ala Glu Lys Gln Phe Gln Lys Ala Leu Ser Ala Val
            805                 810                 815

Lys Phe Asn Lys Pro Thr Gly Ser Ser Pro Lys Ile Phe Ser Asn Val
            820                 825                 830

Thr Gly Gly Val Phe Thr Asp Pro Lys Thr Ala Leu Ser Arg His Met
            835                 840                 845

Thr Ser Ser Val Gln Phe Leu Thr Gln Ile Lys Asn Met Tyr Ala Ala
            850                 855                 860

Gly Ala Arg Val Phe Ile Glu Phe Gly Pro Lys Gln Val Leu Ser Lys
865                 870                 875                 880

Leu Val Asn Glu Ile Phe Pro Gly Asp Thr Ser Val Leu Thr Val Ser
                885                 890                 895

Val Asn Pro Ala Ser Ala Lys Asp Ser Asp Ile Gln Leu Arg Gln Ala
            900                 905                 910

Ala Val Gln Met Ala Val Ala Gly Val Ala Leu Thr Asp Phe Asp Lys
            915                 920                 925

Trp Glu Leu Lys Asp Pro Thr Arg Met Lys Glu Phe Pro Arg Lys Lys
930                 935                 940

Thr Thr Leu Thr Leu Ser Ala Ala Thr Tyr Val Ser Lys Lys Thr Leu
945                 950                 955                 960

Gln Glu Arg Glu Arg Ile Met Asn Asp Gly Arg Thr Val Ser Cys Val
                965                 970                 975

Gln Arg Ile Glu Asn Thr Asn Thr Gly Glu Leu Glu Lys Leu Lys Lys
            980                 985                 990

Gln Leu Gln Asp Lys Glu Asn Glu Val Val Arg Val Gln Ala Leu Ala
            995                 1000                1005

Thr Gln Ala Ser Ala Asp Leu Gln Asn Thr Lys Ala Glu Leu Gln
    1010                1015                1020

Lys Ala Gln Ala Thr Lys Ser Ser Asn Ala Ala Ser Asp Ala Val
    1025                1030                1035

Val Ala Lys His Lys Ala Ile Leu Leu Ala Met Leu Glu Glu Leu
    1040                1045                1050

Glu Thr Gly Lys Ala Val Asp Tyr Ser Ser Phe Ser Lys Gly Gln
    1055                1060                1065

Val Ala Ser Pro Ala Thr Val Arg Val Val Ser Ala Pro Val Gln
    1070                1075                1080

Ala Ala Ala Pro Val Gln Val Ser Ala Ser Val Asp Ser Gly Leu
    1085                1090                1095

Leu Ala Lys Ala Glu Gln Val Val Leu Glu Val Leu Ala Ser Lys
    1100                1105                1110

Thr Gly Tyr Glu Thr Glu Leu Ile Glu Leu Asp Met Glu Leu Glu
    1115                1120                1125

Thr Glu Leu Gly Ile Asp Ser Ile Lys Arg Val Glu Ile Leu Ser
    1130                1135                1140

Glu Val Gln Ala Gln Leu Asn Val Glu Ala Lys Asp Val Asp Ala

-continued

```
              1145                1150                1155
Leu Ser Arg Thr Arg Thr Val Gly Glu Val Ile Asp Ala Met Lys
        1160                1165                1170
Ala Glu Ile Ala Gly Gly Gln Pro Ala Pro Val Gln Val Ala
    1175                1180                1185
Ala Pro Thr Gln Val Val Ala Pro Val Gln Ala Ser Ala Pro Val
    1190                1195                1200
Asp Ser Gly Leu Leu Ala Lys Ala Glu Gln Val Val Leu Glu Val
    1205                1210                1215
Leu Ala Ser Lys Thr Gly Tyr Glu Thr Glu Leu Ile Glu Leu Asp
    1220                1225                1230
Met Glu Leu Glu Thr Glu Leu Gly Ile Asp Ser Ile Lys Arg Val
    1235                1240                1245
Glu Ile Leu Ser Glu Val Gln Ala Gln Leu Ser Val Glu Ala Lys
    1250                1255                1260
Asp Val Asp Ala Leu Ser Arg Thr Arg Thr Val Gly Glu Val Ile
    1265                1270                1275
Asp Ala Met Lys Ala Glu Ile Ala Gly Gly Gln Pro Ala Ala Pro
    1280                1285                1290
Val Gln Val Ala Ala Pro Thr Gln Val Val Ala Pro Val Gln Ala
    1295                1300                1305
Ser Ala Pro Val Asp Ser Gly Leu Leu Ala Lys Ala Glu Gln Val
    1310                1315                1320
Val Leu Glu Val Leu Ala Ser Lys Thr Gly Tyr Glu Thr Glu Leu
    1325                1330                1335
Ile Glu Leu Asp Met Glu Leu Glu Thr Glu Leu Gly Ile Asp Ser
    1340                1345                1350
Ile Lys Arg Val Glu Ile Leu Ser Glu Val Gln Ala Gln Leu Ser
    1355                1360                1365
Val Glu Ala Lys Asp Val Asp Ala Leu Ser Arg Thr Arg Thr Val
    1370                1375                1380
Gly Glu Val Ile Asp Ala Met Lys Ala Glu Ile Ser Gly Gly Gln
    1385                1390                1395
Pro Ala Ala Pro Val Gln Val Ala Ala Pro Thr Gln Ile Val Ala
    1400                1405                1410
Pro Val Gln Val Ser Ala Pro Val Asp Ser Gly Leu Leu Ala Lys
    1415                1420                1425
Ala Glu Gln Val Val Leu Glu Val Leu Ala Ser Lys Thr Gly Tyr
    1430                1435                1440
Glu Thr Glu Leu Ile Glu Leu Asp Met Glu Leu Glu Thr Glu Leu
    1445                1450                1455
Gly Ile Asp Ser Ile Lys Arg Val Glu Ile Leu Ser Glu Val Gln
    1460                1465                1470
Ala Gln Leu Ser Val Glu Ala Lys Asp Val Asp Ala Leu Ser Arg
    1475                1480                1485
Thr Arg Thr Val Gly Glu Val Ile Asp Ala Met Lys Ala Glu Ile
    1490                1495                1500
Ser Gly Gly Gln Pro Thr Ala Pro Val Gln Val Ala Ala Pro Thr
    1505                1510                1515
Gln Ile Val Ala Pro Val Gln Val Ser Ala Pro Val Asp Ser Gly
    1520                1525                1530
Leu Leu Ala Lys Ala Glu Gln Val Val Leu Glu Val Leu Ala Ser
    1535                1540                1545
```

```
Lys Thr Gly Tyr Glu Thr Glu Leu Ile Glu Leu Asp Met Glu Leu
    1550                1555                1560

Glu Thr Glu Leu Gly Ile Asp Ser Ile Lys Arg Val Glu Ile Leu
    1565                1570                1575

Ser Glu Val Gln Ala Gln Leu Ser Val Glu Ala Lys Asp Val Asp
    1580                1585                1590

Ala Leu Ser Arg Thr Arg Thr Val Gly Glu Val Ile Asp Ala Met
    1595                1600                1605

Lys Ala Glu Ile Ser Gly Gly Gln Pro Ala Ala Pro Val Gln Val
    1610                1615                1620

Ala Ala Pro Thr Gln Ile Val Ala Pro Val Gln Ala Ser Ala Pro
    1625                1630                1635

Val Asp Ser Gly Leu Leu Ala Lys Ala Glu Gln Val Val Leu Glu
    1640                1645                1650

Val Leu Ala Ser Lys Thr Gly Tyr Glu Thr Glu Leu Ile Glu Leu
    1655                1660                1665

Asp Met Glu Leu Glu Thr Glu Leu Gly Ile Asp Ser Ile Lys Arg
    1670                1675                1680

Val Glu Ile Leu Ser Glu Val Gln Ala Gln Leu Ser Val Glu Ala
    1685                1690                1695

Lys Asp Val Asp Ala Leu Ser Arg Thr Arg Thr Val Gly Glu Val
    1700                1705                1710

Ile Asp Ala Met Lys Ala Glu Ile Ser Gly Gly Gln Pro Ala Ala
    1715                1720                1725

Pro Val Gln Val Ala Ala Pro Thr Gln Ile Val Ala Pro Val Gln
    1730                1735                1740

Val Ser Ala Pro Val Asp Ser Gly Leu Leu Ala Lys Ala Glu Gln
    1745                1750                1755

Val Val Leu Glu Val Leu Ala Ser Lys Thr Gly Tyr Glu Thr Glu
    1760                1765                1770

Leu Ile Glu Leu Asp Met Glu Leu Glu Thr Glu Leu Gly Ile Asp
    1775                1780                1785

Ser Ile Lys Arg Val Glu Ile Leu Ser Glu Val Gln Ala Gln Leu
    1790                1795                1800

Asn Val Glu Ala Lys Asp Val Asp Ala Leu Ser Arg Thr Arg Thr
    1805                1810                1815

Val Gly Glu Val Ile Asp Ala Met Lys Ala Glu Ile Ala Gly Gly
    1820                1825                1830

Gln Pro Ala Ala Pro Val Gln Val Ala Ala Pro Ala Pro Val Val
    1835                1840                1845

Ala Pro Val Gln Val Ser Thr Pro Val Asp Ser Gly Leu Leu Ala
    1850                1855                1860

Lys Ala Glu Gln Val Val Leu Glu Val Leu Ala Cys Lys Thr Gly
    1865                1870                1875

Tyr Glu Thr Glu Leu Ile Glu Leu Asp Met Glu Leu Glu Thr Glu
    1880                1885                1890

Leu Gly Ile Asp Ser Ile Lys Arg Val Glu Ile Leu Ser Glu Val
    1895                1900                1905

Gln Ala Gln Leu Ser Val Glu Ala Lys Asp Val Asp Ala Leu Ser
    1910                1915                1920

Arg Thr Arg Thr Val Gly Val Ile Asp Ala Met Lys Ala Glu
    1925                1930                1935
```

-continued

```
Ile Ser Gly Gly Gln Pro Thr Ala Pro Val Gln Val Ala Ala Pro
    1940                1945                1950
Thr Gln Val Val Ala Pro Val Lys Val Ser Thr Pro Val Asp Ser
    1955                1960                1965
Gly Leu Leu Ala Lys Ala Glu Gln Val Val Leu Glu Val Leu Ala
    1970                1975                1980
Ser Lys Thr Gly Tyr Glu Thr Glu Leu Ile Glu Leu Asp Met Glu
    1985                1990                1995
Leu Glu Thr Glu Leu Gly Ile Asp Ser Ile Lys Arg Val Glu Ile
    2000                2005                2010
Leu Ser Glu Val Gln Ala Gln Leu Asn Val Glu Ala Lys Asp Val
    2015                2020                2025
Asp Ala Leu Ser Arg Thr Arg Thr Val Gly Glu Val Ile Asp Ala
    2030                2035                2040
Met Lys Ala Glu Ile Ala Gly Asp Gln Pro Ala Pro Ala Val Val
    2045                2050                2055
Pro Val Gln Ala Lys Ser Gly Val Ala Asn Pro Ala Leu Leu Ala
    2060                2065                2070
Lys Ala Glu Gln Val Val Leu Glu Val Leu Ala Ser Lys Thr Gly
    2075                2080                2085
Tyr Glu Thr Glu Leu Ile Glu Leu Asp Met Glu Leu Glu Thr Glu
    2090                2095                2100
Leu Gly Ile Asp Ser Ile Lys Arg Val Glu Ile Leu Ser Glu Val
    2105                2110                2115
Gln Ala Glu Leu Ser Val Glu Ala Lys Asp Val Asp Ala Leu Ser
    2120                2125                2130
Arg Thr Arg Thr Val Gly Glu Val Ile Asp Ala Met Lys Ala Glu
    2135                2140                2145
Ile Ala Gly Ser Ala Val Thr Val Ala Thr Leu Asp Asp Ser Thr
    2150                2155                2160
Ile Met Glu Glu Thr Asp Asp Glu Asp Glu Asp Phe Ile Leu Tyr
    2165                2170                2175
Asp His Val Tyr Gly Ser Glu Cys Glu Asp Leu Ser Leu Ser Phe
    2180                2185                2190
Ser Ser Val Lys Ser Ile Pro Arg Ala Asp Lys Leu Leu Leu Asp
    2195                2200                2205
Asn Ile Ala Glu Arg Pro Ile Val Ile Val Asp Cys Gly Thr Lys
    2210                2215                2220
Leu Thr Thr Glu Leu Ala Lys Ala Ile Gly Glu Arg Ala Val Val
    2225                2230                2235
Ala Thr Phe Ser Ala Gln Ser Leu Val Ser Arg Gly Phe Val Gly
    2240                2245                2250
Lys Ser Phe Thr Leu Gly Asn Thr Glu Glu Ser Glu Ile Glu Lys
    2255                2260                2265
Met Val Ser Ser Ile Glu Ser Ser Tyr Gly Lys Ile Gly Gly Phe
    2270                2275                2280
Val Tyr Gln His Phe His Asp Ser Asp Tyr Gly Met Gln Leu Gly
    2285                2290                2295
Trp Ala Leu Met Ala Ala Lys His Leu Lys Glu Ser Leu Asn Asp
    2300                2305                2310
Pro Ile Lys Asn Gly Arg Thr Phe Phe Leu Ala Val Ala Arg Met
    2315                2320                2325
Asn Gly Lys Leu Gly Met Asp Asn Ala Ser Val His Asp Gln Gly
```

```
                2330                2335                2340
Ile Val Glu Ser Cys Gly Ile Ala Glu Arg Gly Ala Ile Phe Gly
        2345                2350                2355

Leu Cys Lys Thr Leu Asp Leu Glu Trp Pro Asn Val Phe Ala Arg
        2360                2365                2370

Gly Val Asp Ile Ala Glu Gly Met Ser Tyr Ser Leu Ala Ala Glu
        2375                2380                2385

Leu Ile Val Asp Glu Ile Ser Cys Ala Asn Leu Ser Ile Arg Glu
        2390                2395                2400

Ser Gly Tyr Thr Ile Ser Gly Glu Arg Phe Thr Thr Glu Ala His
        2405                2410                2415

Lys Leu Val Thr Gly Lys Pro His Ala Pro Ile Lys Lys Lys Asp
        2420                2425                2430

Ala Phe Leu Val Ser Gly Gly Ala Arg Gly Ile Thr Pro Leu Cys
        2435                2440                2445

Ile Arg Glu Ile Ala Lys Ala Val Lys Gly Gly Thr Tyr Ile Leu
        2450                2455                2460

Met Gly Arg Ser Ala Leu Ala Asp Glu Pro Leu Trp Ala Asn Gly
        2465                2470                2475

Lys Ser Gly Lys Asp Leu Asp Lys Ala Gly Leu Ala Phe Leu Lys
        2480                2485                2490

Glu Glu Phe Ala Ala Gly Arg Gly Ser Lys Pro Thr Pro Lys Val
        2495                2500                2505

His Lys Ser Leu Ile Asp Lys Val Leu Gly Ile Arg Glu Val Arg
        2510                2515                2520

Ala Ser Ile Ala Asn Ile Glu Ala His Gly Ala Lys Ala Ile Tyr
        2525                2530                2535

Leu Ser Cys Asp Val Ser Ser Ala Glu Lys Val Lys Ala Ala Val
        2540                2545                2550

Gln Lys Val Glu Lys Glu His Leu Val Arg Ile Thr Gly Ile Val
        2555                2560                2565

His Ala Ser Gly Val Leu Arg Asp Lys Leu Val Glu Asn Lys Thr
        2570                2575                2580

Leu Asp Asp Phe Asn Ala Val Tyr Gly Thr Lys Val Thr Gly Leu
        2585                2590                2595

Val Asn Leu Leu Ser Ala Val Asn Met Asn Phe Val Arg His Leu
        2600                2605                2610

Val Met Phe Ser Ser Leu Ala Gly Tyr His Gly Asn Val Gly Gln
        2615                2620                2625

Ser Asp Tyr Ala Met Ala Asn Glu Ser Leu Asn Lys Ile Gly Phe
        2630                2635                2640

Arg Leu Gly Ala Ala Tyr Ser Gln Leu Cys Val Lys Ser Ile Cys
        2645                2650                2655

Phe Gly Pro Trp Asp Gly Gly Met Val Thr Pro Ala Leu Lys Lys
        2660                2665                2670

Gln Phe Gln Ser Met Gly Val Gln Ile Ile Pro Arg Glu Gly Gly
        2675                2680                2685

Ala Glu Thr Val Ala Arg Ile Val Leu Ser Ser Asn Pro Ser Gln
        2690                2695                2700

Val Leu Val Gly Asn Trp Gly Val Pro Pro Val Ser Pro Leu Ser
        2705                2710                2715

Lys Ser Ala Thr Ile Val Gln Thr Phe Thr Pro Glu Leu Asn Pro
        2720                2725                2730
```

Phe Leu Lys Ser His Gln Ile His Gly Lys Asn Val Leu Pro Met
2735                2740                2745

Thr Val Ala Ile Gly Tyr Leu Ala His Leu Val Lys Asn Phe Tyr
2750                2755                2760

Ala Gly His His Leu Trp Gly Val Glu Asp Ala Gln Leu Phe Ser
2765                2770                2775

Gly Val Val Ile Asp His Ala Val Gln Ala Gln Val Lys Leu Thr
2780                2785                2790

Glu Gln Ser Leu Asp Asp Asp Gly Lys Val Lys Val Gln Ala Val
2795                2800                2805

Leu Thr Ala Ser Asn Asp Asn Gly Lys Met Val Pro Ala Tyr Lys
2810                2815                2820

Ala Val Ile Val Leu Gly Lys Thr Ser Arg Pro Ala Phe Ile Leu
2825                2830                2835

Lys Asp Phe Ser Leu Gln Glu Ser Asn Ser Arg Ser Ala Asp Glu
2840                2845                2850

Leu Tyr Asp Gly Lys Thr Leu Phe His Gly Pro Leu Phe Arg Gly
2855                2860                2865

Ile Thr Lys Leu Leu Asn Val Ser Asp Thr Ser Leu Thr Thr Gln
2870                2875                2880

Cys Thr Asn Ile Asp Leu Thr Ala Thr Glu Arg Gly Gln Phe Ala
2885                2890                2895

Asp Ile Glu Pro Val Asn Pro Phe Met Ala Asp Ala Ala Phe Gln
2900                2905                2910

Ala Met Leu Val Trp Val Arg Asn Leu Arg Asn Ser Ala Ser Leu
2915                2920                2925

Pro Asn Asn Cys Glu Arg Val Asp Ile Tyr Lys Pro Ile Ala Pro
2930                2935                2940

Gly Glu Lys Tyr Tyr Thr Thr Leu Gln Ala Leu Gly Asn Thr Ser
2945                2950                2955

Gly Ser Val Leu Lys Ser Val Phe Tyr Met His Asp Glu Gln Gly
2960                2965                2970

Glu Val Phe Leu Ser Gly Arg Ala Ser Val Val Asn Asp Lys
2975                2980                2985

Met Glu Phe
2990

<210> SEQ ID NO 70
<211> LENGTH: 5880
<212> TYPE: DNA
<213> ORGANISM: Thraustochytrium sp.

<400> SEQUENCE: 70
atggtgaaat taagtgttgg tgataatatt tgtcatgatc aacgtgttgc tgttgttggt      60
atggctgtta tgtatgctgg ttgtcaaaat caacatgaat tttggcaatc tttacaaggt     120
aaaaatatga attcaaaatc gatttcacaa atcgtttag gttctgagta tagagaagaa      180
cattttaaac ctgaaagaag taaatattcc gataccttt gtaatgaaag atatggttgt      240
attgatgaga atgttcaaag tgaacatgaa cttttattaa acttgcaaa agatgctatt      300 gcggatacaa aggttctat tgatttgaat aaaaccggaa tcgttagtgg ttgcttatct      360
tttccaatgg ataatttaca aggtgattta ttaaatttgt atcaatgtca cattgaaaag     420
aaaattgggc caaatgcatt aaaagatgtg aatttatggt ctaaaagaac caccaacgga     480

```
aaagatgata aaaaagctta ttttgatcct gcctctttcg tagctgaaca attagatatg      540
ggaccattac attatagttt agatgctgct tgtgcgtctg cactttatgt attaagactt      600
gctcaagatc atttattaag tggtgctgct gatacaatgt tatgtggtgc atcttgttta      660
cctgaacctt tttttatttt atctggtttt tctacttttc atgcaatgcc attatctggt      720
gatgtttctg ctcctttgca taaaacttca caaggtctta cacctggtga aggtggtgct      780
attatggtac ttaaacgatt aaatgatgca atccgtgatg gtgatagaat ttatggtact      840
ttacttggtg ctgaattaag taatgctggt tgtggtttac cattgagtcc acatatgcca      900
agtgaatttg attgtatgga aaaagcttta caaagagtac acagattacc atcatctatt      960
caatatgttg agtgtcatgc aactggtaca ccacaaggtg ataaagttga aattgatgct     1020
atgacaaaat gttttggtga acatttacca aggtttggtt caacgaaagg gaattttggt     1080
catacacttg ttgctgctgg ttttgctggt atgtgtaaag ttttattatc aatgcaatat     1140
ggtgaaatac caccaactcc aggtcttgaa aatccagaca atattatgca tgatttagtt     1200
gttactgaaa caattccatg gcctaataca aatggtgatt gaaacgtgc atgtttatct      1260 gcttttggat tcggtggtac taatgcacat gctgtatttg aagagtatcg ttcagattta     1320
caagcaaata aaactcttga aaatgaaagt aaaagtcatg aaatcttttc ttcatttaaa     1380
attgctattg ttggtatgga atctgaattt ggtactttga aaggattaca agaatttgaa     1440
cgtgctattt acaatggtgg tcatggtgca tgtgatttac ctgaaaatag atggagattt     1500
cttggagaag ataaagaatt tttacaagct tgtggtttac aaaaattacc aagaggttgt     1560
tatattaaag aagtggaaac tgattttaaa aggttacgtt taccaatgat acaggaggat     1620
attctaagac ctttacagtt gttagctgtt tcgattatcg acagagcact taacgcatct     1680
ggtgttaaac caaatggcaa agttgcagtt ttagttggat taggtactga tcttgaatta     1740
tatcgtcatc gtgctcgtgt tgcattaaag gaacgcctcc aaactgcggt caaagaagat     1800
attcctttac ttgaaaagtt aatgaactat gtcaatgata gaggtacaag tacatcatat     1860
acatcttata ttggaaattt ggttgcaact cgagtttcat cattatgggg ttttactggt     1920
ccatcattca cgattactga aggtgaaaat tccgtatatc gttgtcttga tttgggaaga     1980
tggttcttag ctaatggtga agtagatgct gttgttgttg ccggggttga tttatgtggt     2040
agtgctgaaa atctttttgt aaaatctcgt agaagtaaag tttccacaca aaatgaacca     2100
tttgcaaatt ttgaatcaaa tgctgatgga tattttgctg gagatggttg tggagctttg     2160
gttttgaaac gattgagtga ttgtacggat tcaactgaaa aaatttatgc aacggtggat     2220
tcaattgctg ttggtgatga agttggccca actattaaac aagctttgaa gaatgcatcc     2280
atagcagcga aagatattga actggcagag ctatcagcaa gttcaggcaa acatcattct     2340
ggtagaatca cttgtgaaga tgaactaaat gaactgggtg aaattttcaa tgaaggtata     2400
caaagagttg caattggtag tgtgaaagct aatgttggag atgttggata tgcatctggt     2460
gcagcaagtt taatcaaaac ggctttgtgc ctgtacaacc gatatttacc aaagttacca     2520
aattggaata agccaacgaa agatgttgaa tggtccaaat cattttttgt atgtgaacat     2580
tctagagcat ggttgaaaaa tgttgatgaa aatagacatg ctgtcgtttc tggagtttgc     2640
gaaaatggtt cgtgttatgg aatcgtaatg tctgatgtac aaggacatca tgaagaatcg     2700
aatcttgtta gtttagacaa aaatgaacca aaagtactgg gtatttacgg agattcagtt     2760
gatgatatcc tagttcagct caacaaatat cttgaaaaat tccttcaaga aactggaacg     2820
gctgcggctg cacaaaaagt taaatcacct acaatagata ttgactccaa tgtgtttgct     2880
```

```
gagatgctta atctaccgca ggataaaaac aaaaaatttg cggtcgcatt ggttaccaca    2940
ccaaataaac tccagcgtga aatagaactt gctgtgaagg gtattccacg ttgcgtaaaa    3000
gcaaaaagag attggtgttc tccatctgga agtattttg cttgtaatcc actcaaaagt    3060
gataatattg catttatgta tggtgaaggc cgaagcccat atgctggact gggatatgat    3120
ttgcatcgaa tttggcctat gctacacgag ttggttaaca atagaactac agaactttgg    3180
gatcaaggtg atagttggta tttacctcga tctagctctg ttgctgaaaa agaaaaagtc    3240
ttcggagatt ttgataagaa tcaaattgaa atgtttagat tgggtatttt tgtatcaatg    3300
tgtttcactg atatggccac tgaacttttg ggtttaaaac ccaaagccgc gtttggttta    3360
agtttgggtg aaatatctat gcttttgca ttttctaaaa agaataccaa gttgtccaaa    3420
gaattgaccc gtcgtctaaa agaagcaaaa gtttgggcat cacaattagc tgttgaattt    3480
gcagctattc gagatttgtg gaatattcca gctgataaat ctattgatga attttggcaa    3540
gggtattttg tttacgcaaa tcgaaccctg gtcgagaaca caattgggga gaataaattt    3600
gttcgtttgt tgattgtaaa tgattcgcaa agttgtctaa ttgccgggaa accagatgaa    3660
tgtcaaaaag ttattgagaa gcttcatttg aagctaccgg cggttccagt aactcagggt    3720
atgatcggtc attgcccaga agcaattcct tatctagatc aaatcagtca tattcatgaa    3780
atgcttgaaa ttccaaaacc cgaaaatgtg aaattgttta caactagtga aaacagagaa    3840
ttagtgtcga tgaaagattc cgtgtcaaaa ttggttgctg agatttatca gcatgttgct    3900
gattttccaa acatcgtgaa caaggttaaa gaaacttgca aaactgatat atttattgaa    3960
ttgggatcga acaattatcg atctggagct gtcaaaacaa ttttaggtcc agaaatcgtt    4020
tctgttgcaa ttgataggca aaatgaaact gcatggggtc aactaatgaa gatggttgca    4080
tcgttgataa gtcatcgagt tccgggtgtt gaattgaaaa aactctatca tcctgaattg    4140
ctgaaatttg atccacaggc aaaaccgaat cgtttcatca gaaatataga actgaatgga    4200 tttttttgatc gtacgaatat tattgttgat aagcaactat cccctgcgga tccgaaactc    4260
gctgaaattg tgaacaatcg aaatatgcct aaagataatg tttatgtacc aattgaacgg    4320
gtgaaaacga tgataaaggc ggaaccagct aatttacaag tcagcgtggg aagtaaacca    4380
gttgttactg aaagaattag ttcggacgat aatctatttg aaaagttgtc agaaattaca    4440
aaatcttttg atggtgtaaa tgcgtgtact gaagcaatgt tgggagactc tggatttctc    4500
aaaacatatg aggttgacta tcctttgtac acaggtgcca tggctaaagg aattgcgtct    4560
gctgatttgg ttattgctgc tggtaaatca agatcttgg catcatttgg agctggtggg    4620
ttggccttac aagtggtaga agatgccatt aaacaaatta agctgaatt ggggaacggt    4680 ccgtttgctg taaatttgat tcattcacca ttcgatccta gcttggagaa gggtaacgtt    4740 gatcttttc taaaatataa cgttcgattt gttgaagtat ccgcatttat gtcattaacc    4800
cctcaggttg tacgatacag agccgctggt ttggccaaag caagagatgg atctgtgaaa    4860
attcaaaatc gtattattgc caaaatttca agaacagagt tagcggaact gttcttgaaa    4920
ccagcaccca aaatatttt agatgcattg gttgcggatg gatctattag tcaagaacaa    4980
gcccaacttg cattacttgt gccaatggct gatgatatta ctgtggaagc tgattctggt    5040
gggcatactg acaatcgacc aattcatgtt ttgttacctt tgataattca gcaaagaaat    5100
agaatttgta acaataccc aaaacattta aagttcgaa tcggagcagc tggtggtatt    5160
ggatgcccga aggcagcatt tgctgcgttt gagatgggtg ctgcatacat tgcaactgga    5220
```

-continued

```
acggtaaatc aactttcaaa ggaagcaggt acttgtgact atgtacgtaa agtattgaat    5280
aaagctacat attcggatgt taccatggct ccagccgcag atatgttcga tcatggtgtt    5340
gaattacaag ttttgaagaa aggtactatg tttccttcac gtgctaaaaa actatacgat    5400
ttgttcaaaa aatacaaatc gattgaggaa ttaccagcag atgaggtgaa aaaacttgag    5460
caaaagtttt caaaaagtc gtttgatgaa gtatgggatg agaccaagaa ttactatatt    5520
aatcgtttac attctcccga aaaaattgaa cgtgctgaaa gagatgcaaa acttaaaatg    5580
tcgttatgtt ttcgttggta tttgtcgaag tcttccagat gggctaatac cggtgaatct    5640
ggaagagtgc aggattatca aatttggtgt ggtccagcaa ttgggtcata taatgatttt    5700
gcgaaaggat caccatgttt ggatcctgag attttgggta gttttccaag tgttgttcag    5760
attaataaac atattttacg tggtgcttgt ttctatcaaa gactctctca gttgaaatat    5820 ctgaattta actatgagga attagatacg ttaacatact ctgcatcgaa ttttatttaa    5880
```

<210> SEQ ID NO 71
<211> LENGTH: 1959
<212> TYPE: PRT
<213> ORGANISM: Thraustochytrium sp.

<400> SEQUENCE: 71

```
Met Val Lys Leu Ser Val Gly Asp Asn Ile Cys His Asp Gln Arg Val
1               5                  10                  15

Ala Val Val Gly Met Ala Val Met Tyr Ala Gly Cys Gln Asn Gln His
            20                  25                  30

Glu Phe Trp Gln Ser Leu Gln Gly Lys Asn Met Asn Ser Lys Ser Ile
        35                  40                  45

Ser Gln Asn Arg Leu Gly Ser Glu Tyr Arg Glu Glu His Phe Lys Pro
    50                  55                  60

Glu Arg Ser Lys Tyr Ser Asp Thr Phe Cys Asn Glu Arg Tyr Gly Cys
65                  70                  75                  80

Ile Asp Glu Asn Val Gln Ser Glu His Glu Leu Leu Lys Leu Ala
                85                  90                  95

Lys Asp Ala Ile Ala Asp Thr Lys Gly Ser Ile Asp Leu Asn Lys Thr
            100                 105                 110

Gly Ile Val Ser Gly Cys Leu Ser Phe Pro Met Asp Asn Leu Gln Gly
        115                 120                 125

Asp Leu Leu Asn Leu Tyr Gln Cys His Ile Glu Lys Lys Ile Gly Pro
    130                 135                 140

Asn Ala Leu Lys Asp Val Asn Leu Trp Ser Lys Arg Thr Thr Asn Gly
145                 150                 155                 160

Lys Asp Asp Lys Lys Ala Tyr Phe Asp Pro Ala Ser Phe Val Ala Glu
                165                 170                 175

Gln Leu Asp Met Gly Pro Leu His Tyr Ser Leu Asp Ala Ala Cys Ala
            180                 185                 190

Ser Ala Leu Tyr Val Leu Arg Leu Ala Gln Asp His Leu Leu Ser Gly
        195                 200                 205

Ala Ala Asp Thr Met Leu Cys Gly Ala Ser Cys Leu Pro Glu Pro Phe
    210                 215                 220

Phe Ile Leu Ser Gly Phe Ser Thr Phe His Ala Met Pro Leu Ser Gly
225                 230                 235                 240

Asp Val Ser Ala Pro Leu His Lys Thr Ser Gln Gly Leu Thr Pro Gly
                245                 250                 255

Glu Gly Gly Ala Ile Met Val Leu Lys Arg Leu Asn Asp Ala Ile Arg
```

```
                260                 265                 270
Asp Gly Asp Arg Ile Tyr Gly Thr Leu Leu Gly Ala Glu Leu Ser Asn
            275                 280                 285

Ala Gly Cys Gly Leu Pro Leu Ser Pro His Met Pro Ser Glu Phe Asp
290                 295                 300

Cys Met Glu Lys Ala Leu Gln Arg Val His Arg Leu Pro Ser Ser Ile
305                 310                 315                 320

Gln Tyr Val Glu Cys His Ala Thr Gly Thr Pro Gln Gly Asp Lys Val
            325                 330                 335

Glu Ile Asp Ala Met Thr Lys Cys Phe Gly Glu His Leu Pro Arg Phe
        340                 345                 350

Gly Ser Thr Lys Gly Asn Phe Gly His Thr Leu Val Ala Ala Gly Phe
    355                 360                 365

Ala Gly Met Cys Lys Val Leu Leu Ser Met Gln Tyr Gly Glu Ile Pro
370                 375                 380

Pro Thr Pro Gly Leu Glu Asn Pro Asp Asn Ile Met His Asp Leu Val
385                 390                 395                 400

Val Thr Glu Thr Ile Pro Trp Pro Asn Thr Asn Gly Asp Leu Lys Arg
            405                 410                 415

Ala Cys Leu Ser Ala Phe Gly Phe Gly Thr Asn Ala His Ala Val
            420                 425                 430

Phe Glu Glu Tyr Arg Ser Asp Leu Gln Ala Asn Lys Thr Leu Glu Asn
        435                 440                 445

Glu Ser Lys Ser His Glu Ile Phe Ser Ser Phe Lys Ile Ala Ile Val
    450                 455                 460

Gly Met Glu Ser Glu Phe Gly Thr Leu Lys Gly Leu Gln Glu Phe Glu
465                 470                 475                 480

Arg Ala Ile Tyr Asn Gly Gly His Gly Ala Cys Asp Leu Pro Glu Asn
            485                 490                 495

Arg Trp Arg Phe Leu Gly Glu Asp Lys Glu Phe Leu Gln Ala Cys Gly
        500                 505                 510

Leu Gln Lys Leu Pro Arg Gly Cys Tyr Ile Lys Glu Val Glu Thr Asp
    515                 520                 525

Phe Lys Arg Leu Arg Leu Pro Met Ile Gln Glu Asp Ile Leu Arg Pro
530                 535                 540

Leu Gln Leu Leu Ala Val Ser Ile Ile Asp Arg Ala Leu Asn Ala Ser
545                 550                 555                 560

Gly Val Lys Pro Asn Gly Lys Val Ala Val Leu Val Gly Leu Gly Thr
            565                 570                 575

Asp Leu Glu Leu Tyr Arg His Arg Ala Arg Val Ala Leu Lys Glu Arg
        580                 585                 590

Leu Gln Thr Ala Val Lys Glu Asp Ile Pro Leu Leu Glu Lys Leu Met
    595                 600                 605

Asn Tyr Val Asn Asp Arg Gly Thr Ser Thr Ser Tyr Thr Ser Tyr Ile
610                 615                 620

Gly Asn Leu Val Ala Thr Arg Val Ser Ser Leu Trp Gly Phe Thr Gly
625                 630                 635                 640

Pro Ser Phe Thr Ile Thr Glu Gly Glu Asn Ser Val Tyr Arg Cys Leu
            645                 650                 655

Asp Leu Gly Arg Trp Phe Leu Ala Asn Gly Glu Val Asp Ala Val Val
        660                 665                 670

Val Ala Gly Val Asp Leu Cys Gly Ser Ala Glu Asn Leu Phe Val Lys
    675                 680                 685
```

```
Ser Arg Arg Ser Lys Val Ser Thr Gln Asn Glu Pro Phe Ala Asn Phe
690                 695                 700

Glu Ser Asn Ala Asp Gly Tyr Phe Ala Gly Asp Cys Gly Ala Leu
705                 710                 715                 720

Val Leu Lys Arg Leu Ser Asp Cys Thr Asp Ser Thr Glu Lys Ile Tyr
                725                 730                 735

Ala Thr Val Asp Ser Ile Ala Val Gly Asp Glu Val Gly Pro Thr Ile
            740                 745                 750

Lys Gln Ala Leu Lys Asn Ala Ser Ile Ala Ala Lys Asp Ile Glu Leu
            755                 760                 765

Ala Glu Leu Ser Ala Ser Gly Lys His His Ser Gly Arg Ile Thr
770                 775                 780

Cys Glu Asp Glu Leu Asn Glu Leu Gly Glu Ile Phe Asn Glu Gly Ile
785                 790                 795                 800

Gln Arg Val Ala Ile Gly Ser Val Lys Ala Asn Val Gly Asp Val Gly
                805                 810                 815

Tyr Ala Ser Gly Ala Ala Ser Leu Ile Lys Thr Ala Leu Cys Leu Tyr
                820                 825                 830

Asn Arg Tyr Leu Pro Lys Leu Pro Asn Trp Asn Lys Pro Thr Lys Asp
                835                 840                 845

Val Glu Trp Ser Lys Ser Phe Phe Val Cys Glu His Ser Arg Ala Trp
850                 855                 860

Leu Lys Asn Val Asp Glu Asn Arg His Ala Val Val Ser Gly Val Cys
865                 870                 875                 880

Glu Asn Gly Ser Cys Tyr Gly Ile Val Met Ser Asp Val Gln Gly His
                885                 890                 895

His Glu Glu Ser Asn Leu Val Ser Leu Asp Lys Asn Glu Pro Lys Val
                900                 905                 910

Leu Gly Ile Tyr Gly Asp Ser Val Asp Asp Ile Leu Val Gln Leu Asn
                915                 920                 925

Lys Tyr Leu Glu Lys Phe Leu Gln Glu Thr Gly Thr Ala Ala Ala Ala
930                 935                 940

Gln Lys Val Lys Ser Pro Thr Ile Asp Ile Asp Ser Asn Val Phe Ala
945                 950                 955                 960

Glu Met Leu Asn Leu Pro Gln Asp Lys Asn Lys Lys Phe Ala Val Ala
                965                 970                 975

Leu Val Thr Thr Pro Asn Lys Leu Gln Arg Glu Ile Glu Leu Ala Val
                980                 985                 990

Lys Gly Ile Pro Arg Cys Val Lys Ala Lys Arg Asp Trp Cys Ser Pro
                995                 1000                1005

Ser Gly Ser Ile Phe Ala Cys Asn Pro Leu Lys Ser Asp Asn Ile
    1010                1015                1020

Ala Phe Met Tyr Gly Glu Gly Arg Ser Pro Tyr Ala Gly Leu Gly
    1025                1030                1035

Tyr Asp Leu His Arg Ile Trp Pro Met Leu His Glu Leu Val Asn
    1040                1045                1050

Asn Arg Thr Thr Glu Leu Trp Asp Gln Gly Asp Ser Trp Tyr Leu
    1055                1060                1065

Pro Arg Ser Ser Ser Val Ala Glu Lys Glu Lys Val Phe Gly Asp
    1070                1075                1080

Phe Asp Lys Asn Gln Ile Glu Met Phe Arg Leu Gly Ile Phe Val
    1085                1090                1095
```

-continued

Ser Met Cys Phe Thr Asp Met Ala Thr Glu Leu Leu Gly Leu Lys
    1100                1105                1110

Pro Lys Ala Ala Phe Gly Leu Ser Leu Gly Glu Ile Ser Met Leu
    1115                1120                1125

Phe Ala Phe Ser Lys Lys Asn Thr Lys Leu Ser Lys Glu Leu Thr
    1130                1135                1140

Arg Arg Leu Lys Glu Ala Lys Val Trp Ala Ser Gln Leu Ala Val
    1145                1150                1155

Glu Phe Ala Ala Ile Arg Asp Leu Trp Asn Ile Pro Ala Asp Lys
    1160                1165                1170

Ser Ile Asp Glu Phe Trp Gln Gly Tyr Phe Val Tyr Ala Asn Arg
    1175                1180                1185

Thr Leu Val Glu Asn Thr Ile Gly Glu Asn Lys Phe Val Arg Leu
    1190                1195                1200

Leu Ile Val Asn Asp Ser Gln Ser Cys Leu Ile Ala Gly Lys Pro
    1205                1210                1215

Asp Glu Cys Gln Lys Val Ile Glu Lys Leu His Leu Lys Leu Pro
    1220                1225                1230

Ala Val Pro Val Thr Gln Gly Met Ile Gly His Cys Pro Glu Ala
    1235                1240                1245

Ile Pro Tyr Leu Asp Gln Ile Ser His Ile His Glu Met Leu Glu
    1250                1255                1260

Ile Pro Lys Pro Glu Asn Val Lys Leu Phe Thr Thr Ser Glu Asn
    1265                1270                1275

Arg Glu Leu Val Ser Met Lys Asp Ser Val Ser Lys Leu Val Ala
    1280                1285                1290

Glu Ile Tyr Gln His Val Ala Asp Phe Pro Asn Ile Val Asn Lys
    1295                1300                1305

Val Lys Glu Thr Cys Lys Thr Asp Ile Phe Ile Glu Leu Gly Ser
    1310                1315                1320

Asn Asn Tyr Arg Ser Gly Ala Val Lys Thr Ile Leu Gly Pro Glu
    1325                1330                1335

Ile Val Ser Val Ala Ile Asp Arg Gln Asn Glu Thr Ala Trp Gly
    1340                1345                1350

Gln Leu Met Lys Met Val Ala Ser Leu Ile Ser His Arg Val Pro
    1355                1360                1365

Gly Val Glu Leu Lys Lys Leu Tyr His Pro Glu Leu Leu Lys Phe
    1370                1375                1380

Asp Pro Gln Ala Lys Pro Asn Arg Phe Ile Arg Asn Ile Glu Leu
    1385                1390                1395

Asn Gly Phe Phe Asp Arg Thr Asn Ile Ile Val Asp Lys Gln Leu
    1400                1405                1410

Ser Pro Ala Asp Pro Lys Leu Ala Glu Ile Val Asn Asn Arg Asn
    1415                1420                1425

Met Pro Lys Asp Asn Val Tyr Val Pro Ile Glu Arg Val Lys Thr
    1430                1435                1440

Met Ile Lys Ala Glu Pro Ala Asn Leu Gln Val Ser Val Gly Ser
    1445                1450                1455

Lys Pro Val Val Thr Glu Arg Ile Ser Ser Asp Asp Asn Leu Phe
    1460                1465                1470

Glu Lys Leu Ser Glu Ile Thr Lys Ser Phe Asp Gly Val Asn Ala
    1475                1480                1485

Cys Thr Glu Ala Met Leu Gly Asp Ser Gly Phe Leu Lys Thr Tyr

-continued

```
            1490                1495                1500
Glu Val Asp Tyr Pro Leu Tyr Thr Gly Ala Met Ala Lys Gly Ile
    1505                1510                1515
Ala Ser Ala Asp Leu Val Ile Ala Ala Gly Lys Ser Lys Ile Leu
    1520                1525                1530
Ala Ser Phe Gly Ala Gly Gly Leu Ala Leu Gln Val Val Glu Asp
    1535                1540                1545
Ala Ile Lys Gln Ile Lys Ala Glu Leu Gly Asn Gly Pro Phe Ala
    1550                1555                1560
Val Asn Leu Ile His Ser Pro Phe Asp Pro Ser Leu Glu Lys Gly
    1565                1570                1575
Asn Val Asp Leu Phe Leu Lys Tyr Asn Val Arg Phe Val Glu Val
    1580                1585                1590
Ser Ala Phe Met Ser Leu Thr Pro Gln Val Val Arg Tyr Arg Ala
    1595                1600                1605
Ala Gly Leu Ala Lys Ala Arg Asp Gly Ser Val Lys Ile Gln Asn
    1610                1615                1620
Arg Ile Ile Ala Lys Ile Ser Arg Thr Glu Leu Ala Glu Leu Phe
    1625                1630                1635
Leu Lys Pro Ala Pro Lys Asn Ile Leu Asp Ala Leu Val Ala Asp
    1640                1645                1650
Gly Ser Ile Ser Gln Glu Gln Ala Gln Leu Ala Leu Leu Val Pro
    1655                1660                1665
Met Ala Asp Asp Ile Thr Val Glu Ala Asp Ser Gly Gly His Thr
    1670                1675                1680
Asp Asn Arg Pro Ile His Val Leu Leu Pro Leu Ile Ile Gln Gln
    1685                1690                1695
Arg Asn Arg Ile Cys Lys Gln Tyr Pro Lys His Leu Lys Val Arg
    1700                1705                1710
Ile Gly Ala Ala Gly Gly Ile Gly Cys Pro Lys Ala Ala Phe Ala
    1715                1720                1725
Ala Phe Glu Met Gly Ala Ala Tyr Ile Ala Thr Gly Thr Val Asn
    1730                1735                1740
Gln Leu Ser Lys Glu Ala Gly Thr Cys Asp Tyr Val Arg Lys Val
    1745                1750                1755
Leu Asn Lys Ala Thr Tyr Ser Asp Val Thr Met Ala Pro Ala Ala
    1760                1765                1770
Asp Met Phe Asp His Gly Val Glu Leu Gln Val Leu Lys Lys Gly
    1775                1780                1785
Thr Met Phe Pro Ser Arg Ala Lys Lys Leu Tyr Asp Leu Phe Lys
    1790                1795                1800
Lys Tyr Lys Ser Ile Glu Glu Leu Pro Ala Asp Glu Val Lys Lys
    1805                1810                1815
Leu Glu Gln Lys Val Phe Lys Ser Phe Asp Glu Val Trp Asp
    1820                1825                1830
Glu Thr Lys Asn Tyr Tyr Ile Asn Arg Leu His Ser Pro Glu Lys
    1835                1840                1845
Ile Glu Arg Ala Glu Arg Asp Ala Lys Leu Lys Met Ser Leu Cys
    1850                1855                1860
Phe Arg Trp Tyr Leu Ser Lys Ser Ser Arg Trp Ala Asn Thr Gly
    1865                1870                1875
Glu Ser Gly Arg Val Gln Asp Tyr Gln Ile Trp Cys Gly Pro Ala
    1880                1885                1890
```

```
Ile Gly Ser Tyr Asn Asp Phe Ala Lys Gly Ser Pro Cys Leu Asp
    1895                1900                1905

Pro Glu Ile Leu Gly Ser Phe Pro Ser Val Val Gln Ile Asn Lys
    1910                1915                1920

His Ile Leu Arg Gly Ala Cys Phe Tyr Gln Arg Leu Ser Gln Leu
    1925                1930                1935

Lys Tyr Leu Asn Phe Asn Tyr Glu Glu Leu Asp Thr Leu Thr Tyr
    1940                1945                1950

Ser Ala Ser Asn Phe Ile
    1955

<210> SEQ ID NO 72
<211> LENGTH: 4368
<212> TYPE: DNA
<213> ORGANISM: Thraustochytrium sp.

<400> SEQUENCE: 72
atggttggtt tacaaatgaa aagaaaacca gtatgggaga tgagtaagga agaacaaagt      60
tctggaaaga atgttgtatt tgactatgat gaattgttgg aatttgctga aggtgatatt    120
ggtaaagtct tggacctaa gtttgatatt atcgataagt atagtcgacg tgtacgttta     180
cctgcgagag aatatcttct agttaccaga gttactttga tggatgctga agttgggaat    240
ttcagagttg gatctagaat ggttactgaa atgatgttc cagtaaatgg tgaactttca    300
caaggtggtg atgttccatg ggctgttctt gttgaatctg acaatgtga tcttatgtta    360 atatcttata tgggtattga ttttcaatgt aaaggtgatc gtgtctatcg attattaaat    420
actacgttga cgttttacgg tgttgctcat gagggtgaaa cactagtata cgatattcgt    480
gtaactggat ttgcaaaagg tatgcacggt gaaatctcca tgttttttttt tgaatatgat    540 tgttatgtga atggacgatt attaatcgaa atgagagatg ttgtgcggg atttttttact    600 gatgaagaac ttgcagcagg taaggagtt attaaaactg ttgctgaact tcataaaaga    660
aaatctattg ttccaaaatc cattaaaacct tttgctctaa atccagcagt acacaaaaca    720 atgtttttctg aaaatgatat ggaaaaattg tgtgagcgtc aatgggaaaa tgtattgggt    780
agtggacttc aaggtattga ctacaagtta tgtgcacgga aaatgcttat gattgatcgt    840
attactaaaa tacaacataa tggtggtgca tggtcttg gattattggt tggcgaaaaa    900
attcttgaac gtgatcattg gtattttcca tgccattttg taaaggatca agttatggct   960
ggctcacttg ttagtgatgg ttgcagtcag ctactaaaac tttatatgtt atggttgggt  1020
ttacatgatg tggttccaga ttttcaattt cgtccagttc ctggacaacc aaataaagtt  1080
cgttgccgtg acaaattag tccacatcgt ggtaaacttg tttatgttat ggaaataaga  1140
gaaatgggat tcaatgaatc aactggacaa ccatatgcta ttgctgatgt tgatattatt  1200
gatgtaaact atgaacttgg tcaatcattt gatatggctg atattgatag ttatggacgt  1260
ggtaatttgt caagagaaat tgtggttgat tttaaaggaa ttgctttgca aatggaaggt  1320
accgtgaaat catcaaatat cattgattct tcaccaaaaat caactattat acaaccacct  1380
ccaaattgtc ttcgtggtga tccactggca ccatacaag ttacatggca tccaatggca  1440
ggagttaatg gggcaccagc tccttcattt agtccatctg attatccacc acgtgctgtt  1500
tgcttcaaac catttcctgg taatcctta gataacgatc atacacctgg taaaatgcct  1560
ttaacatggt ttaatatgtc cgagtttatg tgtggtaaag tatcaaattg tcttggacca  1620
gaatttaaga gattgataa ctctaaaaca tccagaagtc ctgcctttga tcttgcactt  1680
```

```
gttacacgtg ttgtgagtgt atcagatatg gaatttaaac ctcatttaaa tattgatgtt    1740
aatccaagta agggtacaat gataggtgaa tttgattgcc ctgcagatgc gtggtttttt    1800
caaggatcat gtaacgatgg tcatatgccg tattctattg ttatggaaat tgctcttcaa    1860
acttctggtg tattaacttc agttttgaaa gcacctttga ctatggataa agatgatatt    1920
cttttccgca atttggatgc cactgctgaa atggttcgaa gtgatgttga ttgtagaggt    1980
aaaactatca aaaactttac tcaatgtacc ggttacagta tgctcggaaa atgggaatt     2040 catagattca catttgaatt atctgttgat gatgtagttt tctacaaagg atcaacatct    2100
tttggttggt tcacccctga agtattcgag tcacaagttg gtcttgataa tggtaaaaaa    2160
gtacaaccat ggtatttgga acaaaaatca tctaatgtag taacttatga cgttgcgtcc    2220
actgctggca aggataagtt atttccaaag attggatcta aggatgcaca agttcaagaa    2280
agaaatacac aatgtgagtt tctagatact atgcatatta ttccaaatac tggaaagtac    2340
aacaaaggtt atgctcatgg agaaaagaaa gttaatccaa acgactggtt cttttcctgt    2400
catttctggt ttgatcctgt gatgcctggt tcattaggta ttgaaagtat gtttcaactc    2460
attgaagcat tttcaattga tcaaggaatc gcttcaaaac atggtattgt gaatccaact    2520
tttgctcatt ccaatggaaa aacttcttgg aaatacagag gtcaattgaa taacaaaggt    2580
aaacgaatgg atagtgaaat tcatatcaaa gatattgtca aaaatgctga tggtactgtt    2640
gatttgattg ctgatggatt tttattggtt gattcactaa gagtatactc tgcagatgat    2700
cttcgcgtaa aaattgtacc gggaaccaaa gctgcaccta atcagtagc tgctgctcca    2760 agacatgttg caacaccaat tccaggagtg ccttcgaata caagcagtgt tgaaatcagt    2820
ttggaatctt tgaagaaaga attgttaaat cttgagaaac cattgtatct tgaaacttcc    2880
aatcatattg taaacaatt cggtgacgtt aacaatggcc aagcatccgt tattccacca    2940
tgcaccatca atgatttggg tgagcgtagt tttatggaaa catacaatgt tgttgcacca    3000
ctttacactg gagccatggc taaaggtatt gcatctgctg atttggtaat tgcagctggt    3060
aaaagaaaaa tttttgggttc ttttggcgct ggaggcttac caatgcactt ggttcgtgct    3120
tctgttgaaa aaatccaagc cgcacttcca gaaggtccat acgctgtcaa cttgattcat    3180
agtccattcg actcaaatct tgaaaaggga aatgtagatc tatttttgga aaaaggtgtt    3240
catgttgttg aagcatctgc attcactgct ctgaccactc aagtagttcg ttaccgtgca    3300
tgtggtttat ctcgggctaa agacggatct gtattgatca aaaatagaat catcggtaaa    3360
gtttcaagaa ccgaattggc tgaaatgttt ttcagacctg caccacaaaa cttgcttgac    3420
aagcttattg ctagtggaga atcactaaa gaacaagctt cattggcttt ggaagtacca    3480
atggctgatg atgtagctgt tgaagctgat agcggtggac atactgataa tagaccaatt    3540
catgtaatcc tacctttgat tatcaatcta cgaaatagaa ttcataaaga atgtggtttt    3600
cctgctgctt tgagagttcg cgttggtgct ggtggtggaa ttggttgtcc aagtgctgca    3660
gttgctgcat tcaatatggg agctgcattc ttgattactg gcagcgtcaa ccaagttagc    3720
aaacaatctg gtacgtgtga tatcgttaga aagcaattat ctgaagcttc gtattcagat    3780
attaccatgg caccagcggc tgatatgttt gatcaaggag tcgagcttca agtattaaaa    3840
aaaggaacta tgtttccatc tcgtgcaaag aaattgtatg aattattctg tatgtacaac    3900
tcatttgatg acatgccaaa aagcgaactt caaagactag agaagcgaat ttttcaaaaa    3960
tcgcttgcgg aagtttggga agaaactaaa gatttttata tcaatcgttt gaataatcct    4020
```

-continued

```
gagaagattg aacatgctga aagaaagat ccaaagttga agatgtcatt atgctttaga    4080
tggtatttgg gtttaagttc attttgggca acaatggaa ttaaagaaag atcaatggac    4140
tatcaaattt ggtgtggtcc agcgattggt tcatacaatg atttttgtaaa aggaacttat   4200 ttggatcctg cagtagcagg ttcatatcca tgtgttgttc aaattaacat gcaaattcta    4260
cgcggtgctt gttttcttca acgagttcgt gcaatcaagc acgatccacg attggatatt    4320
gatgtcgatg aagatgtatt tacctatcgt ccagaatcaa ccctatag                 4368
```

<210> SEQ ID NO 73
<211> LENGTH: 1455
<212> TYPE: PRT
<213> ORGANISM: Thraustochytrium sp.

<400> SEQUENCE: 73

```
Met Val Gly Leu Gln Met Lys Lys Pro Val Trp Glu Met Ser Lys
1               5                   10                  15

Glu Glu Gln Ser Ser Gly Lys Asn Val Val Phe Asp Tyr Asp Glu Leu
            20                  25                  30

Leu Glu Phe Ala Glu Gly Asp Ile Gly Lys Val Phe Gly Pro Lys Phe
        35                  40                  45

Asp Ile Ile Asp Lys Tyr Ser Arg Arg Val Arg Leu Pro Ala Arg Glu
    50                  55                  60

Tyr Leu Leu Val Thr Arg Val Thr Leu Met Asp Ala Glu Val Gly Asn
65                  70                  75                  80

Phe Arg Val Gly Ser Arg Met Val Thr Glu Tyr Asp Val Pro Val Asn
                85                  90                  95

Gly Glu Leu Ser Gln Gly Gly Asp Val Pro Trp Ala Val Leu Val Glu
            100                 105                 110

Ser Gly Gln Cys Asp Leu Met Leu Ile Ser Tyr Met Gly Ile Asp Phe
        115                 120                 125

Gln Cys Lys Gly Asp Arg Val Tyr Arg Leu Leu Asn Thr Thr Leu Thr
    130                 135                 140

Phe Tyr Gly Val Ala His Glu Gly Glu Thr Leu Val Tyr Asp Ile Arg
145                 150                 155                 160

Val Thr Gly Phe Ala Lys Gly Met His Gly Glu Ile Ser Met Phe Phe
                165                 170                 175

Phe Glu Tyr Asp Cys Tyr Val Asn Gly Arg Leu Leu Ile Glu Met Arg
            180                 185                 190

Asp Gly Cys Ala Gly Phe Phe Thr Asp Glu Glu Leu Ala Ala Gly Lys
        195                 200                 205

Gly Val Ile Lys Thr Val Ala Glu Leu His Lys Arg Lys Ser Ile Val
    210                 215                 220

Pro Lys Ser Ile Lys Pro Phe Ala Leu Asn Pro Ala Val His Lys Thr
225                 230                 235                 240

Met Phe Ser Glu Asn Asp Met Glu Lys Leu Cys Glu Arg Gln Trp Glu
                245                 250                 255

Asn Val Leu Gly Ser Gly Leu Gln Gly Ile Asp Tyr Lys Leu Cys Ala
            260                 265                 270

Arg Lys Met Leu Met Ile Asp Arg Ile Thr Lys Ile Gln His Asn Gly
        275                 280                 285

Gly Ala Tyr Gly Leu Gly Leu Leu Val Gly Glu Lys Ile Leu Glu Arg
    290                 295                 300

Asp His Trp Tyr Phe Pro Cys His Phe Val Lys Asp Gln Val Met Ala
305                 310                 315                 320
```

-continued

```
Gly Ser Leu Val Ser Asp Gly Cys Ser Gln Leu Leu Lys Leu Tyr Met
            325                 330                 335

Leu Trp Leu Gly Leu His Asp Val Val Pro Asp Phe Gln Phe Arg Pro
            340                 345                 350

Val Pro Gly Gln Pro Asn Lys Val Arg Cys Arg Gly Gln Ile Ser Pro
            355                 360                 365

His Arg Gly Lys Leu Val Tyr Val Met Glu Ile Arg Glu Met Gly Phe
    370                 375                 380

Asn Glu Ser Thr Gly Gln Pro Tyr Ala Ile Ala Asp Val Asp Ile Ile
385                 390                 395                 400

Asp Val Asn Tyr Glu Leu Gly Gln Ser Phe Asp Met Ala Asp Ile Asp
            405                 410                 415

Ser Tyr Gly Arg Gly Asn Leu Ser Lys Lys Ile Val Asp Phe Lys
            420                 425                 430

Gly Ile Ala Leu Gln Met Glu Gly Thr Val Lys Ser Ser Asn Ile Ile
            435                 440                 445

Asp Ser Ser Pro Lys Ser Thr Ile Ile Gln Pro Pro Asn Cys Leu
    450                 455                 460

Arg Gly Asp Pro Leu Ala Pro Ser Gln Val Thr Trp His Pro Met Ala
465                 470                 475                 480

Gly Val Asn Gly Ala Pro Ala Pro Ser Phe Ser Pro Ser Asp Tyr Pro
            485                 490                 495

Pro Arg Ala Val Cys Phe Lys Pro Phe Pro Gly Asn Pro Leu Asp Asn
            500                 505                 510

Asp His Thr Pro Gly Lys Met Pro Leu Thr Trp Phe Asn Met Ser Glu
            515                 520                 525

Phe Met Cys Gly Lys Val Ser Asn Cys Leu Gly Pro Glu Phe Lys Arg
    530                 535                 540

Phe Asp Asn Ser Lys Thr Ser Arg Ser Pro Ala Phe Asp Leu Ala Leu
545                 550                 555                 560

Val Thr Arg Val Val Ser Val Ser Asp Met Glu Phe Lys Pro His Leu
            565                 570                 575

Asn Ile Asp Val Asn Pro Ser Lys Gly Thr Met Ile Gly Glu Phe Asp
            580                 585                 590

Cys Pro Ala Asp Ala Trp Phe Phe Gln Gly Ser Cys Asn Asp Gly His
    595                 600                 605

Met Pro Tyr Ser Ile Val Met Glu Ile Ala Leu Gln Thr Ser Gly Val
    610                 615                 620

Leu Thr Ser Val Leu Lys Ala Pro Leu Thr Met Asp Lys Asp Ile
625                 630                 635                 640

Leu Phe Arg Asn Leu Asp Ala Thr Ala Glu Met Val Arg Ser Asp Val
            645                 650                 655

Asp Cys Arg Gly Lys Thr Ile Lys Asn Phe Thr Gln Cys Thr Gly Tyr
            660                 665                 670

Ser Met Leu Gly Lys Met Gly Ile His Arg Phe Thr Phe Glu Leu Ser
            675                 680                 685

Val Asp Asp Val Phe Tyr Lys Gly Ser Thr Ser Phe Gly Trp Phe
    690                 695                 700

Thr Pro Glu Val Phe Glu Ser Gln Val Gly Leu Asp Asn Gly Lys Lys
705                 710                 715                 720

Val Gln Pro Trp Tyr Leu Glu Gln Lys Ser Ser Asn Val Thr Tyr
            725                 730                 735
```

-continued

```
Asp Val Ala Ser Thr Ala Gly Lys Asp Lys Leu Phe Ser Lys Ile Gly
            740                 745                 750

Ser Lys Asp Ala Gln Val Gln Arg Arg Asn Thr Gln Cys Glu Phe Leu
            755                 760                 765

Asp Thr Met His Ile Ile Pro Asn Thr Gly Lys Tyr Asn Lys Gly Tyr
    770                 775                 780

Ala His Gly Glu Lys Lys Val Asn Pro Asn Asp Trp Phe Phe Ser Cys
785                 790                 795                 800

His Phe Trp Phe Asp Pro Val Met Pro Gly Ser Leu Gly Ile Glu Ser
                805                 810                 815

Met Phe Gln Leu Ile Glu Ala Phe Ser Ile Asp Gln Gly Ile Ala Ser
            820                 825                 830

Lys His Gly Ile Val Asn Pro Thr Phe Ala His Ser Asn Gly Lys Thr
            835                 840                 845

Ser Trp Lys Tyr Arg Gly Gln Leu Asn Asn Lys Gly Lys Arg Met Asp
            850                 855                 860

Ser Glu Ile His Ile Lys Asp Ile Val Lys Asn Ala Asp Gly Thr Val
865                 870                 875                 880

Asp Leu Ile Ala Asp Gly Phe Leu Leu Val Asp Ser Leu Arg Val Tyr
                885                 890                 895

Ser Ala Asp Asp Leu Arg Val Lys Ile Val Pro Gly Thr Lys Ala Ala
            900                 905                 910

Pro Lys Ser Val Ala Ala Ala Pro Arg His Val Ala Thr Pro Ile Pro
            915                 920                 925

Gly Val Pro Ser Asn Thr Ser Ser Val Glu Ile Ser Leu Glu Ser Leu
            930                 935                 940

Lys Lys Glu Leu Leu Asn Leu Glu Lys Pro Leu Tyr Leu Glu Thr Ser
945                 950                 955                 960

Asn His Ile Val Lys Gln Phe Gly Asp Val Asn Asn Gly Gln Ala Ser
                965                 970                 975

Val Ile Pro Pro Cys Thr Ile Asn Asp Leu Gly Glu Arg Ser Phe Met
            980                 985                 990

Glu Thr Tyr Asn Val Val Ala Pro Leu Tyr Thr Gly Ala Met Ala Lys
            995                1000                1005

Gly Ile Ala Ser Ala Asp Leu Val Ile Ala Ala Gly Lys Arg Lys
        1010                1015                1020

Ile Leu Gly Ser Phe Gly Ala Gly Gly Leu Pro Met His Leu Val
        1025                1030                1035

Arg Ala Ser Val Glu Lys Ile Gln Ala Ala Leu Pro Glu Gly Pro
        1040                1045                1050

Tyr Ala Val Asn Leu Ile His Ser Pro Phe Asp Ser Asn Leu Glu
        1055                1060                1065

Lys Gly Asn Val Asp Leu Phe Leu Glu Lys Gly Val His Val Val
        1070                1075                1080

Glu Ala Ser Ala Phe Thr Ala Leu Thr Thr Gln Val Val Arg Tyr
        1085                1090                1095

Arg Ala Cys Gly Leu Ser Arg Ala Lys Asp Gly Ser Val Leu Ile
        1100                1105                1110

Lys Asn Arg Ile Ile Gly Lys Val Ser Arg Thr Glu Leu Ala Glu
        1115                1120                1125

Met Phe Phe Arg Pro Ala Pro Gln Asn Leu Leu Asp Lys Leu Ile
        1130                1135                1140

Ala Ser Gly Glu Ile Thr Lys Glu Gln Ala Ser Leu Ala Leu Glu
```

Val Pro Met Ala Asp Asp Val Ala Val Glu Ala Asp Ser Gly Gly
1160                1165                1170

His Thr Asp Asn Arg Pro Ile His Val Ile Leu Pro Leu Ile Ile
1175                1180                1185

Asn Leu Arg Asn Arg Ile His Lys Glu Cys Gly Phe Pro Ala Ala
1190                1195                1200

Leu Arg Val Arg Val Gly Ala Gly Gly Ile Gly Cys Pro Ser
1205                1210                1215

Ala Ala Val Ala Ala Phe Asn Met Gly Ala Ala Phe Leu Ile Thr
1220                1225                1230

Gly Ser Val Asn Gln Val Ser Lys Gln Ser Gly Thr Cys Asp Ile
1235                1240                1245

Val Arg Lys Gln Leu Ser Glu Ala Ser Tyr Ser Asp Ile Thr Met
1250                1255                1260

Ala Pro Ala Ala Asp Met Phe Asp Gln Gly Val Glu Leu Gln Val
1265                1270                1275

Leu Lys Lys Gly Thr Met Phe Pro Ser Arg Ala Lys Lys Leu Tyr
1280                1285                1290

Glu Leu Phe Cys Met Tyr Asn Ser Phe Asp Asp Met Pro Lys Ser
1295                1300                1305

Glu Leu Gln Arg Leu Glu Lys Arg Ile Phe Gln Lys Ser Leu Ala
1310                1315                1320

Glu Val Trp Glu Glu Thr Lys Asp Phe Tyr Ile Asn Arg Leu Asn
1325                1330                1335

Asn Pro Glu Lys Ile Glu His Ala Glu Lys Lys Asp Pro Lys Leu
1340                1345                1350

Lys Met Ser Leu Cys Phe Arg Trp Tyr Leu Gly Leu Ser Ser Phe
1355                1360                1365

Trp Ala Asn Asn Gly Ile Lys Glu Arg Ser Met Asp Tyr Gln Ile
1370                1375                1380

Trp Cys Gly Pro Ala Ile Gly Ser Tyr Asn Asp Phe Val Lys Gly
1385                1390                1395

Thr Tyr Leu Asp Pro Ala Val Ala Gly Ser Tyr Pro Cys Val Val
1400                1405                1410

Gln Ile Asn Met Gln Ile Leu Arg Gly Ala Cys Phe Leu Gln Arg
1415                1420                1425

Val Arg Ala Ile Lys His Asp Pro Arg Leu Asp Ile Asp Val Asp
1430                1435                1440

Glu Asp Val Phe Thr Tyr Arg Pro Glu Ser Thr Leu
1445                1450                1455

<210> SEQ ID NO 74
<211> LENGTH: 1350
<212> TYPE: DNA
<213> ORGANISM: Thraustochytrium sp.

<400> SEQUENCE: 74
agaattgcta ttgttggatt atctgcgatt ttaccaagtg gtgaaaatgt tagagaatct      60
tgggaagcaa tacgtgatgg tttgaattgt ttaagtgatt tacctgcgga tcgtgttgat     120
gttactgcgt attataatcc aacaaaaggt gtaaaggata aaatttattg taaacgtggt     180
gggtttattc ctgaatatga atttgattct agagaatttg gacttaatat gttacaaatg     240
gaagattctg atgctaatca aacgttaact ttattaaagg ttaagaagc attagatgat     300

```
gctaatatac ctgcatttac taatgagaaa aaaaatattg gttgtgttct tggtattggt    360
ggtggtcaaa aagcatctca tgaattttat tcaagactta attatgttgt tgtggataaa    420
gttttaagaa aaatgggatt acctgatgag gatgttgaaa ctgctgttga aaagtttaaa    480
gctaattttc ctgaatggag attagattcc tttcctggtt ttcttggtaa tgttactgct    540
ggccgttgta ctaatacatt caatatggaa ggtatgaatt gtgttgtaga tgctgcttgt    600
gctagttctt taattgctat taaagttgct attgatgaat tattacatgg tgattgtgat    660
gcaatgattg ctggtgcaac ttgtactgat aacgctcttg gtatgtatat ggcattttca    720
aaaacacctg ttttttcaac tgatcaaagt tgtcttgcat atgatgaaaa aacaaaaggt    780
atgcttattg gtgaaggttc agctatgttt gttttaaaac gttatgctga cgcagtgaga    840
gatggtgata ctgtacatgc tgttatacgt tcatgttcat catcatctga cggtaaagca    900
tctggtattt atacaccaac tatttctggt caagaagaag ctattcttag agcatatcgt    960
agagctggtg tatcaccaaa tactattact ttagttgaag acatggtac tggtacacca   1020 gtgggtgata aaattgaatt aacagcttta cgcaatgtat ttgataaagc atatggtcct   1080
ggtcataagg aagaagttgc tgttggaagt attaaaagtc aaattggtca tttgaaagct   1140
gttgctggtt gtgctggtct tgtgaaattg gttatggcat tgaaacataa aacactacct   1200
caaagtatta atgttgaaaa tccacctaat ttagtggatg gtactgtcat tagtgatact   1260
actttatata ttaatacaat gaatcgtcca tggattacta agcctggtgt tccaagaaga   1320
gctggtatat ctagtttcgg atttggtggt                                    1350
```

<210> SEQ ID NO 75
<211> LENGTH: 450
<212> TYPE: PRT
<213> ORGANISM: Thraustochytrium sp.

<400> SEQUENCE: 75

Arg Ile Ala Ile Val Gly Leu Ser Ala Ile Leu Pro Ser Gly Glu Asn
1               5                   10                  15

Val Arg Glu Ser Trp Glu Ala Ile Arg Asp Gly Leu Asn Cys Leu Ser
            20                  25                  30

Asp Leu Pro Ala Asp Arg Val Asp Val Thr Ala Tyr Tyr Asn Pro Thr
        35                  40                  45

Lys Gly Val Lys Asp Lys Ile Tyr Cys Lys Arg Gly Gly Phe Ile Pro
    50                  55                  60

Glu Tyr Glu Phe Asp Ser Arg Glu Phe Gly Leu Asn Met Leu Gln Met
65                  70                  75                  80

Glu Asp Ser Asp Ala Asn Gln Thr Leu Thr Leu Leu Lys Val Lys Glu
                85                  90                  95

Ala Leu Asp Asp Ala Asn Ile Pro Ala Phe Thr Asn Glu Lys Lys Asn
            100                 105                 110

Ile Gly Cys Val Leu Gly Ile Gly Gly Gly Gln Lys Ala Ser His Glu
        115                 120                 125

Phe Tyr Ser Arg Leu Asn Tyr Val Val Val Asp Lys Val Leu Arg Lys
    130                 135                 140

Met Gly Leu Pro Asp Glu Asp Val Glu Thr Ala Val Glu Lys Phe Lys
145                 150                 155                 160

Ala Asn Phe Pro Glu Trp Arg Leu Asp Ser Phe Pro Gly Phe Leu Gly
                165                 170                 175

Asn Val Thr Ala Gly Arg Cys Thr Asn Thr Phe Asn Met Glu Gly Met

```
            180                 185                 190

Asn Cys Val Val Asp Ala Ala Cys Ala Ser Ser Leu Ile Ala Ile Lys
        195                 200                 205

Val Ala Ile Asp Glu Leu Leu His Gly Asp Cys Asp Ala Met Ile Ala
    210                 215                 220

Gly Ala Thr Cys Thr Asp Asn Ala Leu Gly Met Tyr Met Ala Phe Ser
225                 230                 235                 240

Lys Thr Pro Val Phe Ser Thr Asp Gln Ser Cys Leu Ala Tyr Asp Glu
                245                 250                 255

Lys Thr Lys Gly Met Leu Ile Gly Glu Gly Ser Ala Met Phe Val Leu
            260                 265                 270

Lys Arg Tyr Ala Asp Ala Val Arg Asp Gly Asp Thr Val His Ala Val
        275                 280                 285

Ile Arg Ser Cys Ser Ser Ser Ser Asp Gly Lys Ala Ser Gly Ile Tyr
    290                 295                 300

Thr Pro Thr Ile Ser Gly Gln Glu Glu Ala Ile Leu Arg Ala Tyr Arg
305                 310                 315                 320

Arg Ala Gly Val Ser Pro Asn Thr Ile Thr Leu Val Glu Gly His Gly
                325                 330                 335

Thr Gly Thr Pro Val Gly Asp Lys Ile Glu Leu Thr Ala Leu Arg Asn
            340                 345                 350

Val Phe Asp Lys Ala Tyr Gly Pro Gly His Lys Glu Glu Val Ala Val
        355                 360                 365

Gly Ser Ile Lys Ser Gln Ile Gly His Leu Lys Ala Val Ala Gly Cys
    370                 375                 380

Ala Gly Leu Val Lys Leu Val Met Ala Leu Lys His Lys Thr Leu Pro
385                 390                 395                 400

Gln Ser Ile Asn Val Glu Asn Pro Pro Asn Leu Val Asp Gly Thr Val
                405                 410                 415

Ile Ser Asp Thr Thr Leu Tyr Ile Asn Thr Met Asn Arg Pro Trp Ile
            420                 425                 430

Thr Lys Pro Gly Val Pro Arg Arg Ala Gly Ile Ser Ser Phe Gly Phe
        435                 440                 445

Gly Gly
    450

<210> SEQ ID NO 76
<211> LENGTH: 921
<212> TYPE: DNA
<213> ORGANISM: Thraustochytrium sp.

<400> SEQUENCE: 76
ttttctggac aaggcgcaca atatacccat atgtttaatg atgttgcaat gcaatggcca      60
caatttcgtt tatgtgtaaa tgatatggag aaagcacagg aagaagttat caatgataaa     120
agtgtgaaac gtatcagtca agttatgttt cctcgtaaac catatgcaag agaatcacct     180
ttagacaata aagaaatctc taagactgaa tattctcaaa caacaactgt cgctagttca     240
gtaggtttat ttgaaatttt ccgtgatgct ggtttcgctc ctgcttttgt tgctggtcat     300
tctttaggtg aatttagtgc attgtatgca gctggattga ttgatcgcga agatttattc     360
aagttggtat gtaatcgtgc aatggctatg agagatgcac caaaaaaatc tgctgatgga     420
gcaatggctg ctgttattgg tccaaatgct tcttcaatta agctttcagc tcctgaagta     480
tgggttgcta acaataactc tccatctcaa actgttatta ccggtgcaaa ttctggtgta     540
```

```
caagctgaaa caagtaaatt gaaaactcaa ggtttccgtg tggttcattt ggcatgtgat    600
ggggcatttc attcgcctca tatggaaaat gctgaaaagc aatttcaaaa agctctttca    660
gcagttaagt ttaataaacc aactggttct tctccaaaaa ttttcagcaa tgtaactggt    720
ggtgtattta cggatccaaa aactgctttg tcaagacata tgactagttc tgtacaattt    780
cttactcaaa ttaagaatat gtacgcggct ggagctcgtg tctttattga atttggacca    840
aaacaagtac tttccaaatt ggtcaatgaa attttttcctg gtgatacaag cgttttaact   900
gtttcggtga atccagctag t                                              921
```

<210> SEQ ID NO 77
<211> LENGTH: 307
<212> TYPE: PRT
<213> ORGANISM: Thraustochytrium sp.

<400> SEQUENCE: 77

```
Phe Ser Gly Gln Gly Ala Gln Tyr Thr His Met Phe Asn Asp Val Ala
  1               5                  10                  15

Met Gln Trp Pro Gln Phe Arg Leu Cys Val Asn Asp Met Glu Lys Ala
             20                  25                  30

Gln Glu Glu Val Ile Asn Asp Lys Ser Val Lys Arg Ile Ser Gln Val
         35                  40                  45

Met Phe Pro Arg Lys Pro Tyr Ala Arg Glu Ser Pro Leu Asp Asn Lys
     50                  55                  60

Glu Ile Ser Lys Thr Glu Tyr Ser Gln Thr Thr Thr Val Ala Ser Ser
 65                  70                  75                  80

Val Gly Leu Phe Glu Ile Phe Arg Asp Ala Gly Phe Ala Pro Ala Phe
                 85                  90                  95

Val Ala Gly His Ser Leu Gly Glu Phe Ser Ala Leu Tyr Ala Ala Gly
            100                 105                 110

Leu Ile Asp Arg Glu Asp Leu Phe Lys Leu Val Cys Asn Arg Ala Met
        115                 120                 125

Ala Met Arg Asp Ala Pro Lys Lys Ser Ala Asp Gly Ala Met Ala Ala
    130                 135                 140

Val Ile Gly Pro Asn Ala Ser Ser Ile Lys Leu Ser Ala Pro Glu Val
145                 150                 155                 160

Trp Val Ala Asn Asn Ser Pro Ser Gln Thr Val Ile Thr Gly Ala
                165                 170                 175

Asn Ser Gly Val Gln Ala Glu Thr Ser Lys Leu Lys Thr Gln Gly Phe
            180                 185                 190

Arg Val Val His Leu Ala Cys Asp Gly Ala Phe His Ser Pro His Met
        195                 200                 205

Glu Asn Ala Glu Lys Gln Phe Gln Lys Ala Leu Ser Ala Val Lys Phe
    210                 215                 220

Asn Lys Pro Thr Gly Ser Ser Pro Lys Ile Phe Ser Asn Val Thr Gly
225                 230                 235                 240

Gly Val Phe Thr Asp Pro Lys Thr Ala Leu Ser Arg His Met Thr Ser
                245                 250                 255

Ser Val Gln Phe Leu Thr Gln Ile Lys Asn Met Tyr Ala Ala Gly Ala
            260                 265                 270

Arg Val Phe Ile Glu Phe Gly Pro Lys Gln Val Leu Ser Lys Leu Val
        275                 280                 285

Asn Glu Ile Phe Pro Gly Asp Thr Ser Val Leu Thr Val Ser Val Asn
    290                 295                 300
```

Pro Ala Ser
305

<210> SEQ ID NO 78
<211> LENGTH: 3303
<212> TYPE: DNA
<213> ORGANISM: Thraustochytrium sp.

<400> SEQUENCE: 78

```
gcaagtccag ctaccgttcg tgtcgtttca gctcctgttc aagcggctgc tcctgtgcag      60
gtatctgctt ctgttgattc tggtttgttg gcaaaagcgg aacaagttgt attggaagta     120
ttggcatcga agactggtta tgagactgag ttgattgaat tggatatgga attggaaact     180
gaacttggta ttgattctat caagagagta gaaattcttt ctgaagttca agctcaattg     240
aatgttgaag ctaaagatgt agatgctctt agtagaactc gtactgttgg tgaagtgatt     300
gatgcaatga agccgaaat tgctggtggt caaccagctg ctcctgttca agttgcagct     360
cctactcaag tagttgctcc tgttcaagca tctgctcctg ttgattctgg tttgttagca     420
aaagcggaac aagttgtatt ggaagtattg catcgaaga ctggttatga gactgagttg      480
attgaattgg atatggaatt ggaaaccgaa cttggtattg attctatcaa gagagtagaa     540
attctttctg aagttcaagc tcaattgagt gttgaagcta agatgtaga tgctcttagt      600
agaactcgta ctgttggtga agtgattgat gcaatgaaag ccgaaattgc tggtggtcaa     660
ccagctgctc ctgttcaagt tgcagctcct actcaagtag ttgctcctgt tcaagcatct     720
gctcctgttg attctggttt gttagcaaaa gcggaacaag ttgtattgga agtattggca     780
tcgaagactg gttatgagac tgagttgatt gaattggata tggaattgga aaccgaactt     840
ggtattgatt ctatcaagag agtagaaatt ctttctgaag ttcaagctca attgagtgtt     900
gaagctaaag atgtagatgc tcttagtaga actcgtactg ttggtgaagt gattgatgca     960
atgaaagctg aaatttctgg tggtcagcca gctgctcctg ttcaagttgc agctcctact    1020
caaatagttg ctcctgttca gtatccgct cctgttgatt ctggtttgtt agcaaaggcg     1080
gaacaagtag tattggaagt attggcatcc aagactggtt atgagactga gttgattgaa    1140
ttggatatgg aattggaaac tgaacttggt attgattcta tcaagagagt agaaattctt    1200
tctgaagttc aagctcaatt gagtgttgaa gctaaagatg tagatgctct tagtagaact    1260
cgtactgttg gtgaagtgat tgatgcaatg aaagctgaaa tttctggtgg tcaaccaact    1320
gctcctgttc aagttgcagc tcctactcaa atagttgctc tgttcaagt atctgctcct    1380
gttgattctg gtttgttagc aaaggcggaa caagttgtat tggaagtatt ggcatcgaag    1440
actggttatg agactgagtt gattgaattg gatatggaat tggaaaccga acttggtatt    1500
gattctatca gagagtaga aattcttcct gaagttcaag ctcaattgag tgttgaagct    1560
aaagatgtag atgctcttag tagaactcgt actgttggtg aagtgattga tgcaatgaaa    1620
gccgaaattt ctggtggtca gccagctgct cctgttcaag ttgcagctcc tactcaaata    1680
gttgctcctg ttcaagcatc tgctcctgtt gattctggtt tgttggcaaa agcggaacaa    1740
gttgtattgg aagtgttagc atccaagact ggttatgaaa ctgagttgat tgaattagat    1800
atggaattgg aaaccgaact tggtattgat tctatcaaga gagtagaaat tctttctgaa    1860
gttcaagctc aattgagtgt tgaagctaaa gatgtagatg ctcttagtag aactcgtact    1920
gttggtgaag tgattgatgc aatgaaagct gaaatttctg gtggtcaacc agctgctcct    1980
gttcaagttg cagctcctac tcaaatagtt gctcctgttc aagtatctgc tcctgttgat    2040
```

-continued

```
tctggtttgt tagcaaaggc ggaacaagtt gtattggaag tattggcatc taagactggt    2100
tatgagactg agttgattga attggatatg gaattggaaa ctgaacttgg tattgattct    2160
atcaagagag tagaaattct ttctgaagtt caagctcaat tgaatgttga agctaaagat    2220
gtagatgctc ttagtagaac tcgtactgtt ggtgaagtga ttgatgcaat gaaagccgaa    2280
attgctggtg gtcaaccagc tgctcctgtt caagttgcag ctcctgctcc agtagttgct    2340
cctgttcaag tatctactcc tgttgattct ggtttgttgg caaaagcgga acaagttgta    2400
ttggaagtgt tagcatgcaa gactggttat gaaactgagt tgattgaatt ggatatggaa    2460
ttggaaactg aacttggtat tgattctatc aagagagtag aaattctttc tgaagttcaa    2520
gctcaattga gtgttgaagc taagatgta gatgctctta gtagaactcg tactgttggt    2580
gaagtgattg atgcaatgaa agccgaaatt tctggtggtc aaccaactgc tcctgttcaa    2640
gttgcagctc ctactcaagt agttgctcct gttaaagtat ctactcctgt tgattctggt    2700
ttgttagcaa aggcggaaca agtagtattg aagtattgg catctaagac tggttatgaa    2760
actgagttga ttgaattaga tatggaattg aaactgaac ttggtattga ttctatcaag    2820
agagtagaaa ttctttctga agttcaagct caattgaatg tggaagctaa agatgtggat    2880
gctcttagta gaactcgtac tgttggtgaa gtgattgatg caatgaaagc cgaaattgct    2940
ggtgatcaac ctgctccagc tgtagttcca gttcaagcta agagtggtgt agccaaccct    3000
gcacttttgg caaaggcgga acaagtagta ttggaagtat tggcatccaa gaccggttat    3060
gaaactgagc tgattgaatt ggatatggaa ttggaaactg aacttggtat tgattcaatc    3120
aagagagtag aaattctgtc cgaagttcaa gcagaattga gtgttgaagc aaaagatgta    3180
gacgctctaa gtagaacccg tactgttggg gaagtgatcg atgcaatgaa agctgaaatt    3240
gctggcagtg ctgtcacggt tgcaactttg gatgattcaa caattatgga ggagacagat    3300
gat                                                                  3303
```

<210> SEQ ID NO 79
<211> LENGTH: 1101
<212> TYPE: PRT
<213> ORGANISM: Thraustochytrium sp.

<400> SEQUENCE: 79

```
Ala Ser Pro Ala Thr Val Arg Val Ser Ala Pro Val Gln Ala Ala
1               5                   10                  15

Ala Pro Val Gln Val Ser Ala Ser Val Asp Ser Gly Leu Leu Ala Lys
                20                  25                  30

Ala Glu Gln Val Val Leu Glu Val Leu Ala Ser Lys Thr Gly Tyr Glu
            35                  40                  45

Thr Glu Leu Ile Glu Leu Asp Met Glu Leu Glu Thr Glu Leu Gly Ile
        50                  55                  60

Asp Ser Ile Lys Arg Val Glu Ile Leu Ser Glu Val Gln Ala Gln Leu
65                  70                  75                  80

Asn Val Glu Ala Lys Asp Val Asp Ala Leu Ser Arg Thr Arg Thr Val
                85                  90                  95

Gly Glu Val Ile Asp Ala Met Lys Ala Glu Ile Ala Gly Gly Gln Pro
            100                 105                 110

Ala Ala Pro Val Gln Val Ala Ala Pro Thr Gln Val Val Ala Pro Val
        115                 120                 125

Gln Ala Ser Ala Pro Val Asp Ser Gly Leu Leu Ala Lys Ala Glu Gln
    130                 135                 140
```

-continued

```
Val Val Leu Glu Val Leu Ala Ser Lys Thr Gly Tyr Glu Thr Glu Leu
145                 150                 155                 160

Ile Glu Leu Asp Met Glu Leu Glu Thr Glu Leu Gly Ile Asp Ser Ile
                165                 170                 175

Lys Arg Val Glu Ile Leu Ser Glu Val Gln Ala Gln Leu Ser Val Glu
            180                 185                 190

Ala Lys Asp Val Asp Ala Leu Ser Arg Thr Arg Thr Val Gly Glu Val
        195                 200                 205

Ile Asp Ala Met Lys Ala Glu Ile Ala Gly Gly Gln Pro Ala Ala Pro
    210                 215                 220

Val Gln Val Ala Ala Pro Thr Gln Val Ala Pro Val Gln Ala Ser
225                 230                 235                 240

Ala Pro Val Asp Ser Gly Leu Leu Ala Lys Ala Glu Gln Val Val Leu
                245                 250                 255

Glu Val Leu Ala Ser Lys Thr Gly Tyr Glu Thr Glu Leu Ile Glu Leu
            260                 265                 270

Asp Met Glu Leu Glu Thr Glu Leu Gly Ile Asp Ser Ile Lys Arg Val
        275                 280                 285

Glu Ile Leu Ser Glu Val Gln Ala Gln Leu Ser Val Glu Ala Lys Asp
    290                 295                 300

Val Asp Ala Leu Ser Arg Thr Arg Thr Val Gly Glu Val Ile Asp Ala
305                 310                 315                 320

Met Lys Ala Glu Ile Ser Gly Gly Gln Pro Ala Ala Pro Val Gln Val
                325                 330                 335

Ala Ala Pro Thr Gln Ile Val Ala Pro Val Gln Val Ser Ala Pro Val
            340                 345                 350

Asp Ser Gly Leu Leu Ala Lys Ala Glu Gln Val Val Leu Glu Val Leu
        355                 360                 365

Ala Ser Lys Thr Gly Tyr Glu Thr Glu Leu Ile Glu Leu Asp Met Glu
    370                 375                 380

Leu Glu Thr Glu Leu Gly Ile Asp Ser Ile Lys Arg Val Glu Ile Leu
385                 390                 395                 400

Ser Glu Val Gln Ala Gln Leu Ser Val Glu Ala Lys Asp Val Asp Ala
                405                 410                 415

Leu Ser Arg Thr Arg Thr Val Gly Glu Val Ile Asp Ala Met Lys Ala
            420                 425                 430

Glu Ile Ser Gly Gly Gln Pro Thr Ala Pro Val Gln Val Ala Ala Pro
        435                 440                 445

Thr Gln Ile Val Ala Pro Val Gln Val Ser Ala Pro Val Asp Ser Gly
    450                 455                 460

Leu Leu Ala Lys Ala Glu Gln Val Val Leu Glu Val Leu Ala Ser Lys
465                 470                 475                 480

Thr Gly Tyr Glu Thr Glu Leu Ile Glu Leu Asp Met Glu Leu Glu Thr
                485                 490                 495

Glu Leu Gly Ile Asp Ser Ile Lys Arg Val Glu Ile Leu Ser Glu Val
            500                 505                 510

Gln Ala Gln Leu Ser Val Glu Ala Lys Asp Val Asp Ala Leu Ser Arg
        515                 520                 525

Thr Arg Thr Val Gly Glu Val Ile Asp Ala Met Lys Ala Glu Ile Ser
    530                 535                 540

Gly Gly Gln Pro Ala Ala Pro Val Gln Val Ala Ala Pro Thr Gln Ile
545                 550                 555                 560

Val Ala Pro Val Gln Ala Ser Ala Pro Val Asp Ser Gly Leu Leu Ala
```

-continued

```
                565                 570                 575

Lys Ala Glu Gln Val Val Leu Glu Val Leu Ala Ser Lys Thr Gly Tyr
            580                 585                 590

Glu Thr Glu Leu Ile Glu Leu Asp Met Glu Leu Glu Thr Glu Leu Gly
            595                 600                 605

Ile Asp Ser Ile Lys Arg Val Glu Ile Leu Ser Glu Val Gln Ala Gln
        610                 615                 620

Leu Ser Val Glu Ala Lys Asp Val Asp Ala Leu Ser Arg Thr Arg Thr
625                 630                 635                 640

Val Gly Glu Val Ile Asp Ala Met Lys Ala Glu Ile Ser Gly Gly Gln
                645                 650                 655

Pro Ala Ala Pro Val Gln Val Ala Ala Pro Thr Gln Ile Val Ala Pro
            660                 665                 670

Val Gln Val Ser Ala Pro Val Asp Ser Gly Leu Leu Ala Lys Ala Glu
            675                 680                 685

Gln Val Val Leu Glu Val Leu Ala Ser Lys Thr Gly Tyr Glu Thr Glu
            690                 695                 700

Leu Ile Glu Leu Asp Met Glu Leu Glu Thr Glu Leu Gly Ile Asp Ser
705                 710                 715                 720

Ile Lys Arg Val Glu Ile Leu Ser Glu Val Gln Ala Gln Leu Asn Val
                725                 730                 735

Glu Ala Lys Asp Val Asp Ala Leu Ser Arg Thr Arg Thr Val Gly Glu
            740                 745                 750

Val Ile Asp Ala Met Lys Ala Glu Ile Ala Gly Gly Gln Pro Ala Ala
            755                 760                 765

Pro Val Gln Val Ala Ala Pro Ala Pro Val Val Ala Pro Val Gln Val
            770                 775                 780

Ser Thr Pro Val Asp Ser Gly Leu Leu Ala Lys Ala Glu Gln Val Val
785                 790                 795                 800

Leu Glu Val Leu Ala Cys Lys Thr Gly Tyr Glu Thr Glu Leu Ile Glu
                805                 810                 815

Leu Asp Met Glu Leu Glu Thr Glu Leu Gly Ile Asp Ser Ile Lys Arg
            820                 825                 830

Val Glu Ile Leu Ser Glu Val Gln Ala Gln Leu Ser Val Glu Ala Lys
        835                 840                 845

Asp Val Asp Ala Leu Ser Arg Thr Arg Thr Val Gly Glu Val Ile Asp
850                 855                 860

Ala Met Lys Ala Glu Ile Ser Gly Gly Gln Pro Thr Ala Pro Val Gln
865                 870                 875                 880

Val Ala Ala Pro Thr Gln Val Val Ala Pro Val Lys Val Ser Thr Pro
            885                 890                 895

Val Asp Ser Gly Leu Leu Ala Lys Ala Glu Gln Val Val Leu Glu Val
            900                 905                 910

Leu Ala Ser Lys Thr Gly Tyr Glu Thr Glu Leu Ile Glu Leu Asp Met
            915                 920                 925

Glu Leu Glu Thr Glu Leu Gly Ile Asp Ser Ile Lys Arg Val Glu Ile
            930                 935                 940

Leu Ser Glu Val Gln Ala Gln Leu Asn Val Glu Ala Lys Asp Val Asp
945                 950                 955                 960

Ala Leu Ser Arg Thr Arg Thr Val Gly Glu Val Ile Asp Ala Met Lys
                965                 970                 975

Ala Glu Ile Ala Gly Asp Gln Pro Ala Pro Ala Val Val Pro Val Gln
            980                 985                 990
```

Ala Lys Ser Gly Val Ala Asn Pro Ala Leu Leu Ala Lys Ala Glu Gln
        995                 1000                1005

Val Val Leu Glu Val Leu Ala Ser Lys Thr Gly Tyr Glu Thr Glu
    1010                1015                1020

Leu Ile Glu Leu Asp Met Glu Leu Glu Thr Glu Leu Gly Ile Asp
    1025                1030                1035

Ser Ile Lys Arg Val Glu Ile Leu Ser Glu Val Gln Ala Glu Leu
    1040                1045                1050

Ser Val Glu Ala Lys Asp Val Asp Ala Leu Ser Arg Thr Arg Thr
    1055                1060                1065

Val Gly Glu Val Ile Asp Ala Met Lys Ala Glu Ile Ala Gly Ser
    1070                1075                1080

Ala Val Thr Val Ala Thr Leu Asp Asp Ser Thr Ile Met Glu Glu
    1085                1090                1095

Thr Asp Asp
    1100

<210> SEQ ID NO 80
<211> LENGTH: 255
<212> TYPE: DNA
<213> ORGANISM: Thraustochytrium sp.

<400> SEQUENCE: 80
gttgattctg gtttgttggc aaaagcggaa caagttgtat tggaagtatt ggcatcgaag      60
actggttatg agactgagtt gattgaattg gatatggaat tggaaactga acttggtatt     120
gattctatca agagagtaga aattctttct gaagttcaag ctcaattgaa tgttgaagct     180
aaagatgtag atgctcttag tagaactcgt actgttggtg aagtgattga tgcaatgaaa     240
gccgaaattg ctggt                                                      255

<210> SEQ ID NO 81
<211> LENGTH: 85
<212> TYPE: PRT
<213> ORGANISM: Thraustochytrium sp.

<400> SEQUENCE: 81

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
                20                  25                  30

Glu Leu Glu Thr Glu Leu Gly Ile Asp Ser Ile Lys Arg Val Glu Ile
            35                  40                  45

Leu Ser Glu Val Gln Ala Gln Leu Asn Val Glu Ala Lys Asp Val Asp
        50                  55                  60

Ala Leu Ser Arg Thr Arg Thr Val Gly Glu Val Ile Asp Ala Met Lys
65                  70                  75                  80

Ala Glu Ile Ala Gly
                85

<210> SEQ ID NO 82
<211> LENGTH: 255
<212> TYPE: DNA
<213> ORGANISM: Thraustochytrium sp.

<400> SEQUENCE: 82
gttgattctg gtttgttagc aaaagcggaa caagttgtat tggaagtatt ggcatcgaag      60

```
actggttatg agactgagtt gattgaattg gatatggaat tggaaaccga acttggtatt    120
gattctatca agagagtaga aattctttct gaagttcaag ctcaattgag tgttgaagct    180
aaagatgtag atgctcttag tagaactcgt actgttggtg aagtgattga tgcaatgaaa    240
gccgaaattg ctggt                                                    255
```

<210> SEQ ID NO 83
<211> LENGTH: 85
<212> TYPE: PRT
<213> ORGANISM: Thraustochytrium sp.

<400> SEQUENCE: 83

```
Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
            85
```

<210> SEQ ID NO 84
<211> LENGTH: 252
<212> TYPE: DNA
<213> ORGANISM: Thraustochytrium sp.

<400> SEQUENCE: 84

```
gttgattctg gtttgttagc aaaagcggaa caagttgtat tggaagtatt ggcatcgaag     60
actggttatg agactgagtt gattgaattg gatatggaat tggaaaccga acttggtatt    120
gattctatca agagagtaga aattctttct gaagttcaag ctcaattgag tgttgaagct    180
aaagatgtag atgctcttag tagaactcgt actgttggtg aagtgattga tgcaatgaaa    240
gctgaaattt ct                                                       252
```

<210> SEQ ID NO 85
<211> LENGTH: 85
<212> TYPE: PRT
<213> ORGANISM: Thraustochytrium sp.

<400> SEQUENCE: 85

```
Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ser Gly
            85
```

-continued

```
<210> SEQ ID NO 86
<211> LENGTH: 255
<212> TYPE: DNA
<213> ORGANISM: Thraustochytrium sp.

<400> SEQUENCE: 86
gttgattctg gtttgttagc aaaggcggaa caagtagtat tggaagtatt ggcatccaag      60
actggttatg agactgagtt gattgaattg gatatggaat tggaaactga acttggtatt     120
gattctatca agagagtaga aattctttct gaagttcaag ctcaattgag tgttgaagct     180
aaagatgtag atgctcttag tagaactcgt actgttggtg aagtgattga tgcaatgaaa     240
gctgaaattt ctggt                                                      255

<210> SEQ ID NO 87
<211> LENGTH: 85
<212> TYPE: PRT
<213> ORGANISM: Thraustochytrium sp.

<400> SEQUENCE: 87

Val Asp Ser Gly Leu Leu Ala Lys Ala Glu Gln Val Val Leu Glu Val
1               5                  10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ser Gly
            85

<210> SEQ ID NO 88
<211> LENGTH: 254
<212> TYPE: DNA
<213> ORGANISM: Thraustochytrium sp.

<400> SEQUENCE: 88
ttgattctgg tttgttagca aaggcggaac aagttgtatt ggaagtattg gcatcgaaga      60
ctggttatga gactgagttg attgaattgg atatggaatt ggaaaccgaa cttggtattg     120
attctatcaa gagagtagaa attctttctg aagttcaagc tcaattgagt gttgaagcta     180
aagatgtaga tgctcttagt agaactcgta ctgttggtga agtgattgat gcaatgaaag     240
ccgaaatttc tggt                                                       254

<210> SEQ ID NO 89
<211> LENGTH: 85
<212> TYPE: PRT
<213> ORGANISM: Thraustochytrium sp.

<400> SEQUENCE: 89

Val Asp Ser Gly Leu Leu Ala Lys Ala Glu Gln Val Val Leu Glu Val
1               5                  10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
```

```
                50                  55                  60

Ala Leu Ser Arg Thr Arg Thr Val Gly Glu Val Ile Asp Ala Met Lys
 65                  70                  75                  80

Ala Glu Ile Ser Gly
                 85

<210> SEQ ID NO 90
<211> LENGTH: 255
<212> TYPE: DNA
<213> ORGANISM: Thraustochytrium sp.

<400> SEQUENCE: 90
gttgattctg gtttgttggc aaaagcggaa caagttgtat tggaagtgtt agcatccaag      60
actggttatg aaactgagtt gattgaatta gatatggaat tggaaaccga acttggtatt     120
gattctatca agagagtaga aattctttct gaagttcaag ctcaattgag tgttgaagct     180
aaagatgtag atgctcttag tagaactcgt actgttggtg aagtgattga tgcaatgaaa     240
gctgaaattt ctggt                                                     255

<210> SEQ ID NO 91
<211> LENGTH: 85
<212> TYPE: PRT
<213> ORGANISM: Thraustochytrium sp.

<400> SEQUENCE: 91

Val Asp Ser Gly Leu Leu Ala Lys Ala Glu Gln Val Val Leu Glu Val
  1               5                  10                  15

Leu Ala Ser Lys Thr Gly Tyr Glu Thr Glu Leu Ile Glu Leu Asp Met
                 20                  25                  30

Glu Leu Glu Thr Glu Leu Gly Ile Asp Ser Ile Lys Arg Val Glu Ile
         35                  40                  45

Leu Ser Glu Val Gln Ala Gln Leu Ser Val Glu Ala Lys Asp Val Asp
     50                  55                  60

Ala Leu Ser Arg Thr Arg Thr Val Gly Glu Val Ile Asp Ala Met Lys
 65                  70                  75                  80

Ala Glu Ile Ser Gly
                 85

<210> SEQ ID NO 92
<211> LENGTH: 255
<212> TYPE: DNA
<213> ORGANISM: Thraustochytrium sp.

<400> SEQUENCE: 92
gttgattctg gtttgttagc aaaggcggaa caagttgtat tggaagtatt ggcatctaag      60
actggttatg agactgagtt gattgaattg gatatggaat tggaaactga acttggtatt     120
gattctatca agagagtaga aattcttttct gaagttcaag ctcaattgaa tgttgaagct    180
aaagatgtag atgctcttag tagaactcgt actgttggtg aagtgattga tgcaatgaaa     240
gccgaaattg ctggt                                                     255

<210> SEQ ID NO 93
<211> LENGTH: 85
<212> TYPE: PRT
<213> ORGANISM: Thraustochytrium sp.

<400> SEQUENCE: 93

Val Asp Ser Gly Leu Leu Ala Lys Ala Glu Gln Val Val Leu Glu Val
```

```
               1               5                  10                 15
Leu Ala Ser Lys Thr Gly Tyr Glu Thr Glu Leu Ile Glu Leu Asp Met
               20                 25                 30
Glu Leu Glu Thr Glu Leu Gly Ile Asp Ser Ile Lys Arg Val Glu Ile
               35                 40                 45
Leu Ser Glu Val Gln Ala Gln Leu Asn Val Glu Ala Lys Asp Val Asp
               50                 55                 60
Ala Leu Ser Arg Thr Arg Thr Val Gly Glu Val Ile Asp Ala Met Lys
65                 70                 75                 80
Ala Glu Ile Ala Gly
               85

<210> SEQ ID NO 94
<211> LENGTH: 255
<212> TYPE: DNA
<213> ORGANISM: Thraustochytrium sp.

<400> SEQUENCE: 94
gttgattctg gtttgttggc aaaagcggaa caagttgtat tggaagtgtt agcatgcaag        60
actggttatg aaactgagtt gattgaattg gatatggaat tggaaactga acttggtatt       120
gattctatca agagagtaga aattctttct gaagttcaag ctcaattgag tgttgaagct       180
aaagatgtag atgctcttag tagaactcgt actgttggtg aagtgattga tgcaatgaaa       240
gccgaaattt ctggt                                                        255

<210> SEQ ID NO 95
<211> LENGTH: 85
<212> TYPE: PRT
<213> ORGANISM: Thraustochytrium sp.

<400> SEQUENCE: 95

Val Asp Ser Gly Leu Leu Ala Lys Ala Glu Gln Val Val Leu Glu Val
1               5                  10                 15
Leu Ala Cys Lys Thr Gly Tyr Glu Thr Glu Leu Ile Glu Leu Asp Met
               20                 25                 30
Glu Leu Glu Thr Glu Leu Gly Ile Asp Ser Ile Lys Arg Val Glu Ile
               35                 40                 45
Leu Ser Glu Val Gln Ala Gln Leu Ser Val Glu Ala Lys Asp Val Asp
               50                 55                 60
Ala Leu Ser Arg Thr Arg Thr Val Gly Glu Val Ile Asp Ala Met Lys
65                 70                 75                 80
Ala Glu Ile Ser Gly
               85

<210> SEQ ID NO 96
<211> LENGTH: 255
<212> TYPE: DNA
<213> ORGANISM: Thraustochytrium sp.

<400> SEQUENCE: 96
gttgattctg gtttgttagc aaaggcggaa caagtagtat tggaagtatt ggcatctaag        60
actggttatg aaactgagtt gattgaatta gatatggaat tggaaactga acttggtatt       120
gattctatca agagagtaga aattctttct gaagttcaag ctcaattgaa tgtggaagct       180
aaagatgtgg atgctcttag tagaactcgt actgttggtg aagtgattga tgcaatgaaa       240
gccgaaattg ctggt                                                        255
```

<210> SEQ ID NO 97
<211> LENGTH: 85
<212> TYPE: PRT
<213> ORGANISM: Thraustochytrium sp.

<400> SEQUENCE: 97

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Asn Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
                85

<210> SEQ ID NO 98
<211> LENGTH: 255
<212> TYPE: DNA
<213> ORGANISM: Thraustochytrium sp.

<400> SEQUENCE: 98
gccaaccctg cacttttggc aaaggcggaa caagtagtat tggaagtatt ggcatccaag    60
accggttatg aaactgagct gattgaattg gatatggaat tggaaactga acttggtatt   120
gattcaatca agagagtaga aattctgtcc gaagttcaag cagaattgag tgttgaagca   180
aaagatgtag acgctctaag tagaacccgt actgttgggg aagtgatcga tgcaatgaaa   240
gctgaaattg ctggc                                                   255

<210> SEQ ID NO 99
<211> LENGTH: 85
<212> TYPE: PRT
<213> ORGANISM: Thraustochytrium sp.

<400> SEQUENCE: 99

Ala Asn Pro Ala Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Glu Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
                85

<210> SEQ ID NO 100
<211> LENGTH: 2151
<212> TYPE: DNA
<213> ORGANISM: Thraustochytrium sp.

<400> SEQUENCE: 100
gtttcaagca ttgaatcttc gtatggaaaa attggtggct ttgtttatca acatttcat     60

```
gatagcgact atggtatgca acttggatgg gcgttaatgg cagcgaaaca tttgaaagag    120
tccctcaacg acccgattaa gaatggaaga accttctttt tggctgttgc gcgtatgaat    180
ggtaaacttg gtatggacaa tgcttcagtt catgatcaag gaatagtgga atcatgcggt    240
atcgccgaac gtggtgctat ctttggtttg tgcaaaactt tggatttgga atggcctaat    300 gttttttgctc gtggtgttga tattgctgaa ggtatgagtt atagtttggc tgcggaattg    360
attgttgatg agatttcttg tgcaaatctt tccattcggg aatctggtta cacgattagc    420
ggagaaagat tcacaactga agctcacaaa ttggttactg aaagcctca tgctccgatt     480 aagaagaagg atgctttcct agtatctggt ggtgctcgtg gtattactcc actttgtatt    540
cgtgaaattg ctaaagcagt gaaaggtggc acttacattt tgatgggtcg atcagctttg    600
gctgatgaac ccttgtgggc taatggtaaa tccggaaaag atttagataa agctggtttg    660
gcatttttga aggaagagtt tgcagctggg cgtggtagta aaccaactcc aaaagttcac    720
aaatctttga ttgataaagt gctcggtatt agggaggtta gagcatctat tgcaaatata    780
gaagcccatg agcaaaagc tatatatttg tcttgcgatg tatcttccgc tgagaaagta    840
aaggctgcag tgcaaaaagt tgaaaaggag catctagttc gtattactgg tattgtgcat    900
gcatcaggcg ttttgaggga taaattggtt gagaacaaaa ctttggatga tttcaacgca    960
gtatatggaa ccaaagtaac tggactagta aacttgctgt cagcagtgaa catgaatttt   1020
gttcgtcatt tggttatgtt tagttctttg gctggatatc atggaaatgt tggtcaatct   1080
gattatgcaa tggctaacga atcacttaac aagattggtt ttagattggg tgcagcttat   1140
tctcaattgt gtgttaaatc tatttgttt ggaccttggg atggtggaat ggtaactcca    1200
gctttgaaaa aacaatttca atcaatgggt gtccagatta ttcctcgtga aggtggcgcg   1260
gagactgttg caagaatagt cttatcttca aatccttctc aagttttagt tggcaactgg   1320
ggtgttcctc cagtttcacc tttgtcaaaa tcggcaacta ttgttcaaac ttttaccct    1380 gagttaaatc catttctaaa gtctcatcaa attcatggta aaaatgtttt gcctatgact   1440
gtagcaattg gatatcttgc tcacttggtt aagaattttt atgctggtca tcatttgtgg   1500
ggagttgaag atgctcaatt gttcagtggt gttgtaattg accatgcggt gcaagctcaa   1560
gtgaaattaa cggaacagag tttggatgat gatggcaagg taaaagttca agctgttctg   1620
actgcttcaa cgataatgg aaaaatggta cctgcataca aagcagtgat tgttttggga    1680
aaaacaagta gacctgcgtt tatttttgaaa gattttttcat tgcaagaatc taattctcgc   1740
agtgctgatg agttgtatga tggtaaaact ttgtttcatg gtccattatt tcgtggaatt   1800
accaagttgt tgaatgtatc tgatacttca ctaacaactc aatgtaccaa tattgatttg   1860
actgctactg aacgtggtca atttgcggat atcgaacctg tgaatccttt tatggcggat   1920
gctgcatttc aagctatgct tgtatgggtt agaaatttaa ggaatagtgc atctttacca   1980
aacaattgtg aaagagtaga tatctataaa ccaatagcac ctggtgaaaa gtattacact   2040
actttgcaag ctttgggtaa tacctccggt tctgttctca gtctgtatt ttatatgcac     2100 gatgaacaag gagaagtatt tctatctgga agagctagtg ttgttgtgaa t             2151
```

<210> SEQ ID NO 101
<211> LENGTH: 717
<212> TYPE: PRT
<213> ORGANISM: Thraustochytrium sp.

<400> SEQUENCE: 101

-continued

```
Val Ser Ser Ile Glu Ser Ser Tyr Gly Lys Ile Gly Gly Phe Val Tyr
1               5                   10                  15

Gln His Phe His Asp Ser Asp Tyr Gly Met Gln Leu Gly Trp Ala Leu
            20                  25                  30

Met Ala Ala Lys His Leu Lys Glu Ser Leu Asn Asp Pro Ile Lys Asn
            35                  40                  45

Gly Arg Thr Phe Phe Leu Ala Val Ala Arg Met Asn Gly Lys Leu Gly
        50                  55                  60

Met Asp Asn Ala Ser Val His Asp Gln Gly Ile Val Glu Ser Cys Gly
65                  70                  75                  80

Ile Ala Glu Arg Gly Ala Ile Phe Gly Leu Cys Lys Thr Leu Asp Leu
                85                  90                  95

Glu Trp Pro Asn Val Phe Ala Arg Gly Val Asp Ile Ala Glu Gly Met
            100                 105                 110

Ser Tyr Ser Leu Ala Ala Glu Leu Ile Val Asp Glu Ile Ser Cys Ala
            115                 120                 125

Asn Leu Ser Ile Arg Glu Ser Gly Tyr Thr Ile Ser Gly Glu Arg Phe
130                 135                 140

Thr Thr Glu Ala His Lys Leu Val Thr Gly Lys Pro His Ala Pro Ile
145                 150                 155                 160

Lys Lys Lys Asp Ala Phe Leu Val Ser Gly Ala Arg Gly Ile Thr
                165                 170                 175

Pro Leu Cys Ile Arg Glu Ile Ala Lys Ala Val Lys Gly Gly Thr Tyr
                180                 185                 190

Ile Leu Met Gly Arg Ser Ala Leu Ala Asp Glu Pro Leu Trp Ala Asn
                195                 200                 205

Gly Lys Ser Gly Lys Asp Leu Asp Lys Ala Gly Leu Ala Phe Leu Lys
        210                 215                 220

Glu Glu Phe Ala Ala Gly Arg Gly Ser Lys Pro Thr Pro Lys Val His
225                 230                 235                 240

Lys Ser Leu Ile Asp Lys Val Leu Gly Ile Arg Glu Val Arg Ala Ser
                245                 250                 255

Ile Ala Asn Ile Glu Ala His Gly Ala Lys Ala Ile Tyr Leu Ser Cys
                260                 265                 270

Asp Val Ser Ser Ala Glu Lys Val Lys Ala Ala Val Gln Lys Val Glu
            275                 280                 285

Lys Glu His Leu Val Arg Ile Thr Gly Ile Val His Ala Ser Gly Val
            290                 295                 300

Leu Arg Asp Lys Leu Val Glu Asn Lys Thr Leu Asp Asp Phe Asn Ala
305                 310                 315                 320

Val Tyr Gly Thr Lys Val Thr Gly Leu Val Asn Leu Leu Ser Ala Val
                325                 330                 335

Asn Met Asn Phe Val Arg His Leu Val Met Phe Ser Ser Leu Ala Gly
                340                 345                 350

Tyr His Gly Asn Val Gly Gln Ser Asp Tyr Ala Met Ala Asn Glu Ser
            355                 360                 365

Leu Asn Lys Ile Gly Phe Arg Leu Gly Ala Ala Tyr Ser Gln Leu Cys
370                 375                 380

Val Lys Ser Ile Cys Phe Gly Pro Trp Asp Gly Gly Met Val Thr Pro
385                 390                 395                 400

Ala Leu Lys Lys Gln Phe Gln Ser Met Gly Val Gln Ile Ile Pro Arg
                405                 410                 415

Glu Gly Gly Ala Glu Thr Val Ala Arg Ile Val Leu Ser Ser Asn Pro
```

```
                420            425            430
Ser Gln Val Leu Val Gly Asn Trp Gly Val Pro Pro Val Ser Pro Leu
            435                440                445
Ser Lys Ser Ala Thr Ile Val Gln Thr Phe Thr Pro Glu Leu Asn Pro
            450                455                460
Phe Leu Lys Ser His Gln Ile His Gly Lys Asn Val Leu Pro Met Thr
465                470                475                480
Val Ala Ile Gly Tyr Leu Ala His Leu Val Lys Asn Phe Tyr Ala Gly
                485                490                495
His His Leu Trp Gly Val Glu Asp Ala Gln Leu Phe Ser Gly Val Val
            500                505                510
Ile Asp His Ala Val Gln Ala Val Lys Leu Thr Glu Gln Ser Leu
            515                520                525
Asp Asp Asp Gly Lys Val Lys Val Gln Ala Val Leu Thr Ala Ser Asn
            530                535                540
Asp Asn Gly Lys Met Val Pro Ala Tyr Lys Ala Val Ile Val Leu Gly
545                550                555                560
Lys Thr Ser Arg Pro Ala Phe Ile Leu Lys Asp Phe Ser Leu Gln Glu
                565                570                575
Ser Asn Ser Arg Ser Ala Asp Glu Leu Tyr Asp Gly Lys Thr Leu Phe
            580                585                590
His Gly Pro Leu Phe Arg Gly Ile Thr Lys Leu Leu Asn Val Ser Asp
            595                600                605
Thr Ser Leu Thr Thr Gln Cys Thr Asn Ile Asp Leu Thr Ala Thr Glu
            610                615                620
Arg Gly Gln Phe Ala Asp Ile Glu Pro Val Asn Pro Phe Met Ala Asp
625                630                635                640
Ala Ala Phe Gln Ala Met Leu Val Trp Val Arg Asn Leu Arg Asn Ser
                645                650                655
Ala Ser Leu Pro Asn Asn Cys Glu Arg Val Asp Ile Tyr Lys Pro Ile
            660                665                670
Ala Pro Gly Glu Lys Tyr Tyr Thr Thr Leu Gln Ala Leu Gly Asn Thr
            675                680                685
Ser Gly Ser Val Leu Lys Ser Val Phe Tyr Met His Asp Glu Gln Gly
            690                695                700
Glu Val Phe Leu Ser Gly Arg Ala Ser Val Val Asn
705                710                715

<210> SEQ ID NO 102
<211> LENGTH: 1311
<212> TYPE: DNA
<213> ORGANISM: Thraustochytrium sp.

<400> SEQUENCE: 102
ttaagtgttg gtgataatat ttgtcatgat caacgtgttg ctgttgttgg tatggctgtt      60
atgtatgctg ttgtcaaaaa tcaacatgaa ttttggcaat ctttacaagg taaaaatatg     120
aattcaaaat cgatttcaca aaatcgttta ggttctgagt atagagaaga acattttaaa     180
cctgaaagaa gtaaatattc cgatacccttt tgtaatgaaa gatatggttg tattgatgag     240
aatgttcaaa gtgaacatga acttttatta aaacttgcaa agatgctat tgcggataca      300 aaaggttcta ttgatttgaa taaaaccgga atcgttagtg ttgcttatc ttttccaatg      360 gataatttac aaggtgattt attaaatttg tatcaatgtc acattgaaaa gaaaattggg     420
ccaaatgcat taaagatgt gaatttatgg tctaaaagaa ccaccaacgg aaaagatgat      480
```

```
aaaaaagctt attttgatcc tgcctctttc gtagctgaac aattagatat gggaccatta    540
cattatagtt tagatgctgc ttgtgcgtct gcactttatg tattaagact tgctcaagat    600
catttattaa gtggtgctgc tgatacaatg ttatgtggtg catcttgttt acctgaacct    660
ttttttattt tatctggttt ttctactttt catgcaatgc cattatctgg tgatgtttct    720
gctcctttgc ataaaacttc acaaggtctt acacctggtg aaggtggtgc tattatggta    780
cttaaacgat taaatgatgc aatccgtgat ggtgatagaa tttatggtac tttacttggt    840
gctgaattaa gtaatgctgg ttgtggttta ccattgagtc cacatatgcc aagtgaattt    900
gattgtatgg aaaaagcttt acaaagagta cacagattac catcatctat tcaatatgtt    960
gagtgtcatg caactggtac accacaaggt gataaagttg aaattgatgc tatgacaaaa   1020
tgttttggtg aacatttacc aaggtttggt tcaacgaaag ggaattttgg tcatacactt   1080
gttgctgctg gttttgctgg tatgtgtaaa gttttattat caatgcaata tggtgaaata   1140
ccaccaactc caggtcttga aaatccagac aatattatgc atgatttagt tgttactgaa   1200
acaattccat ggcctaatac aaatggtgat ttgaaacgtg catgtttatc tgcttttgga   1260
ttcggtggta ctaatgcaca tgctgtattt gaagagtatc gttcagattt a            1311
```

<210> SEQ ID NO 103
<211> LENGTH: 437
<212> TYPE: PRT
<213> ORGANISM: Thraustochytrium sp.

<400> SEQUENCE: 103

```
Leu Ser Val Gly Asp Asn Ile Cys His Asp Gln Arg Val Ala Val Val
1               5                   10                  15

Gly Met Ala Val Met Tyr Ala Gly Cys Gln Asn Gln His Glu Phe Trp
            20                  25                  30

Gln Ser Leu Gln Gly Lys Asn Met Asn Ser Lys Ser Ile Ser Gln Asn
        35                  40                  45

Arg Leu Gly Ser Glu Tyr Arg Glu His Phe Lys Pro Glu Arg Ser
    50                  55                  60

Lys Tyr Ser Asp Thr Phe Cys Asn Glu Arg Tyr Gly Cys Ile Asp Glu
65                  70                  75                  80

Asn Val Gln Ser Glu His Glu Leu Leu Leu Lys Leu Ala Lys Asp Ala
                85                  90                  95

Ile Ala Asp Thr Lys Gly Ser Ile Asp Leu Asn Lys Thr Gly Ile Val
            100                 105                 110

Ser Gly Cys Leu Ser Phe Pro Met Asp Asn Leu Gln Gly Asp Leu Leu
        115                 120                 125

Asn Leu Tyr Gln Cys His Ile Glu Lys Lys Ile Gly Pro Asn Ala Leu
    130                 135                 140

Lys Asp Val Asn Leu Trp Ser Lys Arg Thr Thr Asn Gly Lys Asp Asp
145                 150                 155                 160

Lys Lys Ala Tyr Phe Asp Pro Ala Ser Phe Val Ala Glu Gln Leu Asp
                165                 170                 175

Met Gly Pro Leu His Tyr Ser Leu Asp Ala Ala Cys Ala Ser Ala Leu
            180                 185                 190

Tyr Val Leu Arg Leu Ala Gln Asp His Leu Leu Ser Gly Ala Ala Asp
        195                 200                 205

Thr Met Leu Cys Gly Ala Ser Cys Leu Pro Glu Pro Phe Phe Ile Leu
    210                 215                 220
```

```
Ser Gly Phe Ser Thr Phe His Ala Met Pro Leu Ser Gly Asp Val Ser
225                 230                 235                 240

Ala Pro Leu His Lys Thr Ser Gln Gly Leu Thr Pro Gly Glu Gly Gly
                245                 250                 255

Ala Ile Met Val Leu Lys Arg Leu Asn Asp Ala Ile Arg Asp Gly Asp
            260                 265                 270

Arg Ile Tyr Gly Thr Leu Leu Gly Ala Glu Leu Ser Asn Ala Gly Cys
        275                 280                 285

Gly Leu Pro Leu Ser Pro His Met Pro Ser Glu Phe Asp Cys Met Glu
    290                 295                 300

Lys Ala Leu Gln Arg Val His Arg Leu Pro Ser Ser Ile Gln Tyr Val
305                 310                 315                 320

Glu Cys His Ala Thr Gly Thr Pro Gln Gly Asp Lys Val Glu Ile Asp
                325                 330                 335

Ala Met Thr Lys Cys Phe Gly Glu His Leu Pro Arg Phe Gly Ser Thr
            340                 345                 350

Lys Gly Asn Phe Gly His Thr Leu Val Ala Ala Gly Phe Ala Gly Met
        355                 360                 365

Cys Lys Val Leu Leu Ser Met Gln Tyr Gly Glu Ile Pro Pro Thr Pro
370                 375                 380

Gly Leu Glu Asn Pro Asp Asn Ile Met His Asp Leu Val Val Thr Glu
385                 390                 395                 400

Thr Ile Pro Trp Pro Asn Thr Asn Gly Asp Leu Lys Arg Ala Cys Leu
                405                 410                 415

Ser Ala Phe Gly Phe Gly Gly Thr Asn Ala His Ala Val Phe Glu Glu
            420                 425                 430

Tyr Arg Ser Asp Leu
        435

<210> SEQ ID NO 104
<211> LENGTH: 1323
<212> TYPE: DNA
<213> ORGANISM: Thraustochytrium sp.

<400> SEQUENCE: 104
aaaattgcta ttgttggtat ggaatctgaa tttggtactt tgaaaggatt acaagaattt      60
gaacgtgcta tttacaatgg tggtcatggt gcatgtgatt tacctgaaaa tagatggaga     120
tttcttggag aagataaaga atttttacaa gcttgtggtt acaaaaaatt accaagaggt     180
tgttatatta agaagtggaa actgattttt aaaaggttac gtttaccaat gatacaggag     240
gatattctaa gacctttaca gttgttagct gtttcgatta tcgacagagc acttaacgca     300
tctggtgtta aaccaaatgg caaagttgca gttttagttg gattaggtac tgatcttgaa     360
ttatatcgtc atcgtgctcg tgttgcatta aggaacgcc tccaaactgc ggtcaaagaa     420
gatattcctt tacttgaaaa gttaatgaac tatgtcaatg atagaggtac aagtacatca     480
tatacatctt atattggaaa tttggttgca actcgagttt catcattatg gggtttttact    540 ggtccatcat tcacgattac tgaaggtgaa aattccgtat atcgttgtct tgatttggga     600
agatggttct tagctaatgg tgaagtagat gctgttgttg ttgccggggt tgatttatgt     660
ggtagtgctg aaaatctttt tgtaaaatct cgtagaagta agtttccac acaaaatgaa     720 ccatttgcaa attttgaatc aaatgctgat ggatattttg ctggagatgg ttgtggagct     780
ttggttttga acgattgag tgattgtacg gattcaactg aaaaaaatta tgcaacggtg     840
gattcaattg ctgttggtga tgaagttggc ccaactatta acaagctttt gaagaatgca     900
```

-continued

```
tccatagcag cgaaagatat tgaactggca gagctatcag caagttcagg caaacatcat    960
tctggtagaa tcacttgtga agatgaacta aatgaactgg gtgaaatttt caatgaaggt   1020
atacaaagag ttgcaattgg tagtgtgaaa gctaatgttg gagatgttgg atatgcatct   1080
ggtgcagcaa gtttaatcaa aacggctttg tgcctgtaca accgatattt accaaagtta   1140
ccaaattgga ataagccaac gaaagatgtt gaatggtcca atcattttt tgtatgtgaa    1200 cattctagag catggttgaa aaatgttgat gaaaatagac atgctgtcgt ttctggagtt   1260
tgcgaaaatg gttcgtgtta tggaatcgta atgtctgatg tacaaggaca tcatgaagaa   1320
tcg                                                                 1323
```

<210> SEQ ID NO 105
<211> LENGTH: 441
<212> TYPE: PRT
<213> ORGANISM: Thraustochytrium sp.

<400> SEQUENCE: 105

```
Lys Ile Ala Ile Val Gly Met Glu Ser Glu Phe Gly Thr Leu Lys Gly
1               5                   10                  15

Leu Gln Glu Phe Glu Arg Ala Ile Tyr Asn Gly Gly His Gly Ala Cys
            20                  25                  30

Asp Leu Pro Glu Asn Arg Trp Arg Phe Leu Gly Glu Asp Lys Glu Phe
        35                  40                  45

Leu Gln Ala Cys Gly Leu Gln Lys Leu Pro Arg Gly Cys Tyr Ile Lys
    50                  55                  60

Glu Val Glu Thr Asp Phe Lys Arg Leu Arg Leu Pro Met Ile Gln Glu
65                  70                  75                  80

Asp Ile Leu Arg Pro Leu Gln Leu Leu Ala Val Ser Ile Ile Asp Arg
                85                  90                  95

Ala Leu Asn Ala Ser Gly Val Lys Pro Asn Gly Lys Val Ala Val Leu
            100                 105                 110

Val Gly Leu Gly Thr Asp Leu Glu Leu Tyr Arg His Arg Ala Arg Val
        115                 120                 125

Ala Leu Lys Glu Arg Leu Gln Thr Ala Val Lys Glu Asp Ile Pro Leu
    130                 135                 140

Leu Glu Lys Leu Met Asn Tyr Val Asn Asp Arg Gly Thr Ser Thr Ser
145                 150                 155                 160

Tyr Thr Ser Tyr Ile Gly Asn Leu Val Ala Thr Arg Val Ser Ser Leu
                165                 170                 175

Trp Gly Phe Thr Gly Pro Ser Phe Thr Ile Thr Glu Gly Glu Asn Ser
            180                 185                 190

Val Tyr Arg Cys Leu Asp Leu Gly Arg Trp Phe Leu Ala Asn Gly Glu
        195                 200                 205

Val Asp Ala Val Val Val Ala Gly Val Asp Leu Cys Gly Ser Ala Glu
    210                 215                 220

Asn Leu Phe Val Lys Ser Arg Arg Ser Lys Val Ser Thr Gln Asn Glu
225                 230                 235                 240

Pro Phe Ala Asn Phe Glu Ser Asn Ala Asp Gly Tyr Phe Ala Gly Asp
                245                 250                 255

Gly Cys Gly Ala Leu Val Leu Lys Arg Leu Ser Asp Cys Thr Asp Ser
            260                 265                 270

Thr Glu Lys Ile Tyr Ala Thr Val Asp Ser Ile Ala Val Gly Asp Glu
        275                 280                 285
```

```
Val Gly Pro Thr Ile Lys Gln Ala Leu Lys Asn Ala Ser Ile Ala Ala
            290                 295                 300

Lys Asp Ile Glu Leu Ala Glu Leu Ser Ala Ser Ser Gly Lys His His
305                 310                 315                 320

Ser Gly Arg Ile Thr Cys Glu Asp Glu Leu Asn Glu Leu Gly Glu Ile
                325                 330                 335

Phe Asn Glu Gly Ile Gln Arg Val Ala Ile Gly Ser Val Lys Ala Asn
                340                 345                 350

Val Gly Asp Val Gly Tyr Ala Ser Gly Ala Ala Ser Leu Ile Lys Thr
            355                 360                 365

Ala Leu Cys Leu Tyr Asn Arg Tyr Leu Pro Lys Leu Pro Asn Trp Asn
370                 375                 380

Lys Pro Thr Lys Asp Val Glu Trp Ser Lys Ser Phe Phe Val Cys Glu
385                 390                 395                 400

His Ser Arg Ala Trp Leu Lys Asn Val Asp Glu Asn Arg His Ala Val
                405                 410                 415

Val Ser Gly Val Cys Glu Asn Gly Ser Cys Tyr Gly Ile Val Met Ser
            420                 425                 430

Asp Val Gln Gly His His Glu Glu Ser
            435                 440

<210> SEQ ID NO 106
<211> LENGTH: 1353
<212> TYPE: DNA
<213> ORGANISM: Thraustochytrium sp.

<400> SEQUENCE: 106
cctacaatag atattgactc aatgtgtttt gctgagatgc ttaatctacc gcaggataaa      60
aacaaaaaat ttgcggtcgc attggttacc acaccaaata aactccagcg tgaaatagaa     120
cttgctgtga agggtattcc acgttgcgta aaagcaaaaa gagattggtg ttctccatct     180
ggaagtattt ttgcttgtaa tccactcaaa agtgataata ttgcatttat gtatggtgaa     240
ggccgaagcc catatgctgg actgggatat gatttgcatc gaatttggcc tatgctacac     300
gagttggtta acaatagaac tacagaactt tgggatcaag gtgatagttg gtatttacct     360
cgatctagct ctgttgctga aaaagaaaaa gtcttcggag attttgataa gaatcaaatt     420
gaaatgttta gattgggtat ttttgtatca atgtgtttca ctgatatggc cactgaactt     480
ttgggtttaa acccaaagc cgcgtttggt ttaagtttgg gtgaaatatc tatgcttttt     540
gcattttcta aaagaatac caagttgtcc aaagaattga cccgtcgtct aaaagaagca     600
aaagtttggg catcacaatt agctgttgaa tttgcagcta ttcgagattt gtggaatatt     660
ccagctgata aatctattga tgaattttgg caagggtatt tgtttacgc aaatcgaacc     720 ctggtcgaga cacaattggg gagaataaaa tttgttcgtt tgttgattgt aaatgattcg     780
caaagttgtc taattgccgg gaaaccagat gaatgtcaaa aagttattga gaagcttcat     840
ttgaagctac cggcggttcc agtaactcag ggtatgatcg gtcattgccc agaagcaatt     900
ccttatctag atcaaatcag tcatattcat gaaatgcttg aaattccaaa acccgaaaat     960
gtgaaattgt ttacaactag tgaaaacaga gaattagtgt cgatgaagaa ttccgtgtca    1020
aaattggttg ctgagattta tcagcatgtt gctgattttc aaacatcgt gaacaaggtt    1080 aaagaaactt gcaaaactga tatttatt gaattgggat cgaacaatta tcgatctgga    1140
gctgtcaaaa caattttagg tccagaaatc gtttctgttg caattgatag gcaaaatgaa    1200
actgcatggg gtcaactaat gaagatggtt gcatcgttga taagtcatcg agttccgggt    1260
```

```
gttgaattga aaaaactcta tcatcctgaa ttgctgaaat ttgatccaca ggcaaaaccg    1320
aatcgtttca tcagaaatat agaactgaat gga                                1353
```

<210> SEQ ID NO 107
<211> LENGTH: 451
<212> TYPE: PRT
<213> ORGANISM: Thraustochytrium sp.

<400> SEQUENCE: 107

| | | | | | | | | | | | | | | |
|---|---|---|---|---|---|---|---|---|---|---|---|---|---|---|
| Pro | Thr | Ile | Asp | Ile | Asp | Ser | Asn | Val | Phe | Ala | Glu | Met | Leu | Asn | Leu |
| 1 | | | | 5 | | | | | 10 | | | | | 15 | |
| Pro | Gln | Asp | Lys | Asn | Lys | Lys | Phe | Ala | Val | Ala | Leu | Val | Thr | Thr | Pro |
| | | | 20 | | | | | 25 | | | | | 30 | | |
| Asn | Lys | Leu | Gln | Arg | Glu | Ile | Glu | Leu | Ala | Val | Lys | Gly | Ile | Pro | Arg |
| | | 35 | | | | | 40 | | | | | 45 | | | |
| Cys | Val | Lys | Ala | Lys | Arg | Asp | Trp | Cys | Ser | Pro | Ser | Gly | Ser | Ile | Phe |
| 50 | | | | | 55 | | | | | 60 | | | | | |
| Ala | Cys | Asn | Pro | Leu | Lys | Ser | Asp | Asn | Ile | Ala | Phe | Met | Tyr | Gly | Glu |
| 65 | | | | 70 | | | | | 75 | | | | | 80 | |
| Gly | Arg | Ser | Pro | Tyr | Ala | Gly | Leu | Gly | Tyr | Asp | Leu | His | Arg | Ile | Trp |
| | | | | 85 | | | | | 90 | | | | | 95 | |
| Pro | Met | Leu | His | Glu | Leu | Val | Asn | Asn | Arg | Thr | Thr | Glu | Leu | Trp | Asp |
| | | | 100 | | | | | 105 | | | | | 110 | | |
| Gln | Gly | Asp | Ser | Trp | Tyr | Leu | Pro | Arg | Ser | Ser | Ser | Val | Ala | Glu | Lys |
| | | 115 | | | | | 120 | | | | | 125 | | | |
| Glu | Lys | Val | Phe | Gly | Asp | Phe | Asp | Lys | Asn | Gln | Ile | Glu | Met | Phe | Arg |
| 130 | | | | | 135 | | | | | 140 | | | | | |
| Leu | Gly | Ile | Phe | Val | Ser | Met | Cys | Phe | Thr | Asp | Met | Ala | Thr | Glu | Leu |
| 145 | | | | 150 | | | | | 155 | | | | | 160 | |
| Leu | Gly | Leu | Lys | Pro | Lys | Ala | Ala | Phe | Gly | Leu | Ser | Leu | Gly | Glu | Ile |
| | | | | 165 | | | | | 170 | | | | | 175 | |
| Ser | Met | Leu | Phe | Ala | Phe | Ser | Lys | Lys | Asn | Thr | Lys | Leu | Ser | Lys | Glu |
| | | | 180 | | | | | 185 | | | | | 190 | | |
| Leu | Thr | Arg | Arg | Leu | Lys | Glu | Ala | Lys | Val | Trp | Ala | Ser | Gln | Leu | Ala |
| | | 195 | | | | | 200 | | | | | 205 | | | |
| Val | Glu | Phe | Ala | Ala | Ile | Arg | Asp | Leu | Trp | Asn | Ile | Pro | Ala | Asp | Lys |
| 210 | | | | | 215 | | | | | 220 | | | | | |
| Ser | Ile | Asp | Glu | Phe | Trp | Gln | Gly | Tyr | Phe | Val | Tyr | Ala | Asn | Arg | Thr |
| 225 | | | | 230 | | | | | 235 | | | | | 240 | |
| Leu | Val | Glu | Asn | Thr | Ile | Gly | Glu | Asn | Lys | Phe | Val | Arg | Leu | Leu | Ile |
| | | | | 245 | | | | | 250 | | | | | 255 | |
| Val | Asn | Asp | Ser | Gln | Ser | Cys | Leu | Ile | Ala | Gly | Lys | Pro | Asp | Glu | Cys |
| | | | 260 | | | | | 265 | | | | | 270 | | |
| Gln | Lys | Val | Ile | Glu | Lys | Leu | His | Leu | Lys | Leu | Pro | Ala | Val | Pro | Val |
| | | 275 | | | | | 280 | | | | | 285 | | | |
| Thr | Gln | Gly | Met | Ile | Gly | His | Cys | Pro | Glu | Ala | Ile | Pro | Tyr | Leu | Asp |
| 290 | | | | | 295 | | | | | 300 | | | | | |
| Gln | Ile | Ser | His | Ile | His | Glu | Met | Leu | Glu | Ile | Pro | Lys | Pro | Glu | Asn |
| 305 | | | | 310 | | | | | 315 | | | | | 320 | |
| Val | Lys | Leu | Phe | Thr | Thr | Ser | Glu | Asn | Arg | Glu | Leu | Val | Ser | Met | Lys |
| | | | | 325 | | | | | 330 | | | | | 335 | |
| Asp | Ser | Val | Ser | Lys | Leu | Val | Ala | Glu | Ile | Tyr | Gln | His | Val | Ala | Asp |
| | | | 340 | | | | | 345 | | | | | 350 | | |

```
Phe Pro Asn Ile Val Asn Lys Val Lys Glu Thr Cys Lys Thr Asp Ile
            355                 360                 365

Phe Ile Glu Leu Gly Ser Asn Asn Tyr Arg Ser Gly Ala Val Lys Thr
    370                 375                 380

Ile Leu Gly Pro Glu Ile Val Ser Val Ala Ile Asp Arg Gln Asn Glu
385                 390                 395                 400

Thr Ala Trp Gly Gln Leu Met Lys Met Val Ala Ser Leu Ile Ser His
                405                 410                 415

Arg Val Pro Gly Val Glu Leu Lys Lys Leu Tyr His Pro Glu Leu Leu
            420                 425                 430

Lys Phe Asp Pro Gln Ala Lys Pro Asn Arg Phe Ile Arg Asn Ile Glu
        435                 440                 445

Leu Asn Gly
    450

<210> SEQ ID NO 108
<211> LENGTH: 1203
<212> TYPE: DNA
<213> ORGANISM: Thraustochytrium sp.

<400> SEQUENCE: 108
ctcaaaacat atgaggttga ctatcctttg tacacaggtg ccatggctaa aggaattgcg      60
tctgctgatt tggttattgc tgctggtaaa tcaaagatct tggcatcatt tggagctggt     120
gggttggcct acaagtggt  agaagatgcc attaaacaaa ttaaagctga attggggaac     180
ggtccgtttg ctgtaaattt gattcattca ccattcgatc ctagcttgga aagggtaac      240 gttgatcttt ttctaaaata taacgttcga tttgttgaag tatccgcatt tatgtcatta     300 accccctcagg ttgtacgata cagagccgct ggtttggcca agcaagaga tggatctgtg    360 aaaattcaaa atcgtattat tgccaaaatt tcaagaacag agttagcgga actgttcttg     420
aaaccagcac ccaaaaatat tttagatgca ttggttgcgg atggatctat tagtcaagaa     480
caagcccaac ttgcattact tgtgccaatg gctgatgata ttactgtgga agctgattct     540
ggtgggcata ctgacaatcg accaattcat gttttgttac ctttgataat tcagcaaaga     600
aatagaattt gtaaacaata cccaaaacat ttaaaagttc gaatcggagc agctggtggt     660
attggatgcc cgaaggcagc atttgctgcg tttgagatgg gtgctgcata cattgcaact     720
ggaacggtaa atcaactttc aaaggaagca ggtacttgtg actatgtacg taaagtattg     780
aataaagcta catattcgga tgttaccatg gctccagccg cagatatgtt cgatcatggt     840
gttgaattac aagttttgaa gaaaggtact atgtttcctt cacgtgctaa aaaactatac     900
gatttgttca aaaatacaa  atcgattgag gaattaccag cagatgaggt gaaaaaactt     960
gagcaaaaag ttttcaaaaa gtcgtttgat gaagtatggg atgagaccaa gaattactat    1020
attaatcgtt tacattctcc cgaaaaaatt gaacgtgctg aaagagatgc aaaacttaaa    1080
atgtcgttat gttttcgttg gtatttgtcg aagtcttcca gatgggctaa taccggtgaa    1140
tctggaagag tgcaggatta tcaaatttgg tgtggtccag caattgggtc atataatgat    1200
ttt                                                                  1203

<210> SEQ ID NO 109
<211> LENGTH: 401
<212> TYPE: PRT
<213> ORGANISM: Thraustochytrium sp.

<400> SEQUENCE: 109
```

```
Leu Lys Thr Tyr Glu Val Asp Tyr Pro Leu Tyr Thr Gly Ala Met Ala
1               5                   10                  15

Lys Gly Ile Ala Ser Ala Asp Leu Val Ile Ala Gly Lys Ser Lys
            20                  25                  30

Ile Leu Ala Ser Phe Gly Ala Gly Gly Leu Ala Leu Gln Val Val Glu
            35                  40                  45

Asp Ala Ile Lys Gln Ile Lys Ala Glu Leu Gly Asn Gly Pro Phe Ala
50                  55                  60

Val Asn Leu Ile His Ser Pro Phe Asp Pro Ser Leu Glu Lys Gly Asn
65                  70                  75                  80

Val Asp Leu Phe Leu Lys Tyr Asn Val Arg Phe Val Glu Val Ser Ala
                85                  90                  95

Phe Met Ser Leu Thr Pro Gln Val Val Arg Tyr Arg Ala Ala Gly Leu
                100                 105                 110

Ala Lys Ala Arg Asp Gly Ser Val Lys Ile Gln Asn Arg Ile Ile Ala
            115                 120                 125

Lys Ile Ser Arg Thr Glu Leu Ala Glu Leu Phe Leu Lys Pro Ala Pro
            130                 135                 140

Lys Asn Ile Leu Asp Ala Leu Val Ala Asp Gly Ser Ile Ser Gln Glu
145                 150                 155                 160

Gln Ala Gln Leu Ala Leu Leu Val Pro Met Ala Asp Asp Ile Thr Val
                165                 170                 175

Glu Ala Asp Ser Gly Gly His Thr Asp Asn Arg Pro Ile His Val Leu
                180                 185                 190

Leu Pro Leu Ile Ile Gln Gln Arg Asn Arg Ile Cys Lys Gln Tyr Pro
                195                 200                 205

Lys His Leu Lys Val Arg Ile Gly Ala Ala Gly Gly Ile Gly Cys Pro
            210                 215                 220

Lys Ala Ala Phe Ala Ala Phe Glu Met Gly Ala Ala Tyr Ile Ala Thr
225                 230                 235                 240

Gly Thr Val Asn Gln Leu Ser Lys Glu Ala Gly Thr Cys Asp Tyr Val
                245                 250                 255

Arg Lys Val Leu Asn Lys Ala Thr Tyr Ser Asp Val Thr Met Ala Pro
                260                 265                 270

Ala Ala Asp Met Phe Asp His Gly Val Glu Leu Gln Val Leu Lys Lys
                275                 280                 285

Gly Thr Met Phe Pro Ser Arg Ala Lys Lys Leu Tyr Asp Leu Phe Lys
            290                 295                 300

Lys Tyr Lys Ser Ile Glu Glu Leu Pro Ala Asp Glu Val Lys Lys Leu
305                 310                 315                 320

Glu Gln Lys Val Phe Lys Lys Ser Phe Asp Glu Val Trp Asp Glu Thr
                325                 330                 335

Lys Asn Tyr Tyr Ile Asn Arg Leu His Ser Pro Glu Lys Ile Glu Arg
            340                 345                 350

Ala Glu Arg Asp Ala Lys Leu Lys Met Ser Leu Cys Phe Arg Trp Tyr
            355                 360                 365

Leu Ser Lys Ser Ser Arg Trp Ala Asn Thr Gly Glu Ser Gly Arg Val
            370                 375                 380

Gln Asp Tyr Gln Ile Trp Cys Gly Pro Ala Ile Gly Ser Tyr Asn Asp
385                 390                 395                 400

Phe

<210> SEQ ID NO 110
```

```
<211> LENGTH: 1350
<212> TYPE: DNA
<213> ORGANISM: Thraustochytrium sp.

<400> SEQUENCE: 110
atggttggtt tacaaatgaa aaagaaacca gtatgggaga tgagtaagga agaacaaagt      60
tctggaaaga atgttgtatt tgactatgat gaattgttgg aatttgctga aggtgatatt     120
ggtaaagtct ttggacctaa gtttgatatt atcgataagt atagtcgacg tgtacgttta     180
cctgcgagag aatatcttct agttaccaga gttactttga tggatgctga agttgggaat     240
ttcagagttg gatctagaat ggttactgaa tatgatgttc cagtaaatgg tgaactttca     300
caaggtggtg atgttccatg ggctgttctt gttgaatctg acaatgtga tcttatgtta      360 atatcttata tgggtattga ttttcaatgt aaaggtgatc gtgtctatcg attattaaat     420
actacgttga cgttttacgg tgttgctcat gagggtgaaa cactagtata cgatattcgt     480
gtaactggat ttgcaaaagg tatgcacggt gaaatctcca tgttttttttt tgaatatgat    540 tgttatgtga atgacgatt attaatcgaa atgagagatt gttgtgcggg attttttact     600
gatgaagaac ttgcagcagg taaggagtt attaaaactg ttgctgaact tcataaaaga     660
aaatctattg ttccaaaatc cattaaacct tttgctctaa atccagcagt acacaaaaca     720
atgttttctg aaaatgatat ggaaaaattg tgtgagcgtc aatgggaaaa tgtattgggt     780
agtggacttc aaggtattga ctacaagtta tgtgcacgga aaatgcttat gattgatcgt     840
attactaaaa tacaacataa tggtggtgca tatggtcttg gattattggt tggcgaaaaa     900
attcttgaac gtgatcattg gtattttcca tgccattttg taaaggatca agttatggct     960
ggctcacttg ttagtgatgg ttgcagtcag ctactaaaac tttatatgtt atggttgggt    1020
ttacatgatg tggttccaga ttttcaattt cgtccagttc ctggacaacc aaataaagtt    1080
cgttgccgtg acaaattag tccacatcgt ggtaaacttg tttatgttat ggaaataaga    1140
gaaatgggat tcaatgaatc aactggacaa ccatatgcta ttgctgatgt tgatattatt    1200
gatgtaaact atgaacttgg tcaatcattt gatatggctg atattgatag ttatggacgt    1260
ggtaatttgt caagagaaat tgtggttgat tttaaaggaa ttgctttgca aatggaaggt    1320
accgtgaaat catcaaatat cattgattct                                     1350

<210> SEQ ID NO 111
<211> LENGTH: 450
<212> TYPE: PRT
<213> ORGANISM: Thraustochytrium sp.

<400> SEQUENCE: 111

Met Val Gly Leu Gln Met Lys Lys Pro Val Trp Glu Met Ser Lys
1               5                   10                  15

Glu Glu Gln Ser Ser Gly Lys Asn Val Val Phe Asp Tyr Asp Glu Leu
            20                  25                  30

Leu Glu Phe Ala Glu Gly Asp Ile Gly Lys Val Phe Gly Pro Lys Phe
        35                  40                  45

Asp Ile Ile Asp Lys Tyr Ser Arg Arg Val Arg Leu Pro Ala Arg Glu
    50                  55                  60

Tyr Leu Leu Val Thr Arg Val Thr Leu Met Asp Ala Glu Val Gly Asn
65                  70                  75                  80

Phe Arg Val Gly Ser Arg Met Val Thr Glu Tyr Asp Val Pro Val Asn
                85                  90                  95

Gly Glu Leu Ser Gln Gly Gly Asp Val Pro Trp Ala Val Leu Val Glu
```

```
            100                 105                 110
Ser Gly Gln Cys Asp Leu Met Leu Ile Ser Tyr Met Gly Ile Asp Phe
            115                 120                 125

Gln Cys Lys Gly Asp Arg Val Tyr Arg Leu Leu Asn Thr Thr Leu Thr
            130                 135                 140

Phe Tyr Gly Val Ala His Glu Gly Glu Thr Leu Val Tyr Asp Ile Arg
145                 150                 155                 160

Val Thr Gly Phe Ala Lys Gly Met His Gly Glu Ile Ser Met Phe Phe
                165                 170                 175

Phe Glu Tyr Asp Cys Tyr Val Asn Gly Arg Leu Leu Ile Glu Met Arg
            180                 185                 190

Asp Gly Cys Ala Gly Phe Phe Thr Asp Glu Glu Leu Ala Ala Gly Lys
            195                 200                 205

Gly Val Ile Lys Thr Val Ala Glu Leu His Lys Arg Lys Ser Ile Val
            210                 215                 220

Pro Lys Ser Ile Lys Pro Phe Ala Leu Asn Pro Ala Val His Lys Thr
225                 230                 235                 240

Met Phe Ser Glu Asn Asp Met Glu Lys Leu Cys Glu Arg Gln Trp Glu
                245                 250                 255

Asn Val Leu Gly Ser Gly Leu Gln Gly Ile Asp Tyr Lys Leu Cys Ala
                260                 265                 270

Arg Lys Met Leu Met Ile Asp Arg Ile Thr Lys Ile Gln His Asn Gly
            275                 280                 285

Gly Ala Tyr Gly Leu Gly Leu Leu Val Gly Glu Lys Ile Leu Glu Arg
            290                 295                 300

Asp His Trp Tyr Phe Pro Cys His Phe Val Lys Asp Gln Val Met Ala
305                 310                 315                 320

Gly Ser Leu Val Ser Asp Gly Cys Ser Gln Leu Leu Lys Leu Tyr Met
                325                 330                 335

Leu Trp Leu Gly Leu His Asp Val Val Pro Asp Phe Gln Phe Arg Pro
            340                 345                 350

Val Pro Gly Gln Pro Asn Lys Val Arg Cys Arg Gly Gln Ile Ser Pro
            355                 360                 365

His Arg Gly Lys Leu Val Tyr Val Met Glu Ile Arg Glu Met Gly Phe
            370                 375                 380

Asn Glu Ser Thr Gly Gln Pro Tyr Ala Ile Ala Asp Val Asp Ile Ile
385                 390                 395                 400

Asp Val Asn Tyr Glu Leu Gly Gln Ser Phe Asp Met Ala Asp Ile Asp
                405                 410                 415

Ser Tyr Gly Arg Gly Asn Leu Ser Lys Lys Ile Val Val Asp Phe Lys
            420                 425                 430

Gly Ile Ala Leu Gln Met Glu Gly Thr Val Lys Ser Ser Asn Ile Ile
            435                 440                 445

Asp Ser
    450

<210> SEQ ID NO 112
<211> LENGTH: 1200
<212> TYPE: DNA
<213> ORGANISM: Thraustochytrium sp.

<400> SEQUENCE: 112
tgcttcaaac catttcctgg taatccttta gataacgatc atacacctgg taaaatgcct      60
ttaacatggt ttaatatgtc cgagtttatg tgtggtaaag tatcaaattg tcttggacca     120
```

```
gaatttaagaa gatttgataa ctctaaaaca tccagaagtc ctgcctttga tcttgcactt    180
gttacacgtg ttgtgagtgt atcagatatg gaatttaaac ctcatttaaa tattgatgtt    240
aatccaagta agggtacaat gataggtgaa tttgattgcc ctgcagatgc gtggttttt     300 caaggatcat gtaacgatgg tcatatgccg tattctattg ttatggaaat tgctcttcaa    360
acttctggtg tattaacttc agttttgaaa gcacctttga ctatggataa agatgatatt    420
cttttccgca atttggatgc cactgctgaa atggttcgaa gtgatgttga ttgtagaggt    480
aaaactatca aaactttac tcaatgtacc ggttacagta tgctcggaaa atgggaatt     540 catagattca catttgaatt atctgttgat gatgtagttt tctacaaagg atcaacatct    600
tttggttggt tcacccctga agtattcgag tcacaagttg gtcttgataa tggtaaaaaa    660
gtacaaccat ggtatttgga acaaaaatca tctaatgtag taacttatga cgttgcgtcc    720
actgctggca aggataagtt atttcaaag attggatcta aggatgcaca agttcaaaga     780
agaaatacac aatgtgagtt tctagatact atgcatatta ttccaaatac tggaaagtac    840
aacaaaggtt atgctcatgg agaaaagaaa gttaatccaa cgactggtt cttttcctgt     900 catttctggt tgatcctgt gatgcctggt tcattaggta ttgaaagtat gtttcaactc     960
attgaagcat tttcaattga tcaaggaatc gcttcaaaac atggtattgt gaatccaact   1020
tttgctcatt ccaatggaaa aacttcttgg aaatacagag gtcaattgaa taacaaaggt   1080
aaacgaatgg atagtgaaat tcatatcaaa gatattgtca aaaatgctga tggtactgtt   1140
gatttgattg ctgatggatt tttattggtt gattcactaa gagtatactc tgcagatgat   1200
```

<210> SEQ ID NO 113
<211> LENGTH: 400
<212> TYPE: PRT
<213> ORGANISM: Thraustochytrium sp.

<400> SEQUENCE: 113

```
Cys Phe Lys Pro Phe Pro Gly Asn Pro Leu Asp Asn Asp His Thr Pro
1               5                   10                  15

Gly Lys Met Pro Leu Thr Trp Phe Asn Met Ser Glu Phe Met Cys Gly
            20                  25                  30

Lys Val Ser Asn Cys Leu Gly Pro Glu Phe Lys Arg Phe Asp Asn Ser
        35                  40                  45

Lys Thr Ser Arg Ser Pro Ala Phe Asp Leu Ala Leu Val Thr Arg Val
    50                  55                  60

Val Ser Val Ser Asp Met Glu Phe Lys Pro His Leu Asn Ile Asp Val
65                  70                  75                  80

Asn Pro Ser Lys Gly Thr Met Ile Gly Glu Phe Asp Cys Pro Ala Asp
                85                  90                  95

Ala Trp Phe Phe Gln Gly Ser Cys Asn Asp Gly His Met Pro Tyr Ser
            100                 105                 110

Ile Val Met Glu Ile Ala Leu Gln Thr Ser Gly Val Leu Thr Ser Val
        115                 120                 125

Leu Lys Ala Pro Leu Thr Met Asp Lys Asp Asp Ile Leu Phe Arg Asn
    130                 135                 140

Leu Asp Ala Thr Ala Glu Met Val Arg Ser Asp Val Asp Cys Arg Gly
145                 150                 155                 160

Lys Thr Ile Lys Asn Phe Thr Gln Cys Thr Gly Tyr Ser Met Leu Gly
                165                 170                 175

Lys Met Gly Ile His Arg Phe Thr Phe Glu Leu Ser Val Asp Asp Val
```

```
                    180                 185                 190
Val Phe Tyr Lys Gly Ser Thr Ser Phe Gly Trp Phe Thr Pro Glu Val
                195                 200                 205
Phe Glu Ser Gln Val Gly Leu Asp Asn Gly Lys Lys Val Gln Pro Trp
            210                 215                 220
Tyr Leu Glu Gln Lys Ser Ser Asn Val Val Thr Tyr Asp Val Ala Ser
225                 230                 235                 240
Thr Ala Gly Lys Asp Lys Leu Phe Ser Lys Ile Gly Ser Lys Asp Ala
                245                 250                 255
Gln Val Gln Arg Arg Asn Thr Gln Cys Glu Phe Leu Asp Thr Met His
            260                 265                 270
Ile Ile Pro Asn Thr Gly Lys Tyr Asn Lys Gly Tyr Ala His Gly Glu
        275                 280                 285
Lys Lys Val Asn Pro Asn Asp Trp Phe Ser Cys His Phe Trp Phe
    290                 295                 300
Asp Pro Val Met Pro Gly Ser Leu Gly Ile Glu Ser Met Phe Gln Leu
305                 310                 315                 320
Ile Glu Ala Phe Ser Ile Asp Gln Gly Ile Ala Ser Lys His Gly Ile
                325                 330                 335
Val Asn Pro Thr Phe Ala His Ser Asn Gly Lys Thr Ser Trp Lys Tyr
            340                 345                 350
Arg Gly Gln Leu Asn Asn Lys Gly Lys Arg Met Asp Ser Glu Ile His
        355                 360                 365
Ile Lys Asp Ile Val Lys Asn Ala Asp Gly Thr Val Asp Leu Ile Ala
    370                 375                 380
Asp Gly Phe Leu Leu Val Asp Ser Leu Arg Val Tyr Ser Ala Asp Asp
385                 390                 395                 400

<210> SEQ ID NO 114
<211> LENGTH: 1729
<212> TYPE: DNA
<213> ORGANISM: Thraustochytrium sp.

<400> SEQUENCE: 114
aggaatcgct tcaaaacatg gtattgtgaa tccaactttt gctcattcca atggaaaaac      60
ttcttggaaa tacagaggtc aattgaataa caaaggtaaa cgaatggata gtgaaattca     120
tatcaaagat attgtcaaaa atgctgatgg tactgttgat tgattgctg atggattttt     180 attggttgat tcactaagag tatactctgc agatgatctt cgcgtaaaaa ttgtaccggg     240
aaccaaagct gcacctaaat cagtagctgc tgctccaaga catgttgcaa caccaattcc     300
aggagtgcct tcgaatacaa gcagtgttga aatcagtttg gaatctttga agaaagaatt     360
gttaaatctt gagaaccat tgtatcttga acttccaat catattgtaa aacaattcgg      420
tgacgttaac aatggccaag catccgttat tccaccatgc accatcaatg atttgggtga     480
gcgtagtttt atggaaacat acaatgttgt tgcaccactt tacactggag ccatggctaa     540
aggtattgca tctgctgatt tggtaattgc agctggtaaa agaaaaattt tgggttcttt     600
tggcgctgga ggcttaccaa tgcacttggt tcgtgcttct gttgaaaaaa tccaagccgc     660
acttccagaa ggtccatacg ctgtcaactt gattcatagt ccattcgact caaatcttga     720
aaagggaaat gtagatctat ttttggaaaa aggtgttcat gttgttgaag catctgcatt     780
cactgctctg accactcaag tagttcgtta ccgtgcatgt ggtttatctc gggctaaaga     840
cggatctgta ttgatcaaaa atagaatcat cggtaaagtt tcaagaaccg aattggctga     900
```

```
aatgtttttc agacctgcac cacaaaactt gcttgacaag cttattgcta gtggagaaat    960
cactaaagaa caagcttcat tggctttgga agtaccaatg gctgatgatg tagctgttga   1020
agctgatagc ggtggacata ctgataatag accaattcat gtaatcctac ctttgattat   1080
caatctacga aatagaattc ataaagaatg tggttttcct gctgctttga gagttcgcgt   1140
tggtgctggt ggtggaattg gttgtccaag tgctgcagtt gctgcattca atatgggagc   1200
tgcattcttg attactggca gcgtcaacca agttagcaaa caatctggta cgtgtgatat   1260
cgttagaaag caattatctg aagcttcgta ttcagatatt accatggcac cagcggctga   1320
tatgtttgat caaggagtcg agcttcaagt attaaaaaaa ggaactatgt ttccatctcg   1380
tgcaaagaaa ttgtatgaat tattctgtat gtacaactca tttgatgaca tgccaaaaag   1440
cgaacttcaa agactagaga agcgaatttt tcaaaaatcg cttgcggaag tttgggaaga   1500
aactaaagat ttttatatca atcgtttgaa taatcctgag aagattgaac atgctgagaa   1560
gaaagatcca aagttgaaga tgtcattatg ctttagatgg tatttgggtt taagttcatt   1620
ttgggcaaac aatggaatta agaaagatc aatggactat caaatttggt gtggtccagc   1680
gattggttca tacaatgatt ttgtaaaagg aacttatttg gatcctgca              1729

<210> SEQ ID NO 115
<211> LENGTH: 455
<212> TYPE: PRT
<213> ORGANISM: Thraustochytrium sp.

<400> SEQUENCE: 115

Asn Leu Glu Lys Pro Leu Tyr Leu Glu Thr Ser Asn His Ile Val Lys
1               5                   10                  15

Gln Phe Gly Asp Val Asn Asn Gly Gln Ala Ser Val Ile Pro Pro Cys
            20                  25                  30

Thr Ile Asn Asp Leu Gly Glu Arg Ser Phe Met Glu Thr Tyr Asn Val
        35                  40                  45

Val Ala Pro Leu Tyr Thr Gly Ala Met Ala Lys Gly Ile Ala Ser Ala
    50                  55                  60

Asp Leu Val Ile Ala Ala Gly Lys Arg Lys Ile Leu Gly Ser Phe Gly
65                  70                  75                  80

Ala Gly Gly Leu Pro Met His Leu Val Arg Ala Ser Val Glu Lys Ile
                85                  90                  95

Gln Ala Ala Leu Pro Glu Gly Pro Tyr Ala Val Asn Leu Ile His Ser
            100                 105                 110

Pro Phe Asp Ser Asn Leu Glu Lys Gly Asn Val Asp Leu Phe Leu Glu
        115                 120                 125

Lys Gly Val His Val Val Glu Ala Ser Ala Phe Thr Ala Leu Thr Thr
    130                 135                 140

Gln Val Val Arg Tyr Arg Ala Cys Gly Leu Ser Arg Ala Lys Asp Gly
145                 150                 155                 160

Ser Val Leu Ile Lys Asn Arg Ile Ile Gly Lys Val Ser Arg Thr Glu
                165                 170                 175

Leu Ala Glu Met Phe Phe Arg Pro Ala Pro Gln Asn Leu Leu Asp Lys
            180                 185                 190

Leu Ile Ala Ser Gly Glu Ile Thr Lys Glu Gln Ala Ser Leu Ala Leu
        195                 200                 205

Glu Val Pro Met Ala Asp Asp Val Ala Val Ala Asp Ser Gly Gly
    210                 215                 220

His Thr Asp Asn Arg Pro Ile His Val Ile Leu Pro Leu Ile Ile Asn
```

```
            225                 230                 235                 240
Leu Arg Asn Arg Ile His Lys Glu Cys Gly Phe Pro Ala Ala Leu Arg
                245                 250                 255

Val Arg Val Gly Ala Gly Gly Ile Gly Cys Pro Ser Ala Ala Val
            260                 265                 270

Ala Ala Phe Asn Met Gly Ala Ala Phe Leu Ile Thr Gly Ser Val Asn
                275                 280                 285

Gln Val Ser Lys Gln Ser Gly Thr Cys Asp Ile Val Arg Lys Gln Leu
            290                 295                 300

Ser Glu Ala Ser Tyr Ser Asp Ile Thr Met Ala Pro Ala Ala Asp Met
305                 310                 315                 320

Phe Asp Gln Gly Val Glu Leu Gln Val Leu Lys Lys Gly Thr Met Phe
                325                 330                 335

Pro Ser Arg Ala Lys Lys Leu Tyr Glu Leu Phe Cys Met Tyr Asn Ser
            340                 345                 350

Phe Asp Asp Met Pro Lys Ser Glu Leu Gln Arg Leu Glu Lys Arg Ile
                355                 360                 365

Phe Gln Lys Ser Leu Ala Glu Val Trp Glu Glu Thr Lys Asp Phe Tyr
        370                 375                 380

Ile Asn Arg Leu Asn Asn Pro Glu Lys Ile Glu His Ala Glu Lys Lys
385                 390                 395                 400

Asp Pro Lys Leu Lys Met Ser Leu Cys Phe Arg Trp Tyr Leu Gly Leu
                405                 410                 415

Ser Ser Phe Trp Ala Asn Asn Gly Ile Lys Glu Arg Ser Met Asp Tyr
            420                 425                 430

Gln Ile Trp Cys Gly Pro Ala Ile Gly Ser Tyr Asn Asp Phe Val Lys
            435                 440                 445

Gly Thr Tyr Leu Asp Pro Ala
            450                 455

<210> SEQ ID NO 116
<211> LENGTH: 903
<212> TYPE: DNA
<213> ORGANISM: Thraustochytrium sp.

<400> SEQUENCE: 116
tccattcggg aatctggtta cacgattagc ggagaaagat tcacaactga agctcacaaa      60
ttggttactg gaaagcctca tgctccgatt aagaagaagg atgctttcct agtatctggt     120
ggtgctcgtg gtattactcc actttgtatt cgtgaaattg ctaaagcagt gaaaggtggc     180
acttacattt tgatgggtcg atcagctttg gctgatgaac ccttgtgggc taatggtaaa     240
tccggaaaag atttagataa agctggtttg cattttttga aggaagagtt tgcagctggg     300
cgtggtagta aaccaactcc aaaagttcac aaatctttga ttgataaagt gctcggtatt     360
agggaggtta gagcatctat tgcaaatata gaagcccatg agcaaaaagc tatatatttg     420
tcttgcgatg tatcttccgc tgagaaagta aaggctgcag tgcaaaaagt tgaaaggag     480 catctagttc gtattactgg tattgtgcat gcatcaggcg ttttgaggga taaattggtt     540
gagaacaaaa ctttggatga tttcaacgca gtatatggaa ccaaagtaac tggactagta     600
aacttgctgt cagcagtgaa catgaatttt gttcgtcatt tggttatgtt tagttctttg     660
gctggatatc atggaaatgt tggtcaatct gattatgcaa tggctaacga atcacttaac     720
aagattggtt ttagattggg tgcagcttat tctcaattgt gtgttaaatc tatttgtttt     780
ggaccttggg atggtggaat ggtaactcca gctttgaaaa aacaatttca atcaatgggt     840
```

```
gtccagatta ttcctcgtga aggtggcgcg gagactgttg caagaatagt cttatcttca    900
aat                                                                  903
```

<210> SEQ ID NO 117
<211> LENGTH: 201
<212> TYPE: PRT
<213> ORGANISM: Thraustochytrium sp.

<400> SEQUENCE: 117

```
Ser Ile Arg Glu Ser Gly Tyr Thr Ile Ser Gly Glu Arg Phe Thr Thr
1               5                   10                  15

Glu Ala His Lys Leu Val Thr Gly Lys Pro His Ala Pro Ile Lys Lys
            20                  25                  30

Lys Asp Ala Phe Leu Val Ser Gly Gly Ala Arg Gly Ile Thr Pro Leu
        35                  40                  45

Cys Ile Arg Glu Ile Ala Lys Ala Val Lys Gly Gly Thr Tyr Ile Leu
    50                  55                  60

Met Gly Arg Ser Ala Leu Ala Asp Glu Pro Leu Trp Ala Asn Gly Lys
65                  70                  75                  80

Ser Gly Lys Asp Leu Asp Lys Ala Gly Leu Ala Phe Leu Lys Glu Glu
                85                  90                  95

Phe Ala Ala Gly Arg Gly Ser Lys Pro Thr Pro Lys Val His Lys Ser
            100                 105                 110

Leu Ile Asp Lys Val Leu Gly Ile Arg Glu Val Arg Ala Ser Ile Ala
        115                 120                 125

Asn Ile Glu Ala His Gly Ala Lys Ala Ile Tyr Leu Ser Cys Asp Val
    130                 135                 140

Ser Ser Ala Glu Lys Val Lys Ala Ala Val Gln Lys Val Glu Lys Glu
145                 150                 155                 160

His Leu Val Arg Ile Thr Gly Ile Val His Ala Ser Gly Val Leu Arg
                165                 170                 175

Asp Lys Leu Val Glu Asn Lys Thr Leu Asp Asp Phe Asn Ala Val Tyr
            180                 185                 190

Gly Thr Lys Val Thr Gly Leu Val Asn
        195                 200
```

<210> SEQ ID NO 118
<211> LENGTH: 39
<212> TYPE: DNA
<213> ORGANISM: Thraustochytrium sp.

<400> SEQUENCE: 118

```
ctaaagtctc atcaaattca tggtaaaaat gttttgcct                           39
```

<210> SEQ ID NO 119
<211> LENGTH: 13
<212> TYPE: PRT
<213> ORGANISM: Thraustochytrium sp.

<400> SEQUENCE: 119

```
Leu Lys Ser His Gln Ile His Gly Lys Asn Val Leu Pro
1               5                   10
```

<210> SEQ ID NO 120
<211> LENGTH: 8976
<212> TYPE: DNA
<213> ORGANISM: Artificial Sequence
<220> FEATURE:

<223> OTHER INFORMATION: Codon-optimized PFA1

<400> SEQUENCE: 120

```
atggaggacc agcgtattgc gatcgttggc cttagcgcga tccttccctc gggcgagaac      60
gtccgcgagt cgtgggaggc gatccgtgac ggcctcaact gcctttccga cctgcccgcc     120
gaccgcgttg acgtcactgc ctactacaac cccacgaagg gcgtcaagga caagatctac     180
tgcaagcgtg gtggcttcat ccccgagtac gagtttgact cgcgcgagtt cggcctcaac     240
atgcttcaga tggaggactc ggacgccaac cagaccctca ccctgctcaa ggttaaggag     300
gccctcgacg acgccaacat tcccgcgttt accaacgaga agaagaacat cggttgcgtc     360
ctcggtattg cggtggtca gaaggcctcg catgagttct acagccgcct caactacgtc      420
gtcgtggata aggtcctccg caagatgggc ctccccggacg aggacgtcga gactgctgtc     480
gagaagttca aggccaactt tcccgagtgg cgccttgact ccttccccgg ctttctcggt     540
aacgtcactg cgggccgctg caccaacacc ttcaacatgg agggcatgaa ctgcgtggtc     600
gatgccgcct gcgcctcgtc cctcatcgct atcaaggtcg ccatcgatga gctgctccac     660
ggcgattgcg acgcgatgat tgctggcgcg acgtgcaccg acaacgccct tggcatgtac     720
atggcctttt ccaagacccc cgtcttttcc acggaccaga gctgcctcgc ctacgacgag     780
aaaaccaagg gtatgctcat tggcgagggt tccgccatgt tcgtccttaa cgctacgcc      840
gacgccgtcc gcgatggcga caccgtccac gccgtcatcc gctcgtgctc gtcctcctcc     900
gacggcaagg cgtcgggtat ctacaccccg accatctcgg gccaggagga ggccatcctt     960
cgcgcctacc gtcgtgccgg cgtgagcccg aacacgatca cccttgtgga gggccatggc    1020
accggcaccc ccgtcggcga caagatcgag ctgaccgccc tccgcaacgt ctttgacaag    1080
gcctacggcc ctggccacaa ggaggaggtc gctgtgggct ccatcaagtc gcagatcggt    1140
cacctcaagg ccgtcgccgg ctgcgctggc ctcgtcaagc tcgtgatggc tctcaagcat    1200
aagacgctcc cgcagtccat caacgtcgag aacccgccca cctcgtcga tggcactgtc     1260
atctcggaca ccacgctcta catcaacacc atgaaccgcc cgtggatcac caagccgggc    1320
gtccccccgtc gtgcgggcat ctccagcttc ggctttggcg cgctaacta ccacgctgtc     1380
cttgaggagt cgagcccga gcagaccaag ccctaccgcc tgaacgtttc ggcccagccg     1440
atgctcctcc acgccgtcaa cgcgaactcg ctccagaagc tctgcgagga ccagctcaag    1500
ctcctcaagg agtcccgcga gaagtgcgtc aacacgaaga caccgactaa cgtcgctttt    1560
tccaagtttc aggactcctt taagctcaag ggctccgtcc ccagccagca cgctcgcgtg    1620
ggctttgctt ccaagagcat cgaggacacg atttccattc ttagcgccat tgtcaaccgc    1680
ttccagaagg acatcacgac caccagctgg gcgctcccga aggagggcgc catctttcgc    1740
agcaccgccc tcatcaacga caacaagtcc gtggccgccc tgttctcggg tcagggcgct    1800
cagtacaccc acatgttcaa cgacgtcgcg atgcagtggc gcagttccg cctctgcgtt     1860
aacgatatgg agaaggccca ggaggaggtg atcaacgaca agtcggttaa gcgcattagc    1920
caggtcatgt ttccccgcaa gccctacgcg cgcgagagcc cctcgacaa caaggagatc     1980
agcaagaccc agtactcgca gacgacgacc gtcgcctcgt ccgtcggcct ctttgagatt    2040
ttccgcgacg ccggctttgc cccggctttt gttgcgggcc actcgctcgg tgagttctcc    2100
gcccttacg ccgctggcct catcgaccgc gaggacctct ttaagctcgt gtgcaaccgc     2160
gccatggcta tgcgcgacgc ccccaagaag tccgctgacg cgccatggc tgccgtcatc     2220
ggtccgaacg cctcgtccat caagctctcg gctcccgagg tttgggtcgc gaacaacaac    2280
```

```
tcgccctcgc agaccgtcat cactggtgcc aacagcggcg tccaggccga gacttcgaag     2340
ctcaagacgc agggtttccg cgtggtccac ctcgcctgcg acggcgcgtt tcacagcccg     2400
cacatggaga acgccgagaa gcagtttcag aaggccctct cggccgtcaa gttcaacaag     2460
cccaccggct cgtcccccaa gattttcagc aacgtcaccg gcggtgtctt taccgatcct     2520
aagacggccc tctcccgcca catgactagc tcggtccagt ttctcaccca gatcaagaac     2580
atgtacgccc tggcgcccg cgttttcatc gagttcggcc ccaagcaggt cctctcgaag     2640
ctcgtcaacg agattttccc gggcgacacc agcgtcctca ctgttagcgt gaaccctgcc     2700
tccgccaagg actcggacat ccagctccgc caggcggccg tgcagatggc ggtcgctggc     2760
gtcgctctca ccgactttga taagtgggag cttaaggacc cgacccgcat gaaggagttc     2820
cctcgcaaga aaacgaccct caccctctcc gccgctacct acgttagcaa gaaaacgctc     2880
caggagcgcg agcgtatcat gaacgacggt cgcactgtca gctgcgtgca gcgcatcgag     2940
aacacgaaca cgggcgagct tgagaagctc aagaagcagc tccaggacaa ggagaacgag     3000
gttgtccgcg tccaggccct tgccacccag gccagcgccg accttcagaa caccaaggct     3060
gagcttcaga aggctcaggc caccaagtcg tcgaacgctg cctcggacgc cgtcgtcgcc     3120
aagcacaagg ccatcctcct cgctatgctg gaggagctgg agactggcaa ggccgtcgat     3180
tactccagct tttccaaggg tcaggttgcc tcccctgcga ccgttcgtgt cgtgtcggct     3240
cccgtgcagg ctgccgcacc ggttcaggtc agcgcctccg tggactcggg cctgctcgcg     3300
aaggcggagc aggtcgtgct tgaggtcctc gcctccaaga ccggctacga gactgagctt     3360
atcgagctgg acatggagct tgagactgag cttggtatcg attcgatcaa gcgcgtcgag     3420
attctttcgg aggtccaggc ccagctcaac gtggaggcca aggacgttga cgccctgtcg     3480
cgcacccgta cggtcggcga ggtcatcgat gccatgaagg cggagattgc cggcggtcag     3540
cctgctgccc ccgtccaggt cgctgcgccg acgcaggtcg tcgccccggt ccaggcctcc     3600
gcgcctgtcg atagcggcct cctcgccaag gcggagcagg tcgtccttga ggtgctcgct     3660
tccaagactg gttacgagac tgagcttatt gagcttgaca tggagctgga gactgagctt     3720
ggcattgact ccatcaagcg cgtggagatt ctgagcgagg tccaggccca gctcagcgtg     3780
gaggccaagg atgtcgatgc cctctcccgt acgcgcaccg tcggcgaggt cattgacgcg     3840
atgaaggccg agatcgcggg tggtcagccg ccgccccccg tccaggtcgc tgcccctacg     3900
caggtcgtcg ctcccgtcca ggccagcgct cccgtcgact cgggccttct tgctaaggcc     3960
gagcaggtcg tccttgaggt ccttgccagc aagactggct acgagactga gcttattgag     4020
cttgacatgg agcttgagac tgagcttggc atcgactcga ttaagcgcgt cgagatcctc     4080
agcgaggtcc aggcccagct ctccgtcgag gctaaggatg tggatgctct cagccgcacg     4140
cgcacggtgg gcgaggtcat tgatgccatg aaggcggaga tttccggcgg tcagcccgct     4200 gccccgtcc aggtcgctgc tccgacccag atcgtcgccc cggtccaggt ttcggctccg     4260
gtggacagcg gcctccttgc caaggccgag caggtcgtcc ttgaggtcct cgccagcaag     4320
accggctacg agactgagct gatcgagctt gacatggagc ttgagactga gctgggcatc     4380
gattccatta gcgcgtcga gatcctctcg gaggtccagg cccagctcag cgtggaggcc     4440
aaggatgtcg atgccctctc gcgtacccgt accgtcggcg aggttatcga tgctatgaag     4500
gccgagatca gcgcggtca gcccacgcgc ccgttcagg tcgctgcccc tacgcagatc     4560
gttgcccctg tccaggtcag cgctcccgtg gacagcggcc tcctcgctaa ggctgagcag     4620
```

```
gtggtgctgg aggtcctggc ctccaagacc ggctacgaga ctgagcttat cgagcttgac    4680
atggagcttg agactgagct tggcattgac agcatcaagc gtgtcgagat cctctccgag    4740
gtgcaggccc agctcagcgt ggaggccaag gacgttgacg cgctcagccg tacgcgcacc    4800
gttggcgagg tgatcgacgc catgaaggcc gagattagcg gtggtcagcc cgctgccccg    4860
gttcaggtgg ctgcccctac gcagatcgtc gcccccgtgc aagcttccgc ccctgtggac    4920
agcggccttc tcgccaaggc cgagcaggtc gtccttgagg tgctggcctc caagaccggc    4980
tacgagactg agctgatcga gcttgacatg gagctggaga ctgagcttgg catcgactcg    5040
atcaagcgcg tggagattct ctcggaggtc caggcccagc tctcggtcga ggccaaggac    5100
gtcgatgcgc tctcccgcac ccgcaccgtg ggcgaggtca tcgacgctat gaaggcggag    5160
atcagcggcg tcagccggc ggcccctgtg caggtggccg ctccgaccca gatcgtcgct    5220
cctgtccagg tttccgcccc ggtggactcg ggcctcctgg ctaaggccga gcaggtcgtc    5280
cttgaggtcc tcgcttccaa gaccggctac gagactgagc tgatcgagct ggacatggag    5340
cttgagactg agctgggcat cgattcgatc aagcgcgtcg agattctctc ggaggtccag    5400
gcccagctca cgttgaggc caaggacgtg acgcccctct cgcgtactcg caccgttggc    5460
gaggttattg atgctatgaa ggccgagatc gccggtggtc agccggctgc ccctgttcag    5520
gttgctgccc ctgcgccggt ggtcgccccg gtccaggtgt ccaccccggt tgacagcggc    5580
ctccttgcca aggccgagca ggttgtgctg gaggtcctcg cctgcaagac gggctacgag    5640
actgagctta tcgagcttga catggagctg gagactgagc ttggcatcga ctccatcaaa    5700
cgcgtcgaga ttctttcgga ggtccaggcc cagctgtcgg tggaggctaa ggatgtcgat    5760
gccctcagcc gcacgcgcac ggtcggtgag gtcatcgatg ctatgaaggc cgagatttcg    5820
ggcggtcagc ccaccgcccc cgtgcaggtc gccgcgccca cccaggtcgt ggccccggtc    5880
aaggtttcca cgcccgtgga ctcgggcctt ctcgccaagg ccgagcaggt cgtgctggag    5940
gttctcgcct ccaagacggg ttacgagact gagctgattg agcttgacat ggagctggag    6000
actgagctgg gcattgactc catcaagcgc gtcgagatcc tctcggaggt ccaggcccag    6060
ctcaacgtcg aggccaagga cgtcgatgcc ctctcgcgca cccgcaccgt cggcgaggtc    6120
attgatgcca tgaaggccga gatcgctggc gatcagcctg ccccggctgt ggtcccggtg    6180
caggccaagt cgggtgtcgc gaaccccgcc ctcctcgcca aggcggagca ggtcgtgctg    6240
gaggtcctgg ccagcaagac gggctacgag actgagctta tcgagcttga catggagctt    6300
gagactgagc ttggtattga ctcgattaag cgcgttgaga tcctttccga ggtccaggcc    6360
gagctgtccg tggaggccaa ggatgtcgat gcgctctccc gcacccgcac ggtgggcgag    6420
gtcatcgacg ctatgaaggc cgagattgcc ggctccgcgg tcactgtcgc tacccttgac    6480
gactcgacca ttatggagga gactgacgac gaggacgagg actttatcct gtacgaccac    6540
gtctacggct ccgagtgcga ggatctctcg ctctcgttct cgtcggtcaa gtcgattcct    6600
cgcgcggaca agctcctgct ggacaacatt gccgagcgcc ccattgtcat tgtcgattgc    6660
ggcacgaagc tcacgaccga gctggcgaag gccatcggcg agcgcgctgt cgttgccacg    6720
ttctcggccc agtcgctcgt gtcccgtggc ttcgtgggca gagcttcac cctcggcaac    6780 accgaggagt cggagatcga aagatggtg tcctccatcg agtcgtccta cggcaagatc    6840
ggcggctttg tctaccagca cttcatgac agcgactacg gtatgcagct cggctgggct    6900
ctcatggccg cgaagcacct caaggagtcc ctcaacgacc cgatcaagaa cggccgcacc    6960
ttttccctgg ctgtcgcccg catgaacggc aagctcggca tggacaacgc ctccgtccac    7020
```

```
gaccagggca tcgtcgagag ctgcggtatc gctgagcgtg gtgccatctt tggcctctgc    7080
aagaccctgg acctggagtg gcctaacgtg tttgcgcgcg gtgtggacat cgcggagggc    7140
atgtcctact ccctcgcggc cgagctgatc gtcgatgaga tcagctgcgc caacctttcg    7200
atccgcgaga gcggctacac tattagcggc gagcgcttca ccacggaggc gcacaagctc    7260
gtcacgggca agcctcacgc gcccatcaag aagaaggacg cctttctcgt gtcgggtggt    7320
gctcgcggca tcacgcccct gtgcattcgc gagattgcca aggccgtcaa gggtggcacc    7380
tacattctca tgggccgctc ggcgctcgcg gacgagcccc tctgggctaa cggcaagagc    7440
ggcaaggacc tcgacaaggc cggcctcgcc ttccttaagg aggagttcgc tgccggccgt    7500
ggctcgaagc ccaccccaa ggtccacaag tcgctcatcg acaaggtcct cggcatccgc    7560
gaggttcgcg cgtccatcgc caacatcgag gcgcacggcg ctaaggccat ctacctctcg    7620
tgcgatgtgt cgagcgccga gaaggtcaag gctgccgtcc agaaggtcga aggagcat    7680 ctcgtccgca tcacgggcat cgtgcacgcc tccggcgtcc tgcgcgacaa gctcgtcgag    7740
aacaagaccc tcgacgactt taacgctgtg tacggcacga aggtcacggg cctcgtcaac    7800
ctccttagcg ccgtcaacat gaacttcgtc cgccacctgg tgatgttctc gtcgctcgct    7860
ggttaccacg gcaacgtcgg ccagtcggac tacgctatgg ccaacgagag ccttaacaag    7920
atcggcttcc gtcttggtgc cgcgtactcc cagctctgcg tcaagtccat ctgcttcggc    7980
ccttgggatg gcggcatggt gacgccggcg ctcaagaagc agttccagtc catgggcgtt    8040
cagatcatcc ctcgcgaggg tggcgccgag actgtcgctc gcattgtgct ctcgtccaac    8100
cccagccagg tcctcgtcgg caactggggc gtcccgcccg tcagcccct ctccaagtcg    8160 gccaccatcg tccagacctt taccctgag cttaacccct tcctcaagtc ccaccagatc    8220
cacggcaaga acgtcctgcc catgacggtc gccattggtt acctcgccca cctcgtgaag    8280
aacttttacg ccggccacca cctctggggc gtggaggacg cgcagctctt ctccggcgtc    8340
gtcatcgacc acgccgtgca ggcccaggtc aagctcactg agcagagcct ggatgacgat    8400
ggcaaggtca aggtccaggc ggtgctcacc gcctcgaacg acaacggcaa gatggtgccg    8460
gcctacaagg ccgtcatcgt gctcggcaag acttcccgtc cggccttcat cctcaaggac    8520
ttttcgctcc aggagtccaa ctcgcgctcg gccgacgagc tgtacgacgg caagaccctg    8580
ttccacggcc cgctgttccg tggcatcacc aagctcctca acgtgtccga cactagcctc    8640
acgacccagt gcaccaacat cgatctcacc gccactgagc gcggccagtt tgccgacatc    8700
gagccggtca accctttcat ggcggacgcc gccttccagg ccatgctcgt ctgggtccgc    8760
aacctccgta actccgccag ccttccgaac aactgcgagc gcgtcgatat ctacaagccc    8820
atcgcgcccg gcgagaagta ctacaccacg ctgcaggccc tcgcaacac ctccggctcg    8880 gttctcaagt ccgttttcta catgcatgac gagcagggcg aggtgttcct ctcgggccgc    8940
gccagcgtcg tggtcaacga taagatggaa ttctaa                              8976

<210> SEQ ID NO 121
<211> LENGTH: 5880
<212> TYPE: DNA
<213> ORGANISM: Artificial Sequence
<220> FEATURE:
<223> OTHER INFORMATION: Codon-optimized PFA2

<400> SEQUENCE: 121
atggtgaagc tttccgttgg tgacaacatt tgccacgatc agcgcgtcgc cgtggtcggc     60
```

-continued

| | |
|---|---|
| atggccgtca tgtacgccgg ctgccagaac cagcacgagt tttggcagag cctccagggt | 120 |
| aagaacatga acagcaagag catcagccag aaccgcctgg gctccgagta ccgcgaggag | 180 |
| cactttaagc cggagcgctc gaagtacagc gacaccttct gcaacgagcg ttacggctgc | 240 |
| atcgacgaga acgtccagag cgagcatgag ctcctcctga agctcgctaa ggacgcgatc | 300 |
| gccgatacca agggcagcat cgaccttaac aagaccggca ttgtctccgg ctgcctctcg | 360 |
| ttccctatgg ataacctcca gggcgacctt ctcaacctct accagtgcca tattgagaag | 420 |
| aagatcggcc cgaacgccct caaggatgtc aacctctggt cgaagcgcac gaccaacggt | 480 |
| aaggacgata agaaggccta cttcgatccc gccagcttcg tcgctgagca gcttgacatg | 540 |
| ggtcccctcc actactcgct cgacgctgcc tgcgcctccg ctctctacgt cctccgcctc | 600 |
| gcccaggacc acctcctcag cggtgccgcc gacaccatgc tctgcggcgc ctcgtgcctc | 660 |
| ccggagccct ttttcatcct ttcgggcttt tcgaccttcc acgccatgcc cctttcgggt | 720 |
| gacgtgtcgg cccctcttca caagacgagc cagggcctca ctccgggcga gggcggtgct | 780 |
| atcatggtcc tgaagcgcct caacgatgcc attcgcgacg cgaccgcat ctacggcacg | 840 |
| ctcctgggcg ccgagctttc caacgcgggt tgcggcctcc cgctctcccc gcacatgccg | 900 |
| tccgagttcg actgcatgga aaggccctc cagcgcgttc accgcctccc gtcctccatc | 960 |
| cagtacgtgg agtgccacgc cactggcacc ccgcagggcg acaaggtcga gatcgacgcc | 1020 |
| atgacgaagt gcttcggcga gcatctgcct cgcttcggct ccaccaaggg taacttcggc | 1080 |
| cacaccctcg tggctgctgg ctttgcgggc atgtgcaagg tcctcctctc gatgcagtac | 1140 |
| ggtgagattc ctcctacgcc tggcctggag aaccccgaca acattatgca cgatcttgtc | 1200 |
| gttaccgaga ctattccctg gccgaacacc aacggcgatc ttaagcgtgc gtgcctcagc | 1260 |
| gcctttggct ttggcggtac taacgcccac gccgtgttcg aggagtaccg cagcgacctt | 1320 |
| caggccaaca agaccccttga gaacgagagc aagtcccacg agatctttttc ctcctttaag | 1380 |
| attgccattg ttggcatgga gtccgagttt ggcactctca gggcctcca ggagttcgag | 1440 |
| cgtgccatct acaacggcgg ccacggcgcg tgcgaccttc cggagaaccg ctggcgcttt | 1500 |
| ctcggtgagg acaaggagtt tctccaggcc tgcggcctcc agaagctccc gcgtggctgc | 1560 |
| tacatcaagg aggtcgagac tgactttaag cgccttcgcc tccccatgat ccaggaggac | 1620 |
| atcctccgcc cctccagct cctcgccgtg tcgatcatcg accgcgccct caacgccagc | 1680 |
| ggcgttaagc ccaacggcaa ggtcgccgtc ctcgtgggcc tcggcaccga tcttgagctc | 1740 |
| taccgccacc gcgctcgcgt cgcccctgaag gagcgccttc agaccgccgt caaggaggac | 1800 |
| atcccccctgc tggagaagct catgaactac gtgaacgacc gcggcacctc cacgtcctac | 1860 |
| acctcgtaca tcggcaacct cgttgcgacc gcgtcagct cgctctgggg cttcaccggc | 1920 |
| cctagcttca cgatcacgga gggcgagaac tcggtttacc gttgcctcga cctcggccgc | 1980 |
| tggttcctcg ccaacggtga ggtcgatgcc gtggttgtcg ctggcgtgga tctctgcggc | 2040 |
| tcggccgaga acctgttcgt caagtcgcgc cgctccaagg tgtccaccca gaacgagccc | 2100 |
| tttgctaact ttgagtcgaa cgccgacggc tacttcgccg cgacggctg cggtgccctc | 2160 |
| gttctcaagc gcctttcgga ctgcactgac tccaccgaga agatctacgc gaccgtggac | 2220 |
| agcattgctg tcggcgacga ggtgggcccg actattaagc aggccctgaa gaacgcctcg | 2280 |
| atcgccgcga aggacatcga gctgcgcgga gctctccgcct ccagcggcaa gcaccactcc | 2340 |
| ggccgcatca cctgcgagga cgagcttaac gagctcggcg agatcttcaa cgagggcatt | 2400 |
| cagcgcgtgg ccatcggcag cgtcaaggcc aacgtcggcg acgtcggcta cgcctccggt | 2460 |

```
gctgccagcc tcatcaagac ggccctctgc ctctacaacc gctacctccc caagctcccc    2520
aactggaaca agccgaccaa ggacgtcgag tggtcgaaga gcttctttgt ctgcgagcac    2580
tcgcgcgcct ggctcaagaa cgtggacgag aaccgccacg cggtcgtgag cggcgtctgc    2640
gagaacggct cctgctacgg catcgtcatg agcgacgtcc agggccacca tgaggagtcg    2700
aacctcgtgt ccctcgataa gaacgagccc aaggtgctcg gtatctacgg cgattccgtg    2760
gacgatattc tggtccagct gaacaagtac ctggagaagt ccttcaggga gactggcact    2820
gctgcggctg cgcagaaggt gaagagccct accattgaca tcgactcgaa cgtctttgcc    2880
gagatgctga accttcccca ggacaagaac aagaagtttg ccgtcgctct ggtcacgacc    2940
cccaacaagc tccagcgcga gattgagctc gccgttaagg gcatccctcg ctgcgtgaag    3000
gccaagcgcg actggtgctc cccctccggc agcatctttg cgtgcaaccc gctcaagtcg    3060
gacaacattg cctttatgta cggcgagggc cgctcgcctt acgccggcct cggctacgat    3120
ctccaccgca tctggcccat gcttcacgag ctcgtgaaca accgcacgac tgagctgtgg    3180
gaccagggtg actcgtggta cctgccgcgc agctcctccg tggccgagaa ggagaaggtc    3240
tttggcgact cgacaagaa ccagatcgag atgttccgcc tcggtatttt cgtcagcatg    3300
tgctttaccg acatggcgac ggagctcctc ggccttaagc cgaaggccgc tttcggcctc    3360
tccctcggcg agatcagcat gctctttgct ttctcgaaga agaacaccaa gctctccaag    3420
gagcttactc gccgcctcaa ggaggccaag gtgtgggcgt cgcagctggc cgtcgagttc    3480
gccgccatcc gcgaccttg gaacatcccg gccgacaagt ccatcgatga gttctggcag    3540
ggttacttcg tttacgccaa ccgtacgctc gtggagaaca ccattggcga gaacaagttc    3600
gtccgcctcc ttatcgtcaa cgactcccag tcctgcctca ttgccggtaa gcccgatgag    3660
tgccagaagg tcatcgagaa gctccacctt aagctccccg ccgtccccgt cacccagggc    3720
atgattggcc actgcccgga ggccattccc tacctcgacc agatcagcca catccacgag    3780
atgcttgaga tcccgaagcc tgagaacgtc aagctcttca cgacgtccga aaccgcgag    3840
cttgtctcga tgaaggactc cgttagcaag ctcgtcgcgg agatctacca gcacgtcgct    3900
gacttcccca acattgtcaa caaggtcaag gagacttgca agacggacat tttcatcgag    3960
ctgggcagca caactaccg ttccggtgcc gtcaagacta tcctcggtcc ggagatcgtg    4020
agcgttgcca tcgaccgtca gaacgagact gcctggggcc agctcatgaa gatggtcgcc    4080
agcctgatct cccaccgcgt ccccggcgtc gagctcaaga agctgtacca tccggagctc    4140
ctgaagttcg atccccaggc caagcccaac cgctttatcc gcaacatcga gctcaacggc    4200
ttttcgacc gcacgaacat catcgtcgat aagcagcttt cccctgcgga cccgaagctc    4260
gccgagatcg tcaacaaccg caacatgccg aaggataacg tgtacgtccc cattgagcgc    4320
gtcaagacga tgatcaaggc cgagcccgct aacctccagg tgtccgtcgg ctcgaagccc    4380
gtggtcaccg agcgtatctc gtcggacgac aacctctttg agaagctctc ggagatcact    4440
aagtccttcg acggtgtcaa cgcctgcacc gaggccatgc tcggcgattc gggctttctc    4500
aagacgtacg aggttgacta cccgctctac accggcgcta tggccaaggg tatcgcctcc    4560
gccgacctcg tcattgcggc gggtaagtcg aagatccttg cgtcctttgg tgctggcggc    4620
ctcgctctcc aggtggtcga ggatgccatt aagcagatca aggctgagct tggcaacggt    4680
cccttttgccg tcaacctcat ccactcgcct ttcgacccct cgcttgagaa gggcaacgtt    4740
gaccttttcc tcaagtacaa cgtccgcttt gtcgaggtga gcgcgttcat gagcctcacc    4800
```

| | |
|---|---|
| cccaggtcg ttcgctaccg cgctgccggc cttgccaagg cccgtgacgg ctcggtcaag | 4860 |
| attcagaacc gcatcatcgc caagatttcg cgcacggagc tggccgagct cttcctcaag | 4920 |
| cccgctccga agaacatcct cgatgccctc gttgccgacg gctcgatttc ccaggagcag | 4980 |
| gctcagctcg cgctcctcgt ccctatggcc gatgacatca ccgttgaggc cgactccggt | 5040 |
| ggccacaccg acaaccgccc cattcatgtg ctcctccccc tcatcatcca gcagcgcaac | 5100 |
| cgcatttgca agcagtaccc gaagcacctc aaggtccgca tcggcgctgc cggtggcatc | 5160 |
| ggttgcccta aggcggcttt tgccgccttt gagatgggtg cggcctacat cgccacgggc | 5220 |
| accgttaacc agctctcgaa ggaggccggc acctgcgact acgtgcgcaa ggtgctcaac | 5280 |
| aaggccacct actccgacgt cacgatggct cccgctgccg acatgttcga ccacggtgtc | 5340 |
| gagctccagg ttctcaagaa gggcaccatg tttccgtcgc gcgccaagaa gctctacgac | 5400 |
| ctctttaaga agtacaagtc gatcgaggag ctccctgccg acgaggtcaa gaagctggag | 5460 |
| cagaaggttt ttaagaagtc gttcgacgag gtctgggacg agactaagaa ctactacatt | 5520 |
| aaccgcctcc actcccctga gaagatcgag cgcgcggagc gtgacgccaa gctgaagatg | 5580 |
| tcgctctgct ttcgttggta cctgagcaag tcgtcccgct gggccaacac cggcgagtcg | 5640 |
| ggccgtgtcc aggactacca gatctggtgc ggccccgcca tcggctcgta caacgacttc | 5700 |
| gcgaagggct cgccctgcct tgaccctgag atccttggct cgttcccgtc ggttgtccag | 5760 |
| atcaacaagc atattctgcg cggcgcttgc ttctaccagc gtctttcgca gctcaagtac | 5820 |
| cttaacttca actacgagga gctcgatacg ctcacctaca gcgctagcaa ctttatctaa | 5880 |

<210> SEQ ID NO 122
<211> LENGTH: 4368
<212> TYPE: DNA
<213> ORGANISM: Codon-optimized PFA3

<400> SEQUENCE: 122

| | |
|---|---|
| atggttggcc tgcagatgaa gaagaagcct gtgtgggaga tgtcgaagga ggagcagtcg | 60 |
| tccggcaaga acgtcgtctt tgactacgac gagctcctcg aattcgcgga gggtgacatc | 120 |
| ggcaaggtgt tcgccccccaa gtttgacatc atcgacaagt acagccgccg tgtgcgcctc | 180 |
| ccggcccgcg agtacctcct cgtcacccgt gtcacgctca tggatgccga ggtcggcaac | 240 |
| ttccgcgtcg gctcgcgcat ggtcaccgag tacgacgtcc cggtgaacgg cgagctttcc | 300 |
| cagggcggcg acgttccctg gccgtcctc gtcgagtcgg gccagtgcga cctcatgctt | 360 |
| atctcgtaca tgggcattga ctttcagtgc aagggtgacc gcgtttaccg ccttctcaac | 420 |
| acgaccctca cgttctacgg tgtcgcccac gagggcgaga ctctcgttta cgacatccgc | 480 |
| gtcactggtt tcgccaaggg catgcacggc gagattagca tgttcttctt cgagtacgac | 540 |
| tgctacgtca acggccgcct gctcatcgag atgcgcgacg gttgcgctgg cttcttcacg | 600 |
| gacgaggagc tcgccgcggg caagggcgtc atcaagaccg tcgctgagct ccacaagcgc | 660 |
| aagtcgattg tgcccaagtc gatcaagcct tttgccctca ccccgccgt ccacaagacg | 720 |
| atgttcagcg agaacgacat ggagaagctt tgcgagcgcc agtgggagaa cgtcctcggc | 780 |
| tccggcctcc agggcatcga ctacaagctg tgcgcccgca agatgctcat gatcgaccgc | 840 |
| atcacgaaga tccagcacaa cggcggtgcg tacggcctcg gcctcctcgt tggcgagaag | 900 |
| attcttgagc gcgaccattg gtacttccct tgccacttcg tcaaggacca ggtgatggcg | 960 |
| ggctccctcg ttagcgacgg ctgctcgcag ctgctcaagc tttacatgct ttggctcggc | 1020 |
| ctccacgacg tggtccccga tttccagttc cgtcctgtcc ctggccagcc caacaaggtg | 1080 |

-continued

```
cgctgccgtg gccagatcag cccccatcgt ggcaagctcg tgtacgtgat ggagattcgc    1140
gagatgggtt tcaacgagtc caccggccag ccctacgcga tcgctgacgt tgacattatc    1200
gatgtgaact acgagctcgg ccagtccttt gacatggccg acatcgactc gtacggccgt    1260
ggcaacctct ccaagaagat tgtcgtcgat ttcaagggca ttgcgctcca gatggagggc    1320
accgtcaaga gctccaacat catcgattcg tcccccaagt ccacgattat ccagccgccg    1380
cccaactgcc tccgcggcga tcctctcgcc ccctcgcagg tcacctggca cccgatggcc    1440
ggtgtcaacg gcgccccgc cccctccttc agcccgtcgg attaccctcc tcgtgccgtt    1500
tgctttaagc ccttccctgg caacccctc gacaacgatc atacgccggg caagatgccg    1560
ctgacctggt ttaacatgtc ggagtttatg tgcggcaagg tcagcaactg ccttggccct    1620
gagtttaagc gcttcgacaa ctccaagacg agccgctccc cggccttcga cctgccctg    1680 gttacgcgcg tggtgtcggt cagcgatatg gagttcaagc cccacctcaa catcgacgtc    1740
aacccgtcga agggcacgat gattggcgag ttcgactgcc ccgctgacgc ctggttcttt    1800
cagggctcct gcaacgacgg ccacatgccg tacagcatcg tcatggagat cgcccttcag    1860
accagcggtg tcctcacctc cgtcctcaag gccccgctca ctatgdacaa ggacgacatt    1920
ctctttcgca acctcgacgc caccgccgag atggtccgtt ccgacgtcga ttgccgcggt    1980
aagaccatca gaacttcac ccagtgcacc ggctacagca tgcttggcaa gatgggcatc    2040
caccgcttca cttttgagct ctcggtcgat gacgtcgtgt tttacaaggg ctcgaccagc    2100
tttggttggt tcacgccgga ggtgtttgag tcgcaggtcg gcctcgataa cggcaagaag    2160
gtccagccgt ggtatctgga gcagaagtcg tcgaacgtgg tgacgtacga tgtcgcctcg    2220
accgccggca aggacaagct cttctcgaag atcggctcga aggacgctca ggtccagcgt    2280
cgcaacaccc agtgcgagtt tctcgacacg atgcacatta ttccgaacac cggcaagtac    2340
aacaagggct acgcgcacgg tgagaagaag gtcaaccccca cgactggtt cttctcctgc    2400 cacttttggt tcgacccggt gatgcccggc tccctcggta ttgagtccat gttccagctc    2460
atcgaggcct tttcgattga ccagggtatc gcgtccaagc atggcatcgt gaaccctacc    2520
ttcgcgcact cgaacggcaa gacctcgtgg aagtaccgcg gccagctcaa caacaagggc    2580
aagcgcatgg acagcgagat tcacatcaag gatattgtca agaacgccga cggtactgtc    2640
gatctcatcg ccgatggttt tcttctcgtg gactcgcttc gcgtttacag cgccgatgac    2700
ctccgcgtca agatcgtccc cggcactaag gctgctccca gagcgtcgc ggccgctccg    2760 cgccatgtgg ccactccgat ccccggcgtc ccctccaaca cctcctcggt ggagatctcg    2820
cttgagtccc ttaagaagga gctcctcaac ctggagaagc ccctctacct tgagacttcc    2880
aaccacatcg tcaagcagtt cggcgacgtt aacaacggcc aggcctccgt catcccctcg    2940
tgcaccatta acgatctcgg tgagcgctcg tttatggaga cttacaacgt cgtcgctccc    3000
ctctacaccg gcgcgatggc gaagggcatc gcttcggcgg acctcgtcat cgctgccggt    3060
aagcgcaaga tcctcggcag cttcggcgcc ggtggcctcc cgatgcacct cgtgcgcgcc    3120
tcggtcgaga agatccaggc cgccctcccg gagggcccgt acgcggtcaa cctcatccac    3180
tcgcctttcg actcgaacct tgagaagggt aacgtggacc tctttctgga aagggcgtc    3240 cacgtggtcg aggcctccgc ctttaccgcc ctcacgaccc aggtcgttcg ctaccgcgcc    3300
tgcggcctct cgcgtgctaa ggacggttcc gtgctgatta agaaccgcat catcggtaag    3360
gtcagccgca cggagcttgc cgagatgttc tttcgcccgt ccccccagaa cctcctcgat    3420
```

| | |
|---|---|
| aagctcatcg ccagcggcga gatcaccaag gagcaggcgt ccctcgctct tgaggttcct | 3480 |
| atggccgacg atgtcgctgt tgaggccgac tccggcggcc acaccgataa ccgtcccatc | 3540 |
| cacgtcatcc tcccgctgat tattaacctc cgcaaccgta tccacaagga gtgcggcttt | 3600 |
| cctgccgctc tccgcgtccg cgtcggcgct ggtggtggca tcggttgccc ctcggccgct | 3660 |
| gtcgccgcct tcaacatggg cgcggccttc ctgatcaccg gctccgttaa ccaggtgagc | 3720 |
| aagcagtccg gcacgtgcga cattgtgcgc aagcagctta gcgaggccag ctactccgac | 3780 |
| atcacgatgg ctcccgccgc tgacatgttc gaccagggcg tggagctcca ggtcctcaag | 3840 |
| aagggtacga tgtttccctc gcgcgccaag aagctctacg agctcttttg catgtacaac | 3900 |
| agctttgacg acatgccgaa gtccgagctc cagcgcctgg agaagcgcat tttccagaag | 3960 |
| agcctcgccg aggtctggga ggagactaag gacttttaca tcaaccgcct caacaacccg | 4020 |
| gagaagatcg agcacgccga gaagaaggac cccaagctca agatgtccct ttgctttcgc | 4080 |
| tggtatctcg gcctttcgag ctttggggcc aacaacggca tcaaggagcg cagcatggat | 4140 |
| taccagattt ggtgcggccc ggccattggc agctacaacg acttcgtgaa gggcacctac | 4200 |
| ctcgaccccg ccgtcgccgg ttcgtacccc tgcgtggtcc agatcaacat gcagatcctc | 4260 |
| cgcggtgcgt gcttcctcca gcgcgtccgc gccattaagc acgacccgcg cctcgatatc | 4320 |
| gacgttgatg aggacgtctt tacctaccgc cccgagagca ccctctaa | 4368 |

<210> SEQ ID NO 123
<211> LENGTH: 33
<212> TYPE: DNA
<213> ORGANISM: Artificial Sequence
<220> FEATURE:
<223> OTHER INFORMATION: Synthetic Primer pDS233
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (28)..(28)
<223> OTHER INFORMATION: y is c or t

<400> SEQUENCE: 123
tgatatggga ggaatgaatt gtgtngtnga ygc      33

<210> SEQ ID NO 124
<211> LENGTH: 36
<212> TYPE: DNA
<213> ORGANISM: Artificial Sequence
<220> FEATURE:
<223> OTHER INFORMATION: Synthetic Primer pDS235
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (34)..(34)
<223> OTHER INFORMATION: r is a or g

<400> SEQUENCE: 124
ttccataaca aatgataat tagctccncc raancc      36

<210> SEQ ID NO 125
<211> LENGTH: 23

```
<212> TYPE: DNA
<213> ORGANISM: Artificial Sequence
<220> FEATURE:
<223> OTHER INFORMATION: Synthetic Primer prDS183
<220> FEATURE:
<221> NAME/KEY: misc_feature
<222> LOCATION: (15)..(15)
<223> OTHER INFORMATION: y is c or t
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (21)..(21)
<223> OTHER INFORMATION: n is a, c, g, or t

<400> SEQUENCE: 125
ggcggccaca ccgayaaymg ncc                                              23

<210> SEQ ID NO 126
<211> LENGTH: 22
<212> TYPE: DNA
<213> ORGANISM: Artificial Sequence
<220> FEATURE:
<223> OTHER INFORMATION: Synthetic Primer prDS184
<220> FEATURE:
<221> NAME/KEY: misc_feature
<222> LOCATION: (14)..(14)
<223> OTHER INFORMATION: r is a or g

<400> SEQUENCE: 126
cggggccgca ccanayytgr ta                                               22

<210> SEQ ID NO 127
<211> LENGTH: 17
<212> TYPE: DNA
<213> ORGANISM: Synthetic Primer prDS181
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: s is c or g
<220> FEATURE:
<221> NAME/KEY: misc_feature
<222> LOCATION: (15)..(15)
<223> OTHER INFORMATION: n is a, c, g, or t

<400> SEQUENCE: 127
tccttcggng cngsngg                                                     17
```

POLYUNSATURATED FATTY ACID SYNTHASE NUCLEIC ACID MOLECULES AND POLYPEPTIDES, COMPOSITIONS, AND METHODS OF MAKING AND USES THEREOF

CROSS-REFERENCE TO RELATED APPLICATION

This application is a divisional application which claims benefit of U.S. application Ser. No. 12/727,851, filed Mar. 19, 2010, which application claims the benefit of the filing date of U.S. Appl. No. 61/161,742, filed Mar. 19, 2009, and U.S. Appl. No. 61/296,460, filed Jan. 19, 2010, which are hereby incorporated by reference in their entireties for all purposes.

REFERENCE TO A SEQUENCE LISTING SUBMITTED ELECTRONICALLY

The content of the electronically submitted sequence listing ("sequence listing.txt", 507,769 bytes, created on Mar. 12, 2010) filed with the application is incorporated herein by reference in its entirety.

BACKGROUND OF THE INVENTION

Field of the Invention

The present invention is directed to isolated nucleic acid molecules and polypeptides of polyunsaturated fatty acid (PUFA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

Background of the Invention

Thraustochytrids are microorganisms of the order Thraustochytriales, including members of the genus *Thraustochytrium* and the genus *Schizochytrium*, and have been recognized as an alternative source of PUFAs. See, e.g., U.S. Pat. No. 5,130,242. It has recently been shown that polyketide synthase (PKS)-like systems in marine bacteria and thraustochytrids are capable of synthesizing polyunsaturated fatty acids (PUFAs) from acetyl-CoA and malonyl-CoA. These PKS synthase-like systems are also referred to herein as PUFA synthase systems. PUFA synthase systems in the marine bacteria *Shewanella* and *Vibrio marinus* are described in U.S. Pat. No. 6,140,486. A PUFA synthase system in a thraustochytrid of the genus *Schizochytrium* is described in U.S. Pat. No. 6,566,583. PUFA synthase systems in thraustochytrids of the genus *Schizochytrium* and the genus *Thraustochytrium* are also described in U.S. Pat. No. 7,247,461. U.S. Pat. No. 7,211,418 describes a PUFA synthase system in a thraustochytrid of the genus *Thraustochytrium* and the production of eicosapentaenoic acid (C20:5, omega-3) (EPA) and other PUFAs using the system. U.S. Pat. No. 7,217,856 describes PUFA synthase systems in *Shewanella olleyana* and *Shewanella japonica*. WO 2005/097982 describes a PUFA synthase system in strain SAM2179. U.S. Pat. Nos. 7,208,590 and 7,368,552 describe PUFA synthase genes and proteins from *Thraustochytrium aureum*.

PKS systems have been traditionally described in the literature as falling into one of three basic types, typically referred to as Type I (modular or iterative), Type II, and Type III. The Type I modular PKS system has also been referred to as a "modular" PKS system, and the Type I iterative PKS system has also been referred to as a "Type I" PKS system. The Type II system is characterized by separable proteins, each of which carries out a distinct enzymatic reaction. The enzymes work in concert to produce the end product and each individual enzyme of the system typically participates several times in the production of the end product. This type of system operates in a manner analogous to the fatty acid synthase (FAS) systems found in plants and bacteria. Type I iterative PKS systems are similar to the Type II system in that the enzymes are used in an iterative fashion to produce the end product. The Type I iterative system differs from the Type II system in that enzymatic activities, instead of being associated with separable proteins, occur as domains of larger proteins. This system is analogous to the Type I FAS systems found in animals and fungi.

In contrast to the Type II systems, each enzyme domain in the Type I modular PKS systems is used only once in the production of the end product. The domains are found in very large proteins and the product of each reaction is passed on to another domain in the PKS protein.

Type III systems have been more recently discovered and belong to the plant chalcone synthase family of condensing enzymes. Type III PKSs are distinct from Type I and Type II PKS systems and utilize free CoA substrates in iterative condensation reactions to usually produce a heterocyclic end product.

In the conventional or standard pathway for PUFA synthesis, medium chain-length saturated fatty acids (products of a fatty acid synthase (FAS) system) are modified by a series of elongation and desaturation reactions. The substrates for the elongation reaction are fatty acyl-CoA (the fatty acid chain to be elongated) and malonyl-CoA (the source of the two carbons added during each elongation reaction). The product of the elongase reaction is a fatty acyl-CoA that has two additional carbons in the linear chain. The desaturases create cis double bonds in the preexisting fatty acid chain by extraction of two hydrogens in an oxygen-dependant reaction. The substrates for the desaturases are either acyl-CoA (in some animals) or the fatty acid that is esterified to the glycerol backbone of a phospholipid (e.g., phosphatidylcholine).

Fatty acids are classified based on the length and saturation characteristics of the carbon chain. Fatty acids are termed short chain, medium chain, or long chain fatty acids based on the number of carbons present in the chain, are termed saturated fatty acids when no double bonds are present between the carbon atoms, and are termed unsaturated fatty acids when double bonds are present. Unsaturated long chain fatty acids are monounsaturated when only one double bond is present and are polyunsaturated when more than one double bond is present.

PUFAs are classified based on the position of the first double bond from the methyl end of the fatty acid: omega-3 (n-3) fatty acids contain a first double bond at the third carbon, while omega-6 (n-6) fatty acids contain a first double bond at the sixth carbon. For example, docosahexaenoic acid ("DHA") is an omega-3 PUFA with a chain length of 22 carbons and 6 double bonds, often designated as "22:6 n-3." Other omega-3 PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 PUFAs include arachidonic acid ("ARA"), designated as "20:4 n-6," and omega-6 docosapentaenoic acid ("DPA n-6"), designated as "22:5 n-6."

Omega-3 fatty acids are biologically important molecules that affect cellular physiology due to their presence in cell membranes, regulate production and gene expression of biologically active compounds, and serve as biosynthetic substrates. Roche, H. M., *Proc. Nutr. Soc.* 58: 397-401 (1999). DHA, for example, accounts for approximately 15%-20% of lipids in the human cerebral cortex, and 30%-60% of lipids in the retina, is concentrated in the testes and sperm, and is an important component of breast milk. Berge, J. P., and Barnathan, G. *Adv. Biochem. Eng. Biotechnol.* 96:49-125 (2005). DHA accounts for up to 97% of the omega-3 fatty acids in the brain and up to 93% of the omega-3 fatty acids in the retina. Moreover, DHA is essential for both fetal and infant development, as well as maintenance of cognitive functions in adults. Id. Because omega-3 fatty acids are not synthesized de novo in the human body, these fatty acids must be derived from nutritional sources.

Flaxseed oil and fish oils are considered good dietary sources of omega-3 fatty acids. Flaxseed oil contains no EPA, DHA, DPA, or ARA but rather contains linolenic acid (C18:3 n-3), a building block enabling the body to manufacture EPA. There is evidence, however, that the rate of metabolic conversion can be slow and variable, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste.

Oils produced from thraustochytrids often have simpler polyunsaturated fatty acid profiles than corresponding fish or microalgal oils. Lewis, T. E., *Mar. Biotechnol.* 1: 580-587 (1999). Strains of thraustrochytrid species have been reported to produce omega-3 fatty acids as a high percentage of the total fatty acids produced by the organisms. U.S. Pat. No. 5,130,242; Huang, J. et al., *J. Am. Oil. Chem. Soc.* 78: 605-610 (2001); Huang, J. et al., *Mar. Biotechnol.* 5: 450-457 (2003). However, isolated thraustochytrids vary in the identity and amounts of PUFAs produced, such that some previously described strains can have undesirable PUFA profiles.

Efforts have been made to produce PUFAs in oil-seed crop plants by modification of the endogenously-produced fatty acids. Genetic modification of these plants with various individual genes for fatty acid elongases and desaturases has produced leaves or seeds containing measurable levels of PUFAs such as EPA, but also containing significant levels of mixed shorter-chain and less unsaturated PUFAs (Qi et al., *Nature Biotech.* 22:739 (2004); PCT Publ. No. WO 04/071467; Abbadi et al., *Plant Cell* 16:1 (2004)); Napier and Sayanova, *Proc. Nutrition Society* 64:387-393 (2005); Robert et al., *Functional Plant Biology* 32:473-479 (2005); and U.S. Appl. Publ. No. 2004/0172682).

As such, a continuing need exists for the isolation of nucleic acid molecules and polypeptides associated with desirable PUFA profiles and methods to produce desirable PUFA profiles through use of such nucleic acid molecules and polypeptides.

BRIEF SUMMARY OF THE INVENTION

The present invention is directed to an isolated nucleic acid molecule selected from the group consisting of: (a) a nucleic acid molecule comprising a polynucleotide sequence at least 80% identical to SEQ ID NO:1, wherein the polynucleotide sequence encodes a polypeptide comprising PUFA synthase activity selected from the group consisting of beta-ketoacyl-ACP synthase (KS) activity, malonyl-CoA: ACP acyltransferase (MAT) activity, acyl carrier protein (ACP) activity, ketoreductase (KR) activity, beta-hydroxyacyl-ACP dehydrase (DH) activity, and combinations thereof; (b) a nucleic acid molecule comprising a polynucleotide sequence at least 80% identical to SEQ ID NO:7, wherein the polynucleotide sequence encodes a polypeptide comprising KS activity; (c) a nucleic acid molecule comprising a polynucleotide sequence at least 80% identical to SEQ ID NO:9, wherein the polynucleotide sequence encodes a polypeptide comprising MAT activity; (d) a nucleic acid molecule comprising a polynucleotide sequence at least 80% identical to any one of SEQ ID NOs:13, 15, 17, 19, 21, or 23, wherein the polynucleotide sequence encodes a polypeptide comprising ACP activity; (e) a nucleic acid molecule comprising a polynucleotide sequence at least 80% identical to SEQ ID NO:11, wherein the polynucleotide sequence encodes a polypeptide comprising ACP activity; (f) a nucleic acid molecule comprising a polynucleotide sequence at least 80% identical to SEQ ID NO:25, wherein the polynucleotide sequence encodes a polypeptide comprising KR activity; and (g) a nucleic acid molecule comprising a polynucleotide sequence at least 80% identical to SEQ ID NO:27, wherein the polynucleotide sequence encodes a polypeptide comprising DH activity. In some embodiments, the polynucleotide sequences are at least 90% identical or at least 95% identical to SEQ ID NOs:1, 7, 9, 11, 13, 15, 17, 19, 21, 23, 25, and 27, respectively. In some embodiments, the nucleic acid molecules comprise the polynucleotide sequences of SEQ ID NOs:1, 7, 9, 11, 13, 15, 17, 19, 21, 23, 25, and 27, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:2, and wherein the polypeptide comprises a PUFA synthase activity selected from the group consisting of KS activity, MAT activity, ACP activity, KR activity, DH activity, and combinations thereof; (b) a nucleic acid molecule comprising a polynucleotide sequence encoding a polypeptide, wherein the polypeptide comprises an amino acid sequence at least 80% identical to SEQ ID NO:8, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:10, and wherein the polypeptide comprises MAT activity; (d) a nucleic acid molecule comprising a polynucleotide sequence encoding a polypeptide, wherein the polypeptide comprises an amino acid sequence at least 80% identical to any one of SEQ ID NOs:14, 16, 18, 20, 22, or 24, and wherein the polypeptide comprises ACP activity; (e) a nucleic acid molecule comprising a polynucleotide sequence encoding a polypeptide, wherein the polypeptide comprises an amino acid sequence at least 80% identical to SEQ ID NO:12, and wherein the polypeptide comprises ACP activity; (f) a nucleic acid molecule comprising a polynucleotide sequence encoding a polypeptide, wherein the polypeptide comprises an amino acid sequence at least 80% identical to SEQ ID NO:26, and wherein the polypeptide comprises KR activity; and (g) a nucleic acid molecule comprising a polynucleotide sequence encoding a polypeptide, wherein the polypeptide comprises an amino acid sequence at least 80% identical to SEQ ID NO:28, and wherein the polypeptide comprises DH activity. In some embodiments, the amino acid sequences are at least 90% identical or at least 95% identical to SEQ ID NOs:2, 8, 10, 12, 14, 16, 18, 20, 22, 24, 26, and 28, respectively. In some embodiments, the polypeptides comprise the amino acid sequences of SEQ ID NOs:2, 8, 10, 12, 14, 16, 18, 20, 22, 24, 26, and 28, respectively.

The present invention is directed to an isolated nucleic acid molecule selected from the group consisting of: (a) a nucleic acid molecule comprising a polynucleotide sequence at least 80% identical to SEQ ID NO:3, wherein the polynucleotide sequence encodes a polypeptide comprising PUFA synthase activity selected from the group consisting of KS activity, chain length factor (CLF) activity, acyltransferase (AT) activity, enoyl-ACP reductase (ER) activity, and combinations thereof; (b) a nucleic acid molecule comprising a polynucleotide sequence at least 80% identical to SEQ ID NO:29, wherein the polynucleotide sequence encodes a polypeptide comprising KS activity; (c) a nucleic acid molecule comprising a polynucleotide sequence at least 80% identical to SEQ ID NO:31, wherein the polynucleotide sequence encodes a polypeptide comprising CLF activity; (d) a nucleic acid molecule comprising a polynucleotide sequence at least 80% identical to SEQ ID NO:33, wherein the polynucleotide sequence encodes a polypeptide comprising AT activity; and (e) a nucleic acid molecule comprising a polynucleotide sequence at least 80% identical to SEQ ID NO:35, wherein the polynucleotide sequence encodes a polypeptide comprising ER activity. In some embodiments, the polynucleotide sequences are at least 90% identical or at least 95% identical to SEQ ID NOs:3, 29, 31, 33, and 35, respectively. In some embodiments, the nucleic acid molecules comprise the polynucleotide sequences of SEQ ID NOs:3, 29, 31, 33, and 35, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:4, and wherein the polypeptide comprises a PUFA synthase activity selected from the group consisting of KS activity, CLF activity, AT activity, ER activity, and combinations thereof; (b) a nucleic acid molecule comprising a polynucleotide sequence encoding a polypeptide, wherein the polypeptide comprises an amino acid sequence at least 80% identical to SEQ ID NO:30, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:32, and wherein the polypeptide comprises CLF activity; (d) a nucleic acid molecule comprising a polynucleotide sequence encoding a polypeptide, wherein the polypeptide comprises an amino acid sequence at least 80% identical to SEQ ID NO:34, and wherein the polypeptide comprises AT activity; and (e) a nucleic acid molecule comprising a polynucleotide sequence encoding a polypeptide, wherein the polypeptide comprises an amino acid sequence at least 80% identical to SEQ ID NO:36, and wherein the polypeptide comprises ER activity. In some embodiments, the amino acid sequences are at least 90% identical or at least 95% identical to SEQ ID NOs:4, 30, 32, 34, and 36, respectively. In some embodiments, the polypeptides comprise the amino acid sequence of SEQ ID NOs:4, 30, 32, 34, and 36, respectively.

The present invention is directed to an isolated nucleic acid molecule selected from the group consisting of: (a) an nucleic acid molecule comprising a polynucleotide sequence at least 80% identical to SEQ ID NO:5, wherein the polynucleotide sequence encodes a polypeptide comprising PUFA synthase activity selected from the group consisting of DH activity, ER activity, and combinations thereof; (b) a nucleic acid molecule comprising a polynucleotide sequence at least 80% identical to SEQ ID NO:37, wherein the polynucleotide sequence encodes a polypeptide comprising DH activity; (c) a nucleic acid molecule comprising a polynucleotide sequence at least 80% identical to SEQ ID NO:39, wherein the polynucleotide sequence encodes a polypeptide comprising DH activity; and (d) a nucleic acid molecule comprising a polynucleotide sequence at least 80% identical to SEQ ID NO:41, wherein the polynucleotide sequence encodes a polypeptide comprising ER activity. In some embodiments, the polynucleotide sequences are at least 90% identical or at least 95% identical to SEQ ID NOs:5, 37, 39, and 41, respectively. In some embodiments, the nucleic acid molecules comprise the polynucleotide sequences of SEQ ID NOs:5, 37, 39, and 41, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:6, wherein the polypeptide comprises PUFA synthase activity selected from the group consisting of DH activity, ER activity, and combinations thereof; (b) a nucleic acid molecule comprising a polynucleotide sequence encoding a polypeptide, wherein the polypeptide comprises an amino acid sequence at least 80% identical to SEQ ID NO:38, and wherein the polypeptide comprises DH activity; (c) a nucleic acid molecule comprising a polynucleotide sequence encoding a polypeptide, wherein the polypeptide comprises an amino acid sequence at least 80% identical to SEQ ID NO:40, and wherein the polypeptide comprises DH activity; and (d) a nucleic acid molecule comprising a polynucleotide sequence encoding a polypeptide, wherein the polypeptide comprises an amino acid sequence at least 80% identical to SEQ ID NO:42, and wherein the polypeptide comprises ER activity. In some embodiments, the amino acid sequences are at least 90% identical or at least 95% identical to SEQ ID NOs:6, 38, 40, and 42, respectively. In some embodiments, the polypeptides comprise the amino acid sequences of SEQ ID NOs:6, 38, 40, and 42, respectively.

The present invention is directed to an isolated nucleic acid molecule selected from the group consisting of: (a) a nucleic acid molecule comprising a polynucleotide sequence at least 80% identical to SEQ ID NO:68 or SEQ ID NO:120, wherein the polynucleotide sequence encodes a polypeptide comprising PUFA synthase activity selected from the group consisting of KS activity, MAT activity, ACP activity, KR activity, DH activity, and combinations thereof; (b) a nucleic acid molecule comprising a polynucleotide sequence at least 80% identical to SEQ ID NO:74, wherein the polynucleotide sequence encodes a polypeptide comprising KS activity; (c) a nucleic acid molecule comprising a polynucleotide sequence at least 80% identical to SEQ ID NO:76, wherein the polynucleotide sequence encodes a polypeptide comprising MAT activity; (d) a nucleic acid molecule comprising a polynucleotide sequence at least 80% identical to any one of SEQ ID NOs: 80, 82, 84, 86, 88, 90, 92, 94, 96, or 98, wherein the polynucleotide sequence encodes a polypeptide comprising ACP activity; (e) a nucleic acid molecule comprising a polynucleotide sequence at least 80% identical to SEQ ID NO:78, wherein the polynucleotide sequence encodes a polypeptide comprising ACP activity; (f) a nucleic acid molecule comprising a polynucleotide sequence at least 80% identical to SEQ ID NO:100, wherein the polynucleotide sequence encodes a polypeptide comprising KR activity; and (g) a nucleic acid molecule comprising a polynucleotide sequence at least 80% identical to SEQ ID NO:118, wherein the polynucleotide sequence encodes a polypeptide comprising DH activity. In some embodiments, the polynucleotide sequences are at least 90% identical or at least 95% identical to SEQ ID NOs:68, 74, 76, 78, 80, 82, 84, 86, 88, 90, 92, 94, 96, 98, 100, 118, and 120, respectively. In some embodiments, the nucleic acid molecules comprise the polynucleotide sequences of SEQ ID NOs:68, 74, 76, 78, 80, 82, 84, 86, 88, 90, 92, 94, 96, 98, 100, 118, and 120, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:69, and wherein the polypeptide comprises a PUFA synthase activity selected from the group consisting of KS activity, MAT activity, ACP activity, KR activity, DH activity, and combinations thereof; (b) a nucleic acid molecule comprising a polynucleotide sequence encoding a polypeptide, wherein the polypeptide comprises an amino acid sequence at least 80% identical to SEQ ID NO:75, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:77, and wherein the polypeptide comprises MAT activity; (d) a nucleic acid molecule comprising a polynucleotide sequence encoding a polypeptide, wherein the polypeptide comprises an amino acid sequence at least 80% identical to any one of SEQ ID NOs:81, 83, 85, 87, 89, 91, 93, 95, 97, or 99, and wherein the polypeptide comprises ACP activity; (e) a nucleic acid molecule comprising a polynucleotide sequence encoding a polypeptide, wherein the polypeptide comprises an amino acid sequence at least 80% identical to SEQ ID NO:79, and wherein the polypeptide comprises ACP activity; (f) a nucleic acid molecule comprising a polynucleotide sequence encoding a polypeptide, wherein the polypeptide comprises an amino acid sequence at least 80% identical to SEQ ID NO:101, and wherein the polypeptide comprises KR activity; and (g) a nucleic acid molecule comprising a polynucleotide sequence encoding a polypeptide, wherein the polypeptide comprises an amino acid sequence at least 80% identical to SEQ ID NO:119, and wherein the polypeptide comprises DH activity. In some embodiments, the amino acid sequences are at least 90% identical or at least 95% identical to SEQ ID NOs:69, 75, 77, 79, 81, 83, 85, 87, 89, 91, 93, 95, 97, 99, 101, and 119, respectively. In some embodiments, the polypeptides comprise the amino acid sequences of SEQ ID NOs:69, 75, 77, 79, 81, 83, 85, 87, 89, 91, 93, 95, 97, 99, 101, and 119, respectively.

The present invention is directed to an isolated nucleic acid molecule selected from the group consisting of: (a) a nucleic acid molecule comprising a polynucleotide sequence at least 80% identical to SEQ ID NO:70 or SEQ ID NO:121, wherein the polynucleotide sequence encodes a polypeptide comprising PUFA synthase activity selected from the group consisting of KS activity, chain length factor (CLF) activity, acyltransferase (AT) activity, enoyl-ACP reductase (ER) activity, and combinations thereof; (b) a nucleic acid molecule comprising a polynucleotide sequence at least 80% identical to SEQ ID NO:102, wherein the polynucleotide sequence encodes a polypeptide comprising KS activity; (c) a nucleic acid molecule comprising a polynucleotide sequence at least 80% identical to SEQ ID NO:104, wherein the polynucleotide sequence encodes a polypeptide comprising CLF activity; (d) a nucleic acid molecule comprising a polynucleotide sequence at least 80% identical to SEQ ID NO:106, wherein the polynucleotide sequence encodes a polypeptide comprising AT activity; and (e) a nucleic acid molecule comprising a polynucleotide sequence at least 80% identical to SEQ ID NO:108, wherein the polynucleotide sequence encodes a polypeptide comprising ER activity. In some embodiments, the polynucleotide sequences are at least 90% identical or at least 95% identical to SEQ ID NOs:70, 102, 104, 106, 108, and 121, respectively. In some embodiments, the nucleic acid molecules comprise the polynucleotide sequences of SEQ ID NOs:70, 102, 104, 106, 108, and 121, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:71, and wherein the polypeptide comprises a PUFA synthase activity selected from the group consisting of KS activity, CLF activity, AT activity, ER activity, and combinations thereof; (b) a nucleic acid molecule comprising a polynucleotide sequence encoding a polypeptide, wherein the polypeptide comprises an amino acid sequence at least 80% identical to SEQ ID NO:103, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:105, and wherein the polypeptide comprises CLF activity; (d) a nucleic acid molecule comprising a polynucleotide sequence encoding a polypeptide, wherein the polypeptide comprises an amino acid sequence at least 80% identical to SEQ ID NO:107, and wherein the polypeptide comprises AT activity; and (e) a nucleic acid molecule comprising a polynucleotide sequence encoding a polypeptide, wherein the polypeptide comprises an amino acid sequence at least 80% identical to SEQ ID NO:109, and wherein the polypeptide comprises ER activity. In some embodiments, the amino acid sequences are at least 90% identical or at least 95% identical to SEQ ID NOs:71, 103, 105, 107, and 109, respectively. In some embodiments, the polypeptides comprise the amino acid sequence of SEQ ID NOs:71, 103, 105, 107, and 109, respectively.

The present invention is directed to an isolated nucleic acid molecule selected from the group consisting of: (a) an nucleic acid molecule comprising a polynucleotide sequence at least 80% identical to SEQ ID NO:72 or SEQ ID NO:122, wherein the polynucleotide sequence encodes a polypeptide comprising PUFA synthase activity selected from the group consisting of DH activity, ER activity, and combinations thereof; (b) a nucleic acid molecule comprising a polynucleotide sequence at least 80% identical to SEQ ID NO:110, wherein the polynucleotide sequence encodes a polypeptide comprising DH activity; (c) a nucleic acid molecule comprising a polynucleotide sequence at least 80% identical to SEQ ID NO:112, wherein the polynucleotide sequence encodes a polypeptide comprising DH activity; and (d) a nucleic acid molecule comprising a polynucleotide sequence at least 80% identical to SEQ ID NO:114, wherein the polynucleotide sequence encodes a polypeptide comprising ER activity. In some embodiments, the polynucleotide sequences are at least 90% identical or at least 95% identical to SEQ ID NOs:72, 110, 112, 114, and 122, respectively. In some embodiments, the nucleic acid molecules comprise the polynucleotide sequences of SEQ ID NOs:72, 110, 112, 114, and 122, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:73, wherein the polypeptide comprises PUFA synthase activity selected from the group consisting of DH activity, ER activity, and combinations thereof; (b) a nucleic acid molecule comprising a polynucleotide sequence encoding a polypeptide, wherein the polypeptide comprises an amino acid sequence at least 80% identical to SEQ ID NO:111, and wherein the polypeptide comprises DH activity; (c) a nucleic acid molecule comprising a polynucleotide sequence encoding a polypeptide, wherein the polypeptide comprises an amino acid sequence at least 80% identical to SEQ ID NO:113, and wherein the polypeptide comprises DH activity; and (d) a nucleic acid molecule comprising a polynucleotide sequence encoding a polypeptide, wherein the polypeptide comprises an amino acid sequence at least 80% identical to SEQ ID NO:115, and wherein the polypeptide comprises ER activity. In some embodiments, the amino acid sequences are at least 90% identical or at least 95% identical to SEQ ID NOs:73, 111, 113, and 115, respectively. In some embodiments, the polypeptides comprise the amino acid sequences of SEQ ID NOs:73, 111, 113, and 115, respectively.

The present invention is directed to an isolated nucleic acid molecule comprising a polynucleotide sequence encoding a polypeptide comprising PUFA synthase activity selected from the group consisting of KS activity, MAT activity, ACP activity, KR activity, CLF activity, AT activity, ER activity, DH activity, and combinations thereof, wherein the polynucleotide hybridizes under stringent conditions to the complement of any of the polynucleotide sequences described above.

The present invention is directed to an isolated nucleic acid molecule comprising a polynucleotide sequence that is fully complementary to any of the polynucleotide sequences described above.

The present invention is directed to a recombinant nucleic acid molecule comprising any of the nucleic acid molecules described above or combinations thereof and a transcription control sequence. In some embodiments, the recombinant nucleic acid molecule is a recombinant vector.

The present invention is directed to a host cell that expresses any of the nucleic acid molecules described above, any of the recombinant nucleic acid molecules described above, and combinations thereof. In some embodiments, the host cell is selected from the group consisting of a plant cell, a microbial cell, and an animal cell. In some embodiments, the microbial cell is a bacterium. In some embodiments, the bacterium is *E. coli*. In some embodiments, the bacterium is a marine bacterium. In some embodiments, the microbial cell is a thraustochytrid. In some embodiments, the thraustochytrid is a *Schizochytrium*. In some embodiments, the thraustochytrid is a *Thraustochytrium*. In some embodiments, the thraustochytrid is an *Ulkenia*.

The present invention is directed to a method to produce at least one PUFA, comprising: expressing a PUFA synthase gene in a host cell under conditions effective to produce PUFA, wherein the PUFA synthase gene comprises any of the isolated nucleic acid molecules described above, any of the recombinant nucleic acid molecules described above, or combinations thereof, and wherein at least one PUFA is produced. In one aspect of this embodiment, the host cell is selected from the group consisting of a plant cell, an isolated animal cell, and a microbial cell. In another aspect of this embodiment, the at least one PUFA comprises docosahexaenoic acid (DHA) or eicosapentaenoic acid (EPA).

The present invention is directed to a method to produce lipids enriched for DHA, EPA, or a combination thereof, comprising: expressing a PUFA synthase gene in a host cell under conditions effective to produce lipids, wherein the PUFA synthase gene comprises any of the isolated nucleic acid molecules described above, any of the recombinant nucleic acid molecules described above, or combinations thereof in the host cell, and wherein lipids enriched with DHA, EPA, or a combination thereof are produced. The present invention is directed to a method for making a recombinant vector comprising inserting any one of the isolated nucleic acid molecules described above into a vector.

The present invention is directed to a method of making a recombinant host cell comprising introducing a recombinant vector as described above into a host cell. In some embodiments, the host cell is selected from the group consisting of a plant cell, an isolated animal cell, and a microbial cell.

The present invention is directed to an isolated polypeptide encoded by any of the polynucleotide sequences described above.

The present invention is directed to an isolated polypeptide selected from the group consisting of: (a) a polypeptide comprising an amino acid sequence at least 80% identical to SEQ ID NO:2, wherein the polypeptide comprises a PUFA synthase activity selected from the group consisting of KS activity, MAT activity, ACP activity, KR activity, DH activity, and combinations thereof; (b) a polypeptide comprising an amino acid sequence at least 80% identical to SEQ ID NO:8, wherein the polypeptide comprises KS activity; (c) a polypeptide comprising an amino acid sequence at least 80% identical to SEQ ID NO:10, wherein the polypeptide comprises MAT activity; (d) a polypeptide comprising an amino acid sequence at least 80% identical to any one of SEQ ID NOs:14, 16, 18, 20, 22, or 24, wherein the polypeptide comprises ACP activity; (e) a polypeptide comprising an amino acid sequence at least 80% identical to SEQ ID NO:12, wherein the polypeptide comprises ACP activity; (f) a polypeptide comprising an amino acid sequence at least 80% identical to SEQ ID NO:26, wherein the polypeptide comprises KR activity; and (g) a polypeptide comprising an amino acid sequence at least 80% identical to SEQ ID NO:28, wherein the polypeptide comprises DH activity. In some embodiments, the amino acid sequences are at least 90% identical or at least 95% identical to SEQ ID NOs:2, 8, 10, 12, 14, 16, 18, 20, 22, 24, 26, and 28, respectively. In some embodiments, the polypeptides comprise the amino acid sequences of SEQ ID NOs:2, 8, 10, 12, 14, 16, 18, 20, 22, 24, 26, and 28, respectively.

The present invention is directed to an isolated polypeptide selected from the group consisting of: (a) a polypeptide comprising an amino acid sequence at least 80% identical to SEQ ID NO:4, wherein the polypeptide comprises a PUFA synthase activity selected from the group consisting of KS activity, CLF activity, AT activity, ER activity, and combinations thereof; (b) a polypeptide comprising an amino acid sequence at least 80% identical to SEQ ID NO:30, wherein the polypeptide comprises KS activity; (c) a polypeptide comprising an amino acid sequence at least 80% identical to SEQ ID NO:32, wherein the polypeptide comprises CLF activity; (d) a polypeptide comprising an amino acid sequence at least 80% identical to SEQ ID NO:34, wherein the polypeptide comprises AT activity; and (e) a polypeptide comprising an amino acid sequence at least 80% identical to SEQ ID NO:36, wherein the polypeptide comprises ER activity. In some embodiments, the amino acid sequences are at least 90% identical or at least 95% identical to SEQ ID NOs:4, 30, 32, 34, and 36, respectively. In some embodiments, the polypeptides comprise the amino acid sequence of SEQ ID NOs:4, 30, 32, 34, and 36, respectively.

The present invention is directed to an isolated polypeptide selected from the group consisting of: (a) a polypeptide comprising an amino acid sequence at least 80% identical to SEQ ID NO:6, wherein the polypeptide comprises a PUFA synthase activity selected from the group consisting of DH activity, ER activity, and combinations thereof; (b) a polypeptide comprising an amino acid sequence at least 80% identical to SEQ ID NO:38, wherein the polypeptide comprises DH activity; (c) a polypeptide comprising an amino acid sequence at least 80% identical to SEQ ID NO:40, wherein the polypeptide comprises DH activity; and (d) a polypeptide comprising an amino acid sequence at least 80% identical to SEQ ID NO:42, wherein the polypeptide comprises ER activity. In some embodiments, the amino acid sequences are at least 90% identical or at least 95% identical to SEQ ID NOs:6, 38, 40, and 42, respectively. In some embodiments, the polypeptides comprise the amino acid sequences of SEQ ID NOs:6, 38, 40, and 42, respectively.

The present invention is directed to an isolated polypeptide selected from the group consisting of: (a) a polypeptide comprising an amino acid sequence at least 80% identical to SEQ ID NO:69, wherein the polypeptide comprises a PUFA synthase activity selected from the group consisting of KS activity, MAT activity, ACP activity, KR activity, DH activity, and combinations thereof; (b) a polypeptide comprising an amino acid sequence at least 80% identical to SEQ ID NO:75, wherein the polypeptide comprises KS activity; (c) a polypeptide comprising an amino acid sequence at least 80% identical to SEQ ID NO:77, wherein the polypeptide comprises MAT activity; (d) a polypeptide comprising an amino acid sequence at least 80% identical to any one of SEQ ID NOs:81, 83, 85, 87, 89, 91, 93, 95, 97, or 99, wherein the polypeptide comprises ACP activity; (e) a polypeptide comprising an amino acid sequence at least 80% identical to SEQ ID NO:79, wherein the polypeptide comprises ACP activity; (f) a polypeptide comprising an amino acid sequence at least 80% identical to SEQ ID NO:101, wherein the polypeptide comprises KR activity; and (g) a polypeptide comprising an amino acid sequence at least 80% identical to SEQ ID NO:119, wherein the polypeptide comprises DH activity. In some embodiments, the amino acid sequences are at least 90% identical or at least 95% identical to SEQ ID NOs:69, 75, 77, 79, 81, 83, 85, 87, 89, 91, 93, 95, 97, 99, 101, and 119, respectively. In some embodiments, the polypeptides comprise the amino acid sequences of SEQ ID NOs:69, 75, 77, 79, 81, 83, 85, 87, 89, 91, 93, 95, 97, 99, 101, and 119, respectively.

The present invention is directed to an isolated polypeptide selected from the group consisting of: (a) a polypeptide comprising an amino acid sequence at least 80% identical to SEQ ID NO:71, wherein the polypeptide comprises a PUFA synthase activity selected from the group consisting of KS activity, CLF activity, AT activity, ER activity, and combinations thereof; (b) a polypeptide comprising an amino acid sequence at least 80% identical to SEQ ID NO:103, wherein the polypeptide comprises KS activity; (c) a polypeptide comprising an amino acid sequence at least 80% identical to SEQ ID NO:105, wherein the polypeptide comprises CLF activity; (d) a polypeptide comprising an amino acid sequence at least 80% identical to SEQ ID NO:107, wherein the polypeptide comprises AT activity; and (e) a polypeptide comprising an amino acid sequence at least 80% identical to SEQ ID NO:109, wherein the polypeptide comprises ER activity. In some embodiments, the amino acid sequences are at least 90% identical or at least 95% identical to SEQ ID NOs:71, 103, 105, 107, and 109, respectively. In some embodiments, the polypeptides comprise the amino acid sequence of SEQ ID NOs:71, 103, 105, 107, and 109, respectively.

The present invention is directed to an isolated polypeptide selected from the group consisting of: (a) a polypeptide comprising an amino acid sequence at least 80% identical to SEQ ID NO:73, wherein the polypeptide comprises a PUFA synthase activity selected from the group consisting of DH activity, ER activity, and combinations thereof; (b) a polypeptide comprising an amino acid sequence at least 80% identical to SEQ ID NO:111, wherein the polypeptide comprises DH activity; (c) a polypeptide comprising an amino acid sequence at least 80% identical to SEQ ID NO:113, wherein the polypeptide comprises DH activity; and (d) a polypeptide comprising an amino acid sequence at least 80% identical to SEQ ID NO:115, wherein the polypeptide comprises ER activity. In some embodiments, the amino acid sequences are at least 90% identical or at least 95% identical to SEQ ID NOs:73, 111, 113, and 115, respectively. In some embodiments, the polypeptides comprise the amino acid sequences of SEQ ID NOs:73, 111, 113, and 115, respectively.

In some embodiments, any of the isolated polypeptides of the invention can be a fusion polypeptide.

The present invention is directed to a composition comprising any of the polypeptides described above and a biologically acceptable carrier.

The present invention is directed to a method of increasing production of DHA, EPA, or a combination thereof in an organism having PUFA synthase activity, comprising: expressing any of the isolated nucleic acid molecules described above, any of the recombinant nucleic acid molecules described above, or combinations thereof in the organism under conditions effective to produce DHA, EPA, or a combination thereof, wherein the PUFA synthase activity replaces an inactive or deleted activity, introduces a new activity, or enhances an existing activity in the organism, and wherein production of DHA, EPA, or a combination thereof in the organism is increased.

The present invention is directed to a method of isolating lipids from a host cell, comprising: (a) expressing a PUFA synthase gene in the host cell under conditions effective to produce lipids, wherein the PUFA synthase gene comprises any of the isolated nucleic acid molecules described above, any of the recombinant nucleic acid molecules described above, or combinations thereof in the host cell, and (b) isolating lipids from the host cell. In some embodiments, the host cell is selected from the group consisting of a plant cell, an isolated animal cell, and a microbial cell. In some embodiments, the lipids comprise DHA, EPA, or a combination thereof.

BRIEF DESCRIPTION OF THE DRAWINGS/FIGURES

FIG. 1 shows the gene architecture of the *Schizochytrium* sp. ATCC PTA-9695 PUFA synthases of the invention.

FIG. 2 shows the gene architecture of the *Thraustochytrium* sp. ATCC PTA-10212 PUFA synthases of the invention.

FIG. 3 shows the domain architecture of the *Schizochytrium* sp. ATCC PTA-9695 and *Thraustochytrium* sp. ATCC PTA-10212 PUFA synthases of the invention and synthases from *Schizochytrium* sp. ATCC 20888, *Thraustochytrium* sp. ATCC 20892, *Thraustochytrium aureum*, and SAM2179.

FIG. 4 shows an alignment of a *Schizochytrium* sp. ATCC PTA-9695 Pfa1p amino acid sequence (SEQ ID NO:2) and a *Thraustochytrium* sp. ATCC PTA-10212 Pfa1p amino acid sequence (SEQ ID NO:69) of the invention with the OrfA sequences from *Schizochytrium* sp. ATCC 20888 (SEQ ID NO:54) and *Thraustochytrium* sp. ATCC 20892 (SEQ ID NO:56) and the ORF A sequence from *Thraustochytrium aureum* (SEQ ID NO:55).

FIG. 5 shows an alignment of a *Schizochytrium* sp. ATCC PTA-9695 Pfa2p amino acid sequence (SEQ ID NO:4) and a *Thraustochytrium* sp. ATCC PTA-10212 Pfa2p amino acid sequence (SEQ ID NO:71) of the invention with the OrfB sequences from *Schizochytrium* sp. ATCC 20888 (SEQ ID NO:57) and *Thraustochytrium* sp. ATCC 20892 (SEQ ID N0:58) and the ORF B sequence from *Thraustochytrium aureum* (SEQ ID NO:59).

Figure 6:
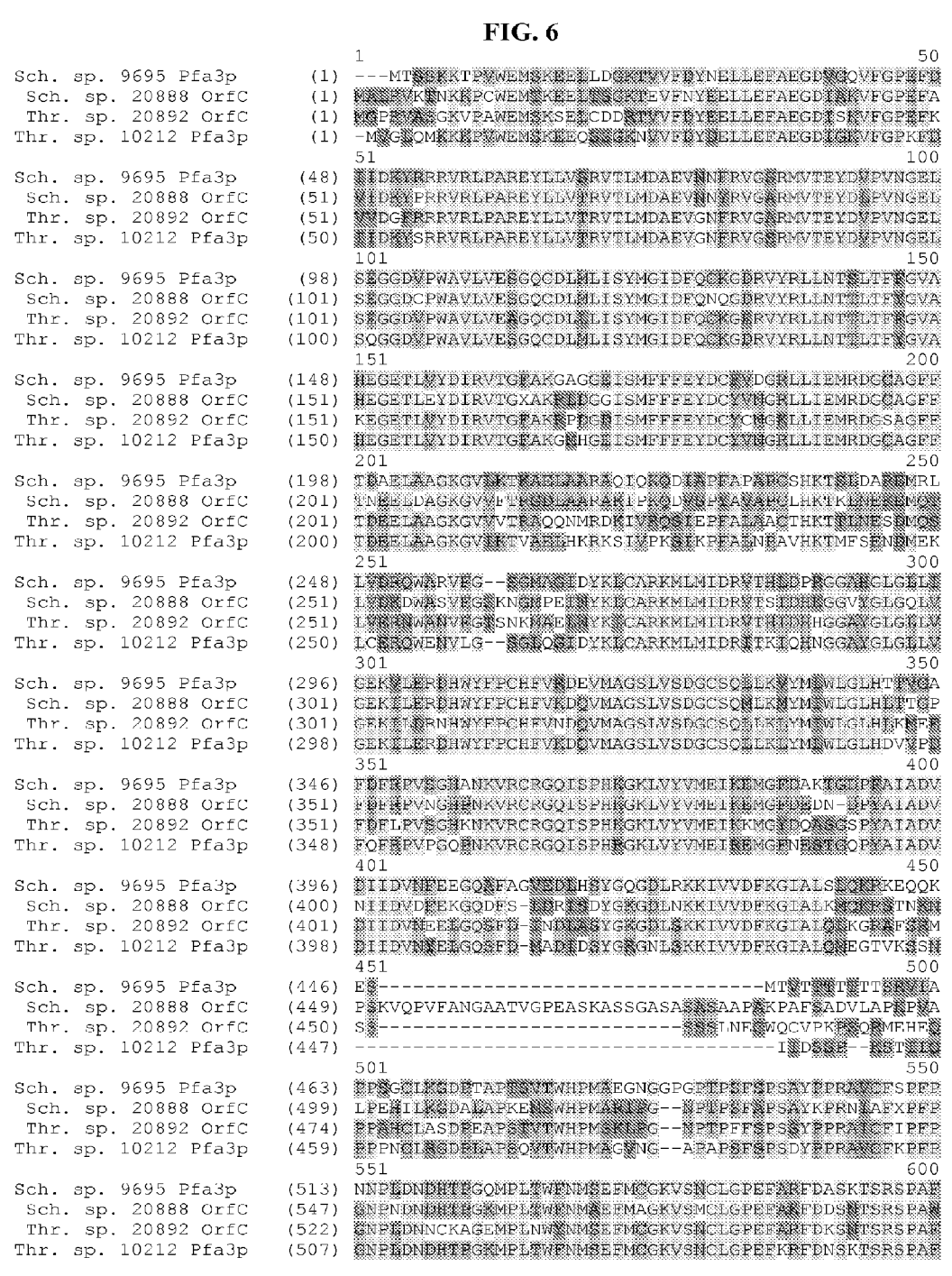

FIG. 6 shows an alignment of a *Schizochytrium* sp. ATCC PTA-9695 Pfa3p amino acid sequence (SEQ ID NO:6) and a *Thraustochytrium* sp. ATCC PTA-10212 Pfa3p amino acid sequence (SEQ ID NO:73) of the invention with the OrfC sequences from *Schizochytrium* sp. ATCC 20888 (SEQ ID NO:61) and *Thraustochytrium* sp. ATCC 20892 (SEQ ID NO:60).

Figure 7:
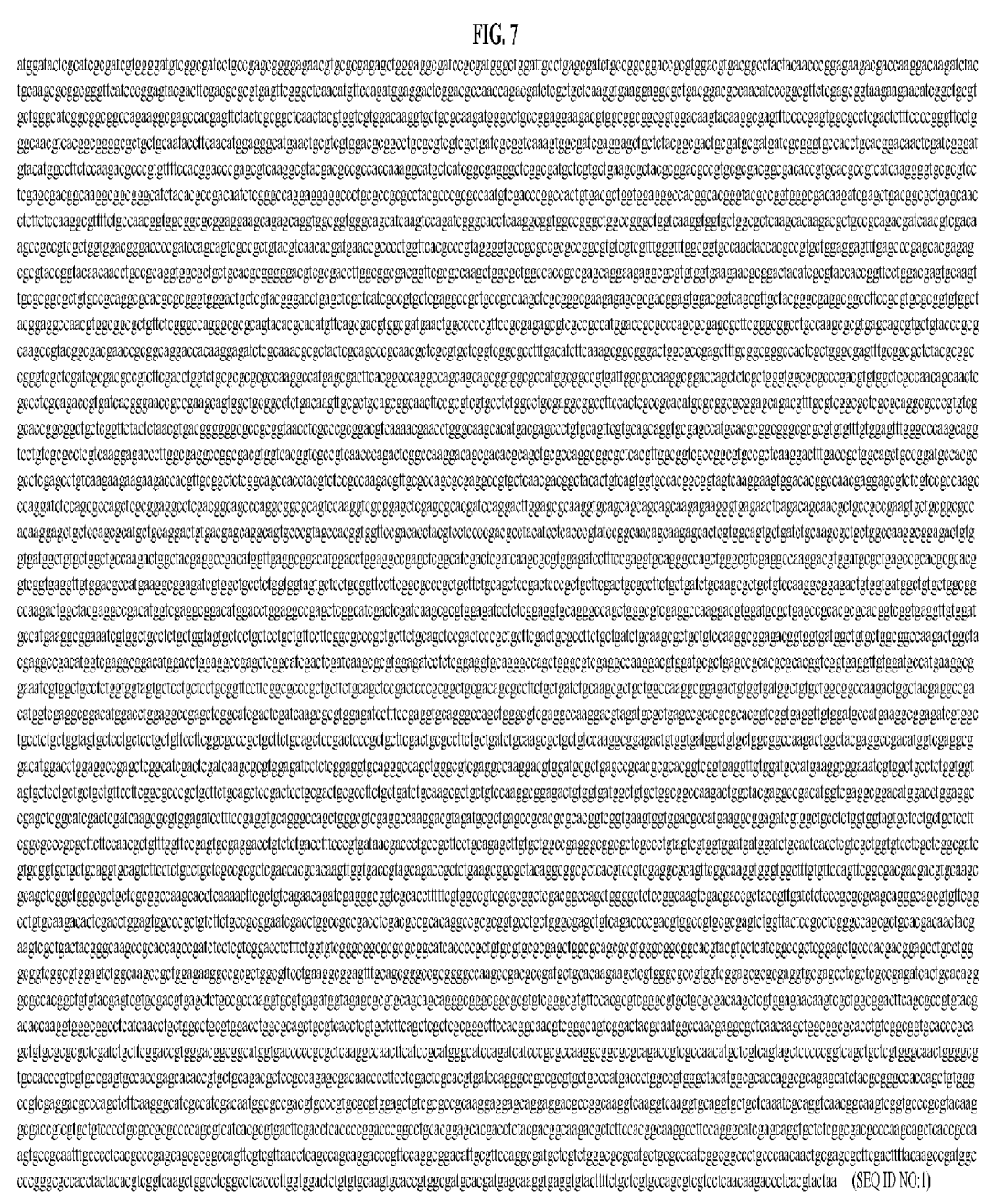

FIG. 7 shows the *Schizochytrium* sp. ATCC PTA-9695 PFA1 polynucleotide sequence (SEQ ID NO:1).

FIG. 8 shows the *Schizochytrium* sp. ATCC PTA-9695 Pfa1p amino acid sequence (SEQ ID NO:2).

FIG. 9 shows the *Schizochytrium* sp. ATCC PTA-9695 PFA2 polynucleotide sequence (SEQ ID NO:3).

FIG. 10 shows the *Schizochytrium* sp. ATCC PTA-9695 Pfa2p amino acid sequence (SEQ ID NO:4).

Figure 11:
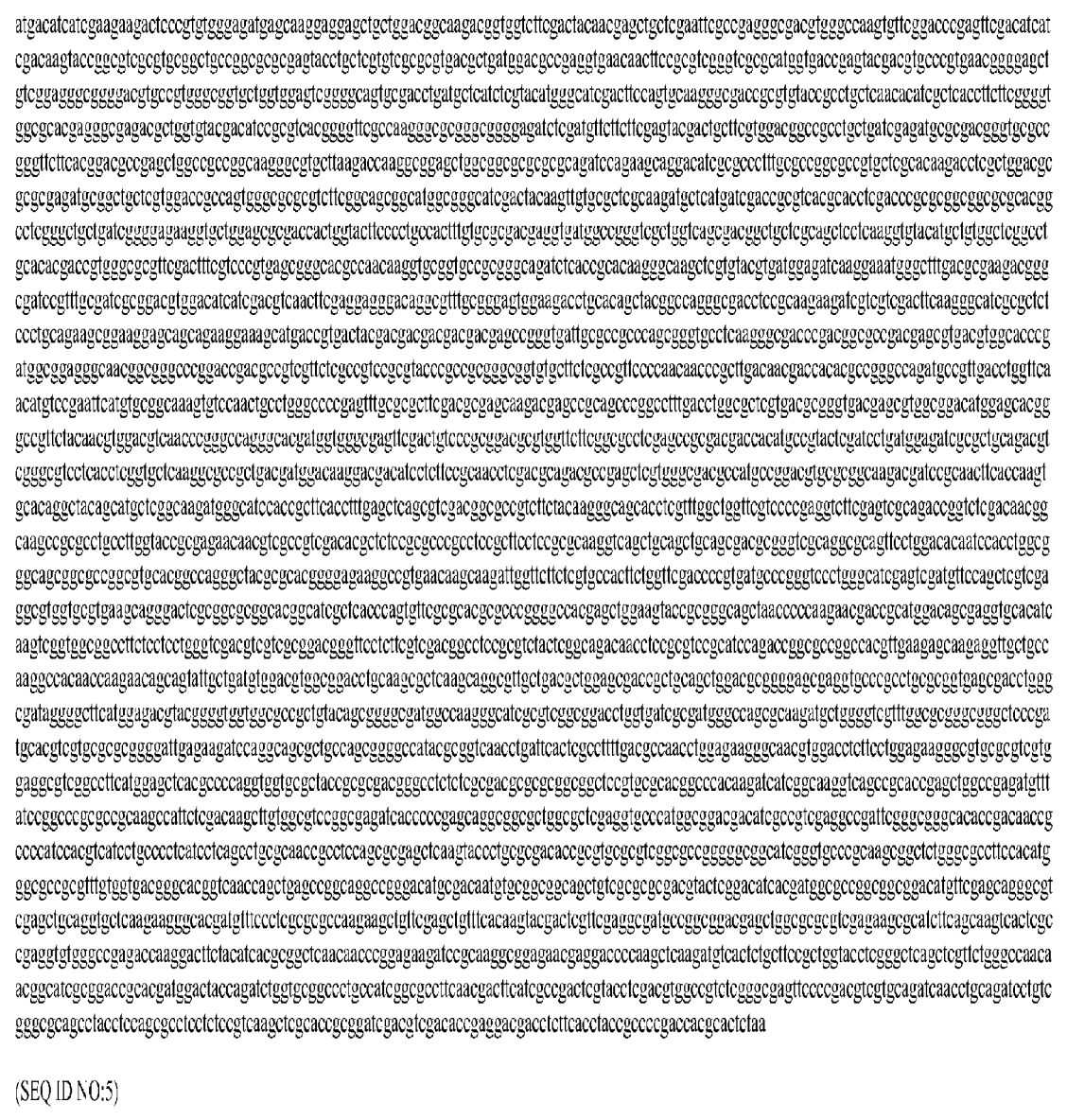

FIG. 11 shows the *Schizochytrium* sp. ATCC PTA-9695 PFA3 polynucleotide sequence (SEQ ID NO:5).

FIG. 12 shows the *Schizochytrium* sp. ATCC PTA-9695 Pfa3p amino acid sequence (SEQ ID NO:6).

FIG. 13 shows the *Thraustochytrium* sp. ATCC PTA-10212 PFA1 polynucleotide sequence (SEQ ID NO:68).

FIG. 14 shows a *Thraustochytrium* sp. ATCC PTA-10212 PFA1 polynucleotide sequence (SEQ ID NO:120) that has been codon-optimized for expression in *Schizochytrium*.

FIG. 15 shows the *Thraustochytrium* sp. ATCC PTA-10212 Pfa1p amino acid sequence (SEQ ID NO:69).

FIG. 16 shows the *Thraustochytrium* sp. ATCC PTA-10212 PFA2 polynucleotide sequence (SEQ ID NO:70).

FIG. 17 shows a *Thraustochytrium* sp. ATCC PTA-10212 PFA2 polynucleotide sequence (SEQ ID NO:121) that has been codon-optimized for expression in *Schizochytrium*.

FIG. 18 shows the *Thraustochytrium* sp. ATCC PTA-10212 Pfa2p amino acid sequence (SEQ ID NO:71).

FIG. 19 shows the *Thraustochytrium* sp. ATCC PTA-10212 PFA3 polynucleotide sequence (SEQ ID NO:72).

FIG. 20 shows a *Thraustochytrium* sp. ATCC PTA-10212 PFA3 polynucleotide sequence (SEQ ID NO:122) that has been codon-optimized for expression in *Schizochytrium*.

FIG. 21 shows the *Thraustochytrium* sp. ATCC PTA-10212 Pfa3p amino acid sequence (SEQ ID NO:73).

FIG. 22 shows a codon usage table for *Schizochytrium*.

DETAILED DESCRIPTION OF THE INVENTION

The present invention is directed to isolated nucleic acid molecules and polypeptides of polyunsaturated fatty acid (PUFA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

PUFA Synthases

As used herein, the term "PUFA synthase" refers to an enzyme that is involved in the production of polyunsaturated fatty acids. See, e.g., Metz et al., *Science* 293:290-293 (2001).

The present invention is directed in part to three PUFA synthase subunits termed Pfa1p (SEQ ID NO:2 or SEQ ID NO:69), Pfa2p (SEQ ID NO:4 or SEQ ID NO:71), and Pfa3p (SEQ ID NO:6 or SEQ ID NO:73), as well as the genes that encode the subunits termed PFA1 (SEQ ID NO:1, SEQ ID NO:68, or SEQ ID NO:120), PFA2 (SEQ ID NO:3, SEQ ID NO:70, or SEQ ID NO:121), and PFA3 (SEQ ID NO:5, SEQ ID NO:72, or SEQ ID NO:122). See, FIGS. 1-3 and 7-21. PUFA synthases in other thraustochytrids have also been designated as ORF 1, ORF 2, and ORF 3, respectively, or as OrfA, OrfB, and OrfC, respectively. See, e.g., *Schizochytrium* sp. (ATCC 20888) and *Thraustochytrium* sp. (ATCC 20892) in U.S. Pat. Nos. 7,247,461 and 7,256,022, referring to orfA, orfB, and orfC genes and corresponding OrfA, OrfB, and OrfC proteins, and *Thraustochytrium aureum* (ATCC 34304) in U.S. Pat. No. 7,368,552, referring to ORF A, ORF B, and ORF C genes and proteins. See also, strain SAM2179 in WO/2005/097982, referring to ORF 1, ORF 2, and ORF 3 genes and proteins.

Nucleic Acid Molecules

The present invention is directed to isolated nucleic acid molecules comprising polynucleotide sequences for PUFA synthase genes and domains derived from an isolated microorganism that is the subject of co-pending U.S. application Ser. No. 12/407,687, filed on Mar. 19, 2009, incorporated herein by reference in its entirety. The microorganism was deposited under the Budapest Treaty at the American Type Culture Collection, Patent Depository, 10801 University Boulevard, Manassas, Va. 20110-2209, on Jan. 7, 2009, and given ATCC Accession No. PTA-9695, and is also referred to as *Schizochytrium* sp. ATCC PTA-9695. When expressed, these genes produce unique fatty acid profiles, characterized in part by high levels of omega-3 fatty acids, in particular high levels of DHA.

The present invention is directed to isolated nucleic acid molecules comprising polynucleotide sequences for PUFA synthase genes and domains derived from an isolated microorganism that is the subject of co-pending U.S. Appl. No. 61/296,456, filed on Jan. 19, 2010, incorporated herein by reference in its entirety. The microorganism was deposited under the Budapest Treaty at the American Type Culture Collection, Patent Depository, 10801 University Boulevard, Manassas, Va. 20110-2209, on Jul. 14, 2009, and given ATCC Accession No. PTA-10212, and is also referred to as *Thraustochytrium* sp. ATCC PTA-10212. When expressed, these genes produce unique fatty acid profiles, characterized in part by high levels of omega-3 fatty acids, in particular high levels of DHA, EPA, or a combination thereof.

As used herein, a "polynucleotide" can comprise a conventional phosphodiester bond or a non-conventional bond (e.g., an amide bond, such as found in peptide nucleic acids (PNA)). A polynucleotide can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotides can be composed of triple-stranded regions comprising RNA or DNA or both RNA and DNA. Polynucleotides can contain ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters. Polynucleotides can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms. The term nucleic acid molecule refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

The terms "isolated" nucleic acid molecule refers to a nucleic acid molecule, DNA or RNA, which has been removed from its native environment. Further examples of isolated nucleic acid molecules include nucleic acid molecules comprising recombinant polynucleotides maintained in heterologous host cells or purified (partially or substantially) polynucleotides in solution. Isolated RNA molecules include in vivo or in vitro RNA transcripts of polynucleotides of the present invention. Isolated nucleic acid molecules according to the present invention further include such molecules produced synthetically. In addition, a nucleic acid molecule or polynucleotide can include a regulatory element such as a promoter, ribosome binding site, or a transcription terminator.

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

The present invention is directed to isolated nucleic acid molecules comprising polynucleotide sequences at least 80% identical to the polynucleotide sequences of *Schizochytrium* sp. ATCC PTA-9695 PFA1 (SEQ ID NO:1), *Schizochytrium* sp. ATCC PTA-9695 PFA2 (SEQ ID NO:3), *Schizochytrium* sp. ATCC PTA-9695 PFA3 (SEQ ID NO:5), *Thraustochytrium* sp. ATCC PTA-10212 PFA1 (SEQ ID NO:68 or SEQ ID NO:120), *Thraustochytrium* sp. ATCC PTA-10212 PFA2 (SEQ ID NO:70 or SEQ ID NO:121), *Thraustochytrium* sp. ATCC PTA-10212 PFA3 (SEQ ID NO:72 or SEQ ID NO:122), and combinations thereof, wherein the polynucleotides encode polypeptides comprising one or more PUFA synthase activities.

The PUFA synthase activities are associated with one or more domains in each synthase polypeptide, wherein the domains can be identified by their conserved structural or functional motifs based on their homology to known motifs and can also be identified based upon their specific biochemical activities. See, e.g., U.S. Pat. No. 7,217,856, incorporated by reference herein in its entirety. Examples of PUFA synthase domains include: the beta-ketoacyl-ACP synthase (KS) domain, malonyl-CoA:ACP acyltransferase (MAT) domain, acyl carrier protein (ACP) domains, ketoreductase (KR) domain, and beta-hydroxyacyl-ACP dehydrase (DH) domain in Pfa1p; the KS domain, chain length factor (CLF) domain, acyltransferase (AT) domain, and enoyl-ACP reductase (ER) domain in Pfa2p; and the DH domains and the ER domain in Pfa3p.

A polypeptide or domain of a polypeptide having beta-ketoacyl-ACP synthase (KS) biological activity (function) has been previously shown to be capable of carrying out the initial step of the fatty acid elongation reaction cycle. The term "beta-ketoacyl-ACP synthase" has been used interchangeably with the terms "3-keto acyl-ACP synthase," "beta-ketoacyl-ACP synthase," and "keto-acyl ACP synthase." In other systems, it has been shown that the acyl group for elongation is linked to a cysteine residue at the active site of KS by a thioester bond, and the acyl-KS undergoes condensation with malonyl-ACP to form -ketoacyl-ACP, $CO_2$, and unbound ("free") KS. In such systems, KS has been shown to possess greater substrate specificity than other polypeptides of the reaction cycle. Polypeptides (or domains of polypeptides) can be readily identified as belonging to the KS family by homology to known KS sequences.

A polypeptide or a domain of a polypeptide having malonyl-CoA:ACP acyltransferase (MAT) activity has been previously shown to be capable of transferring the malonyl moiety from malonyl-CoA to ACP. The term "malonyl-CoA: ACP acyltransferase" has been used interchangeably with "malonyl acyltransferase." In addition to the active site motif (GxSxG), MATs have been shown to possess an extended motif (R and Q amino acids in key positions). Polypeptides (or domains of polypeptides) can be readily identified as belonging to the MAT family by their homology to known MAT sequences and by their extended motif structure.

A polypeptide or a domain of a polypeptide having acyl carrier protein (ACP) activity has been previously shown to be capable of functioning as a carrier for growing fatty acyl chains via a thioester linkage to a covalently bound co-factor. ACPs are typically about 80 to about 100 amino acids long and have been shown to be converted from inactive apo-forms to functional holo-forms by transfer of the phosphopantetheinyl moiety of CoA to a highly conserved serine residue of the ACP. It has also been shown that acyl groups are attached to ACPs by a thioester linkage at the free terminus of the phosphopantetheinyl moiety. The presence of variations of an active site motif (LGIDS*) has also been recognized as a signature of ACPs. The functionality of the active site serine (S*) has been demonstrated in a bacterial PUFA synthase (Jiang et al., *J. Am. Chem. Soc.* 130:6336-7 (2008)). Polypeptides (or domains of polypeptides) can be readily identified as belonging to the ACP family by labeling with radioactive pantetheine and by sequence homology to known ACPs.

A polypeptide or a domain of a polypeptide having dehydrase or dehydratase (DH) activity has been previously shown to be capable of catalyzing a dehydration reaction. Reference to DH activity typically refers to FabA-like beta-hydroxyacyl-ACP dehydrase biological activity. FabA-like beta-hydroxyacyl-ACP dehydrase biological activity removes HOH from a beta-ketoacyl-ACP and initially produces a trans double bond in the carbon chain. The term "FabA-like beta-hydroxyacyl-ACP dehydrase" has been used interchangeably with the terms "FabA-like beta-hydroxy acyl-ACP dehydrase," "beta-hydroxyacyl-ACP dehydrase," and "dehydrase." The DH domains of PUFA synthase systems have previously been demonstrated as showing homology to bacterial DH enzymes associated with FAS systems (rather than to the DH domains of other PKS systems). See, e.g., U.S. Pat. No. 7,217,856, incorporated by reference herein in its entirety. A subset of bacterial DHs, the FabA-like DHs, possesses cis-trans isomerase activity (Heath et al., *J. Biol. Chem.*, 271, 27795 (1996)). Based on homology to the FabA-like DH proteins, one or all of the PUFA synthase system DH domains can be responsible for insertion of cis double bonds in the PUFA synthase products. A polypeptide or domain can also have non-FabA-like DH activity, or non-FabA-like beta-hydroxyacyl-ACP dehydrase (DH) activity. More specifically, a conserved active site motif of about 13 amino acids in length has been previously identified in PUFA synthase DH domains: LxxHxxxGxxxxP (the L position can also be an I in the motif). See, e.g., U.S. Pat. No. 7,217,856, and Donadio S, Katz L., *Gene* 111(1): 51-60 (1992), each of which is incorporated by reference herein in its entirety. This conserved motif is found in a similar region of all known PUFA synthase sequences and could be responsible for a non-FabA like dehydration.

A polypeptide or a domain of a polypeptide having beta-ketoacyl-ACP reductase (KR) activity has been previously shown to be capable of catalyzing the pyridine-nucleotide-dependent reduction of 3-ketoacyl forms of ACP. The term "beta-ketoacyl-ACP reductase" has been used interchangeably with the terms "ketoreductase," "3-ketoacyl-ACP reductase," and "keto-acyl ACP reductase." It has been determined in other systems that KR function involves the first reductive step in the de novo fatty acid biosynthesis elongation cycle. Polypeptides (or domains of polypeptides) can be readily identified as belonging to the KR family by sequence homology to known PUFA synthase KRs.

A polypeptide or a domain of a polypeptide having chain length factor (CLF) activity has been previously defined as having one or more of the following activities or characteristics: (1) it can determine the number of elongation cycles and hence chain length of the end product, (2) it has homology to KS, but lacks the KS active site cysteine, (3) it can heterodimerize with KS, (4) it can provide the initial acyl group to be elongated, or (5) it can decarboxylate malonate (as malonyl-ACP), thus forming an acetate group that can be transferred to the KS active site and that can act as the 'priming' molecule that undergoes the initial elongation (condensation) reaction. A CLF domain is found in all currently identified PUFA synthase systems and in each case is found as part of a multidomain protein. Polypeptides (or domains of polypeptides) can be readily identified as belonging to the CLF family by sequence homology to known PUFA synthase CLFs.

A polypeptide or a domain of a polypeptide having acyltransferase (AT) activity has been previously defined as having one or more of the following activities or characteristics: (1) it can transfer the fatty acyl group from the ACP domain(s) to water (i.e., a thioesterase), releasing the fatty acyl group as a free fatty acid, (2) it can transfer a fatty acyl group to an acceptor such as CoA, (3) it can transfer the acyl group among the various ACP domains, or (4) it can transfer the fatty acyl group to a lipophilic acceptor molecule (e.g. to lysophosphadic acid). Polypeptides (or domains of polypeptides) can be readily identified as belonging to the AT family by sequence homology to known PUFA synthase ATs.

A polypeptide or a domain of a polypeptide having enoyl-ACP reductase (ER) biological activity has been previously shown to be capable of reducing the trans-double bond (introduced by the DH activity) in the fatty acyl-ACP, resulting in saturation of the associated carbons. The ER domain in PUFA synthase systems has previously been shown to have homology to a family of ER enzymes (Heath et al., *Nature* 406: 145-146 (2000), incorporated by reference herein in its entirety), and an ER homolog has been shown to function as an enoyl-ACP reductase in vitro (Bumpus et al. *J. Am. Chem. Soc.*, 130: 11614-11616 (2008), incorporated by reference herein in its entirety). The term "enoyl-ACP reductase" has been used interchangeably with "enoyl reductase," "enoyl ACP-reductase," and "enoyl acyl-ACP reductase." Polypeptides (or domains of polypeptides) can be readily identified as belonging to the ER family by sequence homology to known PUFA synthase ERs.

In some embodiments, the present invention is directed to nucleic acid molecules comprising a polynucleotide sequence at least 80% identical to a polynucleotide sequence within PFA1 (SEQ ID NO:1, SEQ ID NO:68, or SEQ ID NO:120) that encodes one or more PUFA synthase domains. In some embodiments, the nucleic acid molecule comprises a polynucleotide sequence at least 80% identical to a polynucleotide sequence within PFA1 (SEQ ID NO:1, SEQ ID NO:68, or SEQ ID NO:120) that encodes one or more PUFA synthase domains such as a KS domain (SEQ ID NO:7 or SEQ ID NO:74), a MAT domain (SEQ ID NO:9 or SEQ ID NO:76), an ACP domain (such as any one of SEQ ID NOs:13, 15, 17, 19, 21, 23, 80, 82, 84, 86, 88, 90, 92, 94, 96, or 98), a combination of two or more ACP domains, such as two, three, four, five, six, seven, eight, nine, or ten ACP domains, including tandem domains (SEQ ID NO:11 or SEQ ID NO:78, and portions thereof), a KR domain (SEQ ID NO:25 or SEQ ID NO:100), a DH domain (SEQ ID NO:27 or SEQ ID NO:118), and combinations thereof. In some embodiments, the nucleic acid molecule comprises two or more polynucleotide sequences, wherein each of the at least two or more polynucleotide sequences is 80% identical to a polynucleotide sequence within PFA1 (SEQ ID NO:1, SEQ ID NO:68, or SEQ ID NO:120) that encodes one or more PUFA synthase domains. In some embodiments, the at least two or more polynucleotide sequences are 80% identical to the same polynucleotide sequence within SEQ ID NO:1, SEQ ID NO:68, or SEQ ID NO:120 that encodes one or more PUFA synthase domains. In some embodiments, the at least two or more polynucleotide sequences are 80% identical to different polynucleotide sequences within SEQ ID NO:1, SEQ ID NO:68, or SEQ ID NO:120 that each encode one or more PUFA synthase domains. In some embodiments, the at least two or more polynucleotide sequences are 80% identical to different polynucleotide sequences within SEQ ID NO:1, SEQ ID NO:68, or SEQ ID NO:120, wherein the at least two or more polynucleotide sequences are located in the same order or a different order in the nucleic acid molecule as compared to the order of the corresponding sequences within SEQ ID NO:1, SEQ ID NO:68, or SEQ ID NO:120. In some embodiments, each of the at least two or more polynucleotide sequences are 80% identical to a polynucleotide sequence within PFA1 (SEQ ID NO:1, SEQ ID NO:68, or SEQ ID NO:120) that encodes one or more PUFA synthase domains such as a KS domain (SEQ ID NO:7 or SEQ ID NO:74), a MAT domain (SEQ ID NO:9 or SEQ ID NO:76), an ACP domain (such as any one of SEQ ID NOs:13, 15, 17, 19, 21, 23, 80, 82, 84, 86, 88, 90, 92, 94, 96, or 98), a combination of two, three, four, five, six, seven, eight, nine, or ten ACP domains, including tandem domains (SEQ ID NO:11 or SEQ ID NO:78, and portions thereof), a KR domain (SEQ ID NO:25 or SEQ ID NO:100), a DH domain (SEQ ID NO:27 or SEQ ID NO:118), and combinations thereof. In some embodiments, the nucleic acid molecule comprises one or more polynucleotide sequences within PFA1 (SEQ ID NO:1, SEQ ID NO:68, or SEQ ID NO:120) that encodes one or more PUFA synthase domains, including one or more copies of any individual domain in combination with one or more copies of any other individual domain.

In some embodiments, the present invention is directed to nucleic acid molecules comprising a polynucleotide sequence at least 80% identical to a polynucleotide sequence within PFA2 (SEQ ID NO:3, SEQ ID NO:70, or SEQ ID NO:121) that encodes one or more PUFA synthase domains. In some embodiments, the nucleic acid molecule comprises a polynucleotide sequence at least 80% identical to the polynucleotide sequence within PFA2 (SEQ ID NO:3, SEQ ID NO:70, or SEQ ID NO:121) that encodes one or more PUFA synthase domains such as a KS domain (SEQ ID NO:29 or SEQ ID NO:102), a CLF domain (SEQ ID NO:31 or SEQ ID NO:104), an AT domain (SEQ ID NO:33 or SEQ ID NO:106), an ER domain (SEQ ID NO:35 or SEQ ID NO:108), and combinations thereof. In some embodiments, the nucleic acid molecule comprises two or more polynucleotide sequences, wherein each of the at least two or more polynucleotide sequences is 80% identical to a polynucleotide sequence within PFA2 (SEQ ID NO:3, SEQ ID NO:70, or SEQ ID NO:121) that encodes one or more PUFA synthase domains. In some embodiments, the at least two or more polynucleotide sequences are 80% identical to the same polynucleotide sequence within SEQ ID NO:3, SEQ ID NO:70, or SEQ ID NO:121 that encodes one or more PUFA synthase domains. In some embodiments, the at least two or more polynucleotide sequences are 80% identical to different polynucleotide sequences within SEQ ID NO:3, SEQ ID NO:70, or SEQ ID NO:121 that each encode one or more PUFA synthase domains. In some embodiments, the at least two or more polynucleotide sequences are 80% identical to different polynucleotide sequences within SEQ ID NO:3, SEQ ID NO:70, or SEQ ID NO:121, wherein the at least two or more polynucleotide sequences are located in the same order or a different order in the nucleic acid molecule as compared to the order of the corresponding sequences within SEQ ID NO:3, SEQ ID NO:70, or SEQ ID NO:121. In some embodiments, each of the at least two or more polynucleotide sequences are 80% identical to a polynucleotide sequence within PFA2 (SEQ ID NO:3, SEQ ID NO:70, or SEQ ID NO:121) that encodes one or more PUFA synthase domains such as a KS domain (SEQ ID NO:29 or SEQ ID NO:102), a CLF domain (SEQ ID NO:31 or SEQ ID NO:104), an AT domain (SEQ ID NO:33 or SEQ ID NO:106), an ER domain (SEQ ID NO:35 or SEQ ID NO:108), and combinations thereof. In some embodiments, the nucleic acid molecule comprises one or more polynucleotide sequences within PFA2 (SEQ ID NO:3, SEQ ID NO:70, or SEQ ID NO:121) that encodes one or more PUFA synthase domains, including one or more copies of any individual domain in combination with one or more copies of any other individual domain.

In some embodiments, the present invention is directed to nucleic acid molecules comprising a polynucleotide sequence at least 80% identical to a polynucleotide sequence within PFA3 (SEQ ID NO:5, SEQ ID NO:72, or SEQ ID NO:122) that encodes one or more PUFA synthase domains. In some embodiments, the nucleic acid molecule comprises a polynucleotide sequence at least 80% identical to a polynucleotide sequence within PFA3 (SEQ ID NO:5, SEQ ID NO:72, or SEQ ID NO:122) that encodes one or more PUFA synthase domains such as a DH domain (such as SEQ ID NO:37, SEQ ID NO:39, SEQ ID NO:110, or SEQ ID NO:112), an ER domain (SEQ ID NO:41 or SEQ ID NO:114), and combinations thereof. In some embodiments, the nucleic acid molecule comprises two or more polynucleotide sequences, wherein each of the at least two or more polynucleotide sequences is 80% identical to a polynucleotide sequence within PFA3 (SEQ ID NO:5, SEQ ID NO:72, or SEQ ID NO:122) that encodes one or more PUFA synthase domains. In some embodiments, the at least two or more polynucleotide sequences are 80% identical to the same polynucleotide sequence within SEQ ID NO:5, SEQ ID NO:72, or SEQ ID NO:122 that encodes one or more PUFA synthase domains. In some embodiments, the at least two or more polynucleotide sequences are 80% identical to different polynucleotide sequences within SEQ ID NO:5, SEQ ID NO:72, or SEQ ID NO:122 that each encode one or more PUFA synthase domains. In some embodiments, the at least two or more polynucleotide sequences are 80% identical to different polynucleotide sequences within SEQ ID NO:5, SEQ ID NO:72, or SEQ ID NO:122, wherein the at least two or more polynucleotide sequences are located in the same order or a different order in the nucleic acid molecule as compared to the order of the corresponding sequences within SEQ ID NO:5, SEQ ID NO:72, or SEQ ID NO:122. In some embodiments, each of the at least two or more polynucleotide sequences is 80% identical to a polynucleotide sequence within PFA3 (SEQ ID NO:5, SEQ ID NO:72, or SEQ ID NO:122) that encodes one or more PUFA synthase domains such as a DH domain (such as SEQ ID NO:37, SEQ ID NO:39, SEQ ID NO:110, or SEQ ID NO:112), an ER domain (SEQ ID NO:41 or SEQ ID NO:114), and combinations thereof. In some embodiments, the nucleic acid molecule comprises one or more polynucleotide sequences within PFA3 (SEQ ID NO:5, SEQ ID NO:72, or SEQ ID NO:122) that encodes one or more PUFA synthase domains, including one or more copies of any individual domain in combination with one or more copies of any other individual domain.

In some embodiments, the present invention is directed to a nucleic acid molecule comprising a polynucleotide sequence at least 80% identical to SEQ ID NO:1, SEQ ID NO:68, or SEQ ID NO:120, wherein the polynucleotide sequence encodes a polypeptide comprising PUFA synthase activity selected from the group consisting of KS activity, MAT activity, ACP activity, KR activity, DH activity, and combinations thereof.

In some embodiments, the present invention is directed to a nucleic acid molecule comprising a polynucleotide sequence at least 80% identical to SEQ ID NO:7 or SEQ ID NO:74, wherein the polynucleotide sequence encodes a polypeptide comprising KS activity.

In some embodiments, the present invention is directed to a nucleic acid molecule comprising a polynucleotide sequence at least 80% identical to SEQ ID NO:9 or SEQ ID NO:76, wherein the polynucleotide sequence encodes a polypeptide comprising MAT activity.

In some embodiments, the present invention is directed to a nucleic acid molecule comprising a polynucleotide sequence at least 80% identical to any one of SEQ ID NOs:13, 15, 17, 19, 21, 23, 80, 82, 84, 86, 88, 90, 92, 94, 96, or 98, wherein the polynucleotide sequence encodes a polypeptide comprising ACP activity.

In some embodiments, the present invention is directed to a nucleic acid molecule comprising a polynucleotide sequence at least 80% identical to SEQ ID NO:11 or SEQ ID NO:78, wherein the polynucleotide sequence encodes a polypeptide comprising ACP activity.

In some embodiments, the nucleic acid molecule comprises a polynucleotide sequence at least 80% identical to a polynucleotide sequence within SEQ ID NO:11 that encodes one, two, three, four, five, or six ACP domains, wherein the polynucleotide sequence encodes a polypeptide comprising ACP activity associated with one or more ACP domains. SEQ ID NOs:13, 15, 17, 19, 21, and 23 are representative polynucleotides sequence that each encode a single ACP domain within SEQ ID NO:11.

In some embodiments, the nucleic acid molecule comprises a polynucleotide sequence at least 80% identical to a polynucleotide sequence within SEQ ID NO:78 that encodes one, two, three, four, five, six, seven, eight, nine, or ten ACP domains, wherein the polynucleotide sequence encodes a polypeptide comprising ACP activity associated with one or more ACP domains. SEQ ID NOs:80, 82, 84, 86, 88, 90, 92, 94, 96, and 98 are representative polynucleotides sequence that each encode a single ACP domain within SEQ ID NO:78.

In some embodiments, the present invention is directed to a nucleic acid molecule comprising a polynucleotide sequence at least 80% identical to SEQ ID NO:25 or SEQ ID NO:100, wherein the polynucleotide sequence encodes a polypeptide comprising KR activity.

In some embodiments, the present invention is directed to a nucleic acid molecule comprising a polynucleotide sequence at least 80% identical to SEQ ID NO:27 or SEQ ID NO:118, wherein the polynucleotide sequence encodes a polypeptide comprising DH activity.

In some embodiments, the present invention is directed to a nucleic acid molecule comprising a polynucleotide sequence at least 80% identical to SEQ ID NO:3, SEQ ID NO:70, or SEQ ID NO:121, wherein the polynucleotide sequence encodes a polypeptide comprising PUFA synthase activity selected from the group consisting of KS activity, CLF activity, AT activity, ER activity, and combinations thereof.

In some embodiments, the present invention is directed to a nucleic acid molecule comprising a polynucleotide sequence at least 80% identical to SEQ ID NO:29 or SEQ ID NO:102, wherein the polynucleotide sequence encodes a polypeptide comprising KS activity.

In some embodiments, the present invention is directed to a nucleic acid molecule comprising a polynucleotide sequence at least 80% identical to SEQ ID NO:31 or SEQ ID NO:104, wherein the polynucleotide sequence encodes a polypeptide comprising CLF activity.

In some embodiments, the present invention is directed to a nucleic acid molecule comprising a polynucleotide sequence at least 80% identical to SEQ ID NO:33 or SEQ ID NO:106, wherein the polynucleotide sequence encodes a polypeptide comprising AT activity.

In some embodiments, the present invention is directed to a nucleic acid molecule comprising a polynucleotide sequence at least 80% identical to SEQ ID NO:35 or SEQ ID NO:108, wherein the polynucleotide sequence encodes a polypeptide comprising ER activity.

In some embodiments, the present invention is directed to a nucleic acid molecule comprising a polynucleotide sequence at least 80% identical to SEQ ID NO:5, SEQ ID NO:72, or SEQ ID NO:122, wherein the polynucleotide sequence encodes a polypeptide comprising PUFA synthase activity selected from the group consisting of DH activity, ER activity, and combinations thereof.

In some embodiments, the present invention is directed to a nucleic acid molecule comprising a polynucleotide sequence at least 80% identical to SEQ ID NO:37, wherein the polynucleotide sequence encodes a polypeptide comprising DH activity.

In some embodiments, the present invention is directed to a nucleic acid molecule comprising a polynucleotide sequence at least 80% identical to SEQ ID NO:39, wherein the polynucleotide sequence encodes a polypeptide comprising DH activity.

In some embodiments, the present invention is directed to a nucleic acid molecule comprising a polynucleotide sequence at least 80% identical to SEQ ID NO:110, wherein the polynucleotide sequence encodes a polypeptide comprising DH activity.

In some embodiments, the present invention is directed to a nucleic acid molecule comprising a polynucleotide sequence at least 80% identical to SEQ ID NO:112, wherein the polynucleotide sequence encodes a polypeptide comprising DH activity.

In some embodiments, the present invention is directed to a nucleic acid molecule comprising a polynucleotide sequence at least 80% identical to SEQ ID NO:41 or SEQ ID NO:114, wherein the polynucleotide sequence encodes a polypeptide comprising ER activity.

The present invention is directed to isolated nucleic acid molecules comprising polynucleotide sequences encoding polypeptides, wherein the polypeptides comprise amino acid sequences that are at least 80% identical to the amino acid sequences of Pfa1p (SEQ ID NO:2 or SEQ ID NO:69), Pfa2p (SEQ ID NO:4 or SEQ ID NO:71), or Pfa3p (SEQ ID NO:6 or SEQ ID NO:73), wherein the polynucleotides encode polypeptides comprising one or more PUFA synthase activities.

The present invention is directed to nucleic acid molecules comprising a polynucleotide sequence encoding a polypeptide, wherein the polypeptide comprises an amino acid sequence at least 80% identical to the amino acid sequences of one or more PUFA synthase domains of the PUFA synthases of the invention.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa1p (SEQ ID NO:2 or SEQ ID NO:69) comprising one or more PUFA synthase domains. In some embodiments, the polypeptide comprises an amino acid sequence at least 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two or more ACP domains, such as two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises two or more amino acid sequences, wherein each of the at least two or more amino acid sequences is 80% identical to an amino acid sequence within Pfa1p (SEQ ID NO:2 or SEQ ID NO:69) comprising one or more PUFA synthase domains. In some embodiments, the at least two or more amino acid sequences are 80% identical to the same amino acid sequence within Pfa1p (SEQ ID NO:2 or SEQ ID NO:69) comprising one or more PUFA synthase domains. In some embodiments, the at least two or more amino acid sequences are 80% identical to different amino acid sequences within Pfa1p (SEQ ID NO:2 or SEQ ID NO: 69) that each comprise one or more PUFA synthase domains. In some embodiments, the at least two or more amino acid sequences are 80% identical to different amino acid sequences within Pfa1p (SEQ ID NO:2 or SEQ ID NO:69), wherein the at least two or more amino acid sequences are located in the same order or a different order in the polypeptide as compared to the order of the corresponding domains within Pfa1p (SEQ ID NO:2 or SEQ ID NO:69). In some embodiments, the at least two or more amino acid sequences are 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO: 77), an ACP domain (such as any one of SEQ ID NOs:14, 16, 18, 20, 22, 24, 81, 83, 85, 87, 89, 91, 93, 95, 97, or 99), a combination of two, three, four, five, six, seven, eight, nine, or ten ACP domains, including tandem domains (SEQ ID NO:12 or SEQ ID NO: 79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises one or more amino acid sequences within Pfa1p (SEQ ID NO:2 or SEQ ID NO:69) comprising one or more PUFA synthase domains, including one or more copies of any individual domain in combination with one or more copies of any other individual domain.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa2p (SEQ ID NO:4 or SEQ ID NO:71) comprising one or more PUFA synthase domains. In some embodiments, the polypeptide comprises an amino acid sequence at least 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises two or more amino acid sequences, wherein each of the at least two or more amino acid sequences is 80% identical to an amino acid sequence within Pfa2p (SEQ ID NO:4 or SEQ ID NO:71) comprising one or more PUFA synthase domains. In some embodiments, the at least two or more amino acid sequences are 80% identical to the same amino acid sequence within Pfa2p (SEQ ID NO:4 or SEQ ID NO:71). In some embodiments, the at least two or more amino acid sequences are 80% identical to different amino acid sequences within Pfa2p (SEQ ID NO:4 or SEQ ID NO:71) that each comprise one or more PUFA synthase domains. In some embodiments, the at least two or more amino acid sequences are 80% identical to different amino acid sequences within Pfa2p (SEQ ID NO:4 or SEQ ID NO:71), wherein the at least two or more amino acid sequences are located in the same order or a different order in the polypeptide as compared to the order of the corresponding domains within Pfa2p (SEQ ID NO:4 or SEQ ID NO:71). In some embodiments, the at least two or more amino acid sequences are 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises one or more amino acid sequences within Pfa2p (SEQ ID NO:4 or SEQ ID NO:71) comprising one or more PUFA synthase domains, including one or more copies of any individual domain in combination with one or more copies of any other individual domain.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa3p (SEQ ID NO:6 or SEQ ID NO:73) comprising one or more PUFA synthase domains. In some embodiments, the polypeptide comprises an amino acid sequence at least 80% identical to an amino acid sequence within Pfa3p (SEQ ID NO:6 or SEQ ID NO:73) comprising one or more PUFA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises two or more amino acid sequences, wherein each of the at least two or more amino acid sequences is 80% identical to an amino acid sequence within Pfa3p (SEQ ID NO:6 or SEQ ID NO:73) comprising one or more PUFA synthase domains. In some embodiments, the at least two or more amino acid sequences are 80% identical to the same amino acid sequence within Pfa3p (SEQ ID NO:6 or SEQ ID NO:73) comprising one or more PUFA synthase domains. In some embodiments, the at least two or more amino acid sequences are 80% identical to different amino acid sequences within Pfa3p (SEQ ID NO:6 or SEQ ID NO:73) that each comprise one or more PUFA synthase domains. In some embodiments, the at least two or more amino acid sequences are 80% identical to different amino acid sequences within Pfa3p (SEQ ID NO:6 or SEQ ID NO:73), wherein the at least two or more amino acid sequences are located in the same order or a different order in the polypeptide as compared to the order of the corresponding domains within Pfa3p (SEQ ID NO:6 or SEQ ID NO:73). In some embodiments, the at least two or more amino acid sequences are 80% identical to an amino acid sequence within Pfa3p (SEQ ID NO:6 or SEQ ID NO:73) comprising one or more PUFA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises one or more amino acid sequences within Pfa3p (SEQ ID NO:6 or SEQ ID NO:73) comprising one or more PUFA synthase domains, including one or more copies of any individual domain in combination with one or more copies of any other individual domain.

In some embodiments, the present invention is directed to a nucleic acid molecule comprising a polynucleotide sequence encoding a polypeptide, wherein the polypeptide comprises an amino acid sequence at least 80% identical to SEQ ID NO:2 or SEQ ID NO:69, and wherein the polypeptide comprises a PUFA synthase activity selected from the group consisting of KS activity, MAT activity, ACP activity, KR activity, DH activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:8 or SEQ ID NO:75, and wherein the polypeptide comprises KS activity.

In some embodiments, the present invention is directed to a nucleic acid molecule comprising a polynucleotide sequence encoding a polypeptide, wherein the polypeptide comprises an amino acid sequence at least 80% identical to SEQ ID NO:10 or SEQ ID NO:77, and wherein the polypeptide comprises MAT activity.

In some embodiments, the present invention is directed to a nucleic acid molecule comprising a polynucleotide sequence encoding a polypeptide, wherein the polypeptide comprises an amino acid sequence at least 80% identical to any one of SEQ ID NOs:14, 16, 18, 20, 22, 24, 81, 83, 85, 87, 89, 91, 93, 95, 97, or 99, and wherein the polypeptide comprises ACP activity.

In some embodiments, the present invention is directed to a nucleic acid molecule comprising a polynucleotide sequence encoding a polypeptide, wherein the polypeptide comprises an amino acid sequence at least 80% identical to SEQ ID NO:12 or SEQ ID NO:79, and wherein the polypeptide comprises ACP activity.

In some embodiments, the present invention is directed to nucleic acid molecules comprising a polynucleotide sequence encoding a polypeptide, wherein the polypeptide comprises an amino acid sequence at least 80% identical to an amino acid sequence within SEQ ID NO:12, wherein the polypeptide comprises ACP activity. In some embodiments, the amino acid sequence is at least 80% identical to an amino acid sequence within SEQ ID NO:12 comprising one, two, three, four, five, or six ACP domains, wherein the polypeptide comprises ACP activity associated with one or more ACP domains. SEQ ID NOs:14, 16, 18, 20, 22 and 24 are representative amino acid sequences, each comprising a single ACP domain within SEQ ID NO: 12.

In some embodiments, the present invention is directed to nucleic acid molecules comprising a polynucleotide sequence encoding a polypeptide, wherein the polypeptide comprises an amino acid sequence at least 80% identical to an amino acid sequence within SEQ ID NO:79, wherein the polypeptide comprises ACP activity. In some embodiments, the amino acid sequence is at least 80% identical to an amino acid sequence within SEQ ID NO:79 comprising one, two, three, four, five, six, seven, eight, nine, or ten ACP domains, wherein the polypeptide comprises ACP activity associated with one or more ACP domains. SEQ ID NOs:81, 83, 85, 87, 89, 91, 93, 95, 97, and 99 are representative amino acid sequences, each comprising a single ACP domain within SEQ ID NO:79.

In some embodiments, the present invention is directed to a nucleic acid molecule comprising a polynucleotide sequence encoding a polypeptide, wherein the polypeptide comprises an amino acid sequence at least 80% identical to SEQ ID NO:26 or SEQ ID NO:101, and wherein the polypeptide comprises KR activity.

In some embodiments, the present invention is directed to a nucleic acid molecule comprising a polynucleotide sequence encoding a polypeptide, wherein the polypeptide comprises an amino acid sequence at least 80% identical to SEQ ID NO:28 or SEQ ID NO:119, and wherein the polypeptide comprises DH activity.

In some embodiments, the present invention is directed to nucleic acid molecules comprising a polynucleotide sequence encoding a polypeptide, wherein the polypeptide comprises an amino acid sequence at least 80% identical to SEQ ID NO:4 or SEQ ID NO:71, wherein the polypeptide comprises a PUFA synthase activity selected from the group consisting of KS activity, CLF activity, AT activity, ER activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:30 or SEQ ID NO:103, and wherein the polypeptide comprises KS activity.

In some embodiments, the present invention is directed to a nucleic acid molecule comprising a polynucleotide sequence encoding a polypeptide, wherein the polypeptide comprises an amino acid sequence at least 80% identical to SEQ ID NO:32 or SEQ ID NO:105, and wherein the polypeptide comprises CLF activity.

In some embodiments, the present invention is directed to a nucleic acid molecule comprising a polynucleotide sequence encoding a polypeptide, wherein the polypeptide comprises an amino acid sequence at least 80% identical to SEQ ID NO:34 or SEQ ID NO:107, and wherein the polypeptide comprises AT activity.

In some embodiments, the present invention is directed to a nucleic acid molecule comprising a polynucleotide sequence encoding a polypeptide, wherein the polypeptide comprises an amino acid sequence at least 80% identical to SEQ ID NO:36 or SEQ ID NO:109, and wherein the polypeptide comprises ER activity.

In some embodiments, the present invention is directed to a nucleic acid molecule comprising a polynucleotide sequence encoding a polypeptide, wherein the polypeptide comprises an amino acid sequence at least 80% identical to SEQ ID NO:6 or SEQ ID NO:73, wherein the polypeptide comprises a PUFA synthase activity selected from the group consisting of DH activity, ER activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:38, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:40, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:111, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:113, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:42 or SEQ ID NO:115, and wherein the polypeptide comprises ER activity.

In some embodiments, the nucleic acid molecules comprise polynucleotide sequences at least about 80%, 85%, or 90% identical to the polynucleotide sequences reported herein, or at least about 95%, 96%, 97%, 98%, 99%, or 100% identical to the polynucleotide sequences reported herein. The term "percent identity," as known in the art, is a relationship between two or more amino acid sequences or two or more polynucleotide sequences, as determined by comparing the sequences. In the art, "identity" also means the degree of sequence relatedness between amino acid or polynucleotide sequences, as the case may be, as determined by the match between strings of such sequences.

By a nucleic acid molecule having a polynucleotide sequence at least, for example, 95% "identical" to a reference polynucleotide sequence of the present invention, it is intended that the polynucleotide sequence of the nucleic acid molecule is identical to the reference sequence except that the polynucleotide sequence can include up to five nucleotide differences per each 100 nucleotides of the reference polynucleotide sequence. In other words, to obtain a nucleic acid molecule having a polynucleotide sequence at least 95% identical to a reference polynucleotide sequence, up to 5% of the nucleotides in the reference sequence can be deleted or substituted with another nucleotide, or a number of nucleotides up to 5% of the total nucleotides in the reference sequence can be inserted into the reference sequence.

As a practical matter, whether any particular polynucleotide sequence or amino acid sequence is at least 80%, 85%, 90%, 95%, 96%, 97%, 98% or 99% identical to a polynucleotide sequence or amino acid sequence of the present invention can be determined conventionally using known computer programs. A method for determining the best overall match between a query sequence (a sequence of the present invention) and a subject sequence can be determined using the alignment of sequences and calculation of identity scores. The alignments were done using the computer program AlignX, which is a component of the Vector NTI Suite 10.0 package from Invitrogen (www.invitrogen.com). The alignments were performed using a ClustalW alignment (Thompson, J. D., et al. *Nucl. Acids Res.* 22: 4673-4680 (1994)) for both amino acid and polynucleotide sequence alignments. The default scoring matrices Blosum62mt2 and swgapdnamt were used for amino acid and polynucleotide sequence alignments, respectively. For amino acid sequences, the default gap opening penalty is 10 and the gap extension penalty 0.1. For polynucleotide sequences, the default gap opening penalty is 15 and the gap extension penalty is 6.66.

The present invention is directed to an isolated nucleic acid molecule comprising a polynucleotide sequence encoding a polypeptide comprising PUFA synthase activity selected from the group consisting of KS activity, MAT activity, ACP activity, KR activity, CLF activity, AT activity, ER activity, DH activity, and combinations thereof, wherein the polynucleotide hybridizes under stringent conditions to the complement of any of the polynucleotide sequences described above.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified. See, e.g., Sambrook J. and Russell D. 2001. Molecular cloning: A laboratory manual, 3rd edition. Cold Spring Harbor Laboratory Press, Cold Spring Harbor, N.Y. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

The present invention is directed to an isolated nucleic acid molecule comprising a polynucleotide sequence that is fully complementary to any of the polynucleotide sequences described above. The term "complementary" is used to describe the relationship between nucleotide bases that are capable to hybridizing to one another. For example, with respect to DNA, adenosine is complementary to thymine and cytosine is complementary to guanine.

In certain embodiments, the polynucleotide or nucleic acid is DNA. In the case of DNA, a nucleic acid molecule comprising a polynucleotide sequence which encodes a polypeptide can normally include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a polynucleotide sequence encoding a polypeptide if the promoter was capable of effecting transcription of that polynucleotide sequence. The promoter can be a cell-specific promoter that directs substantial transcription of the DNA only in predetermined cells. In general, a coding region is located 3' to a promoter. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths can have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

Suitable regulatory regions include nucleic acid regions located upstream (5' non-coding sequences), within, or downstream (3' non-coding sequences) of a coding region, and which influence the transcription, RNA processing or stability, or translation of the associated coding region. Regulatory regions can include promoters, translation leader sequences, RNA processing sites, effector binding sites, and stem-loop structures. Other transcription control elements, besides a promoter, for example enhancers, operators, repressors, and transcription termination signals, can be operably associated with the polynucleotide to direct cell-specific transcription. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

In certain aspects of the invention, polynucleotide sequences having at least 20 bases, at least 30 bases, or at least 50 bases and that hybridize to a polynucleotide sequence of the present invention can be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally two short segments of the instant sequences can be used in polymerase chain reaction (PCR) protocols to amplify longer nucleic acid fragments encoding homologous genes from DNA or RNA. The polymerase chain reaction can also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence can be based upon sequences derived from the cloning vector.

In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Therefore, the nucleic acid molecules of the present invention can be used to isolate genes encoding homologous proteins from the same or other species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683,202; ligase chain reaction (LCR) (Tabor, S. et al., *Proc. Acad. Sci. USA* 82: 1074 (1985)); or strand displacement amplification (SDA; Walker, et al., *Proc. Natl. Acad. Sci. U.S.A.* 89: 392 (1992)).

In some embodiments, the isolated nucleic acid molecules of the present invention are used to isolate homologous nucleic acid molecules from other organisms in order to identify PUFA synthases that produce similar or improved PUFA profiles. In some embodiments, the isolated nucleic acid molecules of the present invention are used to isolate homologous nucleic acid molecules from other organisms that are involved in producing high amounts of DHA.

The nucleic acid molecules of the present invention also comprise polynucleotide sequences encoding a PUFA synthase gene, a domain of a PUFA synthase gene, or a fragment of the PUFA synthase gene fused in frame to a marker sequence which allows for detection of the polypeptide of the present invention. Marker sequences include auxotrophic or dominant markers known to one of ordinary skill in the art such as ZEO (zeocin), NEO (G418), hygromycin, arsenite, HPH, NAT, and the like.

The present invention also encompasses variants of the PUFA synthase gene. Variants can contain alterations in the coding regions, non-coding regions, or both. Examples are polynucleotide sequence variants containing alterations which produce silent substitutions, additions, or deletions, but do not alter the properties or activities of the encoded polypeptide. In certain embodiments, polynucleotide sequence variants are produced by silent substitutions due to the degeneracy of the genetic code. In further embodiments, polynucleotide sequence variants can be produced for a variety of reasons, e.g., to optimize codon expression for a particular host (e.g., changing codons in the thraustochytrid mRNA to those preferred by other organisms such as *E. coli* or *Saccharomyces cerevisiae*).

Also provided in the present invention are allelic variants, orthologs, and/or species homologs. Procedures known in the art can be used to obtain full-length genes, allelic variants, splice variants, full-length coding portions, orthologs, and/or species homologs of the genes described herein using information from the sequences disclosed herein. For example, allelic variants and/or species homologs can be isolated and identified by making suitable probes or primers from the sequences provided herein and screening a suitable nucleic acid source for allelic variants and/or the desired homologue.

The present invention is directed to a recombinant nucleic acid molecule comprising any of the nucleic acid molecules described above or combinations thereof and a transcription control sequence. In some embodiments, the recombinant nucleic acid molecule is a recombinant vector.

The present invention is directed to a method for making a recombinant vector comprising inserting one or more isolated nucleic acid molecules as described herein into a vector.

The vectors of this invention can be, for example, a cloning vector or an expression vector. The vector can be, for example, in the form of a plasmid, a viral particle, a phage, etc.

The polynucleotide sequences of the invention can be included in any one of a variety of expression vectors for expressing a polypeptide. Such vectors include chromosomal, nonchromosomal, and synthetic DNA or RNA sequences, e.g., derivatives of SV40; bacterial plasmids; and yeast plasmids. However, any other appropriate vector known to one of ordinary skill in the art can be used.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The present invention also includes recombinant constructs comprising one or more of the polynucleotide sequences described above. The constructs comprise a vector, such as a plasmid or viral vector, into which one or more sequences of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available.

Polypeptides

The present invention is directed to isolated polypeptides comprising amino acid sequences for PUFA synthase proteins and domains derived from the isolated microorganisms deposited as ATCC Accession Nos. PTA-9695 and PTA-10212.

As used herein, the term "polypeptide" is intended to encompass a singular "polypeptide" as well as plural "polypeptides" and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids.

Polypeptides as described herein can include fragment, variant, or derivative molecules thereof without limitation. The terms "fragment," "variant," "derivative" and "analog" when referring to a polypeptide include any polypeptide which retains at least some biological activity. Polypeptide fragments can include proteolytic fragments, deletion fragments, and fragments which more easily reach the site of action when delivered to an animal. Polypeptide fragments further include any portion of the polypeptide which comprises an antigenic or immunogenic epitope of the native polypeptide, including linear as well as three-dimensional epitopes. Polypeptide fragments can comprise variant regions, including fragments as described above, and also polypeptides with altered amino acid sequences due to amino acid substitutions, deletions, or insertions. Variants can occur naturally, such as an allelic variant. By an "allelic variant" is intended alternate forms of a gene occupying a given locus on a chromosome of an organism. Non-naturally occurring variants can be produced using art-known mutagenesis techniques. Polypeptide fragments of the invention can comprise conservative or non-conservative amino acid substitutions, deletions, or additions. Variant polypeptides can also be referred to herein as "polypeptide analogs." Polypeptide fragments of the present invention can also include derivative molecules. As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

Polypeptides of the invention can be encoded by any of the nucleic acid molecules of the invention.

The present invention is directed to isolated polypeptides comprising amino acid sequences that are at least 80% identical to the amino acid sequences of Pfa1p (SEQ ID NO:2 or SEQ ID NO:69), Pfa2p (SEQ ID NO:4 or SEQ ID NO:71), Pfa3p (SEQ ID NO:6 or SEQ ID NO:73), and combinations thereof, wherein the polypeptides comprise one or more PUFA synthase activities.

The present invention is directed to polypeptides comprising amino acid sequences that are at least 80% identical to the amino acid sequences of one or more PUFA synthase domains of the PUFA synthases of the invention.

In some embodiments, the present invention is directed to polypeptides comprising amino acid sequences that are at least 80% identical to an amino acid sequence within Pfa1p (SEQ ID NO:2 or SEQ ID NO:69) comprising one or more PUFA synthase domains. In some embodiments, the polypeptide comprises an amino acid sequence at least 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two or more ACP domains such as two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises two or more amino acid sequences, wherein each of the at least two or more amino acid sequences is 80% identical to an amino acid sequence within Pfa1p (SEQ ID NO:2 or SEQ ID NO:69) comprising one or more PUFA synthase domains. In some embodiments, the at least two or more amino acid sequences are 80% identical to the same amino acid sequence within Pfa1p (SEQ ID NO:2 or SEQ ID NO:69) comprising one or more PUFA synthase domains. In some embodiments, the at least two or more amino acid sequences are 80% identical to different amino acid sequences within Pfa1p (SEQ ID NO:2 or SEQ ID NO:69) that each comprise one or more PUFA synthase domains. In some embodiments, the at least two or more amino acid sequences are 80% identical to different amino acid sequences within Pfa1p (SEQ ID NO:2 or SEQ ID NO:69), wherein the at least two or more amino acid sequences are located in the same order or a different order in the polypeptide as compared to the order of the corresponding domains within Pfa1p (SEQ ID NO:2 or SEQ ID NO:69). In some embodiments, the at least two or more amino acid sequences are 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises one or more amino acid sequences within Pfa1p (SEQ ID NO:2 or SEQ ID NO:69) comprising one or more PUFA synthase domains, including one or more copies of any individual domain in combination with one or more copies of any other individual domain.

In some embodiments, the present invention is directed to polypeptides comprising amino acid sequences that are at least 80% identical to an amino acid sequence within Pfa2p (SEQ ID NO:4 or SEQ ID NO:71) comprising one or more PUFA synthase domains. In some embodiments, the polypeptide comprises an amino acid sequence at least 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises two or more amino acid sequences, wherein each of the at least two or more amino acid sequences is 80% identical to an amino acid sequence within Pfa2p (SEQ ID NO:4 or SEQ ID NO:71) comprising one or more PUFA synthase domains. In some embodiments, the at least two or more amino acid sequences are 80% identical to the same amino acid sequence within Pfa2p (SEQ ID NO:4 or SEQ ID NO:71). In some embodiments, the at least two or more amino acid sequences are 80% identical to different amino acid sequences within Pfa2p (SEQ ID NO:4 or SEQ ID NO:71) that each comprise one or more PUFA synthase domains. In some embodiments, the at least two or more amino acid sequences are 80% identical to different amino acid sequences within Pfa2p (SEQ ID NO:4 or SEQ ID NO:71), wherein the at least two or more amino acid sequences are located in the same order or a different order in the polypeptide as compared to the order of the corresponding domains within Pfa2p (SEQ ID NO:4 or SEQ ID NO:71). In some embodiments, the at least two or more amino acid sequences are 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:24 or SEQ ID NO:107), an ER domain (SEQ ID NO:36 or SEQ ID NO:109), and combinations thereof. In some embodiments, the polypeptide comprises one or more amino acid sequences sequence within Pfa2p (SEQ ID NO:4 or SEQ ID NO:71) comprising one or more PUFA synthase domains, including one or more copies of any individual domain in combination with one or more copies of any other individual domain.

In some embodiments, the present invention is directed to polypeptides comprising amino acid sequences that are at least 80% identical to an amino acid sequence within Pfa3p (SEQ ID NO:6 or SEQ ID NO:73) comprising one or more PUFA synthase domains. In some embodiments, the polypeptide comprises an amino acid sequence at least 80% identical to an amino acid sequence within Pfa3p (SEQ ID NO:6 or SEQ ID NO:73) comprising one or more PUFA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises two or more amino acid sequences, wherein each of the at least two or more amino acid sequences is 80% identical to an amino acid sequence within Pfa3p (SEQ ID NO:6 or SEQ ID NO:73) comprising one or more PUFA synthase domains. In some embodiments, the at least two or more amino acid sequences are 80% identical to the same amino acid sequence within Pfa3p (SEQ ID NO:6 or SEQ ID NO:73) comprising one or more PUFA synthase domains. In some embodiments, the at least two or more amino acid sequences are 80% identical to different amino acid sequences within Pfa3p (SEQ ID NO:6 or SEQ ID NO:73) that each comprise one or more PUFA synthase domains. In some embodiments, the at least two or more amino acid sequences are 80% identical to different amino acid sequences within Pfa3p (SEQ ID NO:6 or SEQ ID NO:73), wherein the at least two or more amino acid sequences are located in the same order or a different order in the polypeptide as compared to the order of the corresponding domains within Pfa3p (SEQ ID NO:6 or SEQ ID NO:73). In some embodiments, the at least two or more amino acid sequences are 80% identical to an amino acid sequence within Pfa3p (SEQ ID NO:6 or SEQ ID NO:73) comprising one or more PUFA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises one or more amino acid sequences within Pfa3p (SEQ ID NO:6 or SEQ ID NO:73) comprising one or more PUFA synthase domains, including one or more copies of any individual domain in combination with one or more copies of any other individual domain.

In some embodiments, the present invention is directed to a polypeptide comprising an amino acid sequence at least 80% identical to SEQ ID NO:2 or SEQ ID NO:69, wherein the polypeptide comprises a PUFA synthase activity selected from the group consisting of KS activity, MAT activity, ACP activity, KR activity, DH activity, and combinations thereof.

In some embodiments, the present invention is directed to a polypeptide comprising an amino acid sequence at least 80% identical to SEQ ID NO:8 or SEQ ID NO:75, wherein the polypeptide comprises KS activity.

In some embodiments, the present invention is directed to a polypeptide comprising an amino acid sequence at least 80% identical to SEQ ID NO:10 or SEQ ID NO:77, wherein the polypeptide comprises MAT activity.

In some embodiments, the present invention is directed to a polypeptide comprising an amino acid sequence at least 80% identical to such as any one of SEQ ID NOs:14, 16, 18, 20, 22, 24, 81, 83, 85, 87, 89, 91, 93, 95, 97, or 99, wherein the polypeptide comprises ACP activity.

In some embodiments, the present invention is directed to a polypeptide comprising an amino acid sequence at least 80% identical to SEQ ID NO:12 or SEQ ID NO:79, wherein the polypeptide comprises ACP activity.

In some embodiments, the present invention is directed to a polypeptide comprising an amino acid sequence at least 80% identical to an amino acid sequence within SEQ ID NO:12, wherein the polypeptide comprises ACP activity. In some embodiments, the amino acid sequence is at least 80% identical to an amino acid sequence within SEQ ID NO:12 comprising one, two, three, four, five, or six ACP domains, wherein the polypeptide comprises ACP activity associated with one or more ACP domains. SEQ ID NOs:14, 16, 18, 20, 22, and 24 are representative amino acid sequences comprising a single ACP domain within SEQ ID NO: 12.

In some embodiments, the present invention is directed to a polypeptide comprising an amino acid sequence at least 80% identical to an amino acid sequence within SEQ ID NO:79, wherein the polypeptide comprises ACP activity. In some embodiments, the amino acid sequence is at least 80% identical to an amino acid sequence within SEQ ID NO:79 comprising one, two, three, four, five, six, seven, eight, nine, or ten ACP domains, wherein the polypeptide comprises ACP activity associated with one or more ACP domains. SEQ ID NOs:81, 83, 85, 87, 89, 91, 93, 95, 97, and 99 are representative amino acid sequences comprising a single ACP domain within SEQ ID NO:79.

In some embodiments, the present invention is directed to a polypeptide comprising an amino acid sequence at least 80% identical to SEQ ID NO:26 or SEQ ID NO:101, wherein the polypeptide comprises KR activity.

In some embodiments, the present invention is directed to a polypeptide comprising an amino acid sequence at least 80% identical to SEQ ID NO:28 or SEQ ID NO:119, wherein the polypeptide comprises DH activity.

In some embodiments, the present invention is directed to a polypeptide comprising an amino acid sequence at least 80% identical to SEQ ID NO:4 or SEQ ID NO:71, wherein the polypeptide comprises a PUFA synthase activity selected from the group consisting of KS activity, CLF activity, AT activity, ER activity, and combinations thereof.

In some embodiments, the present invention is directed to a polypeptide comprising an amino acid sequence at least 80% identical to SEQ ID NO:30 or SEQ ID NO:103, wherein the polypeptide comprises KS activity.

In some embodiments, the present invention is directed to a polypeptide comprising an amino acid sequence at least 80% identical to SEQ ID NO:32 or SEQ ID NO:105, wherein the polypeptide comprises CLF activity.

In some embodiments, the present invention is directed to a polypeptide comprising an amino acid sequence at least 80% identical to SEQ ID NO:34 or SEQ ID NO:107, wherein the polypeptide comprises AT activity.

In some embodiments, the present invention is directed to a polypeptide comprising an amino acid sequence at least 80% identical to SEQ ID NO:36 or SEQ ID NO:109, wherein the polypeptide comprises ER activity.

In some embodiments, the present invention is directed to a polypeptide comprising an amino acid sequence at least 80% identical to SEQ ID NO:6 or SEQ ID NO:73, wherein the polypeptide comprises a PUFA synthase activity selected from the group consisting of DH activity, ER activity, and combinations thereof.

In some embodiments, the present invention is directed to a polypeptide comprising an amino acid sequence at least 80% identical to SEQ ID NO:38, wherein the polypeptide comprises DH activity.

In some embodiments, the present invention is directed to a polypeptide comprising an amino acid sequence at least 80% identical to SEQ ID NO:40, wherein the polypeptide comprises DH activity.

In some embodiments, the present invention is directed to a polypeptide comprising an amino acid sequence at least 80% identical to SEQ ID NO:111, wherein the polypeptide comprises DH activity.

In some embodiments, the present invention is directed to a polypeptide comprising an amino acid sequence at least 80% identical to SEQ ID NO:113, wherein the polypeptide comprises DH activity.

In some embodiments, the present invention is directed to a polypeptide comprising an amino acid sequence at least 80% identical to SEQ ID NO:42 or SEQ ID NO:115, wherein the polypeptide comprises ER activity.

In some embodiments, the polypeptides comprise amino acid sequences at least about 80%, 85%, or 90% identical to the amino acid sequences reported herein, or at least about 95%, 96%, 97%, 98%, 99%, or 100% identical to the amino acid sequences reported herein.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide having an amino acid sequence that is at least 80%, 85%, 90%, 95%, 96%, 97%, 98% or 99% identical to, for instance, the amino acid sequence of the present invention can be determined conventionally using known computer programs. As discussed above, a method for determining the best overall match between a query sequence (a sequence of the present invention) and a subject sequence can be determined using the alignment of sequences and calculation of identity scores. The alignments were done using the computer program AlignX, which is a component of the Vector NTI Suite 10.0 package from Invitrogen (www.invitrogen.com). The alignments were performed using a ClustalW alignment (J. Thompson et al., *Nucleic Acids Res.* 22(22): 4673-4680 (1994). The default scoring matrix Blosum62mt2 was used. The default gap opening penalty is 10 and the gap extension penalty 0.1.

In further aspects of the invention, nucleic acid molecules having polynucleotide sequences at least 80%, 85%, 90%, 95%, 96%, 97%, 98% or 99% identical to the polynucleotide sequences disclosed herein, encode a polypeptide having one or more PUFA synthase activities. Polypeptides having one or more PUFA synthase activities exhibit one or more activities similar to, but not necessarily identical to, one or more activities of a PUFA synthase of the present invention.

Of course, due to the degeneracy of the genetic code, one of ordinary skill in the art will immediately recognize that a large portion of the nucleic acid molecules having a polynucleotide sequence at least 80%, 85%, 90%, 95%, 96%, 97%, 98%, or 99% identical to the polynucleotide sequences described herein will encode polypeptides "having PUFA synthase functional activity." In fact, since degenerate variants of any of these polynucleotide sequences all encode the same polypeptide, in many instances, it can be predicted by the skilled artisan based on knowledge of conservative substitutions as well as conserved functional domains, which polypeptides will exhibit activity. In certain aspects of the invention, the polypeptides and polynucleotides of the present invention are provided in an isolated form, e.g., purified to homogeneity. Alternatively, the polypeptides and polynucleotides of the invention can be synthetically produced by conventional synthesizers.

As known in the art "similarity" between two polypeptides is determined by comparing the amino acid sequence and conserved amino acid substitutes thereto of the polypeptide to the sequence of a second polypeptide.

In some embodiments, a polypeptide of the invention is a fusion polypeptide.

As used herein, "fusion polypeptide" means a polypeptide comprising a first polypeptide linearly connected, via peptide bonds, to a second polypeptide. The first polypeptide and the second polypeptide can be identical or different, and they can be directly connected, or connected via a peptide linker. As used herein, the terms "linked," "fused," or "fusion" are used interchangeably. These terms refer to the joining together of two more elements or components by any means including chemical conjugation or recombinant means. An "in-frame fusion" refers to the joining of two or more open reading frames to form a continuous longer open reading frame, in a manner that maintains the correct reading frame of the original open reading frames. Thus, the resulting recombinant fusion protein is a single protein containing two or more segments that correspond to polypeptides encoded by the original open reading frames (which segments are not normally so joined in nature). Although the reading frame is thus made continuous throughout the fused segments, the segments can be physically or spatially separated by, for example, in-frame linker sequence. A "linker" sequence is a series of one or more amino acids separating two polypeptide coding regions in a fusion protein.

The invention is directed to a composition comprising one or more polypeptides of the invention and a biologically acceptable carrier.

In some embodiments, the composition includes a biologically acceptable "excipient," wherein the excipient is a component, or mixture of components, that is used in a composition of the present invention to give desirable characteristics to the composition, and also include carriers. "Biologically acceptable" means a compound, material, composition, salt, and/or dosage form which is, within the scope of sound medical judgment, suitable for contact with the tissues of living cells without excessive toxicity, irritation, inflammatory response, or other problematic complications over the desired duration of contact commensurate with a reasonable benefit/risk ratio. Various excipients can be used. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, *Remington: The Science and Practice of Pharmacy*, 21$^{st}$ ed. (2005). Inclusion of an excipient in a particular classification herein (e.g., "solvent") is intended to illustrate rather than limit the role of the excipient. A particular excipient can fall within multiple classifications.

The present invention further relates to a fragment, variant, derivative, or analog of any of the polypeptide disclosed herein.

The polypeptide of the present invention can be a recombinant polypeptide, a natural polypeptide, or a synthetic polypeptide.

Host Cells

The present invention is directed to a host cell that expresses any of the nucleic acid molecules and recombinant nucleic acid molecules described above as well as combinations thereof.

The term "expression" as used herein refers to a process by which a gene produces a biochemical, for example, a RNA or polypeptide. The process includes any manifestation of the functional presence of the gene within the cell including, without limitation, gene knockdown as well as both transient expression and stable expression. It includes, without limitation, transcription of the gene into messenger RNA (mRNA), transfer RNA (tRNA), small hairpin RNA (shRNA), small interfering RNA (siRNA), or any other RNA product, and the translation of such mRNA into polypeptide(s). If the final desired product is biochemical, expression includes the creation of that biochemical and any precursors.

To produce one or more desired polyunsaturated fatty acids, a host cell can be genetically modified to introduce a PUFA synthase system of the present invention into the host cell.

When genetically modifying organisms to express a PUFA synthase system according to the present invention, some host organisms can endogenously express accessory proteins that are required in conjunction with a PUFA synthase system in order to produce PUFAs. However, it may be necessary to transform some organisms with nucleic acid molecules encoding one or more accessory protein(s) in order to enable or to enhance production of PUFAs by the organism, even if the organism endogenously produces a homologous accessory protein. Some heterologous accessory proteins can operate more effectively or efficiently with the transformed PUFA synthase proteins than the host cells' endogenous accessory protein(s).

Accessory proteins are defined herein as proteins that are not considered to be part of the core PUFA synthase system (i.e., not part of the PUFA synthase enzyme complex itself) but which may be necessary for PUFA production or efficient PUFA production using the core PUFA synthase enzyme complex of the present invention. For example, in order to produce PUFAs, a PUFA synthase system must work with an accessory protein that transfers a 4'-phosphopantetheinyl moiety from coenzyme A to the acyl carrier protein (ACP) domain(s). Therefore, a PUFA synthase system can be considered to include at least one 4'-phosphopantetheinyl transferase (PPTase) domain, or such a domain can be considered to be an accessory domain or protein to the PUFA synthase system. Structural and functional characteristics of PPTases have been described in detail, e.g., in U.S. Appl. Publ. Nos. 2002/0194641; 2004/0235127; and 2005/0100995.

A domain or protein having 4'-phosphopantetheinyl transferase (PPTase) biological activity (function) is characterized as the enzyme that transfers a 4'-phosphopantetheinyl moiety from Coenzyme A to the acyl carrier protein (ACP). This transfer to an invariant serine reside of the ACP activates the inactive apo-form to the holo-form. In both polyketide and fatty acid synthesis, the phosphopantetheine group forms thioesters with the growing acyl chains. The PPTases are a family of enzymes that have been well characterized in fatty acid synthesis, polyketide synthesis, and non-ribosomal peptide synthesis. The sequences of many PPTases are known, crystal structures have been determined (e.g., Reuter K., et al., *EMBO J.* 18(23):6823-31 (1999)), and mutational analysis has identified amino acid residues important for activity (Mofid M. R., et al., *Biochemistry* 43(14):4128-36 (2004)).

One heterologous PPTase which has been previously demonstrated to recognize *Schizochytrium* ACP domains as substrates is the Het I protein of *Nostoc* sp. PCC 7120 (formerly called *Anabaena* sp. PCC 7120). Het I is present in a cluster of genes in *Nostoc* known to be responsible for the synthesis of long chain hydroxy-fatty acids that are a component of a glyco-lipid layer present in heterocysts of that organism (Black and Wolk, J. Bacteriol. 176: 2282-2292 (1994); Campbell et al., *Arch. Microbiol.* 167: 251-258 (1997)). Het I is likely to activate the ACP domains of a protein, Hgl E, present in that cluster. Sequences and constructs containing Het I have been described in, e.g., U.S. Appl. Publ. No. 2007/0244192, incorporated by reference herein in its entirety.

Another heterologous PPTase which has been demonstrated previously to recognize the *Schizochytrium* ACP domains is Sfp, derived from *Bacillus subtilis*. Sfp has been well characterized and is widely used due to its ability to recognize a broad range of substrates. Based on published sequence information (Nakana, et al., *Molecular and General Genetics* 232: 313-321 (1992)), an expression vector was previously produced for Sfp by cloning the coding region, along with defined up- and downstream flanking DNA sequences, into a pACYC-184 cloning vector. This construct encodes a functional PPTase as demonstrated by its ability to be co-expressed with *Schizochytrium* Orfs in *E. coli* which, under appropriate conditions, resulted in the accumulation of DHA in those cells (see, U.S. Appl. Publ. No. 2004/0235127, incorporated by reference herein in its entirety).

Host cells can include microbial cells; animal cells; plant cells; and insect cells. Representative examples of appropriate hosts include bacterial cells; thermophilic or mesophilic bacteria; marine bacteria; thraustochytrids; fungal cells, such as yeast; plant cells; insect cells; and isolated animal cells. Host cells can be either untransfected cells or cells that are already transfected with at least one other recombinant nucleic acid molecule. Host cells can also include transgenic cells that have been engineered to express a PUFA synthase. The selection of an appropriate host is deemed to be within the scope of those skilled in the art from the teachings herein.

Host cells include any microorganism of the order Thraustochytriales, such as microorganisms from a genus including, but not limited to: *Thraustochytrium, Labyrinthuloides, Japonochytrium*, and *Schizochytrium*. Species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium* striatum, *Thraustochytrium aureum, Thraustochytrium roseum*; and any *Japonochytrium* species. Strains of Thraustochytriales include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); *Schizochytrium aggregatum* (Goldstein et Belsky) (ATCC 28209); *Schizochytrium limacinum* (Honda et Yokochi) (IFO 32693); *Thraustochytrium* sp. (23B) (ATCC 20891); *Thraustochytrium* striatum (Schneider) (ATCC 24473); *Thraustochytrium aureum* (Goldstein) (ATCC 34304); *Thraustochytrium roseum* (Goldstein) (ATCC 28210); and *Japonochytrium* sp. (L1) (ATCC 28207). Other examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also can be used as hosts. This includes *Escherichia coli*, which can be useful in fermentation processes. Alternatively, a host such as a *Lactobacillus* species or *Bacillus* species can be used as a host.

Plant host cells include, but are not limited to, any higher plants, including both dicotyledonous and monocotyledonous plants, and consumable plants, including crop plants and plants used for their oils. Such plants can include, for example: canola, soybeans, rapeseed, linseed, corn, safflowers, sunflowers, and tobacco. Other plants include those plants that are known to produce compounds used as pharmaceutical agents, flavoring agents, neutraceutical agents, functional food ingredients, cosmetically active agents, or plants that are genetically engineered to produce these compounds/agents. Thus, any plant species or plant cell can be selected. Examples of plants and plant cells, and plants grown or derived therefrom, include, but are not limited to, plants and plant cells obtainable from canola (*Brassica rapa* L.); canola cultivars NQC02CNX12 (ATCC PTA-6011), NQC02CNX21 (ATCC PTA-6644), and NQC02CNX25 (ATCC PTA-6012) as well as cultivars, breeding cultivars, and plant parts derived from canola cultivars NQC02CNX12, NQC02CNX21, and NQC02CNX25 (see, U.S. Pat. Nos. 7,355,100, 7,456,340, and 7,348,473, respectively); soybean (*Glycine max*); rapeseed (*Brassica* spp.); linseed/flax (*Linum usitatissimum*); maize (corn) (*Zea mays*); safflower (*Carthamus tinctorius*); sunflower (*Helianthus annuus*); tobacco (*Nicotiana tabacum*); *Arabidopsis thaliana*, Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); mustard (*Brassica* spp. and *Sinapis alba*); oil palm (*Elaeis guineeis*); olive ((*ilea eurpaea*); rice (*Oryza sativa*); squash (*Cucurbita maxima*); barley (*Hordeum vulgare*); wheat (*Traeticum aestivum*); and duckweed (*Lemnaceae* sp.). Plant lines from these and other plants can be produced, selected, or optimized for a desirable trait such as or associated with, but not limited to, seed yield, lodging resistance, emergence, disease resistance or tolerance, maturity, late season plant intactness, plant height, shattering resistance, ease of plant transformation, oil content, or oil profile. Plant lines can be selected through plant breeding such as pedigree breeding, recurrent selection breeding, intercross and backcross breeding, as well as methods such as marker assisted breeding and tilling. See, e.g., U.S. Pat. No. 7,348,473.

Animal cells include any isolated animal cells.

The present invention is directed to a host cell that expresses one or more nucleic acid molecules or recombinant nucleic acid molecules, including vectors, of the invention.

The present invention is directed to a method for making a recombinant host cell comprising introducing a recombinant vector into a host cell.

Host cells can be genetically engineered (transduced or transformed or transfected) with the vectors of this invention that can be, for example, a cloning vector or an expression vector. The vector can be, for example, in the form of a plasmid, a viral particle, a phage, etc. The vector containing a polynucleotide sequence as described herein, as well as an appropriate promoter or control sequence, can be employed to transform an appropriate host to permit expression of the polypeptide encoded by the polynucleotide sequence. The genetic modification of host cells can also include the optimization of genes for preferred or optimal host codon usage.

The engineered host cells can be cultured in conventional nutrient media modified as appropriate for activating promoters, selecting transformants, or amplifying the genes of the present invention. The culture conditions, such as temperature, pH, and the like, are those previously used with the host cell selected for expression, and will be apparent to the ordinarily skilled artisan.

In some embodiments, the present invention is directed to genetically modifying a plant or part of a plant to express a PUFA synthase system described herein, which includes at least the core PUFA synthase enzyme complex. A "part of a plant" or "plant part" as defined herein includes any part of a plant, such as, but not limited to, seeds (immature or mature), oils, pollen, embryos, flowers, fruits, shoots, leaves, roots, stems, explants, etc. In some embodiments, the genetically modified plant or part of a plant produces one or more PUFAs, such as EPA, DHA, DPA (n-3 or n-6), ARA, GLA, SDA, other PUFAs, and combinations thereof. Plants are not known to endogenously contain a PUFA synthase system; therefore, the PUFA synthase systems of the present invention can be used to engineer plants with unique fatty acid production capabilities. In a further embodiment, the plant or part of a plant is further genetically modified to express at least one PUFA synthase accessory protein, (e.g., a PPTase). In some embodiments, the plant is an oil seed plant, wherein the oil seeds, and/or the oil in the oil seeds, contain PUFAs produced by the PUFA synthase system. In some embodiments, the genetically modified plants, parts of plants, oil seeds, and/or oils in the oil seeds contain a detectable amount of at least one PUFA that is the product of the PUFA synthase system. In further embodiments, such plants, parts of plants, oil seeds, and/or oils in the oil seeds can be substantially free of intermediate or side products that are not the primary PUFA products of the introduced PUFA synthase system and that are not naturally produced by the endogenous FAS system in the wild-type plants. While wild-type plants produce some short or medium chain PUFAs, such as 18 carbon PUFAs via the FAS system, new or additional PUFAs will be produced in the plant, parts of plants, oil seeds, and/or oils in the oil seeds as a result of genetic modification with a PUFA synthase system described herein.

Genetic modification of a plant can be accomplished using classical strain development and/or molecular genetic techniques. See, U.S. Appl. Publ. No. 2007/0244192. Methods for producing a transgenic plant, wherein a recombinant nucleic acid molecule encoding a desired amino acid sequence is incorporated into the genome of the plant, are known in the art. For example, viral vectors can be used to produce transgenic plants, such as by transformation of a monocotyledonous plant with a viral vector using the methods described in U.S. Pat. Nos. 5,569,597; 5,589,367; and 5,316,931. Methods for the genetic engineering or modification of plants by transformation are also well known in the art, including biological and physical transformation protocols. See, e.g., B. L. Miki et al., *Procedures for Introducing Foreign DNA into Plants*, in METHODS IN PLANT MOLECULAR BIOLOGY AND BIOTECHNOLOGY 67-88 (Glick, B. R. and Thompson, J. E. eds., CRC Press, Inc., Boca Raton, 1993). In addition, vectors and in vitro culture methods for plant cell or tissue transformation and regeneration of plants are available. See, e.g., M. Y. Gruber et al., *Vectors for Plant Transformation*, in METHODS IN PLANT MOLECULAR BIOLOGY AND BIOTECHNOLOGY 89-119 (Glick, B. R. and Thompson, J. E. eds., CRC Press, Inc., Boca Raton, 1993).

A widely utilized method for introducing an expression vector into plants is based on the natural transformation system of *Agrobacterium*. See, e.g., Horsch et al., *Science* 227:1229 (1985) and U.S. Pat. No. 6,051,757. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, e.g., Kado, C. I., Crit. Rev. Plant. Sci. 10:1 (1991). Descriptions of *Agrobacterium* vector systems and methods for *Agrobacterium*-mediated gene transfer are provided by numerous references, including Gruber et al., supra; Miki et al., supra; Moloney et al., *Plant Cell Reports* 8:238 (1989); U.S. Pat. Nos. 5,177,010; 5,104,310; 5,149,645; 5,469,976; 5,464,763; 4,940,838; 4,693,976; 5,591,616; 5,231,019; 5,463,174; 4,762,785; 5,004,863; and 5,159,135; and European Patent Appl. Nos. 0131624, 120516, 159418, 176112, 116718, 290799, 320500, 604662, 627752, 0267159, and 0292435.

Other methods of plant transformation include microprojectile-mediated transformation, wherein DNA is carried on the surface of microprojectiles. The expression vector is introduced into plant tissues with a biolistic device that accelerates the microprojectiles to speeds sufficient to penetrate plant cell walls and membranes. See, e.g., Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992), and U.S. Pat. Nos. 5,015,580 and 5,322,783. Techniques for accelerating genetic material coated onto microparticles directed into cells is also described, e.g., in U.S. Pat. Nos. 4,945,050 and 5,141,141. Another method for physical delivery of DNA to plants is sonication of target cells. See, e.g., Zhang et al., *Bio/Technology* 9:996 (1991). Alternatively, liposome or spheroplast fusion have been used to introduce expression vectors into plants. See, e.g., Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, DNA injection, polyvinyl alcohol or poly-L-ornithine have also been reported. See, e.g., Hain et al., *Mol. Gen. Genet.* 199:161 (1985) and Draper et al., *Plant Cell Physiol.* 23:451 (1982). Electroporation of protoplasts and whole cells and tissues has also been described. See, e.g., Donn et al., in Abstracts of VIIth International Congress on Plant Cell and Tissue Culture IAPTC, A2-38, p. 53 (1990); D'Halluin et al., *Plant Cell* 4:1495-1505 (1992); Spencer et al., *Plant Mol. Biol.* 24:51-61 (1994); International Appl. Publ. Nos. WO 87/06614, WO 92/09696, and WO 93/21335; and U.S. Pat. Nos. 5,472,869 and 5,384,253. Other transformation technology includes whiskers technology, see, e.g., U.S. Pat. Nos. 5,302,523 and 5,464,765.

Chloroplasts or plastids can also be directly transformed. As such, recombinant plants can be produced in which only the chloroplast or plastid DNA has been modified with any of the nucleic acid molecules and recombinant nucleic acid molecules described above as well as combinations thereof. Promoters which function in chloroplasts and plastids are known in the art. See, e.g., Hanley-Bowden et al., *Trends in Biochemical Sciences* 12:67-70 (1987). Methods and compositions for obtaining cells containing chloroplasts into which heterologous DNA has been inserted have been described, e.g., in U.S. Pat. Nos. 5,693,507 and 5,451,513.

Any other methods which provide for efficient transformation can also be employed.

Vectors suitable for use in plant transformation are known in the art. See, e.g., U.S. Pat. Nos. 6,495,738; 7,271,315; 7,348,473; 7,355,100; 7,456,340; and references disclosed therein.

Expression vectors can include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which can be an antibiotic or an herbicide, or genes that encode an altered target which is insensitive to the inhibitor. Selectable markers suitable for use in plant transformation include, but are not limited to, the aminoglycoside phosphotransferase gene of transposon Tn5 (Aph II) which encodes resistance to the antibiotics kanamycin, neomycin, and G418, as well as those genes which encode for resistance or tolerance to glyphosate, hygromycin, methotrexate, phosphinothricin (bialophos), imidazolinones, sulfonylureas and triazolopyrimidine herbicides, such as chlorsulfuron, bromoxynil, dalapon, and the like. One commonly used selectable marker gene for plant transformation is the neomycin phosphotransferase II (nptII) gene under the control of plant regulatory signals which confers resistance to kanamycin. See, e.g., Fraley et al., *Proc. Natl. Acad. Sci. U.S.A.* 80: 4803 (1983). Another commonly used selectable marker gene is the hygromycin phosphotransferase gene which confers resistance to the antibiotic hygromycin. See, e.g., Vanden Elzen et al., *Plant Mol. Biol.* 5:299 (1985). Additional selectable marker genes of bacterial origin that confer resistance to antibiotics include gentamycin acetyl transferase, streptomycin phosphotransferase, aminoglycoside-3'-adenyl transferase, and the bleomycin resistance determinant. See, e.g., Hayford et al., *Plant Physiol.* 86:1216 (1988), Jones et al., *Mol. Gen. Genet.* 210: 86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate, or bromoxynil. See, e.g., Comai et al., *Nature* 317:741-744 (1985), Gordon-Kamm et al., *Plant Cell* 2:603-618 (1990) and Stalker et al., *Science* 242:419-423 (1988). Other selectable marker genes for plant transformation are not of bacterial origin. These genes include, for example, mouse dihydrofolate reductase, plant 5-enolpyruvylshikimate-3-phosphate synthase and plant acetolactate synthase. See, e.g., Eichholtz et al., *Somatic Cell Mol. Genet.* 13:67 (1987), Shah et al., *Science* 233:478 (1986), Charest et al., *Plant Cell Rep.* 8:643 (1990).

A reporter gene can be used with or without a selectable marker. Reporter genes are genes which are typically not present in the recipient organism or tissue and typically encode for proteins resulting in some phenotypic change or enzymatic property. See, e.g., K. Weising et al., *Ann. Rev. Genetics* 22: 421 (1988). Reporter genes include, but are not limited to beta-glucuronidase (GUS), beta-galactosidase, chloramphenicol acetyltransferase, green fluorescent protein, and luciferase genes. See, e.g., Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), and Chalfie et al., *Science* 263:802 (1994). An assay for detecting reporter gene expression can be performed at a suitable time after the gene has been introduced into recipient cells. One such assay entails the use of the gene encoding beta-glucuronidase (GUS) of the uida locus of *E. coli* as described by Jefferson et al., *Biochem. Soc. Trans.* 15: 17-19 (1987).

Promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter, as well as promoters of viral origin, such as the cauliflower mosaic virus (35S and 19S), 35T (which is a re-engineered 35S promoter, see International Appl. Publ. No. WO 97/13402) can be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Matrix attachment regions, scaffold attachment regions, introns, enhancers, and polyadenylation sequences can also be used to improve transcription efficiency or DNA integration. Such elements can be included to obtain optimal performance of the transformed DNA in the plant. Typical elements include, but are not limited to, Adh-intron 1, Adh-intron 6, the alfalfa mosaic virus coat protein leader sequence, the maize streak virus coat protein leader sequence, as well as others available to a skilled artisan. Constitutive promoter regulatory elements can also be used to direct continuous gene expression. Constitutive promoters include, but are not limited to, promoters from plant viruses such as the 35S promoter from CaMV (Odell et al., *Nature* 313:810-812 (1985)), and promoters from such genes as rice actin (McElroy et al., *Plant Cell* 2:163-171 (1990)), ubiquitin (Christensen et al., *Plant Mol. Biol.* 12:619-632 (1989) and Christensen et al., *Plant Mol. Biol.* 18:675-689 (1992)), pEMU (Last et al., *Theor. Appl. Genet.* 81:581-588 (1991)), MAS (Velten et al., *EMBO J.* 3:2723-2730 (1984)), maize H3 histone (Lepetit et al., *Mol. Gen. Genetics* 231:276-285 (1992) and Atanassova et al., *Plant Journal* 2(3): 291-300 (1992)), and the ALS promoter, XbaI/NcoI fragment 5' to the *Brassica napus* ALS3 structural gene (or a nucleotide sequence similar to the XbaI/NcoI fragment) (International Appl. Publ. No. WO 96/30530). Tissue-specific promoter regulatory elements can also be used for gene expression in specific cell or tissue types, such as leaves or seeds (e.g., zein, oleosin, napin, ACP, globulin, and the like). Tissue-specific or tissue-preferred promoters include, but are not limited to, a root-preferred promoter, such as from the phaseolin gene (Murai et al., *Science* 23:476-482 (1983) and Sengupta-Gopalan et al., *Proc. Natl. Acad.* Sci. U.S.A. 82:3320-3324 (1985)); a leaf-specific and light-induced promoter such as from cab or rubisco (Simpson et al., *EMBO J.* 4(11):2723-2729 (1985) and Timko et al., *Nature* 318:579-582 (1985)); an anther-specific promoter such as from LAT52 (Twell et al., *Mol. Gen. Genetics* 217:240-245 (1989)); a pollen-specific promoter such as from Zm13 (Guerrero et al., *Mol. Gen. Genetics* 244:161-168 (1993)); or a microspore-preferred promoter such as from apg (Twell et al., *Sex. Plant Reprod.*

6:217-224 (1993)). Promoter regulatory elements can also be active during a certain stage of a plants' development as well as plant tissues and organs, including, but not limited to, pollen-specific, embryo specific, corn silk specific, cotton fiber specific, root specific, and seed endosperm specific promoter regulatory elements. An inducible promoter regulatory element can be used, which is responsible for expression of genes in response to a specific signal, such as: physical stimulus (heat shock genes); light (RUBP carboxylase); hormone (Em); metabolites; chemicals; and stress. Inducible promoters include, but are not limited to, a promoter from the ACEI system which responds to copper (Mett et al., *PNAS* 90:4567-4571 (1993)); from the In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)), from the Tet repressor from Tn10 (Gatz et al., *Mol. Gen. Genetics* 227:229-237 (1991)); and from a steroid hormone gene, the transcriptional activity of which is induced by a glucocorticosteroid hormone (Schena et al., *Proc. Natl. Acad. Sci. U.S.A.* 88:0421 (1991).

Signal sequences can also be used to direct a polypeptide to either an intracellular organelle or subcellular compartment or for secretion to the apoplast. See, e.g., Becker et al., *Plant Mol. Biol.* 20:49 (1992), Knox, C., et al., *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., *Cell* 39:499-509 (1984), and Steifel et al., *Plant Cell* 2:785-793 (1990). Such targeting sequences provide for the desired expressed protein to be transferred to the cell structure in which it most effectively functions or to areas of the cell in which cellular processes necessary for desired phenotypic functions are concentrated.

In some embodiments, signal sequences are used to direct proteins of the invention to a subcellular compartment, for example, to the plastid or chloroplast. Gene products, including heterologous gene products, can be targeted to the plastid or chloroplast by fusing the gene product to a signal sequence which is cleaved during chloroplast import yielding the mature protein. See, e.g., Comai et al., *J. Biol. Chem.* 263: 15104-15109 (1988) and van den Broeck et al., *Nature* 313: 358-363 (1985). DNA encoding for appropriate signal sequences can be isolated from cDNAs encoding the RUBISCO protein, the CAB protein, the EPSP synthase enzyme, the GS2 protein, or from any naturally occurring chloroplast targeted protein that contains a signal sequence (also termed a chloroplast transit peptide (CTP)) that directs the targeted protein to the chloroplast. Such chloroplast targeted proteins are well known in the art. The chloroplast targeted proteins are synthesized as larger precursor proteins that contain an amino-terminal CTP, which directs the precursor to the chloroplast import machinery. CTPs are generally cleaved by specific endoproteases located within the chloroplast organelle, thus releasing the targeted mature protein, including active proteins such as enzymes, from the precursor into the chloroplast milieu. Examples of sequences encoding peptides suitable for targeting a gene or gene product to the chloroplast or plastid of the plant cell include the *petunia* EPSPS CTP, the *Arabidopsis* EPSPS CTP2 and intron, and other sequences known in the art. Specific examples of CTPs include, but are not limited to, the *Arabidopsis thaliana* ribulose bisphosphate carboxylase small subunit ats1A transit peptide, an *Arabidopsis thaliana* EPSPS transit peptide, and a *Zea* maize ribulose bisphosphate carboxylase small subunit transit peptide. An optimized transit peptide is described, e.g., by Van den Broeck et al., *Nature* 313:358-363 (1985). Prokaryotic and eukaryotic signal sequences are disclosed, e.g., by Michaelis et al., *Ann. Rev. Microbiol.* 36: 425 (1982). Additional examples of transit peptides that can be used in the invention include chloroplast transit peptides described in Von Heijne et al., *Plant Mol. Biol. Rep.* 9:104-126(1991); Mazur et al., *Plant Physiol.* 85: 1110 (1987); Vorst et al., *Gene* 65: 59 (1988); Chen & Jagendorf, *J. Biol. Chem.* 268: 2363-2367 (1993); a transit peptide from the rbcS gene from *Nicotiana plumbaginifolia* (Poulsen et al. *Mol. Gen. Genet.* 205: 193-200 (1986)); and a transit peptide derived from *Brassica napus* acyl-ACP thioesterase (Loader et al., *Plant Mol. Biol.* 23: 769-778 (1993); Loader et al., *Plant Physiol.* 110:336-336 (1995).

Genetically modified plants of the invention can be further modified to delete or inactivate an endogenous fatty acid synthase, to reduce endogenous competition with the exogenous PUFA synthase system for malonyl CoA, to increase the level of malonyl CoA in the organism, and combinations thereof. See, e.g., U.S. Appl. Publ. No. 2007/0245431.

A genetically modified plant can be cultured in a fermentation medium or grown in a suitable medium such as soil. A suitable growth medium for higher plants includes any growth medium for plants, such as, but not limited to, soil, sand, any other particulate media that support root growth (e.g. vermiculite, perlite, etc.) or hydroponic culture as well as suitable light, water, and nutritional supplements which optimize the growth of the higher plant. PUFAs can be recovered from the genetically modified plants through purification processes which extract the compounds from the plant. PUFAs can be recovered by harvesting the plant as well as by harvesting the oil from the plant (e.g., from the oil seeds). The plant can also be consumed in its natural state or further processed into consumable products. In some embodiments, the present invention is directed to a genetically modified plant, wherein the plant produces at least one PUFA as a result of the genetic modification, and wherein the total fatty acid profile in the plant, or the part of the plant that accumulates PUFAs, comprises a detectable amount of the PUFA produced as a result of genetic modification of the plant. In some embodiments, the plant is an oil seed plant. In some embodiments, the oil seed plant produces PUFAs in its mature seeds or contains the PUFAs in the oil of its seeds.

Various mammalian cell culture systems can also be employed to express recombinant protein. Expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences.

Methods Involving Heterologous Expression

The present invention is directed to a method to produce at least one PUFA comprising expressing a PUFA synthase system in a host cell under conditions effective to produce PUFA, wherein the PUFA synthase system comprises any of the isolated nucleic acid molecules and recombinant nucleic acid molecules described herein as well as combinations thereof, wherein at least on PUFA is produced. In some embodiments, the at least one PUFA includes DHA, EPA, or a combination thereof. In some embodiments, the host cell is a plant cell, an isolated animal cell, or a microbial cell. In some embodiments the host cell is a thraustochytrid.

The present invention is directed to a method to produce lipids enriched for DHA, EPA, or a combination thereof, comprising expressing a PUFA synthase gene in a host cell under conditions effective to produce lipids, wherein the PUFA synthase gene comprises any of the isolated nucleic acid molecules and recombinant nucleic acid molecules described herein as well as combinations thereof in the host cell, wherein lipids enriched with DHA, EPA, or a combination thereof are produced.

The invention is directed to a method of isolating lipids from a host cell, comprising expressing a PUFA synthase gene in the host cell under conditions effective to produce lipids, and isolating lipids from the host cell, wherein the PUFA synthase system in the host cell comprises any of the isolated nucleic acid molecules and recombinant nucleic acid molecules described herein as well as combinations thereof.

In some embodiments, one or more lipid fractions containing PUFAs are isolated from the host cells. In some embodiments, the one or more fractions isolated from the host cell includes the total fatty acid fraction, the sterol esters fraction, the triglyceride fraction, the free fatty acid fraction, the sterol fraction, the diglycerol fraction, the phospholipid fraction, or combination thereof. In some embodiments, PUFAs are isolated from the host cells, wherein the PUFAs are enriched for omega-3 fatty acids omega-6 fatty acids, or combinations thereof based on the composition of the PUFA synthase system introduced into a host cell. In some embodiments, the PUFAs are enriched for DHA, EPA, DPA n-6, ARA, or combinations thereof based on the composition of the PUFA synthase system introduced into a host cell. In some embodiments, the PUFAs are enriched for DHA, EPA, or a combination thereof. In some embodiments, the PUFA profile of PUFAs isolated from a host cell include high concentrations of DHA and lower concentrations of EPA, ARA, DPA n-6, or combinations thereof. In some embodiments, the PUFA profile of PUFAs isolated from a host cell include high concentrations of DHA and EPA, and lower concentrations of ARA, DPA n-6, or combinations thereof. In some embodiments, the PUFA profile of PUFAs isolated from a host cell include high concentrations of EPA and lower concentrations of DHA, ARA, DPA n-6, or combinations thereof.

The invention is directed to a method of replacing an inactive or deleted PUFA synthase activity, introducing a new PUFA synthase activity, or enhancing an existing PUFA synthase activity in an organism having PUFA synthase activity, comprising expressing any of the isolated nucleic acid molecules and recombinant nucleic acid molecules described herein as well as combinations thereof in the organism under conditions effective to express the PUFA synthase activity. In some embodiments, the nucleic acid molecule comprises one or more PFA1, PFA2, or PFA3 PUFA synthase polynucleotide sequences described herein that encode one or more PUFA synthase domains. In some embodiments, the PUFA profiles of the organisms are altered by the introduction of the one or more nucleic acid molecules of the invention. In some embodiments, the altered PUFA profiles include an increase in omega-3 fatty acids and a decrease in omega-6 fatty acids. In some embodiments, the altered PUFA profiles include an increase in omega-6 fatty acids and a decrease in omega-3 fatty acids. In some embodiments, both omega-3 and omega-6 fatty acids are increased. In some embodiments, the amount of DHA is increased while the amounts of one or more of EPA, ARA, DPA n-6, or combinations thereof are maintained or decrease. In some embodiments, the amounts of EPA and DHA are increased while the amounts of ARA, DPA n-6, or a combination thereof are maintained or decrease. In some embodiments, the amount of EPA is increased while the amounts of one or more of EPA, ARA, DPA n-6, or combinations thereof are maintained or decrease. In some embodiments, the nucleic acid molecule comprises the polynucleotide sequence of PFA3 or one or more domains therein. In some embodiments, the nucleic acid molecule comprises the polynucleotide sequence of PFA3 or one or more domains therein and the amount of omega-3 fatty acids in the organism is increased while the amount of omega-6 fatty acids is decreased. In some embodiments, the nucleic acid molecule comprises the polynucleotide sequence of PFA2 or one or more domains therein and the amount of DHA in the organism is increased while the amount of EPA is decreased.

The invention is directed to methods of increasing production of DHA, EPA, or a combination thereof in an organism having PUFA synthase activity, comprising expressing any of the isolated nucleic acid molecules and recombinant nucleic acid molecules described herein as well as combinations thereof in the organism under conditions effective to produce DHA, EPA, or a combination thereof, wherein the PUFA synthase activity replaces an inactive or deleted activity, introduces a new activity, or enhances an existing activity in the organism, and wherein production of DHA, EPA, or a combination thereof in the organism is increased.

Having generally described this invention, a further understanding can be obtained by reference to the examples provided herein. These examples are for purposes of illustration only and are not intended to be limiting.

Example 1

Degenerate primers for the KS and DH PUFA synthase domains were designed in order to isolate the corresponding sequences from the isolated microorganism deposited under ATCC Accession No. PTA-9695, also known as *Schizochytrium* sp. ATCC PTA-9695.

Degenerate primers for the KS region of *Schizochytrium* sp. ATCC PTA-9695 PFA1 (i.e., the region containing the KS domain) were designed based on the published PFA1 (previously termed orfA or ORF 1) sequences for *Shewanella japonica, Schizochytrium* sp. ATCC 20888, *Thraustochytrium aureum* (ATCC 34304), and *Thraustochytrium* sp. 23B ATCC 20892:

```
                                        (SEQ ID NO: 62)
prDS173 (forward):
GATCTACTGCAAGCGCGGNGGNTTYAT,
and (SEQ ID NO: 63)
prDS174 (reverse):
GGCGCAGGCGGCRTCNACNAC.
```

Degenerate primers for the DH region of *Schizochytrium* sp. ATCC PTA-9695 PFA3 (previously termed orfC or ORF 3) were designed based on the published sequences for *Moritella marina; Schizochytrium* sp. ATCC 20888; *Shewanella* sp. SCRC-2738; *Photobacter profundum*; and *Thraustochytrium* sp. 23B ATCC 20892:

```
                                        (SEQ ID NO: 64)
JGM190 (forward): CAYTGGTAYTTYCCNTGYCAYTT;
and (SEQ ID NO: 65)
BLR242 (reverse): CCNGGCATNACNGGRTC.
```

The PCR conditions with chromosomal DNA template were as follows: 0.2 µM dNTPs, 0.1 uM each primer, 8% DMSO, 200 ng chromosomal DNA, 2.5 U Herculase® II fusion polymerase (Stratagene), and 1× Herculase® buffer (Stratagene) in a 50 µL total volume. The PCR Protocol included the following steps: (1) 98° C. for 3 minutes; (2) 98° C. for 30 seconds; (3) 50° C. for 30 seconds; (4) 72° C. for 2 minutes; (5) repeat steps 2-4 for 40 cycles; (6) 72° C. for 5 minutes; and (7) hold at 6° C.

For both primer pairs, PCR yielded distinct DNA products with the expected sizes using chromosomal templates from *Schizochytrium* sp. ATCC Accession No. PTA-9695. The respective PCR products were cloned into the vector pJET1.2/blunt (Fermentas) according to the manufacturer's instructions, and the insert sequence was determined using supplied standard primers.

The DNA sequences obtained from the PCR products were compared with known sequences available from the NCBI GenBank in a standard BLASTx search (BLASTx parameters: Low complexity filter on; Matrix: BLOSUM62; Gap cost; Existence 11, Extenstion1. Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", *Nucleic Acids Res.* 25:3389-3402.).

At the amino acid level, the sequences with the highest level of homology to deduced amino acid sequence derived from the cloned DNA containing the KS fragment from *Schizochytrium* sp. ATCC PTA-9695 were: *Schizochytrium* sp. ATCC 20888 "polyunsaturated fatty acid synthase subunit A" (Identity=87%; positives=92%); *Shewanella oneidensis* MR-1 "multi-domain beta-ketoacyl synthase" (Identity=49%; positives=64%); and *Shewanella* sp. MR-4 "beta-ketoacyl synthase" (Identity=49%; positives=64%).

At the amino acid level, the sequences with the highest level of homology to the deduced amino acid sequence derived from the cloned DNA containing the DH fragment from *Schizochytrium* sp. ATCC PTA-9695 were: *Schizochytrium* sp. ATCC 20888 "polyunsaturated fatty acid synthase subunit C" (Identity=61%; positives=71%); *Shewanella pealeana* ATCC 700345 "Beta-hydroxyacyl- (acyl-carrier-protein) dehydratase FabA/FabZ" (Identity=35%; positives=50%); and *Shewanella sediminis* HAW-EB3 "omega-3 polyunsaturated fatty acid synthase PfaC" (Identity=34%; positives=50%).

Example 2

PUFA synthase genes were identified from *Schizochytrium* sp. ATCC PTA-9695.

Genomic DNA was prepared from the microorganism by standard procedures. See, e.g., Sambrook J. and Russell D. 2001. *Molecular cloning: A laboratory manual*, 3rd edition. Cold Spring Harbor Laboratory Press, Cold Spring Harbor, N.Y. Briefly: (1) 500 µL of cells were pelleted from mid-log culture. The cells were Re-spun, and all traces of liquid were removed from the cell pellet with a small-bore tip; (2) pellets were resuspended with 200 µL lysis buffer (20 mM Tris pH 8.0, 125 µg/mL Proteinase K, 50 mM NaCl, 10 mM EDTA pH 8.0, 0.5% SDS); (3) cells were lysed at 50° C. for 1 hour; (4) the lysis mixture was pipetted into phase-lock gel (PLG-Eppendorf) 2 mL tubes; (5) equal volume of P:C:I was added and allowed to mix for 1.5 hours; (6) the tubes were centrifuged at 12 k×g for 5 minutes; (7) the aqueous phase was removed from above the gel within the PLG tube and an equal volume of chloroform was added to the aqueous phase, and mixed for 30 minutes; (8) the tubes were centrifuged at 14 k for approximately 5 minutes; (9) the top layer (aqueous phase) was pipetted away from the chloroform, and placed in a new tube; (10) 0.1 volume of 3M NaOAC was added and mixed (inverted several times); (11) 2 volumes of 100% EtOH were added and mixed (inverted several times) with genomic DNA precipitant forming at this stage; (12) the tubes were spun at 4° C. in a microcentrifuge at 14 k for approximately 15 minutes; (13) the liquid was gently poured off with genomic DNA remaining at the bottom of the tube; (14) the pellet was washed with 0.5 mL 70% EtOH; (15) the tubes were spun at 4° C. in a microcentrifuge at 14 k for approximately 5 minutes; (16) the EtOH was gently poured off and the genomic DNA pellet was dried; and (17) a suitable volume of $H_2O$ and RNase was added directly to the genomic DNA pellet.

The isolated genomic DNA was used to generate recombinant libraries consisting of large fragments (approximately 40 kB) according to the manufacturer's instructions in the cosmid pWEB-TNC™ (Epicentre). The cosmid libraries were screened by standard colony hybridization procedures using $^{32}P$ radioactively labeled probes (Sambrook J. and Russell D. 2001. *Molecular cloning: A laboratory manual*, 3rd edition. Cold Spring Harbor Laboratory Press, Cold Spring Harbor, N.Y.). The probes contained DNA homologous to published PUFA synthase sequences from other organisms as described in Example 1. These probes were generated by a DNA restriction digest of the cloned fragments from respective clones from pJET1.2/blunt described above and labeled by standard methods. In all cases, strong hybridization of the individual probes to certain cosmids indicated clones containing DNA homologous to PUFA synthase genes.

Cosmid clone pDS115 demonstrated strong hybridization of probe to the KS region and was selected for DNA sequencing of the *Schizochytrium* sp. ATCC PTA-9695 PFA1 gene. Cosmid clone pDS115, containing the *Schizochytrium* sp. ATCC PTA-9695 PFA1 and PFA2 genes, was deposited under the Budapest Treaty, at the American Type Culture Collection, Patent Depository, 10801 University Boulevard, Manassas, Va. 20110-2209, on Jan. 27, 2009, and given ATCC Accession No. PTA-9737. Sequencing primers to the DNA sequence of the KS region determined in Example 1 were designed using standard methods. To determine the DNA sequence of *Schizochytrium* sp. ATCC PTA-9695 PFA1, successive rounds of DNA sequencing, involving subsequent sequencing primer design by standard methods, was carried out in order to "walk" the cosmid clone.

In previously published thraustochytrid PUFA synthase systems, the PUFA synthase genes PFA1 and PFA2 have been clustered together and arranged as to be divergently transcribed. This is also the case for PFA1 and PFA2 from *Schizochytrium* sp. ATCC PTA-9695. Through the "walking" of DNA sequence from cosmid clone pDS115, the conceptual start of PFA2 was found to be 493 nucleotides from the start of PFA1 and divergently transcribed. Each nucleotide base pair of the *Schizochytrium* sp. ATCC PTA-9695 PFA1 and PFA2 PUFA synthase genes were covered by at least two separate DNA sequencing reactions with high-quality with at least a minimum aggregated Phred score of 40 (confidence level of 99.99%).

Cosmid clone pBS4 demonstrated strong hybridization of probe to the DH region and was selected for DNA sequencing of the *Schizochytrium* sp. ATCC PTA-9695 PFA3 gene. Cosmid clone pBS4, containing the *Schizochytrium* sp. ATCC PTA-9695 PFA3 gene, was deposited under the Budapest Treaty, at the American Type Culture Collection, Patent Depository, 10801 University Boulevard, Manassas, Va. 20110-2209, on Jan. 27, 2009, and given ATCC Accession No. PTA-9736. Sequencing primers were designed using standard methods to the DH region DNA sequence determined in Example 1. To determine the DNA sequence of the *Schizochytrium* sp. ATCC PTA-9695 PFA3 gene, successive rounds of DNA sequencing, involving subsequent sequencing primer design by standard methods, was carried out in order to "walk" the cosmid clone. Each nucleotide base pair of the *Schizochytrium* sp. ATCC PTA-9695 PFA3 gene was covered by at least two separate DNA sequencing reactions of high-quality with at least a minimum aggregated Phred score of 40 (confidence level of 99.99%).

Table 1 shows identities for the *Schizochytrium* sp. ATCC PTA-9695 PFA1 (SEQ ID NO:1), PFA2 (SEQ ID NO:3), and PFA3 (SEQ ID NO:5) polynucleotide sequences as compared to previously published sequences. Identities were determined by the scoring matrix "swgapdnamt" within the "AlignX" program of the VectorNTI program, a standard for DNA alignment.

TABLE 1

PERCENT IDENTITY TO PFA1, PFA2, AND PFA3 POLYNUCLEOTIDE Sequences

| Source of Published PFA1, PFA2, and PFA3 Sequences | % Identity of published PFA1 (orfA) to PFA1 (SEQ ID NO: 1) | % Identity of published PFA2 (orfB) to PFA2 (SEQ ID NO: 3) | % Identity of published PFA3 (orfC) to PFA3 (SEQ ID NO: 5) |
|---|---|---|---|
| *Schizochytrium* sp. ATCC 20888 | 70 | 66 | 75 |
| *Thraustochytrium aureum* ATCC 34304 | 65 | 62 | not published |
| *Thraustochytrium* sp. 23B ATCC 20892 | 56 | 55 | 67 |

Table 2 shows identities for the *Schizochytrium* sp. ATCC PTA-9695 Pfa1p (SEQ ID NO:2), Pfa2p (SEQ ID NO:4), and Pfa3p (SEQ ID NO:6) amino acid sequences as compared to previously published PUFA synthase amino acid sequences. Identities were determined through use of the scoring matrix "blosum62mt2" within the "AlignX" program of the VectorNTI program, a standard for protein alignment.

TABLE 2

Percent Identity to Pfa1p, Pfa2p, and Pfa3p Amino Acid Sequences

| Source of Published Pfa1p, Pfa2p, and Pfa3p Sequences | % Identity of published Pfa1p (OrfA) to Pfa1p (SEQ ID NO: 2) | % Identity of published Pfa2p (OrfB) to Pfa2p (SEQ ID NO: 4) | % Identity of published Pfa3p (OrfC) to Pfa3p (SEQ ID NO: 6) |
|---|---|---|---|
| *Schizochytrium* sp. ATCC 20888 | 60 | 53 | 70 |
| *Thraustochytrium aureum* ATCC 34304 | 60 | 54 | not published |
| *Thraustochytrium* sp. 23B ATCC 20892 | 52 | 52 | 70 |

Example 3

Domain analysis was performed to annotate the sequence coordinates for the PUFA synthase domains and active sites of *Schizochytrium* sp. ATCC PTA-9695 PFA1, PFA2, and PFA3, respectively. Domains were identified based on homology to known PUFA synthase, fatty acid synthase, and polyketide synthase domains.

Table 3 shows the domains and active sites associated with *Schizochytrium* sp. ATCC PTA-9695 PFA1.

TABLE 3

*Schizochytrium* sp. ATCC PTA-9695 PFA1 Domain Analysis

| Domain | DNA position | AA position | Sites | DNA position | AA position |
|---|---|---|---|---|---|
| KS | 7-1401 of SEQ ID NO: 1 (SEQ ID NO: 7) | 3-467 of SEQ ID NO: 2 (SEQ ID NO: 8) | Active - DXAC* (SEQ ID NO:43) | 607-609 of SEQ ID NO: 1 | C203 of SEQ ID NO: 2 |
| | | | End - GFGG (SEQ ID NO: 44) | 1363-1374 of SEQ ID NO: 1 (SEQ ID NO: 45) | 455-458 of SEQ ID NO: 2 |
| MAT | 1798-2700 of SEQ ID NO: 1 (SEQ ID NO: 9) | 600-900 of SEQ ID NO: 2 (SEQ ID NO: 10) | Active GHS * LG (SEQ ID NO: 46) | 2095-2097 of SEQ ID NO: 1 | S699 of SEQ ID NO: 2 |
| ACP | 3298-5400 of SEQ ID NO: 1 (SEQ ID NO: 11) | 1100-1800 of SEQ ID NO: 2 (SEQ ID NO: 12) | ACP1 domain | 3325-3600 of SEQ ID NO: 1 (SEQ ID NO: 13) | 1109-1200 of SEQ ID NO: 2 (SEQ ID NO: 14) |
| | | | ACP1 Active LGIDS* (SEQ ID NO: 47) | 3454-3456 of SEQ ID NO: 1 | S1152 of SEQ ID NO: 2 |
| | | | ACP2 domain | 3667-3942 of SEQ ID NO: 1 (SEQ ID NO: 15) | 1223-1314 of SEQ ID NO: 2 (SEQ ID NO: 16) |
| | | | ACP2 Active LGIDS* (SEQ ID NO: 47) | 3796-3798 of SEQ ID NO: 1 | S1266 of SEQ ID NO: 2 |
| | | | ACP3 domain | 4015-4290 of SEQ ID NO: 1 (SEQ ID NO: 17) | 1339-1430 of SEQ ID NO: 2 (SEQ ID NO: 18) |

TABLE 3-continued

Schizochytrium sp. ATCC PTA-9695 PFA1 Domain Analysis

| Domain | DNA position | AA position | Sites | DNA position | AA position |
|---|---|---|---|---|---|
| | | | ACP3 Active LGIDS* (SEQ ID NO: 47) | 4144-4146 of SEQ ID NO: 1 | S1382 of SEQ ID NO: 2 |
| | | | ACP4 domain | 4363-4638 of SEQ ID NO: 1 (SEQ ID NO: 19) | 1455-1546 of SEQ ID NO: 2 (SEQ ID NO: 20) |
| | | | ACP4 Active LGIDS* (SEQ ID NO: 47) | 4492-4494 of SEQ ID NO: 1 | S1498 of SEQ ID NO: 2 |
| | | | ACP5 domain | 4711-4986 of SEQ ID NO: 1 (SEQ ID NO: 21) | 1571-1662 of SEQ ID NO: 2 (SEQ ID NO: 22) |
| | | | ACP5 Active LGIDS* (SEQ ID NO: 47) | 4840-4842 of SEQ ID NO: 1 | S1614 of SEQ ID NO: 2 |
| | | | ACP6 domain | 5053-5328 of SEQ ID NO: 1 (SEQ ID NO: 23) | 1685-1776 of SEQ ID NO: 2 (SEQ ID NO: 24) |
| | | | ACP6 Active LGIDS* (SEQ ID NO: 47) | 5182-5184 of SEQ ID NO: 1 | S1728 of SEQ ID NO: 2 |
| KR | 5623-7800 of SEQ ID NO: 1 (SEQ ID NO: 25) | 1875-2600 of SEQ ID NO: 2 (SEQ ID NO: 26) | "core region" | 5998-6900 of SEQ ID NO: 1 (SEQ ID NO: 48) | 2000-2300 of SEQ ID NO: 2 (SEQ ID NO: 49) |
| DH Motif | 7027-7065 of SEQ ID NO: 1 (SEQ ID NO: 27) | 2343-2355 of SEQ ID NO: 2 (SEQ ID NO: 28) | LxxHxxxGxxxxP (SEQ ID NO: 50) | 7027-7065 of SEQ ID NO: 1 (SEQ ID NO: 27) | 2343-2355 of SEQ ID NO: 2 (SEQ ID NO: 28) |

The first domain in Schizochytrium sp. ATCC PTA-9695 Pfa1 is a KS domain. The nucleotide sequence containing the sequence encoding the Schizochytrium sp. ATCC PTA-9695 Pfa1 KS domain is represented herein as SEQ ID NO:7, corresponding to positions 7-1401 of SEQ ID NO:1. The amino acid sequence containing the Schizochytrium sp. ATCC PTA-9695 Pfa1 KS domain is represented herein as SEQ ID NO:8, corresponding to positions 3-467 of SEQ ID NO:2. The KS domain contains an active site motif: DXAC* (SEQ ID NO:43), with an *acyl binding cite corresponding to C203 of SEQ ID NO:2. Also, a characteristic motif is present at the end of the KS domain: GFGG (SEQ ID NO:44), corresponding to positions 455-458 of SEQ ID NO:2 and positions 453-456 of SEQ ID NO:8.

The second domain in Schizochytrium sp. ATCC PTA-9695 Pfa1 is a MAT domain. The nucleotide sequence containing the sequence encoding the Schizochytrium sp. ATCC PTA-9695 Pfa1 MAT domain is represented herein as SEQ ID NO:9, corresponding to positions 1798-2700 of SEQ ID NO:1. The amino acid sequence containing the Schizochytrium sp. ATCC PTA-9695 Pfa1 MAT domain is represented herein as SEQ ID NO:10, corresponding to positions 600-900 of SEQ ID NO:2. The MAT domain contains an active site motif: GHS*XG (SEQ ID NO:46), with an *acyl binding cite corresponding to 5699 of SEQ ID NO:2.

The third through eighth domains of Schizochytrium sp. ATCC PTA-9695 Pfa1 are six tandem ACP domains, also referred to herein as ACP1, ACP2, ACP3, ACP4, ACP5, and ACP6. The nucleotide sequence containing the first ACP domain, ACP1, is represented herein as SEQ ID NO:13 and is contained within the nucleotide sequence spanning from about position 3325 to about position 3600 of SEQ ID NO:1. The amino acid sequence containing ACP1, represented herein as SEQ ID NO:14, is contained within the amino acid sequence spanning from about position 1109 to about position 1200 of SEQ ID NO:2. The nucleotide sequence containing ACP2, represented herein as SEQ ID NO:15, is contained within the nucleotide sequence spanning from about position 3667 to about position 3942 of SEQ ID NO:1. The amino acid sequence containing ACP2, represented herein as SEQ ID NO:16, is contained within the amino acid sequence spanning from about position 1223 to about position 1314 of SEQ ID NO:2. The nucleotide sequence containing ACP3, represented herein as SEQ ID NO:17, is contained within the nucleotide sequence spanning from about position 4015 to about position 4290 of SEQ ID NO:1. The amino acid sequence containing ACP3, represented herein as SEQ ID NO:18, is contained within the amino acid sequence spanning from about position 1339 to about position 1430 of SEQ ID NO:2. The nucleotide sequence containing ACP4, represented herein as SEQ ID NO:19, is contained within the nucleotide sequence spanning from about position 4363 to about position 4638 of SEQ ID NO:1. The amino acid sequence containing ACP4, represented herein as SEQ ID NO:20, is contained within the amino acid sequence spanning from about position 1455 to about position 1546 of SEQ ID NO:2. The nucleotide sequence containing ACP5, represented herein as SEQ ID NO:21, is contained within the nucleotide sequence spanning from about position 4711 to about position 4986 of SEQ ID NO:1. The amino acid sequence containing ACP5, represented herein as SEQ ID NO:22, is contained within the amino acid sequence spanning from about position 1571 to about position 1662 of SEQ ID NO:2. The nucleotide sequence containing ACP6, represented herein as SEQ ID NO:23, is contained within the nucleotide sequence spanning from about position 5053 to about position 5328 of SEQ ID NO:1. The amino acid sequence containing ACP6, represented herein as SEQ ID NO:24, is contained within the amino acid sequence spanning from about position 1685 to about position 1776 of SEQ ID NO:2. All six ACP domains together span a region of Schizochytrium sp. ATCC PTA-9695 Pfa1 of from about position 3298 to about position 5400 of SEQ ID NO:1, corresponding to amino acid positions of about 1100 to about 1800 of SEQ ID NO:2. The nucleotide sequence for the entire ACP region containing all six domains is represented herein as SEQ ID NO:11; while the amino acid sequence for the entire ACP region containing all six domains is represented herein as SEQ ID NO:12. The repeat interval for the six ACP domains within SEQ ID NO:11 was found to be approximately every 342 nucleotides (the actual number of amino acids measured between adjacent active site serines ranges from 114 to 116 amino acids). Each of the six ACP domains contains a pantetheine binding motif LGIDS* (SEQ ID NO:47) wherein S* is the pantetheine binding site serine (S). The pantetheine binding site serine (S) is located near the center of each ACP domain sequence. The locations of the active site serine residues (i.e., the pantetheine binding site) for each of the six ACPD domains, with respect to the amino acid sequence of SEQ ID NO:2 are: ACP1=S1152, ACP2=S1266, ACP3=S1382, ACP4=S1498, ACP5=S1614, and ACP6=S1728.

The ninth domain in *Schizochytrium* sp. ATCC PTA-9695 Pfa1 is a KR domain. The nucleotide sequence containing the sequence encoding the *Schizochytrium* sp. ATCC PTA-9695 Pfa1 KR domain is represented herein as SEQ ID NO:25, corresponding to positions 5623-7800 of SEQ ID NO:1. The amino acid sequence containing the *Schizochytrium* sp. ATCC PTA-9695 Pfa1 KR domain is represented herein as SEQ ID NO:26, corresponding to positions 1875-2600 of SEQ ID NO:2. Within the KR domain is a core region (contained within the nucleotide sequence of SEQ ID NO:48, and the amino acid sequence of SEQ ID NO:49) with homology to short chain aldehyde-dehydrogenases (KR is a member of this family). This core region spans from about position 5998 to about 6900 of SEQ ID NO:1, which corresponds to amino acid positions 2000-2300 of SEQ ID NO:2.

The tenth domain in *Schizochytrium* sp. ATCC PTA-9695 Pfa1 is a DH domain. The nucleotide sequence containing the sequence encoding the *Schizochytrium* sp. ATCC PTA-9695 Pfa1 DH domain is represented herein as SEQ ID NO:27, corresponding to positions 7027-7065 of SEQ ID NO:1. The amino acid sequence containing the *Schizochytrium* sp. ATCC PTA-9695 Pfa1 DH domain is represented herein as SEQ ID NO:28, corresponding to positions 2343-2355 of SEQ ID NO:2. The DH domain contains a conserved active site motif (See, Donadio, S. and Katz., L., Gene 111(1): 51-60 (1992)): LxxHxxxGxxxxP (SEQ ID NO:50).

Table 4 shows the domains and active sites associated with *Schizochytrium* sp. ATCC PTA-9695 PFA2.

The first domain in *Schizochytrium* sp. ATCC PTA-9695 Pfa2 is a KS domain. The nucleotide sequence containing the sequence encoding the *Schizochytrium* sp. ATCC PTA-9695 Pfa2 KS domain is represented herein as SEQ ID NO:29, corresponding to positions 10-1350 of SEQ ID NO:3. The amino acid sequence containing the *Schizochytrium* sp. ATCC PTA-9695 Pfa2 KS domain is represented herein as SEQ ID NO:30, corresponding to positions 4-450 of SEQ ID NO:4. The KS domain contains an active site motif: DXAC* (SEQ ID NO:43), with an *acyl binding cite corresponding to C191 of SEQ ID NO:4. Also, a characteristic motif is present at the end of the KS domain: GFGG (SEQ ID NO:44), corresponding to positions 438-441 of SEQ ID NO:4 and positions 435-438 of SEQ ID NO:30.

The third domain in *Schizochytrium* sp. ATCC PTA-9695 Pfa2 is a CLF domain. The nucleotide sequence containing the sequence encoding the *Schizochytrium* sp. ATCC PTA-9695 Pfa2 CLF domain is represented herein as SEQ ID NO:31, corresponding to positions 1408-2700 of SEQ ID NO:3. The amino acid sequence containing the *Schizochytrium* sp. ATCC PTA-9695 Pfa2 CLF domain is represented herein as SEQ ID NO:32, corresponding to positions 470-900 of SEQ ID NO:4.

The third domain in *Schizochytrium* sp. ATCC PTA-9695 Pfa2 is an AT domain. The nucleotide sequence containing the sequence encoding the *Schizochytrium* sp. ATCC PTA-9695 Pfa2 AT domain is represented herein as SEQ ID NO:33, corresponding to positions 2998-4200 of SEQ ID NO:3. The amino acid sequence containing the *Schizochytrium* sp. ATCC PTA-9695 Pfa2 AT domain is represented herein as SEQ ID NO:34, corresponding to positions 1000-1400 of SEQ ID NO:4. The AT domain contains an active site motif of GxS*xG (SEQ ID NO:52) that is characteristic of acyltransferse (AT) proteins, with an active site serine residue corresponding to 51141 of SEQ ID NO:4.

The fourth domain of *Schizochytrium* sp. ATCC PTA-9695 Pfa2 is an ER domain. The nucleotide sequence containing the sequence encoding the *Schizochytrium* sp. ATCC PTA-9695 Pfa2 ER domain is represented herein as SEQ ID NO:35, corresponding to positions 4498-5700 of SEQ ID NO:3. The amino acid sequence containing the Pfa2 ER domain is represented herein as SEQ ID NO:36, corresponding to positions 1500-1900 of SEQ ID NO:4.

Table 5 shows the domains and active sites associated with *Schizochytrium* sp. ATCC PTA-9695 PFA3.

TABLE 4

*Schizochytrium* sp. ATCC PTA-9695 PFA2 Domain Analysis

| Domain | DNA positions | AA positions | Sites | DNA positions | AA positions |
|---|---|---|---|---|---|
| KS | 10-1350 of SEQ ID NO: 3 (SEQ ID NO: 29) | 4-450 of SEQ ID NO: 4 (SEQ ID NO: 30) | DXAC* (SEQ ID NO: 43) | 571-573 of SEQ ID NO: 3 | C191 of SEQ ID NO: 4 |
| | | | End - GFGG (SEQ ID NO: 44) | 1312-1323 of SEQ ID NO: 3 (SEQ ID NO: 51) | 438-441 of SEQ ID NO: 4 |
| CLF | 1408-2700 of SEQ ID NO: 3 (SEQ ID NO: 31) | 470-900 of SEQ ID NO:4 (SEQ ID NO: 32) | | | |
| AT | 2998-4200 of SEQ ID NO: 3 (SEQ ID NO: 33) | 1000-1400 of SEQ ID NO: 4 (SEQ ID NO: 34) | GxS*xG (SEQ ID NO: 52) | 3421-3423 of SEQ ID NO: 3 | S1141 of SEQ ID NO: 4 |
| ER | 4498-5700 of SEQ ID NO: 3 (SEQ ID NO: 35) | 1500-1900 of SEQ ID NO: 4 (SEQ ID NO: 36) | | | |

TABLE 5

Schizochytrium sp. ATCC PTA-9695 PFA3 Domain Analysis

| Domain | DNA positions | AA positions | Sites | DNA positions | AA positions |
|---|---|---|---|---|---|
| DH1 | 1-1350 of SEQ ID NO: 5 (SEQ ID NO: 37) | 1-450 of SEQ ID NO: 6 (SEQ ID NO: 38) | FxxH*F (SEQ ID NO: 53) | 931-933 of SEQ ID NO: 5 | H310 of SEQ ID NO: 6 |
| DH2 | 1501-2700 of SEQ ID NO: 5 (SEQ ID NO: 39) | 501-900 of SEQ ID NO: 6 (SEQ ID NO: 40) | FxxH*F (SEQ ID NO: 53) | 2401-2403 of SEQ ID NO: 5 | H801 of SEQ ID NO: 6 |
| ER | 2848-4200 of SEQ ID NO: 5 (SEQ ID NO: 41) | 950-1400 of SEQ ID NO: 6 (SEQ ID NO: 42) | | | |

The first and second domains of *Schizochytrium* sp. ATCC PTA-9695 Pfa3 are DH domains, referred to herein as DH1 and DH2, respectively. The nucleotide sequence containing the sequence encoding the *Schizochytrium* sp. ATCC PTA-9695 Pfa3 DH1 domain is represented herein as SEQ ID NO:37, corresponding to positions 1-1350 of SEQ ID NO:5. The amino acid sequence containing the *Schizochytrium* sp. ATCC PTA-9695 Pfa3 DH1 domain is represented herein as SEQ ID NO:38, corresponding to positions 1-450 of SEQ ID NO:6. The nucleotide sequence containing the sequence encoding the *Schizochytrium* sp. ATCC PTA-9695 Pfa3 DH2 domain is represented herein as SEQ ID NO:39, corresponding to positions 1501-2700 of SEQ ID NO:5. The amino acid sequence containing the *Schizochytrium* sp. ATCC PTA-9695 Pfa3 DH2 domain is represented herein as SEQ ID NO:40, corresponding to positions 501-900 of SEQ ID NO:6. The DH domains contain an active site motif: FxxH*F (SEQ ID NO:53). The nucleotide sequence containing the active site motif in DH1 corresponds to positions 931-933 of SEQ ID NO:5, while the nucleotide sequence containing the active site motif in DH2 corresponds to positions 2401-2403 of SEQ ID NO:5. The active site H* in the motif FxxH*F is based on data from Leesong et al., *Structure* 4:253-64 (1996) and Kimber et al. *J Biol Chem.* 279:52593-602 (2004), with the active site H* in DH1 corresponding to H310 of SEQ ID NO:6 and the active site H* in DH2 corresponding to H801 of SEQ ID NO:6.

The third domain of *Schizochytrium* sp. ATCC PTA-9695 Pfa3 is an ER domain. The nucleotide sequence containing the sequence encoding the *Schizochytrium* sp. ATCC PTA-9695 Pfa3 ER domain is represented herein as SEQ ID NO:41, corresponding to positions 2848-4200 of SEQ ID NO:5. The amino acid sequence containing the *Schizochytrium* sp. ATCC PTA-9695 Pfa3 ER domain is represented herein as SEQ ID NO:42, corresponding to positions 950-1400 of SEQ ID NO:6.

Example 4

Degenerate primers for the KS, ER, and DH PUFA synthase domains were designed in order to isolate the corresponding sequences from the isolated microorganism deposited under ATCC Accession No. PTA-10212, also known as *Thraustochytrium* sp. ATCC PTA-10212.

Degenerate primers for the KS region of *Thraustochytrium* sp. ATCC PTA-10212 PFA1 (i.e., the region containing the KS domain) were designed based on the published PFA1 (previously termed orfA or ORF 1) sequences for *Schizochytrium* sp. ATCC 20888, *Thraustochytrium aureum* (ATCC 34304), and *Thraustochytrium* sp. 23B ATCC 20892:

```
                                      (SEQ ID NO: 123)
prDS233 (forward):
TGATATGGGAGGAATGAATTGTGTNGTNGAYGC (SEQ ID NO: 124)
prDS235 (reverse):
TTCCATAACAAAATGATAATTAGCTCCNCCRAANCC.
```

Degenerate primers for the ER region of *Thraustochyirium* sp. ATCC PTA-10212 PFA2 (i.e., the region containing the ER domain) were designed based on the published PFA2 (previously termed orfB or ORF 2) sequences for *Shewanella japonica, Schizochytrium* sp. ATCC 20888, *Thraustochytrium aureum* (ATCC 34304), and *Thraustochytrium* sp. 23B ATCC 20892:

```
                                      (SEQ ID NO: 125)
prDS183 (forward): GGCGGCCACACCGAYAAYMGNCC (SEQ ID NO: 126)
prDS184 (reverse): CGGGGCCGCACCANAYYTGRTA.
```

Degenerate primers for the ER region of *Thraustochytrium* sp. ATCC PTA-10212 PFA3 (i.e., the region containing the ER domain) were designed based on the published PFA3 (previously termed orfC or ORF 3) sequences for *Shewanella japonica, Schizochytrium* sp. ATCC 20888, *Thraustochytrium aureum* (ATCC 34304), and *Thraustochytrium* sp. 23B ATCC 20892:

```
                                      (SEQ ID NO: 127)
prDS181 (forward): TCCTTCGGNGCNGSNGG (SEQ ID NO: 126)
prDS184 (reverse): CGGGGCCGCACCANAYYTGRTA.
```

Degenerate primers JGM190 (forward, SEQ ID NO:64) and BLR242 (reverse, SEQ ID NO:65), as described above, were used to amplify the DH region of PFA3 from *Thraustochytrium* sp. ATCC PTA-10212.

The PCR conditions with chromosomal DNA template were as follows: 0.2 μM dNTPs, 0.1 uM each primer, 6% DMSO, 200 ng chromosomal DNA, 2.5 U Herculase® II fusion polymerase (Stratagene), and 1× Herculase® buffer (Stratagene) in a 50 μL total volume. The PCR Protocol included the following steps: (1) 98° C. for 3 minutes; (2) 98° C. for 30 seconds; (3) 54° C. for 45 seconds; (4) 72° C. for 1 minutes; (5) repeat steps 2-4 for 40 cycles; (6) 72° C. for 5 minutes; and (7) hold at 6° C.

For all primer pairs, PCR yielded distinct DNA products with the expected sizes using chromosomal templates from *Thraustochytrium* sp. ATCC PTA-10212. The respective PCR products were cloned into the vector pJET1.2/blunt (Fermentas) according to the manufacturer's instructions, and the insert sequence was determined using supplied standard primers.

The DNA sequences obtained from the PCR products were compared with known sequences available from the NCBI GenBank as described in Example 1.

At the amino acid level, the sequences with the highest level of homology to deduced amino acid sequence derived from the cloned DNA containing the KS fragment from PFA1 from *Thraustochytrium* sp. ATCC PTA-10212 were: *Schizochytrium* sp. ATCC 20888 "polyunsaturated fatty acid synthase subunit A" (Identity=80%; positives=90%); *Shewanella benthica* KT99 "omega-3 polyunsaturated fatty acid synthase PfaA" (Identity=51%; positives=67%); *Shewanella loihica* PV-4 "beta-ketoacyl synthase" (Identity=50%; positives=67%); *Shewanella woodyi* ATCC 51908 "polyketide-type polyunsaturated fatty acid synthase PfaA" (Identity=51%; positives=66%).

At the amino acid level, the sequences with the highest level of homology to deduced amino acid sequence derived from the cloned DNA containing the ER fragment from PFA2 from *Thraustochytrium* sp. ATCC PTA-10212 were: *Schizochytrium* sp. ATCC 20888 "polyunsaturated fatty acid synthase subunit B" (Identity=70%; positives=85%); *Schizochytrium* sp. ATCC 20888 "polyunsaturated fatty acid synthase subunit C" (Identity=66%; positives=83%); *Nodularia spumigena* CCY9414 "2-nitropropane dioxygenase" (Identity=57%; positives=74%); *Moritella* sp. PE36 "polyunsaturated fatty acid synthase PfaD" (Identity=57%; positives=71%).

At the amino acid level, the sequences with the highest level of homology to deduced amino acid sequence derived from the cloned DNA containing the ER fragment from PFA3 from *Thraustochytrium* sp. ATCC PTA-10212 were: *Schizochytrium* sp. ATCC 20888 "polyunsaturated fatty acid synthase subunit C" (Identity=80%; positives=90%); *Schizochytrium* sp. ATCC 20888 "polyunsaturated fatty acid synthase subunit B" (Identity=78%; positives=89%); *Moritella* sp. PE36 "polyunsaturated fatty acid synthase PfaD" (Identity=56%; positives=71%); *Shewanella amazonensis* SB2B "omega-3 polyunsaturated fatty acid synthase PfaD" (Identity=55%; positives=73%).

At the amino acid level, the sequences with the highest level of homology to deduced amino acid sequence derived from the cloned DNA containing the DH fragment from PFA3 from *Thraustochytrium* sp. ATCC PTA-10212 were: *Schizochytrium* sp. ATCC 20888 "polyunsaturated fatty acid synthase subunit C" (Identity=63%; positives=76%); *Shewanella pealeana* ATCC 700345 "Beta-hydroxyacyl-(acyl-carrier-protein) dehydratase FabA/FabZ" (Identity=35%; positives=53%); *Shewanella piezotolerans* WP3 "Multi-domain beta-ketoacyl synthase" (Identity=36%; positives=52%); *Shewanella benthica* KT99 "omega-3 polyunsaturated fatty acid synthase PfaC" (Identity=35%; positives=51%).

Example 5

PUFA synthase genes were identified from *Thraustochytrium* sp. ATCC PTA-10212.

From a −80° C. cyrovial, 1 mL of cells were thawed at room temperature and added to 50 mL of liquid HSFM media (below) in a 250 mL non-baffled flask. The flask was incubated at 23° C. for 3 days. Cells were collected and utilized for standard Bacterial Artificial Chromosome (BAC) library construction (Lucigen Corporation, Middleton, Wis. USA).

TABLE 6

| HSFM Media | | | |
|---|---|---|---|
| Ingredient | concentration | | ranges |
| $Na_2SO_4$ | g/L | 31.0 | 0-50, 15-45, or 25-35 |
| NaCl | g/L | 0.625 | 0-25, 0.1-10, or 0.5-5 |
| KCl | g/L | 1.0 | 0-5, 0.25-3, or 0.5-2 |
| $MgSO_4 \cdot 7H_2O$ | g/L | 5.0 | 0-10, 2-8, or 3-6 |
| $(NH_4)_2SO_4$ | g/L | 0.44 | 0-10, 0.25-5, or 0.05-3 |
| MSG * $1H_2O$ | g/L | 6.0 | 0-10, 4-8, or 5-7 |
| $CaCl_2$ | g/L | 0.29 | 0.1-5, 0.15-3, or 0.2-1 |
| T 154 (yeast extract) | g/L | 6.0 | 0-20, 0.1-10, or 1-7 |
| $KH_2PO_4$ | g/L | 0.8 | 0.1-10, 0.5-5, or 0.6-1.8 |
| Post autoclave (Metals) | | | |
| Citric acid | mg/L | 3.5 | 0.1-5000, 10-3000, or 3-2500 |
| $FeSO_4 \cdot 7H_2O$ | mg/L | 10.30 | 0.1-100, 1-50, or 5-25 |
| $MnCl_2 \cdot 4H_2O$ | mg/L | 3.10 | 0.1-100, 1-50, or 2-25 |
| $ZnSO_4 \cdot 7H_2O$ | mg/L | 3.10 | 0.01-100, 1-50, or 2-25 |
| $CoCl_2 \cdot 6H_2O$ | mg/L | 0.04 | 0-1, 0.001-0.1, or 0.01-0.1 |
| $Na_2MoO_4 \cdot 2H_2O$ | mg/L | 0.04 | 0.001-1, 0.005-0.5, or 0.01-0.1 |
| $CuSO_4 \cdot 5H_2O$ | mg/L | 2.07 | 0.1-100, 0.5-50, or 1-25 |
| $NiSO_4 \cdot 6H_2O$ | mg/L | 2.07 | 0.1-100, 0.5-50, or 1-25 |
| Post autoclave (Vitamins) | | | |
| Thiamine | mg/L | 9.75 | 0.1-100, 1-50, or 5-25 |
| Vitamin B12 | mg/L | 0.16 | 0.01-100, 0.05-5, or 0.1-1 |
| Ca½-pantothenate | mg/L | 2.06 | 0.1-100, 0.1-50, or 1-10 |
| Biotin | mg/L | 3.21 | 0.1-100, 0.1-50, or 1-10 |
| Post autoclave (Carbon) | | | |
| Glycerol | g/L | 30.0 | 5-150, 10-100, or 20-50 |
| Nitrogen Feed: | | | |
| MSG•$1H_2O$ | g/L | 17 | 0-150, 10-100, or 15-50 |

Typical cultivation conditions would include the following:

pH about 6.5-about 9.5, about 6.5-about 8.0, or about 6.8 about 7.8;

temperature: about 15-about 30 degrees Celsius, about 18-about 28 degrees Celsius, or about 21 to about 23 degrees Celsius;

dissolved oxygen: about 0.1-about 100% saturation, about 5-about 50% saturation, or about 10-about 30% saturation; and/or glycerol controlled 0: about 5-about 50 g/L, about 10-about 40 g/L, or about 15-about 35 g/L.

The recombinant BAC libraries, consisting of large fragments (average of approximately 120 kB) were handled according to the manufacturer's instructions in the BAC vector pSMART® (Lucigen Corporation). The BAC libraries were screened by standard colony hybridization procedures using $^{32}$P radioactively labeled probes (Sambrook J. and Russell D. 2001. Molecular cloning: A laboratory manual, 3rd edition. Cold Spring Harbor Laboratory Press, Cold Spring Harbor, N.Y.). The probes contained DNA homologous to published PUFA synthase sequences from other organisms as described in Example 4. These probes were generated by a DNA restriction digest of the cloned fragments from respective clones from pJET1.2/blunt described above and labeled by standard methods. In all cases, strong hybridization of the individual probes to certain BACs indicated clones containing DNA homologous to PUFA synthase genes.

BAC clone pLR130 (also known as LuMaBAC 2M23) demonstrated strong hybridization of probe to both the KS region and ER region, indicating that it contained the PFA1 and PFA2 genes, and was selected for DNA sequencing of the *Thraustochytrium* sp. ATCC PTA-10212 PFA1 and PFA2 genes. The BAC was sequenced by standard procedures (Eurofins MWG Operon, Huntsville, Ala.). BAC clone pLR130, containing the PFA1 and PFA2 genes, was deposited under the Budapest Treaty, at the American Type Culture Collection, Patent Depository, 10801 University Boulevard, Manassas, Va. 20110-2209, on Dec. 1, 2009, and given ATCC Accession No. PTA-10511.

In previously published thraustochytrid PUFA synthase systems, the PUFA synthase genes PFA1 and PFA2 have been clustered together and arranged as to be divergently transcribed. This is also the case for PFA1 and PFA2 from *Thraustochytrium* sp. ATCC PTA-10212. The conceptual start of PFA2 was found to be 693 nucleotides from the start of PFA1 and divergently transcribed.

BAC clone pDS127 (also known as LuMaBAC 9K17) demonstrated strong hybridization of probe to both the DH region and ER region of PFA3 and was selected for DNA sequencing of the PFA3 gene. BAC clone pDS127, containing the PFA3 gene, was deposited under the Budapest Treaty, at the American Type Culture Collection, Patent Depository, 10801 University Boulevard, Manassas, Va. 20110-2209, on Dec. 1, 2009, and given ATCC Accession No. PTA-10510. Sequencing primers were designed using standard methods to the DH region and ER region and the DNA sequence determined in Example 4. To determine the DNA sequence of the *Thraustochytrium* sp. ATCC PTA-10212 PFA3 gene, successive rounds of DNA sequencing, involving subsequent sequencing primer design by standard methods, was carried out in order to "walk" the BAC clone. Each nucleotide base pair of the PFA3 gene was covered by at least two separate DNA sequencing reactions of high-quality with at least a minimum aggregated Phred score of 40 (confidence level of 99.99%).

Table 7 shows identities for the *Thraustochytrium* sp. ATCC PTA-10212 PFA1 (SEQ ID NO:68), PFA2 (SEQ ID NO:70), and PFA3 (SEQ ID NO:72) polynucleotide sequences as compared to previously published sequences and the sequences from *Schizochytrium* sp. PTA-9695. Identities were determined by the scoring matrix "swgapdnamt" within the "AlignX" program of the VectorNTI program, a standard for DNA alignment.

TABLE 7

Percent Identity to PFA1, PFA2, and PFA3 Polynucleotide Sequences

| Source of Comparison PFA1, PFA2, and PFA3 Sequences | % Identity of Comparison PFA1 (orfA) to PFA1 | % Identity of Comparison PFA2 (orfB) to PFA2 | % Identity of Comparison PFA3 (orfC) to PFA3 |
|---|---|---|---|
| *Schizochytrium* sp. ATCC 20888 | 55 | 54 | 59 |
| *Thraustochytrium aureum* ATCC 34304 | 55 | 53 | not published |
| *Thraustochytrium* sp. 23B ATCC 20892 | 55 | 57 | 62 |
| *Schizochytrium* sp. PTA-9695 | 55 | 52 | 59 |

Table 8 shows identities for the *Thraustochytrium* sp. ATCC PTA-10212 Pfa1p (SEQ ID NO:69), Pfa2p (SEQ ID NO:71), and Pfa3p (SEQ ID NO:73) amino acid sequences as compared to previously published PUFA synthase amino acid sequences and the sequences from *Schizochytrium* sp. PTA-9695. Identities were determined through use of the scoring matrix "blosum62mt2" within the "AlignX" program of the VectorNTI program, a standard for protein alignment.

TABLE 8

Percent Identity to Pfa1p, Pfa2p, and Pfa3p Amino Acid Sequences

| Source of Comparison Pfa1p, Pfa2p, and Pfa3p Sequences | % Identity of Comparison Pfa1p (OrfA) to Pfa1p | % Identity of Comparison Pfa2p (OrfB) to Pfa2p | % Identity of Comparison Pfa3p (OrfC) to Pfa3p |
|---|---|---|---|
| *Schizochytrium* sp. ATCC 20888 | 62 | 57 | 69 |
| *Thraustochytrium aureum* ATCC 34304 | 58 | 54 | not published |
| *Thraustochytrium* sp. 23B ATCC 20892 | 54 | 54 | 71 |
| *Schizochytrium* sp. PTA-9695 | 59 | 53 | 73 |

Example 6

Domain analysis was performed to annotate the sequence coordinates for the PUFA synthase domains and active sites of *Thraustochytrium* sp. ATCC PTA-10212 PFA1, PFA2, and PFA3, respectively. Domains were identified based on homology to known PUFA synthase, fatty acid synthase, and polyketide synthase domains.

Table 9 shows the domains and active sites associated with *Thraustochytrium* sp. ATCC PTA-10212 PFA1.

TABLE 9

*Thraustochytrium* sp. ATCC PTA-10212 PFA1 Domain Analysis

| Domain | DNA position | AA position | Sites | DNA position | AA position |
|---|---|---|---|---|---|
| KS | 13-1362 of SEQ ID NO: 68 (SEQ ID NO: 74) | 5-545 of SEQ ID NO: 69 (SEQ ID NO: 75) | Active - DXAC* (SEQ ID NO: 43) | 601-612 of SEQ ID NO: 68 | C204 of SEQ ID NO: 69 |
| | | | End - GFGG (SEQ ID NO: 44) | 1351-1362 of SEQ ID NO: 68 (SEQ ID NO: 45) | 451-454 of SEQ ID NO: 69 |
| MAT | 1783-2703 of SEQ ID NO: 68 (SEQ ID NO: 76) | 595-901 of SEQ ID NO: 69 (SEQ ID NO: 77) | Active GHS*LG (SEQ ID NO: 46) | 2083-2085 of SEQ ID NO: 68 (SEQ ID NO: 116) | S695 of SEQ ID NO: 69 |

TABLE 9-continued

*Thraustochytrium* sp. ATCC PTA-10212 PFA1 Domain Analysis

| Domain | DNA position | AA position | Sites | DNA position | AA position |
|---|---|---|---|---|---|
| ACP | 3208-6510 of SEQ ID NO: 68 (SEQ ID NO: 78) | 1070-2170 of SEQ ID NO: 69 (SEQ ID NO: 79) | ACP1 domain | 3280-3534 of SEQ ID NO: 68 (SEQ ID NO: 80) | 1094-1178 of SEQ ID NO: 69 (SEQ ID NO: 81) |
| | | | ACP1 Active LGIDS* (SEQ ID NO: 47) | 3403-3405 of SEQ ID NO: 68 | S1135 of SEQ ID NO: 69 |
| | | | ACP2 domain | 3607-3861 of SEQ ID NO: 68 (SEQ ID NO: 82) | 1203-1287 of SEQ ID NO: 69 (SEQ ID NO: 83) |
| | | | ACP2 Active LGIDS* (SEQ ID NO: 47) | 3730-3732 of SEQ ID NO: 68 | S1244 of SEQ ID NO: 69 |
| | | | ACP3 domain | 3934-4185 of SEQ ID NO: 68 (SEQ ID NO: 84) | 1312-1396 of SEQ ID NO: 69 (SEQ ID NO: 85) |
| | | | ACP3 Active LGIDS* (SEQ ID NO: 47) | 4057-4059 of SEQ ID NO: 68 | S1353 of SEQ ID NO: 69 |
| | | | ACP4 domain | 4261-4515 of SEQ ID NO: 68 (SEQ ID NO: 86) | 1421-1505 of SEQ ID NO: 69 (SEQ ID NO: 87) |
| | | | ACP4 Active LGIDS* (SEQ ID NO: 47) | 4384-4386 of SEQ ID NO: 68 | S1462 of SEQ ID NO: 69 |
| | | | ACP5 domain | 4589-4842 of SEQ ID NO: 68 (SEQ ID NO: 88) | 1530-1614 of SEQ ID NO: 69 (SEQ ID NO: 89) |
| | | | ACP5 Active LGIDS* (SEQ ID NO: 47) | 4711-4713 of SEQ ID NO: 68 | S1571 of SEQ ID NO: 69 |
| | | | AGP6 domain | 4915-5169 of SEQ ID NO: 68 (SEQ ID NO: 90) | 1639-1723 of SEQ ID NO: 69 (SEQ ID NO: 91) |
| | | | ACP6 Active LGIDS* (SEQ ID NO: 47) | 5038-5040 of SEQ ID NO: 68 | S1680 of SEQ ID NO: 69 |
| | | | ACP7 domain | 5242-5496 of SEQ ID NO: 68 (SEQ ID NO: 92) | 1748-1832 of SEQ ID NO: 69 (SEQ ID NO: 93) |
| | | | ACP7 Active LGIDS* (SEQ ID NO: 47) | 5365-5367 of SEQ ID NO: 68 | S1789 of SEQ ID NO: 69 |
| | | | ACP8 domain | 5569-5823 of SEQ ID NO: 68 (SEQ ID NO: 94) | 1857-1941 of SEQ ID NO: 69 (SEQ ID NO: 95) |
| | | | ACP8 Active LGIDS* (SEQ ID NO: 47) | 5692-5694 of SEQ ID NO: 68 | S1898 of SEQ ID NO: 69 |
| | | | ACP9 domain | 5896-6150 of SEQ ID NO: 68 (SEQ ID NO: 96) | 1966-2050 of SEQ ID NO: 69 (SEQ ID NO: 97) |
| | | | ACP9 Active LGIDS* (SEQ ID NO: 47) | 6019-6021 of SEQ ID NO: 68 | S2007 of SEQ ID NO: 69 |
| | | | ACP10 domain | 6199-6453 of SEQ ID NO: 68 (SEQ ID NO: 98) | 2067-2151 of SEQ ID NO: 69 (SEQ ID NO: 99) |
| | | | ACP10 Active LGIDS* (SEQ ID NO: 47) | 6322-6324 of SEQ ID NO: 68 | S2108 of SEQ ID NO: 69 |
| KR | 6808-8958 of SEQ ID NO: 68 (SEQ ID NO: 100) | 2270-2986 of SEQ ID NO: 69 (SEQ ID NO: 101) | "core region" | 7198-8100 of SEQ ID NO: 68 (SEQ ID NO: 116) | 2400-2600 of SEQ ID NO: 69 (SEQ ID NO: 117) |
| DH Motif | 8203-8241 of SEQ ID NO: 68 (SEQ ID NO: 118) | 2735-2747 of SEQ ID NO: 69 (SEQ ID NO: 119) | LxxHxxxGxxxxP (SEQ ID NO: 50) | 8203-8241 of SEQ ID NO: 68 (SEQ ID NO: 118) | 2735-2747 of SEQ ID NO: 69 (SEQ ID NO: 119) |

The first domain in *Thraustochytrium* sp. ATCC PTA-10212 Pfa1 is a KS domain. The nucleotide sequence containing the sequence encoding the *Thraustochytrium* sp. ATCC PTA-10212 Pfa1 KS domain is represented herein as SEQ ID NO:74, corresponding to positions 13-1362 of SEQ ID NO:68. The amino acid sequence containing the *Thraustochytrium* sp. ATCC PTA-10212 Pfa1 KS domain is represented herein as SEQ ID NO:75, corresponding to positions 5-454 of SEQ ID NO:69. The KS domain contains an active site motif: DXAC* (SEQ ID NO:43), with an *acyl binding cite corresponding to C204 of SEQ ID NO:69. Also, a characteristic motif is present at the end of the KS domain: GFGG (SEQ ID NO:44), corresponding to positions 451-454 of SEQ ID NO:69 and positions 447-450 of SEQ ID NO:75.

The second domain in *Thraustochytrium* sp. ATCC PTA-10212 Pfa1 is a MAT domain. The nucleotide sequence containing the sequence encoding the *Thraustochytrium* sp. ATCC PTA-10212 Pfa1 MAT domain is represented herein as SEQ ID NO:76, corresponding to positions 1783-2703 of SEQ ID NO:68. The amino acid sequence containing the *Thraustochytrium* sp. ATCC PTA-10212 Pfa1 MAT domain is represented herein as SEQ ID NO:77, corresponding to positions 595-901 of SEQ ID NO:69. The MAT domain contains an active site motif: GHS*XG (SEQ ID NO:46), with an *acyl binding cite corresponding to 5695 of SEQ ID NO:69.

The third through twelfth domains of *Thraustochytrium* sp. ATCC PTA-10212 Pfa1p are ten tandem ACP domains, also referred to herein as ACP1, ACP2, ACP3, ACP4, ACP5, ACP6, ACP7, ACP8, ACP9, and ACP10. The nucleotide sequence containing the first ACP domain, ACP1, is represented herein as SEQ ID NO:80 and is contained within the nucleotide sequence spanning from about position 3280 to about position 3534 of SEQ ID NO:68. The amino acid sequence containing ACP1, represented herein as SEQ ID NO:81, is contained within the amino acid sequence spanning from about position 1094 to about position 1178 of SEQ ID NO:69. The nucleotide sequence containing ACP2, represented herein as SEQ ID NO:82, is contained within the nucleotide sequence spanning from about position 3607 to about position 3861 of SEQ ID NO:68. The amino acid sequence containing ACP2, represented herein as SEQ ID NO:83, is contained within the amino acid sequence spanning from about position 1203 to about position 1287 of SEQ ID NO:69. The nucleotide sequence containing ACP3, represented herein as SEQ ID NO:84, is contained within the nucleotide sequence spanning from about position 3934 to about position 4185 of SEQ ID NO:68. The amino acid sequence containing ACP3, represented herein as SEQ ID NO:85, is contained within the amino acid sequence spanning from about position 1312 to about position 1396 of SEQ ID NO:69. The nucleotide sequence containing ACP4, represented herein as SEQ ID NO:86, is contained within the nucleotide sequence spanning from about position 4261 to about position 4515 of SEQ ID NO:68. The amino acid sequence containing ACP4, represented herein as SEQ ID NO:87, is contained within the amino acid sequence spanning from about position 1421 to about position 1505 of SEQ ID NO:69. The nucleotide sequence containing ACP5, represented herein as SEQ ID NO:88, is contained within the nucleotide sequence spanning from about position 4589 to about position 4842 of SEQ ID NO:68. The amino acid sequence containing ACP5, represented herein as SEQ ID NO:89, is contained within the amino acid sequence spanning from about position 1530 to about position 1614 of SEQ ID NO:69. The nucleotide sequence containing ACP6, represented herein as SEQ ID NO:90, is contained within the nucleotide sequence spanning from about position 4915 to about position 5169 of SEQ ID NO:68. The amino acid sequence containing ACP6, represented herein as SEQ ID NO:91, is contained within the amino acid sequence spanning from about position 1639 to about position 1723 of SEQ ID NO:69. The nucleotide sequence containing ACP7, represented herein as SEQ ID NO:92, is contained within the nucleotide sequence spanning from about position 5242 to about position 5496 of SEQ ID NO:68. The amino acid sequence containing ACP7, represented herein as SEQ ID NO:93, is contained within the amino acid sequence spanning from about position 1748 to about position 1832 of SEQ ID NO:69. The nucleotide sequence containing ACP8, represented herein as SEQ ID NO:94, is contained within the nucleotide sequence spanning from about position 5569 to about position 5832 of SEQ ID NO:68. The amino acid sequence containing ACP8, represented herein as SEQ ID NO:95, is contained within the amino acid sequence spanning from about position 1857 to about position 1941 of SEQ ID NO:69. The nucleotide sequence containing ACP9, represented herein as SEQ ID NO:96, is contained within the nucleotide sequence spanning from about position 5896 to about position 6150 of SEQ ID NO:68. The amino acid sequence containing ACP9, represented herein as SEQ ID NO:97, is contained within the amino acid sequence spanning from about position 1966 to about position 2050 of SEQ ID NO:69. The nucleotide sequence containing ACP10, represented herein as SEQ ID NO:98, is contained within the nucleotide sequence spanning from about position 6199 to about position 6453 of SEQ ID NO:68. The amino acid sequence containing ACP10, represented herein as SEQ ID NO:99, is contained within the amino acid sequence spanning from about position 2067 to about position 2151 of SEQ ID NO:69. All ten ACP domains together span a region of *Thraustochytrium* sp. ATCC PTA-10212 Pfa1 of from about position 3208 to about position 6510 of SEQ ID NO:68, corresponding to amino acid positions of about 1070 to about 2170 of SEQ ID NO:69. The nucleotide sequence for the entire ACP region containing all 10 domains is represented herein as SEQ ID NO:78; while the amino acid sequence for the entire ACP region containing all six domains is represented herein as SEQ ID NO:79. The repeat interval for the 10 ACP domains within SEQ ID NO:78 was found to be approximately every 327 nucleotides (the actual number of amino acids measured between adjacent active site serines ranges from 101 to 109 amino acids). Each of the ten ACP domains contains a pantetheine binding motif LGIDS* (SEQ ID NO:47) wherein S* is the pantetheine binding site serine (S). The pantetheine binding site serine (S) is located near the center of each ACP domain sequence. The locations of the active site serine residues (i.e., the pantetheine binding site) for each of the six ACPD domains, with respect to the amino acid sequence of SEQ ID NO:69 are: ACP1=S1135, ACP2=S1244, ACP3=S1353, ACP4=S1462, ACP5=S1571, ACP6=S1680, APC7=S1789, ACP7=S1789, ACP8=S1898, ACP9=S=2007, and ACP10=S2108.

The thirteenth domain in *Thraustochytrium* sp. ATCC PTA-10212 Pfa1 is a KR domain. The nucleotide sequence containing the sequence encoding the Pfa1 KR domain is represented herein as SEQ ID NO:100, corresponding to positions 6808-8958 of SEQ ID NO:68. The amino acid sequence containing the Pfa1 KR domain is represented herein as SEQ ID NO:101, corresponding to positions 2270-2986 of SEQ ID NO:69. Within the KR domain is a core region (contained within the nucleotide sequence of SEQ ID NO:116, and the amino acid sequence of SEQ ID NO:117) with homology to short chain aldehyde-dehydrogenases (KR is a member of this family). This core region spans from about position 5998 to about position 6900 of SEQ ID NO:68, which corresponds to amino acid positions 2000-2300 of SEQ ID NO:69.

The fourteenth domain in *Thraustochytrium* sp. ATCC PTA-10212 Pfa1 is a DH domain. The nucleotide sequence containing the sequence encoding the Pfa1 DH domain is represented herein as SEQ ID NO:118, corresponding to positions 7027-7065 of SEQ ID NO:68. The amino acid sequence containing the Pfa1 DH domain is represented herein as SEQ ID NO:119, corresponding to positions 2343-2355 of SEQ ID NO:69. The DH domain contains a conserved active site motif (see, Donadio, S. and Katz., L., Gene 111(1): 51-60 (1992)): LxxHxxxGxxxxP (SEQ ID NO:50).

Table 10 shows the domains and active sites associated with *Thraustochytrium* sp. ATCC PTA-10212 PFA2.

as SEQ ID NO:104, corresponding to positions 1378-2700 of SEQ ID NO:70. The amino acid sequence containing the *Thraustochytrium* sp. ATCC PTA-10212 Pfa2 CLF domain is represented herein as SEQ ID NO:105, corresponding to positions 460-900 of SEQ ID NO:71.

The third domain in *Thraustochytrium* sp. ATCC PTA-10212 Pfa2 is an AT domain. The nucleotide sequence containing the sequence encoding the *Thraustochytrium* sp. ATCC PTA-10212 Pfa2 AT domain is represented herein as

TABLE 10

*Thraustochytrium* sp. ATCC PTA-10212 PFA2 Domain Analysis

| Domain | DNA positions | AA positions | Sites | DNA positions | AA positions |
| --- | --- | --- | --- | --- | --- |
| KS | 10-1320 of SEQ ID NO: 70 (SEQ ID NO: 102) | 4-440 of SEQ ID NO: 71 (SEQ ID NO: 103) | DXAC* (SEQ ID NO: 43) | 571-573 of SEQ ID NO: 70 | C191 of SEQ ID NO: 71 |
|  |  |  | End - GFGG (SEQ ID NO: 44) | 1267-1278 of SEQ ID NO: 70 | 423-426 of SEQ ID NO: 71 |
| CLF | 1378-2700 of SEQ ID NO: 70 (SEQ ID NO: 104) | 460-900 of SEQ ID NO: 71 (SEQ ID NO: 105) |  |  |  |
| AT | 2848-4200 of SEQ ID NO: 70 (SEQ ID NO: 106) | 950-1400 of SEQ ID NO: 71 (SEQ ID NO: 107) | GxS*xG (SEQ ID NO: 52) | 3361-3363 of SEQ ID NO: 70 | S1121 of SEQ ID NO: 71 |
| ER | 4498-5700 of SEQ ID NO: 70 (SEQ ID NO: 108) | 1500-1900 of SEQ ID NO: 71 (SEQ ID NO: 109) |  |  |  |

The first domain in *Thraustochytrium* sp. ATCC PTA-10212 Pfa2 is a KS domain. The nucleotide sequence containing the sequence encoding the *Thraustochytrium* sp. ATCC PTA-10212 Pfa2 KS domain is represented herein as SEQ ID NO:102, corresponding to positions 10-1320 of SEQ ID NO:70. The amino acid sequence containing the *Thraustochytrium* sp. ATCC PTA-10212 Pfa2 KS domain is represented herein as SEQ ID NO:103, corresponding to positions 4-440 of SEQ ID NO:71. The KS domain contains an active site motif: DXAC* (SEQ ID NO:43), with an *acyl binding cite corresponding to C191 of SEQ ID NO:71. Also, a characteristic motif is present at the end of the KS domain: GFGG (SEQ ID NO:44), corresponding to positions 423-426 of SEQ ID NO:71 and positions 1267-1278 of SEQ ID NO:70.

The second domain in *Thraustochytrium* sp. ATCC PTA-10212 Pfa2 is a CLF domain. The nucleotide sequence containing the sequence encoding the *Thraustochytrium* sp. ATCC PTA-10212 Pfa2 CLF domain is represented herein SEQ ID NO:106, corresponding to positions 2848-4200 of SEQ ID NO:70. The amino acid sequence containing the *Thraustochytrium* sp. ATCC PTA-10212 Pfa2 AT domain is represented herein as SEQ ID NO:107, corresponding to positions 950-1400 of SEQ ID NO:71. The AT domain contains an active site motif of GxS*xG (SEQ ID NO:50) that is characteristic of acyltransferse (AT) proteins, with an active site serine residue corresponding to S1121 of SEQ ID NO:71.

The fourth domain of *Thraustochytrium* sp. ATCC PTA-10212 Pfa2 is an ER domain. The nucleotide sequence containing the sequence encoding the *Thraustochytrium* sp. ATCC PTA-10212 Pfa2 ER domain is represented herein as SEQ ID NO:108, corresponding to positions 4498-5700 of SEQ ID NO:70. The amino acid sequence containing the *Thraustochytrium* sp. ATCC PTA-10212 Pfa2 ER domain is represented herein as SEQ ID NO:109, corresponding to positions 1500-1900 of SEQ ID NO:71.

Table 11 shows the domains and active sites associated with *Thraustochytrium* sp. ATCC PTA-10212 PFA3.

TABLE 11

*Thraustochytrium* sp. ATCC PTA-10212 PFA3 Domain Analysis

| Domain | DNA positions | AA positions | Sites | DNA positions | AA positions |
| --- | --- | --- | --- | --- | --- |
| DH1 | 1-1350 of SEQ ID NO: 72 (SEQ ID NO: 110) | 1-450 of SEQ ID NO: 73 (SEQ ID NO: 111) | FxxH*F (SEQ ID NO: 53) | 934-936 of SEQ ID NO: 72 | H312 of SEQ ID NO: 73 |
| DH2 | 1501-2700 of SEQ ID NO: 72 (SEQ ID NO: 112) | 501-900 of SEQ ID NO: 73 (SEQ ID NO: 113) | FxxH*F (SEQ ID NO: 53) | 2401-2403 of SEQ ID NO: 72 | H801 of SEQ ID NO: 73 |
| ER | 2848-4212 of SEQ ID NO: 72 (SEQ ID NO: 114) | 950-1404 of SEQ ID NO: 73 (SEQ ID NO: 115) |  |  |  |

The first and second domains of *Thraustochytrium* sp. ATCC PTA-10212 Pfa3 are DH domains, referred to herein as DH1 and DH2, respectively. The nucleotide sequence containing the sequence encoding the *Thraustochytrium* sp. ATCC PTA-10212 Pfa3 DH1 domain is represented herein as SEQ ID NO:110, corresponding to positions 1-1350 of SEQ ID NO:72. The amino acid sequence containing the *Thraustochytrium* sp. ATCC PTA-10212 Pfa3 DH1 domain is represented herein as SEQ ID NO:111, corresponding to positions 1-450 of SEQ ID NO:73. The nucleotide sequence containing the sequence encoding the *Thraustochytrium* sp. ATCC PTA-10212 Pfa3 DH2 domain is represented herein as SEQ ID NO:112, corresponding to positions 1501-2700 of SEQ ID NO:72. The amino acid sequence containing the *Thraustochytrium* sp. ATCC PTA-10212 Pfa3 DH2 domain is represented herein as SEQ ID NO:113, corresponding to positions 501-900 of SEQ ID NO:73. The DH domains contain an active site motif: FxxH*F (SEQ ID NO:53). The nucleotide sequence containing the active site motif in DH1 corresponds to positions 934-936 of SEQ ID NO:72, while the nucleotide sequence containing the active site motif in DH2 corresponds to positions 2401-2403 of SEQ ID NO:72. The active site H* in the motif FxxH*F is based on data from Leesong et al., *Structure* 4:253-64 (1996) and Kimber et al. *J Biol Chem.* 279:52593-602 (2004), with the active site H* in DH1 corresponding to H312 of SEQ ID NO:73 and the active site H* in DH2 corresponding to H801 of SEQ ID NO:73.

The third domain of *Thraustochytrium* sp. ATCC PTA-10212 Pfa3 is an ER domain. The nucleotide sequence containing the sequence encoding the *Thraustochytrium* sp. ATCC PTA-10212 Pfa3 ER domain is represented herein as SEQ ID NO:114, corresponding to positions 2848-4200 of SEQ ID NO:72. The amino acid sequence containing the *Thraustochytrium* sp. ATCC PTA-10212 Pfa3 ER domain is represented herein as SEQ ID NO:115, corresponding to positions 950-1400 of SEQ ID NO:73.

Example 7

The inactivation of native PUFA synthase genes in *Schizochytrium* sp. ATCC 20888, to generate PUFA auxotrophs, and the replacement of such inactivated genes with exogenously introduced homologous genes to restore PUFA synthesis has been previously demonstrated and described. See, e.g., U.S. Pat. No. 7,217,856, incorporated by reference herein in its entirety. The three PUFA synthase genes from *Schizochytrium* sp. ATCC 20888 have been previously termed orfA, orfB, and orfC, corresponding to the PFA1, PFA2, and PFA3 nomenclature used herein, respectively. Id.

The native orfA gene in *Schizochytrium* sp. ATCC 20888 was replaced by homologous recombination following transformation with a vector containing the Zeocin™ resistance marker surrounded by sequences from the orfA flanking region. A mutant strain was generated lacking a functional orfA gene. The mutant strain was auxotrophic and required PUFA supplementation for growth.

*Schizochytrium* sp. ATCC PTA-9695 PFA1 (SEQ ID NO:1) was cloned into expression vector pREZ37 to generate pREZ345. The expression vector contained approximately 2 kb of DNA from the flanking region of the native orfA gene locus from *Schizochytrium* sp. ATCC 20888. The *Schizochytrium* sp. ATCC 20888 mutant lacking functional orfA was transformed via electroporation with enzyme pretreatment (see below) with pREZ345 containing PFA1. Based on homologous regions flanking the Zeocin™ resistance marker in the mutant and flanking the PFA1 gene in pREZ345, double-crossover recombination occurred such that PFA1 was inserted into the native orfA locus. Recombination with *Schizochytrium* sp. ATCC PTA-9695 PFA1 (SEQ ID NO:1) restored PUFA production in the *Schizochytrium* sp. ATCC 20888 mutant lacking orfA. In brief, cells were grown in M2B liquid media (see following paragraph) at 30° C. with 200 rpm shaking for 3 days. Cells were harvested and the fatty acids were converted to methylesters using standard techniques. Fatty acid profiles were determined using gas chromatography with flame ionization detection (GC-FID) as fatty acid methyl esters (FAME). The native *Schizochytrium* sp. ATCC 20888 strain containing a functional orfA gene produced DHA and DPA n-6 in a ratio of 2.3:1. The recombinant strain containing *Schizochytrium* sp. ATCC PTA-9695 PFA1 (SEQ ID NO:1) in place of the inactivated orfA gene also produced DHA and DPA n-6 in a ratio of 2.4:1. The EPA content of the recombinant strain was 2.7% of fatty acid methyl-esters (FAME), the DPA n-3 content was 0.7%, the DPA n-6 content was 8.8%, and the DHA content was 21.2%.

M2B medium—10 g/L glucose, 0.8 g/L $(NH_4)_2SO_4$, 5 g/L $Na_2SO_4$, 2 g/L $MgSO_4.7H_2O$, 0.5 g/L $KH_2PO_4$, 0.5 g/L KCl, 0.1 g/L $CaCl_2.2H_2O$, 0.1 M MES (pH 6.0) 0.1% PB26 metals, and 0.1% PB26 Vitamins (v/v). PB26 vitamins consisted of 50 mg/mL vitamin B12, 100 µg/mL thiamine, and 100 µg/mL Ca-pantothenate. PB26 metals were adjusted to pH 4.5 and consisted of 3 g/L $FeSO_4.7H_2O$, 1 g/L $MnCl_2.4H_2O$, 800 mg/mL $ZnSO_4.7H_2O$, 20 mg/mL $CoCl_2.6H_2O$, 10 mg/mL $Na_2MoO_4.2H_2O$, 600 mg/mL $CuSO_4.5H_2O$, and 800 mg/mL $NiSO_4.6H_2O$. PB26 stock solutions were filter-sterilized separately and added to the broth after autoclaving. Glucose, $KH_2PO_4$, and $CaCl_2.2H_2O$ were each autoclaved separately from the remainder of the broth ingredients before mixing to prevent salt precipitation and carbohydrate caramelizing. All medium ingredients were purchased from Sigma Chemical (St. Louis, Mo.).

Electroporation with Enzyme Pretreatment—

Cells were grown in 50 mL of M50-20 media (see U.S. Publ. No. 2008/0022422) on a shaker at 200 rpm for 2 days at 30° C. The cells were diluted at 1:100 into M2B media and grown overnight (16-24 h), attempting to reach mid-log phase growth (OD600 of 1.5-2.5). The cells were centrifuged in a 50 mL conical tube for 5 min at about 3000×g. The supernatant was removed and the cells were resuspended in 1 M mannitol, pH 5.5, in a suitable volume to reach a final concentration of 2 $OD_{600}$ units. 5 mL of cells were aliquoted into a 25 mL shaker flask and amended with 10 mM $CaCl_2$ (1.0 M stock, filter sterilized) and 0.25 mg/mL Protease XIV (10 mg/mL stock, filter sterilized; Sigma-Aldrich, St. Louis, Mo.). Flasks were incubated on a shaker at 30° C. and about 100 rpm for 4 h. Cells were monitored under the microscope to determine the degree of protoplasting, with single cells desired. The cells were centrifuged for 5 min at about 2500×g in round-bottom tubes (i.e., 14 mL Falcon™ tubes, BD Biosciences, San Jose, Calif.). The supernatant was removed and the cells were gently resuspended with 5 mL of ice cold 10% glycerol. The cells were re-centrifuged for 5 min at about 2500×g in round-bottom tubes. The supernatant was removed and the cells were gently resuspended with 500 µL of ice cold 10% glycerol, using wide-bore pipette tips. 90 µL of cells were aliquoted into a prechilled electro-cuvette (Gene Pulser® cuvette—0.1 cm gap or 0.2 cm gap, Bio-Rad, Hercules, Calif.). One µg to 5 µg of DNA (in less than or equal to a 10 µL volume) was added to the cuvette, mixed gently with a pipette tip, and placed on ice for 5 min. Cells were electroporated at 200 ohms (resistance), 25 µF (capacitance), and either 250V (for 0.1 cm gap) or 500V (0.2 cm gap). 0.5 mL of M50-20 media was added immediately to the cuvette. The cells were then transferred to 4.5 mL of M50-20 media in a 25 mL shaker flask and incubated for 2-3 h at 30° C. and about 100 rpm on a shaker. The cells were centrifuged for 5 min at about 2500×g in round bottom tubes. The supernatant was removed and the cell pellet was resuspended in 0.5 mL of M50-20 media. Cells were plated onto an appropriate number (2 to 5) of M2B plates with appropriate selection and incubated at 30° C.

The *Schizochytrium* sp. ATCC 20888 mutant lacking functional orfA is also transformed with pREZ345 containing PFA1, such that PFA1 is randomly integrated in the mutant and restores PUFA production.

Example 8

*Thraustochytrium* sp. ATCC PTA-10212 PFA1 (SEQ ID NO:68) was re-synthesized (DNA2.0) and codon-optimized for expression in *Schizochytrium* (SEQ ID NO:120) and was cloned into an expression vector to generate pLR95. Codon-optimization occurred using the *Schizochytrium* codon usage table in FIG. 22. The expression vector contained approximately 2 kb of DNA from the flanking region of the native orfA gene locus from *Schizochytrium* sp. ATCC 20888.

The *Schizochytrium* sp. ATCC 20888 mutant lacking functional orfA from Example 7 was transformed via electroporation with enzyme pretreatment (See Example 7) with pLR95 containing codon-optimized *Thraustochytrium* sp. ATCC PTA-10212 PFA1 (SEQ ID NO:120). Based on homologous regions flanking the Zeocin™ resistance marker in the mutant and flanking the PFA1 gene in pLR95, double-crossover recombination occurred such that codon-optimized *Thraustochytrium* sp. ATCC PTA-10212 PFA1 was inserted into the native orfA locus. Recombination with codon-optimized *Thraustochytrium* sp. ATCC PTA-10212 PFA1 (SEQ ID NO:120) restored PUFA production in the *Schizochytrium* sp. ATCC 20888 mutant lacking orfA. Cells were grown and analyzed for FAMEs as described in Example 7. The native *Schizochytrium* sp. ATCC 20888 strain containing a functional orfA gene produced DHA and EPA in a ratio of 25:1. The recombinant strain containing codon-optimized *Thraustochytrium* sp. ATCC PTA-10212 PFA1 (SEQ ID NO:120) in place of the inactivated orfA gene produced DHA and EPA in a ratio of 5.4:1, further demonstrating that the PUFA profile of *Schizochytrium* can be altered by the nucleic acid molecules described herein. The EPA content of the recombinant strain was 4.4% of FAME, the DPA n-3 content was 2.3%, the DPA n-6 content was 4.9%, and the DHA content was 24.0%.

The *Schizochytrium* sp. ATCC 20888 mutant lacking functional orfA is also transformed with pLR95 containing PFA1, such that PFA1 is randomly integrated in the mutant and restores PUFA production.

Example 9

The native orfB gene in *Schizochytrium* sp. ATCC 20888 was replaced by homologous recombination following transformation via electroporation with enzyme pretreatment (See Example 7) with a vector containing the Zeocin™ resistance marker surrounded by sequences from the orfB flanking region. A mutant strain was generated lacking a functional orfB gene. The mutant strain was auxotrophic and required PUFA supplementation for growth.

*Schizochytrium* sp. ATCC PTA-9695 PFA2 (SEQ ID NO:3) was cloned into expression vector pDS04 to generate pREZ331. The expression vector contained approximately 2 kb of DNA from the flanking region of the native orfB gene locus from *Schizochytrium* sp. ATCC 20888.

The *Schizochytrium* sp. ATCC 20888 mutant lacking functional orfB was transformed with pREZ331 containing PFA2. Based on random integration in the mutant, PUFA production was restored by *Schizochytrium* sp. ATCC PTA-9695 PFA2 (SEQ ID NO:3). Cells were grown and analyzed for FAMEs as described in Example 7. The native *Schizochytrium* sp. ATCC 20888 strain containing a functional orfB gene produced DHA and DPA n-6 in a ratio of 2.3:1. The recombinant strain containing *Schizochytrium* sp. ATCC PTA-9695 PFA2 (SEQ ID NO:3) as a replacement of the inactivated orfB gene produced DHA and DPA n-6 in a ratio of 3.5:1. The EPA content of the recombinant strain was 0.8% of FAME, the DPA n-3 content was 0.1%, the DPA n-6 content was 7.1%, and the DHA content was 25.1%.

The *Schizochytrium* sp. ATCC 20888 mutant lacking functional orfB is also transformed with pREZ331 containing PFA2, such that PFA2 is inserted into the native orfB locus and restores PUFA production.

Example 10

*Thraustochytrium* sp. ATCC PTA-10212 PFA2 (SEQ ID NO:70) was re-synthesized (DNA2.0) and codon-optimized for expression in *Schizochytrium* (SEQ ID NO:121) and was cloned into an expression vector to generate pLR85. Codon-optimization occurred using the *Schizochytrium* codon usage table in FIG. 22. The expression vector contained approximately 2 kb of DNA from the flanking region of the native orfB gene locus from *Schizochytrium* sp. ATCC 20888.

Replacement of orf genes was also studied in a daughter strain of *Schizochytrium* sp. ATCC 20888 having improved DHA productivity. The native orfB gene in the daughter strain was replaced by homologous recombination following transformation via electroporation with enzyme pretreatment (See Example 7) with a vector containing the Zeocin™ resistance marker surrounded by sequences from the orfB flanking region. A mutant strain was generated lacking a functional orfB gene. The mutant strain was auxotrophic and required PUFA supplementation for growth. The mutant strain was transformed via electroporation with enzyme pretreatment (see Example 8) with pLR85 containing codon-optimized *Thraustochytrium* sp. ATCC PTA-10212 PFA2 (SEQ ID NO:121). Based on homologous regions flanking the Zeocin™ resistance marker in the mutant and flanking the PFA2 gene in pLR85, double-crossover recombination occurred such that codon-optimized *Thraustochytrium* sp. ATCC PTA-10212 PFA2 (SEQ ID NO:121) was inserted into the native orfB locus of the mutant strain. Recombination with codon-optimized *Thraustochytrium* sp. ATCC PTA-10212 PFA2 (SEQ ID NO:121) restored PUFA production in the daughter strain mutant lacking orfB. Cells were grown and analyzed for FAMEs as described in Example 7. The EPA content of the recombinant strain was 1.0% of FAME, the DPA n-3 content was 0.3%, the DPA n-6 content was 7.0%, and the DHA content was 31.0%.

In an experiment to be performed, the *Schizochytrium* sp. ATCC 20888 mutant lacking functional orfB from Example 9 is transformed via electroporation with enzyme pretreatment (see Example 8) with pLR85 containing codon-optimized *Thraustochytrium* sp. ATCC PTA-10212 PFA2 (SEQ ID NO:121). Based on homologous regions flanking the Zeocin™ resistance marker in the mutant and flanking the PFA2 gene in pLR85, double-crossover recombination occurs such that codon-optimized *Thraustochytrium* sp. ATCC PTA-10212 PFA2 (SEQ ID NO:121) is inserted into the native orfB locus. Recombination with codon-optimized *Thraustochytrium* sp. ATCC PTA-10212 PFA2 (SEQ ID NO:121) restores PUFA production in the *Schizochytrium* sp. ATCC 20888 mutant lacking orfB.

The *Schizochytrium* sp. ATCC 20888 and daughter strain mutants lacking functional orfB are also transformed with pLR85 containing PFA2, such that PFA2 is randomly integrated in the mutants and restores PUFA production in each of the mutants.

Example 11

A plasmid containing a paromomycin resistance marker cassette functional in *Schizochytrium* was developed for *Schizochytrium* sp. ATCC 20888 by replacement of the bleomycin/Zeocin™ resistance gene (ble) coding region in pMON50000/pTUBZEO11-2 (U.S. Pat. No. 7,001,772 B2) with that of neomycin phosphotransferase II (npt), originally from bacterial transposon Tn5. In pMON50000, the ble resistance gene is driven by the *Schizochytrium* α-tubulin promoter and is followed by the SV40 transcription terminator. The ble region in pMON50000 encompasses a NcoI restriction site at the ATG start codon and a PmlI restriction site immediately following the TGA stop signal. PCR was used to amplify the npt coding region present in pCaMVnpt (Shimizu et al., *Plant J.* 26(4):375 (2001)) such that the product included a BspHI restriction site (underlined below, primer CAX055) at the start ATG (bold) and a PmlI restriction site (underlined below, primer CAX056) immediately following the stop signal (bold—reverse complement):

```
                              (SEQ ID NO: 66)
CAX055 (forward):
GTCATGATTGAACAAGATGGATTGCAC (SEQ ID NO: 67)
CAX056 (reverse):
CCACGTGTCAGAAGAACTCGTCAAGAA.
```

PCR was carried out with the TaqMaster polymerase kit (5Prime), products were cloned into pCR4-TOPO (Invitrogen), and resulting plasmids were transformed into *E. coli* TOP10 (Invitrogen). DNA sequence analysis using vector primers identified multiple clones containing the desired 805 bp structure (i.e., the sequences match those of the source template plus the engineered restriction sites). The modified npt coding region was isolated by digestion with BspHI plus PmlI restriction enzymes, and the purified DNA fragment was ligated with a pMON50000 vector fragment generated by digestion with NcoI plus PmlI enzymes. Restriction enzymes BspHI and NcoI leave compatible overlapping ends, and PmlI leaves blunt ends. The resulting plasmid, pTS-NPT, contains the npt neomycin/paromomycin resistance gene in the identical context as that of the original ble gene in pMON50000.

Particle bombardment of *Schizochytrium* (U.S. Pat. No. 7,001,772 B2) was used to evaluate the function of the novel paromomycin resistance cassette in pTS-NPT. Selection for paromomycin (PAR) resistance was carried out on agar plates containing 50 μg/mL paromomycin sulfate (Sigma). Paromomycin-resistant *Schizochytrium* transformants were found at frequencies similar to those for Zeocin™-resistance from pMON50000. The "α-tubulin promoter/npt/SV40 ter-minator" cassette can be freed from pTS-NPT with various restriction enzymes for subsequent use in other development efforts.

Example 12

The native orfC gene in *Schizochytrium* sp. ATCC 20888 was replaced by homologous recombination following transformation with a vector containing the paromomycin resistance marker surrounded by sequences from the orfC flanking region. A mutant strain was generated lacking a functional orfC gene. The mutant strain was auxotrophic and required PUFA supplementation for growth.

*Schizochytrium* sp. ATCC PTA-9695 PFA3 (SEQ ID NO:5) was cloned into expression vector pREZ22 to generate pREZ324. The expression vector contained approximately 2 kb of DNA from the flanking region of the native orfC gene locus from *Schizochytrium* sp. ATCC 20888.

The *Schizochytrium* sp. ATCC 20888 mutant lacking functional orfC was transformed with pREZ324 containing *Schizochytrium* sp. ATCC PTA-9695 PFA3. Based on homologous regions flanking the paromomycin resistance marker in the mutant and flanking the *Schizochytrium* sp. ATCC PTA-9695 PFA3 gene in pREZ324, double-crossover recombination occurred such that *Schizochytrium* sp. ATCC PTA-9695 PFA3 was inserted into the native orfC locus. Homologous recombination with *Schizochytrium* sp. ATCC PTA-9695 PFA3 (SEQ ID NO:5) restored PUFA production in the *Schizochytrium* sp. ATCC 20888 mutant lacking orfC. Cells were grown and analyzed for FAMEs as described in Example 7. The native *Schizochytrium* sp. ATCC 20888 strain containing a functional orfC gene produced DHA and DPA n-6 in a ratio of 2.3:1. The recombinant strain containing *Schizochytrium* sp. ATCC PTA-9695 PFA3 (SEQ ID NO:5) in place of the inactivated orfC gene produced DHA and DPA n-6 in a ratio of 14:9, further demonstrating that the PUFA profile of *Schizochytrium* can be altered by the nucleic acid molecules described herein. The EPA content of the recombinant strain was 1.2% of FAME, the DPA n-3 content was 0.2%, the DPA n-6 content was 2.9%, and the DHA content was 43.4%.

The *Schizochytrium* sp. ATCC 20888 mutant lacking functional orfC was also transformed with pREZ324 containing PFA3, such that PFA3 was randomly integrated in the mutant and restored PUFA production. The EPA content of the recombinant strain was 1.2% of FAME, the DPA n-3 content was 0.2%, the DPA n-6 content was 2.5%, and the DHA content was 39.1%.

The native orfC gene in the daughter strain discussed in Example 10 was replaced by homologous recombination following transformation with a vector containing the paromomycin resistance marker surrounded by sequences from the orfC flanking region. A mutant strain was generated lacking a functional orfC gene. The mutant strain was auxotrophic and required PUFA supplementation for growth. The mutant lacking functional orfC was transformed with pREZ324. Double-crossover recombination occurred such that *Schizochytrium* sp. ATCC PTA-9695 PFA3 was inserted into the native orfC locus of the mutant strain. Homologous recombination with *Schizochytrium* sp. ATCC PTA-9695 PFA3 (SEQ ID NO:5) restored PUFA production in the daughter strain mutant lacking orfC. Cells were grown and analyzed for FAMEs as described in Example 7. The EPA content of the recombinant strain was 1.2% of FAME, the DPA n-3 content was 0.3%, the DPA n-6 content was 2.8%, and the DHA content was 43.1%.

The daughter strain mutant lacking functional orfB is also transformed with pREZ324 containing PFA3, such that PFA3 is randomly integrated in the mutant and restores PUFA production.

Example 13

*Thraustochytrium* sp. ATCC PTA-10212 PFA3 (SEQ ID NO:72) was re-synthesized (DNA2.0) and codon-optimized for expression in *Schizochytrium* (SEQ ID NO:122) and was cloned into expression vector pREZ22 to generate pREZ337. Codon-optimization occurred using the *Schizochytrium* codon usage table in FIG. 22. The expression vector contained approximately 2 kb of DNA from the flanking region of the native orfC gene locus from *Schizochytrium* sp. ATCC 20888.

The daughter strain mutant lacking functional orfC from Example 12 was transformed via electroporation with enzyme pretreatment (see Example 8) with pREZ337 containing codon-optimized *Thraustochytrium* sp. ATCC PTA-10212 PFA3 (SEQ ID NO:122). Based on homologous regions flanking the Zeocin™ resistance marker in the mutant and flanking the PFA3 gene in pREZ337, double-crossover recombination occurred such that codon-optimized *Thraustochytrium* sp. ATCC PTA-10212 PFA3 (SEQ ID NO:122) was inserted into the native orfC locus. Recombination with codon-optimized *Thraustochytrium* sp. ATCC PTA-10212 PFA3 (SEQ ID NO:122) restored PUFA production in the daughter strain mutant lacking orfC. Cells were grown and analyzed for FAMEs as described in Example 7. The EPA content of the recombinant strain was 1.3% of FAME, the DPA n-3 content was 0.4%, the DPA n-6 content was 2.7%, and the DHA content was 50.2%.

In an experiment to be performed, the *Schizochytrium* sp. ATCC 20888 mutant lacking functional orfC from Example 12 is transformed via electroporation with enzyme pretreatment (see Example 8) with pREZ337 containing codon-optimized *Thraustochytrium* sp. ATCC PTA-10212 PFA3 (SEQ ID NO:122). Based on homologous regions flanking the Zeocin™ resistance marker in the mutant and flanking the PFA3 gene in pREZ337, double-crossover recombination occurs such that codon-optimized *Thraustochytrium* sp. ATCC PTA-10212 PFA3 (SEQ ID NO:122) is inserted into the native orfC locus. Recombination with codon-optimized *Thraustochytrium* sp. ATCC PTA-10212 PFA3 (SEQ ID NO:122) restores PUFA production in the *Schizochytrium* sp. ATCC 20888 mutant lacking orfC.

The *Schizochytrium* sp. ATCC 20888 and daughter strain mutants lacking functional orfC are also transformed with pREZ337 containing PFA3, such that PFA3 is randomly integrated in the mutants and restores PUFA production in each of the mutants.

Example 14

Any two or all three of the orfA, orfB, and orfC genes in *Schizochytrium* sp. ATCC 20888 are replaced by homologous recombination following transformation with vectors containing either the Zeocin™ or paromomycin resistance marker surrounded by sequences from the appropriate orf flanking region. Mutant strains are generated lacking functional genes for any two or all three of orfA, orfB, and orfC. The mutant strains are auxotrophic and require PUFA supplementation for growth.

The *Schizochytrium* sp. ATCC 20888 mutants lacking functional orf genes are transformed with one or more expression vectors containing corresponding PFA genes (one or more of SEQ ID NOs: 1, 3, 5, 120, 121, or 122). Based on homologous regions flanking the Zeocin™ or paromomycin resistance markers in the mutants and flanking the PFA genes in the respective expression vectors, double-crossover recombination can occur such that PFA genes are inserted into the native orf loci. Random integration of these expression vectors can also occur with the selection of transformants based solely on the restoration of PUFA production. Homologous recombination with PFA genes restores PUFA production in the mutants, such that native PUFA profiles are restored or altered based on the combination of PFA genes inserted into the mutants.

In one performed experiment, the *Schizochytrium* sp. ATCC 20888 strain from Example 12 lacking a functional orfC gene and containing randomly integrated *Schizochytrium* sp. ATCC PTA-9695 PFA3 (SEQ ID NO:5) was used for replacement of the orfA and orfB genes. The native orfA and orfB genes in the strain were replaced by homologous recombination following transformation with a vector containing the Zeocin™ resistance marker surrounded by sequences from the orfA and orfB flanking regions. A strain was generated lacking functional orfA, orfB, and orfC, and containing randomly integrated *Schizochytrium* sp. ATCC PTA-9695 PFA3. The strain was transformed with pREZ345 containing codon-optimized *Schizochytrium* sp. ATCC PTA-9695 PFA1 (SEQ ID NO:1) and pREZ331 containing codon-optimized *Schizochytrium* sp. ATCC PTA-9695 PFA2 (SEQ ID N0:3) such that random integration of PFA1 and PFA2 occurred. The resulting recombinant strain lacked functional orfA, orfB, and orfC and contained random integrations of *Schizochytrium* sp. ATCC PTA-9695 PFA1, PFA2, and PFA3. Cells were grown and analyzed for FAMEs as described in Example 7. The EPA content of the recombinant strain was 6.6% of FAME, the DPA n-3 content was 0.8%, the DPA n-6 content was 1.6%, and the DHA content was 20.9%.

In another performed experiment, the daughter strain from Example 12 lacking a functional orfC gene and containing *Schizochytrium* sp. ATCC PTA-9695 PFA3 (SEQ ID NO:5) inserted into the native orfC locus was used for replacement of the orfA and orfB genes. The native orfA and orfB genes in the strain were replaced by homologous recombination following transformation with a vector containing the paromomycin resistance marker surrounded by sequences from the orfA and orfB flanking regions. A strain was generated lacking functional orfA, orfB, and orfC, and containing *Schizochytrium* sp. ATCC PTA-9695 PFA3 inserted into the native orfC locus. The strain was transformed with pREZ345 containing codon-optimized *Schizochytrium* sp. ATCC PTA-9695 PFA1 (SEQ ID NO:1) and pREZ331 containing codon-optimized *Schizochytrium* sp. ATCC PTA-9695 PFA2 (SEQ ID NO:3). Double-crossover recombinations occurred such that *Schizochytrium* sp. ATCC PTA-9695 PFA1 was inserted into the native orfA locus and *Schizochytrium* sp. ATCC PTA-9695 PFA2 was inserted into the native orfB locus of the strain. The resulting recombinant strain lacked functional orfA, orfB, and orfC and contained *Schizochytrium* sp. ATCC PTA-9695 PFA1, PFA2, and PFA3 inserted into the respective orfA, orfB, and orfC loci. Cells were grown and analyzed for FAMEs as described in Example 7. The EPA content of the recombinant strain was 7.3% of FAME, the DPA n-3 content was 0.4%, the DPA n-6 content was 1.5%, and the DHA content was 23.9%.

In another performed experiment, the daughter strain from Example 12 lacking a functional orfC gene and containing randomly integrated *Schizochytrium* sp. ATCC PTA- 9695 PFA3 (SEQ ID NO:5) was used for replacement of the orfA and orfB genes. The native orfA and orfB genes in the strain were replaced by homologous recombination following transformation with a vector containing the Zeocin™ resistance marker surrounded by sequences from the orfA and orfB flanking regions. A strain was generated lacking functional orfA, orfB, and orfC, and containing randomly integrated Schizochytrium sp. ATCC PTA-9695 PFA3. The strain was transformed with pREZ345 containing codon-optimized Schizochytrium sp. ATCC PTA-9695 PFA1 (SEQ ID NO:1) and pREZ331 containing codon-optimized Schizochytrium sp. ATCC PTA-9695 PFA2 (SEQ ID NO:3) such that random integration of PFA1 and PFA2 occurred. The resulting recombinant strain lacked functional orfA, orfB, and orfC and contained random integrations of Schizochytrium sp. ATCC PTA-9695 PFA1, PFA2, and PFA3. Cells were grown and analyzed for FAMEs as described in Example 7. The EPA content of the recombinant strain was 6.2% of FAME, the DPA n-3 content was 1.3%, the DPA n-6 content was 0.9%, and the DHA content was 16.6%.

In another performed experiment, the daughter strain from Example 13 lacking a functional orfC gene and containing Schizochytrium sp. ATCC PTA-10212 PFA3 (SEQ ID NO:122) inserted into the native orfC locus was used for replacement of the orfA and orfB genes. The native orfA and orfB genes in the strain were replaced by homologous recombination following transformation with a vector containing the paromomycin resistance marker surrounded by sequences from the orfA and orfB flanking regions. A strain was generated lacking functional orfA, orfB, and orfC, and containing Schizochytrium sp. ATCC PTA-10212 PFA3 inserted into the native orfC locus. The strain was transformed with pLR95 containing codon-optimized Schizochytrium sp. ATCC PTA-10212 PFA1 (SEQ ID NO:120) and pLR85 containing codon-optimized Schizochytrium sp. ATCC PTA-10212 PFA2 (SEQ ID NO:121). Double-crossover recombinations occurred such that Schizochytrium sp. ATCC PTA-10212 PFA1 was inserted into the native orfA locus and Schizochytrium sp. ATCC PTA-10212 PFA2 was inserted into the native orfB locus of the strain. The resulting recombinant strain lacked functional orfA, orfB, and orfC and contained Schizochytrium sp. ATCC PTA-10212 PFA1, PFA2, and PFA3 inserted into the respective orfA, orfB, and orfC loci. Cells were grown and analyzed for FAMEs as described in Example 7. The EPA content of the recombinant strain was 5.2% of FAME, the DPA n-3 content was 0.6%, the DPA n-6 content was 2.1%, and the DHA content was 47.1%.

In another performed experiment, the daughter strain from Example 13 lacking a functional orfC gene and containing randomly integrated Schizochytrium sp. ATCC PTA-10212 PFA3 (SEQ ID NO:122) was used for replacement of the orfA and orfB genes. The native orfA and orfB genes in the strain were replaced by homologous recombination following transformation with a vector containing the Zeocin™ resistance marker surrounded by sequences from the orfA and orfB flanking regions. A strain was generated lacking functional orfA, orfB, and orfC, and containing randomly integrated Schizochytrium sp. ATCC PTA-10212 PFA3. The strain was transformed with pLR95 containing codon-optimized Schizochytrium sp. ATCC PTA-10212 PFA1 (SEQ ID NO:120) and pLR85 containing codon-optimized Schizochytrium sp. ATCC PTA-10212 PFA2 (SEQ ID NO:121) such that random integration of PFA1 and PFA2 occurred. The resulting recombinant strain lacked functional orfA, orfB, and orfC and contained random integrations of Schizochytrium sp. ATCC PTA-10212 PFA1, PFA2, and PFA3. Cells were grown and analyzed for FAMEs as described in Example 7. The EPA content of the recombinant strain was 1.8% of FAME, the DPA n-3 content was 1.8%, the DPA n-6 content was 2.3%, and the DHA content was 34.1%.

Example 15

The orfA, orfB, and orfC genes from Schizochytrium sp. ATCC 20888 were cloned into a series of Duet vectors (Novagen). The Duet expression vectors are a set of compatible plasmids in which multiple target genes are cloned and co-expressed from the T7 inducible promoter in E. coli. Duet plasmid pREZ91 contained Schizochytrium sp. ATCC 20888 orfA in pETDuet-1; duet plasmid pREZ96 contained Schizochytrium sp. ATCC 20888 orfB in pCDFDuet-1; and duet plasmid pREZ101 contained Schizochytrium sp. ATCC 20888 orfC in pCOLADuet-1. Duet plasmids pREZ91, pREZ96, and pREZ101, along with plasmid pJK737, which contained the required accessory gene HetI (described in U.S. Pat. No. 7,217,856, incorporated by reference herein in its entirety), were transformed into E. coli strain BLR(DE3), which contains an inducible T7 RNA polymerase gene. Upon cell growth and addition of IPTG, according to manufacturer's instructions (Novagen), DHA and DPA n-6 were produced. Briefly, 1 mM IPTG was added for induction when cells reached an optical density of about 0.5 at 600 nm. Cells were the grown for 12 hours at 30° C. in Luria broth and harvested. The fatty acids were converted to methylesters using standard techniques. Fatty acid profiles were determined using gas chromatography with flame ionization detection (GC-FID) as fatty acid methyl esters (FAME).

The Schizochytrium sp. ATCC PTA-9695 PFA1 (SEQ ID NO:1) gene was cloned into the expression vector pETDuet-1, generating pREZ346. Duet plasmids pREZ346 (containing Schizochytrium sp. ATCC PTA-9695 PFA1), pREZ96 (containing orfB), and pREZ101 (containing orfC) were transformed into E. coli strain BLR(DE3) along with pJK737 (containing HetI). The Schizochytrium sp. ATCC PTA-9695 PFA1 gene was coexpressed with the Schizochytrium sp. ATCC 20888 orfB and orfC genes. The expression of Schizochytrium sp. ATCC PTA-9695 PFA1, in combination with Schizochytrium sp. ATCC 20888 orfB and orfC, supported DHA production in E. coli under induction conditions. The DHA content of the transformed E. coli was 2.8% of FAME, the DPA n-6 content was 1.1%, the DPA n-3 content was 0.6%, and the EPA content was 3.7%.

Example 16

The codon-optimized Thraustochytrium sp. ATCC PTA-10212 PFA1 (SEQ ID NO:120) gene was cloned into the expression vector pETDuet-1, generating pLR100. Duet plasmids pLR100 (containing codon-optimized Thraustochytrium sp. ATCC PTA-10212 PFA1), pREZ96 (containing Schizochytrium sp. ATCC 20888 orfB), and pREZ101 (containing Schizochytrium sp. ATCC 20888 orfC) are transformed into E. coli strain BLR(DE3) along with pJK737 (containing HetI). See Example 15. The Thraustochytrium sp. ATCC PTA-10212 PFA1 gene is coexpressed with the Schizochytrium sp. ATCC 20888 orfB and orfC genes. The expression of Thraustochytrium sp. ATCC PTA-10212 PFA1, in combination with Schizochytrium sp. ATCC 20888 orfB and orfC, supports DHA and EPA production in E. coli under induction conditions.

Example 17

The *Schizochytrium* sp. ATCC PTA-9695 PFA3 (SEQ ID NO:5) gene was cloned into the expression vector pCOLADuet-1, generating pREZ326. Duet plasmids pREZ326 (containing *Schizochytrium* sp. ATCC PTA-9695 PFA3), pREZ91 (containing *Schizochytrium* sp. ATCC 20888 orfA), and pREZ96 (containing *Schizochytrium* sp. ATCC 20888 orfB) were transformed into *E. coli* strain BLR(DE3) along with pJK737 (containing HetI). See Example 15. The expression of *Schizochytrium* sp. ATCC PTA-9695 PFA3, in combination with *Schizochytrium* sp. ATCC 20888 orfA and orfB, supported DHA production in *E. coli* under induction conditions. Cells were grown and analyzed for FAMEs as described in Example 15. The DHA content of the transformed *E. coli* was 0.3% of FAME.

Example 18

The codon-optimized *Thraustochytrium* sp. ATCC PTA-10212 PFA3 (SEQ ID NO:122) gene was cloned into the expression vector pCOLADuet-1, generating pREZ348. Duet plasmids pREZ348 (containing codon-optimized *Thraustochytrium* sp. ATCC PTA-10212 PFA3), pREZ91 (containing *Schizochytrium* sp. ATCC 20888 orfA), and pREZ96 (containing *Schizochytrium* sp. ATCC 20888 orfB) were transformed into *E. coli* strain BLR(DE3) along with pJK737 (containing HetI). See Example 15. The expression of *Thraustochytrium* sp. ATCC PTA-10212 PFA3, in combination with *Schizochytrium* sp. ATCC 20888 orfA and orfB, supported DHA production in *E. coli* under induction conditions. Cells were grown and analyzed for FAMEs as described in Example 15. The DHA content of the transformed *E. coli* was 2.9% of FAME and the DPA n-6 content was 0.4%.

Example 19

The *Schizochytrium* sp. ATCC PTA-9695 PFA2 (SEQ ID NO:3) gene was cloned into the expression vector pCDFDuet-1, generating pREZ330. Duet plasmids pREZ330 (containing *Schizochytrium* sp. ATCC PTA-9695 PFA2), pREZ326 (containing *Schizochytrium* sp. ATCC PTA-9695 PFA3), and pREZ91 (containing *Schizochytrium* sp. ATCC 20888 orfA), were transformed into *E. coli* strain BLR(DE3) along with pJK737 (containing HetI). See Example 9. The expression of *Schizochytrium* sp. ATCC PTA-9695 PFA2 and PFA3, in combination with *Schizochytrium* sp. ATCC 20888 orfA, supported DHA production in *E. coli* under induction conditions. Cells were grown and analyzed for FAMEs as described in Example 15. The DHA content of the transformed *E. coli* was 0.8% of FAME and the DPA n-6 content was 0.2%.

Example 20

The codon-optimized *Thraustochytrium* sp. ATCC PTA-10212 PFA2 (SEQ ID NO:121) gene was cloned into the expression vector pCDFDuet-1, generating pLR87. Duet plasmids pLR87 (containing codon-optimized *Thraustochytrium* sp. ATCC PTA-10212 PFA2), pREZ348 (containing codon-optimized *Thraustochytrium* sp. ATCC PTA-10212 PFA3), and pREZ91 (containing *Schizochytrium* sp. ATCC 20888 orfA), were transformed into *E. coli* strain BLR(DE3) along with pJK737 (containing HetI). See Example 15. The expression of codon-optimized *Thraustochytrium* sp. ATCC PTA-10212 PFA2 and PFA3, in combination with *Schizochytrium* sp. ATCC 20888 orfA, supported DHA and low levels of EPA production in *E. coli* under induction conditions. Cells were grown and analyzed for FAMEs as described in Example 15. The DHA content of the transformed *E. coli* was 4.4% of FAME, the DPA n-6 content was 1.1%, and the EPA content was 0.1%.

Example 21

Duet plasmids pREZ346 (containing *Schizochytrium* sp. ATCC PTA-9695 PFA1), pREZ330 (containing *Schizochytrium* sp. ATCC PTA-9695 PFA2), and pREZ326 (containing *Schizochytrium* sp. ATCC PTA-9695 PFA3) were transformed into *E. coli* strain BLR(DE3) along with pJK737 (containing HetI). See Example 15. The expression of *Schizochytrium* sp. ATCC PTA-9695 PFA1, PFA2, and PFA3 supported DHA production in *E. coli* under induction conditions. Cells were grown and analyzed for FAMEs as described in Example 15. The DHA content of the transformed *E. coli* was 0.3% of FAME and the EPA content was 0.3%.

Example 22

Duet plasmids pLR100 (containing codon-optimized *Thraustochytrium* sp. ATCC PTA-10212 PFA1), pLR87 (containing codon-optimized *Thraustochytrium* sp. ATCC PTA-10212 PFA2), and pREZ348 (containing codon-optimized *Thraustochytrium* sp. ATCC PTA-10212 PFA3) are transformed into *E. coli* strain BLR(DE3) along with pJK737 (containing HetI). See Example 15. The expression of codon-optimized *Thraustochytrium* sp. ATCC PTA-10212 PFA1, PFA2, and PFA3 supports DHA and EPA production in *E. coli* under induction conditions.

Example 23

Duet plasmids pREZ330 (containing *Schizochytrium* sp. ATCC PTA-9695 PFA2), pREZ91 (containing *Schizochytrium* sp. ATCC 20888 orfA), and pREZ101 (containing *Schizochytrium* sp. ATCC 20888 orfC) were transformed into *E. coli* strain BLR(DE3) along with pJK737 (containing HetI). See Example 15. The expression of *Schizochytrium* sp. ATCC PTA-9695 PFA2, in combination with *Schizochytrium* sp. ATCC 20888 orfA and orfC, supported DHA production in *E. coli* under induction conditions. Cells were grown and analyzed for FAMEs as described in Example 15. The DHA content of the transformed *E. coli* was 0.6% of FAME and the DPA n-6 content was 0.3%.

Example 24

Duet plasmids pLR87 (containing codon-optimized *Thraustochytrium* sp. ATCC PTA-10212 PFA2), pREZ91 (containing *Schizochytrium* sp. ATCC 20888 orfA), and pREZ101 (containing *Schizochytrium* sp. ATCC 20888 orfC) were transformed into *E. coli* strain BLR(DE3) along with pJK737 (containing HetI). See Example 15. The expression of codon-optimized *Thraustochytrium* sp. ATCC PTA-10212 PFA2, in combination with *Schizochytrium* sp. ATCC 20888 orfA and orfC, supported DHA and low levels of EPA production in *E. coli* under induction conditions. Cells were grown and analyzed for FAMEs as described in Example 15. The DHA content of the transformed *E. coli* was 1.7% of FAME, the DPA n-6 content was 0.9%, and the EPA content was 0.1%.

Example 25

Duet plasmids pREZ346 (containing *Schizochytrium* sp. ATCC PTA-9695 PFA1), pREZ330 (containing *Schizochytrium* sp. ATCC PTA-9695 PFA2), and pREZ101 (containing *Schizochytrium* sp. ATCC 20888 orfC) were transformed into *E. coli* strain BLR(DE3) along with pJK737 (containing HetI). See Example 15. The expression of PFA1 and PFA2, in combination with *Schizochytrium* sp. ATCC 20888 orfC, supported DHA production in *E. coli* under induction conditions. Cells were grown and analyzed for FAMEs as described in Example 15. The DHA content of the transformed *E. coli* was 0.3% of FAME, the DPA n-6 content was 0.1%, and the EPA content was 0.5%.

Example 26

Duet plasmids pLR100 (containing codon-optimized *Thraustochytrium* sp. ATCC PTA-10212 PFA1), pLR87 (containing codon-optimized *Thraustochytrium* sp. ATCC PTA-10212 PFA2), and pREZ101 (containing *Schizochytrium* sp. ATCC 20888 orfC) are transformed into *E. coli* strain BLR(DE3) along with pJK737 (containing HetI). See Example 15. The expression of codon-optimized *Thraustochytrium* sp. ATCC PTA-10212 PFA1 and PFA2, in combination with *Schizochytrium* sp. ATCC 20888 orfC, supports DHA and EPA production in *E. coli* under induction conditions.

Example 27

Duet plasmids pREZ346 (containing *Schizochytrium* sp. ATCC PTA-9695 PFA1), pREZ96 (containing *Schizochytrium* sp. ATCC 20888 orfB), and pREZ326 (containing *Schizochytrium* sp. ATCC PTA-9695 PFA3) were transformed into *E. coli* strain BLR(DE3) along with pJK737 (containing HetI). See Example 15. The expression of *Schizochytrium* sp. ATCC PTA-9695 PFA1 and PFA3, in combination with *Schizochytrium* sp. ATCC 20888 orfB, supported DHA production in *E. coli* under induction conditions. Cells were grown and analyzed for FAMEs as described in Example 15. The DHA content of the transformed *E. coli* was 0.1% of FAME and the EPA content was 0.1%.

Example 28

Duet plasmids pLR100 (containing codon-optimized *Thraustochytrium* sp. ATCC PTA-10212 PFA1), pREZ96 (containing *Schizochytrium* sp. ATCC 20888 orfB), and pREZ348 (containing codon-optimized *Thraustochytrium* sp. ATCC PTA-10212 PFA3) are transformed into *E. coli* strain BLR(DE3) along with pJK737 (containing HetI). See Example 15. The expression of codon-optimized *Thraustochytrium* sp. ATCC PTA-10212 PFA1 and PFA3, in combination with *Schizochytrium* sp. ATCC 20888 orfB, supports DHA and EPA production in *E. coli* under induction conditions.

Example 29

Pfa1p, Pfa2p, and Pfa3p PUFA synthase activities in *Schizochytrium* sp. ATCC PTA-9695 and *Thraustochytrium* sp. ATCC PTA-10212 are individually knocked-out by standard procedures. See, e.g., U.S. Pat. No. 7,217,856, incorporated by reference herein in its entirety.

The Zeocin™, hygromycin, blasticidin, or other appropriate resistance marker is inserted into a restriction site of the PFA1 gene (SEQ ID NO:1 or SEQ ID NO:68) that is contained in a plasmid. Following insertion of the resistance marker, the plasmid is introduced into *Schizochytrium* sp. ATCC PTA-9695 or *Thraustochytrium* sp. ATCC PTA-10212, respectively, by particle bombardment, electroporation, or other appropriate transformation method. Homologous recombination occurs, generating mutants in which the native PFA1 gene is either replaced or disrupted by the Zeocin™, hygromycin, blasticidin, or other appropriate resistance marker. Transformants are selected on plates containing Zeocin™, hygromycin, blasticidin, or other appropriate selection agent, supplemented with PUFAs. Colonies are further examined for the capacity to grow in the absence of PUFA supplementation. Genomic DNA is isolated from the colonies that are resistant to the selection agent and unable to grow in the absence of PUFA supplementation. PCR and Southern Blot analysis of the DNA is performed to demonstrate that the PFA1 gene is either deleted or disrupted.

PFA2 is knocked-out by similar procedures. Resultant knock-out mutants requiring PUFA supplementation are found to lack full-length PFA2.

PFA3 is knocked-out by similar procedures. Resultant knock-out mutants requiring PUFA supplementation are found to lack full-length PFA3.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A recombinant nucleic acid molecule comprising a polynucleotide sequence at least 95% identical to SEQ ID NO:72 and a transcription control sequence, wherein the polynucleotide sequence encodes a polypeptide comprising beta-hydroxyacyl-ACP dehydrase (DH) activity, and enoyl-ACP reductase (ER) activity, wherein said polynucleotide sequence is heterologous to said transcription control sequence.

2. The recombinant nucleic acid molecule of claim 1, wherein the nucleic acid molecule comprises the polynucleotide sequence of SEQ ID NO: 72.

3. A recombinant nucleic acid molecule comprising a polynucleotide sequence encoding a polypeptide and a transcription control sequence, wherein the polypeptide comprises an amino acid sequence at least 95% identical to SEQ ID NO: 73, wherein the polypeptide comprises beta-hydroxyacyl-ACP dehydrase (DH) activity and enoyl-ACP reductase (ER) activity, wherein said polynucleotide sequence is heterologous to said transcription control sequence.

4. The recombinant nucleic acid molecule of claim 3, wherein the polypeptide comprises the amino acid sequence of SEQ ID NO:73.

5. A host cell that expresses the nucleic acid molecule of claim 1 or claim 3, wherein said nucleic acid molecule is heterologous to the host cell, and wherein said host cell is not a human cell.

6. The host cell of claim 5, wherein the host cell is selected from the group consisting of a plant cell, a microbial cell, and an isolated animal cell.

7. The host cell of claim 6, wherein the microbial cell is a thraustochytrid, excluding *Thraustochytrium* sp. ATCC PTA-10212.

8. The host cell of claim 7, wherein the thraustochytrid is a *Schizochytrium* or a *Thraustochytrium*.

9. The host cell of claim 6, wherein the plant cell is selected from the group consisting of: canola, soybean, rapeseed, linseed/flax, maize, safflower, sunflower, tobacco, *Arabidopsis thaliana*, Brazil nut, castor bean, coconut, coriander, cotton, groundnut, jojoba, mustard, oil palm, olive, rice, squash, barley, wheat, and duckweed.

10. A method to produce at least one PUFA, comprising: expressing a PUFA synthase gene in a host cell under conditions effective to produce PUFA, wherein the PUFA synthase gene comprises a nucleic acid molecule comprising a polynucleotide sequence at least 95% identical to SEQ ID NO:72 or a polynucleotide sequence encoding a polypeptide which comprises an amino acid sequence at least 95% identical to SEQ ID NO:73, wherein said nucleic acid molecule is heterologous to the host cell, wherein said polynucleotide sequence encodes a PUFA synthase polypeptide comprising beta-hydroxyacyl-ACP dehydrase (DH) activity and enoyl-ACP reductase (ER) activity, and wherein at least one PUFA is produced.

11. A method to produce lipids enriched for DHA, EPA, or a combination thereof, comprising: expressing a PUFA synthase gene in a host cell under conditions effective to produce lipids, wherein the PUFA synthase gene comprises a nucleic acid molecule comprising a polynucleotide sequence at least 95% identical to SEQ ID NO:72 or a polynucleotide sequence encoding a polypeptide which comprises an amino acid sequence at least 95% identical to SEQ ID NO:73, wherein said nucleic acid molecule is heterologous to the host cell, wherein said polynucleotide sequence encodes a PUFA synthase polypeptide comprising beta-hydroxyacyl-ACP dehydrase (DH) activity and enoyl-ACP reductase (ER) activity, and wherein lipids enriched with DHA, EPA, or a combination thereof are produced.

12. A method of increasing production of DHA, EPA, or a combination thereof in an organism having PUFA synthase activity, comprising:
expressing the recombinant nucleic acid molecule of claim 1 or claim 3 in the organism under conditions effective to produce DHA, EPA, or a combination thereof, wherein said nucleic acid molecule is heterologous to the host organism, and wherein the PUFA synthase activity replaces an inactive or deleted activity, introduces a new activity, or enhances an existing activity in the organism, and wherein production of DHA, EPA, or a combination thereof in the organism is increased.

* * * * *